United States Patent
Chassaing et al.

(10) Patent No.: US 9,096,524 B2
(45) Date of Patent: Aug. 4, 2015

(54) ANTHELMINTIC AGENTS AND THEIR USE

(75) Inventors: Christophe Pierre Alain Chassaing, Schwabenheim (DE); Thorsten Meyer, Schwabenheim (DE)

(73) Assignee: Intervet International B.V., Boxmeer (NL)

( * ) Notice: Subject to any disclaimer, the term of this patent is extended or adjusted under 35 U.S.C. 154(b) by 692 days.

(21) Appl. No.: 13/256,369

(22) PCT Filed: Mar. 17, 2010

(86) PCT No.: PCT/EP2010/053448
§ 371 (c)(1),
(2), (4) Date: Sep. 13, 2011

(87) PCT Pub. No.: WO2010/115688
PCT Pub. Date: Oct. 14, 2010

(65) Prior Publication Data
US 2011/0319393 A1     Dec. 29, 2011

Related U.S. Application Data

(60) Provisional application No. 61/162,506, filed on Mar. 23, 2009.

(30) Foreign Application Priority Data

Mar. 20, 2009    (EP) .................................. 09155780

(51) Int. Cl.
| | | |
|---|---|---|
| *A01N 43/66* | (2006.01) | |
| *A01N 43/60* | (2006.01) | |
| *A01N 43/40* | (2006.01) | |
| *A01N 43/54* | (2006.01) | |
| *C07D 239/42* | (2006.01) | |
| *C07D 401/04* | (2006.01) | |
| *C07D 213/74* | (2006.01) | |
| *C07D 207/14* | (2006.01) | |
| *C07D 211/46* | (2006.01) | |
| *C07D 211/58* | (2006.01) | |
| *C07D 295/185* | (2006.01) | |
| *C07D 401/12* | (2006.01) | |
| *C07D 401/14* | (2006.01) | |
| *C07D 417/12* | (2006.01) | |
| *C07D 487/04* | (2006.01) | |

(52) U.S. Cl.
CPC ............ *C07D 213/74* (2013.01); *C07D 207/14* (2013.01); *C07D 211/46* (2013.01); *C07D 211/58* (2013.01); *C07D 295/185* (2013.01); *C07D 401/04* (2013.01); *C07D 401/12* (2013.01); *C07D 401/14* (2013.01); *C07D 417/12* (2013.01); *C07D 487/04* (2013.01)

(58) Field of Classification Search
CPC ... A61K 31/33; A61K 31/335; A61K 31/336; A61K 31/337; A61K 31/34; A61K 31/341; A61K 31/343; A61K 31/345; A61K 31/35; A61K 31/351; A61K 31/352; A61K 31/353; A61K 31/355; A61K 31/357; A61K 31/36; A61K 31/38; A61K 31/381; A61K 31/382
USPC ........... 514/171, 250, 275, 233.2, 235.8, 245, 514/255.06, 210.02, 210.09, 249, 252.02, 514/252.11, 253.01, 254.01, 254.1, 255.03, 514/256, 259.31, 267, 274, 291, 300, 304, 514/312, 315, 318, 319, 321, 351, 411, 161, 514/195, 210.16, 210.18, 210.2, 212.06, 514/217, 217.02, 218, 221.2, 220, 229.5, 514/230.5, 233.5, 235.2, 235.5, 236.2, 514/236.8, 243, 246, 248, 252.1, 252.14, 514/252.16, 252.18, 253.04, 253.1, 254.06, 514/254.11, 255.04, 255.05, 262.1, 263.2, 514/263.23, 263.34, 278, 290, 302, 303, 514/305, 307, 309, 311, 316, 317, 327, 333, 514/335, 336, 338, 342, 343, 344, 35, 350, 514/352, 354, 356, 357, 361, 370, 376, 378, 514/381, 387, 393, 394, 399, 4, 293
See application file for complete search history.

(56) References Cited

U.S. PATENT DOCUMENTS

| | | |
|---|---|---|
| 3,943,135 A | 3/1976 | Fujii |
| 4,203,986 A | 5/1980 | Joullie et al. |
| 5,077,288 A | 12/1991 | Lavielle et al. |
| 5,658,921 A | 8/1997 | Perregaard et al. |
| 6,642,228 B1 | 11/2003 | Hayashi et al. |
| 2003/0027814 A1 | 2/2003 | Ishiwata et al. |
| 2007/0021609 A1 * | 1/2007 | Dos Santos et al. .......... 544/120 |

FOREIGN PATENT DOCUMENTS

| | | |
|---|---|---|
| WO | WO 2005/021521 | 3/2005 |
| WO | WO2007/106525 | * 9/2007 |

OTHER PUBLICATIONS

European Search Report (Partial) corresponding to EP 09 15 5780, dated Sep. 1, 2009.
International Search Report corresponding to PCT/EP2010/053448, mailed Jun. 10, 2010.

* cited by examiner

*Primary Examiner* — San-Ming Hui

(57) ABSTRACT

This invention is directed to compounds and salts that are generally useful as anthelmintic agents or as intermediates in processes for making anthelmintic agents. This invention also is directed to processes for making the compounds and salts, pharmaceutical compositions and kits comprising the compounds and salts, uses of the compounds and salts to make medicaments, and treatments comprising the administration of the compounds and salts to animals in need of the treatments.

(I)

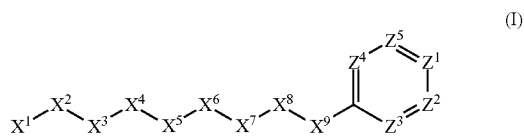

9 Claims, No Drawings

ANTHELMINTIC AGENTS AND THEIR USE

RELATED APPLICATIONS

This application is a national stage entry under 35 U.S.C. §371 of PCT/EP2010/053448 filed on Mar. 17, 2010, which claims priority to U.S. Provisional Application No. 61/162,506 filed on Mar. 23, 2009 and to EP Application No. 09155780.1 filed on Mar. 20, 2009.

FIELD OF THE INVENTION

This invention relates to compounds (and salts thereof) that are generally useful as anthelmintic agents or as intermediates in processes for making anthelmintic agents. This invention also relates to processes for making the compounds and salts, pharmaceutical compositions and kits comprising the compounds and salts, uses of the compounds and salts to make medicaments, and treatments comprising the administration of the compounds and salts to animals in need of the treatments.

BACKGROUND OF THE INVENTION

Parasitic diseases in humans and animals cause substantial suffering and economic losses throughout the world. Thus, control of parasitic infections remains an important global endeavor. The causative organisms include endoparasites, such as nematodes, cestodes, and trematodes. These organisms can infect, for example, the stomach, intestinal tract, lymphatic system, tissues, liver, lungs, heart, and brain.

There are many known drugs (or "anthelmintic agents") available to treat various endoparasitic infections. These reportedly include, for example, various avermectins (e.g., ivermectin, selamectin, doramectin, abamectin, and eprinomectin); milbemycins (moxidectin and milbemycin oxime); pro-benzimidazoles (e.g., febantel, netobimin, and thiophanate); a thiazole benzimidazole derivatives (e.g., thiabendazole and cambendazole); carbamate benzimidazole derivatives (e.g., fenbendazole, albendazole (oxide), mebendazole, oxfendazole, parbendazole, oxibendazole, flubendazole, and triclabendazole); imidazothiazoles (e.g., levamisole and tetramisole); tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulphonamides (e.g., clorsulon); pyrazino isoquinoline and benzazepine (e.g., praziquantel and epsiprantel); heterocyclic compounds (e.g., piperazine, diethylcarbamazine, and phenothiazine); arsenicals (e.g., thiacetarsamide, melorsamine, and arsenamide); cyclooctadepsipeptides (e.g., emodepside); and paraherquamides. See, e.g., McKellar, Q. A., et al., "Veterinary anthelmintics: old and new," *Review: Trends in Parasitology,* 20(10), 456-61 (October 2004).

While many endoparasitic infections can be treated with known drugs, evolutionary development of resistance by the parasites can render such drugs obsolete over time. See, e.g., Jabbar, A., et al., "Anthelmintic resistance: the state of play revisited," *Life Sciences,* 79, 2413-31 (2006). In addition, known drugs may have other deficiencies, such as limited spectrum of activity and the need for repeated treatments. Thus, there still exists a need for new anthelmintic agents to ensure safe, effective, and convenient treatment of a wide range of endoparasitic infections over a long period of time.

The following disclosure describes a group of such agents, as well as methods for making and using them.

SUMMARY OF THE INVENTION

Briefly, this invention is related to compounds (and salts thereof) that can generally be used as anthelmintic agents. The compounds correspond in structure to Formula I:

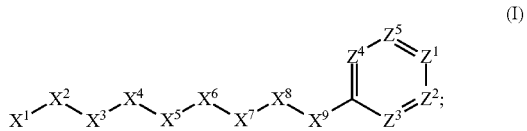

In Formula (I), $X^1$ is selected from the group consisting of $C_3$-$C_6$-alkyl, $C_3$-$C_6$-alkenyl, $C_3$-$C_6$-alkynyl, cyclopentyl, cyclohexyl, phenyl, 5-member heterocycloalkyl, 5-member heterocycloalkenyl, 5-member heteroaryl, 6-member heterocycloalkyl, 6-member heterocycloalkenyl, and 6-member heteroaryl. The $C_3$-$C_6$-alkyl, $C_3$-$C_6$-alkenyl, $C_3$-$C_6$-alkynyl, cyclopentyl, 5-member heterocycloalkyl, 5-member heterocycloalkenyl, and 5-member heteroaryl are optionally substituted by one or more substituents independently selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl, wherein the alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and hetero arylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl. The cyclohexyl, phenyl, 6-member heterocycloalkyl, 6-member heterocycloalkenyl, and 6-member heteroaryl are optionally substituted by one or more substituents independently selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl, wherein the alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl.

$X^2$ is selected from the group consisting of a bond, —O—, —C(O)—, —C(S)—, —NH—, —S—, —S(O)—, —S(O)$_2$—, —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$—. The —NH— is optionally substituted with alkyl, and the —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$— are optionally substituted with one or more independently selected alkyl;

$X^3$ is a linker, wherein the linker is a hydrocarbon, except as follows: the linker comprises one or more nitrogen atoms, and one or more of the carbons in the hydrocarbon are optionally substituted with one or more substituents independently selected from the group consisting of halogen, alkyl, alkoxy, and oxo, the linker comprises at least one chain of from 3 to 6 atoms that link $X^2$ to $X^4$, wherein from 1 to 2 of the chain atoms are nitrogen, and the linker comprises no chain of less than 3 atoms that links $X^2$ and $X^4$.

$X^4$ is selected from the group consisting of a bond, —$CH_2$—, —O—, —C(S)—, —C(O)—, —S(O)—, and —$S(O)_2$—, wherein the —$CH_2$— is optionally substituted with up to two substituents independently selected from the group consisting of alkyl, alkenyl, and carbocyclyl.

$X^5$ is selected from the group consisting of a bond, —$CH_2$—, and carbocyclyl, wherein the —$CH_2$— is optionally substituted with up to two substituents independently selected from the group consisting of alkyl, alkenyl, and carbocyclyl.

$X^6$ is selected from the group consisting of a bond, —$CH_2$—, and carbocyclyl, wherein the —$CH_2$— is optionally substituted with up to two substituents independently selected from the group consisting of alkyl, alkenyl, and carbocyclyl.

$X^7$ is selected from the group consisting of —$CH_2$—, —O—, —C(O)—, —C(S)—, —S—, —S(O)—, —$S(O)_2$—, —NH—, —C(O)—NH—, —C(S)—NH—, —NH—C(O)—, —NH—C(S)—, wherein the —$CH_2$— is optionally substituted with up to two substituents independently selected from the group consisting of alkyl, alkenyl, and carbocyclyl, and any —NH— is optionally substituted at a substitutable position with a substituent selected from the group consisting of alkyl, alkenyl, alkynyl, alkoxyalkyl, carbocyclyl, and carbocyclylalkyl, wherein any such substituent is optionally substituted with one or more independently selected halogen.

$X^8$ is selected from the group consisting of piperidinyl, piperazinyl, homopiperazinyl, and pyrrolidinyl, wherein the piperidinyl, piperazinyl, homopiperazinyl or pyrrolidinyl is optionally substituted with one or more independently selected alkyl;

$X^4$—$X^5$—$X^6$—$X^7$ comprises at least one chain of 3 to 5 atoms that links $X^3$ to $X^8$.

$X^4$—$X^5$—$X^6$—$X^7$ comprises no chain of less than 3 atoms that links $X^3$ to $X^8$.

$X^9$ is selected from the group consisting of a bond, —O—, —C(O)—, —S—, —S(O)—, —$S(O)_2$—, and —NH—, wherein the —NH— is optionally substituted at a substitutable position with a substituent selected from the group consisting of alkyl, alkenyl, alkynyl, alkoxyalkyl, carbocyclyl, and carbocyclylalkyl, wherein any such substituent is optionally substituted with one or more independently selected halogen.

$Z^1$ is selected from the group consisting of N and CH, wherein the CH is optionally substituted with a substituent selected from the group consisting of halogen, nitro, cyano, aminosulfonyl, alkyl, alkoxy, alkoxycarbonyl, alkylsulfanyl, alkylsulfinyl, alkylsulfonyl, aryl, arylsulfanyl, arylsulfinyl, arylsulfonyl, hetero aryl, heteroarylsulfanyl, heteroarylsulfinyl, and heteroarylsulfonyl, wherein the alkyl, alkoxy, alkoxycarbonyl, alkylsulfanyl, alkylsulfinyl, alkylsulfonyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl, and the aminosulfonyl is optionally substituted with up to two independently selected alkyl.

$Z^2$ is selected from the group consisting of N and CH, wherein the CH is optionally substituted with a substituent selected from the group consisting of cyano, halogen, nitro, alkyl, alkoxy, haloalkyl, alkylsulfanyl, and haloalkylsulfanyl.

$Z^3$, $Z^4$, and $Z^5$ are each independently selected from the group consisting of N and CH, wherein the CH is optionally substituted with a substituent selected from the group consisting of halogen, cyano, nitro, alkyl, alkoxy, alkylsulfanyl, haloalkyl, haloalkoxy, and haloalkylsulfanyl; and only one of $Z^1$, $Z^2$, $Z^3$, $Z^4$, and $Z^5$ may be N.

This invention also is directed, in part, to methods for making the above-described compounds and salts of this invention.

This invention also is directed, in part, to pharmaceutical compositions. The pharmaceutical compositions comprise at least one compound or salt of this invention, and at least one excipient.

This invention also is directed, in part, to methods for treating a disease in an animal, particularly a parasitic infection. The methods comprise administering at least one compound or salt of this invention to the animal.

This invention also is directed, in part, to a use of at least one compound or salt of this invention to prepare a medicament for treating a disease (e.g., a parasitic infection) in an animal.

This invention also is directed, in part, to a kit. The kit comprises at least one compound or salt of this invention. In addition, the kit comprises at least one other component, such as another ingredient (e.g., an excipient or active ingredient), instructions and/or an apparatus for combining the compound or salt with another ingredient, instructions and/or an apparatus for administering the compound or salt, and/or a diagnostic tool.

Further benefits of Applicants' invention will be apparent to one skilled in the art from reading this specification.

DETAILED DESCRIPTION OF PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this specification, and may be variously modified.

I. Compounds of this Invention

The compounds of this invention generally correspond in structure to Formula (I):

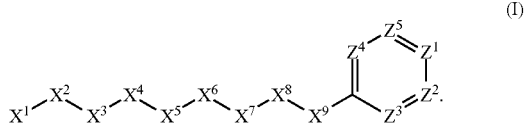

The substituents in Formula (I) are defined as follows:

A. Preferred Embodiments of $X^1$ $X^1$ is selected from the group consisting of $C_3$-$C_6$-alkyl, $C_3$-$C_6$-alkenyl, $C_3$-$C_6$-alkynyl, cyclopentyl, cyclohexyl, phenyl, 5-member heterocycloalkyl, 5-member heterocycloalkenyl, 5-member heteroaryl, 6-member heterocycloalkyl, 6-member heterocycloalkenyl, and 6-member heteroaryl.

The $C_3$-$C_6$-alkyl, $C_3$-$C_6$-alkenyl, $C_3$-$C_6$-alkynyl, cyclopentyl, 5-member heterocycloalkyl, 5-member heterocycloalkenyl, and 5-member heteroaryl are optionally substituted by one or more substituents independently selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl.

The cyclohexyl, phenyl, 6-member heterocycloalkyl, 6-member heterocycloalkenyl, and 6-member heteroaryl are optionally substituted by one or more substituents independently selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl.

In some embodiments, the cyclohexyl, phenyl, 6-member heterocycloalkyl, 6-member heterocycloalkenyl, and 6-member heteroaryl are optionally substituted at the meta and para positions by one or more substituents independently selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl. The alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl. The cyclohexyl, phenyl, 6-member heterocycloalkyl, 6-member heterocycloalkenyl, 6-member heteroaryl are optionally substituted at the ortho positions by one or more independently selected halogen.

In some embodiments, $X^1$ is $C_3$-$C_6$-alkyl.
In some embodiments, $X^1$ is $C_3$-$C_4$-alkyl.
In some embodiments, $X^1$ is $C_3$-alkyl. In some such embodiments, $X^1$ is isopropyl. In these embodiments, the compound is encompassed by the following formula:

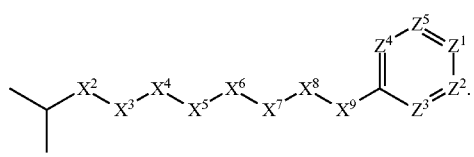

In some embodiments, $X^1$ is $C_4$-alkyl. In some such embodiments, $X^1$ is butyl. In such embodiments, the compound is encompassed by the following formula:

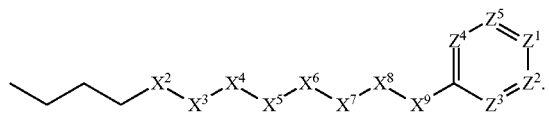

In some embodiments, $X^1$ is $C_3$-$C_6$-cycloalkyl. In some such embodiments, for example, $X^1$ is $C_6$-cycloalkyl (i.e., cyclohexyl). In such embodiments, the compound is encompassed by the following formula:

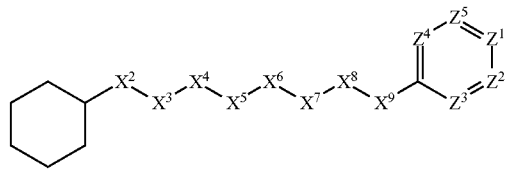

In some embodiments, $X^1$ is phenyl optionally substituted at the meta and para positions with one or more substituents selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and hetero arylalkylsulfanyl. The alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and hetero arylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl. The phenyl is also optionally substituted at the ortho positions by one or more independently selected halogen.

In some embodiments, $X^1$ is phenyl. In such embodiments, the compound is encompassed by the following formula:

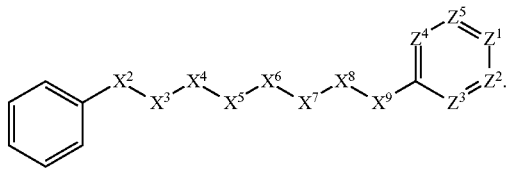

In some embodiments, $X^1$ is phenyl substituted with one substituent.

In some embodiments, $X^1$ is phenyl substituted with one substituent at an ortho position.

In some embodiments, $X^1$ is phenyl substituted with one halogen substituent at an ortho position. In some such embodiments, $X^1$ is phenyl substituted with chloro at an ortho position. Such embodiments are encompassed by the following formula:

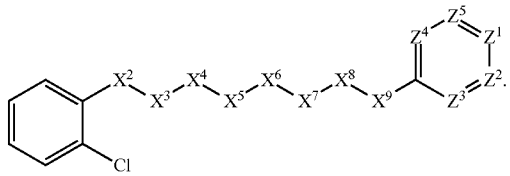

In some embodiments, $X^1$ is phenyl substituted with one substituent at a meta position.

In some embodiments, $X^1$ is phenyl substituted with haloalkyl at a meta position. In some such embodiments $X^1$ is phenyl substituted with trifluoromethyl at a meta position. Such embodiments are encompassed by the following formula:

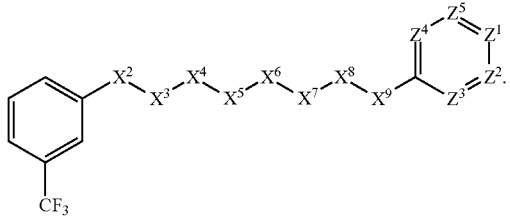

In other such embodiments, $X^1$ is phenyl substituted with chloro at a meta position. In such embodiments, the compound is encompassed by the following formula:

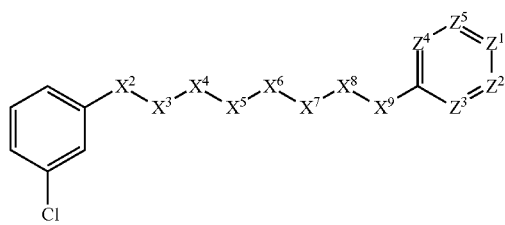

In other such embodiments, $X^1$ is phenyl substituted with halo-$C_1$-$C_6$-alkoxy at a meta position. In some such embodiments, for example, $X^1$ is phenyl substituted with fluoro-$C_1$-alkoxy (i.e., —$OCF_3$). Such embodiments are encompassed by the following formula:

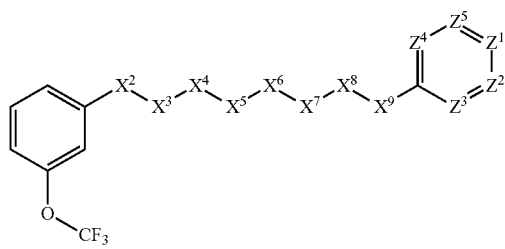

In some embodiments, $X^1$ is phenyl substituted with one substituent at the para position.

In some embodiments, $X^1$ is phenyl substituted with halo-$C_1$-$C_6$-alkyl at the para position. In some such embodiments, for example, $X^1$ is phenyl substituted with trifluoromethyl (i.e., —$CF_3$). at the para position. Such embodiments are encompassed by the following formula:

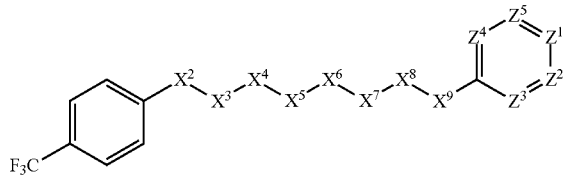

In some embodiments, $X^1$ is phenyl substituted with $C_1$-$C_6$-alkyl. In some such embodiments, for example, $X^1$ is phenyl substituted with tert-butyl at the para position. Such embodiments are encompassed by the following formula:

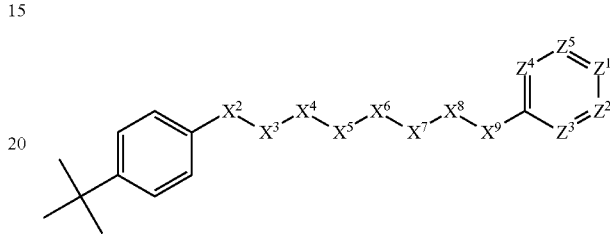

In other such embodiments, $X^1$ is phenyl substituted with $C_3$-alkyl (i.e. propyl) at the para position. In such embodiments, the compound is encompassed by the following formula:

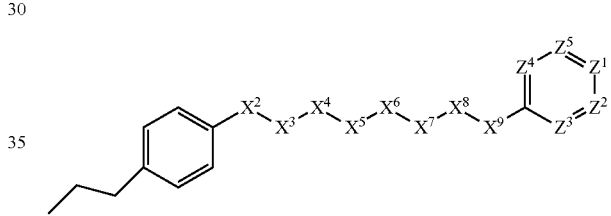

In yet other such embodiments, $X^1$ is phenyl substituted with $C_1$-alkyl (i.e. methyl) at the para position. In such embodiments, the compound is encompassed by the following formula:

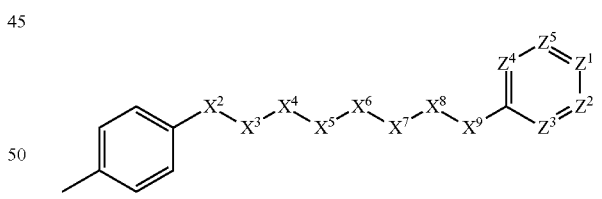

In some embodiments, $X^1$ is phenyl substituted with halo at the para position. In some such embodiments, for example, $X^1$ is phenyl substituted with chloro at the para position. Such embodiments are encompassed by the following formula:

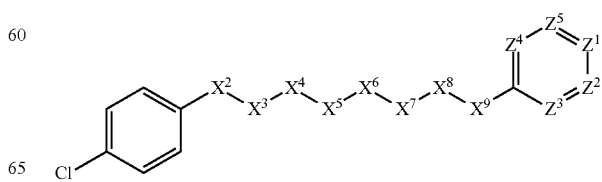

In other such embodiments, $X^1$ is phenyl substituted with fluoro at the para position. In such embodiments, the compound is encompassed by the following formula:

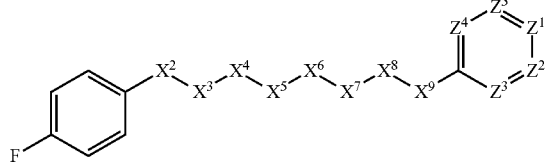

In some embodiments, $X^1$ is phenyl substituted with $C_1$-$C_6$-alkoxy. In some such embodiments, for example, $X^1$ is phenyl substituted with $C_2$-alkoxy (i.e. ethoxy) at the para position. Such embodiments are encompassed by the following formula:

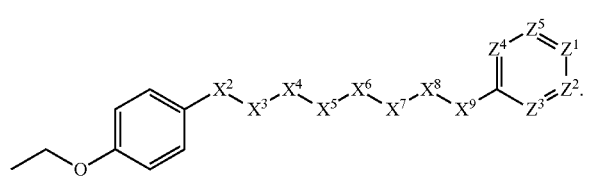

In some such embodiments, for example, $X^1$ is phenyl substituted with $C_1$-alkoxy (i.e. methoxy) at the para position. Such embodiments are encompassed by the following formula:

In some embodiments, $X^1$ is phenyl substituted with cyano at the para position. In those embodiments, the compound is encompassed by the following formula:

In some embodiments, $X^1$ is phenyl substituted with aryl at the para position. In some such embodiments, for example, $X^1$ is phenyl substituted with phenyl at the para position. Such embodiments are encompassed by the following formula:

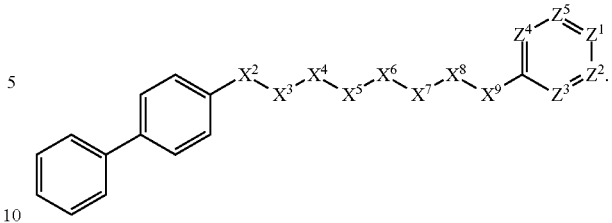

In some embodiments, $X^1$ is phenyl substituted with aryloxy at the para position. In some such embodiments, for example, $X^1$ is phenyl substituted with phenoxy at the para position. Such embodiments are encompassed by the following formula:

In some embodiments, $X^1$ is phenyl substituted with aryl-$C_1$-$C_6$-alkoxy at the para position. In some such embodiments, for example, $X^1$ is phenyl substituted with phenylmethoxy at the para position. Such embodiments are encompassed by the following formula:

In some embodiments, $X^1$ is phenyl substituted $C_1$-$C_6$-alkoxy. In some such embodiments, for example, $X^1$ is phenyl para-substituted with $C_4$-alkoxy (i.e., isobutyloxy). Such embodiments are encompassed by the following formula:

In some embodiments, $X^1$ is phenyl substituted with halo-$C_1$-$C_6$-alkyl-aryl-$C_1$-$C_6$-alkoxy. In some such embodiments, for example, $X^1$ is phenyl substituted with trifluoro-$C_1$-alkylphenyl-$C_1$-alkoxy (i.e., trifluoromethylphenylmethoxy). Such embodiments are encompassed by the following formula:

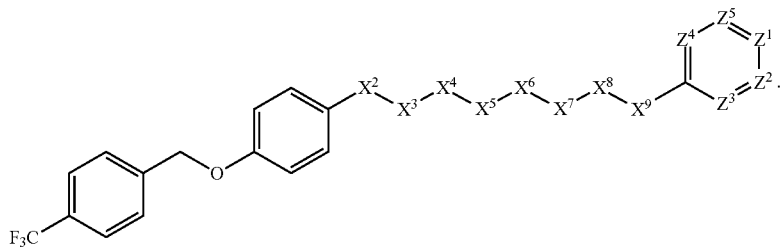

In some embodiments, $X^1$ is phenyl substituted with two substituents.

In some embodiments, $X^1$ is phenyl substituted at the ortho and para positions.

In some embodiments, $X^1$ is phenyl substituted at the ortho and para positions with two independently selected halo substituents. In some such embodiments, for example, $X^1$ is phenyl substituted with two chloro substituents. Such embodiments are encompassed by the following formula:

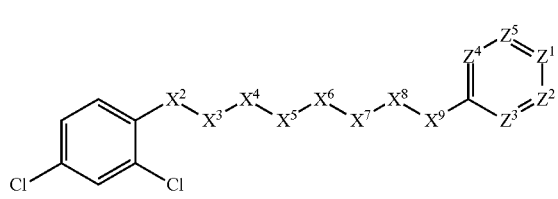

In other such embodiments, for example, $X^1$ is phenyl substituted with two fluoro substituents. Such embodiments are encompassed by the following formula:

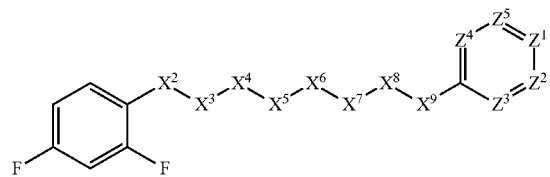

In yet other such embodiments, for example, $X^1$ is phenyl substituted with a fluoro at the ortho position and a chloro at the para position. Such embodiments are encompassed by the following formula:

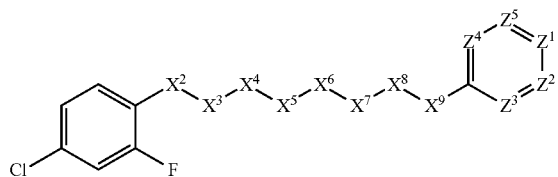

In some embodiments, $X^1$ is phenyl substituted at the meta and para positions.

In some embodiments, $X^1$ is phenyl substituted at meta and para positions. In some such embodiments, for example, $X^1$ is phenyl substituted with two chloro substituents. Such embodiments are encompassed by the following formula:

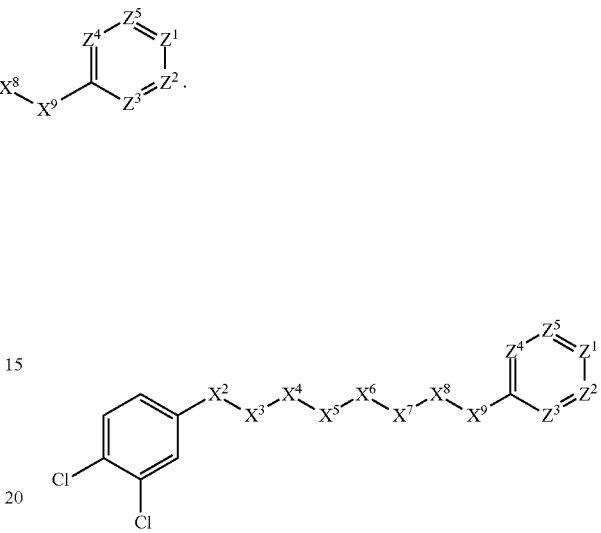

In other such embodiments, for example, $X^1$ is phenyl substituted with two independently selected $C_1$-$C_6$-alkoxy substituents. For example, $X^1$ is phenyl substituted with two $C_1$-alkoxy substituents (i.e., methoxy). Such embodiments are encompassed by the following formula:

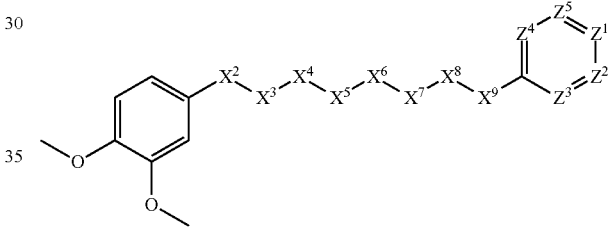

In other such embodiments, the compound corresponds in structure to the following formula:

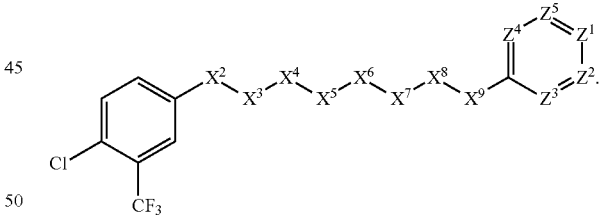

In yet other such embodiments, the compound corresponds in structure to the following formula:

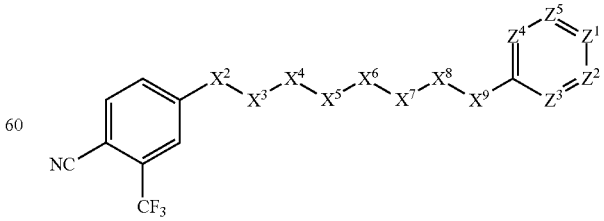

In some embodiments, $X^1$ is phenyl substituted at both meta positions.

In some embodiments, $X^1$ is phenyl substituted with two halo-$C_1$-$C_6$-alkyl substituents. For example, some such embodiments are encompassed by the following formula:

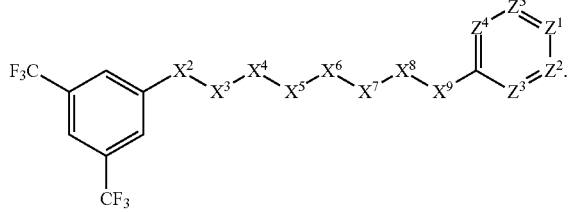

In some embodiments, $X^1$ is 5-membered heteroaryl optionally substituted by one or more substituents independently selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and hetero arylalkylsulfanyl. The alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and hetero arylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl.

In some embodiments, $X^1$ is optionally substituted thiadiazoyl, optionally substituted with a haloalkyl substituent. In some such embodiments, $X^1$ is thiadiazoyl substituted with trifluoromethyl. In such embodiments, the compound is encompassed by the following formula:

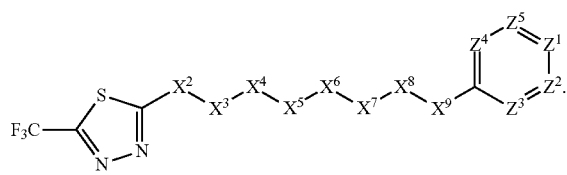

In some embodiments, $X^1$ is 6-membered heteroaryl optionally substituted by one or more substituents independently selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and hetero arylalkylsulfanyl. The alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and hetero arylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl. The cyclohexyl, phenyl, 6-member heterocycloalkyl, 6-member heterocycloalkenyl, 6-member heteroaryl are optionally substituted at the ortho positions by one or more independently selected halogen.

In some embodiments, $X^1$ is optionally substituted pyridinyl.

In some embodiments, $X^1$ is 2-pyridinyl. In such embodiments, the compound is encompassed by the following formula:

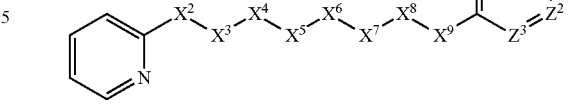

In some embodiments, $X^1$ is 2-pyridinyl substituted with haloalkyl. In such embodiments, the compound is encompassed by the following formula:

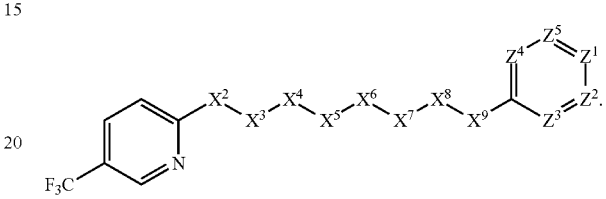

In some embodiments, $X^1$ is 2-pyridinyl substituted with chloro at the para position. In such embodiments, the compound is encompassed by the following formula:

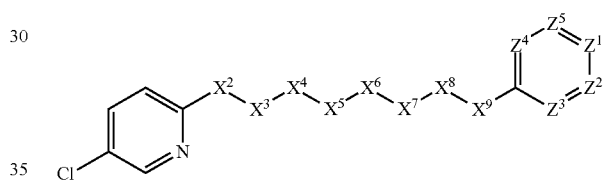

In some embodiments, $X^1$ is 3-pyridinyl. In such embodiments, the compound is encompassed by the following formula:

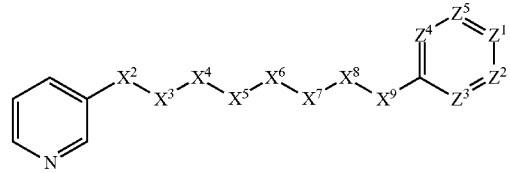

In some embodiments, $X^1$ is 3-pyridinyl substituted with halo-$C_1$-$C_6$-alkyl. In such embodiments, for example, the compound is encompassed by the following formula:

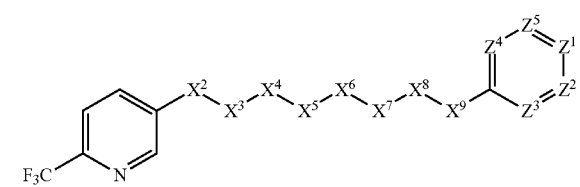

In some embodiments, $X^1$ is 3-pyridinyl substituted with $C_1$-$C_6$-alkoxy. In such embodiments, for example, the compound is encompassed by the following formula:

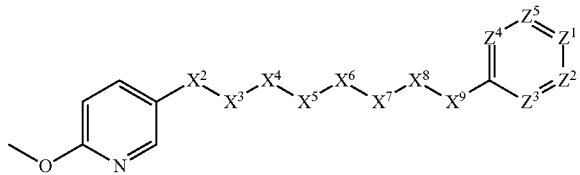

In yet other such embodiments, $X^1$ is 4-pyridinyl. In such embodiments, the compound is encompassed by the following formula:

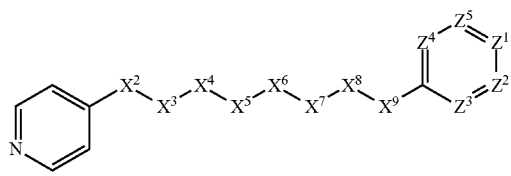

B. Preferred Embodiments of $X^2$ $X^2$ is selected from the group consisting of a bond, —O—, —C(O)—, —C(S)—, —NH—, —S—, —S(O)—, —S(O)$_2$—, —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$—. Here, the —NH— is optionally substituted with alkyl. The —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$— are optionally substituted with one or more independently selected alkyl.

In some embodiments, $X^2$ is selected from the group consisting of a bond, —O—, —C(O)—, —C(S)—, —NH—, —S—, —S(O)—, —S(O)$_2$—, —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$—. Here, the —NH— is optionally substituted with $C_1$-$C_6$-alkyl. The —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$— are optionally substituted with one or more independently selected $C_1$-$C_6$-alkyl.

In some embodiments, $X^2$ is a single bond. In such embodiments, the compound is encompassed by the following formula:

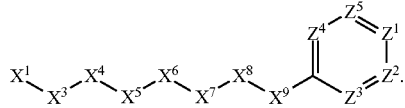

In some embodiments, $X^2$ is —O—. In such embodiments, the compound is encompassed by the following formula:

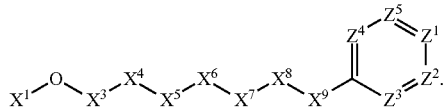

In some embodiments, $X^2$ is —C(O)—. In such embodiments, the compound is encompassed by the following formula:

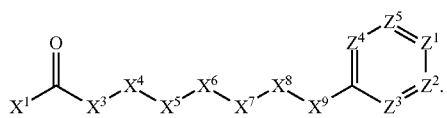

In some embodiments, $X^2$ is —C(S)—. In such embodiments, the compound is encompassed by the following formula:

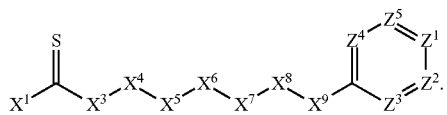

In some embodiments, $X^2$ is —NH—. In such embodiments, the compound is encompassed by the following formula:

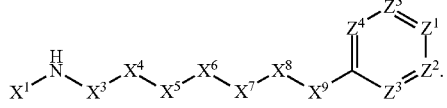

In some embodiments, $X^2$ is —S—. In such embodiments, the compound is encompassed by the following formula:

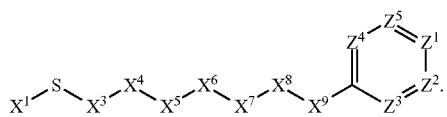

In some embodiments, $X^2$ is —S(O)—. In such embodiments, the compound is encompassed by the following formula:

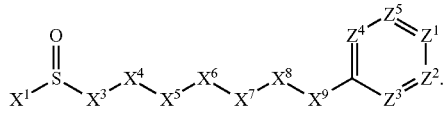

In some embodiments, $X^2$ is —S(O)$_2$—. In such embodiments, the compound is encompassed by the following formula:

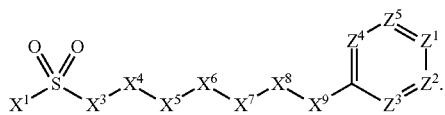

In some embodiments, $X^2$ is —CH$_2$—. In such embodiments, the compound is encompassed by the following formula:

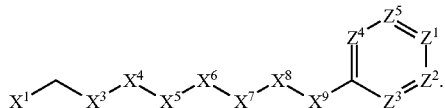

In some embodiments, $X^2$ is —CH$_2$CH$_2$—. In such embodiments, the compound is encompassed by the following formula:

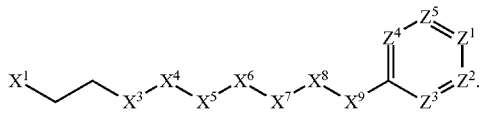

In some embodiments, $X^2$ is —C(O)—CH$_2$—. In such embodiments, the compound is encompassed by the following formula:

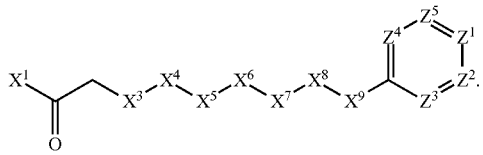

In some embodiments, $X^2$ is —CH$_2$—C(O)—. In such embodiments, the compound is encompassed by the following formula:

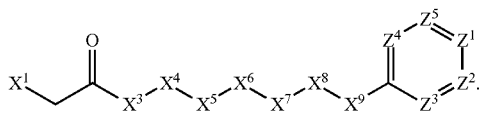

In some embodiments, $X^2$ is —O—CH$_2$—. In such embodiments, the compound is encompassed by the following formula:

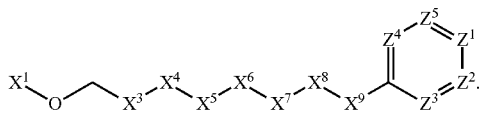

In some embodiments, $X^2$ is —CH$_2$—O—. In such embodiments, the compound is encompassed by the following formula:

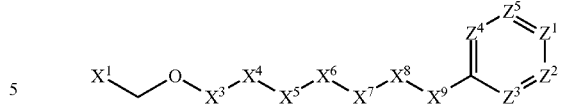

In some embodiments, $X^2$ is —NH—CH$_2$—. In such embodiments, the compound is encompassed by the following formula:

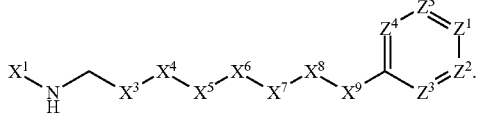

In some embodiments, $X^2$ is —CH$_2$NH—. In such embodiments, the compound is encompassed by the following formula:

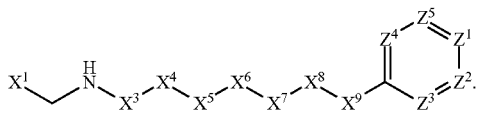

In some embodiments, $X^2$ is —S—CH$_2$—. In such embodiments, the compound is encompassed by the following formula:

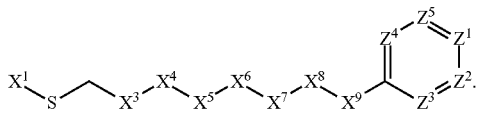

In some embodiments, $X^2$ is —CH$_2$—S—. In such embodiments, the compound is encompassed by the following formula:

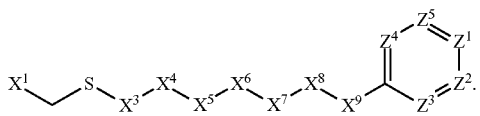

In some embodiments, $X^2$ is —S(O)—CH$_2$—. In such embodiments, the compound is encompassed by the following formula:

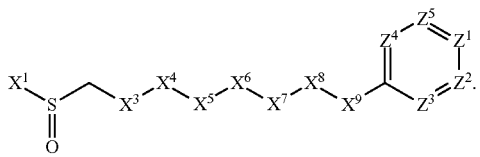

In some embodiments, $X^2$ is —CH$_2$—S(O)—. In such embodiments, the compound is encompassed by the following formula:

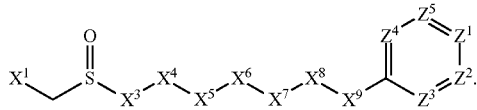

In some embodiments, $X^2$ is —S(O)$_2$—CH$_2$—. In such embodiments, the compound is encompassed by the following formula:

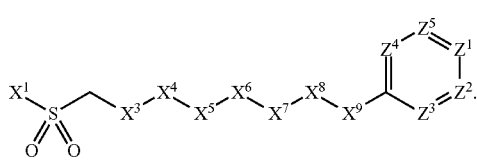

In some embodiments, $X^2$ is —CH$_2$—S(O)$_2$—. In such embodiments, the compound is encompassed by the following formula:

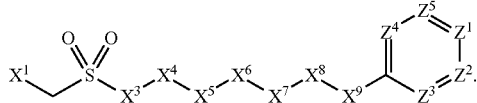

C. Preferred Embodiments of $X^3$ $X^3$ is a linker. The linker is a hydrocarbon group, except: (a) the linker comprises one or more nitrogen atoms, and (b) one or more of the carbons in the hydrocarbon optionally are substituted with one or more substituents independently selected from the group consisting of oxo, halogen, hydroxy, alkyl, and alkoxy. The linker comprises at least one chain of from 3 to 6 atoms that bridges $X^2$ to $X^4$. From 1 to 2 of the chain atoms are nitrogen. The linker has no chain of less than 3 atoms that bridges $X^2$ and $X^4$.

In some embodiments, the linker is a hydrocarbon group, except: (a) the linker comprises one or more nitrogen atoms, and (b) one or more of the carbons in the hydrocarbon optionally are substituted with one or more substituents independently selected from the group consisting of oxo, halogen, alkyl, and alkoxy. The linker comprises at least one chain of from 3 to 5 atoms that bridges $X^2$ to $X^4$. From 1 to 2 of the chain atoms are nitrogen. The linker has no chain of less than 3 atoms that bridges $X^2$ and $X^4$.

In some embodiments, the linker is a hydrocarbon group, except: (a) the linker comprises one or more nitrogen atoms, and (b) one or more of the carbons in the hydrocarbon optionally are substituted with one or more substituents independently selected from the group consisting of oxo, halogen, hydroxy, $C_1$-$C_6$-alkyl, and $C_1$-$C_6$-alkoxy.

In some embodiments, the linker is a hydrocarbon group, except: (a) the linker comprises one or more nitrogen atoms, and (b) one or more of the carbons in the hydrocarbon optionally are substituted with oxo.

In some embodiments, the linker is a hydrocarbon group, except: (a) the linker comprises one or more nitrogen atoms, and (b) one carbon in the hydrocarbon is substituted with oxo.

In some embodiments, the linker is a hydrocarbon group, except for comprising one or more nitrogen atoms.

In some embodiments, the linker comprises no greater than one nitrogen atom.

In other embodiments, the linker comprises no greater and no less than two nitrogen atoms.

In some embodiments, the linker comprises at least one chain of from 3 to 6 atoms that bridges $X^2$ to $X^4$.

In some embodiments, the linker comprises at least one 3-atom chain that bridges $X^2$ to $X^4$.

In some embodiments, the linker comprises at least one 4-atom chain that bridges $X^2$ to $X^4$. In some such embodiments, the linker has no chain of less than 4 atoms that bridges $X^2$ to $X^4$.

In some embodiments, the linker comprises at least one 5-atom chain that bridges $X^2$ to $X^4$. In some such embodiments, the linker has no chain of less than 5 atoms that bridges $X^2$ to $X^4$.

In some embodiments, $X^3$ is selected from the group of linkers consisting of those shown in Table I:

TABLE I

Example of $X^3$ Linkers

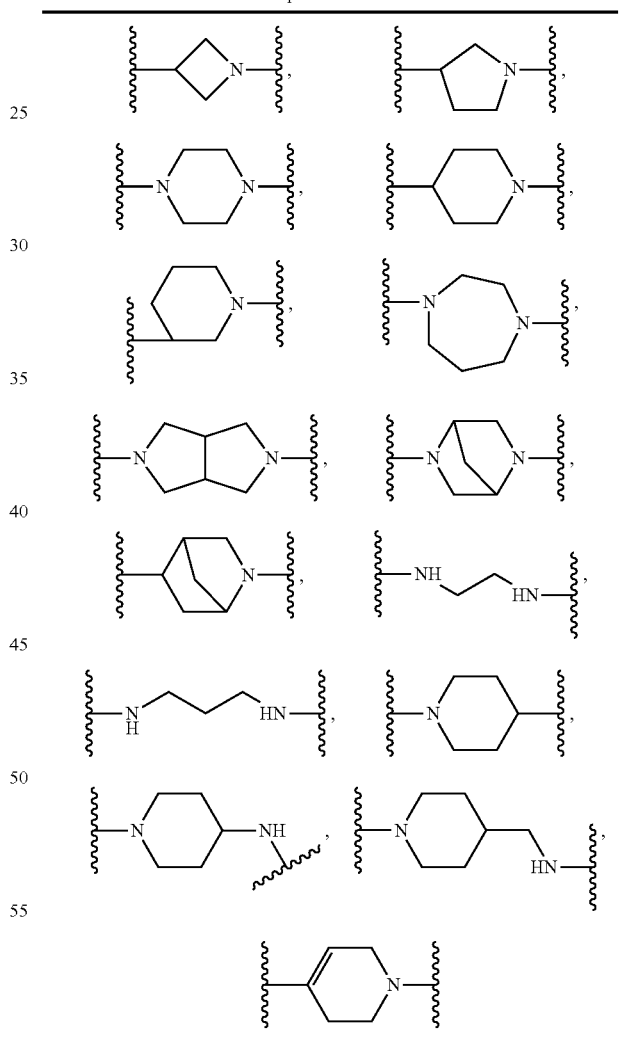

Any such group is optionally substituted with one or more substituents independently selected from the group consisting of halogen, $C_1$-$C_6$-alkyl, $C_1$-$C_6$-alkoxy, oxo, and thiocarbonyl.

In some embodiments, $X^3$ is selected from the group consisting of:

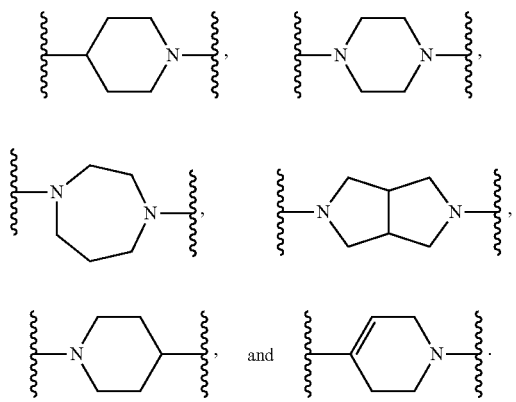

In some embodiments, the linker comprises at least one 3-atom chain that bridges $X^2$ to $X^4$. To illustrate, the following are some of the structures from Table I that exemplify such linkers:

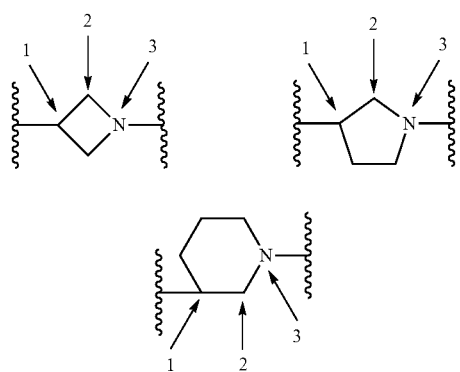

In some embodiments, the linker comprises at least one 4-atom chain that bridges $X^2$ to $X^4$. To illustrate, the following are some of the structures from Table I that exemplify such linkers:

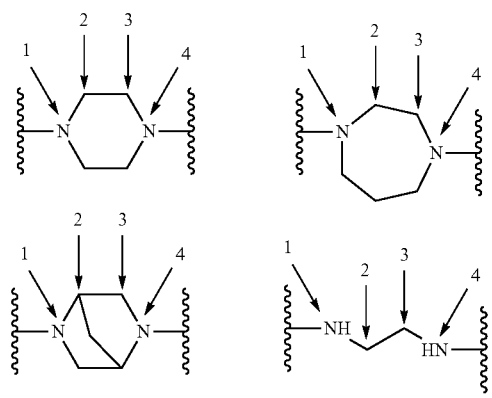

In some embodiments, the linker comprises at least one 5-atom chain that bridges $X^2$ to $X^4$. To illustrate, the following are some of the structures from Table I that exemplify such linkers:

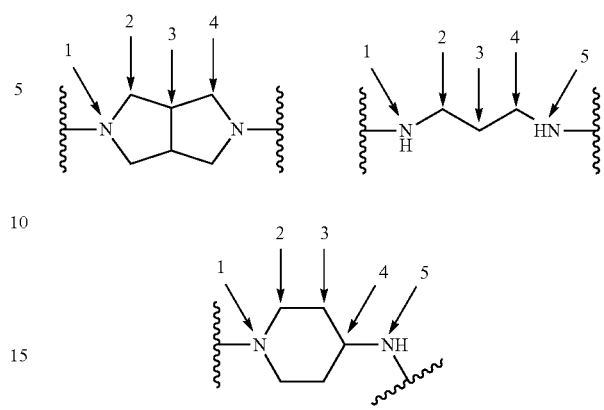

In some embodiments, the structures in Table I are not substituted with any $C_1$-$C_6$-alkyl or oxo.

In some embodiments, $X^3$ does not comprise a ring. In some such embodiments, $X^6$ is a linker selected from the group consisting of:

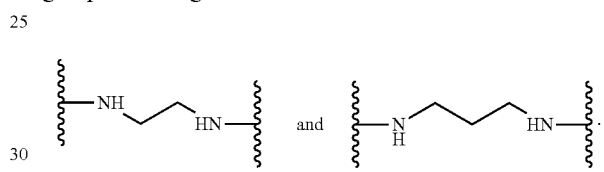

Any such group is optionally substituted with one or more substituents independently selected from the group consisting of $C_1$-$C_6$-alkyl and oxo.

In some embodiments, $X^3$ is one of the single- or double-ring structures in Table I. The ring(s) is/are optionally substituted with one or more substituents independently selected from the group consisting of halogen, hydroxy, $C_1$-$C_6$-alkyl, $C_1$-$C_6$-alkoxy, oxo, and thiocarbonyl.

In some embodiments, $X^3$ is one of the 4- to 7-member single ring structures in Table I. The ring is optionally substituted with one or more substituents independently selected from the group consisting of halogen, hydroxy, $C_1$-$C_6$-alkyl, $C_1$-$C_6$-alkoxy, oxo, and thiocarbonyl.

In some embodiments, $X^3$ is one of the 4- to 7-member single ring structures in Table I. The ring is optionally substituted with one or more substituents independently selected from the group consisting of halogen, hydroxy, $C_1$-$C_6$-alkyl, $C_1$-$C_6$-alkoxy, and oxo.

In some embodiments, $X^3$ is one of the 4- to 7-member single ring structures in Table I. The ring is optionally substituted with one or more substituents independently selected from the group consisting of $C_1$-$C_6$-alkyl and oxo.

In some embodiments, $X^3$ is:

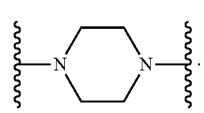 [SMILES: *N1CCN(*)CC1 ; ","]

In those embodiments, the compound is encompassed by the following formula:

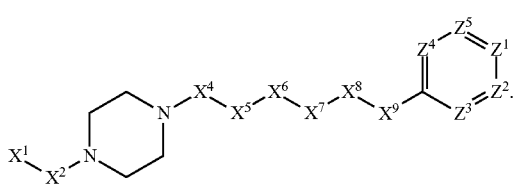

In some embodiments, $X^3$ is:

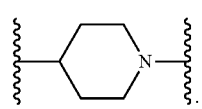 [SMILES: *C1CCN(*)CC1]

In such embodiments, the compound is encompassed by the following formula:

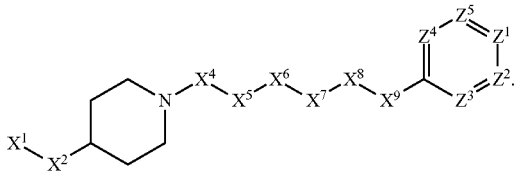

In some embodiments, $X^3$ is:

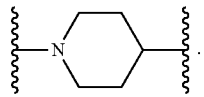

In such embodiments, the compound is encompassed by the following formula:

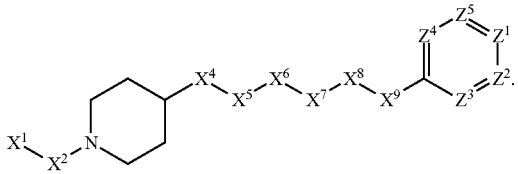

In some embodiments, $X^3$ is:

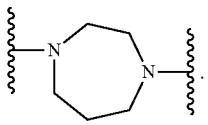

In such embodiments, the compound is encompassed by the following formula:

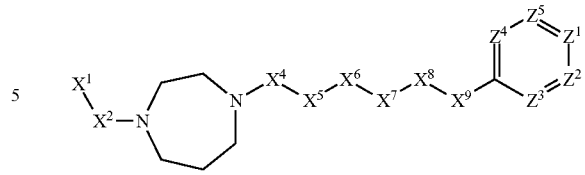

In some embodiments, $X^3$ is:

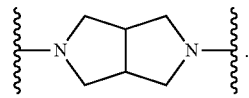 [SMILES: *N1CC2CN(*)CC2C1]

In such embodiments, the compound is encompassed by the following formula:

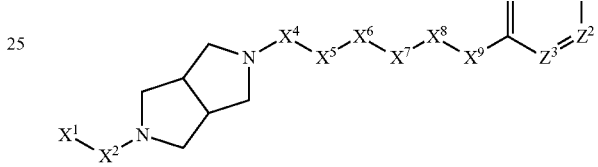

In some embodiments, $X^3$ is:

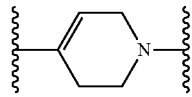

In such embodiments, the compound is encompassed by the following formula:

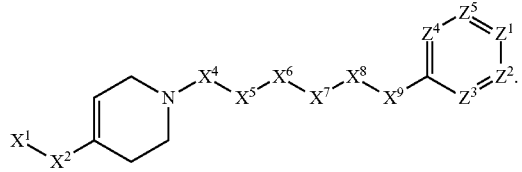

In some embodiments, one or more carbon atoms in the linker are substituted with one or two substituents independently selected from the group consisting of halogen, hydroxy, $C_1$-$C_6$-alkyl, $C_1$-$C_6$-alkoxy, oxo, and thiocarbonyl.

In some embodiments, one or more carbon atoms in the linker are substituted with one or two substituents independently selected from the group consisting of halogen, hydroxy, $C_1$-$C_6$-alkyl, $C_1$-$C_6$-alkoxy, and oxo.

In some embodiments, $X^3$ is one of the single- or double-ring structures in Table I, and one or two of the ring atoms in the ring structure are substituted with a substituent independently selected from the group consisting of methyl and oxo. To illustrate, in some embodiments, a ring atom is substituted with an oxo substituent. The linker in such an instance may be, for example:

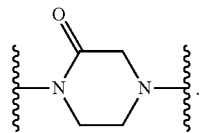 [SMILES: *N1CCN(*)C(=O)C1]

In other embodiments, for example, one or two of the ring atoms are substituted with methyl. To illustrate, the linker in such an instance may be, for example:

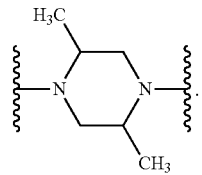 [SMILES: *N1CC(C)N(*)CC1C]

To further illustrate, the linker may alternatively be, for example:

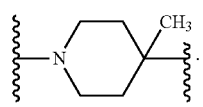 [SMILES: *N1CCC(*)(C)CC1]

D. Preferred Embodiments of $X^4$ $X^4$ is selected from the group consisting of a bond, —CH$_2$—, —O—, —C(S)—, —C(O)—, —S(O)—, and —S(O)$_2$—. The —CH$_2$— is optionally substituted with up to two substituents independently selected from the group consisting of alkyl, alkenyl, and carbocyclyl.

In some embodiments, $X^4$ is selected from the group consisting of a bond, —CH$_2$—, —O—, —C(S)—, —C(O)—, —S(O)—, and —S(O)$_2$—. The —CH$_2$— is optionally substituted with up to two substituents independently selected from the group consisting of C$_1$-C$_6$-alkyl, C$_2$-C$_6$-alkenyl, and C$_3$-C$_6$-carbocyclyl.

In some embodiments, $X^4$ is selected from the group consisting of a bond, —CH$_2$—, —O—, —C(S)—, —C(O)—, —S(O)—, and —S(O)$_2$—. The —CH$_2$— is optionally substituted with up to two substituents independently selected from the group consisting of C$_1$-C$_6$-alkyl, C$_2$-C$_6$-alkenyl, and C$_3$-C$_6$-cycloalkyl.

In some embodiments, $X^4$ is a single bond. In such embodiments, the compound is encompassed by the following formula:

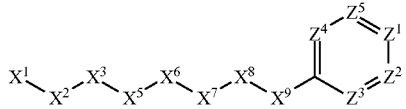

In some embodiments, $X^4$ is —CH$_2$—. In such embodiments, the compound is encompassed by the following formula:

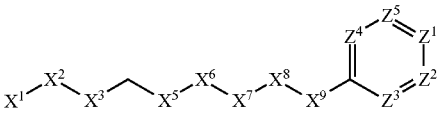

In some embodiments, $X^4$ is —O—. In those embodiments, the compound is encompassed by the following formula:

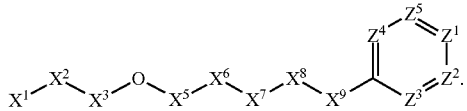

In some embodiments, $X^4$ is —C(S)—. In such embodiments, the compound is encompassed by the following formula:

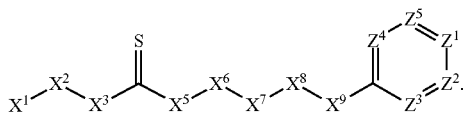

In some embodiments, $X^4$ is —C(O)—. In such embodiments, the compound is encompassed by the following formula:

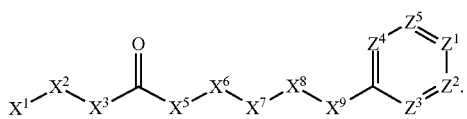

In some embodiments, $X^4$ is —S(O)—. In such embodiments, the compound is encompassed by the following formula:

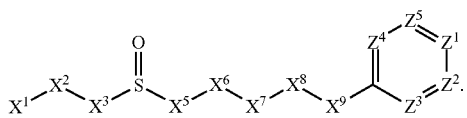

In some embodiments, $X^4$ is —S(O)$_2$—. In such embodiments, the compound is encompassed by the following formula:

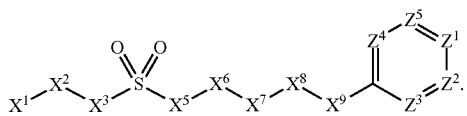

E. Preferred Embodiments of $X^5$ $X^5$ is selected from the group consisting of a bond, —CH$_2$—, and carbocyclyl. The —CH$_2$— is optionally substituted with up to two substituents independently selected from the group consisting of alkyl, alkenyl, and carbocyclyl.

In some embodiments, $X^5$ is selected from the group consisting of a bond, —$CH_2$—, and carbocyclyl. The —$CH_2$— is optionally substituted with up to two substituents independently selected from the group consisting of $C_1$-$C_6$-alkyl, $C_2$-$C_6$-alkenyl, and $C_1$-$C_6$-carbocyclyl.

$X^5$ is selected from the group consisting of a bond and —$CH_2$—. The —$CH_2$— is optionally substituted with up to two substituents independently selected from the group consisting of alkyl, alkenyl, and carbocyclyl.

In some embodiments, $X^5$ is selected from the group consisting of a bond and —$CH_2$—. The —$CH_2$— is optionally substituted with up to two substituents independently selected from the group consisting of $C_1$-$C_6$-alkyl, $C_2$-$C_6$-alkenyl, and $C_1$-$C_6$-carbocyclyl.

In some embodiments, $X^5$ is a single bond. In such embodiments, the compound is encompassed by the following formula:

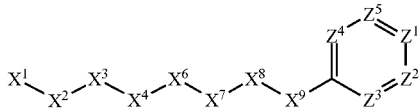

In some embodiments, $X^5$ is —$CH_2$—. In such embodiments, the compound is encompassed by the following formula:

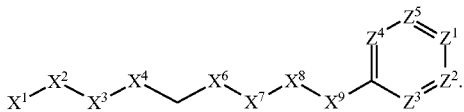

In some embodiments, $X^5$ is —$CH_2$— substituted with up to two independently selected $C_1$-$C_6$-alkyl. For example, in some embodiments, $X^5$ is —$CH_2$— substituted with $C_1$-alkyl (i.e., methyl). In such embodiments, the compound is encompassed by the following formula:

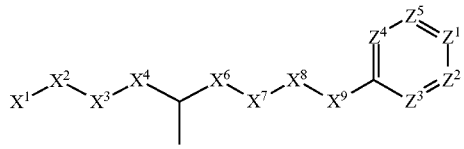

In other embodiments, $X^5$ is —$CH_2$— substituted with two $C_1$-alkyl (i.e., methyl) groups. In such embodiments, the compound is encompassed by the following formula:

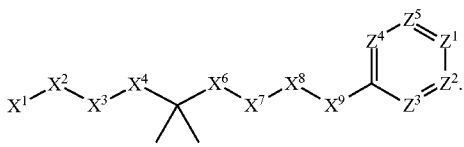

In some embodiments, $X^5$ is carbocyclyl. For example, in some such embodiments, $X^5$ is $C_6$-cycloalkyl (e.g., cyclohexyl). In such embodiments, the compound is encompassed by the following formula:

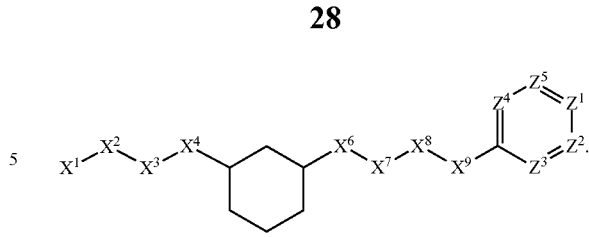

F. Preferred Embodiments of $X^6$ $X^6$ is selected from the group consisting of a bond, —$CH_2$—, and carbocyclyl. The —$CH_2$— is optionally substituted with up to two substituents independently selected from the group consisting of alkyl, alkenyl, and carbocyclyl.

In some embodiments, $X^6$ is selected from the group consisting of a bond, —$CH_2$—, and carbocyclyl. The —$CH_2$— is optionally substituted with up to two substituents independently selected from the group consisting of $C_1$-$C_6$-alkyl, $C_2$-$C_6$-alkenyl, and $C_1$-$C_6$-carbocyclyl.

$X^6$ is selected from the group consisting of a bond and —$CH_2$—. The —$CH_2$— is optionally substituted with up to two substituents independently selected from the group consisting of alkyl, alkenyl, and carbocyclyl.

In some embodiments, $X^6$ is selected from the group consisting of a bond and —$CH_2$—. The —$CH_2$— is optionally substituted with up to two substituents independently selected from the group consisting of $C_1$-$C_6$-alkyl, $C_2$-$C_6$-alkenyl, and $C_1$-$C_6$-carbocyclyl.

In some embodiments, $X^6$ is a single bond. In such embodiments, the compound is encompassed by the following formula:

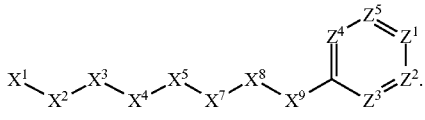

In some embodiments, $X^6$ is —$CH_2$—. In such embodiments, the compound is encompassed by the following formula:

In some embodiments, $X^6$ is —$CH_2$— substituted with up to two independently selected $C_1$-$C_6$-alkyl. For example, in some embodiments, $X^6$ is —$CH_2$— substituted with $C_1$-alkyl (i.e., methyl). In such embodiments, the compound is encompassed by the following formula:

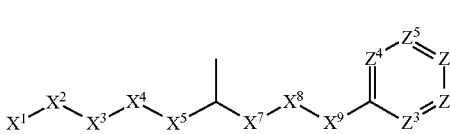

In other embodiments, $X^5$ is —$CH_2$— substituted with two $C_1$-alkyl (i.e., methyl) groups. In such embodiments, the compound is encompassed by the following formula:

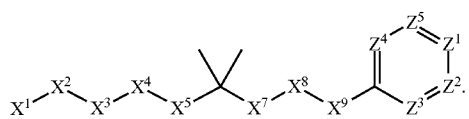

In some embodiments, $X^6$ is carbocyclyl. For example, in some such embodiments, $X^6$ is $C_6$-cycloalkyl (e.g., cyclohexyl). In such embodiments, the compound is encompassed by the following formula:

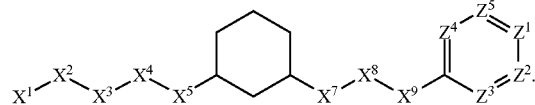

G. Preferred Embodiments of $X^7$ $X^7$ is selected from the group consisting of —$CH_2$—, —O—, —C(O)—, —C(S)—, —S—, —S(O)—, —S(O)$_2$—, —NH—, —C(O)—NH—, —C(S)—NH—, —NH—C(O)—, and —NH—C(S)—. The —$CH_2$— is optionally substituted with up to two substituents independently selected from the group consisting of alkyl, alkenyl, and carbocyclyl. The —NH— is optionally substituted with a substituent selected from the group consisting of alkyl, alkenyl, alkynyl, alkoxyalkyl, carbocyclyl, and carbocyclylalkyl, wherein any such substituent is optionally substituted with one or more independently selected halogen.

In some embodiments, $X^7$ is selected from the group consisting of —$CH_2$—, —O—, —C(O)—, —C(S)—, —S—, —S(O)—, —S(O)$_2$—, —NH—, —C(O)—NH—, —C(S)—NH—, —NH—C(O)—, and —NH—C(S)—. The —$CH_2$— is optionally substituted with up to two substituents independently selected from the group consisting of $C_1$-$C_6$-alkyl, $C_2$-$C_6$-alkenyl, and $C_3$-$C_6$-carbocyclyl. The —NH— is optionally substituted with a substituent selected from the group consisting of $C_1$-$C_6$-alkyl, $C_2$-$C_6$-alkenyl, $C_2$-$C_6$-alkynyl, $C_1$-$C_6$-alkoxy-$C_1$-$C_6$-alkyl, $C_3$-$C_6$-carbocyclyl, and $C_3$-$C_6$-carbocyclyl-$C_1$-$C_6$-alkyl, wherein any such substituent is optionally substituted with one or more independently selected halogen.

In some embodiments, $X^7$ is —$CH_2$—. In some such embodiments, for example, $X^7$ is —$CH_2$—. In these embodiments, the compound is encompassed by the following formula:

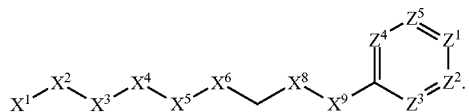

In some embodiments, $X^7$ is —O—. In these embodiments, the compound is encompassed by the following formula:

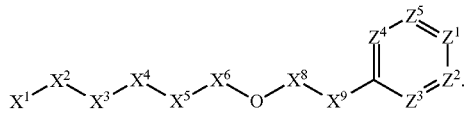

In some embodiments, $X^7$ is —C(O)—. In these embodiments, the compound is encompassed by the following formula:

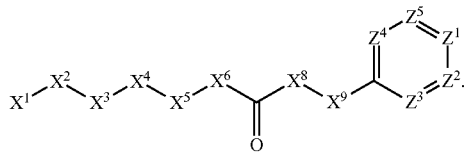

In some embodiments, $X^7$ is —C(S)—. In these embodiments, the compound is encompassed by the following formula:

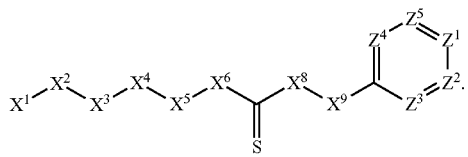

In some embodiments, $X^7$ is —S—. In these embodiments, the compound is encompassed by the following formula:

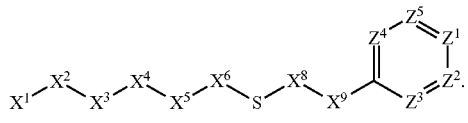

In some embodiments, $X^7$ is —S(O)—. In these embodiments, the compound is encompassed by the following formula:

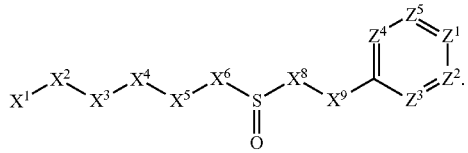

In some embodiments, $X^7$ is —S(O)$_2$—. In these embodiments, the compound is encompassed by the following formula:

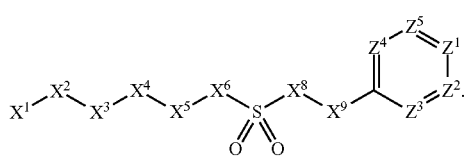

In some embodiments, $X^7$ is —NH—. In these embodiments, the compound is encompassed by the following formula:

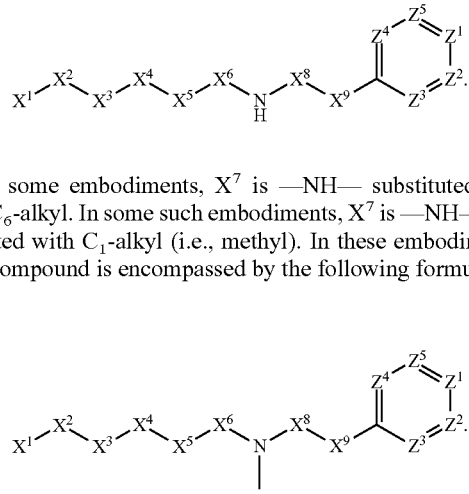

In some embodiments, $X^7$ is —NH— substituted with $C_1$-$C_6$-alkyl. In some such embodiments, $X^7$ is —NH— substituted with $C_1$-alkyl (i.e., methyl). In these embodiments, the compound is encompassed by the following formula:

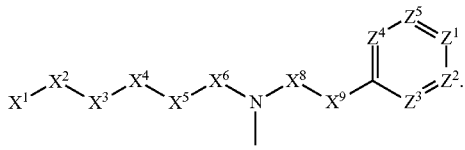

In some embodiments, $X^7$ is —C(O)—NH—. In these embodiments, the compound is encompassed by the following formula:

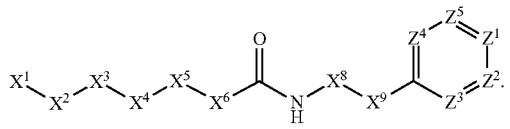

In some embodiments, $X^7$ is —C(S)—NH—. In these embodiments, the compound is encompassed by the following formula:

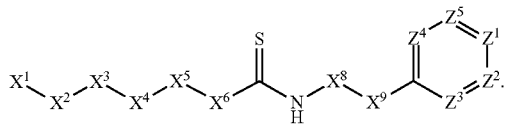

In some embodiments, $X^7$ is —NH—C(O)—. In these embodiments, the compound is encompassed by the following formula:

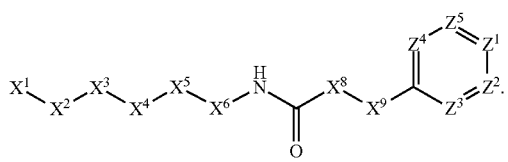

In some embodiments, $X^7$ is —NH—C(O)— substituted with methyl. In these embodiments, the compound is encompassed by the following formula:

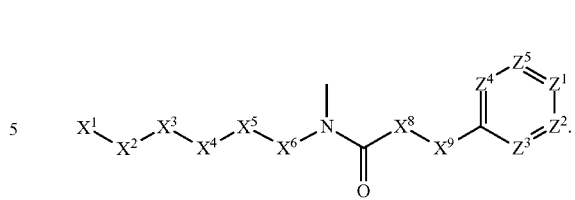

In some embodiments, $X^7$ is —NH—C(S)—. In these embodiments, the compound is encompassed by the following formula:

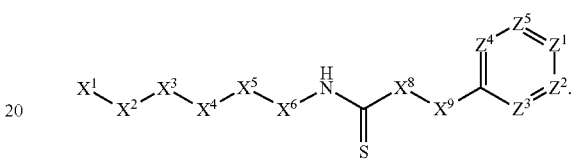

In some embodiments, $X^7$ is —NH—C(S)— substituted with methyl. In these embodiments, the compound is encompassed by the following formula:

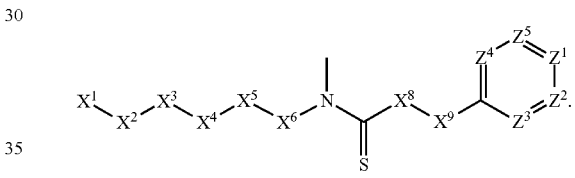

H. Preferred Embodiments of $X^4$, $X^5$, $X^6$, and $X^7$

In some embodiments of this invention, the compound corresponds in structure to the following formula:

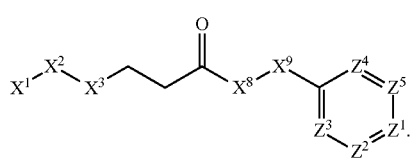

In some embodiments of this invention, the compound corresponds in structure to the following formula:

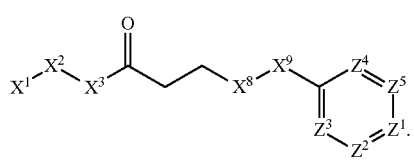

In some embodiments of this invention, the compound corresponds in structure to the following formula:

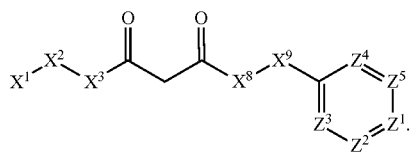

In some embodiments of this invention, the compound corresponds in structure to the following formula:

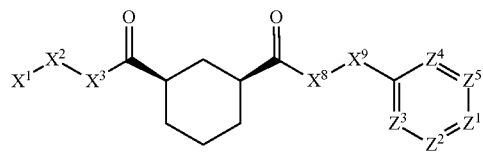

In some embodiments of this invention, the compound corresponds in structure to the following formula:

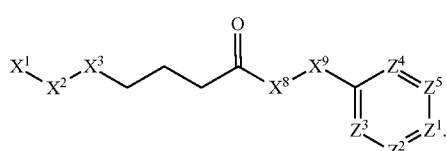

In some embodiments of this invention, the compound corresponds in structure to the following formula:

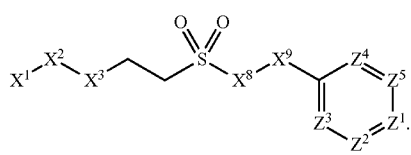

In some embodiments of this invention, the compound corresponds in structure to the following formula:

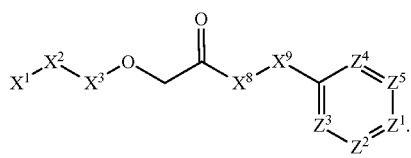

In some embodiments of this invention, the compound corresponds in structure to the following formula:

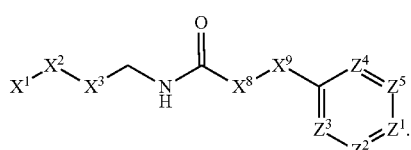

In some embodiments of this invention, the compound corresponds in structure to the following formula:

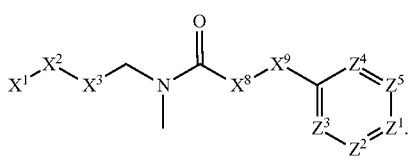

In some embodiments of this invention, the compound corresponds in structure to the following formula:

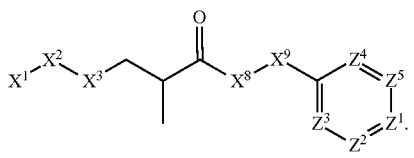

In some embodiments of this invention, the compound corresponds in structure to the following formula:

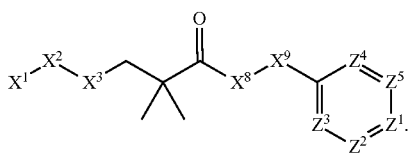

In some embodiments of this invention, the compound corresponds in structure to the following formula:

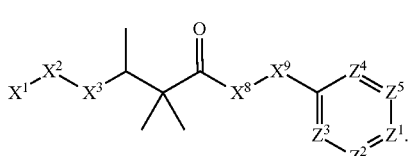

In some embodiments of this invention, the compound corresponds in structure to the following formula:

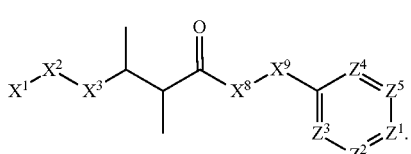

In some embodiments of this invention, the compound corresponds in structure to the following formula:

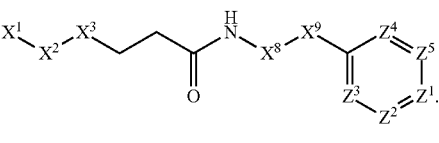

In some embodiments of this invention, the compound corresponds in structure to the following formula:

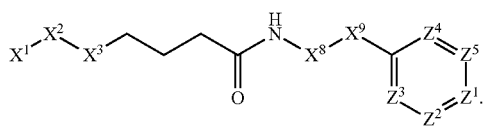

In some embodiments of this invention, the compound corresponds in structure to the following formula:

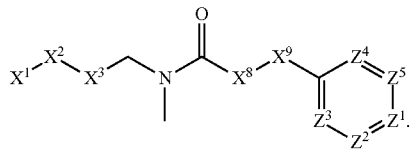

In some embodiments of this invention, the compound corresponds in structure to the following formula:

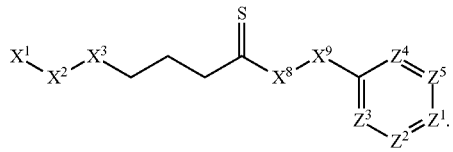

In some embodiments of this invention, the compound corresponds in structure to the following formula:

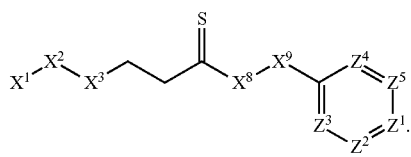

In some embodiments of this invention, the compound corresponds in structure to the following formula:

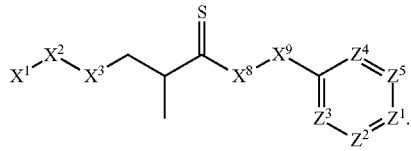

In some embodiments of this invention, the compound corresponds in structure to the following formula:

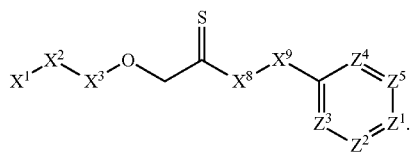

In some embodiments of this invention, the compound corresponds in structure to the following formula:

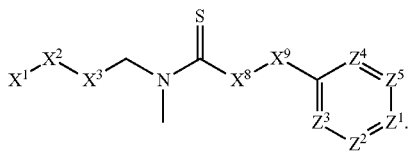

In some embodiments of this invention, the compound corresponds in structure to the following formula:

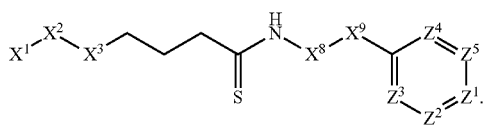

In some embodiments of this invention, the compound corresponds in structure to the following formula:

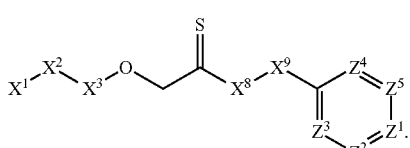

I. Preferred Embodiments of $X^8$ $X^8$ is selected from the group consisting of piperidinyl, piperazinyl, homopiperazinyl, and pyrrolidinyl. The piperidinyl, piperazinyl, homopiperazinyl or pyrrolidinyl is optionally substituted with one or more independently selected alkyl.

In some embodiments, $X^8$ is piperidinyl or pyrrolidinyl. The piperidinyl or pyrrolidinyl is optionally substituted with one or more independently selected alkyl.

In some embodiments, $X^8$ is piperidinyl or pyrrolidinyl. The piperidinyl or pyrrolidinyl is optionally substituted with one or more independently selected $C_1$-$C_6$-alkyl.

In some embodiments, $X^8$ is piperidinyl optionally substituted with one or more independently selected $C_1$-$C_6$-alkyl. To illustrate, in some such embodiments, $X^8$ is piperidinyl. In some such embodiments, the compound is encompassed by the following formula:

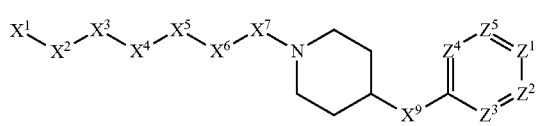

In other such embodiments, the compound is encompassed by the following formula:

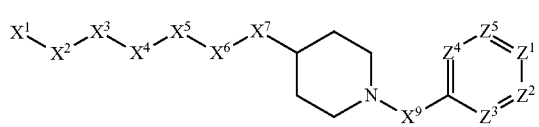

In some embodiments, $X^8$ is piperidinyl optionally substituted with one or more independently selected $C_1$-$C_6$-alkyl.

To illustrate, in some such embodiments, $X^8$ is piperidinyl. In some such embodiments, the compound is encompassed by the following formula:

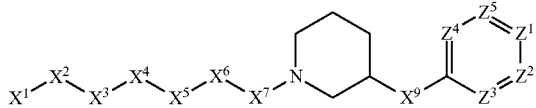

In some embodiments, $X^8$ is pyrrolidinyl optionally substituted with one or more independently selected alkyl. To illustrate, in some such embodiments, $X^8$ is pyrrolidinyl. In some such embodiments, the compound is encompassed by the following formula:

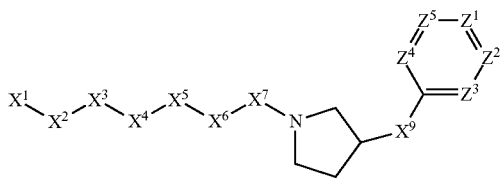

In some embodiments, $X^8$ is piperazinyl optionally substituted with one or more independently selected alkyl. To illustrate, in some such embodiments, $X^8$ is piperazinyl. In some such embodiments, the compound is encompassed by the following formula:

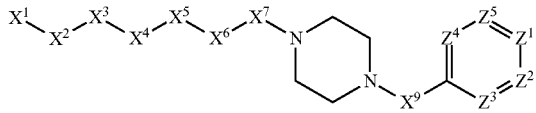

In some embodiments, $X^8$ is homopiperazinyl optionally substituted with one or more independently selected alkyl. To illustrate, in some such embodiments, $X^8$ is homopiperazinyl. In some such embodiments, the compound is encompassed by the following formula:

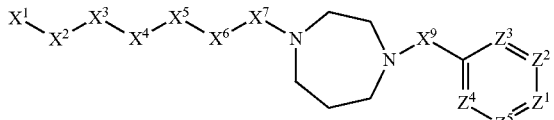

J. Preferred Embodiments of $X^9$ $X^9$ is selected from the group consisting of a bond, —O—, —C(O)—, —S—, —S(O)—, —S(O)$_2$—, and —NH—, preferably —O—, —C(O)—, —S—, —S(O)—, —S(O)$_2$—, and —NH—. Here, the —NH— optionally is substituted with a substituent selected from the group consisting of alkyl, alkenyl, alkynyl, alkoxyalkyl, carbocyclyl, and carbocyclylalkyl. Any such substituent is optionally substituted with one or more independently selected halogen.

In some embodiments, $X^9$ is selected from the group consisting of a bond, —O—, —C(O)—, —S—, —S(O)—, —S(O)$_2$—, and —NH—, preferably —O—, —C(O)—, —S—, —S(O)—, —S(O)$_2$—, and —NH—. Here, the —NH— optionally is substituted with a substituent selected from the group consisting of $C_1$-$C_6$-alkyl, $C_2$-$C_6$-alkenyl, $C_2$-$C_6$-alkynyl, $C_1$-$C_6$-alkoxy $C_1$-$C_6$-alkyl, $C_3$-$C_6$-carbocyclyl, and $C_3$-$C_6$-carbocyclyl-$C_1$-$C_6$-alkyl. Any such substituent is optionally substituted with one or more independently selected halogen.

In some embodiments $X^9$ is different from a bond.

In some embodiments, $X^9$ is —NH— optionally substituted with a substituent selected from the group consisting of $C_1$-$C_6$-alkyl, $C_2$-$C_6$-alkenyl, $C_2$-$C_6$-alkynyl, $C_1$-$C_6$-alkoxy $C_1$-$C_6$-alkyl, $C_3$-$C_6$-carbocyclyl, and $C_3$-$C_6$-carbocyclyl-$C_1$-$C_6$-alkyl. Any such substituent is optionally substituted with one or more independently selected halogen. To illustrate, in some such embodiments, $X^1$ is —NH—. In such embodiments, the compound is encompassed by the following formula:

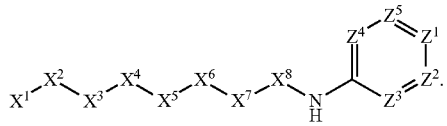

In other such embodiments, the compound is encompassed by the following formula:

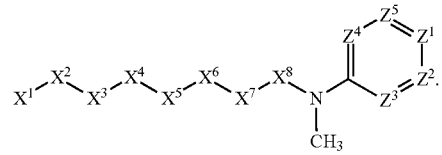

In some embodiments, for example, $X^9$ is a single bond. Here, the compound is encompassed by the following formula:

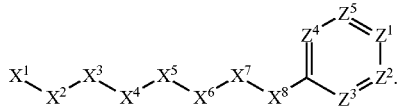

In some embodiments, $X^9$ is —O—. In such embodiments, the compound is encompassed by the following formula:

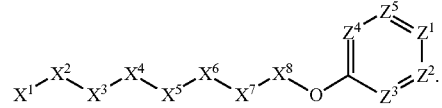

In some embodiments, $X^9$ is —C(O)—. In such embodiments, the compound is encompassed by the following formula:

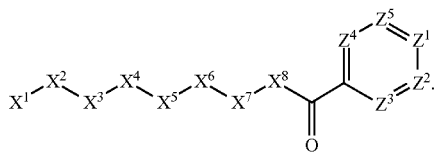

In some embodiments, $X^9$ is —S—. In such embodiments, the compound is encompassed by the following formula:

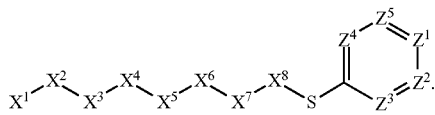

In some embodiments, $X^9$ is —S(O)—. In such embodiments, the compound is encompassed by the following formula:

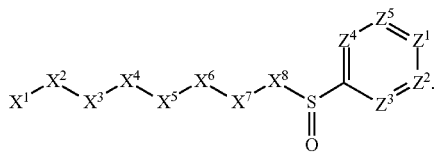

In some embodiments, $X^9$ is —S(O)$_2$—. In such embodiments, the compound is encompassed by the following formula:

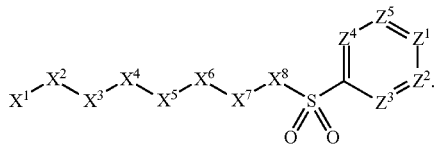

K. Preferred Embodiments of $Z^1$, $Z^2$, $Z^3$, $Z^4$, and $Z^5$ $Z^1$ is selected from the group consisting of N and CH. The CH is optionally substituted with a substituent selected from the group consisting of halogen, nitro, cyano, aminosulfonyl, alkyl, alkoxy, alkoxycarbonyl, alkylsulfanyl, alkylsulfinyl, alkylsulfonyl, aryl, arylsulfanyl, arylsulfinyl, arylsulfonyl, heteroaryl, heteroarylsulfanyl, heteroarylsulfinyl, and heteroarylsulfonyl. The alkyl, alkoxy, alkoxycarbonyl, alkylsulfanyl, alkylsulfinyl, alkylsulfonyl, aryl, arylsulfanyl, arylsulfinyl, arylsulfonyl, hetero aryl, heteroarylsulfanyl, heteroarylsulfinyl, and heteroarylsulfonyl are optionally substituted with one or more substituents independently selected from the group consisting of halogen and alkyl. The aminosulfonyl is optionally substituted with up to two independently selected alkyl.

In some embodiments, $Z^1$ is selected from the group consisting of N and CH. The CH is optionally substituted with a substituent selected from the group consisting of halogen, nitro, cyano, aminosulfonyl, $C_1$-$C_6$-alkyl, $C_1$-$C_6$-alkoxy, $C_1$-$C_6$-alkoxycarbonyl, $C_1$-$C_6$-alkylsulfanyl, $C_1$-$C_6$-alkylsulfinyl, $C_1$-$C_6$-alkylsulfonyl, aryl, arylsulfanyl, arylsulfinyl, arylsulfonyl, heteroaryl, heteroarylsulfanyl, heteroarylsulfinyl, and heteroarylsulfonyl. The $C_1$-$C_6$-alkyl, $C_1$-$C_6$-alkoxy, $C_1$-$C_6$-alkoxycarbonyl, $C_1$-$C_6$-$C_1$-$C_6$-alkylsulfanyl, $C_1$-$C_6$-alkylsulfinyl, $C_1$-$C_6$-alkylsulfonyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and $C_1$-$C_6$-alkyl. The aminosulfonyl is optionally substituted with up to two independently selected $C_1$-$C_6$-alkyl.

In some embodiments, $Z^1$ is N. Such embodiments are encompassed by the following structure:

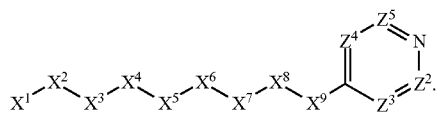

In some embodiments, $Z^1$ is optionally substituted CH. In some such embodiments, for example, $Z^1$ is CH. Such embodiments are encompassed by the following structure:

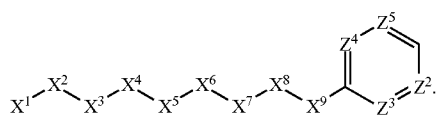

In other embodiments, $Z^1$ is CH substituted with a substituent selected from the group consisting of alkylsulfonyl, alkoxy, cyano, haloalkyl, halogen, nitro, haloarylsulfonyl, haloalkylsulfanyl, haloalkoxy, alkoxycarbonyl, 5-membered heteroaryl, alkylsulfanyl, alkylsulfinyl, and dialkylaminosulfonyl, wherein the 5-membered heteroaryl optionally is substituted with $C_1$-$C_6$-alkyl.

In some embodiments, $Z^1$ is CH substituted with an electron-withdrawing substituent. Such substituents include, for example, halogen, nitro, cyano, halo-$C_1$-$C_6$-alkyl, halo-$C_1$-$C_6$-alkoxy, and halo-$C_1$-$C_6$-alkylsulfanyl, alkylsulfinyl, alkylsulfonyl, and dialkylaminosulfonyl.

In some embodiments, $Z^1$ is CH substituted with a halogen. For example, in some such embodiments, $Z^1$ is CH substituted with chloro. These embodiments are encompassed by the following structure:

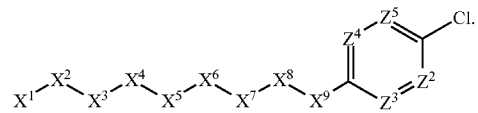

In some embodiments, $Z^1$ is CH substituted with nitro. Such embodiments are encompassed by the following structure:

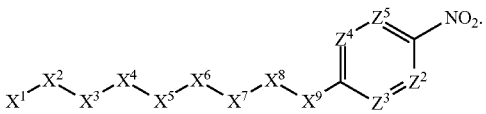

In some embodiments, $Z^1$ is CH substituted with cyano. Such embodiments are encompassed by the following structure:

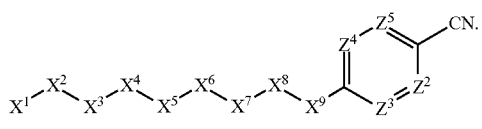

In some embodiments, $Z^1$ is CH substituted with halo-$C_1$-$C_6$-alkyl. For example, in some such embodiments, $Z^1$ is CH substituted with trifluoro-$C_1$-alkyl (i.e., trifluoromethyl). Such embodiments are encompassed by the following structure:

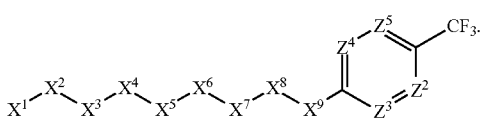

In some embodiments, $Z^1$ is CH substituted with $C_1$-$C_6$-alkoxy. For example, in some such embodiments, $Z^1$ is CH substituted with $C_1$-alkoxy (i.e., methoxy). Such embodiments are encompassed by the following structure:

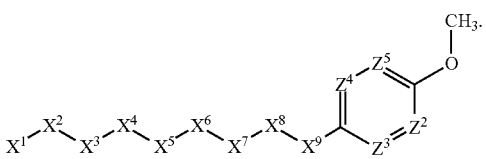

In some embodiments, $Z^1$ is CH substituted with $C_1$-$C_6$-alkylsulfanyl. For example, in some such embodiments, $Z^1$ is CH substituted with $C_1$-alkylsulfanyl (i.e., methylsulfinyl). Such embodiments are encompassed by the following structure:

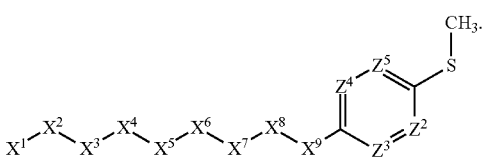

In some embodiments, $Z^1$ is CH substituted with halo-$C_1$-$C_6$-alkoxy. For example, in some such embodiments, $Z^1$ is CH substituted with fluoro-$C_1$-alkoxy. Such embodiments are encompassed by the following structure:

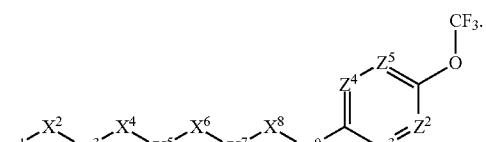

In some embodiments, $Z^1$ is CH substituted with halo-$C_1$-$C_6$-alkylsulfanyl. For example, in some such embodiments, $Z^1$ is CH substituted with fluoro-$C_1$-alkylsulfanyl. Such embodiments are encompassed by the following structure:

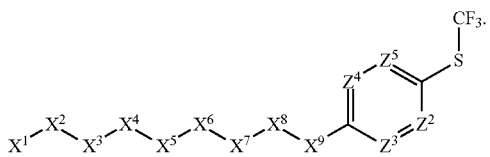

In some embodiments, $Z^1$ is CH substituted with $C_1$-$C_6$-alkylsulfinyl. For example, in some such embodiments, $Z^1$ is CH substituted with $C_1$-alkylsulfinyl (i.e., methylsulfinyl). Such embodiments are encompassed by the following structure:

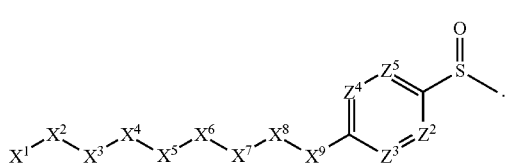

In some embodiments, $Z^1$ is CH substituted with $C_1$-$C_6$-alkylsulfonyl. For example, in some such embodiments, $Z^1$ is CH substituted with $C_1$-alkylsulfonyl (i.e., methylsulfonyl). Such embodiments are encompassed by the following structure:

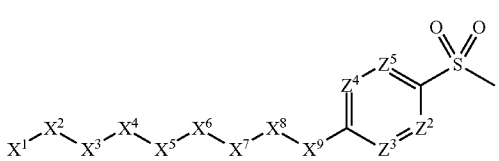

In some embodiments, $Z^1$ is CH substituted with di-$C_1$-$C_6$-alkylaminosulfonyl. For example, in some such embodiments, $Z^1$ is CH substituted with di-$C_1$-alkylaminosulfonyl (i.e., dimethylaminosulfonyl). Such embodiments are encompassed by the following structure:

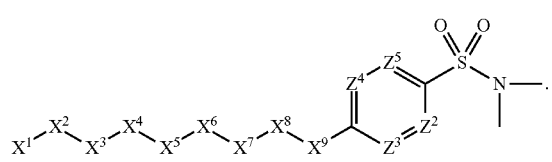

In some embodiments, $Z^1$ is CH substituted with haloarylsulfonyl. For example, in some such embodiments, $Z^1$ is CH substituted with 4-fluoro-phenyl-sulfonyl. Such embodiments are encompassed by the following structure:

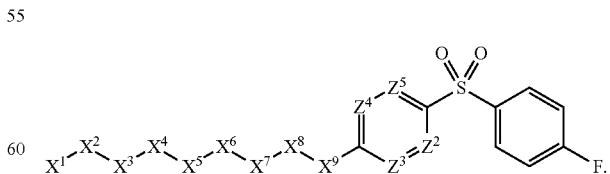

In some embodiments, $Z^1$ is CH substituted with $C_1$-$C_6$-alkoxycarbonyl. For example, in some such embodiments, $Z^1$ is CH substituted with $C_2$-alkoxycarbonyl (i.e., ethoxycarbonyl). Such embodiments are encompassed by the following structure:

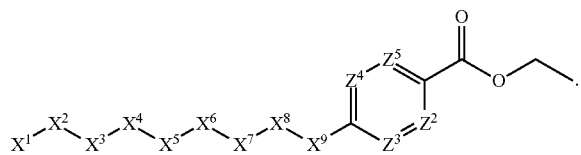

In some embodiments, $Z^1$ is CH substituted with heteroaryl optionally substituted with $C_1$-$C_6$-alkyl. For example, in some such embodiments, $Z^1$ is CH substituted with methyltetrazoyl). And is encompassed by the following structure:

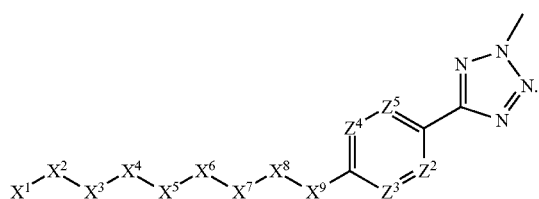

$Z^2$ is selected from the group consisting of N and CH. The CH is optionally substituted with a substituent selected from the group consisting of cyano, halogen, nitro, alkyl, alkoxy, haloalkyl, and haloalkylsulfanyl.

In some embodiments, $Z^2$ is selected from the group consisting of N and CH. The CH is optionally substituted with a substituent selected from the group consisting of cyano, halogen, nitro, $C_1$-$C_6$-alkyl, $C_1$-$C_6$-alkoxy, halo-$C_1$-$C_6$-alkyl, halo-$C_1$-$C_6$-sulfanyl.

In some embodiments, $Z^2$ is selected from the group consisting of N and CH. The CH is optionally substituted with a substituent selected from the group consisting of cyano, halogen, $C_1$-$C_6$-alkyl, $C_1$-$C_6$-alkoxy, halo-$C_1$-$C_6$-alkyl, halo-$C_1$-$C_6$-sulfanyl.

In some embodiments, $Z^2$ is N. Such embodiments are encompassed by the following structure:

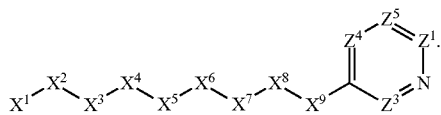

In some embodiments, $Z^2$ is CH substituted with a substituent selected from the group consisting of cyano, halogen, nitro, $C_1$-$C_6$-alkyl, $C_1$-$C_6$-alkoxy, halo-$C_1$-$C_6$-alkyl, and halo-$C_1$-$C_6$-alkylsulfanyl. In some such embodiments, for example, $Z^2$ is CH. Such embodiments are encompassed by the following structure:

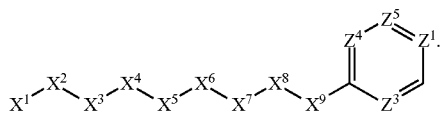

In some embodiments, $Z^2$ is CH substituted with halo-$C_1$-$C_6$-alkyl. For example, in some such embodiments, $Z^2$ is CH substituted with fluoro-$C_1$-$C_6$-alkyl. To illustrate, $Z^2$ can be, for example, CH substituted with trifluoromethyl such that the compound is encompassed by the following structure:

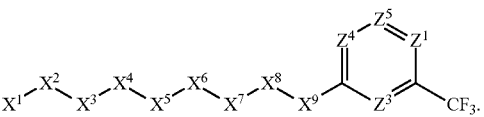

In some embodiments, $Z^2$ is CH substituted with cyano. Such embodiments are encompassed by the following structure:

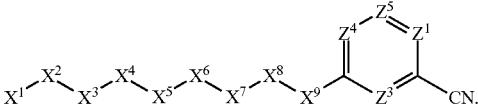

In some embodiments, $Z^2$ is CH substituted with halogen. For example, in some such embodiments, $Z^2$ is CH substituted with chloro. These embodiments are encompassed by the following structure:

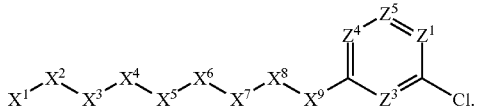

In some embodiments, $Z^2$ is CH substituted with $C_1$-$C_6$-alkyl. For example, in some such embodiments, $Z^2$ is CH substituted with $C_1$-alkyl (i.e., methyl). Such embodiments are encompassed by the following structure:

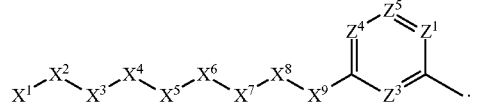

In some embodiments, $Z^2$ is CH substituted with $C_1$-$C_6$-alkoxy. For example, in some such embodiments, $Z^2$ is CH substituted with $C_4$-alkoxy (e.g., isobutoxy). Such embodiments are encompassed by the following structure:

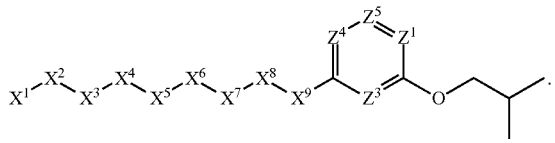

In other such embodiments, $Z^2$ is CH substituted with $C_2$-alkoxy (e.g., ethoxy). Such embodiments are encompassed by the following structure:

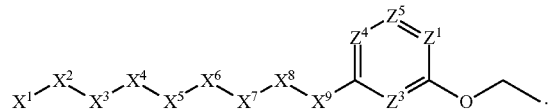

In yet other such embodiments, $Z^2$ is CH substituted with $C_1$-alkoxy (e.g., methoxy). Such embodiments are encompassed by the following structure:

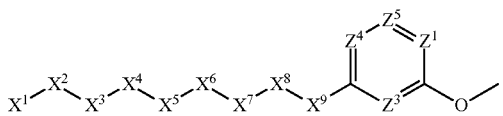

In some embodiments, $Z^2$ is CH substituted with halo-$C_1$-$C_6$-alkylsulfanyl. For example, in some such embodiments, $Z^2$ is CH substituted with fluoro-$C_1$-$C_6$-alkylsulfanyl (e.g., trifluoromethylsulfanyl). Such embodiments are encompassed by the following structure:

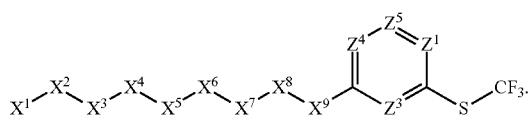

Each of $Z^3$, $Z^4$, and $Z^5$ is independently selected from the group consisting of N and CH. The CH is optionally substituted with a substituent selected from the group consisting of halogen, cyano, nitro, alkyl, alkoxy, alkylsulfanyl, haloalkyl, haloalkoxy, and haloalkylsulfanyl.

In some embodiments, each of $Z^3$, $Z^4$, and $Z^5$ is independently selected from the group consisting of N and CH. The CH is optionally substituted with a substituent selected from the group consisting of halogen, cyano, nitro, $C_1$-$C_6$-alkyl, $C_1$-$C_6$-alkoxy, $C_1$-$C_6$-alkylsulfanyl, halo-$C_1$-$C_6$-alkyl, halo-$C_1$-$C_6$-alkoxy, and halo-$C_1$-$C_6$-alkylsulfanyl.

In some embodiments, $Z^3$ is halo-$C_1$-$C_6$-alkyl. For example, in some such embodiments, $Z^3$ is trifluoromethyl. Such embodiments are encompassed by the following structure:

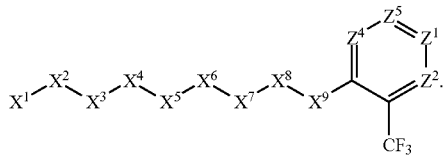

In some embodiments, $Z^2$, $Z^3$, $Z^4$, and $Z^5$ are each CH. Such embodiments are encompassed by the following structure:

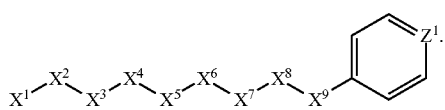

In some embodiments, $Z^1$, $Z^3$, $Z^4$, and $Z^5$ are each CH. Such embodiments are encompassed by the following structure:

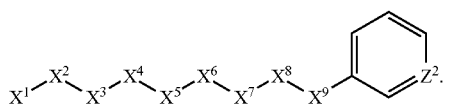

In some embodiments, $Z^2$, $Z^4$, and $Z^5$ are each CH. Such embodiments are encompassed by the following structure:

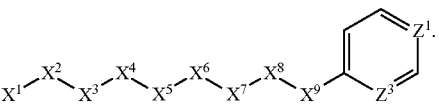

In some embodiments, $Z^2$, $Z^4$, and $Z^5$ are each CH and $Z^3$ is N. Such embodiments are encompassed by the following structure:

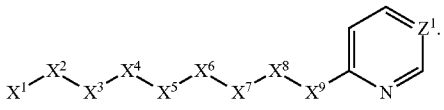

In some embodiments, $Z^3$, $Z^4$, and $Z^5$ are each CH and $Z^1$ is N. Such embodiments are encompassed by the following structure:

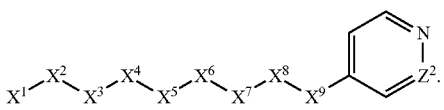

In some embodiments, $Z^1$, $Z^3$, and $Z^4$ are each CH and $Z^2$ is N. Such embodiments are encompassed by the following structure:

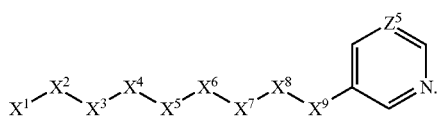

In some embodiments, $Z^2$, $Z^4$, and $Z^5$ are each CH and $Z^5$ is N. Such embodiments are encompassed by the following structure:

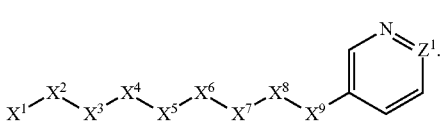

In some embodiments, $Z^2$ and $Z^4$ are each CH and $Z^3$ is N. Such embodiments are encompassed by the following structure:

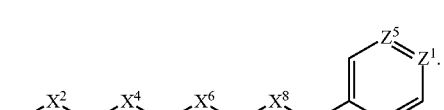

L. Preferred Embodiments of $Z^1$, $Z^2$, $Z^3$, $Z^4$, and $Z^5$

In some embodiments, none of $Z^1$, $Z^2$, $Z^3$, $Z^4$, and $Z^5$ are N. In some such embodiments, $Z^1$, $Z^2$, $Z^3$, $Z^4$, and $Z^5$ together with the atom to which they are bonded form a 6-membered ring, wherein only one of $Z^1$, $Z^2$, $Z^3$, $Z^4$, and $Z^5$ is substituted CH. Table II shows examples of such groups.

TABLE II

Example of $Z^1, Z^2, Z^3, Z^4,$ and $Z^5$

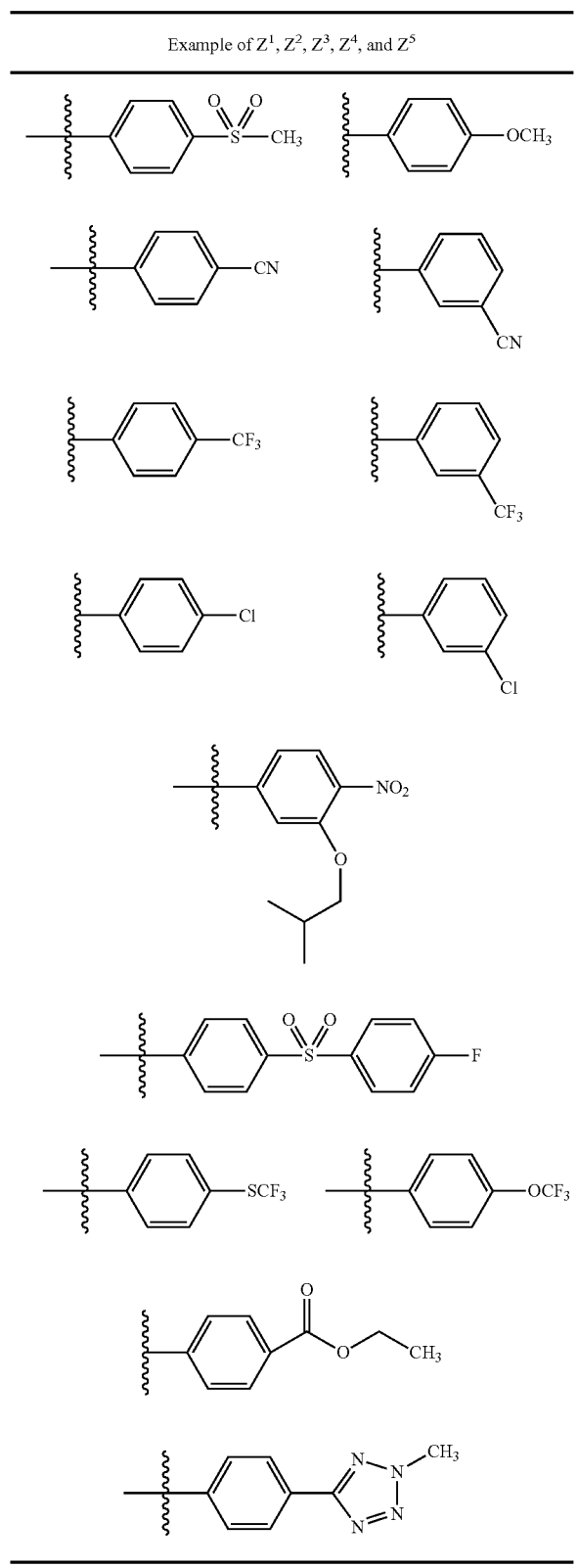

In other such embodiments, only two of $Z^1, Z^2, Z^3, Z^4,$ and $Z^5$ are substituted CH. Table III shows examples of such groups:

TABLE III

Example of $Z^1, Z^2, Z^3, Z^4,$ and $Z^5$

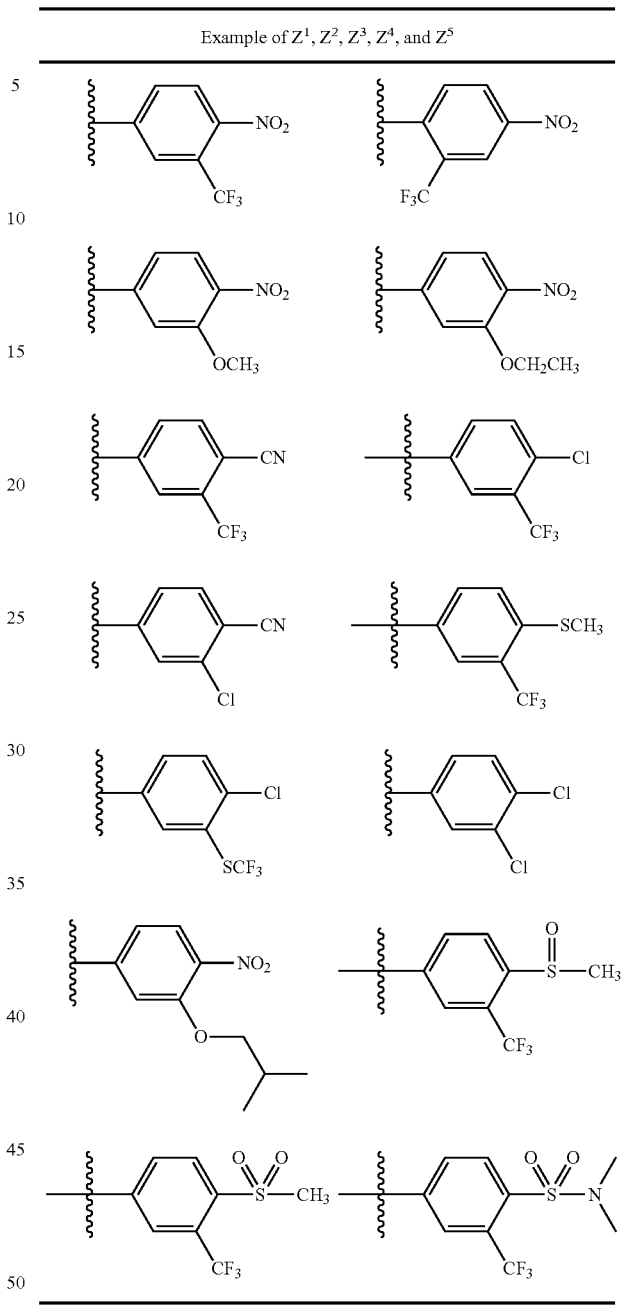

In some embodiments, at least one of $Z^1, Z^2, Z^3, Z^4,$ and $Z^5$ is N.

In some embodiments, two of $Z^1, Z^2, Z^3, Z^4,$ and $Z^5$ are each N. In other embodiments, only one of $Z^1, Z^2, Z^3, Z^4,$ and $Z^5$ is N. Table IV shows examples of such groups.

TABLE IV

Example of $Z^1, Z^2, Z^3, Z^4,$ and $Z^5$

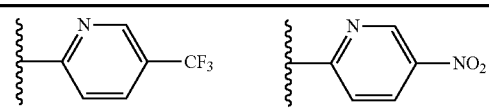

TABLE IV-continued

Example of $Z^1$, $Z^2$, $Z^3$, $Z^4$, and $Z^5$

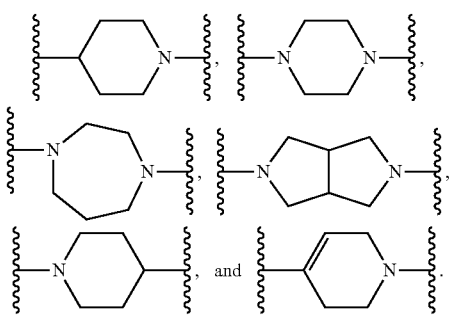

M. Examples of Various Specific Preferred Embodiments

In some embodiments of this invention, the compound is defined as corresponding in structure to the following formula:

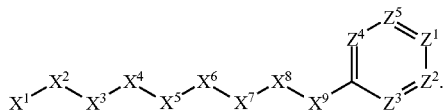

In some such embodiments, $X^1$ is selected from the group consisting of phenyl, 5-member heteroaryl, 6-member heteroaryl and alkyl wherein:
the 5-member heteroaryl is substituted with haloalkyl;
the phenyl and 6-member heteroaryl are optionally substituted with one or more substituents independently selected from the group consisting of alkyl, haloalkyl, halogen, alkoxy, haloalkoxy, phenylalkoxy, aryl, cyano and phenoxy wherein:
the phenylalkoxy are optionally substituted with one or more haloalkyl; and $X^2$ is selected from the group consisting of a bond, —CH$_2$—O—, —C(O)—, —N(H)— and —C(S)—;

$X^3$ is selected from the group consisting of $X^4$ is selected from the group consisting of a bond, —CH$_2$—, —O—, and —C(O)—, wherein the —CH$_2$— is optionally substituted with up to two independently selected alkyl;

$X^5$ is selected from the group consisting of a bond and —CH$_2$—;

$X^6$ is selected from the group consisting of a bond, —CH$_2$— and cycloalkyl wherein the —CH$_2$— is optionally substituted with up to two independently selected alkyl;

$X^7$ is selected from the group consisting of —C(O)—, —C(S)—, —NH—C(O)—, —C(O)—NH—, —C(S)—NH—, —S(O)$_2$— and —C(O)—NH— wherein:
the —NH—C(O)— and —NH—C(S)— are optionally substituted with alkyl;

$X^8$ is selected from the group consisting of piperidinyl, piperazinyl, homopiperazinyl, and pyrrolidinyl;

$Z^1$ is selected from the group consisting of N and CH, wherein:
the CH is optionally substituted with a substituent selected from the group consisting of nitro, halogen, cyano, alkyl, alkoxy, alkylsulfanyl, alkylsulfinyl, alkylsulfonyl, arylsulfonyl, heteroaryl, aminosulfonyl and alkoxycarbonyl wherein:
the alkyl, alkoxy, alkylsulfanyl, arylsulfonyl, heteroaryl and aminosulfonyl are optionally substituted with one or more substituents independently selected from the group consisting of halogen and alkyl;

$Z^2$ is selected from the group consisting of N and CH, wherein:
the CH is optionally substituted with a substituent selected from the group consisting of alkyl, halogen, cyano, alkoxy, haloalkyl, and haloalkylsulfanyl;

$Z^3$, $Z^4$, and $Z^5$ are independently selected from the group consisting of N and CH.

In some embodiments of this invention, the compound is defined as corresponding in structure to the following formula:

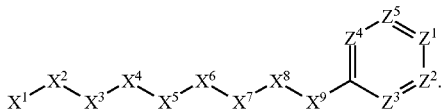

In some such embodiments, $X^1$ is selected from the group consisting of phenyl, 5-member heteroaryl, 6-member heteroaryl and alkyl wherein:
the 5-member heteroaryl is substituted with haloalkyl;
the phenyl and 6-member heteroaryl are optionally substituted with one or more substituents independently selected from the group consisting of alkyl, haloalkyl, halogen, alkoxy, haloalkoxy, phenylalkoxy, aryl, cyano and phenoxy wherein:
the phenylalkoxy are optionally substituted with one or more haloalkyl; and $X^2$ is selected from the group consisting of a bond, —CH$_2$—O—, —C(O)—, —N(H)— and —C(S)—;

$X^3$ is selected from the group consisting of $X^4$ is selected from the group consisting of a bond, —CH$_2$—, —O—, and —C(O)—, wherein the —CH$_2$— is optionally substituted with up to two independently selected alkyl;

$X^5$ is selected from the group consisting of a bond and —CH$_2$—;

$X^6$ is selected from the group consisting of a bond, —CH$_2$— and cycloalkyl wherein the —CH$_2$— is optionally substituted with up to two independently selected alkyl;

$X^7$ is selected from the group consisting of —C(O)—, —C(S)—, —NH—C(O)—, —C(O)—NH—, —C(S)—NH—, —S(O)$_2$— and —C(O)—NH— wherein:
  the —NH—C(O)— and —NH—C(S)— are optionally substituted with alkyl;

$X^8$ is piperidinyl or pyrrolidinyl;

$Z^1$ is selected from the group consisting of N and CH, wherein:
  the CH is optionally substituted with a substituent selected from the group consisting of nitro, halogen, cyano, alkyl, alkoxy, alkylsulfanyl, alkylsulfinyl, alkylsulfonyl, arylsulfonyl, heteroaryl, aminosulfonyl and alkoxycarbonyl wherein:
    the alkyl, alkoxy, alkylsulfanyl, arylsulfonyl, heteroaryl and aminosulfonyl are optionally substituted with one or more substituents independently selected from the group consisting of halogen and alkyl;

$Z^2$ is selected from the group consisting of N and CH, wherein:
  the CH is optionally substituted with a substituent selected from the group consisting of alkyl, halogen, cyano, alkoxy, haloalkyl, and haloalkylsulfanyl;

$Z^3$, $Z^4$, and $Z^5$ are independently selected from the group consisting of N and CH.

In some embodiments of this invention, the compound is defined as corresponding in structure to the following formula:

In some such embodiments,
  the compound has no mirror-symmetry plane.
In some such embodiments,
  $X^9$ is selected from the group consisting of —O—, —C(O)—, —S—, —S(O)—, —S(O)$_2$—, and —NH—, wherein the —NH— optionally is substituted with a substituent selected from the group consisting of alkyl, alkenyl, alkynyl, alkoxyalkyl, carbocyclyl, and carbocyclylalkyl, wherein any such substituent is optionally substituted with one or more independently selected halogen.

In some such embodiments,
  $X^9$ is selected from the group consisting of —O—, —C(O)—, —S—, —S(O)—, —S(O)$_2$—, and —NH—, wherein the —NH— optionally is substituted with a substituent selected from the group consisting of alkyl, alkenyl, alkynyl, alkoxyalkyl, carbocyclyl, and carbocyclylalkyl, wherein any such substituent is optionally substituted with one or more independently selected halogen, and the compound has no mirror-symmetry plane.

In some such embodiments,
  at least one of $X^4$, $X^5$, $X^6$ is different from a bond and from —CH$_2$—, or $X^7$ is different from —CH$_2$—.

In some such embodiments,
  at least one of $X^4$, $X^5$, $X^6$ is different from a bond and from —CH$_2$—, or $X^7$ is different from —CH$_2$—, and the compound has no mirror-symmetry plane.

In some such embodiments,
  $X^1$ is selected from the group consisting of phenyl, 5-member heteroaryl, 6-member heteroaryl and C$_3$-C$_6$-alkyl wherein:
    the 5-member heteroaryl is optionally substituted by one or more alkyl wherein:
      the alkyl is optionally substituted with one or more independently selected halogen,
    the phenyl and 6-member heteroaryl are optionally substituted at the meta and para positions by one or more substituents selected from the group consisting of alkyl, halogen, alkoxy, arylalkoxy, aryl, cyano and aryloxy wherein:
      the alkyl and alkoxy are optionally substituted with one or more independently selected halogen;
      the arylalkoxy is optionally substituted with one or more haloalkyl; and
    the phenyl is optionally substituted at the ortho positions with one or two independently selected halogen;

$X^2$ is selected from the group consisting of a bond, —CH$_2$—O—, —C(O)—, —N(H)— and —C(S)—;

$X^4$ is selected from the group consisting of a bond, —CH$_2$—, —O—, and —C(O)—, wherein:
    the —CH$_2$— is optionally substituted with up to two independently selected alkyl;

$X^5$ is selected from the group consisting of a bond and —CH$_2$—;

$X^6$ is selected from the group consisting of a bond, —CH$_2$— and cycloalkyl wherein:
    the —CH$_2$— is optionally substituted with up to two independently selected alkyl;

$X^7$ is selected from the group consisting of —C(O)—, —C(S)—, —NH—C(O)—, —C(O)—NH—, —C(S)—NH—, —S(O)$_2$— and —C(O)—NH— wherein:
    the —NH—C(O)— and —NH—C(S)— are optionally substituted with alkyl;

$X^8$ is piperidinyl or pyrrolidinyl;

$X^9$ is selected from the group consisting of —O—, —C(O)—, —S—, —S(O)—, —S(O)$_2$—, and —NH—, wherein the —NH— optionally is substituted with a substituent selected from the group consisting of alkyl, alkenyl, alkynyl, alkoxyalkyl, carbocyclyl, and carbocyclylalkyl, wherein any such substituent is optionally substituted with one or more independently selected halogen, $Z^1$ is selected from the group consisting of N and CH, wherein:
the CH is optionally substituted with a substituent selected from the group consisting of nitro, halogen, cyano, alkyl, alkoxy, alkylsulfanyl, alkylsulfinyl, alkylsulfonyl, arylsulfonyl, heteroaryl, aminosulfonyl and alkoxycarbonyl wherein:
the alkyl, alkoxy, alkylsulfanyl, arylsulfonyl, heteroaryl and aminosulfonyl are optionally substituted with one or more substituents independently selected from the group consisting of halogen and alkyl;

$Z^2$ is selected from the group consisting of N and CH, wherein:
the CH is optionally substituted with a substituent selected from the group consisting of alkyl, halogen, cyano, alkoxy, haloalkyl, alkylsulfanyl and haloalkylsulfanyl;

$Z^3$ and $Z^4$ are independently selected from the group consisting of N and CH; and $Z^5$ is CH.

In some such embodiments, $X^1$ is selected from the group consisting of phenyl, 5-member heteroaryl, 6-member heteroaryl and $C_3$-$C_6$-alkyl wherein:
the 5-member heteroaryl is optionally substituted by one or more alkyl wherein:
the alkyl is optionally substituted with one or more independently selected halogen,
the phenyl and 6-member heteroaryl are optionally substituted at the meta and para positions by one or more substituents selected from the group consisting of alkyl, halogen, alkoxy, arylalkoxy, aryl, cyano and aryloxy wherein:
the alkyl and alkoxy are optionally substituted with one or more independently selected halogen;
the arylalkoxy is optionally substituted with one or more haloalkyl; and
the phenyl is optionally substituted at the ortho positions with one or two independently selected halogen;

$X^2$ is selected from the group consisting of a bond, —CH$_2$—O—, —C(O)—, —N(H)— and —C(S)—;

$X^4$ is selected from the group consisting of a bond, —CH$_2$—, —O—, and —C(O)—, wherein:
the —CH$_2$— is optionally substituted with up to two independently selected alkyl;

$X^5$ is selected from the group consisting of a bond and —CH$_2$—;

$X^6$ is selected from the group consisting of a bond, —CH$_2$— and cycloalkyl wherein:
the —CH$_2$— is optionally substituted with up to two independently selected alkyl;

$X^7$ is selected from the group consisting of —C(O)—, —C(S)—, —NH—C(O)—, —C(O)—NH—, —C(S)—NH—, —S(O)$_2$— and —C(O)—NH— wherein:
the —NH—C(O)— and —NH—C(S)— are optionally substituted with alkyl;

$X^8$ is piperidinyl or pyrrolidinyl;

$X^9$ is selected from the group consisting of —O—, —C(O)—, —S—, —S(O)—, —S(O)$_2$—, and —NH—, wherein the —NH— optionally is substituted with a substituent selected from the group consisting of alkyl, alkenyl, alkynyl, alkoxyalkyl, carbocyclyl, and carbocyclylalkyl, wherein any such substituent is optionally substituted with one or more independently selected halogen, $Z^1$ is selected from the group consisting of N and CH, wherein:
the CH is optionally substituted with a substituent selected from the group consisting of nitro, halogen, cyano, alkyl, alkoxy, alkylsulfanyl, alkylsulfinyl, alkylsulfonyl, arylsulfonyl, heteroaryl, aminosulfonyl and alkoxycarbonyl wherein:
the alkyl, alkoxy, alkylsulfanyl, arylsulfonyl, heteroaryl and aminosulfonyl are optionally substituted with one or more substituents independently selected from the group consisting of halogen and alkyl;

$Z^2$ is selected from the group consisting of N and CH, wherein:
the CH is optionally substituted with a substituent selected from the group consisting of alkyl, halogen, cyano, alkoxy, haloalkyl, alkylsulfanyl and haloalkylsulfanyl;

$Z^3$ and $Z^4$ are independently selected from the group consisting of N and CH; and $Z^5$ is CH, and the compound has no mirror-symmetry plane.

In some such embodiments, $X^1$ is selected from the group consisting of phenyl, pyridyl and thiadiazoyl, substituted by halogen, ($C_1$-$C_6$)alkyl, ($C_1$-$C_6$)alkyloxy, ($C_1$-$C_6$)haloalkyl, ($C_1$-$C_6$)haloalkyloxy, phenyloxy, halophenyloxy, benzyloxy and halobenzyloxy, preferably ($C_1$-$C_6$)alkyl, ($C_1$-$C_6$)alkyloxy, ($C_1$-$C_6$)haloalkyl, ($C_1$-$C_6$)haloalkyloxy, $X^2$ is a bond, $X^3$ is piperazinyl, $X^4$ is —CH$_2$—, $X^5$ is selected from the group consisting of is —CH$_2$— and —CH($C_1$-$C_6$)alkyl, $X^6$ is selected from the group consisting of —CH$_2$— and a bond, $X^7$ is CO or CS, $X^8$ is piperidinyl, $X^9$ is NH or S, preferably NH, $Z^1$ is selected from the group consisting of C—NO$_2$, C—CN, C—S—($C_1$-$C_6$)alkyl and C—S—($C_1$-$C_6$)haloalkyl, preferably C—NO$_2$ or C—CN, $Z^2$ is C—CF$_3$ or CH, $Z^3$ is CH or N, $Z^4$ is CH, and $Z^5$ is CH.

In some such embodiments, $X^1$ is selected from the group consisting of phenyl, pyridyl and thiadiazoyl, substituted by halogen, ($C_1$-$C_6$)alkyl, ($C_1$-$C_6$)alkyloxy, ($C_1$-$C_6$)haloalkyl, ($C_1$-$C_6$)haloalkyloxy, phenyloxy, halophenyloxy, benzyloxy and halobenzyloxy, preferably ($C_1$-$C_6$)alkyl, ($C_1$-$C_6$)alkyloxy, ($C_1$-$C_6$)haloalkyl, ($C_1$-$C_6$)haloalkyloxy, $X^2$ is a bond, $X^3$ is piperazinyl, $X^4$ is —CH$_2$—, $X^5$ is selected from the group consisting of is —CH$_2$— and —CH($C_1$-$C_6$)alkyl, $X^6$ is selected from the group consisting of —CH$_2$— and a bond, $X^7$ is CO or CS, $X^8$ is piperidinyl, $X^9$ is NH or S, preferably NH, $Z^1$ is selected from the group consisting of C—NO$_2$, C—CN, C—S—(C$_1$-C$_6$)alkyl and C—S—(C$_1$-C$_6$)haloalkyl, preferably C—NO$_2$ or C—CN, $Z^2$ is —CF$_3$ or CH, $Z^3$ is CH or N, $Z^4$ is CH, and $Z^5$ is CH, and the compound has no mirror-symmetry plane.

In some embodiments of this invention, the compound is defined as corresponding in structure to the following formula:

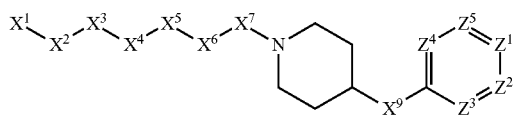

In some such embodiments,
the compound has no mirror-symmetry plane.

In some such embodiments,
$X^9$ is selected from the group consisting of —O—, —C(O)—, —S—, —S(O)—, —S(O)$_2$—, and —NH—, wherein the —NH— optionally is substituted with a substituent selected from the group consisting of alkyl, alkenyl, alkynyl, alkoxyalkyl, carbocyclyl, and carbocyclylalkyl, wherein any such substituent is optionally substituted with one or more independently selected halogen.

In some such embodiments,
$X^9$ is selected from the group consisting of —O—, —C(O)—, —S—, —S(O)—, —S(O)$_2$—, and —NH—, wherein the —NH— optionally is substituted with a substituent selected from the group consisting of alkyl, alkenyl, alkynyl, alkoxyalkyl, carbocyclyl, and carbocyclylalkyl, wherein any such substituent is optionally substituted with one or more independently selected halogen, and the compound has no mirror-symmetry plane.

In some such embodiments,
at least one of $X^4$, $X^5$, $X^6$ is different from a bond and from —CH$_2$—, or $X^7$ is different from —CH$_2$—.

In some such embodiments,
at least one of $X^4$, $X^5$, $X^6$ is different from a bond and from —CH$_2$—, or $X^7$ is different from —CH$_2$—, and the compound has no mirror-symmetry plane.

In some such embodiments,
$X^1$ is selected from the group consisting of phenyl, 5-member heteroaryl, 6-member heteroaryl and C$_3$-C$_6$-alkyl wherein:
the 5-member heteroaryl is optionally substituted by one or more alkyl wherein:
the alkyl is optionally substituted with one or more independently selected halogen,
the phenyl and 6-member heteroaryl are optionally substituted at the meta and para positions by one or more substituents selected from the group consisting of alkyl, halogen, alkoxy, arylalkoxy, aryl, cyano and aryloxy wherein:
the alkyl and alkoxy are optionally substituted with one or more independently selected halogen;
the arylalkoxy is optionally substituted with one or more haloalkyl; and
the phenyl is optionally substituted at the ortho positions with one or two independently selected halogen;

$X^2$ is selected from the group consisting of a bond, —CH$_2$—O—, —C(O)—, —N(H)— and —C(S)—;

$X^4$ is selected from the group consisting of a bond, —CH$_2$—, —O—, and —C(O)—, wherein:
the —CH$_2$— is optionally substituted with up to two independently selected alkyl;

$X^5$ is selected from the group consisting of a bond and —CH$_2$—;

$X^6$ is selected from the group consisting of a bond, —CH$_2$— and cycloalkyl wherein:
the —CH$_2$— is optionally substituted with up to two independently selected alkyl;

$X^7$ is selected from the group consisting of —C(O)—, —C(S)—, —NH—C(O)—, —C(O)—NH—, —C(S)—NH—, —S(O)$_2$— and —C(O)—NH— wherein:
the —NH—C(O)— and —NH—C(S)— are optionally substituted with alkyl;

$X^9$ is selected from the group consisting of —O—, —C(O)—, —S—, —S(O)—, —S(O)$_2$—, and —NH—, wherein the —NH— optionally is substituted with a substituent selected from the group consisting of alkyl, alkenyl, alkynyl, alkoxyalkyl, carbocyclyl, and carbocyclylalkyl, wherein any such substituent is optionally substituted with one or more independently selected halogen, $Z^1$ is selected from the group consisting of N and CH, wherein:
the CH is optionally substituted with a substituent selected from the group consisting of nitro, halogen, cyano, alkyl, alkoxy, alkylsulfanyl, alkylsulfinyl, alkylsulfonyl, arylsulfonyl, heteroaryl, aminosulfonyl and alkoxycarbonyl wherein:
the alkyl, alkoxy, alkylsulfanyl, arylsulfonyl, heteroaryl and aminosulfonyl are optionally substituted with one or more substituents independently selected from the group consisting of halogen and alkyl;

$Z^2$ is selected from the group consisting of N and CH, wherein:
the CH is optionally substituted with a substituent selected from the group consisting of alkyl, halogen, cyano, alkoxy, haloalkyl, alkylsulfanyl and haloalkylsulfanyl;

$Z^3$ and $Z^4$ are independently selected from the group consisting of N and CH; and $Z^5$ is CH.

In some such embodiments,
$X^1$ is selected from the group consisting of phenyl, 5-member heteroaryl, 6-member heteroaryl and C$_3$-C$_6$-alkyl wherein:
the 5-member heteroaryl is optionally substituted by one or more alkyl wherein:
the alkyl is optionally substituted with one or more independently selected halogen,
the phenyl and 6-member heteroaryl are optionally substituted at the meta and para positions by one or more substituents selected from the group consisting of alkyl, halogen, alkoxy, arylalkoxy, aryl, cyano and aryloxy wherein:
the alkyl and alkoxy are optionally substituted with one or more independently selected halogen;
the arylalkoxy is optionally substituted with one or more haloalkyl; and
the phenyl is optionally substituted at the ortho positions with one or two independently selected halogen;

$X^2$ is selected from the group consisting of a bond, —CH$_2$—O—, —C(O)—, —N(H)— and —C(S)—;

$X^4$ is selected from the group consisting of a bond, —CH$_2$—, —O—, and —C(O)—, wherein:
the —CH$_2$— is optionally substituted with up to two independently selected alkyl;

$X^5$ is selected from the group consisting of a bond and —CH$_2$—;

$X^6$ is selected from the group consisting of a bond, —CH$_2$— and cycloalkyl wherein:
the —CH$_2$— is optionally substituted with up to two independently selected alkyl;

$X^7$ is selected from the group consisting of —C(O)—, —C(S)—, —NH—C(O)—, —C(O)—NH—, —C(S)—NH—, —S(O)$_2$— and —C(O)—NH— wherein:
the —NH—C(O)— and —NH—C(S)— are optionally substituted with alkyl;

$X^9$ is selected from the group consisting of —O—, —C(O)—, —S—, —S(O)—, —S(O)$_2$—, and —NH—, wherein the —NH— optionally is substituted with a substituent selected from the group consisting of alkyl, alkenyl, alkynyl, alkoxyalkyl, carbocyclyl, and carbocyclylalkyl, wherein any such substituent is optionally substituted with one or more independently selected halogen, $Z^1$ is selected from the group consisting of N and CH, wherein:
the CH is optionally substituted with a substituent selected from the group consisting of nitro, halogen, cyano, alkyl, alkoxy, alkylsulfanyl, alkylsulfinyl, alkylsulfonyl, arylsulfonyl, heteroaryl, aminosulfonyl and alkoxycarbonyl wherein:
the alkyl, alkoxy, alkylsulfanyl, arylsulfonyl, heteroaryl and aminosulfonyl are optionally substituted with one or more substituents independently selected from the group consisting of halogen and alkyl;

$Z^2$ is selected from the group consisting of N and CH, wherein:
the CH is optionally substituted with a substituent selected from the group consisting of alkyl, halogen, cyano, alkoxy, haloalkyl, alkylsulfanyl and haloalkylsulfanyl;

$Z^3$ and $Z^4$ are independently selected from the group consisting of N and CH; and $Z^5$ is CH, and the compound has no mirror-symmetry plane.

In some such embodiments,
$X^1$ is selected from the group consisting of phenyl, pyridyl and thiadiazoyl, substituted by halogen, (C$_1$-C$_6$)alkyl, (C$_1$-C$_6$)alkyloxy, (C$_1$-C$_6$)haloalkyl, (C$_1$-C$_6$)haloalkyloxy, phenyloxy, halophenyloxy, benzyloxy and halobenzyloxy, preferably (C$_1$-C$_6$)alkyl, (C$_1$-C$_6$)alkyloxy, (C$_1$-C$_6$)haloalkyl, (C$_1$-C$_6$)haloalkyloxy, $X^2$ is a bond,
$X^3$ is piperazinyl,
$X^4$ is —CH$_2$—,
$X^5$ is selected from the group consisting of is —CH$_2$— and —CH(C$_1$-C$_6$)alkyl,
$X^6$ is selected from the group consisting of —CH$_2$— and a bond,
$X^7$ is CO or CS,
$X^8$ is piperidinyl,
$X^9$ is NH or S, preferably NH,
$Z^1$ is selected from the group consisting of C—NO$_2$, C—CN, C—S—(C$_1$-C$_6$)alkyl and C—S—(C$_1$-C$_6$)haloalkyl, preferably C—NO$_2$ or C—CN,
$Z^2$ is C—CF$_3$ or CH,
$Z^3$ is CH or N, $Z^4$ is CH, and
$Z^5$ is CH.

In some such embodiments,
$X^1$ is selected from the group consisting of phenyl, pyridyl and thiadiazoyl, substituted by halogen, (C$_1$-C$_6$)alkyl, (C$_1$-C$_6$)alkyloxy, (C$_1$-C$_6$)haloalkyl, (C$_1$-C$_6$)haloalkyloxy, phenyloxy, halophenyloxy, benzyloxy and halobenzyloxy, preferably (C$_1$-C$_6$)alkyl, (C$_1$-C$_6$)alkyloxy, (C$_1$-C$_6$)haloalkyl, (C$_1$-C$_6$)haloalkyloxy, $X^2$ is a bond,
$X^3$ is piperazinyl,
$X^4$ is —CH$_2$—,
$X^5$ is selected from the group consisting of is —CH$_2$— and —CH(C$_1$-C$_6$)alkyl,
$X^6$ is selected from the group consisting of —CH$_2$— and a bond,
$X^7$ is CO or CS,
$X^8$ is piperidinyl,
$X^9$ is NH or S, preferably NH,
$Z^1$ is selected from the group consisting of C—NO$_2$, C—CN, C—S—(C$_1$-C$_6$)alkyl and C—S—(C$_1$-C$_6$)haloalkyl, preferably C—NO$_2$ or C—CN,
$Z^2$ is C—CF$_3$ or CH,
$Z^3$ is CH or N,
$Z^4$ is CH, and
$Z^5$ is CH, and the compound has no mirror-symmetry plane.

In some embodiments of this invention, the compound is defined as corresponding in structure to the following formula:

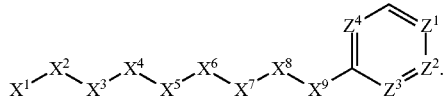

In some such embodiments,
$X^1$ is selected from the group consisting of phenyl, 5-member heteroaryl, and 6-member heteroaryl, and C$_3$-C$_6$-alkyl wherein:
the 5-member heteroaryl is optionally substituted by one or more alkyl wherein:
the alkyl is optionally substituted with one or more independently selected halogen,
the phenyl and 6-member heteroaryl are optionally substituted at the meta and para positions by one or more substituents selected from the group consisting of alkyl, halogen, aryloxy, alkoxy, arylalkoxy and cyano wherein:
the alkyl is optionally substituted with one or more independently selected halogen;
the arylalkoxy is optionally substituted with one or more haloalkyl;
the phenyl is optionally substituted at the ortho position with one or more halogen; and $X^2$ is selected from the group consisting of a bond, —C(O)—, and —CH$_2$—O—;
$X^3$ is selected from the group consisting of

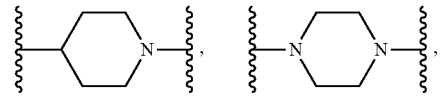

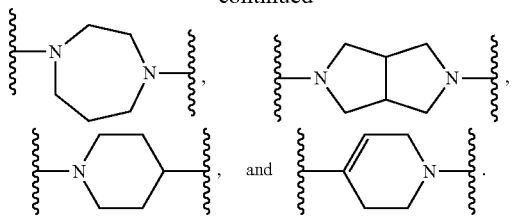

$X^4$ is selected from the group consisting of a bond, —CH$_2$—, —O—, and —C(O)—, wherein:
  the —CH$_2$— is optionally substituted with up to two substituents independently selected alkyl;
$X^5$ is selected from the group consisting of a bond and —CH$_2$—;
$X^6$ is selected from the group consisting of a bond and —CH$_2$—, wherein:
  the —CH$_2$— is optionally substituted with up to two substituents independently selected alkyl;
$X^1$ is selected from the group consisting of —C(O)—, —C(S)—, —NH—C(O)—, —C(O)—NH—, S(O)$_2$, and —C(S)—NH— wherein:
  the —NH—C(O)— is optionally substituted with alkyl;
$X^8$ is selected from the group consisting of

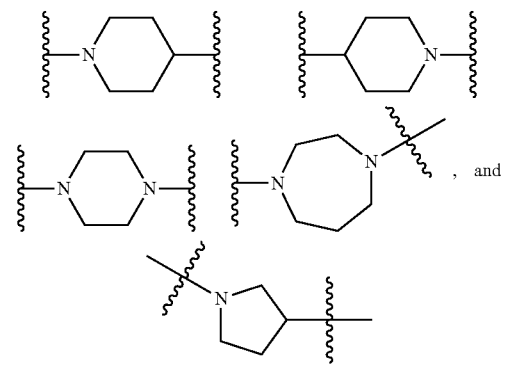

$X^9$ is selected from the group consisting of a bond, —NH—, and —O—;
$Z^1$ is selected from the group consisting of N and CH, wherein:
  the CH is optionally substituted with a substituent selected from the group consisting of nitro, halogen, cyano, alkyl, alkoxy, alkylsulfinyl, alkylsulfanyl, alkylsulfonyl, arylsulfonyl, aminosulfonyl, and 5-membered heteroaryl, wherein:
    the alkyl, alkoxy, alkylsulfanyl, arylsulfonyl, aminosulfonyl, and 5-membered heteroaryl are optionally substituted with one or more substituents independently selected from the group consisting of halogen and alkyl;
$Z^2$ is selected from the group consisting of N and CH, wherein:
  the CH is optionally substituted with a substituent selected from the group consisting of alkyl, halogen, cyano, alkoxy, haloalkyl and haloalkylsulfanyl; and
$Z^3$ and $Z^4$ are independently selected from the group consisting of N and CH.

In some embodiments of this invention, the compound is defined as corresponding in structure to the following formula:

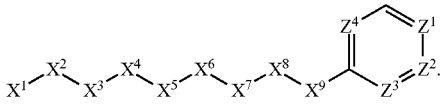

In some such embodiments,
$X^1$ is selected from the group consisting of phenyl, 5-member heteroaryl, and 6-member heteroaryl, and C$_3$-C$_6$-alkyl wherein:
  the 5-member heteroaryl is optionally substituted by one or more alkyl wherein:
    the alkyl is optionally substituted with one or more independently selected halogen,
  the phenyl and 6-member heteroaryl are optionally substituted at the meta and para positions by one or more substituents selected from the group consisting of alkyl, halogen, aryloxy, alkoxy, arylalkoxy and cyano wherein:
    the alkyl is optionally substituted with one or more independently selected halogen;
    the arylalkoxy is optionally substituted with one or more haloalkyl;
  the phenyl is optionally substituted at the ortho position with one or more halogen; and
$X^2$ is selected from the group consisting of a bond, —C(O)—, and —CH$_2$—O—;
$X^3$ is selected from the group consisting of

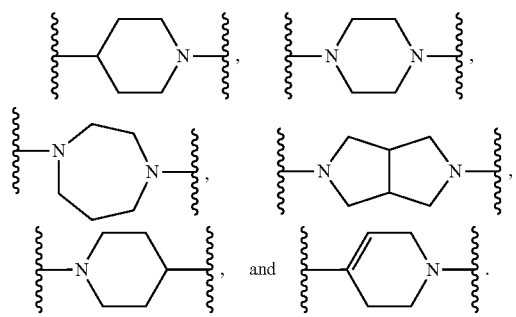

$X^4$ is selected from the group consisting of a bond, —CH$_2$—, —O—, and —C(O)—, wherein:
  the —CH$_2$— is optionally substituted with up to two substituents independently selected alkyl;
$X^5$ is selected from the group consisting of a bond and —CH$_2$—;
$X^6$ is selected from the group consisting of a bond and —CH$_2$—, wherein:
  the —CH$_2$— is optionally substituted with up to two substituents independently selected alkyl;
$X^1$ is selected from the group consisting of —C(O)—, —C(S)—, —NH—C(O)—, —C(O)—NH—, S(O)$_2$, and —C(S)—NH— wherein:
  the —NH—C(O)— is optionally substituted with alkyl;
$X^8$ is selected from the group consisting of

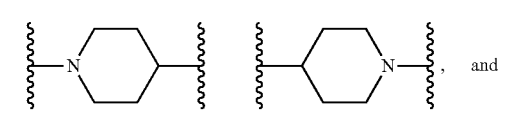

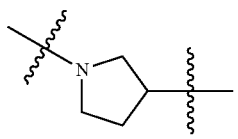

$X^9$ is selected from the group consisting of a bond, —NH—, and —O—;

$Z^1$ is selected from the group consisting of N and CH, wherein:
the CH is optionally substituted with a substituent selected from the group consisting of nitro, halogen, cyano, alkyl, alkoxy, alkylsulfinyl, alkylsulfanyl, alkylsulfonyl, arylsulfonyl, aminosulfonyl, and 5-membered heteroaryl, wherein:
the alkyl, alkoxy, alkylsulfanyl, arylsulfonyl, aminosulfonyl, and 5-membered heteroaryl are optionally substituted with one or more substituents independently selected from the group consisting of halogen and alkyl;

$Z^2$ is selected from the group consisting of N and CH, wherein:
the CH is optionally substituted with a substituent selected from the group consisting of alkyl, halogen, cyano, alkoxy, haloalkyl and haloalkylsulfanyl; and $Z^3$ and $Z^4$ are independently selected from the group consisting of N and CH.

In some embodiments, the compound or salt thereof corresponds to a structure selected from the group consisting of:

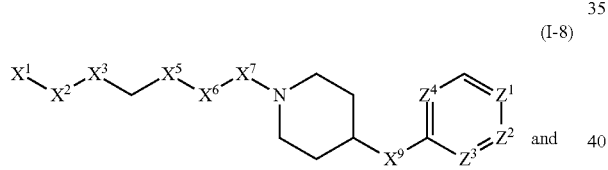

(I-8)

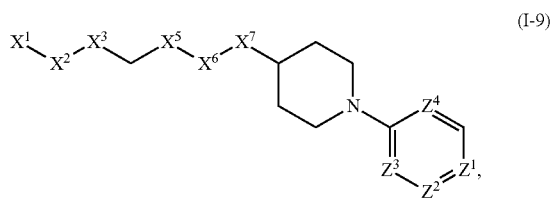

(I-9)

$X^1$ is selected from the group consisting of phenyl, 5-member heteroaryl, and 6-member heteroaryl, wherein:
the 5-member heteroaryl is substituted with trifluoromethyl;

the phenyl and 6-member heteroaryl are optionally substituted at the meta and para positions by one or more substituents selected from the group consisting of alkyl, trifluoromethyl, halogen, phenoxy, alkoxy, and trifluoromethylphenylalkoxy wherein:

$X^2$ is selected from the group consisting of a bond and —CH$_2$—O—;

$X^3$ is a linker selected from the group consisting of:

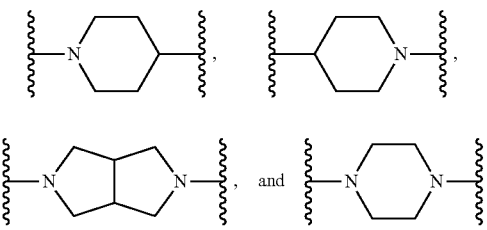

$X^5$ is selected from the group consisting of a bond and —CH$_2$—;

$X^6$ is selected from the group consisting of a bond and —CH$_2$—, wherein:
the —CH$_2$— is optionally substituted with up to two substituents independently selected alkyl;

$X^7$ is selected from the group consisting of —C(O)—, —C(S)—, —NH—C(O)—, —C(O)—NH—, and —C(S)—NH— wherein:
the —NH—C(O)— is optionally substituted with alkyl;

$X^9$ is selected from the group consisting of a bond, —NH—, and —O—;

$Z^1$ is selected from the group consisting of N and CH, wherein:
the CH is optionally substituted with a substituent selected from the group consisting of nitro, halogen, cyano, trifluoromethyl, trifluoromethoxy, alkylsulfanyl, trifluoromethylsulfanyl, alkylsulfonyl, trifluormethylsulfonyl, phenylsulfonyl and 5-membered-heteroaryl, wherein:
the 5-membered-heteroaryl is optionally substituted with C$_1$-C$_3$-alkyl;

$Z^2$ is selected from the group consisting of N and CH, wherein:
the CH is optionally substituted with a substituent selected from the group consisting of alkyl, halogen, cyano, alkoxy, trifluoromethyl and trifluoromethylsulfanyl; and $Z^3$ and $Z^4$ are independently selected from the group consisting of N and CH. Compounds encompassed by these embodiments include, for example:

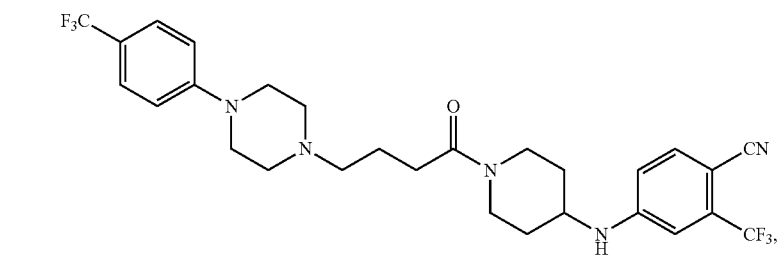

-continued
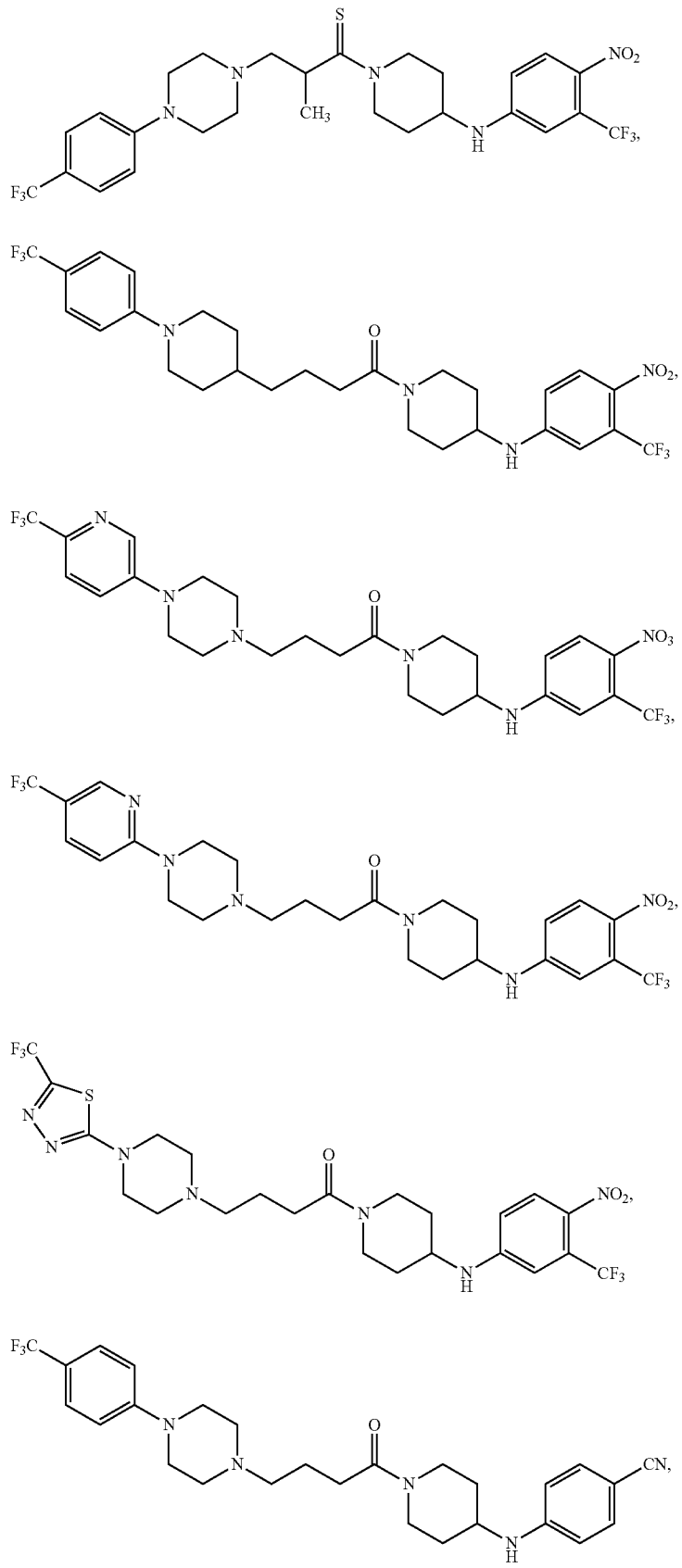

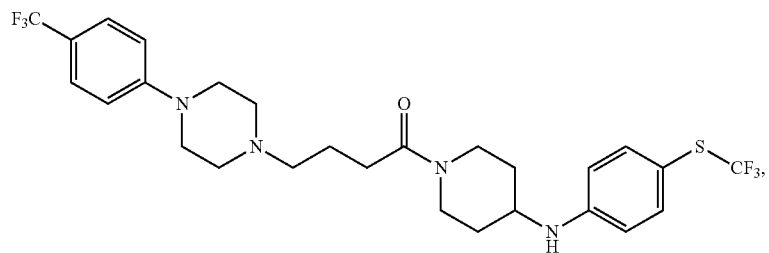
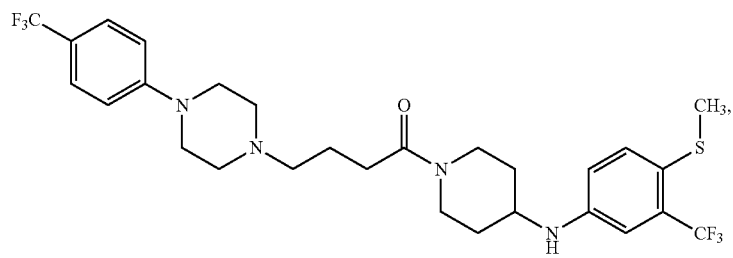
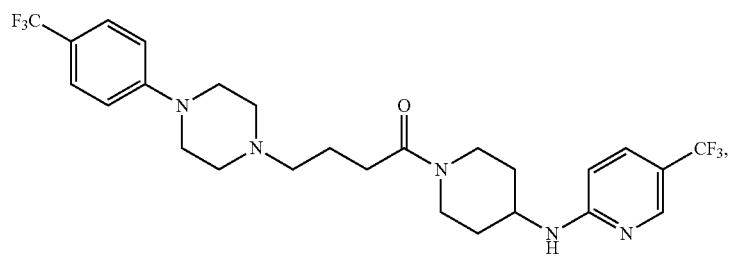
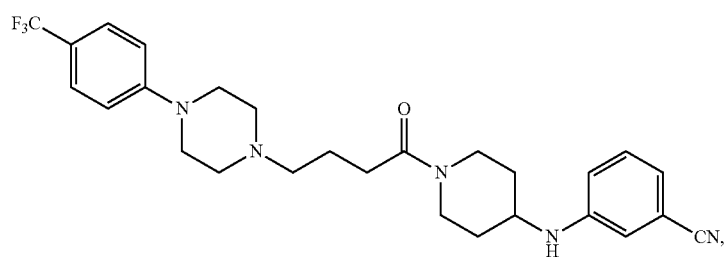
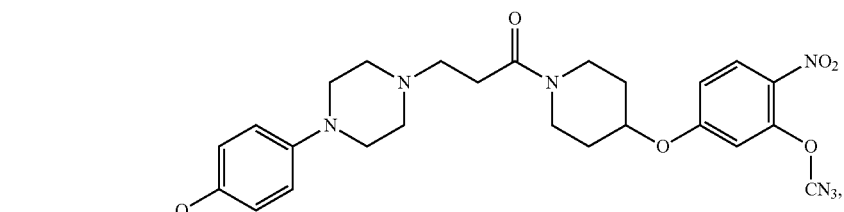
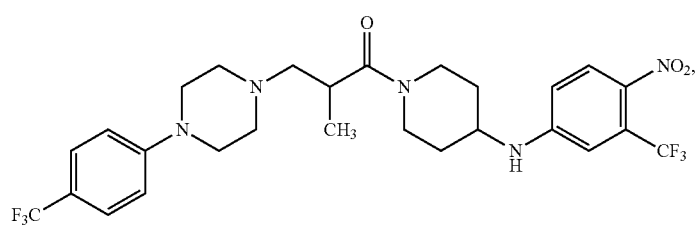

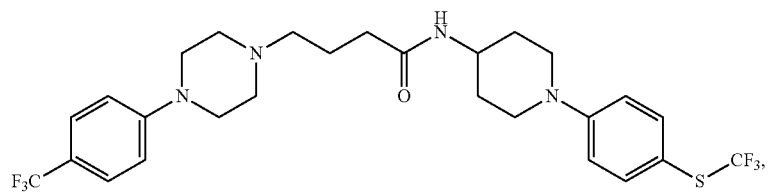
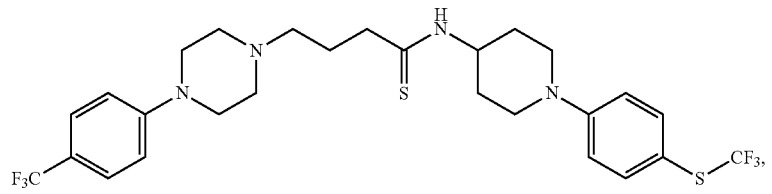
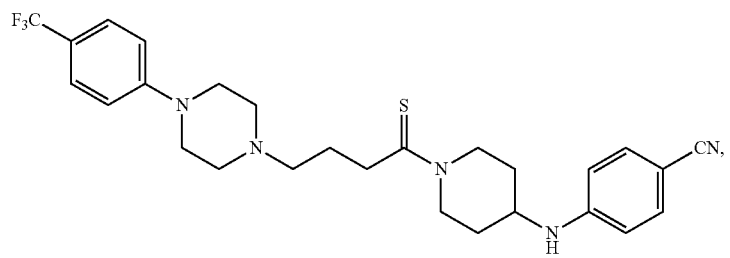
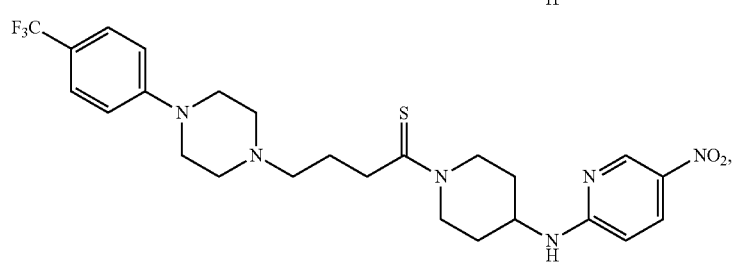
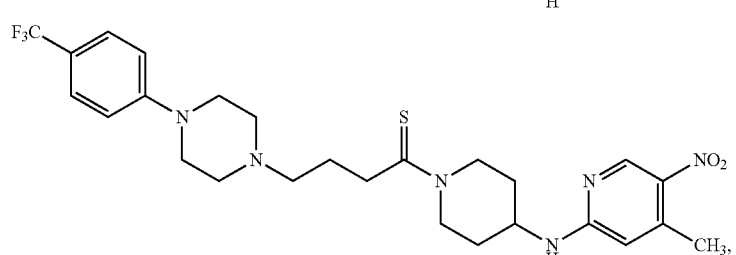
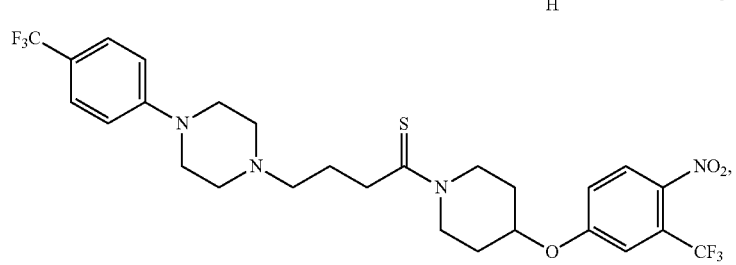
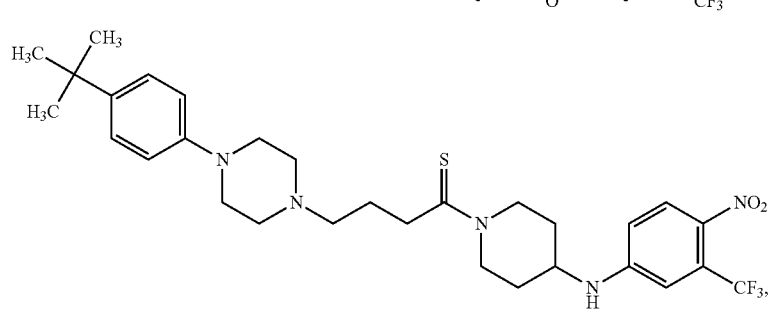

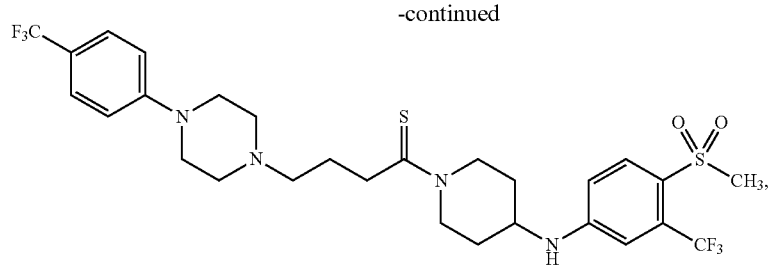
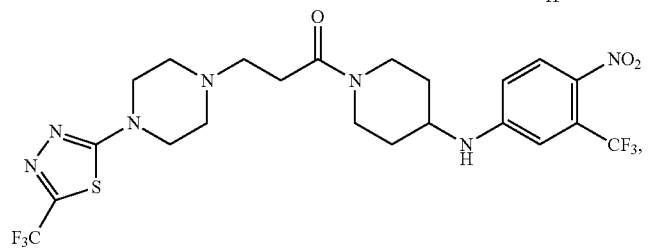
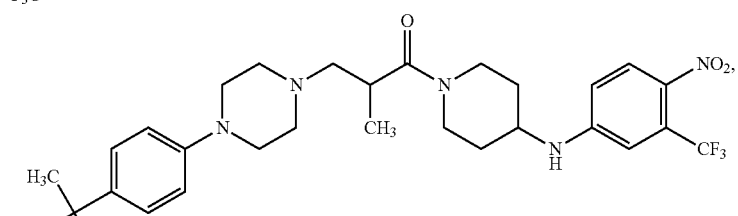
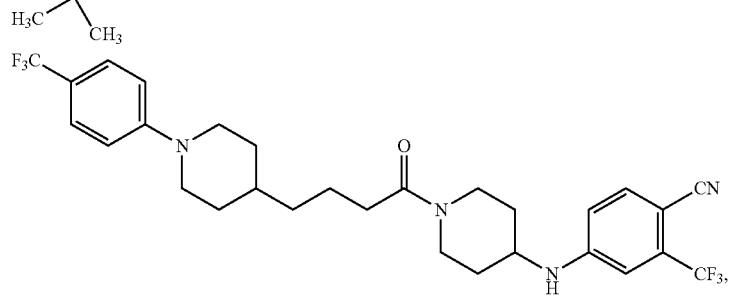
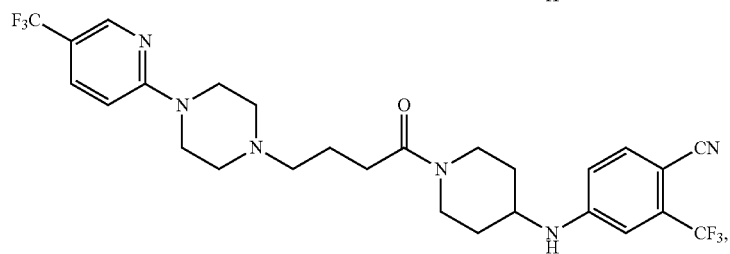
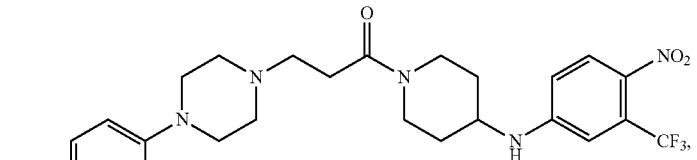
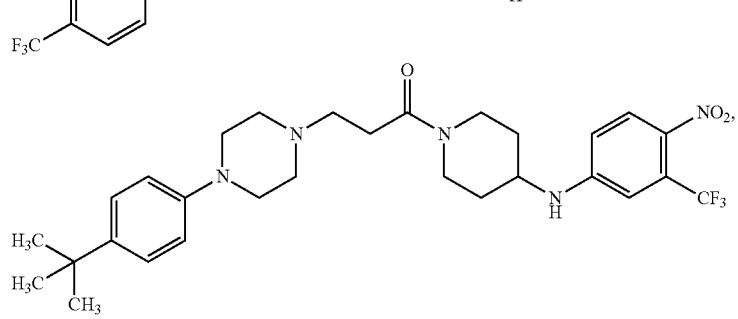

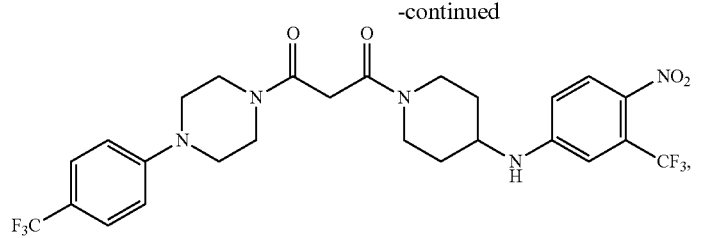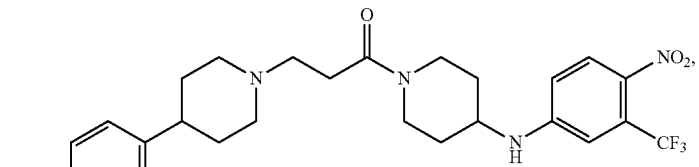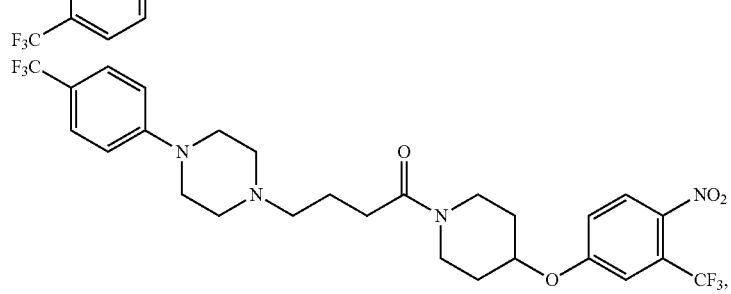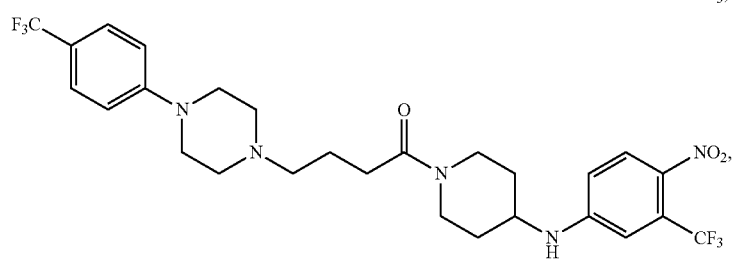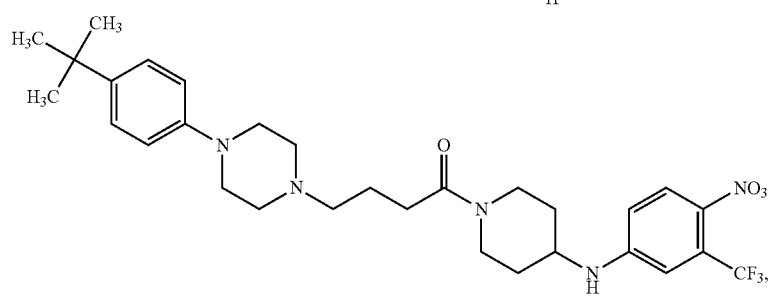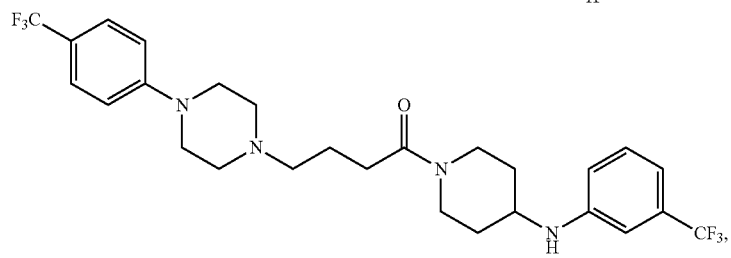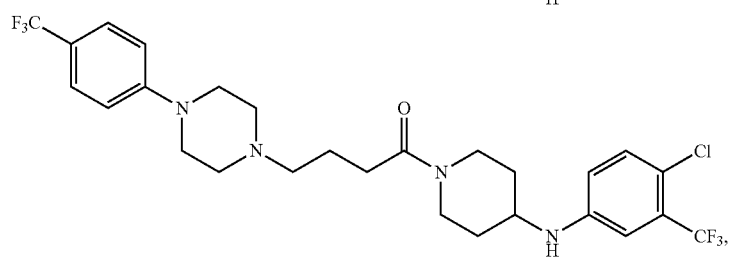

-continued
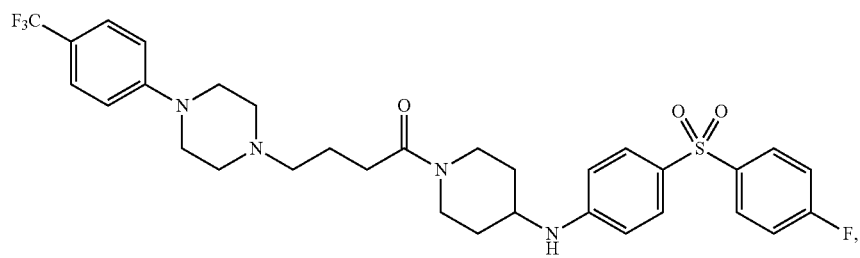
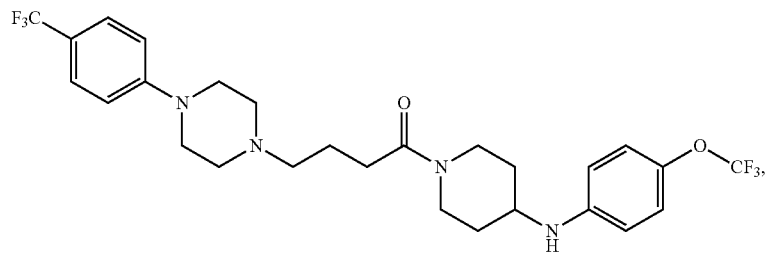
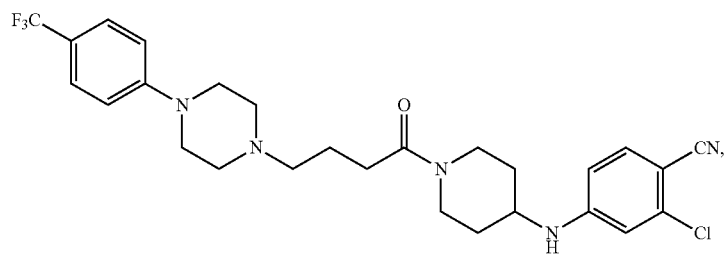
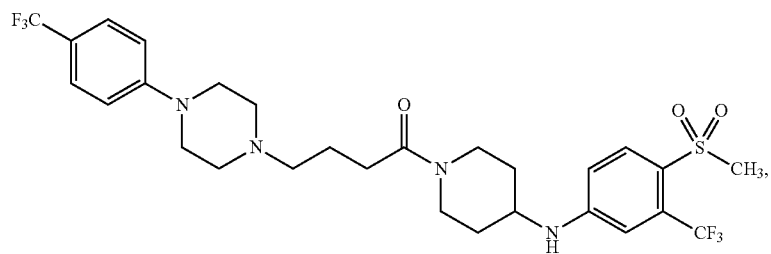
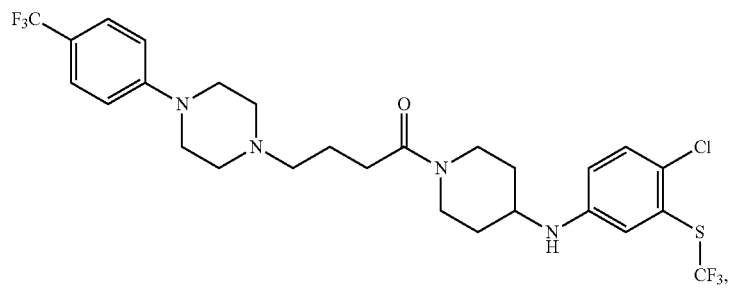
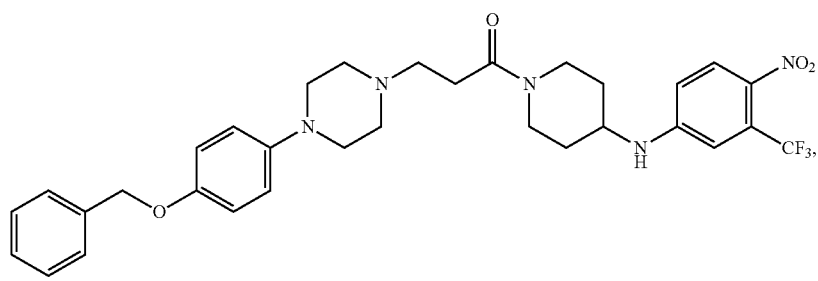

-continued
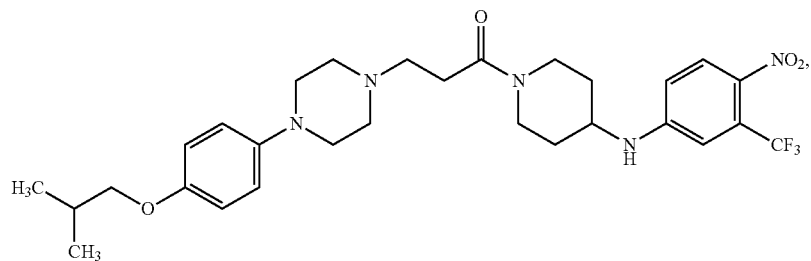
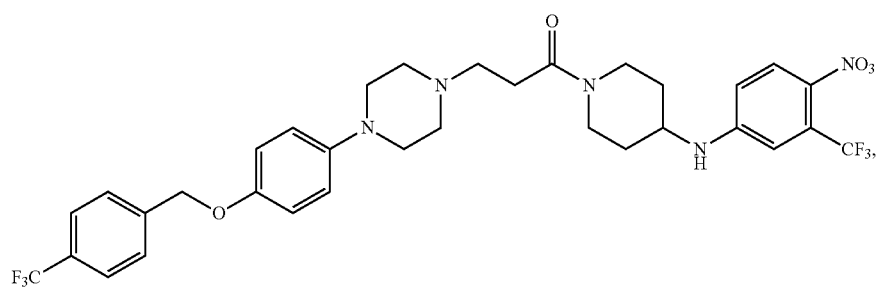
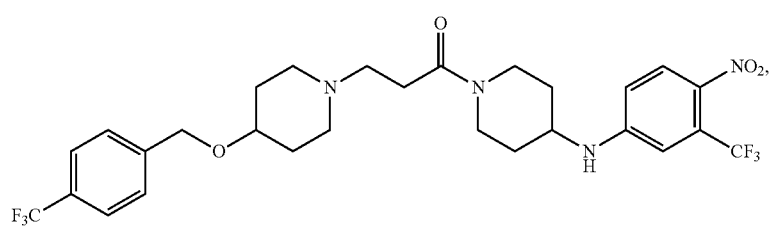
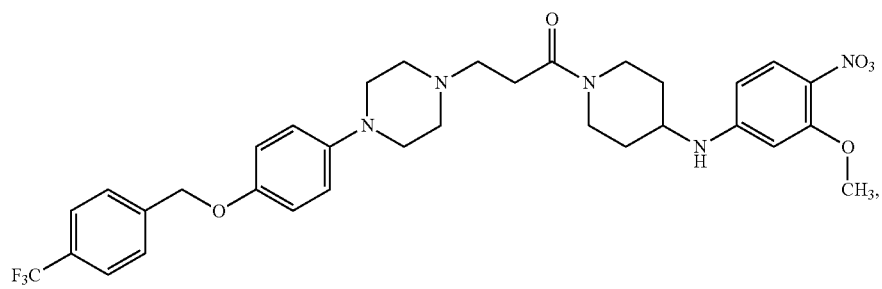
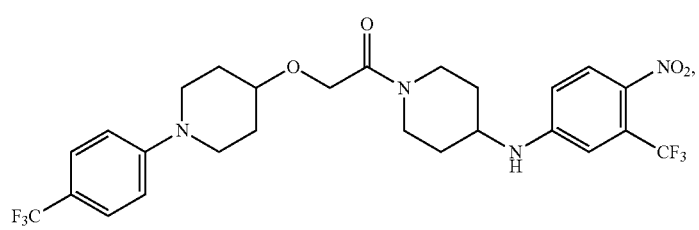
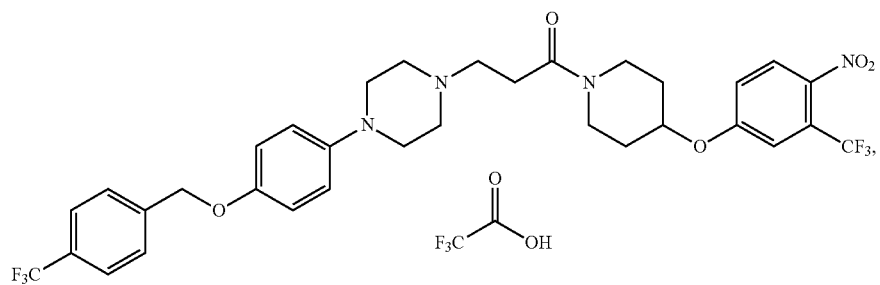

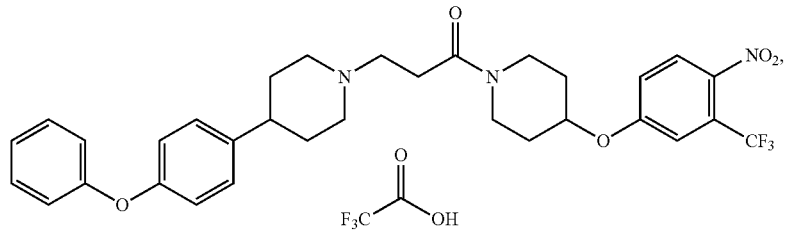
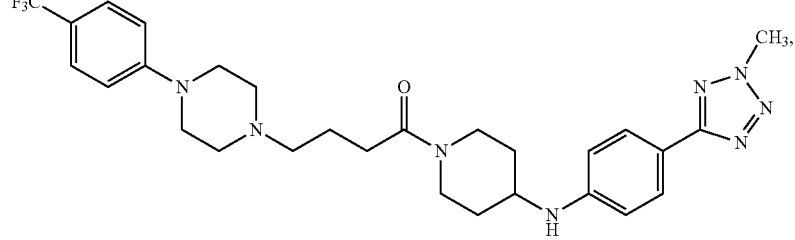
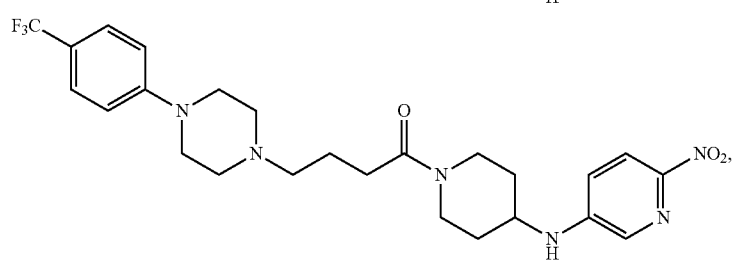
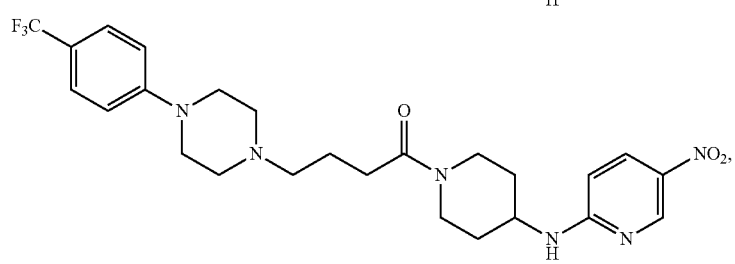
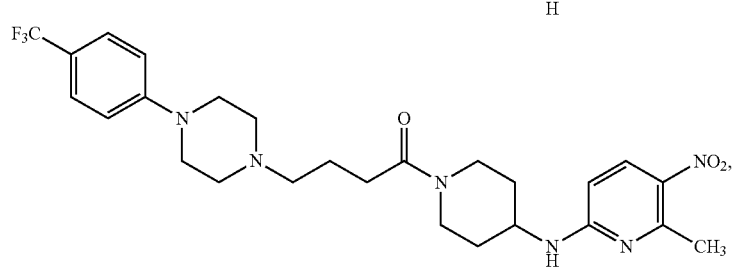
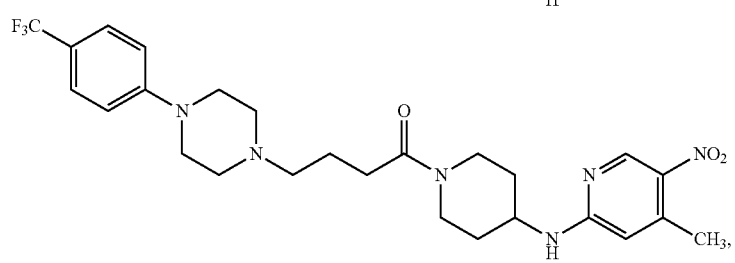
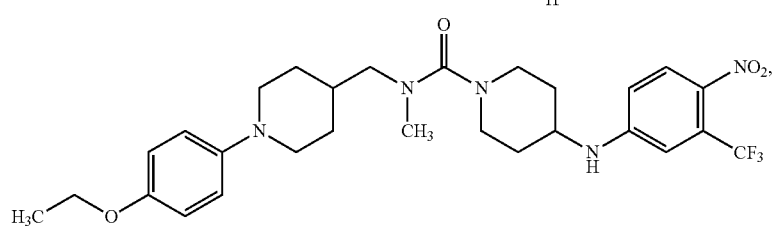

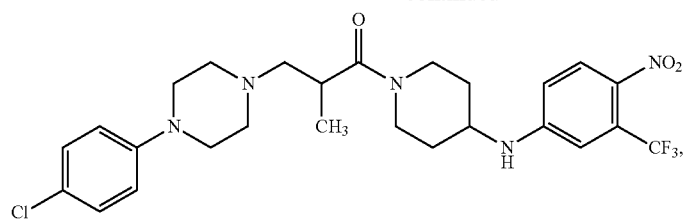
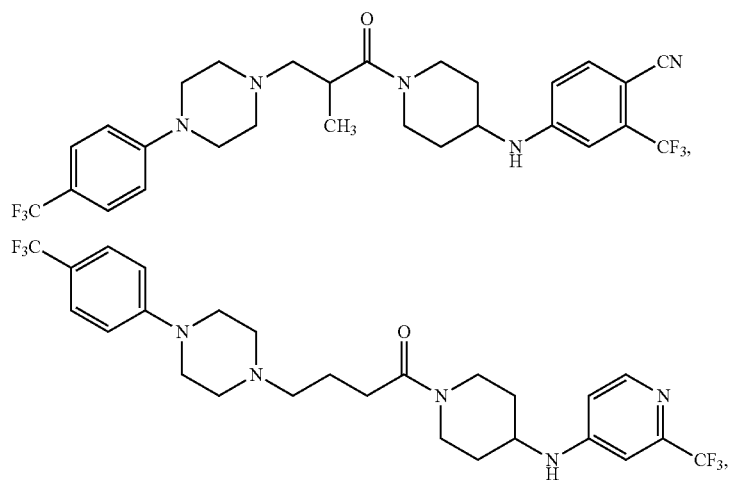
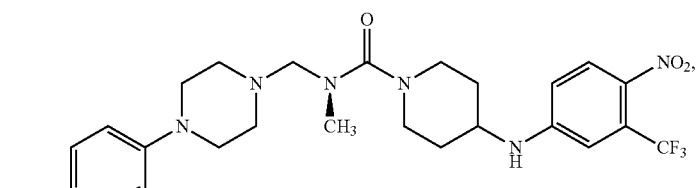
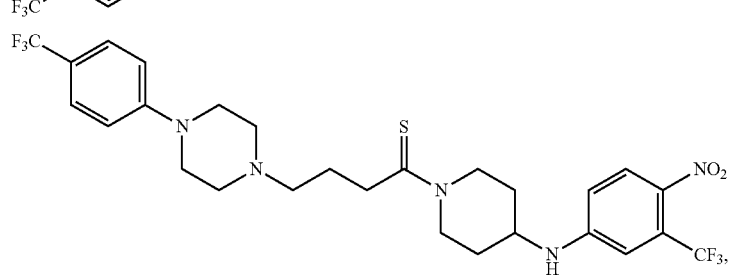
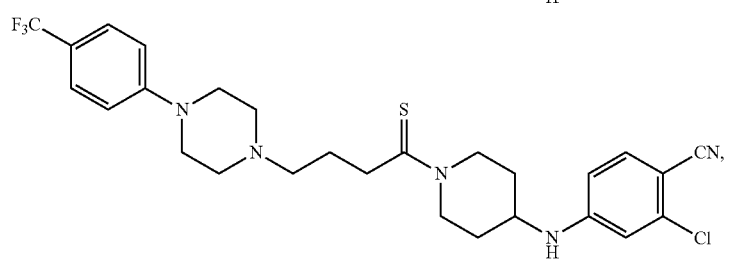
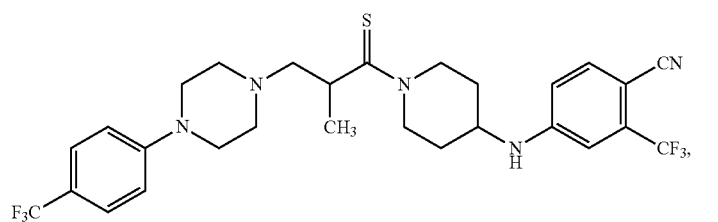

-continued
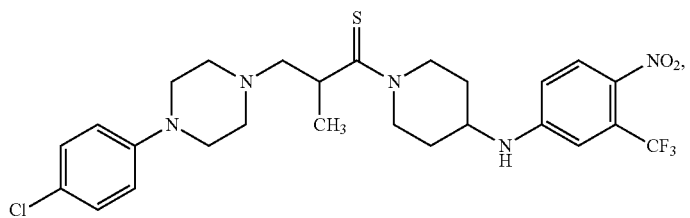
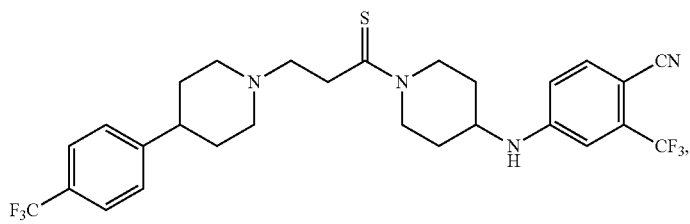
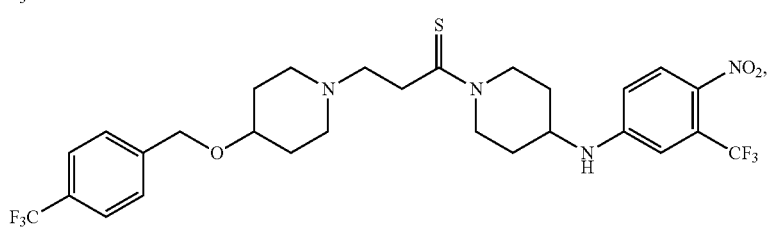
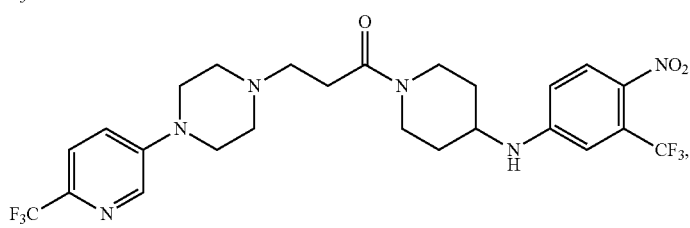
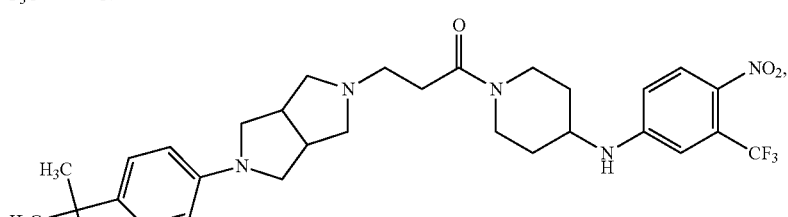
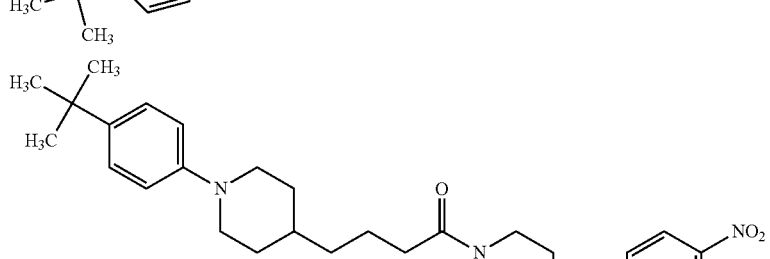
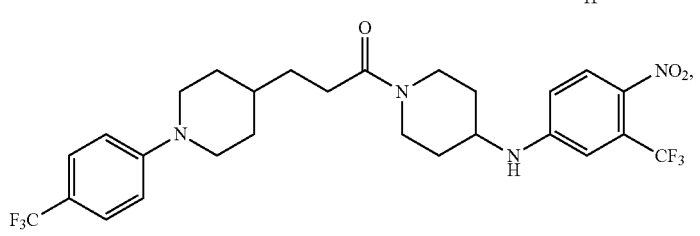

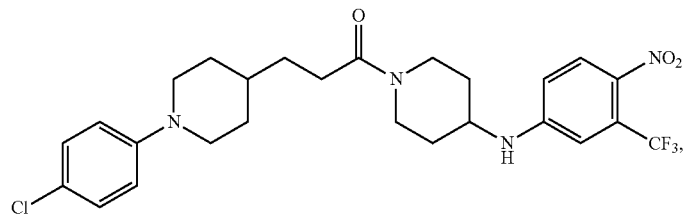
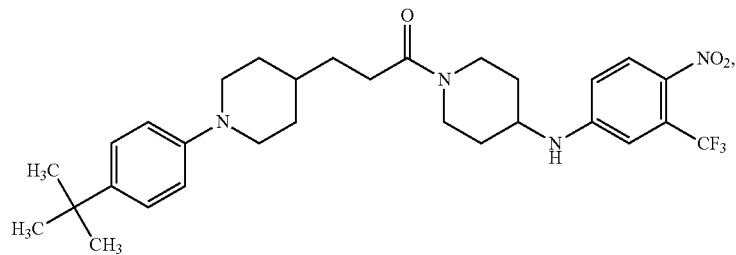
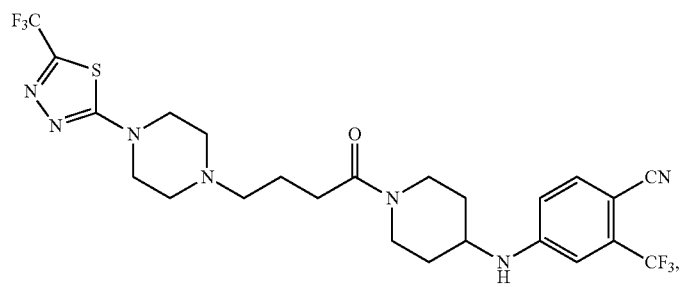
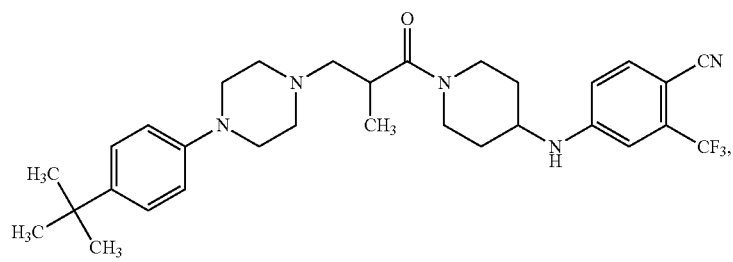
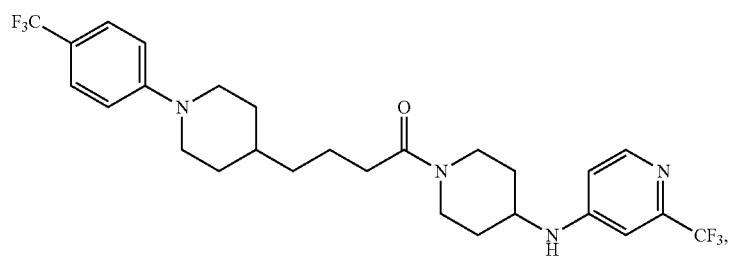
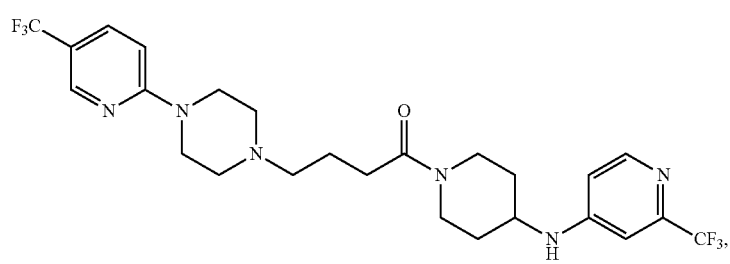

-continued
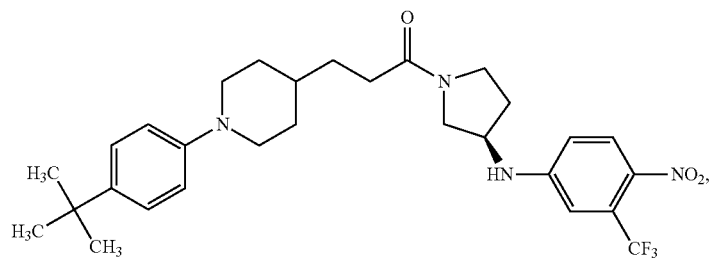
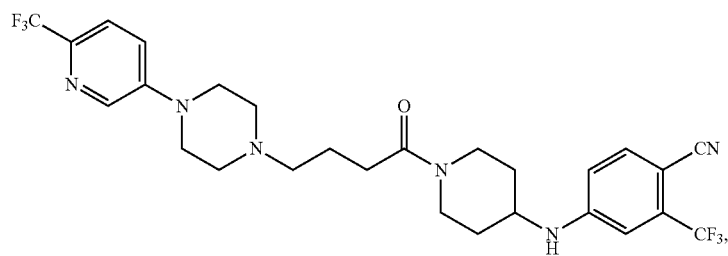
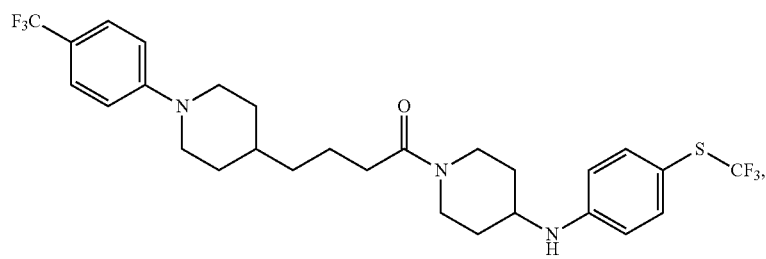
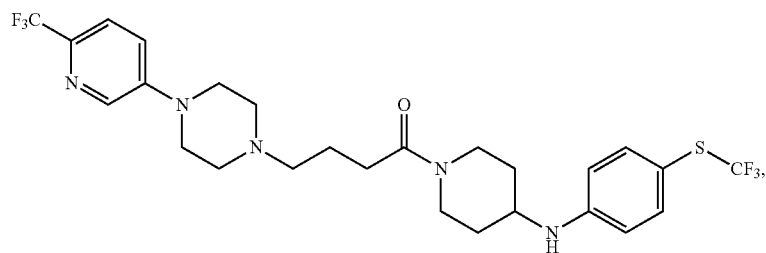
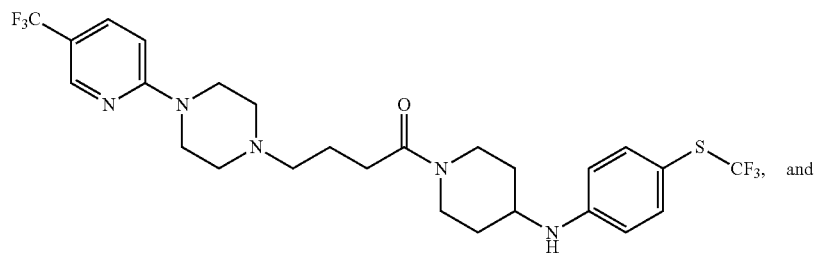
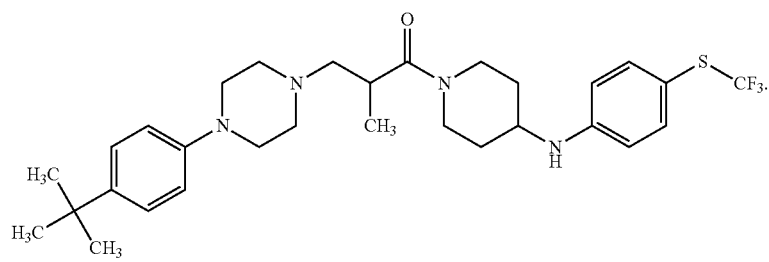 [SMILES: CC(CN1CCN(c2ccc(C(C)(C)C)cc2)CC1)C(=O)N1CCC(Nc2ccc(SC(F)(F)F)cc2)CC1]

In some embodiments, the compound or salt thereof corresponds to a structure selected from the group consisting of:

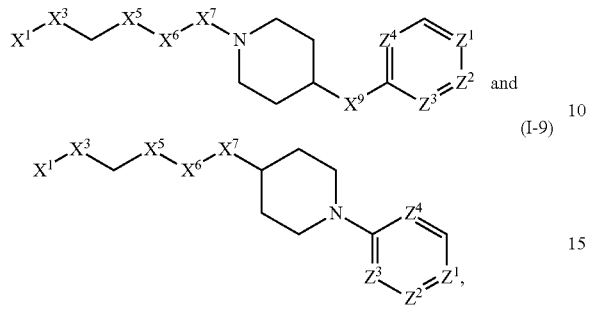

(I-8)

(I-9)

$X^1$ is selected from the group consisting of phenyl, 5-member heteroaryl, and 6-member heteroaryl, wherein:
  the 5-member heteroaryl is substituted with trifluoromethyl;
  the phenyl and 6-member heteroaryl are optionally substituted at the para position by a substituent selected from the group consisting of $C_1$-$C_4$-alkyl, trifluoromethyl, and trifluorophenyl-$C_1$-$C_3$-alkoxy;
$X^3$ is a linker selected from the group consisting of:

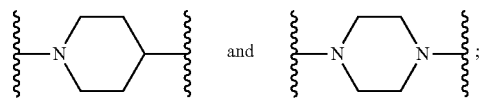

and $X^5$ is selected from the group consisting of a bond and —$CH_2$—;
$X^6$ is —$CH_2$—, optionally substituted with $C_1$-$C_3$-alkyl;
$X^7$ is selected from the group consisting of —C(O)—, —C(S), —C(O)—NH—, and —C(S)—NH—;
$X^9$ is selected from the group consisting of —NH— and —O—;
$Z^1$ is CH, wherein:
  the CH is optionally substituted with a substituent selected from the group consisting of nitro, cyano, alkyl, alkylsulfanyl and alkylsulfonyl, wherein:
    the alkyl and alkylsulfanyl are optionally substituted with one or more halogen;
$Z^2$ is CH, wherein:
  the CH is optionally substituted with a substituent selected from the group consisting of trifluoromethyl and $C_1$-$C_3$-alkoxy; and
$Z^3$ and $Z^4$ are independently selected from the group consisting of N and CH. Compounds encompassed by these embodiments include, for example:

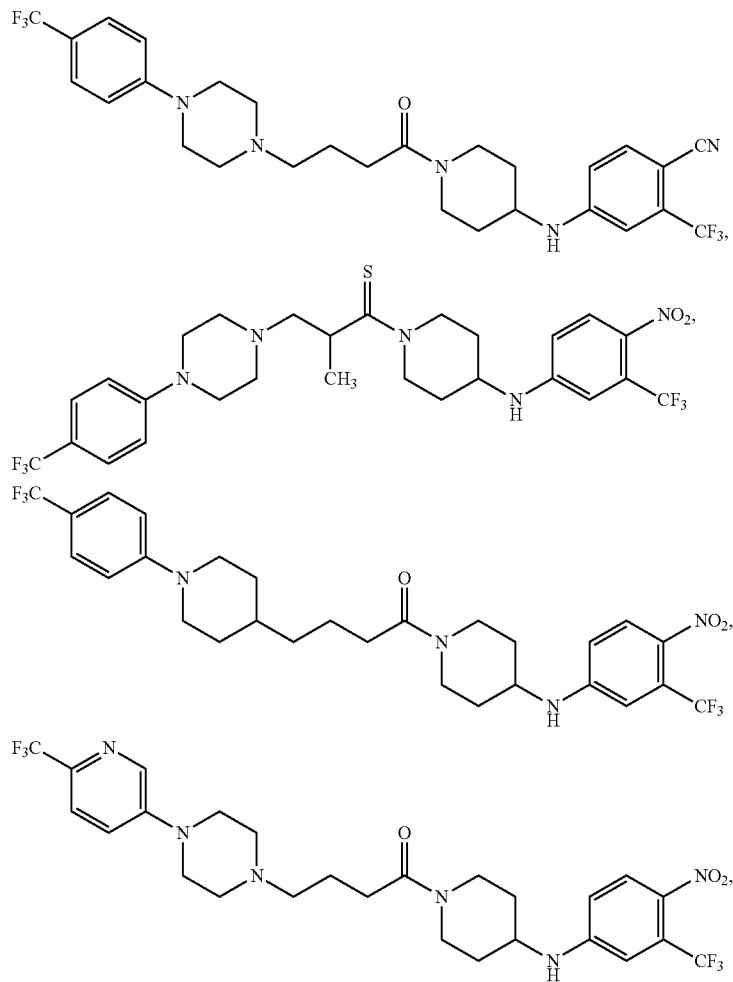

-continued
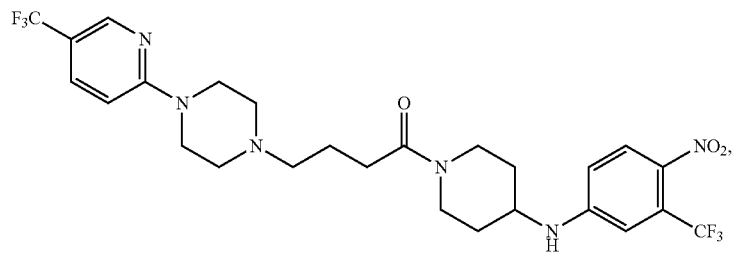
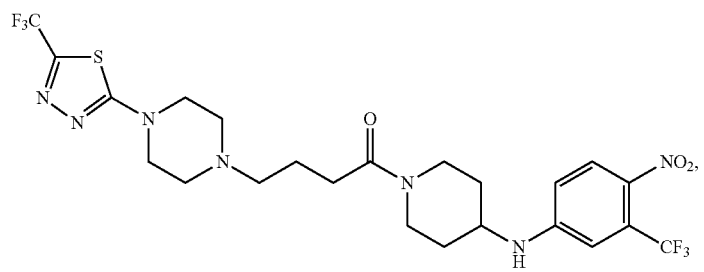
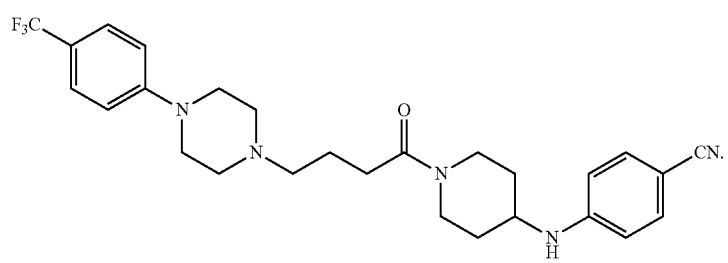
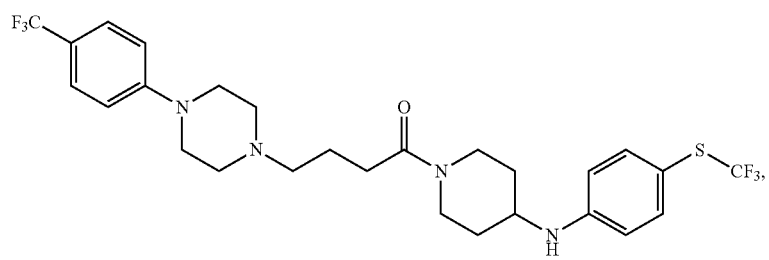
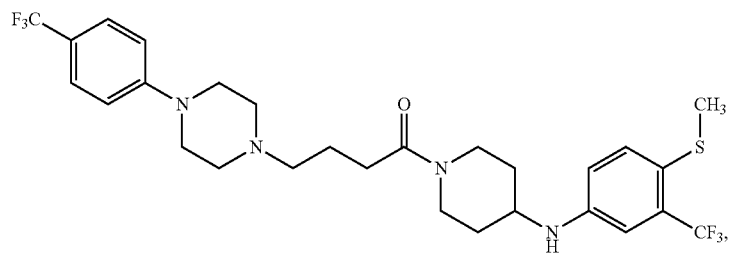
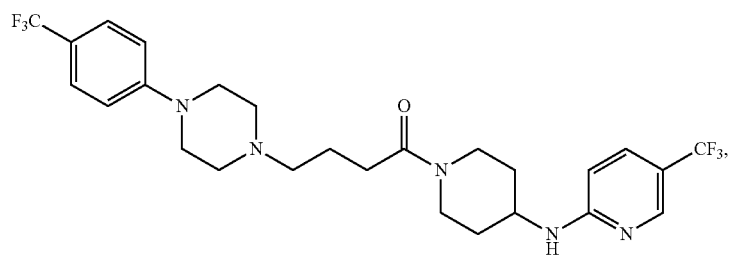

-continued
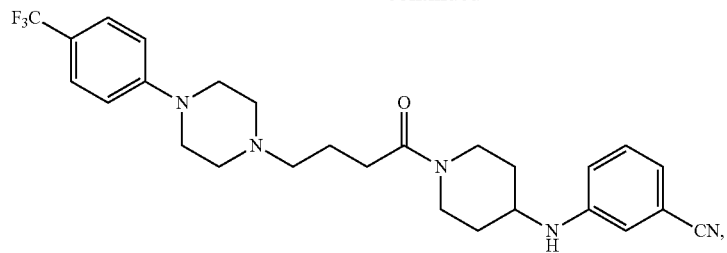
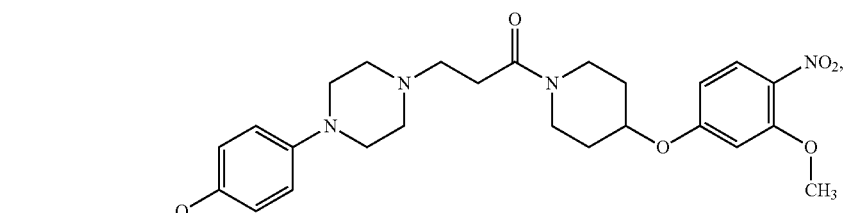
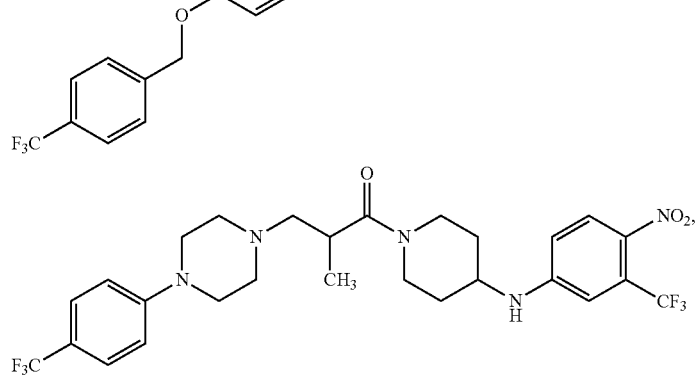
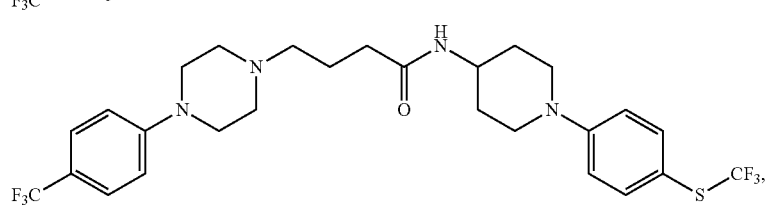
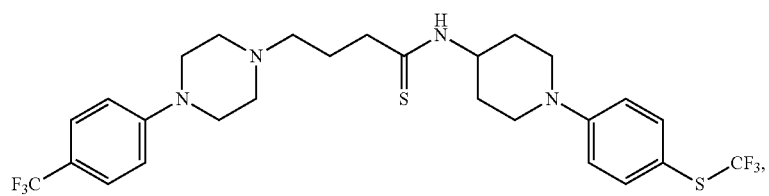
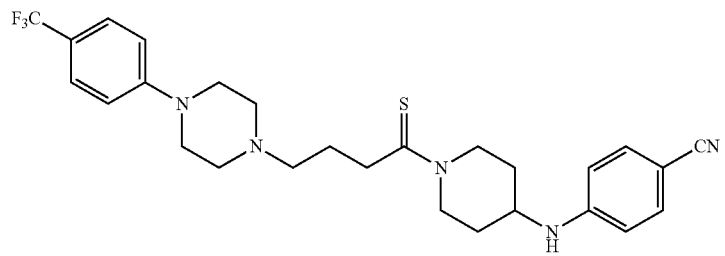
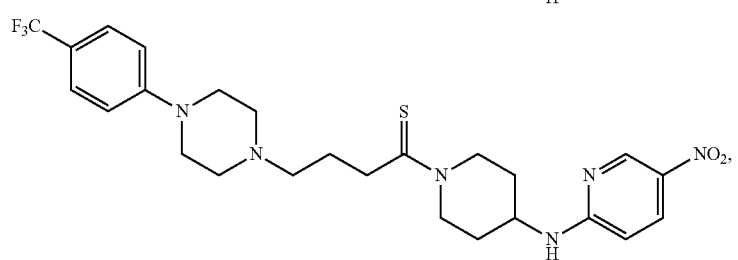

-continued
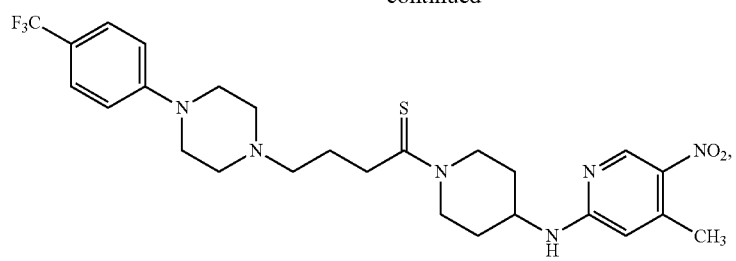
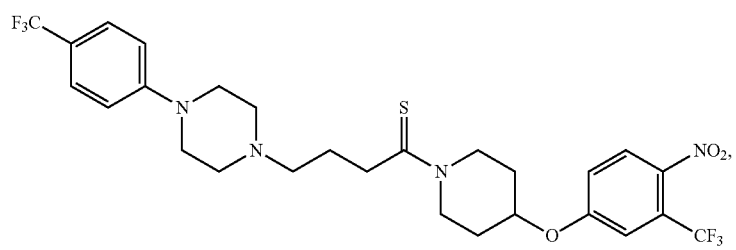
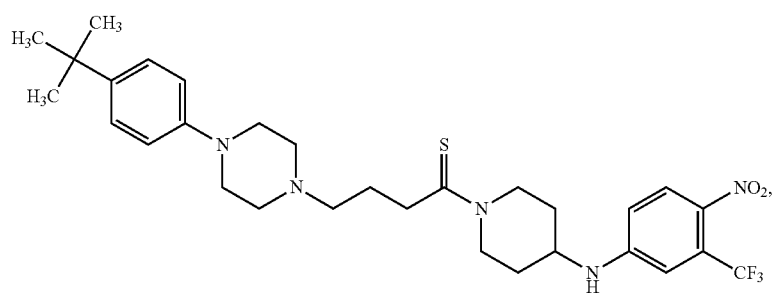
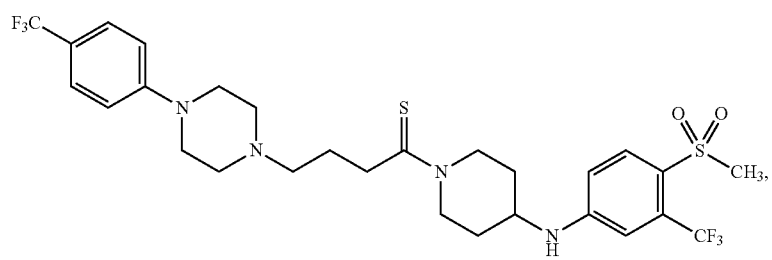
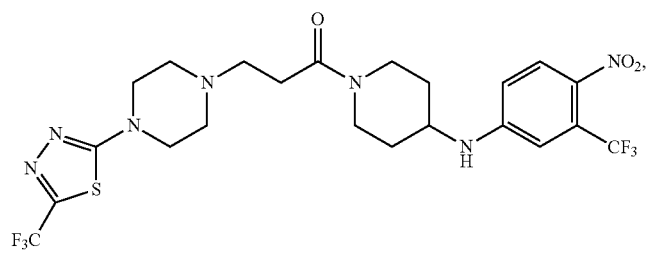
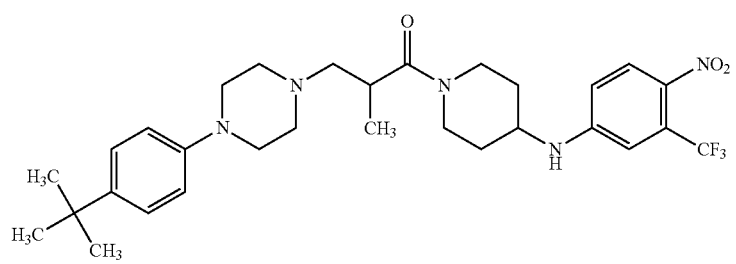

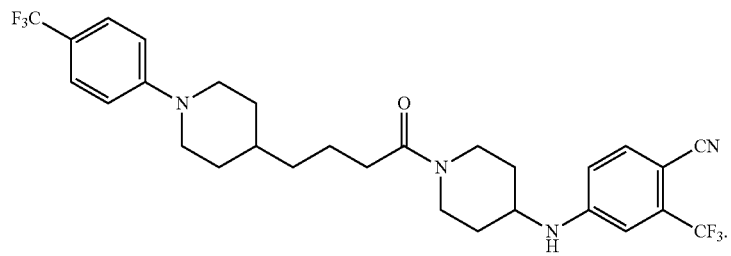

In some embodiments, the compound or salt thereof corresponds in structure to:

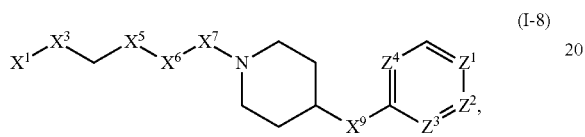
(I-8)

wherein

X⁹ is selected from the group consisting of —NH— and —O—.

In some embodiments, the compound or salt thereof corresponds in structure to:

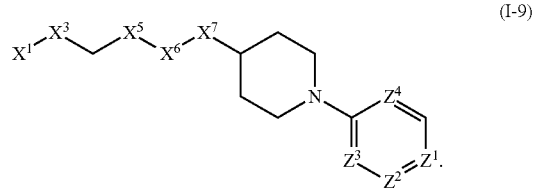
(I-9)

In some embodiments, the compound or salt thereof corresponds in structure to:

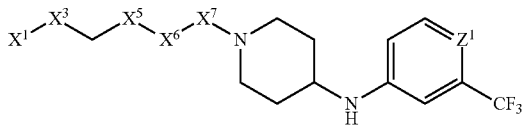

$X^1$ is selected from the group consisting of phenyl, 5-member heteroaryl, and 6-member heteroaryl, wherein:
  the 5-member heteroaryl is substituted with trifluoromethyl;
  the phenyl and 6-member heteroaryl are substituted at the para position with trifluoromethyl;
$X^3$ is a linker selected from the group consisting of:

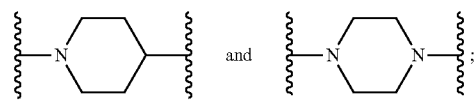

$X^5$ is selected from the group consisting of a bond and —CH₂—;
$X^6$ is —CH₂—, optionally substituted with C₁-C₃-alkyl;
$X^7$ is selected from the group consisting of —C(O)— and —C(S); and
$Z^1$ is CH optionally substituted with a substituent selected from the group consisting of nitro and cyano.

Compounds encompassed by these embodiments include, for example:

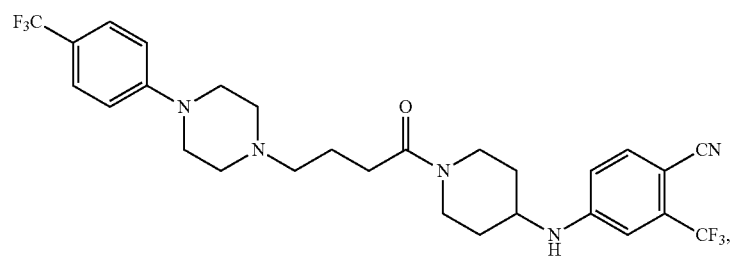

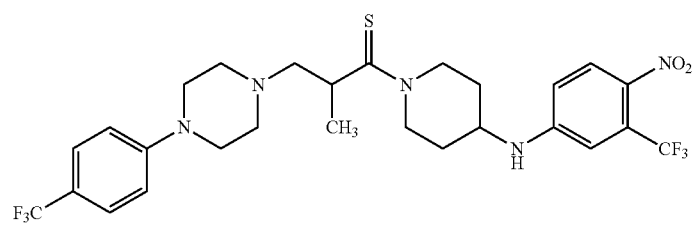

-continued

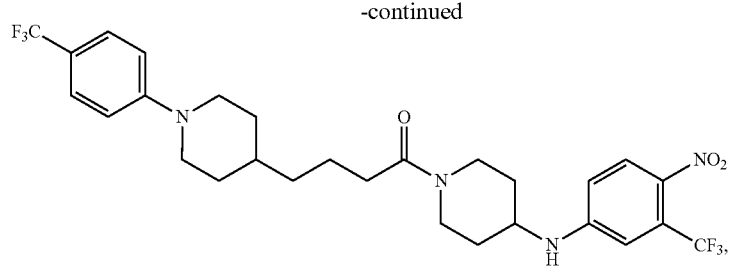

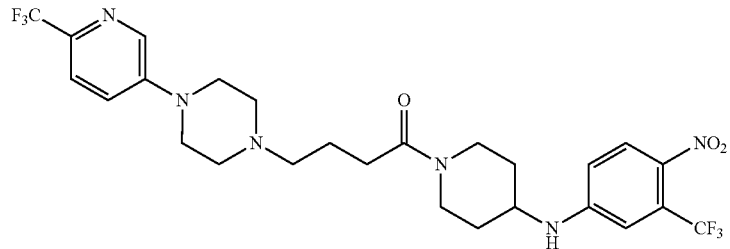

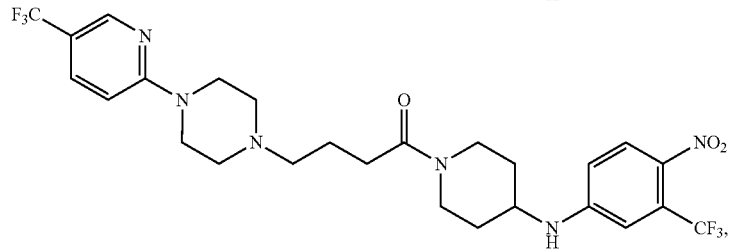

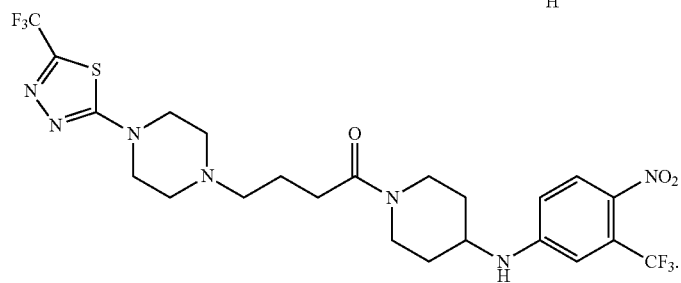

In some such embodiments of this invention, the compound is defined as corresponding in structure to the following formula:

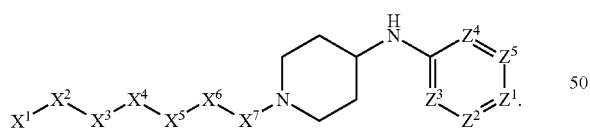

In some such embodiments of this invention, the compound is defined as corresponding in structure to the following formula:

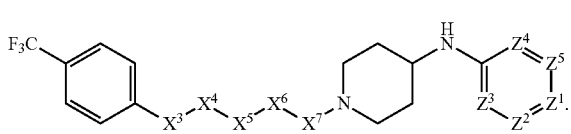

In some such embodiments of this invention, the compound is defined as corresponding in structure to the following formula:

In some such embodiments of this invention, the compound is defined as corresponding in structure to the following formula:

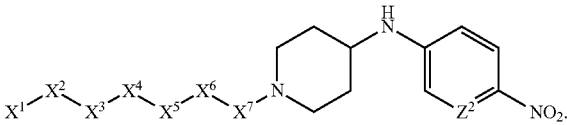

In some such embodiments of this invention, the compound is defined as corresponding in structure to the following formula:

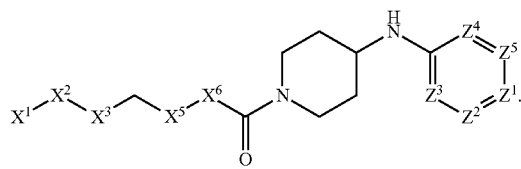

In some such embodiments of this invention, the compound is defined as corresponding in structure to the following formula:

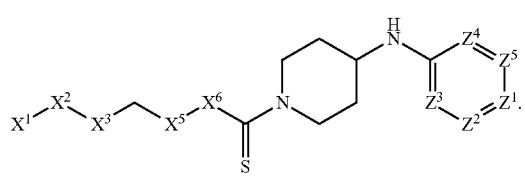

In some such embodiments of this invention, the compound is defined as corresponding in structure to the following formula:

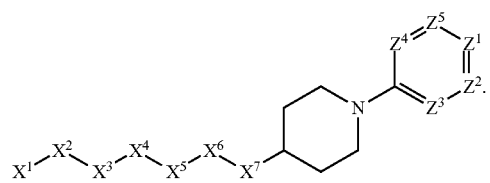

In some such embodiments of this invention, the compound is defined as corresponding in structure to the following formula:

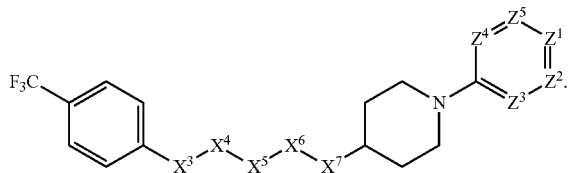

In some such embodiments of this invention, the compound is defined as corresponding in structure to the following formula:

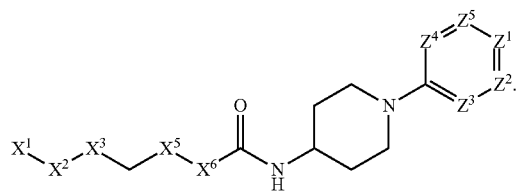

In some such embodiments of this invention, the compound is defined as corresponding in structure to the following formula:

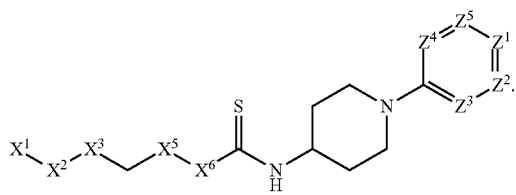

In some embodiments of this invention, the compound is defined as corresponding in structure to the following formula:

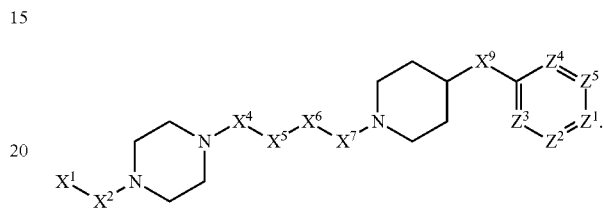

In some such embodiments of this invention, the compound is defined as corresponding in structure to the following formula:

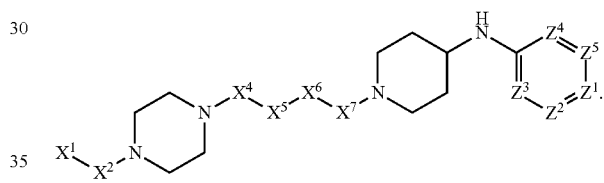

In some such embodiments of this invention, the compound is defined as corresponding in structure to the following formula:

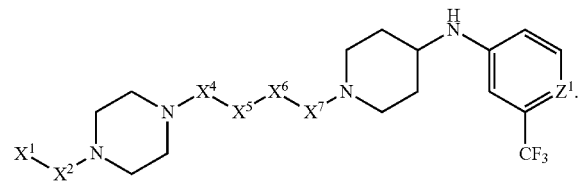

In other some embodiments of this invention, the compound is defined as corresponding in structure to the following formula:

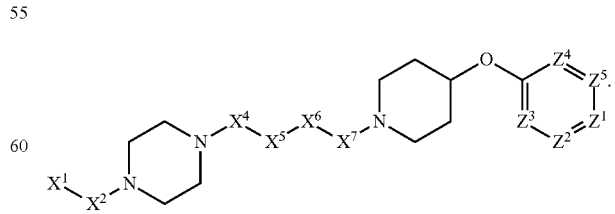

In some such embodiments of this invention, the compound is defined as corresponding in structure to the following formula:

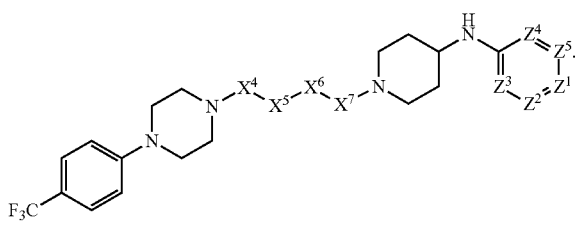

In some embodiments of this invention, the compound is defined as corresponding in structure to the following formula:

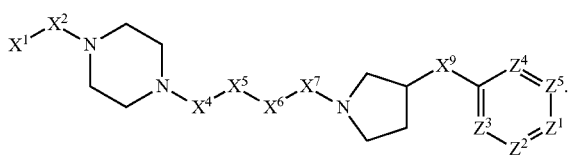

In some embodiments of this invention, the compound is defined as corresponding in structure to the following formula:

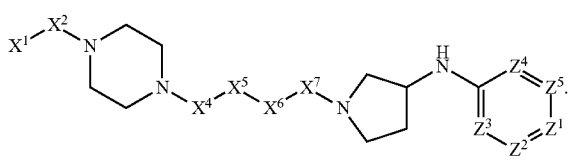

In some embodiments of this invention, the compound is defined as corresponding in structure to the following formula:

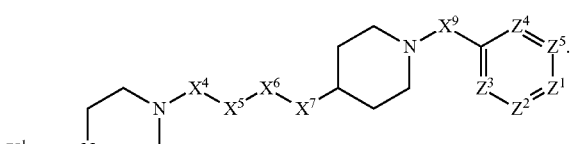

In some embodiments of this invention, the compound is defined as corresponding in structure to the following formula:

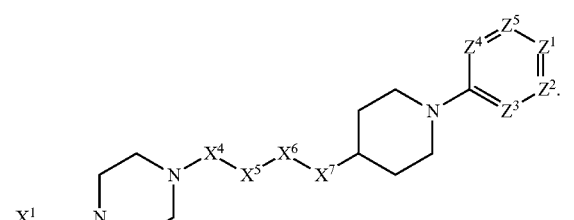

In some such embodiments of this invention, the compound is defined as corresponding in structure to the following formula:

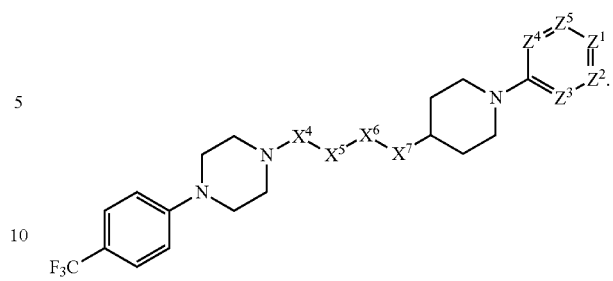

In some embodiments of this invention, the compound is defined as corresponding in structure to the following formula:

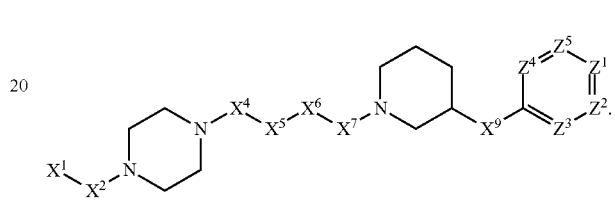

In some embodiments of this invention, the compound is defined as corresponding in structure to the following formula:

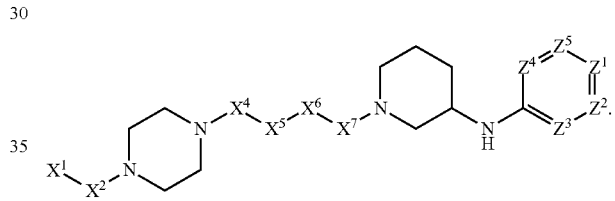

In some embodiments of this invention, the compound is defined as corresponding in structure to the following formula:

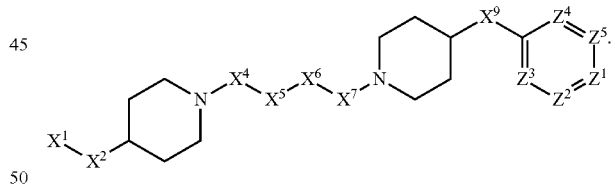

In some such embodiments of this invention, the compound is defined as corresponding in structure to the following formula:

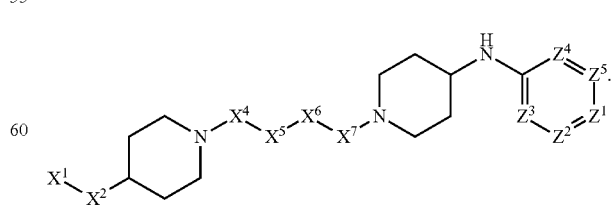

In other such embodiments of this invention, the compound is defined as corresponding in structure to the following formula:

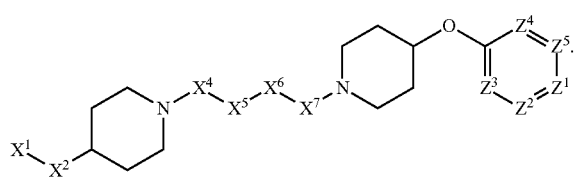

In some embodiments of this invention, the compound is defined as corresponding in structure to the following formula:

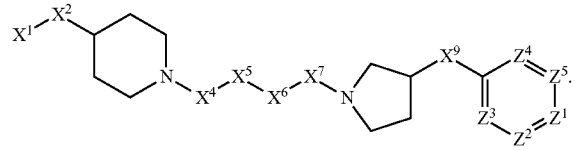

In some embodiments of this invention, the compound is defined as corresponding in structure to the following formula:

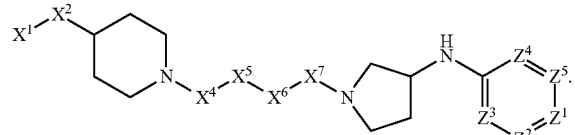

In some embodiments of this invention, the compound is defined as corresponding in structure to the following formula:

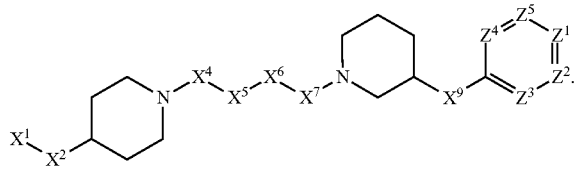

In some embodiments of this invention, the compound is defined as corresponding in structure to the following formula:

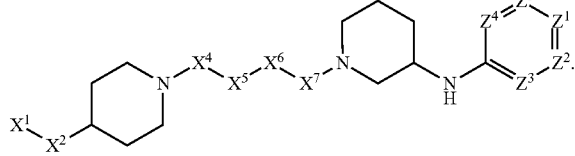

In some embodiments of this invention, the compound is defined as corresponding in structure to the following formula:

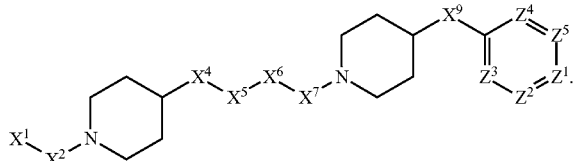

In some embodiments of this invention, the compound is defined as corresponding in structure to the following formula:

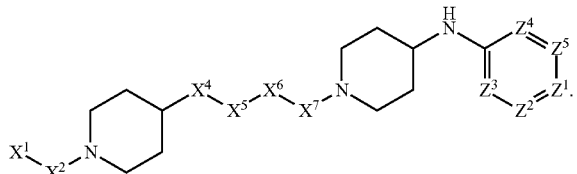

In some embodiments of this invention, the compound is defined as corresponding in structure to the following formula:

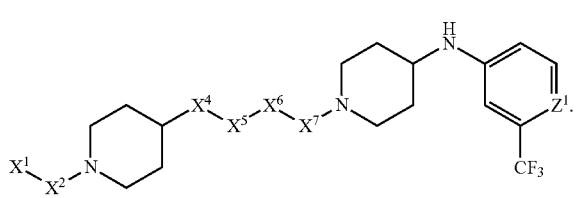

In some embodiments of this invention, the compound is defined as corresponding in structure to the following formula:

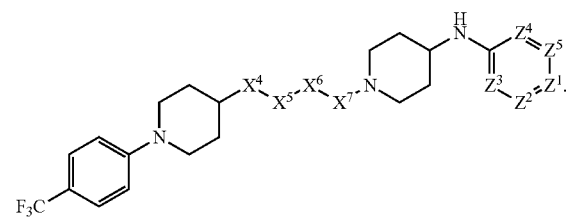

In some embodiments of this invention, the compound is defined as corresponding in structure to the following formula:

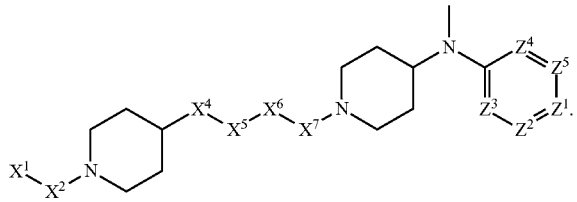

In some embodiments of this invention, the compound is defined as corresponding in structure to the following formula:

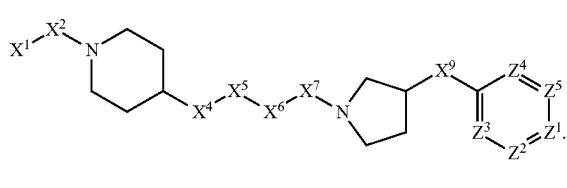

In some embodiments of this invention, the compound is defined as corresponding in structure to the following formula:

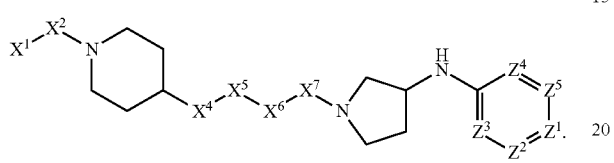

In some embodiments of this invention, the compound is defined as corresponding in structure to the following formula:

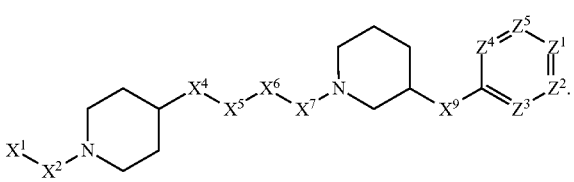

In some embodiments of this invention, the compound is defined as corresponding in structure to the following formula:

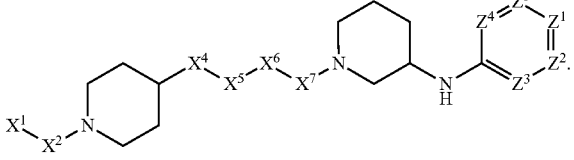

In some embodiments of this invention, the compound is defined as corresponding in structure to the following formula:

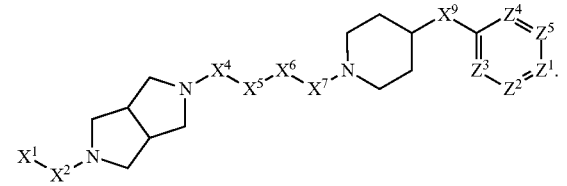

In some embodiments of this invention, the compound is defined as corresponding in structure to the following formula:

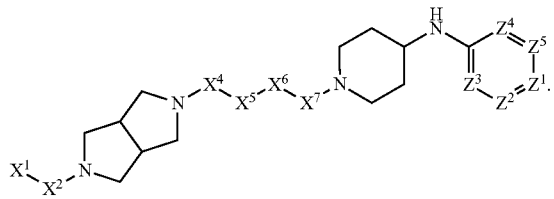

In some embodiments of this invention, the compound is defined as corresponding in structure to the following formula:

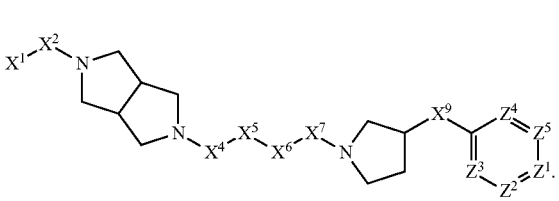

In some embodiments of this invention, the compound is defined as corresponding in structure to the following formula:

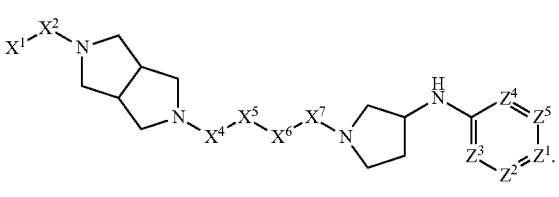

In some embodiments of this invention, the compound is defined as corresponding in structure to the following formula:

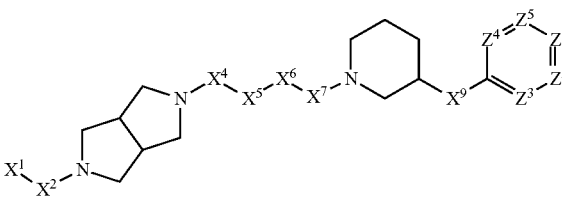

In some embodiments of this invention, the compound is defined as corresponding in structure to the following formula:

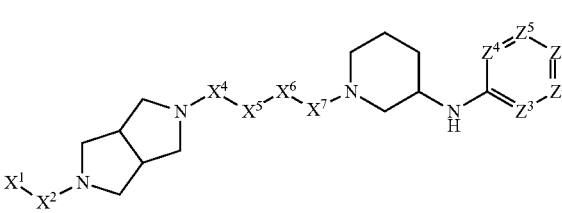

In some embodiments of this invention, the compound is defined as corresponding in structure to the following formula:

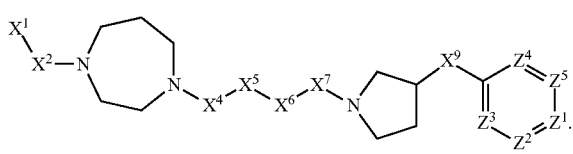

In some embodiments of this invention, the compound is defined as corresponding in structure to the following formula:

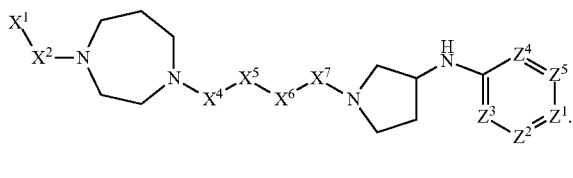

In some embodiments of this invention, the compound is defined as corresponding in structure to the following formula:

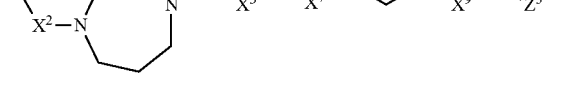

In some embodiments of this invention, the compound is defined as corresponding in structure to the following formula:

In some embodiments of this invention, the compound is defined as corresponding in structure to the following formula:

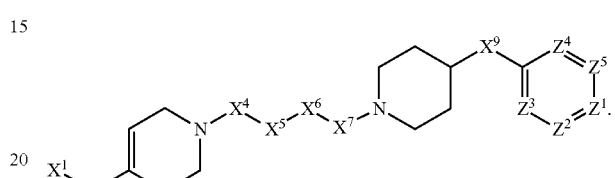

In some embodiments of this invention, the compound is defined as corresponding in structure to the following formula:

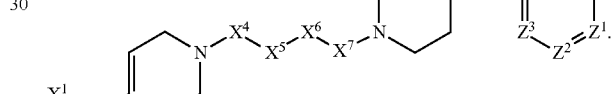

In some embodiments of this invention, the compound is defined as corresponding in structure to the following formula:

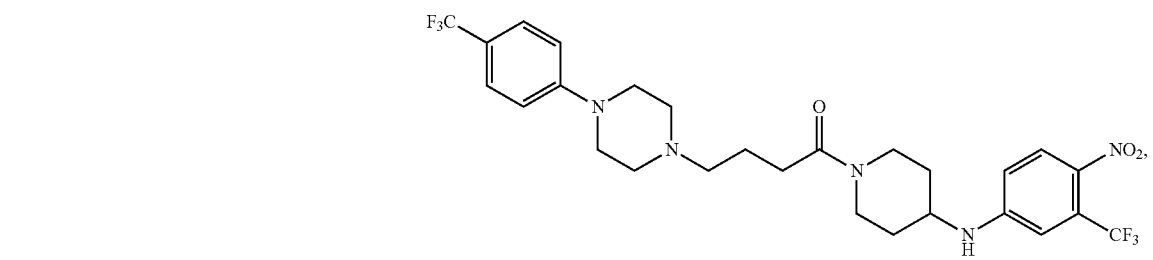

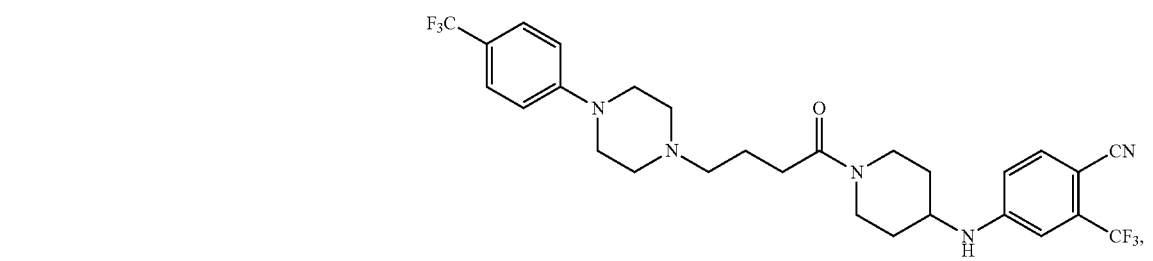

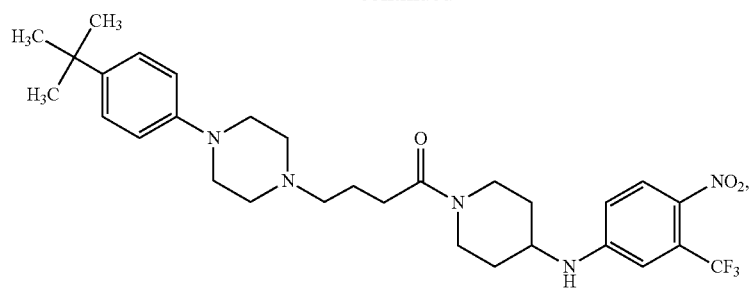
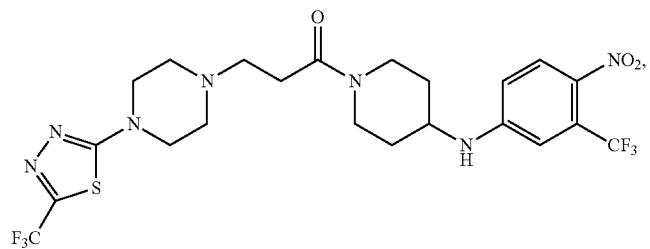
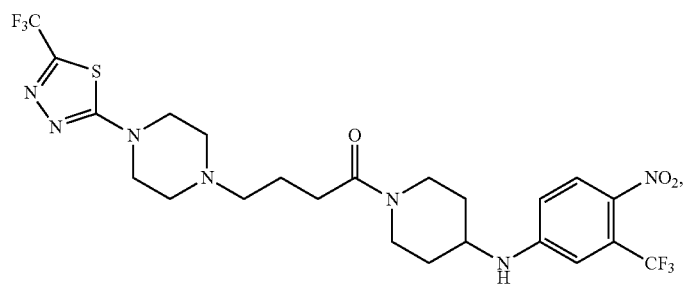
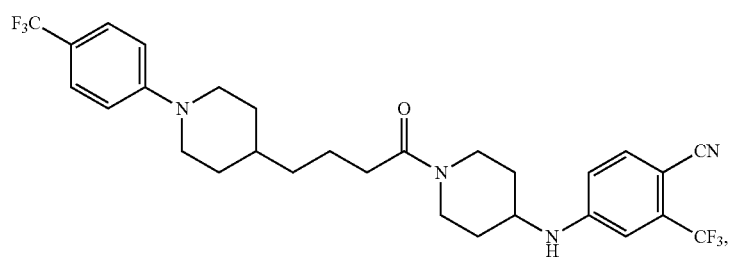
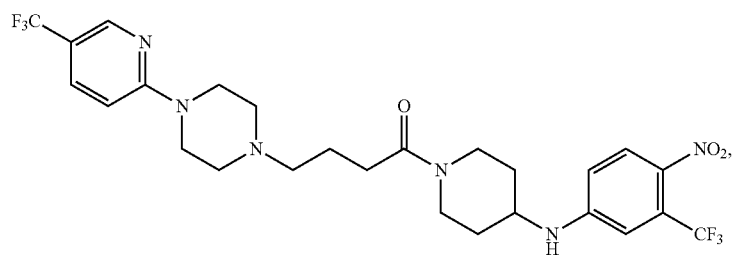
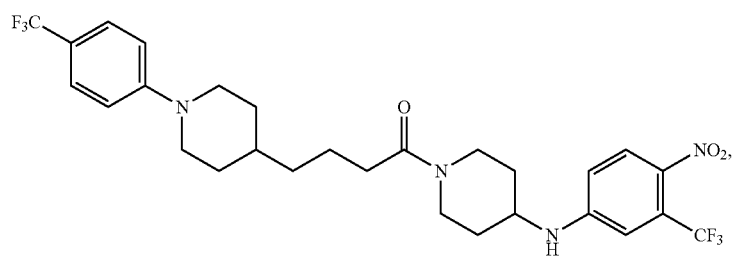

-continued
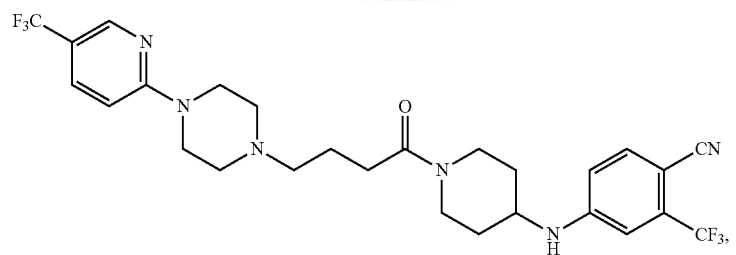
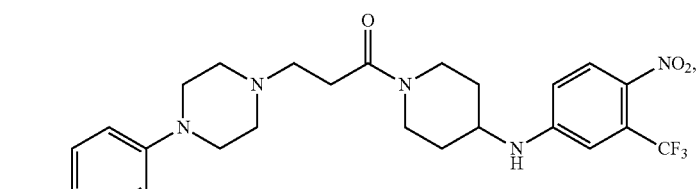
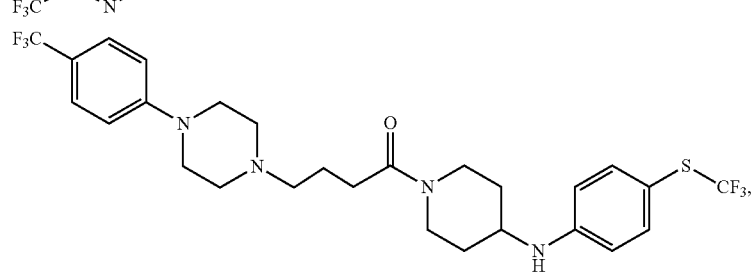
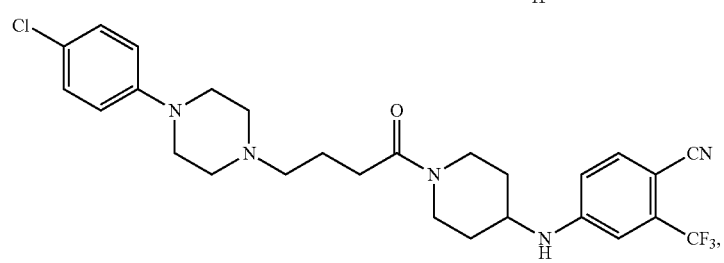
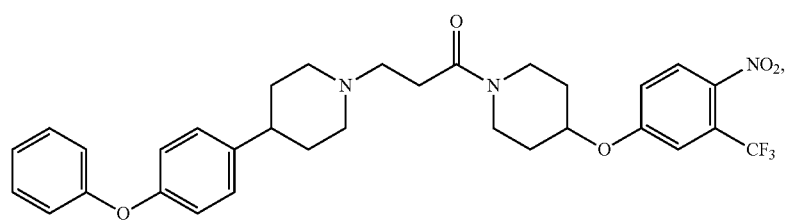
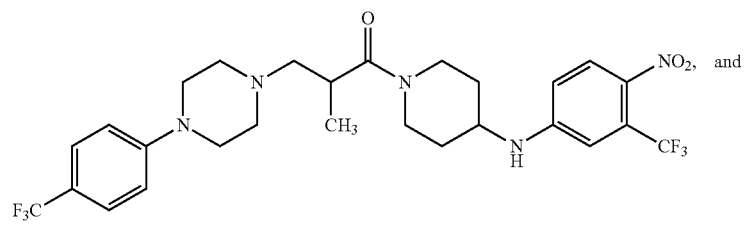
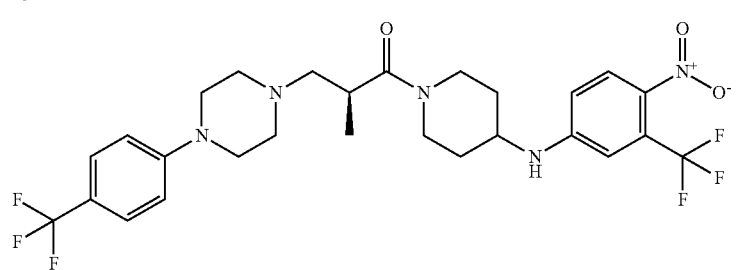 [SMILES: C[C@@H](CN1CCN(c2ccc(C(F)(F)F)cc2)CC1)C(=O)N1CCC(Nc2ccc([N+](=O)[O-])c(C(F)(F)F)c2)CC1]
and In other embodiments, the compound is selected from the group consisting of:
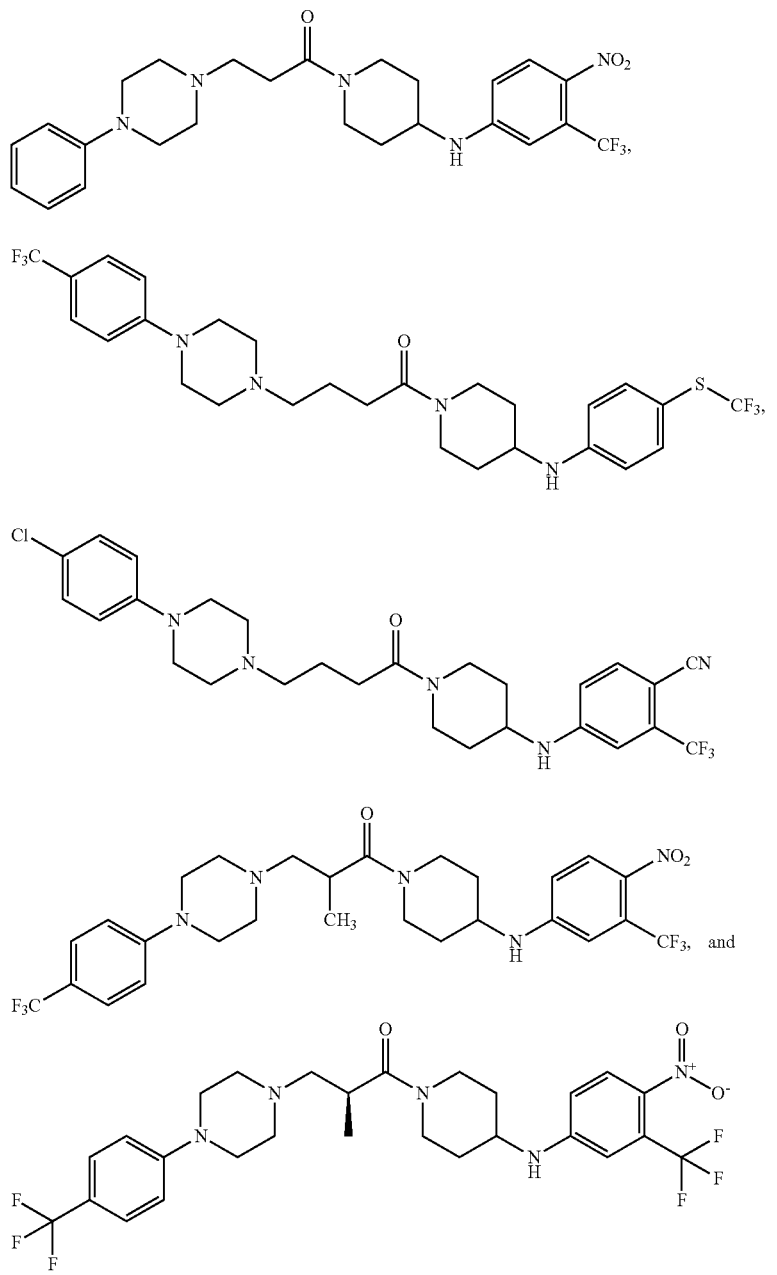
In other embodiments, the compound is selected from the group consisting of:
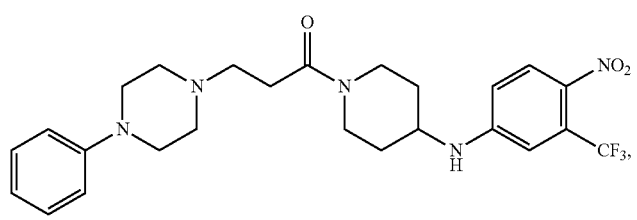

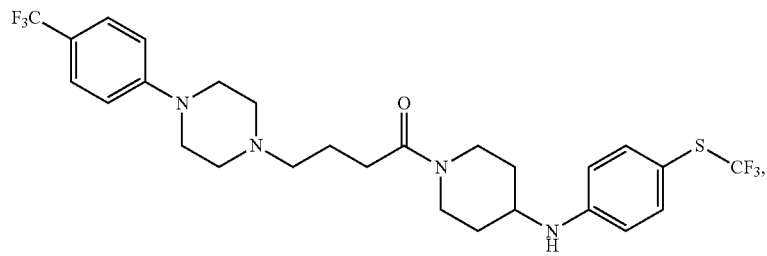

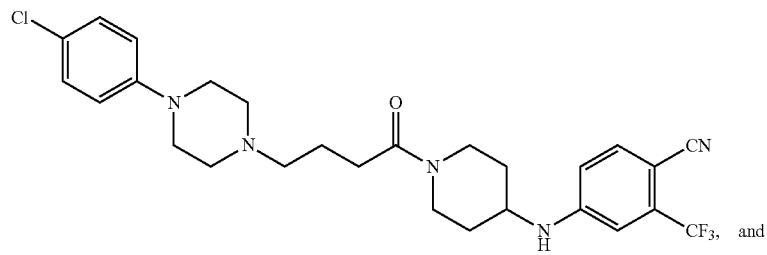

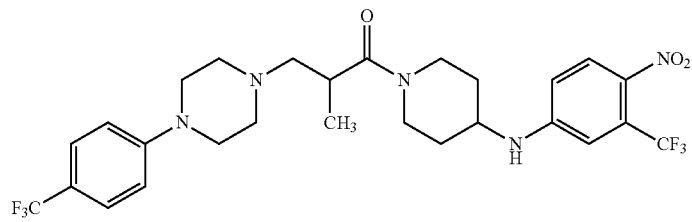

N. Isomers

In some embodiments, a compound of this invention may have two or more conformational or geometric structures. For example, the following compound can have a cis or trans configuration:

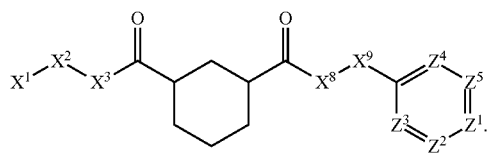

In some embodiments, this compound has the trans configuration such that the compound is encompassed by following formula:

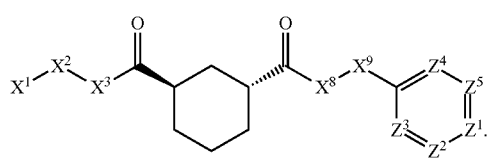

In other embodiments, the compound has the cis configuration such that the compound is encompassed by the following formula:

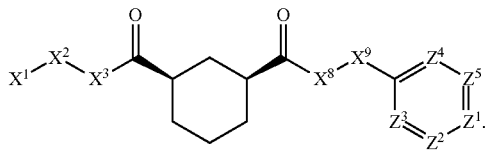

Unless otherwise stated, a compound structure that does not indicate a particular conformation is intended to encompass compositions of all the possible conformational isomers of the compound, as well as compositions comprising fewer than all the possible conformational isomers.

In some embodiments, a compound of this invention is a chiral compound. For example, the following compound can have an R or S configuration:

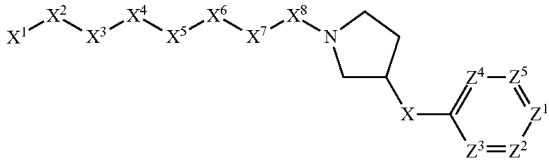

In some embodiments, this compound is one enantiomer such that the compound is encompassed by the following formula:

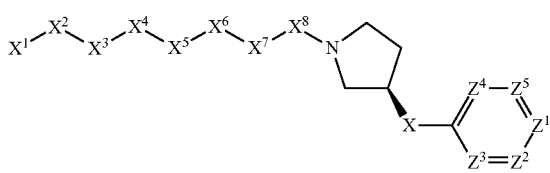

In some embodiments, this compound is the other enantiomer such that the compound is encompassed by the following formula:

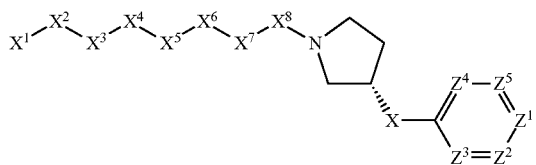

In some embodiments, the compound of this invention is a non-chiral compound.

Unless otherwise stated, a chiral compound structure that does not indicate a particular enantiomer is intended to encompass compositions of all possible enantiomers, diastereomers, and stereoisomers of the compound, as well as compositions comprising fewer than all the possible enantiomers, diastereomers, and stereoisomers, including racemic mixtures.

II. Salts of Compounds of this Invention

A salt of the above-described compounds may be advantageous due to one or more of the salt's physical properties, such as pharmaceutical stability in differing temperatures and humidities; crystalline properties; and/or a desirable solubility in water, oil, or other solvent. In some instances, a salt may be used as an aid in the isolation, purification, and/or resolution of the compound. Acid and base salts can typically be formed by, for example, mixing the compound with an acid or base, respectively, using various known methods in the art. To the extent a salt of the compound is intended to be administered in vivo (i.e., to an animal) for a therapeutic benefit, the salt preferably is pharmaceutically acceptable.

In general, an acid addition salt can be prepared by reacting a free base compound with an approximately stoichiometric amount of an inorganic or organic acid. Examples of often suitable inorganic acids for making pharmaceutically acceptable salts include hydrochloric, hydrobromic, hydroiodic, nitric, carbonic, sulfuric, and phosphoric acid. Examples of often suitable organic acids for making pharmaceutically acceptable salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt.

In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as $C_1$-$C_6$-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

III. Treatment Methods Using Compounds and Salts of this Invention

Compounds and salts of this invention may generally be used as anthelmintics. In accordance with this invention, it has been discovered that these compounds and salts are particularly useful for treating helminth infections, such as nematode, cestode or trematode infections, preferably nematode infections, such as infections by *Trichostrongylus axei, Trichostrongylus colubriformis, Haemonchus contortus, Ascaridia galli,* and/or *Oesophagostomum dentatum.* It is contemplated that the compounds and salts of this invention may be used to treat a range of animals, especially mammals. Such mammals include, for example, humans. Other mammals include, for example, farm or livestock mammals (e.g., swine, bovines, sheep, goats, etc.), laboratory mammals (e.g., mice, rats, jirds, etc.), companion mammals (e.g., dogs, cats, equines, etc.), and wild and zoo mammals (e.g., buffalo, deer, etc.). In some embodiments, the compounds and salts are used to treat goats. In other embodiments, the compounds and salts are used to treat sheep. It is contemplated that the compounds and salts of this invention also are suitable to treat non-mammals, such as birds (e.g., turkeys, chickens, etc.) and fish (e.g., salmon, trout, koi, etc.).

In some embodiments, one or more compounds or salts of this invention are used to treat an infection by a nematode (for example, *H. contortus*) that is resistant to one or more other anthelmintic agents. In some embodiments, the compound or salt is active against a nematode (for example, *H contortus*) resistant to one or more of the following: an avermectin (e.g., ivermectin, selamectin, doramectin, abamectin, and eprinomectin); a milbemycin (moxidectin and milbemycin oxime); a pro-benzimidazole (e.g., febantel, netobimin, and thiophanate); a benzimidazole derivative, such as a thiazole benzimidazole derivative (e.g., thiabendazole and cambendazole) or a carbamate benzimidazole derivative (e.g., fenbendazole, albendazole (oxide), mebendazole, oxfendazole, parbendazole, oxibendazole, flubendazole, and triclabendazole); an imidazothiazole (e.g., levamisole and tetramisole); a tetrahydropyrimidine (morantel and pyrantel), an organophosphate (e.g., trichlorphon, haloxon, dichlorvos, and naphthalophos); a salicylanilide (e.g., closantel, oxyclozanide, rafoxanide, and niclosamide); a nitrophenolic compound (e.g., nitroxynil and nitroscanate); benzenedisulphonamide (e.g., clorsulon); a pyrazino isoquinoline and benzazepine (e.g., praziquantel and epsiprantel); a heterocyclic compound (e.g., piperazine, diethylcarbamazine, and phenothiazine); an arsenical (e.g., thiacetarsamide, melorsamine, and arsenamide); cyclooctadepsipeptide (e.g., emodepside); and a paraherquamide. In some such embodiments, for example, the compound or salt is active against a nematode (for example, *H contortus*) resistant to an avermectin, such as ivermectin. In other embodiments, the compound or salt is alternatively or additionally active against a nematode (for example, *H contortus*) resistant to a benzimidazole derivative, such as fenbendazole. In other embodiments, the compound or salt is alternatively or additionally active against a nematode (for example, *H contortus*) resistant to levamisole. And, in other embodiments, the compound or salt is alternatively or additionally active against a nematode (for example, *H contortus*) resistant to pyrantel.

The compounds of this invention may be administered in various dosage forms. The term "dosage form" means that the active ingredient(s) are formulated into a product suitable for administering to the animal via the envisaged dosage route.

The compounds and salts of this invention may be administered orally. For example, the compound or salt may be added to the intended recipient's feed, either directly or as part of a premix. The compound or salt alternatively may be administered as, for example, a separate solid dosage form (e.g., a tablet, a hard or soft capsule, granules, powders, etc.), paste, or liquid dosage form (e.g., a solution, suspension, syrup, etc.). Several modified-release delivery systems have been developed, that take advantage of the unique anatomy of the ruminant forestomach. These systems generally comprise intraruminal boluses with a controlled rate of release and are administered using a balling gun. As an alternative the compounds may be administered to a non-human animal with the feedstuff and for this purpose a concentrated feed additive or premix may be prepared for mixing with the normal animal feed or a concentrate (liquid or dry) is mixed with the drinking water for the animal. Other forms of non-direct oral administration include for example the application of the composition onto the coat of the animal and its later ingestion during the self cleaning of the animal.

A dosage form may comprise one or more suitable excipients. Such excipients generally include, for example, sweetening agents, flavoring agents, coloring agents, preservative agents, inert diluents (e.g., calcium carbonate, sodium carbonate, lactose, calcium phosphate, sodium phosphate, or kaolin), granulating and disintegrating agents (e.g., corn starch or alginic acid), binding agents (e.g., gelatin, acacia, or carboxymethyl cellulose), and lubricating agents (e.g., magnesium stearate, stearic acid, or talc). Liquid compositions will generally comprise a solvent, such as, for example, one or more of dimethylformamide, N,N-dimethylacetamide, pyrrolidone, N-methylpyrrolidone, polyethyleneglycol, diethyleneglycolmonoethyl ester, dimethylsulfoxide, and ethyl lactate. The solvent preferably has sufficient chemical properties and quantity to keep the compound or salt solubilized under normal storage conditions. In some instances, it may be desirable for the compositions to comprise one or more preservatives. The presence of a preservative may, for example, allow for the compositions to be stored for longer periods. Every excipient in the composition preferably is pharmaceutically acceptable.

It is contemplated that the compounds and salts of this invention may alternatively be administered via non-oral routes, such as rectally, via inhalation (e.g., via a mist or aerosol), transdermally (e.g., via a transdermal patch), or parenterally (e.g., subcutaneous injection, intravenous injection, intramuscular injection, etc.). For instance the compounds of this invention may be administered topically using a transdermal formulation (i.e. a formulation that passes through the skin). Alternatively the compounds of this invention may be administered topically via the mucosa. Typical formulations for transdermal and mucosal administration include, for example, pour-ons, spot-ons, dips, sprays, mousses, shampoos, powders, gels, hydrogels, lotions, solutions, creams, ointments, dusting powders, dressings, foams, films, skin patches, limb bands, collars, ear tags, wafers, sponges, fibers, bandages, and microemulsions. The pour-on or spot-on methods, for example, comprise applying the composition to a specific location of the skin or coat, such as on the neck or backbone of the animal. This may be achieved by, for example, applying a swab or drop of the pour-on or spot-on formulation to a relatively small area of the recipient animal's skin or coat (i.e., generally no greater than about 10% of the animal recipient's skin or coat). In some embodiments, the compound of this invention is dispersed from the application site to wide areas of the fur due to the spreading nature of the components in the formulation and the animal's movements while, in parallel, being absorbed through the skin and distributed via the animal recipient's fluids and/or tissues.

Parenteral dosage forms and delivery systems for non-oral routes include injectables (solutions, suspensions, emulsions, and dry powders for reconstitution), and implants. A solution for injection is a mixture of two or more components that form a single phase that is homogeneous down to the molecular level. A suspension for injection consists of insoluble solid particles dispersed in a liquid medium, with the solid particles accounting for about 0.5% to about 30% of the suspension. The liquid may be aqueous, oily, or both. An emulsion for injection is a heterogeneous dispersion of one immiscible liquid in another; it relies on an emulsifying agent for stability. A dry powder for parenteral administration is reconstituted as a solution or as a suspension immediately prior to injection. The principal advantage of this dosage form is that it overcomes the problem of instability in solution. The majority of implants used in veterinary medicine are compressed tablets or dispersed matrix systems in which the drug is uniformly dispersed within a nondegradable polymer.

In general, the compositions of this invention are administered in a dosage form that provides a therapeutically effective amount of the compound or salt to the site of infection. A "therapeutically effective amount" is an amount that is sufficient to ameliorate, suppress, or eradicate a target pathogen(s) infection. Generally, the therapeutically effective amount is defined as the amount necessary to achieve a concentration efficacious to control the target pathogen(s) at the site of infection. The concentration at the site of infection is preferably at least equal to the $MIC_{90}$ level (minimum inhibitory concentration, i.e., the concentration that inhibits the growth of 90% of the target pathogen) of the compound or salt thereof for the target pathogen. To the extent the compound or salt is administered with another active ingredient(s) (e.g., one or more other anthelmintics), the dosage preferably comprises an amount of the compound or salt that, together with the amount of other active ingredient(s), constitutes a therapeutically effective amount.

A single administration of the compound or salt is typically sufficient to treat a nematode infection. Although such a single dose is typically preferred, it is contemplated that multiple doses can be used. When the compound or salt is orally administered, the total dose to treat an infection is generally greater than about 0.01 mg/kg (i.e., milligram of compound or salt per kilogram body weight). In some such embodiments, the total dose is from about 0.01 to about 100 mg/kg, from about 0.01 to about 50 mg/kg, from about 0.1 to about 25 mg/kg, or from about 1 to about 20. For sheep, for example, the dose is generally from about 1 to about 15 mg/kg, from about 8 to about 12 mg/kg, or about 10 mg/kg. The same dose range may be suitable for other routes of administration. For example, in some embodiments, the same dose range is used for subcutaneous administration. The desired dose, however, may be less in some instances where the compound or salt is administered parenterally, particularly intravenously. For example, in some such embodiments, the dose is from about 0.01 to about 50 mg/kg, from about 0.01 to about 15 mg/kg, or from about 0.1 to about 10. For sheep, for example, a suitable intravenous dose may be from about 0.01 to about 10 mg/kg, from about 0.1 to about 5 mg/kg, or about 1 mg/kg.

If the compound or salt is administered parenterally via an injection, the concentration of the compound or salt in the dosage form preferably is sufficient to provide the desired therapeutically effective amount of the compound or salt in a volume that is acceptable for parenteral administration.

Factors affecting the preferred dosage may include, for example, the type (e.g., species and breed), age, size, sex, diet, activity, and condition of the intended recipient; the administration route; pharmacological considerations, such as the activity, efficacy, pharmacokinetic, and toxicology profiles of the particular composition administered; and whether the compound or salt is being administered as part of a combination of active ingredients. Thus, the preferred amount of the compound or salt can vary, and, therefore, can deviate from the typical dosages set forth above. Determining such dosage adjustments is generally within the skill of those in the art.

This invention is also directed to combinations which are useful for pharmaceutical compositions comprising a) one or more compounds of this invention with b) one or more active compounds which differ in structure from component a). The active compounds b) are preferably anthelmintic compounds, more preferably selected from the group consisting of avermectins (e.g., ivermectin, selamectin, doramectin, abamectin, and eprinomectin); milbemycins (moxidectin and milbemycin oxime); pro-benzimidazoles (e.g., febantel, netobimin, and thiophanate); benzimidazole derivatives, such as a thiazole benzimidazole derivative (e.g., thiabendazole and cambendazole) or a carbamate benzimidazole derivatives (e.g., fenbendazole, albendazole (oxide), mebendazole, oxfendazole, parbendazole, oxibendazole, flubendazole, and triclabendazole); an imidazothiazoles (e.g., levamisole and tetramisole); a tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzoenedisulphonamides (e.g., clorsulon); pyrazinaisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside); paraherquamides (e.g. derquantel); amino-acetonitrile compounds (e.g. monepantel, AAD 1566); and amidine compounds (e.g., amidantel and tribendimidin) (including all pharmaceutically acceptable forms, such as salts).

In the contemplated combination therapies, the compounds according to this invention may be administered before, simultaneously, and/or after the other active ingredient(s). In addition, the compounds according to this invention may be administered in the same composition as the other active ingredient(s) and/or in a separate compositions from the other active ingredient(s). Further, the compounds according to this invention and other active ingredient(s) may be administered via the same and/or different routes of administration.

This invention also is directed to kits that are, for example, suitable for use in performing the methods of treatment described above. The kit comprises a therapeutically effective amount of at least one compound or salt of this invention, and an additional component. The additional component(s) may be, for example, one or more of the following: another ingredient (e.g., an excipient or active ingredient), instructions for combining the compound or salt with another ingredient, an apparatus for combining the compound or salt with another ingredient and/or administering the compound or salt, instructions for using an apparatus to combine the compound or salt with another ingredient and/or administer the compound or salt, or a diagnostic tool.

EXAMPLES

The following examples are merely illustrative, and not limiting to the remainder of this disclosure in any way.

Example 1

Protocols for Analyzing Compounds Prepared in Accordance with this Invention

Applicants prepared a plethora of compounds of this invention. The identities and purities were characterized and verified using various analytical high performance liquid chromatography ("HPLC") and mass spectroscopy ("MS") protocols. These protocols are discussed below.

System I

In some instances, the compound analysis was conducted using an HPLC/MSD 1100 (Agilent, Santa Clara, Calif., USA) having a binary pump (G1312A) with a degasser (G1379A), a well plate sampler (G1367A), a column oven (G1316A), a diode array detector (G1315B), a mass detector (G1946D SL) with an ESI-source, and an evaporating light detector (Sedex 75). Four different columns and detection methods were used with this system:

Protocol I-A

The column used for this protocol was a Zorbax SB-C18 (Agilent), having a 4.6 mm diameter, a 30 mm length, and 3.5 μm packing. The column was operated at 30° C. (ambient temperature). The injection volume was 5.0 μL, the flow rate was 1.0 ml/min, and the run time was 8 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 90 | 10 |
| 0.2 | 90 | 10 |

-continued

| Time (min) | Solvent A (%) water/formic acid, 99.9/0.1 (v/v) | Solvent B (%) acetonitrile/formic acid, 99.9/0.1 (v/v) |
|---|---|---|
| 4.2 | 2 | 98 |
| 5.5 | 2 | 98 |

The samples were diluted in a 1:1 mixture of solvents A and B before analysis. The detection methods were UV at 210 and 254 nm; ESI/MS (100-1000 m/z), positive ions; and ELSD (Sedex 75).

Protocol I-B

The column used for this protocol was an Atlantis dC18 (Waters, Milford, Mass., USA), having a 4.6 mm diameter, a 50 mm length, and 3 µm packing. The column was operated at 30° C. The injection volume was 2.0 µL, the flow rate was 1.0 ml/min, and the run time was 10 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 95 | 5 |
| 1.0 | 95 | 5 |
| 5.0 | 2 | 98 |
| 7.0 | 2 | 98 |

The samples were diluted in a 1:1 mixture of solvents A and B before analysis. The detection methods were UV at 210 and 254 nm; ESI/MS (100-1000 m/z), positive ions; and ELSD (Sedex 75).

Protocol I-C

The column used for this protocol was an Atlantis dC18, having a 4.6 mm diameter, a 50 mm length, and 3 µm packing. The column was operated at 30° C. The injection volume was 2.0 µL, the flow rate was 1.5 ml/min, and the run time was 6 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 90 | 10 |
| 0.5 | 90 | 10 |
| 3.0 | 2 | 98 |
| 4.0 | 2 | 98 |

The samples were diluted in a 1:1 mixture of solvents A and B before analysis. The detection methods were UV at 210 and 254 nm; ESI/MS (85-1000 m/z), positive ions; and ELSD (Sedex 75).

Protocol I-D

The column used for this protocol was a Chromolith Fast Gradient, RP-18e, 2 mm diameter and a 50 mm length. The column was operated at 35° C. The injection volumen was 1.0 µL, the flow rate was 1.2 mL/min, and the run time was 3.5 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 90 | 10 |
| 2.0 | 0 | 100 |
| 2.7 | 0 | 100 |
| 3.0 | 90 | 10 |

The samples were diluted in a 1:1 mixture of A and B before analysis. The diction methods were UV at 210 and 254 nm; ESI/MS (100-1000 m/z), positive ions; and ELSD (Sedex 75).

System II

In some instances, the compound analysis was conducted using an LC/MSD Trap 1100 (Agilent, Santa Clara, Calif., USA) having a binary pump (G1312A) with a degasser (G1379A), a well plate sampler (G1367A), a column oven (G1316A), a diode array detector (G1315B), a mass detector (G2445D SL) with an APCI-source, and an evaporating light detector (Alltech ELSD2000). Three different columns and detection methods were used with this system:

Protocol II-A

The column used for this protocol was a Zorbax SB-C18 (Agilent), having a 4.6 mm diameter, a 30 mm length, and 3.5 µm packing. The column was operated at 30° C. The injection volume was 5.0 µL, the flow rate was 1.0 ml/min, and the run time was 8 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 90 | 10 |
| 0.2 | 90 | 10 |
| 4.2 | 2 | 98 |
| 5.5 | 2 | 98 |

The samples were diluted in a 1:1 mixture of solvents A and B before analysis. The detection methods were UV at 210 and 254 nm; and APCI/MS (80-1000 m/z), positive ions.

Protocol II-B

The column used for this protocol was an XBridge C18 (Waters), having a 4.6 mm diameter, a 50 mm length, and 2.5 µm packing. The column was operated at 40° C. The injection volume was 2.0 µL, the flow rate was 1.0 ml/min, and the run time was 10 min (equilibration included). Two eluents were used with the following gradients:

| Time (min) | Solvent A (%) water/ammonia, 99.9/0.1 (v/v) | Solvent B (%) acetonitrile |
|---|---|---|
| 0.0 | 75 | 25 |
| 5.0 | 0 | 100 |
| 7.0 | 0 | 100 |
| 7.5 | 75 | 25 |

The samples were diluted in a 1:1 mixture of solvents A and B before analysis. The detection methods were UV at 254 and 210 nm; and APCI/MS (100-1500 m/z), positive ions.

Protocol II-C

The column used for this protocol was an Atlantis dC18 (Waters), having a 4.6 mm diameter, a 150 mm length, and 3 μm packing. The column was operated at 40° C. The injection volume was 5.0 μL, the flow rate was 1.0 ml/min, and the run time was 16 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 98 | 2 |
| 10 | 0 | 100 |
| 12 | 0 | 100 |
| 13 | 98 | 2 |

The samples were diluted in a 1:1 mixture of solvents A and B before analysis. The detection methods were UV at 254 and 210 nm; and APCI/MS (100-1000 m/z), positive ions.

Protocol II-D

The column used for this protocol was an Atlantis dC18 (Waters), having a 4.6 mm diameter, a 50 mm length, and 3 μm packing. The column was operated at 40° C. The injection volume was 5.0 μL, the flow rate was 1.0 ml/min, and the run time was 8 min (equilibration included). Two eluents were used with the following gradients:

| Time (min) | Solvent A (%) water/formic acid, 99.9/0.1 (v/v) | Solvent B (%) acetonitrile/formic acid, 99.9/0.1 (v/v) |
|---|---|---|
| 0.0 | 90 | 10 |
| 10 | 0 | 100 |
| 12 | 0 | 100 |
| 13 | 90 | 10 |

The samples were diluted in a 1:1 mixture of solvents A and B before analysis. The detection methods were UV at 254 and 210 nm; and APCI/MS (100-1000 m/z), positive ions Protocol II-E The column used for this protocol was a Phenomenex (Gemini), having a 4.6 mm diameter, a 150 mm length, and 5 μm packing. The column was operated at 35° C. The injection volume was 1.0 μL, the flow rate was 1.0 ml/min. Two eluents were used with the following gradients:

| Time (min) | Solvent A (%) 10 mM formic acid/acetonitrile | Solvent B (%) 10 mM formic acid/water |
|---|---|---|
| 0.0 | 2 | 98 |
| 10.5 | 98 | 2 |
| 18 | 98 | 2 |

The samples were diluted in a 1:1 mixture of solvents A and B before analysis. The detection methods were UV at 320 and 220 nm; and ESI/MS (100-800 m/z), positive and negative ions.

Protocol II-F

The column used for this protocol was a Phenomenex (Gemini), having a 4.6 mm diameter, a 150 mm length, and 5 μm packing. The column was operated at 35° C. The injection volume was 1.0 μL, the flow rate was 1.0 ml/min Two eluents were used with the following gradients:

| Time (min) | Solvent A (%) 10 mM ammonia/acetonitrile | Solvent B (%) 10 mM ammonia/water |
|---|---|---|
| 0.0 | 2 | 98 |
| 10.5 | 98 | 2 |
| 18 | 98 | 2 |

The samples were diluted in a 1:1 mixture of solvents A and B before analysis. The detection methods were UV at 320 and 220 nm; and ESI/MS (100-800 m/z), positive and negative ions.

Example 2

Preparation of 4-[4-(4-trifluoromethyl-phenyl)-piperazin-1-yl]-butyric acid ethyl ester intermediate

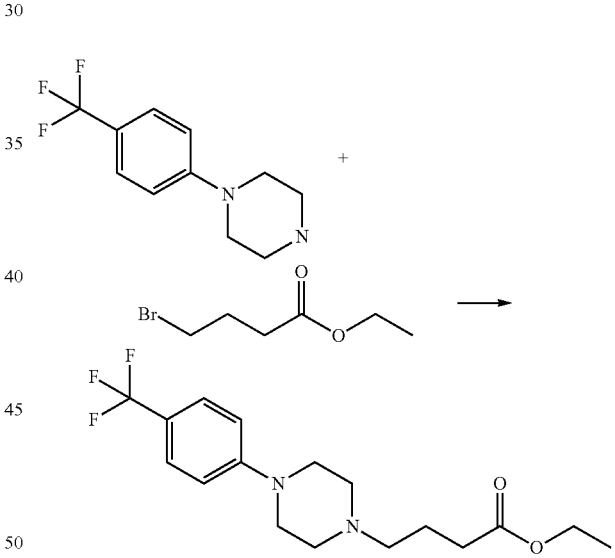

Ethyl-4-bromobutyrate (390 mg, 2.00 mmol) and triethylamine (280 μL; 2.00 mmol) were added to a solution of 1-(4-trifluoromethylphenyl)-piperazine (460 mg; 2.00 mmol) in tetrahydrofuran (3 mL). Potassium iodide (332 mg; 2.00 mmol) was added and the resulting suspension is irradiated in a mono-mode microwave oven for 2 hours at 100° C. The suspension is then diluted with dichloromethane (15 mL) and washed twice with water (5 mL). The organic phase is then dried over sodium sulphate and is concentrated under reduced pressure to afford the desired product (660 mg; 1.96 mmol).

In many instances, the method of Example 2 can be adapted to make other compounds that are useful as intermediates for making the compounds and salts of this invention. An illustrative generic scheme is as follows:

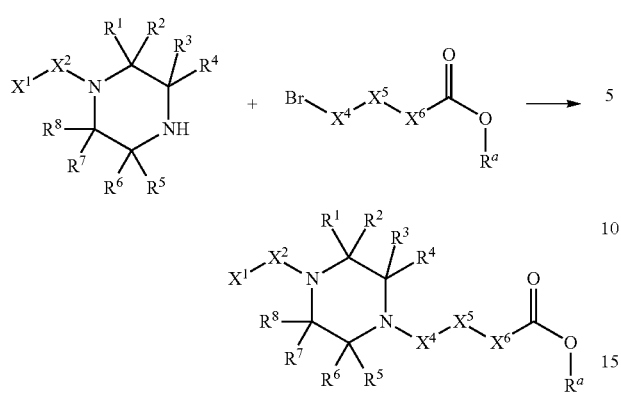

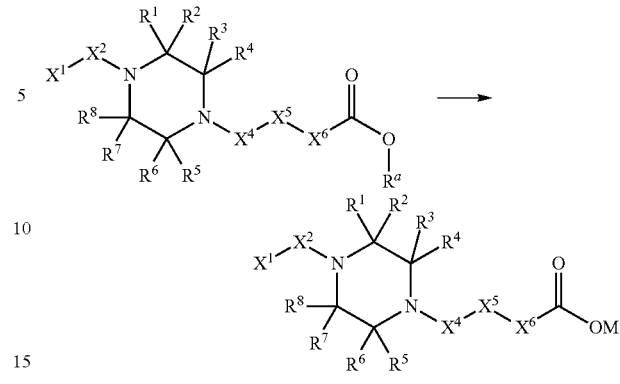

Here $X^1$, $X^2$, $X^3$, $X^4$, $X^5$ and $X^6$ are as defined above for the compounds of this invention. $R^1$, $R^2$, $R^3$, $R^4$, $R^5$, $R^6$, $R^7$ and $R^8$ are each independently selected from the group consisting of halogen, alkyl, alkoxy and oxo. $R^a$ is alkyl. Determining the suitability of the method (and any necessary routine adaptations) or making a particular intermediate is generally with the skill of those in the art after reading this patent.

Here $X^1$, $X^2$, $X^3$, $X^4$, $X^5$ and $X^6$ are as defined above for the compounds of this invention. $R^1$, $R^2$, $R^3$, $R^4$, $R^5$, $R^6$, $R^7$ and $R^8$ are each independently selected from the group consisting of halogen, alkyl, alkoxy and oxo. $R^a$ is independently selected from alkyl. M is selected from the group consisting of hydrogen, lithium, sodium, and potassium. Determining the suitability of the method (and any necessary routine adaptations) or making a particular intermediate is generally with the skill of those in the art after reading this patent.

Example 3

Preparation of 4-[4-(4-trifluoromethyl-phenyl)-piperazin-1-yl]-butyric acid lithium salt intermediate Example 4

Preparation of (4-methylsulfanyl-3-trifluoromethyl-phenyl)-piperidin-4-yl-amine hydrochloride intermediate

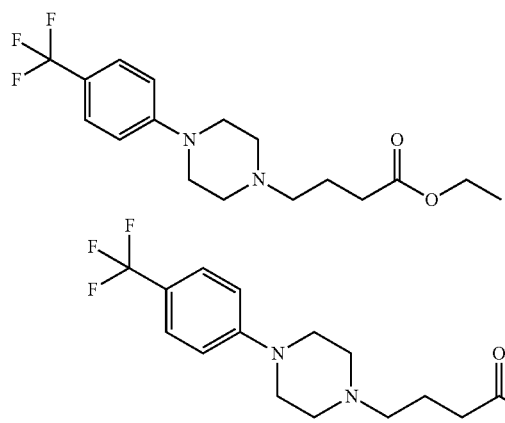

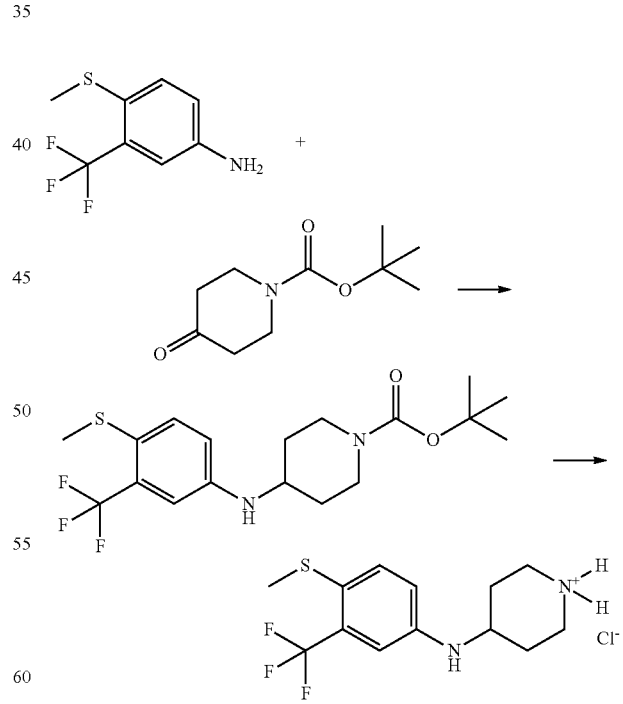

4-[4-(4-Trifluoromethyl-phenyl)-piperazin-1-yl]-butyric acid ethyl ester (660 mg; 1.92 mmol, prepared in accordance with Example 2) and lithium hydroxide are dissolved in a mixture of tetrahydrofuran (2.8 mL) and water (1.2 mL). The resulting mixture is irradiated in a mono-mode microwave oven for 30 minutes at 70° C. The mixture is then diluted with acetonitrile (20 mL) and the precipitate formed is filtered and rinsed with acetonitrile (10 mL). The solid obtained is then dried under high vacuum to deliver the desired product (584 mg; 1.81 mmol).

In many instances, the method of Example 3 can be adapted to make other compounds that are useful as intermediates for making the compounds and salts of this invention. An illustrative generic scheme is as follows:

4-Methylsulfanyl-3-trifluoromethyl-phenylamine (414 mg; 2.00 mmol), 4-oxo-piperidine-1-carboxylic acid tert-butyl ester (400 mg; 2.00 mmol) and sodium triacetoxyborohydride (1.27 g; 6.00 mmol) are suspended in dichloromethane (10 mL) and the resulting mixture is stirred for 2 days. The suspension is then diluted with dichloromethane (50 mL) and is washed with water (30 mL) and aq. sat. ammonium chloride (3×30 mL). The organic phase is dried over magnesium sulphate, filtered and concentrated under reduced pressure to deliver the desired intermediate. The crude intermediate is then dissolved in dichloromethane (5 mL) and trifluoroacetic acid is added (2.5 mL). After 90 minutes reaction time, the mixture is concentrated under reduced pressure and co-evaporated twice with dichloromethane (10 mL). The crude residue is then triturated with a 4N solution of hydrochloric acid in dioxane (5 mL) until a precipitate forms. The solid is filtered and dried under high vacuum to afford the desired product as hydrochloride (354 mg; 1.09 mmol).

In many instances, the method of Example 4 can be adapted to make other compounds that are useful as intermediates for making the compounds and salts of this invention. An illustrative generic scheme is as follows:

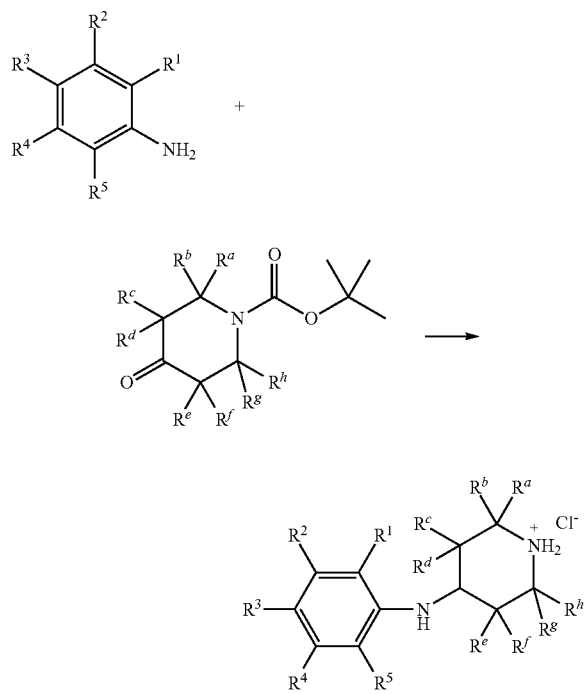

Here $R^1$, $R^2$, $R^3$, $R^4$ and $R^5$ are each independently selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl, wherein the alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl. $R^a$, $R^b$, $R^c$, $R^d$, $R^e$, $R^f$, $R^g$, and $R^h$ are each independently selected from the group consisting of halogen, alkyl, alkoxy and oxo. Determining the suitability of the method (and any necessary routine adaptations) or making a particular intermediate is generally with the skill of those in the art after reading this patent.

Example 5

Preparation of 1-[4-(4-methylsulfanyl-3-trifluoromethyl-phenylamino)-piperidin-1-yl]-4-[4-(4-trifluoromethyl-phenyl)-piperazin-1-yl]-butan-1-one

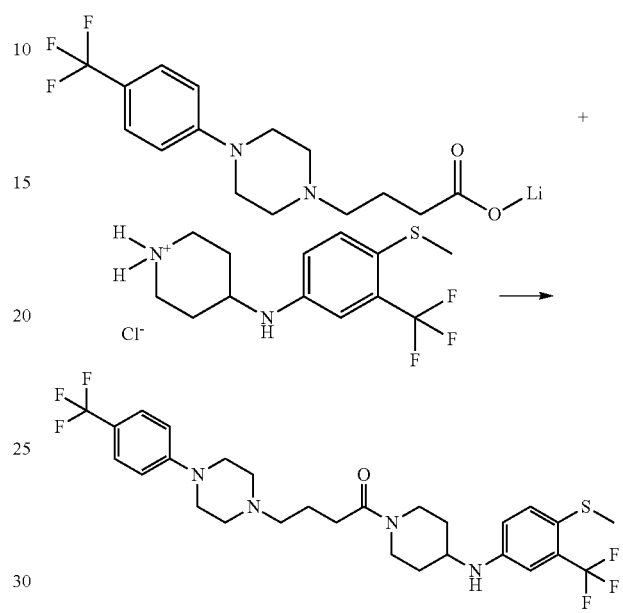

4-[4-(4-Trifluoromethyl-phenyl)-piperazin-1-yl]-butyric acid lithium salt (16 mg; 0.05 mmol, prepared in accordance with Example 3), diisopropylethyl amine (18 µL; 0.10 mmol) and tetramethyl-O-(1H-benzotriazol-1-yl)uronium hexafluorophosphate (19 mg; 0.05 mmol) are diluted in a 2 to 1 mixture of dimethylformamide and tetrahydrofuran (1.5 mL) and the resulting solution is stirred for 5 minutes. A solution of (4-methylsulfanyl-3-trifluoromethyl-phenyl)-piperidin-4-yl-amine hydrochloride (16 mg; 0.05 mmol, prepared in accordance with Example 4) in dimethylformamide (0.5 mL) is added and the reaction is then stirred for 3 hours at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (5 mg; 0.01 mmol). The structure was confirmed using Protocol I-B. Calculated mass=589; observed mass=589; HPLC retention time=4.83 min.

In many instances, the method of Example 5 can be adapted to make other compounds that are useful as intermediates for making the compounds and salts of this invention. An illustrative generic scheme is as follows:

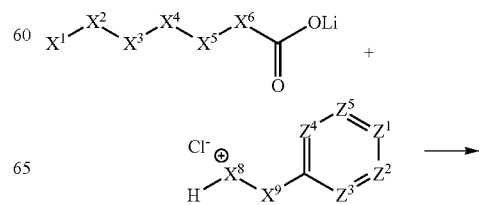

131

-continued

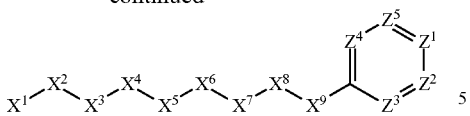

Here, $X^1$, $X^2$, $X^3$, $X^4$, $X^5$, $X^6$, $X^7$, $X^8$, $X^9$, $Z^1$, $Z^2$, $Z^3$, $Z^4$ and $Z^5$ are as defined above for the compounds of this invention. Determining the suitability of the method (and any necessary routine adaptations) or making a particular intermediate is generally with the skill of those in the art after reading this patent.

Example 6

Preparation of 3-(piperidin-4-ylamino)-benzonitrile hydrochloride intermediate

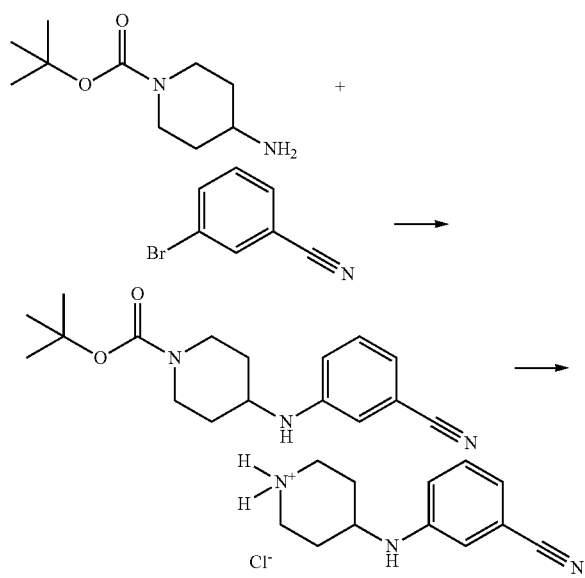

Tris(dibenzylideneacetone)dipalladium (33 mg; 0.04 mmol), 2,2'-bis(diphenylphosphino)-1,1'-binaphthyl (67 mg; 0.11 mmol), sodium tert-butoxide (259 mg; 2.70 mmol), 3-bromobenzonitrile (331 mg; 1.80 mmol) and 4-amino-piperidine-1-carboxylic acid tert-butyl ester (400 mg; 2.0 mmol) are suspended in dry toluene (1 mL) and the mixture is irradiated in a mono-mode microwave oven for 20 minutes at 120° C. The mixture is then cooled down to room temperature, is diluted with ethyl acetate (15 mL), is filtered and is concentrated under reduced pressure. The crude residue is then diluted in dichloromethane (15 mL) and filtered over a short silica gel pad. The desired product is eluted from the silica gel pad with diethyl ether (about 30 mL) and the organic layer is concentrated under reduced pressure to afford the desired intermediate.

The intermediate is dissolved in a 1 to 1 mixture of dichloromethane and trifluoroacetic acid (10 mL), and stirred for 30 minutes. The mixture is then concentrated under reduced pressure and is co-evaporated with dichloromethane (2×10 mL). The resulting residue is diluted in diethylether (5 mL) and a molar solution of hydrochloric acid in diethylether is added (10 mL). A precipitate is formed which is filtered and dried under high vacuum to yield the desired product as hydrochloride (303 mg; 1.28 mmol).

132

In many instances, the method of Example 6 can be adapted to make other compounds that are useful as intermediates for making the compounds and salts of this invention. An illustrative generic scheme is as follows:

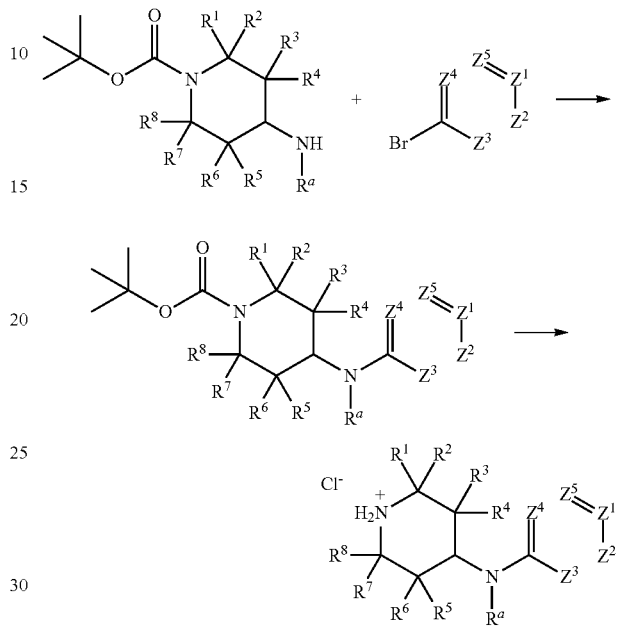

Here, $Z^1$, $Z^2$, $Z^3$, $Z^4$ and $Z^5$ are as defined above for the compounds of this invention, and at least one $Z^1$, $Z^2$, $Z^3$, $Z^4$ and $Z^5$ mustbe cyano. $R^1$, $R^2$, $R^3$, $R^4$, $R^5$, $R^6$, $R^7$ and $R^8$ are each independently selected from the group consisting of halogen, alkyl, alkoxy and oxo. $R^a$ is hydrogen. Determining the suitability of the method (and any necessary routine adaptations) or making a particular intermediate is generally with the skill of those in the art after reading this patent.

Example 7

Preparation of 3-(1-{4-[4-(4-trifluoromethyl-phenyl)-piperazin-1-yl]-butyryl}-piperidin-4-ylamino)-benzonitrile

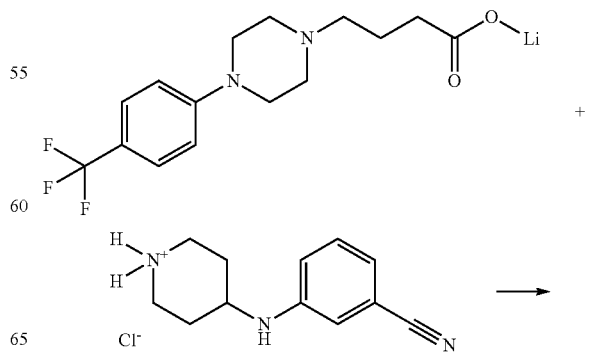

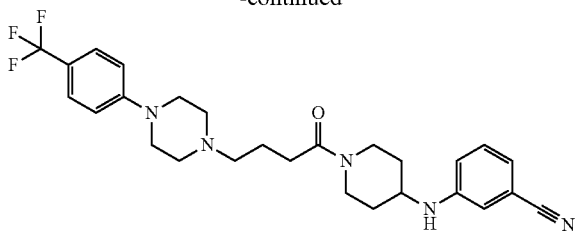

4-[4-(4-Trifluoromethyl-phenyl)-piperazin-1-yl]-butyric acid lithium salt (120 mg; 0.37 mmol, prepared in accordance with Example 3), diisopropylethyl amine (150 µL; 0.85 mmol) and tetramethyl-O-(1H-benzotriazol-1-yl)uronium hexafluorophosphate (129 mg; 0.34 mmol) are diluted in a 2 to 1 mixture of dimethylformamide and tetrahydrofuran (2.5 mL) and the resulting solution is stirred for 5 minutes. A solution 3-(piperidin-4-ylamino)-benzonitrile hydrochloride (80 mg; 0.34 mmol, prepared in accordance with Example 6) in dimethylformamide (850 µL) is added and the reaction is then stirred for 60 minutes at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (67 mg; 0.14 mmol). The structure was confirmed using Protocol I-B. Calculated mass=500; observed mass=500; HPLC retention time=4.40 min.

Example 8

Preparation of (4-nitro-3-trifluoromethyl-phenyl)-piperidin-4-yl-amine hydrochloride intermediate

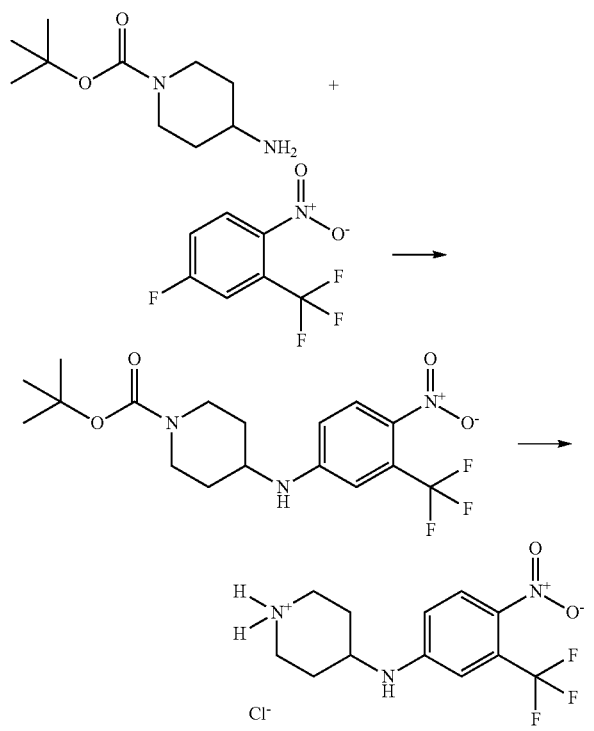

A solution of 4-amino-piperidine-1-carboxylic acid tert-butyl ester (47.8 g; 0.23 mol), 5-fluoro-2-nitrobenzotrifluoride (50.0 g; 0.23 mol) and potassium carbonate (99.7 g; 0.69 mol) in dimethylsulfoxide (600 mL) is heated at 100° C. for 3.5 hours. The mixture is then diluted with dichloromethane (200 mL) and is washed aq. sat ammonium chloride (2×55 mL) and with brine (25 mL). The organic layer is then dried over magnesium sulfate, filtered and concentrated under reduced pressure. The residue obtained is then dissolved in a minimum volume of diethylether and petrol ether is added until precipitation is observed. The precipitate is filtered, washed with petrol ether (10 mL) and dried under high vacuum to afford the desired product (75.4 g; 0.19 mol).

The product is dissolved in a 1 to 1 mixture of dichloromethane and trifluoroacetic acid (600 mL) and the resulting solution is stirred at room temperature until complete conversion is observed. A 4N aq. solution of sodium hydroxide is added until the pH of the aqueous layer reaches 8-9. The organic phase is separated, dried over sodium sulfate, filtered and concentrated under vacuum. The residue obtained is diluted in diethylether (200 mL) and a molar solution of hydrochloric acid in diethylether (150 mL) is added. The precipitate obtained is filtered and dried under high vacuum to afford the desired product as hydrochloride (59.0 g; 0.18 mol).

In many instances, the method of Example 8 can be adapted to make other compounds that are useful as intermediates for making the compounds and salts of this invention. An illustrative generic scheme is as follows:

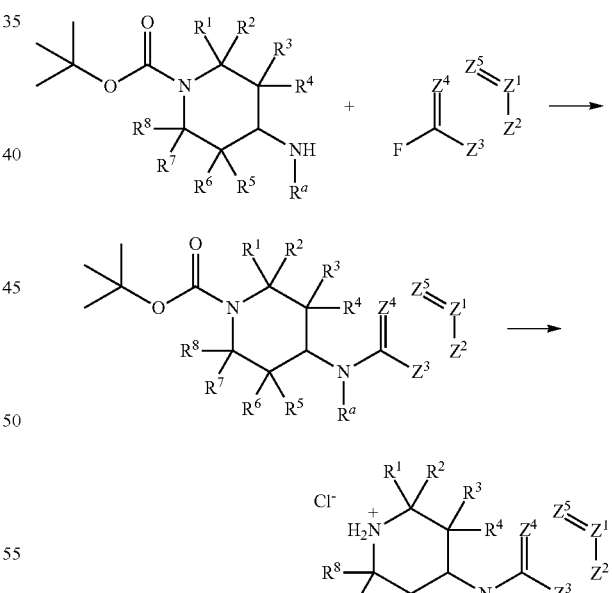

Here, $Z^1$, $Z^2$, $Z^3$, $Z^4$ and $Z^5$ are as defined above for the compounds of this invention. $R^1$, $R^2$, $R^3$, $R^4$, $R^5$, $R^6$, $R^7$ and $R^8$ are each independently selected from the group consisting of halogen, alkyl, alkoxy and oxo. $R^a$ is hydrogen. Determining the suitability of the method (and any necessary routine adaptations) or making a particular intermediate is generally with the skill of those in the art after reading this patent.

Example 9

Preparation of
1-(4-trifluoromethyl-phenyl)-piperidin-4-ol
Intermediate

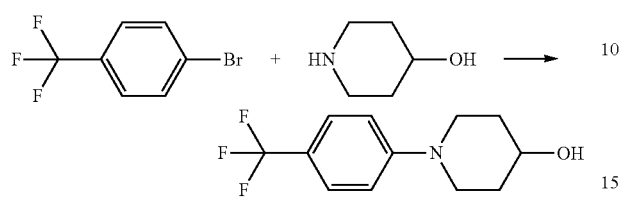

A mixture of 4-hydroxypiperidine (100 mg; 0.99 mmol), 4-bromo benzotrifluoride (0.167 mL, 1.19 mmol), tris(dibenzylideneacetone)dipalladium (37 mg; 0.04 mmol) and 2-(dicyclohexylphosphino)-2-methylbiphenyl (29 mg; 0.08 mmol) is thoroughly flushed with argon and tetrahydrofuran is added (1 mL). A molar solution of bis-(trimethylsilyl)-lithium amide in tetrahydrofuran (1.9 mL, 1.90 mmol) is added and the reaction mixture is heated at 65° C. After 17 hours reaction time, aq. 1M hydrochloric acid (7.5 mL) is added and the mixture is stirred for 15 minutes before neutralization by addition of aq. sat. sodium hydrogencarbonate. The mixture is extracted with ethyl acetate (2×10 mL). The combined organic layers are dried over sodium sulfate, filtered and evaporated under reduced pressure to yield crude 1-(4-trifluoromethyl-phenyl)-piperidin-4-ol.

In many instances, the method of Example 9 can be adapted to make other compounds that are useful as intermediates for making the compounds and salts of this invention. An illustrative generic scheme is as follows:

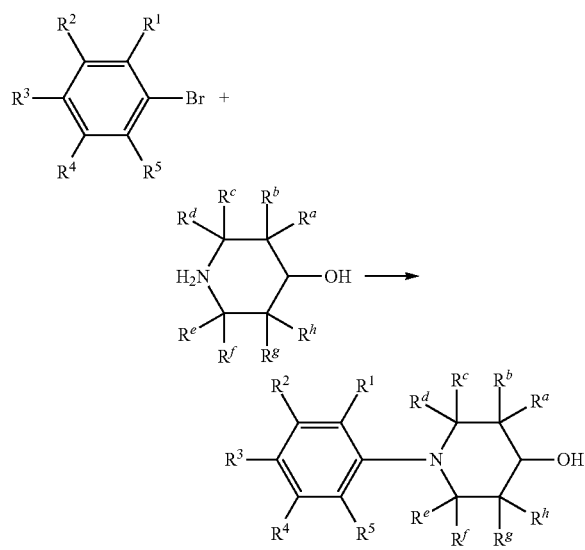

Here $R^1$, $R^2$, $R^3$, $R^4$ and $R^5$ are each independently selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl, wherein the alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl. $R^a$, $R^b$, $R^c$, $R^d$, $R^e$, $R^f$, $R^g$, and $R^h$ are each independently selected from the group consisting of halogen, alkyl, alkoxy and oxo. Determining the suitability of the method (and any necessary routine adaptations) or making a particular intermediate is generally with the skill of those in the art after reading this patent.

Example 10

Preparation of [1-(4-trifluoromethyl-phenyl)-piperidin-4-yloxy]-acetic acid tert-butyl ester intermediate

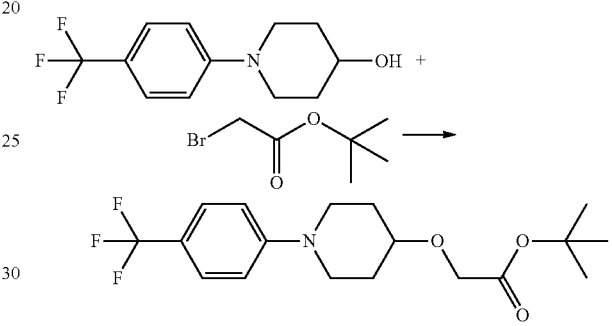

Tetrabutylammonium bromide (275 mg; 0.85 mmol) is added to a solution of the crude 1-(4-trifluoromethyl-phenyl)-piperidin-4-ol (627 mg, prepared in accordance with Example 9) in toluene (8 mL). The reaction mixture is cooled to 0° C. and aq. 35% sodium hydroxide (8 mL) is added followed by a drop wise addition of tert-butyl bromoacetate (749 mg; 3.84 mmol).

The mixture is then allowed to reach room temperature and is stirred for 17 hours at this temperature. The layers are separated and the organic layer is washed twice with water (4 mL), is dried over sodium sulfate, concentrated under vacuum and is co-evaporated with dichloromethane (2×4 mL). Purification of the crude material by flash column chromatography on silica gel (ethyl acetate:heptane 2:8) yields the desired pure material (769 mg; 2.14 mmol).

In many instances, the method of Example 10 can be adapted to make other compounds that are useful as intermediates for making the compounds and salts of this invention. An illustrative generic scheme is as follows:

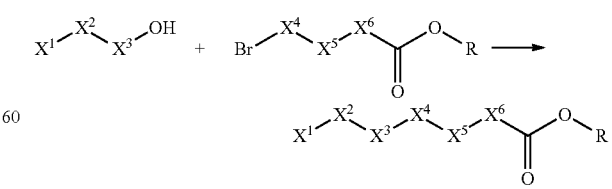

Here, $X^1$, $X^2$, $X^3$, $X^4$, $X^5$ and $X^6$ are as defined above for the compounds of this invention. R is alkyl. Determining the suitability of the method (and any necessary routine adapta-

Example 11

Preparation of [(4-trifluoromethyl-phenyl)-piperidin-4-yloxy]-acetic acid intermediate

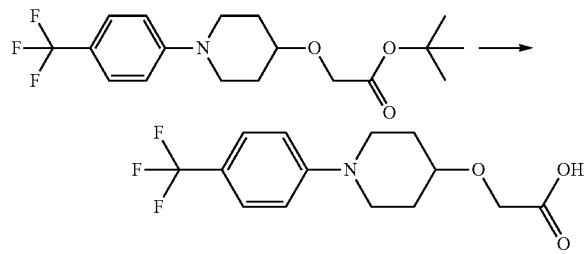

Trifluoroacetic acid (2 mL) is added to a solution of [1-(4-trifluoromethyl-phenyl)-piperidin-4-yloxy]-acetic acid tert-butyl ester (769 mg; 2.14 mmol, prepared in accordance with Example 10) in dichloromethane (2 mL). The reaction mixture is stirred until complete conversion is observed, is then concentrated under reduced pressure and co-evaporated with toluene (10 mL) to yield the desired product (985 mg, 2.14 mmol).

Example 12

Preparation of 1-[4-(4-nitro-3-trifluoromethyl-phenylamino)-piperidin-1-yl]-2-[1-(4-trifluoromethyl-phenyl)-piperidin-4-yloxy]-ethanone

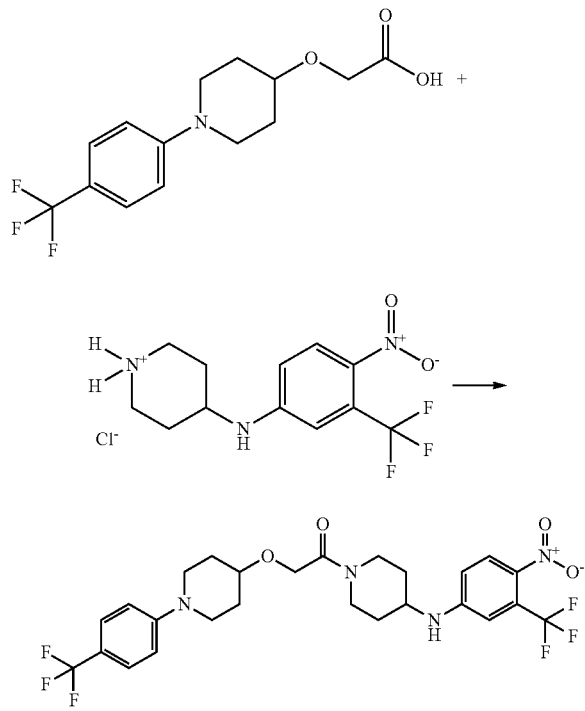

[1-(4-Trifluoromethyl-phenyl)-piperidin-4-yloxy]-acetic acid (186 mg; 0.61 mmol, prepared according to Example 11), diisopropylethyl amine (220 μL; 1.22 mmol) and tetramethyl-β-(1H-benzotriazol-1-yl)uronium hexafluorophosphate (232 mg; 0.61 mmol) are diluted in a 2 to 1 mixture of dimethylformamide and tetrahydrofuran (18 mL) and the resulting solution is stirred for 5 minutes. A solution of (4-nitro-3-trifluoromethyl-phenyl)-piperidin-4-yl-amine hydrochloride (200 mg; 0.61 mmol, prepared in accordance with Example 8) in dimethylformamide (6 mL) is added and the reaction is then stirred for 3 hours at room temperature. Following dilution with dichloromethane (50 mL), the organic layer is sequentially washed with water (15 mL), aq. sat. sodium hydrogen carbonate (15 mL), is dried over magnesium sulfate and concentrated under reduced pressure. The desired product (209 mg; 0.36 mmol) is isolated in pure form following purification by column chromatography on silica gel (dichloromethane:methanol from 100:0 to 95:5). The structure was confirmed using Protocol II-E. Calculated mass=575; observed mass=576; HPLC retention time=11.52 min.

Example 13

Preparation of 3-[4-(4-trifluoromethyl-phenyl)-piperidin-1-yl]-propionic acid lithium salt intermediate

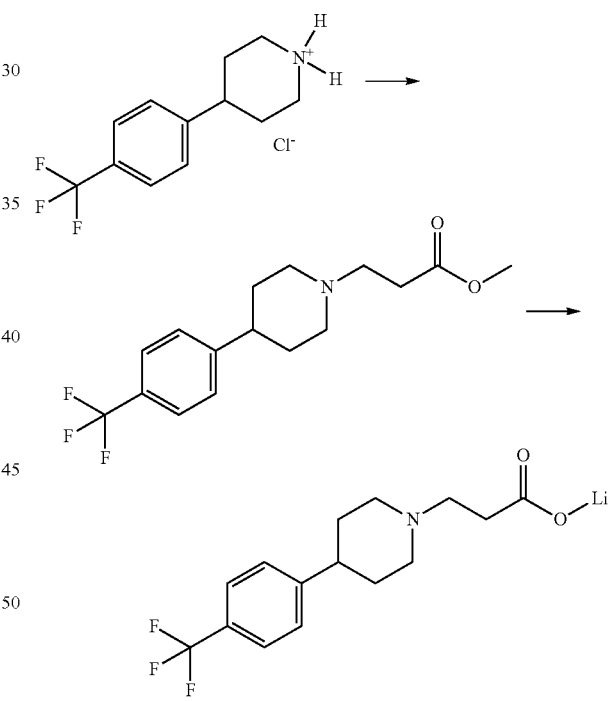

4-(4-Trifluoromethylphenyl)-piperidine hydrochloride (797 mg; 3.0 mmol) and triethylamine (420 μL; 3.0 mmol) are suspended in water (1.2 mL). Methylacrylate (301 mg; 3.5 mmol) is added and the resulting mixture is irradiated in a mono-mode microwave oven for 20 minutes at 120° C.

Lithium hydroxide (143 mg; 6.0 mmol) is added and a second irradiation is applied for 10 minutes at 100° C. The reaction is diluted with acetonitrile (15 mL), the precipitate is filtered and dried in a vacuum oven. The desired product is obtained as lithium salt (906 mg; 2.95 mmol).

Example 14

Preparation of 1-[4-(4-nitro-3-trifluoromethyl-phenylamino)-piperidin-1-yl]-3-[4-(4-trifluoromethyl-phenyl)-piperidin-1-yl]-propan-1-one

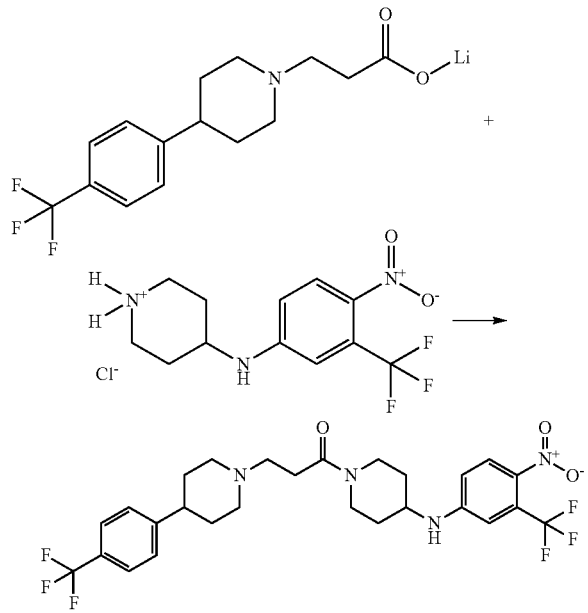

3-[4-(4-Trifluoromethyl-phenyl)-piperidin-1-yl]-propionic acid lithium salt (118 mg; 0.38 mmol, prepared in accordance with Example 13), diisopropylethyl amine (137 µL; 0.76 mmol) and tetramethyl-O-(1H-benzotriazol-1-yl)uronium hexafluorophosphate (145 mg; 0.38 mmol) are diluted in a 2 to 1 mixture of dimethylformamide and tetrahydrofuran (12 mL) and the resulting solution is stirred for 5 minutes. A solution of (4-nitro-3-trifluoromethyl-phenyl)-piperidin-4-yl-amine hydrochloride (114 mg; 0.35 mmol, prepared in accordance with Example 8) in dimethylformamide (4 mL) is added and the reaction is then stirred for 2 hours at room temperature. Following dilution with dichloromethane (50 mL), the organic layer is sequentially washed with water (15 mL), aq. sat. sodium hydrogen carbonate (15 mL), is dried over magnesium sulfate and concentrated under reduced pressure. The desired product is finally obtained in pure form (103 mg; 0.18 mmol) following purification by preparative HPLC. The structure was confirmed using Protocol II-A. Calculated mass=572; observed mass=573; HPLC retention time=3.62 min.

Example 15

Preparation of 4-(4-chloro-3-trifluoromethylsulfanyl-phenylamino)-piperidine-1-carboxylic acid tert-butyl ester intermediate

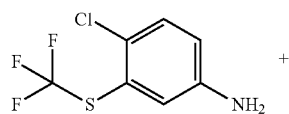

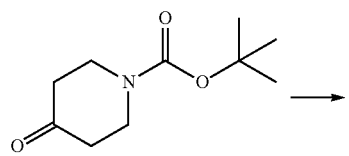

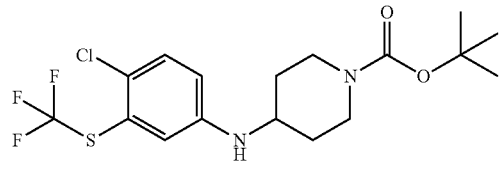

4-Chloro-3-trifluoromethylsulfanyl-phenylamine (683 mg; 3.00 mmol), 4-oxo-piperidine-1-carboxylic acid tert-butyl ester (598 mg; 3.00 mmol) and sodium triacetoxyborohydride (1.9 g; 9.00 mmol) are suspended in dichloroethane (25 mL) and the resulting mixture is stirred for 1 day. Acetic acid is then added (0.18 mL) and the reaction mixture is stirred for additional 9 days. The suspension is then diluted with dichloromethane (10 mL) and is washed with water (20 mL). The organic phase is then washed with aq. sat. sodium carbonate (10 mL), water (10 mL) and is then dried over magnesium sulphate, filtered and concentrated under reduced pressure. Purification of the crude by column chromatography on silica gel (dichloromethane) affords the desired product (580 mg; 1.41 mmol).

Example 16

Preparation of (4-chloro-3-trifluoromethylsulfanyl-phenyl)-piperidin-4-yl-amine hydrochloride intermediate

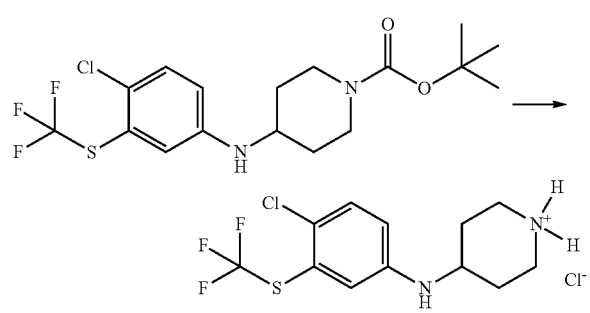

4-(4-Chloro-3-trifluoromethylsulfanyl-phenylamino)-piperidine-1-carboxylic acid tert-butyl ester (580 mg; 1.41 mmol, prepared in accordance with Example 15) is dissolved in dichloromethane (8 mL) and trifluoroacetic acid (2 mL) is slowly added under stirring. After 60 minutes reaction time, the mixture is concentrated under reduced pressure and co-evaporated twice with dichloromethane (10 mL). The crude residue is then diluted in dioxane (2 mL) and a 4N solution of hydrochloric acid in dioxane (3 mL) is added under stirring. A solid is formed which is then filtered and dried under high vacuum to afford the desired product as hydrochloride (484 mg; 1.40 mmol).

Example 17

Preparation of 1-[4-(4-chloro-3-trifluoromethylsulfanyl-phenylamino)-piperidin-1-yl]-4-[4-(4-trifluoromethyl-phenyl)-piperazin-1-yl]-butan-1-one

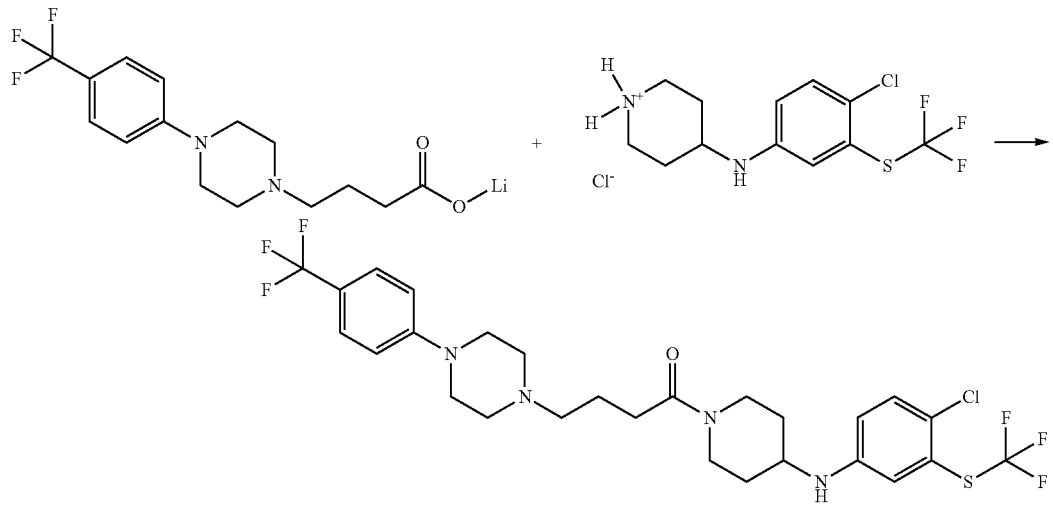

4-[4-(4-Trifluoromethyl-phenyl)-piperazin-1-yl]-butyric acid lithium salt (16 mg; 0.05 mmol, prepared in accordance with Example 3), diisopropylethyl amine (18 µL; 0.10 mmol) and tetramethyl-O-(1H-benzotriazol-1-yl)uronium hexafluorophosphate (19 mg; 0.05 mmol) are diluted in a 2 to 1 mixture of dimethylformamide and tetrahydrofuran (1.5 mL) and the resulting solution is stirred for 5 minutes. A solution of (4-chloro-3-trifluoromethylsulfanyl-phenyl)-piperidin-4-yl-amine hydrochloride (17 mg; 0.05 mmol, prepared in accordance with Example 16) in dimethylformamide (0.5 mL) is added and the reaction is then stirred for 90 minutes at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (5 mg; 0.01 mmol). The structure was confirmed using Protocol I-B. Calculated mass=609; observed mass=609; HPLC retention time=4.89 min.

Example 18

Preparation of 5-(4-bromo-phenyl)-2-methyl-1H-tetrazole intermediate

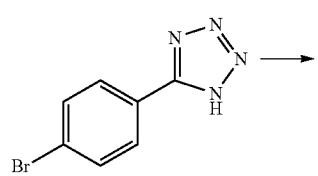

-continued

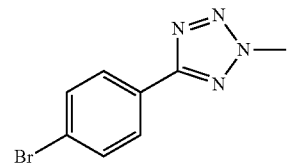

4-Bromophenyltetrazole (225 mg; 1.0 mmol) and potassium carbonate (140 mg; 1.0 mmol) are dissolved in dimethylformamide (3 mL), and a solution of methyliodide (140 mg; 1.0 mmol) in dimethylformamide (1 mL) is added dropwise under stirring. After 2 hours reaction time at room temperature methyliodide (28 mg; 0.2 mmol) is added and the mixture is stirred further for 90 minutes. The reaction is then diluted with water (4 mL), the precipitated white solid is filtered off and is rinsed once with water. After drying under high vacuum the desired product is obtained as a 95:5 mixture of regioisomers (188 mg; 0.79 mmol).

Example 19

Preparation of 4-[4-(2-methyl-1H-tetrazol-5-yl)-phenylamino]-piperidine-1-carboxylic acid tert-butyl ester intermediate

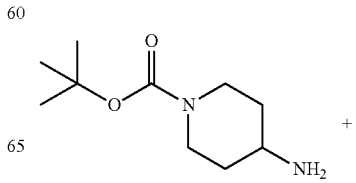

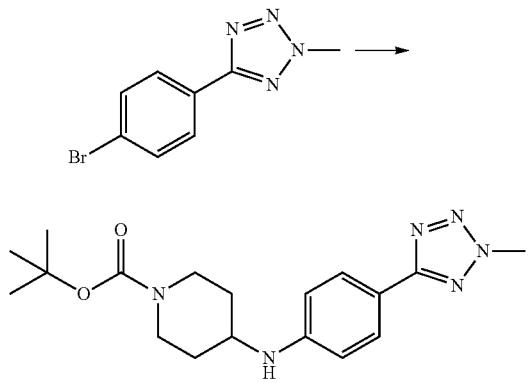

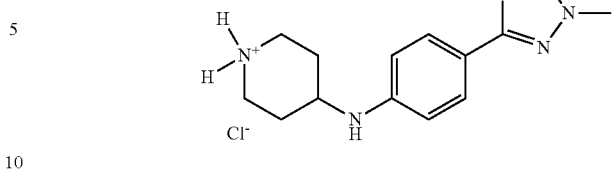

4-[4-(1-Methyl-1H-tetrazol-5-yl)-phenylamino]-piperidine-1-carboxylic acid tert-butyl ester (401 mg; 1.12 mmol, prepared in accordance with Example 19) is dissolved in dichloromethane (3 mL) and trifluoroacetic acid (1 mL) is slowly added under stirring. After 60 minutes reaction time, the mixture is concentrated under reduced pressure and co-evaporated twice with dichloromethane (10 mL). The crude residue is then diluted in dioxane (2 mL) and a 4N solution of hydrochloric acid in dioxane (3 mL) is added under stiffing. The solid formed is filtered and is dried under high vacuum to afford the desired product as hydrochloride (257 mg; 0.87 mmol).

Tris(dibenzylideneacetone)dipalladium (30 mg; 0.03 mmol), 2,2'-bis(diphenylphosphino)-1,1'-binaphthyl (62 mg; 0.10 mmol), sodium tert-butoxide (240 mg; 2.50 mmol), 5-(4-bromo-phenyl)-1-methyl-1H-tetrazole (406 mg; 1.70 mmol, prepared in accordance with Example 18) and 4-amino-piperidine-1-carboxylic acid tert-butyl ester (421 mg; 2.1 mmol) are suspended in dry toluene (7 mL) and the mixture is irradiated in a mono-mode microwave oven for 20 min. at 120° C. The mixture is then cooled down to room temperature, is diluted with ethyl acetate (15 mL), is filtered and is concentrated under reduced pressure. The crude residue is finally purified by chromatography on silica gel (dichloromethane: methanol 100:0 to 98:2) to afford the desired product (401 mg; 1.12 mmol).

In many instances, the method of Example 20 can be adapted to make other compounds that are useful as intermediates for making the compounds and salts of this invention. An illustrative generic scheme is as follows:

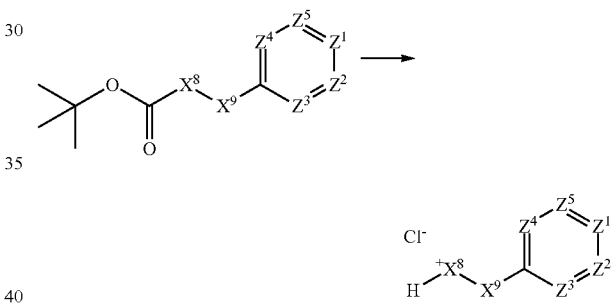

Here, $X^8, X^9, Z^1, Z^2, Z^3, Z^4$ and $Z^5$ are as defined above for the compounds of this invention. Determining the suitability of the method (and any necessary routine adaptations) or making a particular intermediate is generally with the skill of those in the art after reading this patent.

Example 20

Preparation of [4-(2-methyl-1H-tetrazol-5-yl)-phenyl]-piperidin-4-yl-amine hydrochloride intermediate

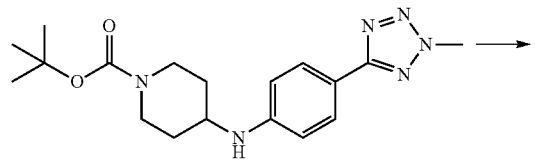

Example 21

Preparation of 1-{4-[4-(2-methyl-1H-tetrazol-5-yl)-phenylamino]-piperidin-1-yl}-4-[4-(4-trifluoromethyl-phenyl)-piperazin-1-yl]-butan-1-one

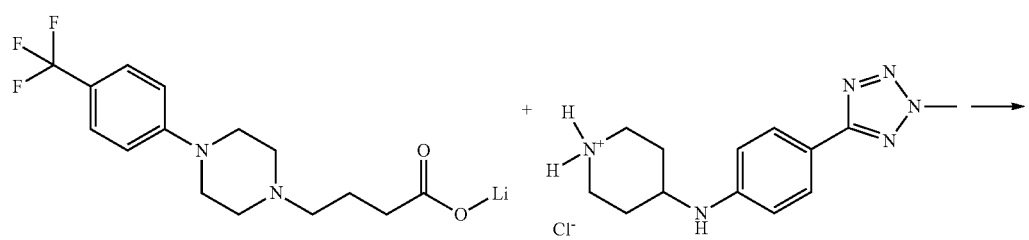

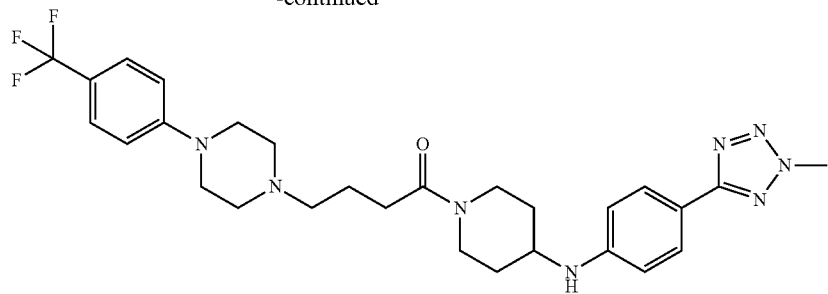

4-[4-(4-Trifluoromethyl-phenyl)-piperazin-1-yl]-butyric acid lithium salt (16 mg; 0.05 mmol, prepared in accordance with Example 3), diisopropylethyl amine (18 μL; 0.10 mmol) and tetramethyl-O-(1H-benzotriazol-1-yl)uronium hexafluorophosphate (19 mg; 0.05 mmol) are diluted in a 2 to 1 mixture of dimethylformamide and tetrahydrofuran (1.5 mL) and the resulting solution is stirred for 5 minutes. A solution of [4-(1-methyl-1H-tetrazol-5-yl)-phenyl]-piperidin-4-yl-amine hydrochloride (16 mg; 0.05 mmol, prepared in accordance with Example 20) in dimethylformamide (0.5 mL) is added and the reaction is then stirred for 45 minutes at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (19 mg; 0.03 mmol). The structure was confirmed using Protocol I-B. Calculated mass=557; observed mass=557; HPLC retention time=4.36 min.

Example 22

Preparation of 3-[4-(4-benzyloxy-phenyl)-piperazin-1-yl]-propionic acid lithium intermediate

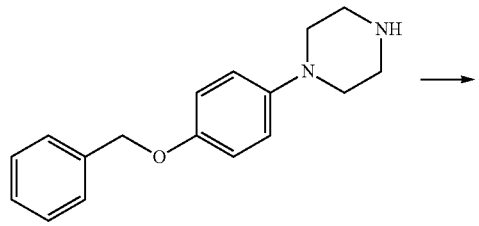

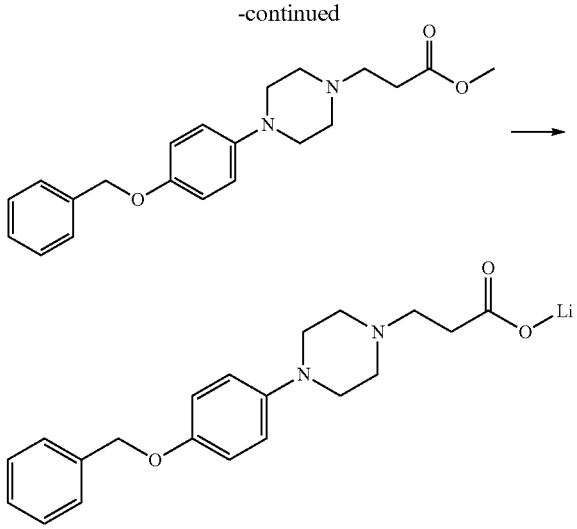

1-(4-Benzyloxy-phenyl)-piperazine (800 mg; 2.98 mmol) and methylacrylate (774 mg; 9.00 mmol) are diluted in a 4 to 1 mixture of tetrahydrofuran and water (1.5 mL). The resulting mixture is irradiated in a mono-mode microwave oven for 20 minutes at 120° C.

Lithium hydroxide (290 mg; 12.1 mmol) is added and the mixture is stirred at 70° C. for 2 hours. The reaction is diluted with acetonitrile (100 mL), the precipitate obtained is filtered and dried in a vacuum oven. The desired product is obtained as lithium salt in pure form (585 mg; 1.69 mmol).

Example 23

Preparation of 3-[4-(4-benzyloxy-phenyl)-piperazin-1-yl]-1-[4-(4-nitro-3-trifluoromethyl-phenylamino)-piperidin-1-yl]-propan-1-one

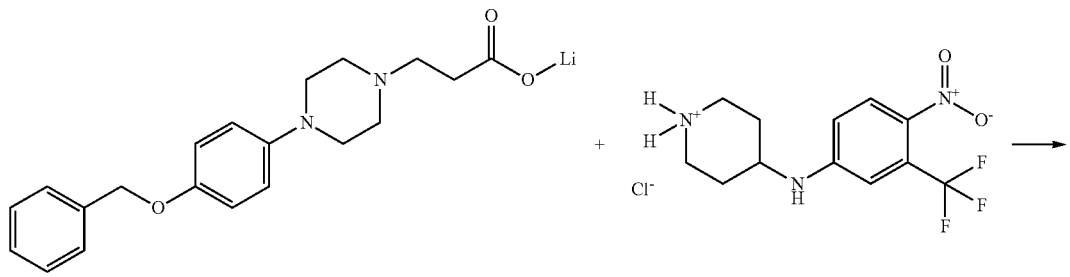

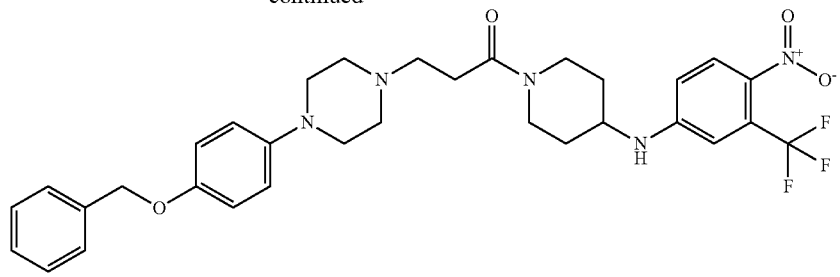

3-[4-(4-Benzyloxy-phenyl)-piperazin-1-yl]-propionic acid lithium salt (134 mg; 0.39 mmol, prepared in accordance with Example 22), diisopropylethyl amine (174 μL; 0.35 mmol) and tetramethyl-O-(1H-benzotriazol-1-yl)uronium hexafluorophosphate (133 mg; 0.35 mmol) are diluted in a 2 to 1 mixture of dimethylformamide and tetrahydrofuran (1.5 mL) and the resulting solution is stirred for 5 minutes. A solution of (4-nitro-3-trifluoromethyl-phenyl)-piperidin-4-yl-amine hydrochloride (114 mg; 0.35 mmol, prepared in accordance with Example 8) in dimethylformamide (0.5 mL) is added and the reaction is then stirred for 3 hours at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (61 mg; 0.10 mmol). The structure was confirmed using Protocol II-A. Calculated mass=612; observed mass=612; HPLC retention time=3.57 min.

Example 24

Preparation of 1-(4-isobutoxy-phenyl)-piperazine hydrochloride intermediate

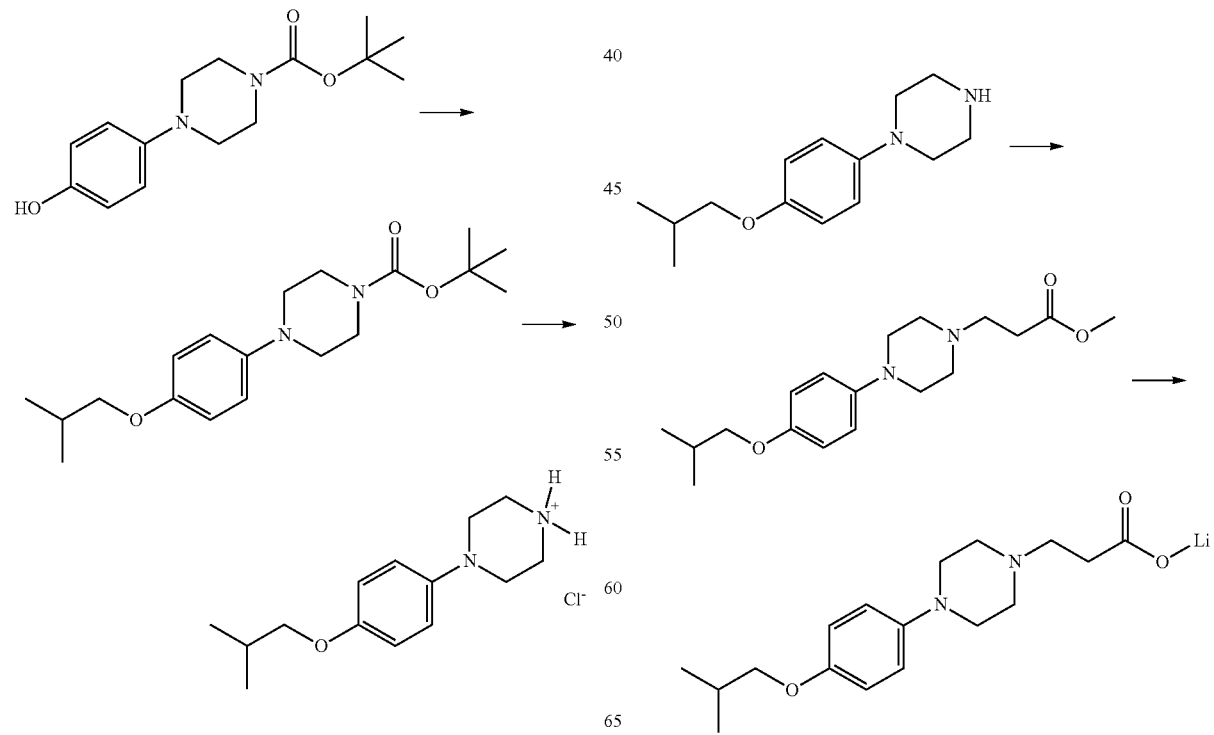

A solution of 4-(4-hydroxy-phenyl)-piperazine-1-carboxylic acid tert-butyl ester (1.5 g; 5.39 mmol) in tetrahydrofuran (5 mL) is added to a suspension of sodium hydride (647 mg of a 60% suspension in oil; 16.2 mmol) in tetrahydrofuran (35 mL) under inert atmosphere. The resulting mixture is stirred for 5 minutes and a solution of 1-bromo-2-methyl-propane (1.1 g; 8.09 mmol) in tetrahydrofuran (5 mL) is added. The reaction is stirred for 16 hours at room temperature. The organic layer is then washed with aq. sat. ammonium chloride (10 mL), and water (10 mL). The organic layer is separated, is dried over magnesium sulfate, filtered and concentrated under reduced pressure.

The crude product is dissolved in dichloromethane (10 mL) and trifluoroacetic acid (10 mL) is added. After 60 minutes reaction time, the mixture is concentrated under reduced pressure and co-evaporated twice with dichloromethane (10 mL). The crude residue is then diluted in diethylether (4 mL) and a 1M solution of hydrochloric acid in diethylether (10 mL) is added under stirring. The solid formed is filtered and is dried under high vacuum to afford the desired product as hydrochloride (600 mg; 2.22 mmol).

Example 25

Preparation of 3-[4-(4-isobutoxy-phenyl)-piperazin-1-yl]-propionic acid lithium salt intermediate 1-(4-Isobutoxy-phenyl)-piperazine [(800 mg; 3.41 mmol, free base of Example 24) and methylacrylate (774 mg; 9.00 mmol) are diluted in a 4 to 1 mixture of tetrahydrofuran and water (1.5 mL). The resulting mixture is irradiated in a mono-mode microwave oven for 20 minutes at 120° C.
Lithium hydroxide (290 mg; 12.1 mmol) is added and the mixture is stirred at 70° C. for 2 hours. The reaction is diluted with acetonitrile (100 mL), the precipitate obtained is filtered and dried in a vacuum oven. The desired product is obtained as lithium salt in pure form (515 mg; 1.65 mmol).

In many instances, the method of Example 25 can be adapted to make other compounds that are useful as intermediates for making the compounds and salts of this invention. An illustrative generic scheme is as follows:

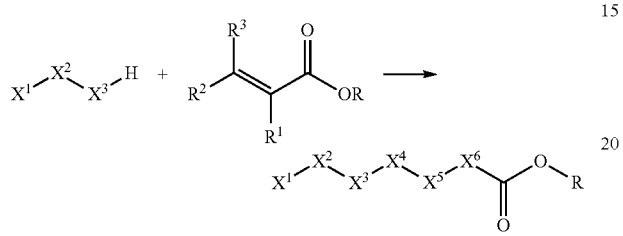

Here, $X^1$, $X^2$, $X^3$, $X^4$, $X^5$ and $X^6$ are as defined above for the compounds of this invention. R is alkyl. $R^1$, $R^2$, $R^3$ are each independently selected from the group consisting of hydrogen, alkyl, alkenyl and carboxyclyl. Determining the suitability of the method (and any necessary routine adaptations) or making a particular intermediate is generally with the skill of those in the art after reading this patent.

Example 26

Preparation of 3-[4-(4-isobutoxy-phenyl)-piperazin-1-yl]-1-[4-(4-nitro-3-trifluoromethyl-phenylamino)-piperidin-1-yl]-propan-1-one

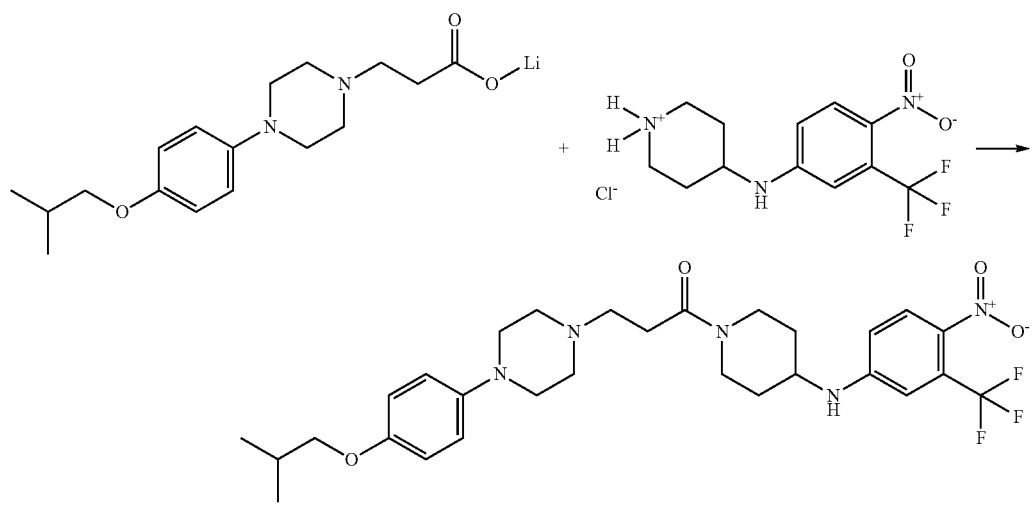

3-[4-(4-Isobutoxy-phenyl)-piperazin-1-yl]-propionic acid lithium salt (35 mg; 0.11 mmol, prepared in accordance with Example 25), diisopropylethyl amine (50 µL; 0.10 mmol) and tetramethyl-O-(1H-benzotriazol-1-yl)uronium hexafluorophosphate (38 mg; 0.10 mmol) are diluted in a 2 to 1 mixture of dimethylformamide and tetrahydrofuran (1.5 mL) and the resulting solution is stirred for 5 minutes. A solution of (4-nitro-3-trifluoromethyl-phenyl)-piperidin-4-yl-amine hydrochloride (33 mg; 0.10 mmol, prepared in accordance with Example 8) in dimethylformamide (0.5 mL) is added and the reaction is then stirred for 3 hours at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (30 mg; 0.05 mmol). The structure was confirmed using Protocol II-A. Calculated mass=578; observed mass=578; HPLC retention time=3.54 min.

Example 27

Preparation of 4-(4-methylsulfanyl-3-trifluoromethyl-phenylamino)-piperidine-1-carboxylic acid tert-butyl ester intermediate

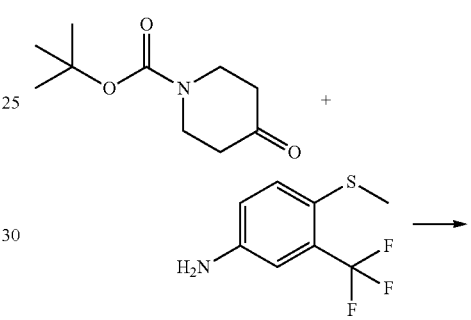

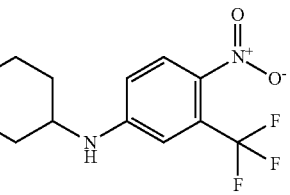

-continued

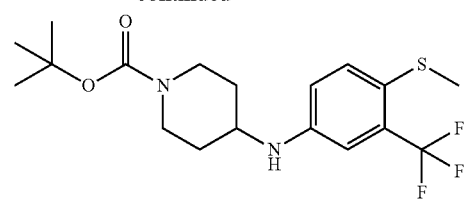

4-Methylsulfanyl-3-trifluoromethyl-phenylamine (828 mg; 4.00 mmol), 4-oxo-piperidine-1-carboxylic acid tert-butyl ester (876 mg; 4.40 mmol) and sodium triacetoxyborohydride (2.52 g; 12.00 mmol) are suspended in dichloromethane (18 mL) and the resulting mixture is stirred for 1 day. The suspension is then diluted with dichloromethane (50 mL) and is washed with water (30 mL) and aq. sat. ammonium chloride (3×30 mL). The organic phase is dried over magnesium sulphate, filtered and concentrated under reduced pressure to deliver the desired product in the presence of remaining traces of solvent (1.8 g; 4.6 mmol).

Example 28

Preparation of 4-(4-methanesulfonyl-3-trifluoromethyl-phenylamino)-piperidine-1-carboxylic acid tert-butyl ester intermediate

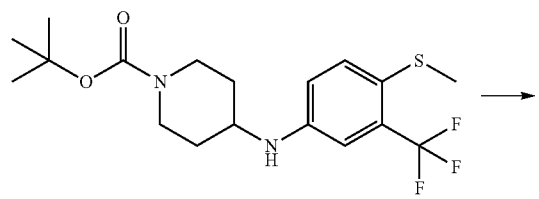

4-(4-Methylsulfanyl-3-trifluoromethyl-phenylamino)-piperidine-1-carboxylic acid tert-butyl ester (1.8 g; 4.6 mmol, prepared in accordance with Example 27) and 3-chloro-benzenecarboperoxoic acid (2.09 g 70% wt/wt; 12.1 mmol) are dissolved in pre-cooled dichloromethane (22 mL) and the resulting mixture is stirred at this temperature for 3 days. After filtration, the filtrate is washed with aq. sat. potassium carbonate (15 mL), is dried over magnesium sulphate and concentrated under reduced pressure. The crude product is then purified by column chromatography on silica gel (dichloromethane:methanol 1:0 to 3:2) to afford the desired product (650 mg; 1.54 mmol).

In many instances, the method of Example 28 can be adapted to make other compounds that are useful as intermediates for making the compounds and salts of this invention. An illustrative generic scheme is as follows:

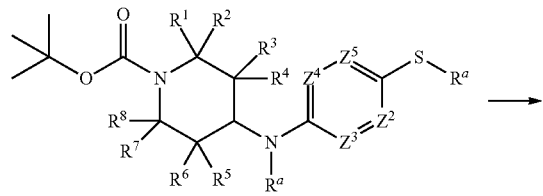

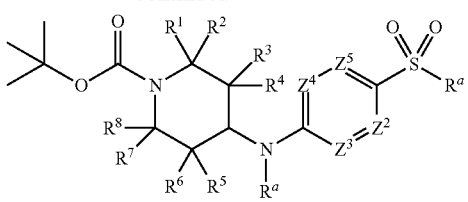

Here, $Z^2$, $Z^3$, $Z^4$ and $Z^5$ are as defined above for the compounds of this invention. $R^1$, $R^2$, $R^3$, $R^4$, $R^5$, $R^6$, $R^7$ and $R^8$ are each independently selected from the group consisting of halogen, alkyl, alkoxy and oxo. $R^a$ is independently selected from the group consisting of hydrogen, alkyl and haloalkyl. Determining the suitability of the method (and any necessary routine adaptations) or making a particular intermediate is generally with the skill of those in the art after reading this patent.

Example 29

Preparation of 4-[4-(4-trifluoromethyl-phenyl)-piperazin-1-yl]-butyric acid lithium salt intermediate

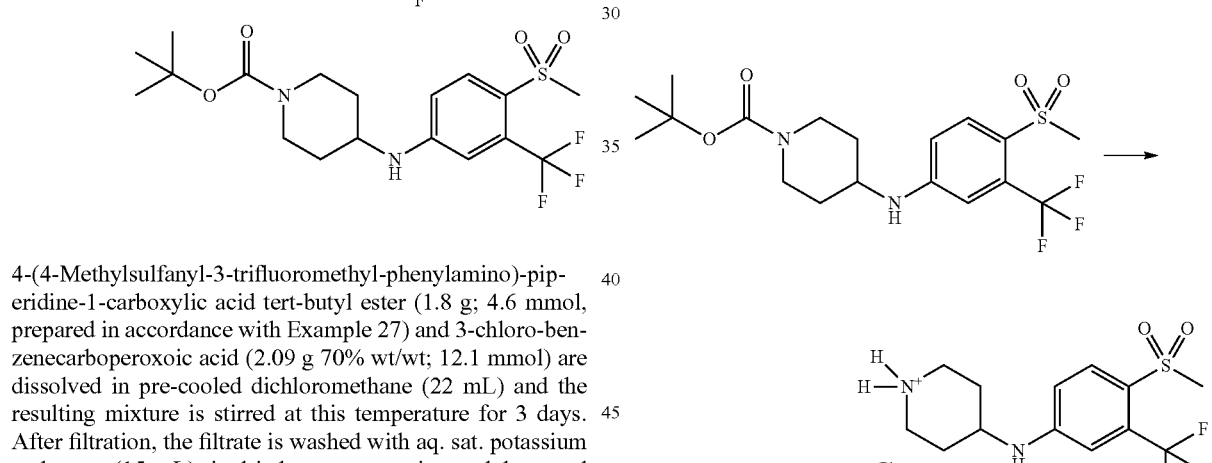

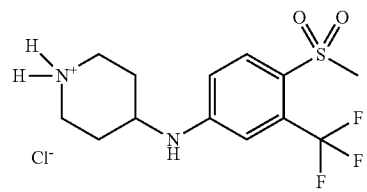

Trifluoroacetic acid (1 mL) is added to a solution of 4-(4-methanesulfonyl-3-trifluoromethyl-phenylamino)-piperidine-1-carboxylic acid tert-butyl ester (490 mg; 1.16 mmol, prepared in accordance with Example 28) in dichloromethane (1 mL) and the resulting solution is stirred for 30 minutes at room temperature. The mixture is then concentrated under reduced pressure and is co-evaporated with dichloromethane (2×10 mL). The residue obtained is dissolved in dioxane (5 mL) and a 4N solution of hydrochloric acid in dioxane (5 mL) is added. The precipitate formed is filtered, triturated with ethylacetate (5 mL) and filtered. After drying under high vacuum, the desired product is isolated as hydrochloride (390 mg; 1.09 mmol).

Example 30

Preparation of 1-[4-(4-methanesulfonyl-3-trifluoromethyl-phenylamino)-piperidin-1-yl]-4-[4-(4-trifluoromethyl-phenyl)-piperazin-1-yl]-butan-1-one

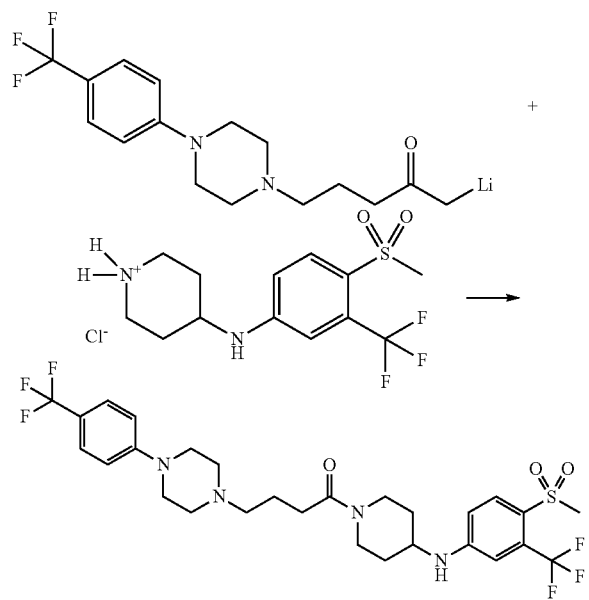

4-[4-(4-Trifluoromethyl-phenyl)-piperazin-1-yl]-butyric acid lithium salt (120 mg; 0.38 mmol, prepared in accordance with Example 3), diisopropylethyl amine (174 µL; 1.00 mmol) and tetramethyl-O-(1H-benzotriazol-1-yl)uronium hexafluorophosphate (121 mg; 0.28 mmol) are diluted in a 2 to 1 mixture of dimethylformamide and tetrahydrofuran (1.5 mL) and the resulting solution is stirred for 5 minutes. A solution (4-methanesulfonyl-3-trifluoromethyl-phenyl)-piperidin-4-yl-amine hydrochloride (103 mg; 0.32 mmol, prepared in accordance with Example 29) in dimethylformamide (0.5 mL) is added and the reaction is then stirred for 2 hours at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (36 mg; 0.06 mmol). The structure was confirmed using Protocol I-B. Calculated mass=621; observed mass=621; HPLC retention time=4.39 min.

Example 31

Preparation of 4-[4-(4-fluoro-benzenesulfonyl)-phenylamino]-piperidine-1-carboxylic acid tert-butyl ester intermediate

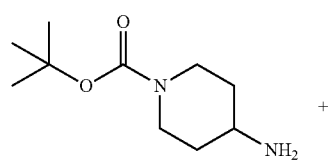

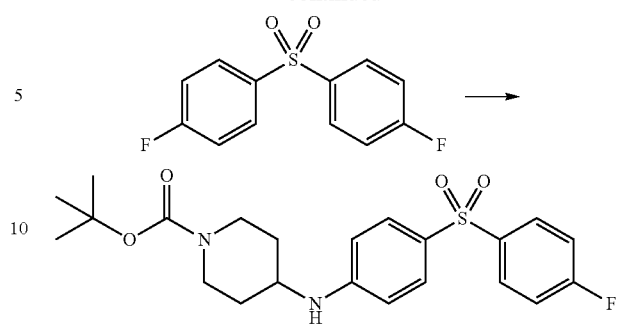

A solution of 4-amino-piperidine-1-carboxylic acid tert-butyl ester (427 mg; 2.13 mmol), bis(4-fluorophenyl) sulfone (493 mg; 1.94 mmol) and potassium carbonate (1.01 g; 7.76 mmol) in dimethylsulfoxide (5 mL) is heated over night at 100° C. The temperature is then increased to 120° C. and the mixture is reacted at this temperature for 24 hours. The reaction is then diluted with dichloromethane (100 mL), filtered and the filtrate is washed with aq. 1N hydrochloric acid (2×20 mL), and water (2×20 mL). The organic layer is dried over magnesium sulfate, filtered and concentrated under reduced pressure. The residue obtained is finally purified by column chromatography on silica gel (dichloromethane:methanol 100:0 (200 mL) and then 98:2 (150 mL)) to afford the desired product (653 mg; 1.50 mmol).

Example 32

Preparation of [4-(4-fluoro-benzenesulfonyl)-phenyl]-piperidin-4-yl-amine hydrochloride intermediate

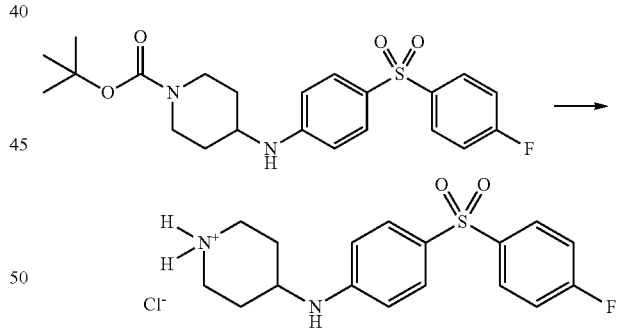

4-[4-(4-Fluoro-benzenesulfonyl)-phenylamino]-piperidine-1-carboxylic acid tert-butyl ester (640 mg; 1.47 mmol, prepared in accordance with Example 31) is dissolved in a 1 to 1 mixture of dichloromethane and trifluoroacetic acid (2 mL) and the resulting solution is stirred at room temperature until complete conversion is observed (about 90 minutes). After concentration under reduced pressure, the residue obtained is co-evaporated with dichloromethane (2×10 mL). The crude residue is then diluted in ethylacetate (2 mL) and a 4N solution of hydrochloric acid in dioxane (3 mL) is added under stirring. The solid formed is filtered and dried under high vacuum to afford the desired product as hydrochloride (546 mg; 1.47 mmol).

Example 33

Preparation of 1-{4-[4-(4-fluoro-benzenesulfonyl)-phenylamino]-piperidin-1-yl}-4-[4-(4-trifluoromethyl-phenyl)-piperazin-1-yl]-butan-1-one

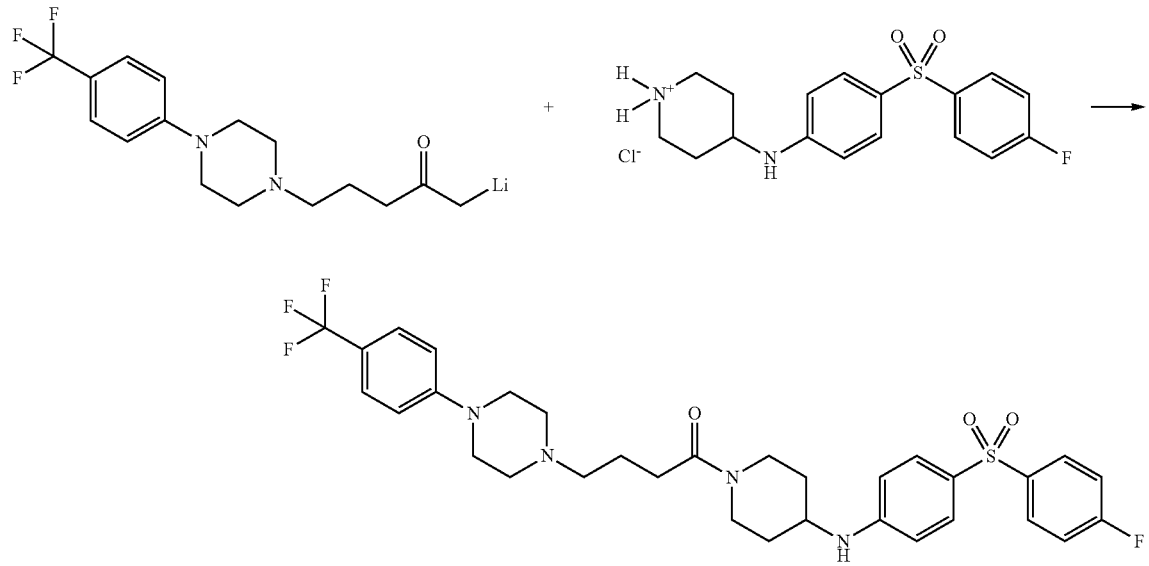

4-[4-(4-Trifluoromethyl-phenyl)-piperazin-1-yl]-butyric acid lithium salt (16 mg; 0.05 mmol, prepared in accordance with Example 3), diisopropylethyl amine (18 μL; 0.10 mmol) and tetramethyl-O-(1H-benzotriazol-1-yl)uronium hexafluorophosphate (19 mg; 0.05 mmol) are diluted in a 2 to 1 mixture of dimethylformamide and tetrahydrofuran (1.5 mL) and the resulting solution is stirred for 5 minutes. A solution [4-(4-fluoro-benzenesulfonyl)-phenyl]-piperidin-4-yl-amine hydrochloride (19 mg; 0.05 mmol, prepared in accordance with Example 32) in dimethylformamide (0.5 mL) is added and the reaction is then stirred for 45 minutes at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (16 mg; 0.03 mmol). The structure was confirmed using Protocol I-B. Calculated mass=633; observed mass=633; HPLC retention time=4.90 min.

Example 34

Preparation of 3-[4-(4-tert-butyl-phenyl)-piperazin-1-yl]-propionic acid lithium salt intermediate

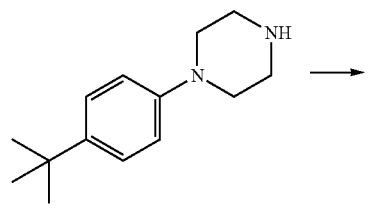

1-(4-tert-Butyl-phenyl)-piperazine (436 mg; 2.00 mmol) and methylacrylate (198 μL; 2.00 mmol) are diluted with water (1.6 mL). The resulting mixture is irradiated in a mono-mode microwave oven for 30 minutes at 120° C.

The reaction is diluted with water (3.4 mL) and lithium hydroxide (96 mg; 4.0 mmol) is added. The mixture is then irradiated twice in a mono-mode microwave oven for 10 minutes at 100° C. The reaction is diluted with acetonitrile (50 mL); the precipitate obtained is filtered and dried in a vacuum oven. The desired product is obtained as lithium salt in pure form (410 mg; 1.39 mmol).

Example 35

Preparation of 3-[4-(4-tert-butyl-phenyl)-piperazin-1-yl]-1-[4-(4-nitro-3-trifluoromethyl-phenylamino)-piperidin-1-yl]-propan-1-one

Example 36

Preparation of 1-[4-(4-trifluoromethyl-benzyloxy)-phenyl]-piperazine intermediate

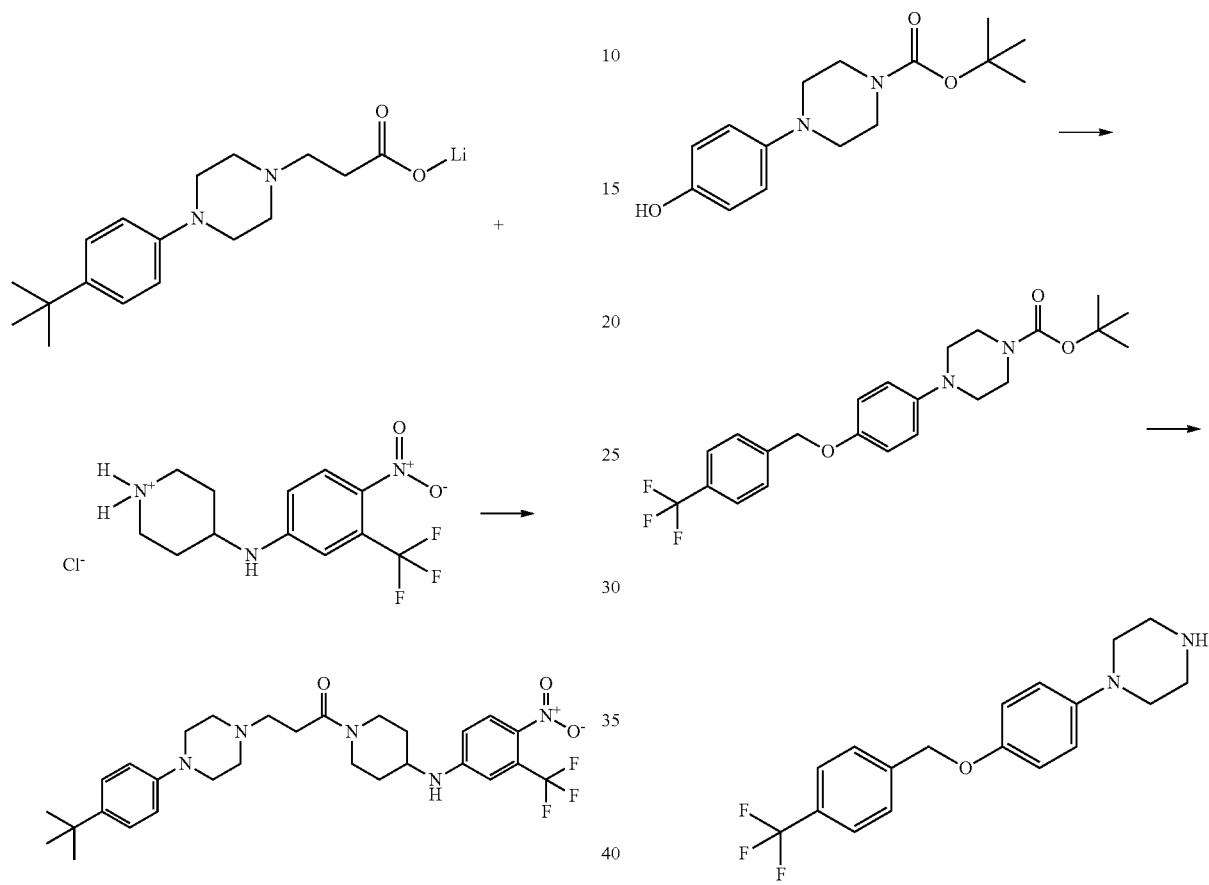

3-[4-(4-tert-Butyl-phenyl)-piperazin-1-yl]-propionic acid lithium salt (114 mg; 0.39 mmol, prepared in accordance with Example 34), diisopropylethylamine (174 µL; 1.0 mmol) and tetramethyl-O-(1H-benzotriazol-1-yl)uronium hexafluorophosphate (133 mg; 0.35 mmol) are diluted in a 2 to 1 mixture of dimethylformamide and tetrahydrofuran (1.5 mL) and the resulting solution is stirred for 5 minutes. A solution (4-nitro-3-trifluoromethyl-phenyl)-piperidin-4-yl-amine hydrochloride (114 mg; 0.35 mmol, prepared in accordance with Example 8) in dimethylformamide (0.5 mL) is added and the reaction is then stirred for 2 hours at room temperature. Following dilution with dichloromethane (10 mL), the organic layer is sequentially washed with water (5 mL), aq. sat. sodium hydrogen carbonate (2×5 mL), is dried over magnesium sulfate and concentrated under reduced pressure. The residue obtained is finally purified by preparative HPLC to deliver the desired product in pure form (18 mg; 0.05 mmol). The structure was confirmed using Protocol II-F. Calculated mass=562; observed mass=563; HPLC retention time=12.14 min.

A solution of 4-(4-hydroxy-phenyl)-piperazine-1-carboxylic acid tert-butyl ester (1.5 g, 5.4 mmol) in dry tetrahydrofuran (5 mL) is added to suspension of sodium hydride (431 mg, 60% in oil, 10.8 mmol) in dry tetrahydrofuran (35 mL). After 15 minutes reaction time, a solution of 1-bromomethyl-4-trifluoromethyl-benzene (1.9 g, 8.1 mmol) in tetrahydrofuran (5 mL) is added. The reaction is stirred for 16 hours at room temperature, is filtered and concentrated under vacuum. The residue obtained is diluted in ethyl acetate (40 mL) and the organic layer is washed with water (3×20 mL), is dried over magnesium sulfate, filtered and concentrated under vacuum. The residue obtained is dissolved in a 1 to 1 mixture of dichloromethane and trifluoroacetic acid (30 mL), and stirred for 30 minutes. The mixture is then concentrated under vacuum, and co-evaporated in dichloromethane (30 mL). The resulting residue is diluted in diethylether (5 mL) and a molar solution of hydrochloric acid in diethylether is added (10 mL). The precipitate formed is filtered, washed with diethylether (10 mL) and dried under vacuum. The desired product is isolated as hydrochloride as a colorless solid in the presence of traces of solvent.

Example 37

Preparation of 3-{4-[4-(4-trifluoromethyl-benzyloxy)-phenyl]-piperazin-1-yl}-propionic acid lithium salt intermediate

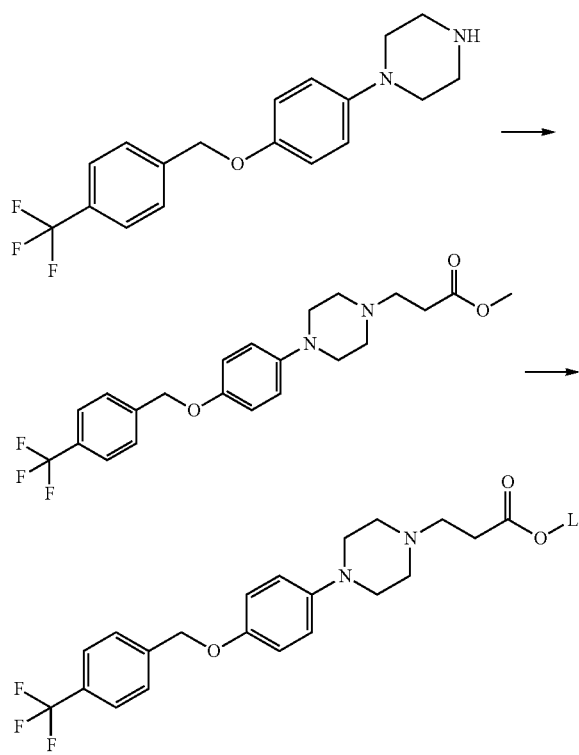

1-[4-(4-Trifluoromethyl-benzyloxy)-phenyl]-piperazine (277 mg; 0.82 mmol, prepared in accordance with Example 36) and methylacrylate (189 mg; 1.37 mmol) are diluted with water (1.5 mL). The resulting mixture is irradiated in a monomode microwave oven for 30 minutes at 120° C.

The reaction is diluted with water (2.5 mL) and lithium hydroxide (47 mg; 0.90 mmol) is added. The mixture is then irradiated twice in a mono-mode microwave oven for 10 minutes at 100° C. The reaction is diluted with acetonitrile (20 mL); the precipitate obtained is filtered and dried in a vacuum oven. The desired product is obtained as lithium salt in pure form (163 mg; 0.40 mmol).

Example 38

Preparation of 4-fluoro-2-methoxy-1-nitro-benzene Intermediate

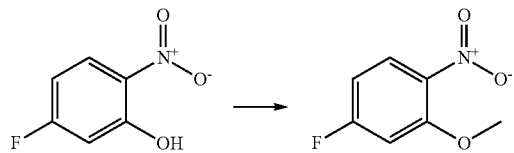

5-Fluoro-2-nitrophenol (3.14 g; 20 mmol) and potassium carbonate (2.76 g; 20 mmol) are place in a round bottom flask and are flushed with argon. Dry dimethylformamide (60 mL) is added followed by dimethylsulfate (3.8 mL; 40 mmol). The reaction is stirred for 2 days at room temperature. Dichloromethane (120 mL) and water (60 mL) are then added. The aqueous phase is extracted with dichloromethane (100 mL) and the combined organic layers are washed three times with aq. sat. sodium hydrogencarbonate (50 mL), twice with aq. 1N hydrochloric acid (50 mL) and with brine (50 mL). The organic layer is then dried over magnesium sulfate and is concentrated under reduced pressure. The desired product is isolated in the presence of dimethylformamide (4.39 g).

Example 39

Preparation of (3-methoxy-4-nitro-phenyl)-piperidin-4-yl-amine hydrochloride intermediate

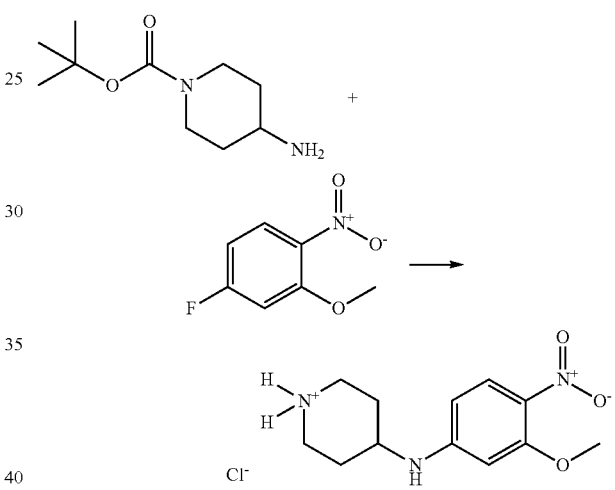

Crude 4-fluoro-2-methoxy-1-nitro-benzene (2.10 g; 12.3 mmol, prepared in accordance with Example 38) is dissolved in dimethylsulfoxide (15 mL) and 4-amino-piperidine-1-carboxylic acid tert-butyl ester (2.40 g; 12.0 mmol) followed by potassium carbonate (3.31 g; 24.0 mmol) are added. The resulting mixture is heated to 100° C. and is reacted for 17 hours. The reaction is then allowed to reach room temperature and is diluted with dichloromethane (100 mL). The organic layer is then washed with water (50 mL), aq. sat ammonium chloride (50 mL), water (50 mL) and brine (30 mL). The organic layer is dried over magnesium sulfate and is concentrated under reduce pressure to afford the desired Boc-protected intermediate. The crude product is dissolved in dichloromethane (20 mL) and trifluoroacetic acid (10 mL) is slowly added under vigorous stirring. After 1 hour reaction time, the reaction mixture is concentrated under reduced pressure and co-evaporated twice with dichlolomethane (20 mL each). The residue obtained is triturated with a 4N solution of hydrochloric acid in dioxane (20 mL). The precipitate formed is then filtered and dried under vacuum to afford the desired (3-Methoxy-4-nitro-phenyl)-piperidin-4-yl-amine as hydrochloride (3.22 g; 11.2 mmol).

Example 40

Preparation of 1-[4-(3-methoxy-4-nitro-phenylamino)-piperidin-1-yl]-3-{4-[4-(4-trifluoromethyl-benzyloxy)-phenyl]-piperazin-1-yl}-propan-1-one

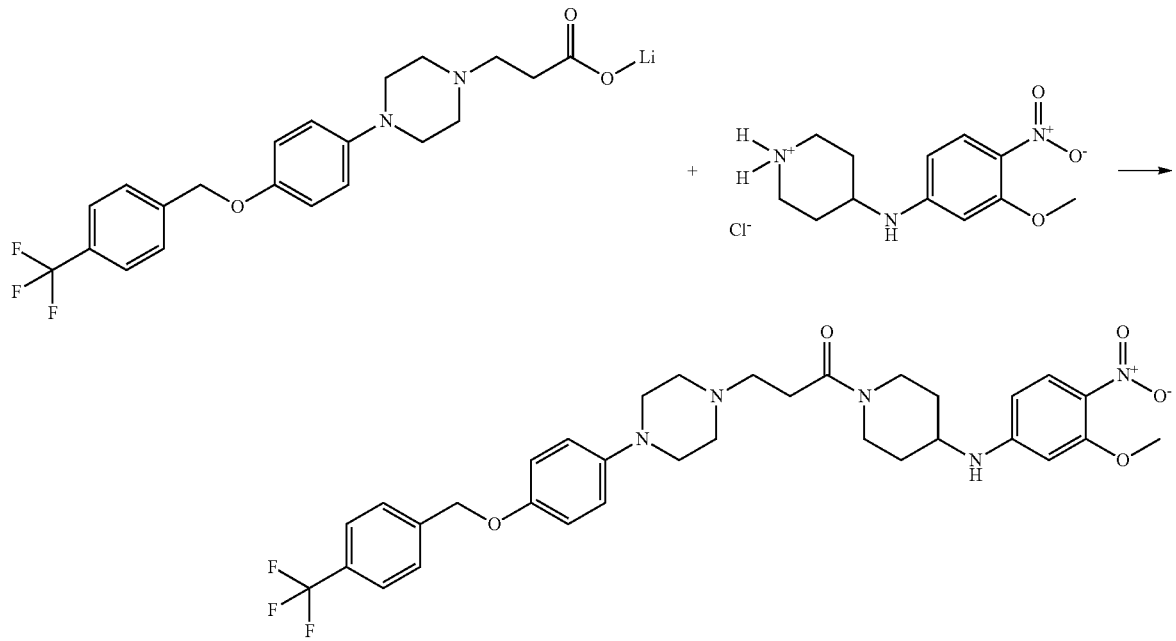

3-{4-[4-(4-Trifluoromethyl-benzyloxy)-phenyl]-piperazin-1-yl}-propionic acid lithium salt (160 mg; 0.39 mmol, prepared in accordance with Example 37), diisopropylethyl amine (134 μL; 0.77 mmol) and tetramethyl-O-(1H-benzotriazol-1-yl)uronium hexafluorophosphate (127 mg; 0.39 mmol) are diluted in a 2 to 1 mixture of dimethylformamide and tetrahydrofuran (1.5 mL) and the resulting solution is stirred for 5 minutes. A solution (3-methoxy-4-nitro-phenyl)-piperidin-4-yl-amine hydrochloride (100 mg; 0.35 mmol, prepared in accordance with Example 39) in dimethylformamide (0.5 mL) is added and the reaction is stirred for 3 hours at room temperature. Following dilution with dichloromethane (10 mL), the organic layer is sequentially washed with water (5 mL), aq. sat. sodium hydrogen carbonate (2×5 mL), is dried over magnesium sulfate and concentrated under reduced pressure. The residue obtained is finally purified by preparative HPLC to deliver the desired product in pure form (29.5 mg; 0.05 mmol). The structure was confirmed using Protocol II-A. Calculated mass=642; observed mass=642; HPLC retention time=3.68 min.

Example 41

Preparation of 1-benzyl-4-(4-phenoxy-phenyl)-piperidin-4-ol Intermediate

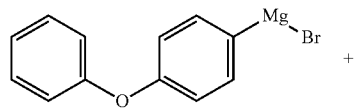

A solution of 4-phenoxyphenylmagnesium bromide in tetrahydrofuran (30 mL, 15 mmol) is introduced in a flame dried flask placed under argon atmosphere. A solution of 1-benzyl-4-piperidone (2.84 g, 15 mmol) in dry tetrahydrofuran (12 mL) is added dropwise, while the temperature is maintained below 20° C. with an ice bath. After completion of the addition, the mixture is allowed to reach room temperature and is further stirred for 2 hours. Ice is then added to the reaction mixture and 1 N hydrochloric acid is added until the precipitate formed is completely dissolved. The reaction is then diluted with diethyl ether (100 mL) and washed with water (50 mL). The aqueous layer is then extracted with diethyl ether (2×50 mL) and the combined organic layers are sequentially washed with saturated aqueous sodium hydrogencarbonate (2×50 mL) and with water (50 mL), are then dried over magnesium sulphate, filtered and concentrated under vacuum. The crude product is then purified by column chromatography on silica gel (dichloromethane and then diethyl ether). The desired product is isolated as a colorless solid (1.74 g, 33% yield).

Example 42

Preparation of 4-(4-phenoxy-phenyl)-piperidine trifluoroacetate intermediate

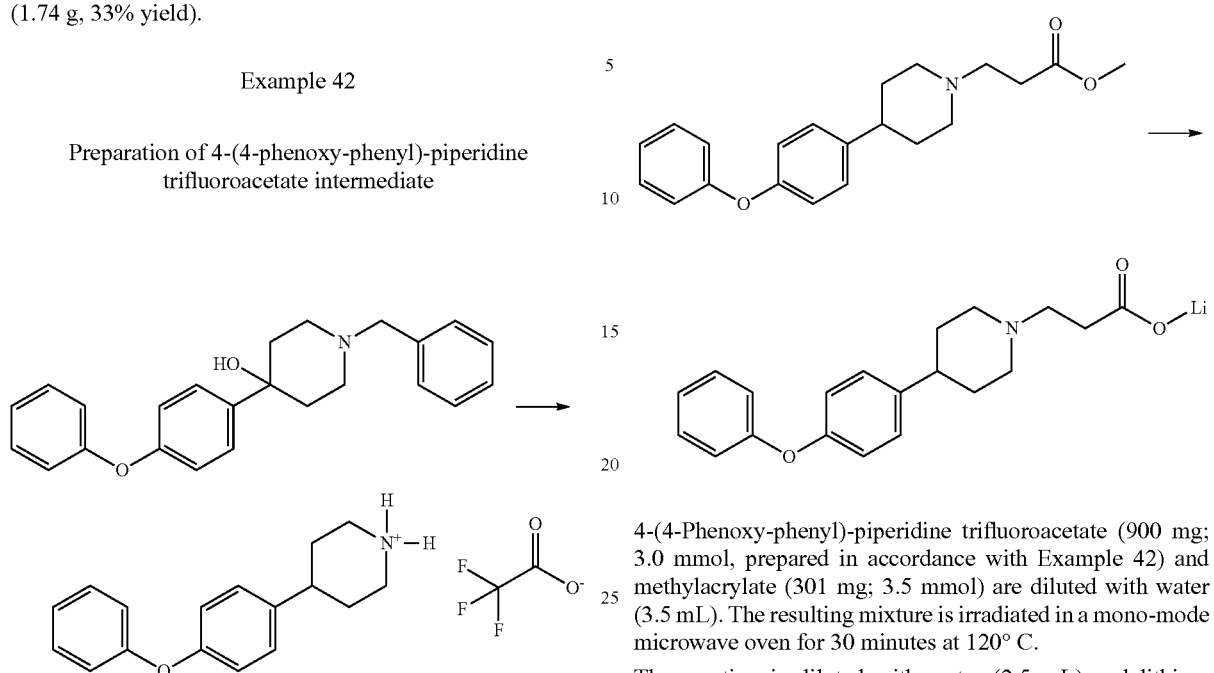

The starting alcohol (3.47 g, 9.6 mmol, prepared in accordance with Example 41) is treated with trifluoroacetic acid (6 mL) and the resulting mixture is irradiated at 130° C. in the mono-mode microwave oven for 15 minutes. The mixture is concentrated under vacuum, the obtained residue is triturated with diethyl ether (20 mL) and the solvent is finally removed under reduced pressure. The product isolated (6.6 g) is dissolved in methanol (350 mL) and 10% palladium on charcoal is added (800 mg). The resulting suspension is then reacted under hydrogen pressure (4 bar) for 5 hours at 75° C. After removal of the catalyst by filtration, the filtrate is concentrated under vacuum. The obtained residue is triturated with diethyl ether (50 mL) the precipitate is filtered and finally dried under vacuum. The desired product is obtained as a light yellow solid (3.26 g, 92% yield).

Example 43

Preparation of 3-[4-(4-phenoxy-phenyl)-piperidin-1-yl]-propionic acid lithium salt intermediate

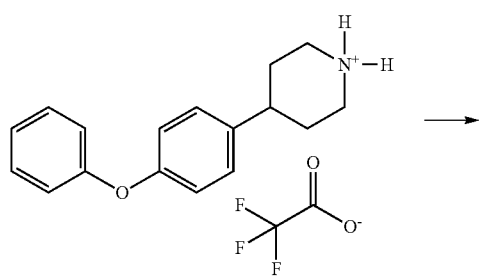

4-(4-Phenoxy-phenyl)-piperidine trifluoroacetate (900 mg; 3.0 mmol, prepared in accordance with Example 42) and methylacrylate (301 mg; 3.5 mmol) are diluted with water (3.5 mL). The resulting mixture is irradiated in a mono-mode microwave oven for 30 minutes at 120° C.

The reaction is diluted with water (2.5 mL) and lithium hydroxide (143 mg; 6.0 mmol) is added. The mixture is then irradiated twice in a mono-mode microwave oven for 10 minutes at 100° C. The reaction is diluted with acetonitrile (20 mL); the precipitate obtained is filtered and dried in a vacuum oven. The desired product is obtained as lithium salt in pure form (810 mg; 2.44 mmol).

Example 44

Preparation of 4-(4-nitro-3-trifluoromethyl-phenoxy)-piperidine hydrochloride intermediate

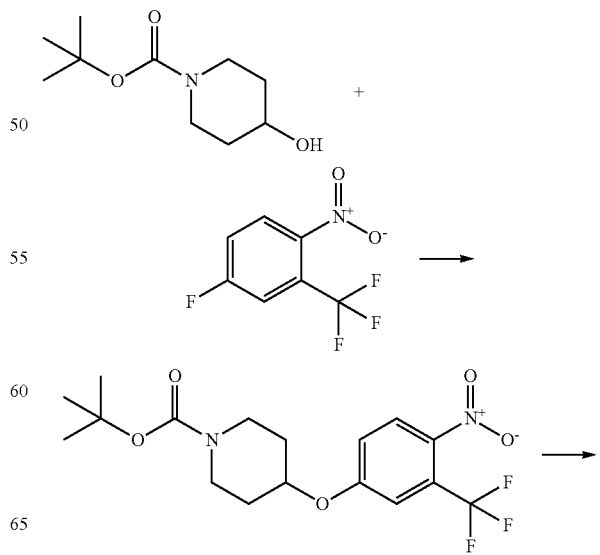

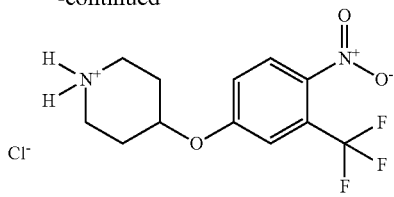

A solution of 4-hydroxy-piperidine-1-carboxylic acid tert-butyl ester (2.2 g; 11.0 mmol), 5-fluoro-2-nitrobenzotrifluoride (2.5 g; 11.9 mmol) and potassium carbonate (3.0 g; 22.0 mmol) in dimethylsulfoxide (25 mL) is heated over night at 100° C. The mixture is then diluted with dichloromethane (200 mL) and is washed with water (25 mL), aq. sat. ammonium chloride (25 mL) and twice with water (25 mL). The organic layer is then filtered and the filtrate is evaporated under reduced pressure.

The product is dissolved in a 1 to 1 mixture of dichloromethane and trifluoroacetic acid (16 mL) and the resulting solution is stirred at room temperature until complete conversion is observed (about 30 minutes). After concentration under reduced pressure, the residue obtained is co-evaporated with dichloromethane (3×30 mL). The crude product is diluted in diethylether (25 mL) and a molar solution of hydrochloric acid in diethylether (15 mL) is added under stirring. The solid obtained is finally filtered and is dried under high vacuum to yield the desired product as hydrochloride (1.86 g; 5.7 mmol).

Example 45

Preparation of 1-[4-(4-nitro-3-trifluoromethyl-phenoxy)-piperidin-1-yl]-3-[4-(4-phenoxy-phenyl)-piperidin-1-yl]-propan-1-one

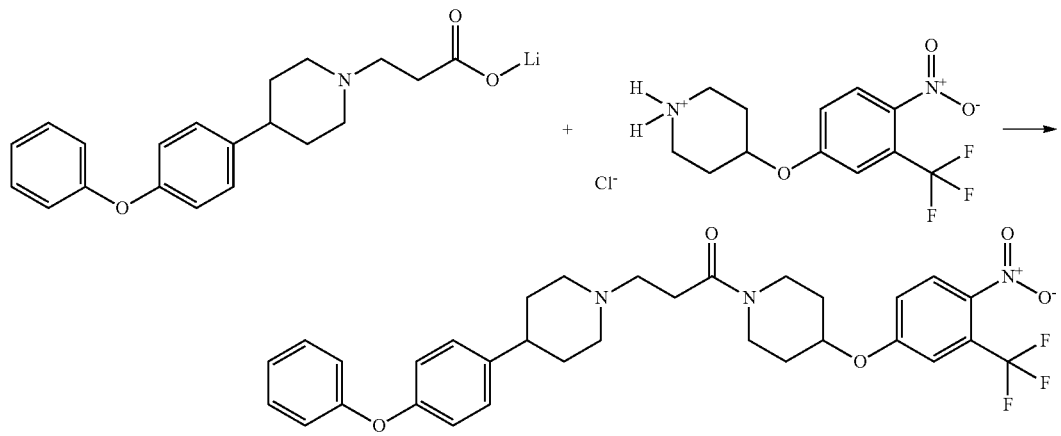

3-[4-(4-Phenoxy-phenyl)-piperidin-1-yl]-propionic acid lithium salt (115 mg; 0.36 mmol, prepared in accordance with Example 43), diisopropylethyl amine (124 µL; 0.71 mmol) and tetramethyl-O-(1H-benzotriazol-1-yl)uronium hexafluorophosphate (117 mg; 0.36 mmol) are diluted in a 2 to 1 mixture of dimethylformamide and tetrahydrofuran (1.5 mL) and the resulting solution is stirred for 5 minutes. A solution 4-(4-nitro-3-trifluoromethyl-phenoxy)-piperidine hydrochloride (103 mg; 0.32 mmol, prepared in accordance with Example 44) in dimethylformamide (0.5 mL) is added and the reaction is then stirred for 3 hours at room temperature. Following dilution with dichloromethane (10 mL), the organic layer is sequentially washed with water (5 mL), aq. sat. sodium hydrogen carbonate (2×5 mL), is dried over magnesium sulfate and concentrated under reduced pressure. The residue obtained is finally purified by preparative HPLC to deliver the desired product in pure form (56 mg; 0.09 mmol). The structure was confirmed using Protocol I-B. Calculated mass=598; observed mass=598; HPLC retention time=5.22 min.

Example 46

Preparation of 4-(4-trifluoromethylsulfanyl-phenylamino)-piperidine-1-carboxylic acid tert-butyl ester intermediate

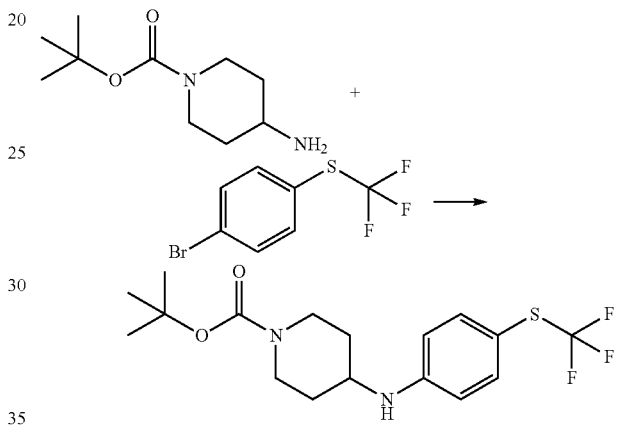

Tris(dibenzylideneacetone)dipalladium (23 mg; 0.03 mmol), 2,2'-bis(diphenylphosphino)-1,1'-binaphthyl (46 mg; 0.07 mmol), sodium tert-butoxide (176 mg; 1.83 mmol), 1-bromo-4-trifluoromethylsulfanyl-benzene (314 mg; 1.22 mmol) and 4-amino-piperidine-1-carboxylic acid tert-butyl ester (302 mg; 1.51 mmol) are suspended in dry toluene (5 mL) and the mixture is irradiated in a mono-mode microwave oven for 20 minutes at 120° C. The mixture is then cooled down to room temperature, is diluted with ethyl acetate (15 mL), filtered and concentrated under reduced pressure. The crude residue is then diluted in dichloromethane (15 mL) and filtered over a short silica gel pad. The desired product is eluted from the silica gel pad with dichloromethane and the fractions of interest are concentred under reduced pressure to afford the desired product (220 mg; 0.59 mmol).

Example 47

Preparation of piperidin-4-yl-(4-trifluoromethylsulfanyl-phenyl)-amine hydrochloride intermediate

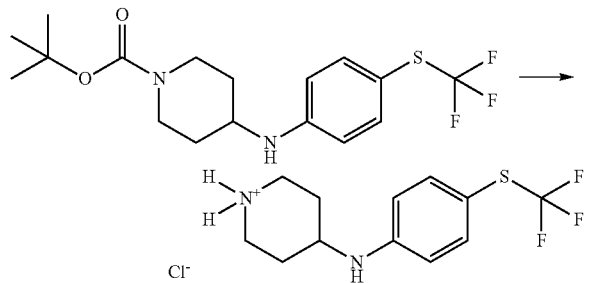

4-(4-Trifluoromethylsulfanyl-phenylamino)-piperidine-1-carboxylic acid tert-butyl ester (200 mg; 0.53 mmol, prepared in accordance with Example 46) is dissolved in a 1 to 1 mixture of dichloromethane and trifluoroacetic acid (2 mL), and stirred for 90 minutes. The mixture is concentrated under reduced pressure and co-evaporated with dichloromethane (2×10 mL). The resulting residue is diluted in ethylacetate (5 mL) and a 4N solution of hydrochloric acid in dioxane (5 mL) is added. A precipitate is obtained which is filtered and dried under high vacuum to afford the desired product as hydrochloride (168 mg; 0.53 mmol).

Example 48

Preparation of 4-[4-(4-trifluoromethyl-phenyl)-piperazin-1-yl]-1-[4-(4-trifluoromethylsulfanyl-phenylamino)-piperidin-1-yl]-butan-1-one 4-[4-(4-Trifluoromethyl-phenyl)-piperazin-1-yl]-butyric acid lithium salt (16 mg; 0.05 mmol, prepared in accordance with Example 3) diisopropylethyl amine (18 µL; 0.10 mmol) and tetramethyl-O-(1H-benzotriazol-1-yl)uronium hexafluorophosphate (19 mg; 0.05 mmol) are diluted in a 2 to 1 mixture of dimethylformamide and tetrahydrofuran (1.5 mL) and the resulting solution is stirred for 5 minutes. A solution piperidin-4-yl-(4-trifluoromethylsulfanyl-phenyl)-amine hydrochloride (16 mg; 0.05 mmol, prepared in accordance with Example 47) in dimethylformamide (0.5 mL) is added and the reaction is then stirred for 105 minutes at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (10 mg; 0.02 mmol). The structure was confirmed using Protocol II-A. Calculated mass=575; observed mass=575; HPLC retention time=3.65 min.

Example 49

Preparation of 4-(5-trifluoromethyl-pyridin-2-ylamino)-piperidine-1-carboxylic acid tert-butyl ester intermediate

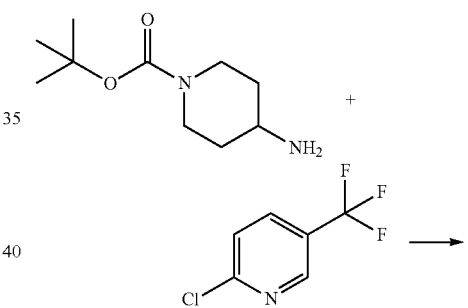

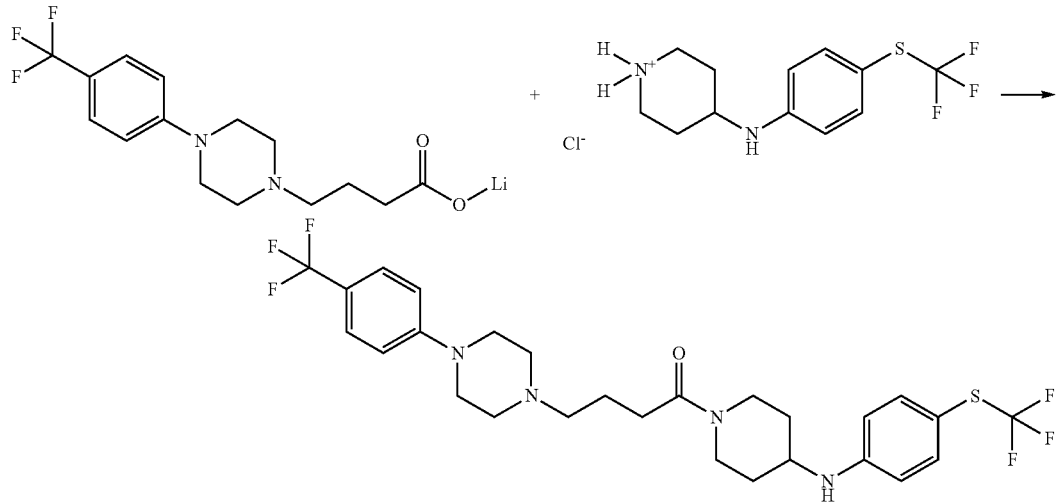

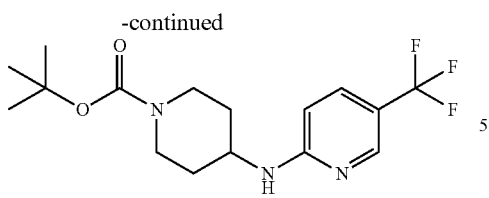

A solution of 4-amino-piperidine-1-carboxylic acid tert-butyl ester (400 mg; 2.0 mmol), 2-chloro-5-trifluoromethyl-pyridine (362 mg; 2.0 mmol) and potassium carbonate (280 mg; 2.0 mmol) in dimethylsulfoxide (3 mL) is heated 10 hours at 120° C. The reaction is then cooled to room temperature, water (20 mL) is added and the pH is set to 4-5 by addition of aq. 1N hydrochloric acid. The aqueous layer is then extracted with dichloromethane (4×20 mL), the combined organic layers are dried over magnesium sulfate, filtered and concentrated under reduced pressure. The residue obtained is finally purified by column chromatography on silica gel (dichloromethane and then dichloromethane:ethylacetate 8:1) to afford the desired product (380 mg; 1.10 mmol).

Example 50

Preparation of piperidin-4-yl-(5-trifluoromethyl-pyridin-2-yl)-amine hydrochloride intermediate

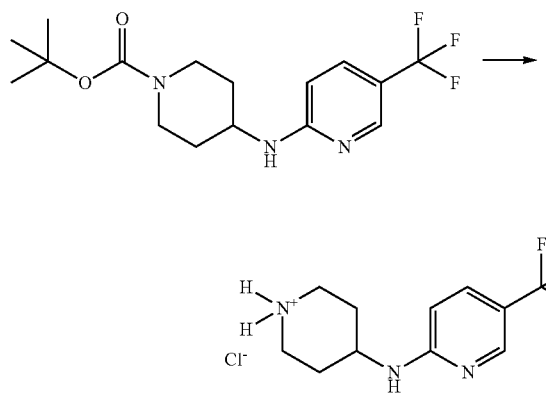

4-(5-Trifluoromethyl-pyridin-2-ylamino)-piperidine-1-carboxylic acid tert-butyl ester (460 mg; 1.33 mmol, prepared in accordance with Example 49) is dissolved in dichloromethane (6 mL) and trifluoroacetic acid (1 mL) is added under stirring. After 30 minutes reaction time, the solution is concentrated under reduced pressure and the residue obtained is co-evaporated with dichloromethane (5 mL). The product isolated is dissolved in dioxane (2 mL) and a 4N solution of hydrochloric acid in dioxane (3 mL) is added. The precipitate formed is filtered, rapidly rinsed with a small amount of dioxane and is dried under high vacuum to afford the desired product as hydrochloride (352 mg; 1.25 mmol).

Example 51

Preparation of 4-[4-(4-trifluoromethyl-phenyl)-piperazin-1-yl]-1-[4-(5-trifluoromethyl-pyridin-2-ylamino)-piperidin-1-yl]-butan-1-one

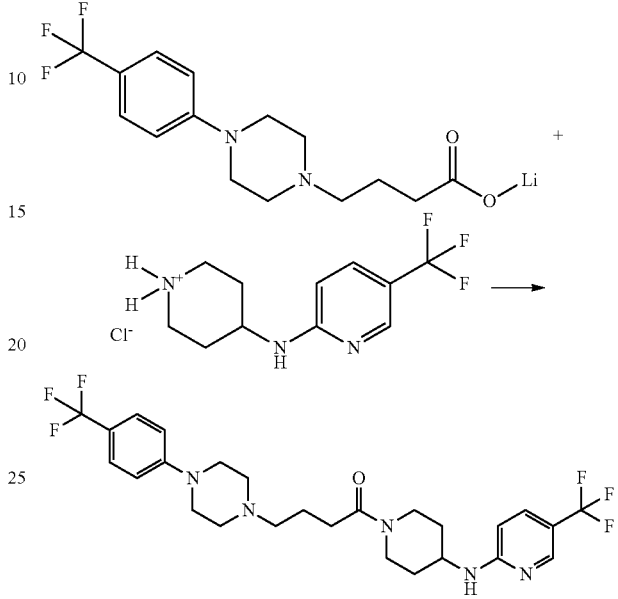

4-[4-(4-Trifluoromethyl-phenyl)-piperazin-1-yl]-butyric acid lithium salt (16 mg; 0.05 mmol, prepared in accordance with Example 3), diisopropylethyl amine (18 µL; 0.10 mmol) and tetramethyl-O-(1H-benzotriazol-1-yl)uronium hexafluorophosphate (19 mg; 0.05 mmol, prepared in accordance with Example 50) are diluted in a 2 to 1 mixture of dimethylformamide and tetrahydrofuran (1.5 mL) and the resulting solution is stirred for 5 minutes. A solution piperidin-4-yl-(5-trifluoromethyl-pyridin-2-yl)-amine hydrochloride (14 mg; 0.05 mmol) in dimethylformamide (0.5 mL) is added and the reaction is then stirred for 150 minutes at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (14 mg; 0.03 mmol). The structure was confirmed using Protocol I-B. Calculated mass=544; observed mass=544; HPLC retention time=4.47 min.

Example 52

Preparation of 4-(4-trifluoromethoxy-phenylamino)-piperidine-1-carboxylic acid tert-butyl ester intermediate

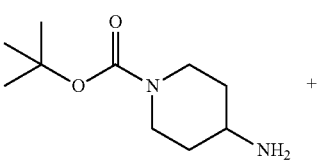

-continued

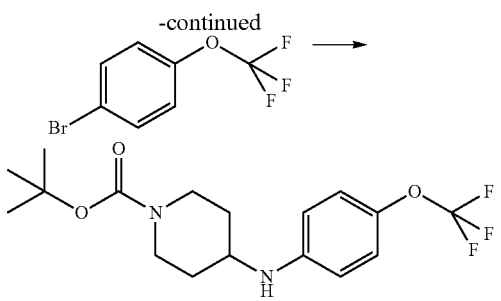

Tris(dibenzylideneacetone)dipalladium (30 mg; 0.03 mmol), 2,2'-bis(diphenylphosphino)-1,1'-binaphthyl (62 mg; 0.1 mmol), sodium tert-butoxide (240 mg; 2.5 mmol), 1-bromo-4-trifluoromethoxy-benzene (410 mg; 1.7 mmol) and 4-amino-piperidine-1-carboxylic acid tert-butyl ester (421 mg; 2.1 mmol) are suspended in dry toluene (5 mL) and the mixture is irradiated in a mono-mode microwave oven for 30 minutes at 120° C. The mixture is then cooled down to room temperature, is diluted with ethyl acetate (15 mL), filtered over Celite and concentrated under reduced pressure. The crude residue is then diluted in dichloromethane (15 mL) and filtered over a short silica gel pad. The desired product is eluted from the silica gel pad (dichloromethane (150 mL) followed by dichloromethane:methanol 98:2 (100 mL)). The fractions of interest are collected, pooled and concentrated under reduced pressure to afford the desired product (396 mg; 1.1 mmol).

Example 53

Preparation of piperidin-4-yl-(4-trifluoromethoxy-phenyl)-amine hydrochloride intermediate

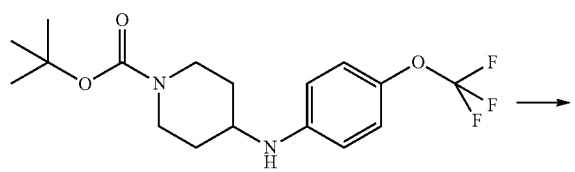

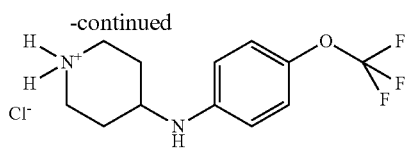

4-(4-Trifluoromethoxy-phenylamino)-piperidine-1-carboxylic acid tert-butyl ester (380 mg; 1.06 mmol, prepared in accordance with Example 52) is dissolved in a 1 to 1 mixture of dichloromethane and trifluoroacetic acid (2 mL), and stirred for 90 minutes. The mixture is concentrated under reduced pressure and co-evaporated with dichloromethane (2×10 mL). The resulting residue is diluted in ethylacetate (5 mL) and a 4N solution of hydrochloric acid in dioxane (5 mL) is added. A precipitate is obtained which is filtered and dried under high vacuum to afford the desired product as hydrochloride (275 mg; 0.93 mmol).

Example 54

Preparation of 1-[4-(4-trifluoromethoxy-phenylamino)-piperidin-1-yl]-4-[4-(4-trifluoromethyl-phenyl)-piperazin-1-yl]-butan-1-one

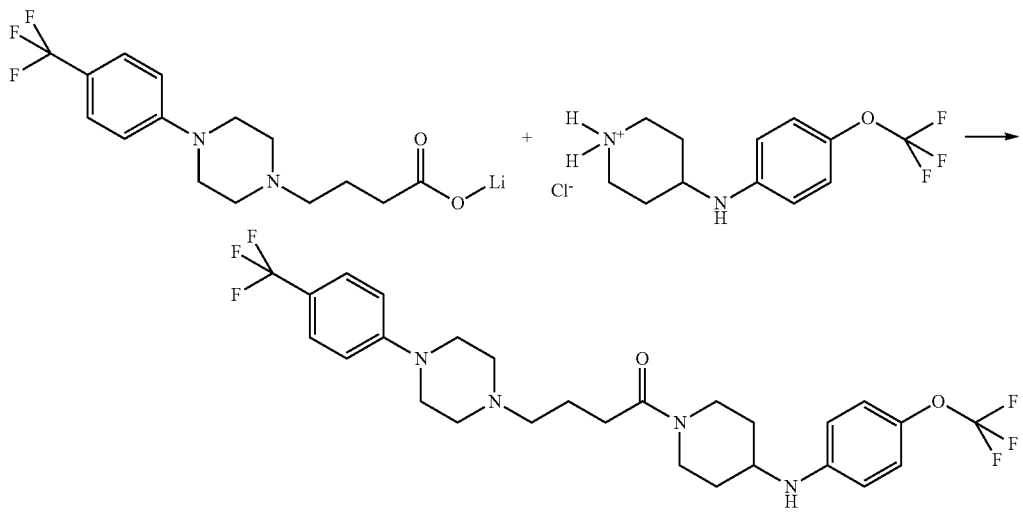

4-[4-(4-Trifluoromethyl-phenyl)-piperazin-1-yl]-butyric acid lithium salt (16 mg; 0.05 mmol, prepared in accordance with Example 3), diisopropylethyl amine (18 µL; 0.10 mmol) and tetramethyl-O-(1H-benzotriazol-1-yl)uronium hexafluorophosphate (19 mg; 0.05 mmol) are diluted in a 2 to 1 mixture of dimethylformamide and tetrahydrofuran (1.5 mL) and the resulting solution is stirred for 5 minutes. A solution piperidin-4-yl-(4-trifluoromethoxy-phenyl)-amine hydrochloride (15 mg; 0.05 mmol, prepared in accordance with Example 53) in dimethylformamide (0.5 mL) is added and the reaction is then stirred for 105 minutes at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (23 mg; 0.04 mmol). The structure was confirmed using Protocol I-B. Calculated mass=559; observed mass=559; HPLC retention time=4.78 min.

Example 55

Preparation of 4-(4-trifluoromethyl-benzyloxy)-piperidine hydrochloride intermediate

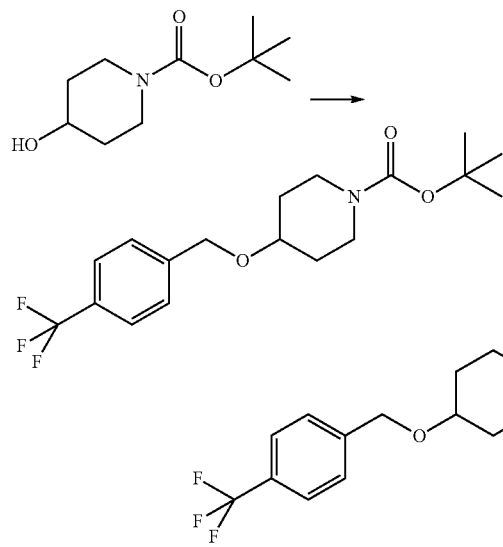

As solution of 4-hydroxy-piperidine-1-carboxylic acid tert-butyl ester (2 g; 9.9 mmol) in tetrahydrofuran (5 mL) is added to a suspension of sodium hydride (1.19 g of a 60% suspension in oil; 29.8 mmol) in tetrahydrofuran (35 mL) under inert atmosphere. After 10 minutes, a solution of 1-bromomethyl-4-trifluoromethyl-benzene (3.6 g; 14.9 mmol) in tetrahydrofuran (5 mL) is added and the resulting mixture is stirred for 16 hours at room temperature. The organic layer is then washed with aq. sat. ammonium chloride (10 mL), and water (10 mL). The organic layer is separated, is dried over magnesium sulfate, filtered and concentrated under reduced pressure.

The crude product is dissolved in dichloromethane (10 mL) and trifluoroacetic acid (10 mL) is added. After 30 minutes reaction time, the mixture is concentrated under reduced pressure and co-evaporated twice with dichloromethane (10 mL). The crude residue is then diluted in diethylether (4 mL) and a 1M solution of hydrochloric acid in diethylether (10 mL) is added under stirring. The solid formed is filtered and is dried under high vacuum to afford the desired product as hydrochloride (1.3 g; 4.41 mmol).

Example 56

Preparation of 3-[4-(4-trifluoromethyl-benzyloxy)-piperidin-1-yl]-propionic acid lithium salt intermediate

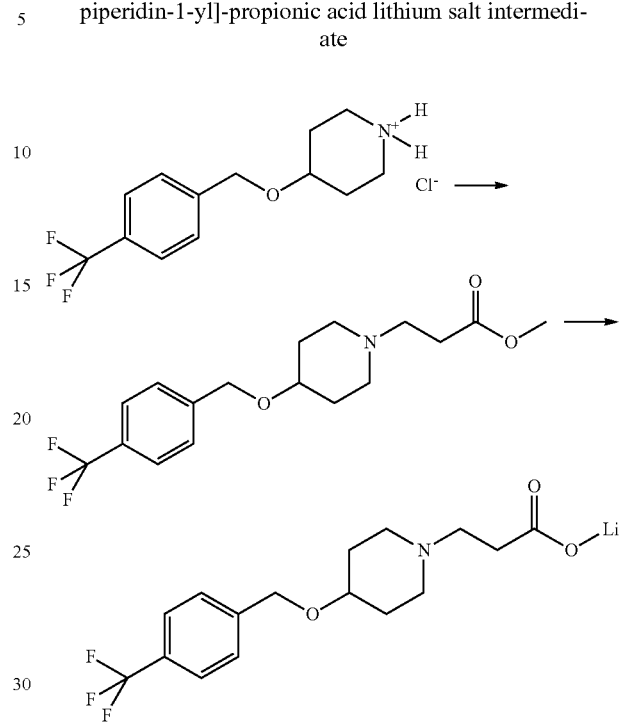

4-(4-Trifluoromethyl-benzyloxy)-piperidine hydrochloride (910 mg; 3.09 mmol, prepared in accordance with Example 55) and triethylamine (433 µL; 3.09 mmol) are suspended in water (1.2 mL). Methylacrylate (310 mg; 3.6 mmol) is added and the resulting mixture is irradiated in a mono-mode microwave oven for 20 minutes at 120° C.

Lithium hydroxide (148 mg; 6.2 mmol) is added and a second irradiation is applied for 10 minutes at 100° C. The reaction is diluted with acetonitrile (15 mL), the precipitate is filtered and dried in a vacuum oven. The desired product is obtained as lithium salt (587 mg; 1.74 mmol).

Example 57

Preparation of 1-[4-(4-nitro-3-trifluoromethyl-phenylamino)-piperidin-1-yl]-3-[4-(4-trifluoromethyl-benzyloxy)-piperidin-1-yl]-propan-1-one

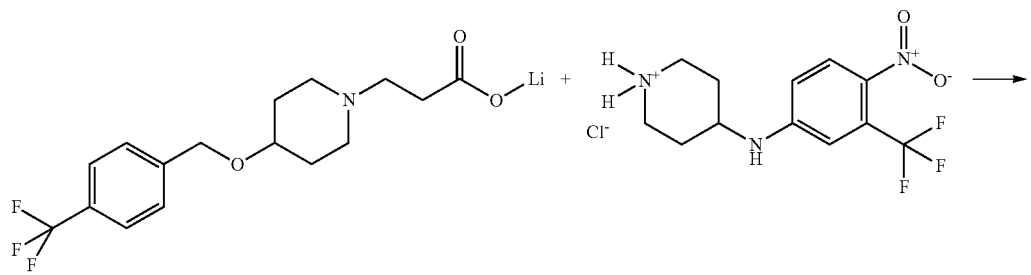

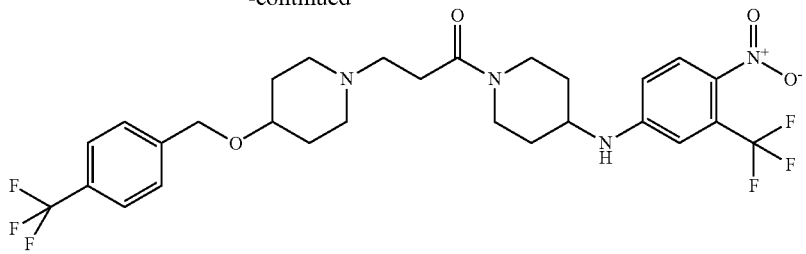

3-[4-(4-Trifluoromethyl-benzyloxy)-piperidin-1-yl]-propionic acid lithium salt (130 mg; 0.36 mmol, prepared in accordance with Example 56), diisopropylethyl amine (87 μL; 0.50 mmol) and tetramethyl-O-(1H-benzotriazol-1-yl)uronium hexafluorophosphate (132 mg; 0.35 mmol) are diluted in a 2 to 1 mixture of dimethylformamide and tetrahydrofuran (1.5 mL) and the resulting solution is stirred for 5 minutes. A solution (4-nitro-3-trifluoromethyl-phenyl)-piperidin-4-yl-amine hydrochloride (15 mg; 0.05 mmol, prepared in accordance with Example 8) in dimethylformamide (0.5 mL) is added and the reaction is then stirred for 105 minutes at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (96 mg; 0.16 mmol). The structure was confirmed using Protocol I-B. Calculated mass=603; observed mass=603; HPLC retention time=5.038 min.

Example 58

Preparation of 3-[4-(4-benzyloxy-phenyl)-piperazin-1-yl]-1-[4-(4-nitro-3-trifluoromethyl-phenoxy)-piperidin-1-yl]-propan-1-one 3-[4-(4-Benzyloxy-phenyl)-piperazin-1-yl]-propionic acid lithium salt (34 mg; 0.10 mmol, prepared in accordance with Example 22), diisopropylethyl amine (35 μL; 0.20 mmol) and tetramethyl-O-(1H-benzotriazol-1-yl)uronium hexafluorophosphate (38 mg; 0.10 mmol) are diluted in a 2 to 1 mixture of dimethylformamide and tetrahydrofuran (1.5 mL) and the resulting solution is stirred for 5 minutes. A solution of 4-(4-nitro-3-trifluoromethyl-phenoxy)-piperidine hydrochloride (33 mg; 0.10 mmol, prepared in accordance with Example 44) in dimethylformamide (0.5 mL) is added and the reaction is then stirred for 2 hours at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (19 mg; 0.03 mmol). The structure was confirmed using Protocol I-B. Calculated mass=613; observed mass=613; HPLC retention time=4.74 min.

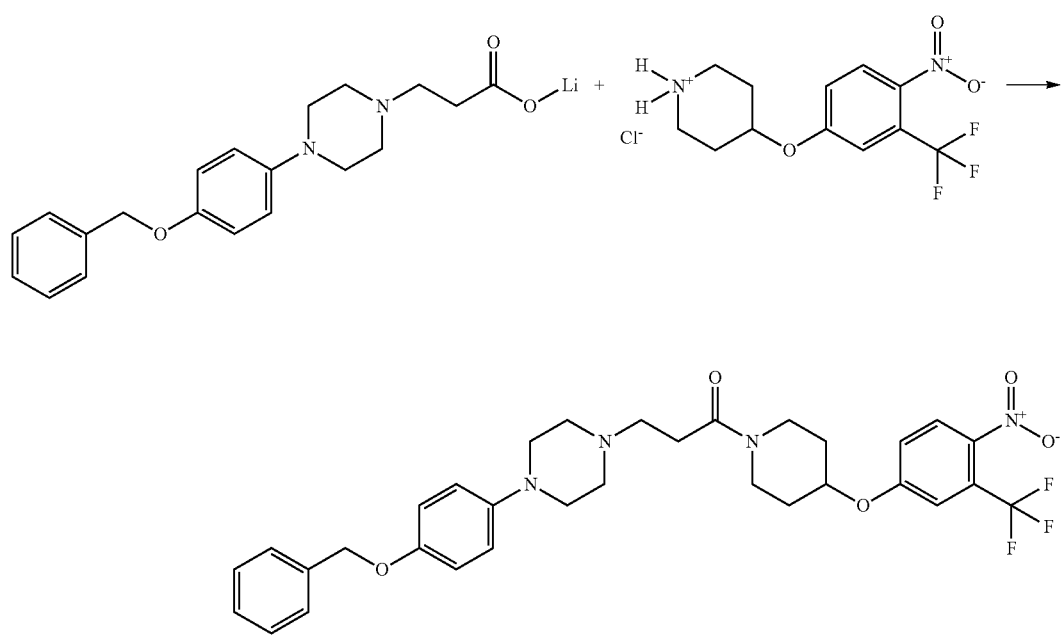

Example 59

Preparation of 3-[4-(4-chloro-phenyl)-piperazin-1-yl]-2-methyl-propionic acid methyl ester intermediate

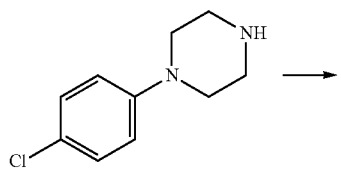

1-(4-Chloro-phenyl)-piperazine (392 mg; 2.0 mmol) and sodium ethoxide (150 mg; 2.21 mmol) are dissolved in ethanol (2 mL) and irradiated for 5 minutes in a mono-mode microwave oven at 60° C. 2-Methyl-acrylic acid methyl ester (400 µL; 4.0 mmol) is then added and the resulting mixture is irradiated for 50 minutes in a mono-mode microwave oven at 100° C. The reaction is concentrated under reduced pressure, diluted in ethylacetate (10 mL) and extracted with water (2×5 mL). The organic phase is dried over magnesium sulphate, filtered and concentrated under reduced pressure to afford the desired product (586 mg; 1.98 mmol).

Example 60

Preparation of 3-[4-(4-chloro-phenyl)-piperazin-1-yl]-2-methyl-propionic acid lithium salt intermediate

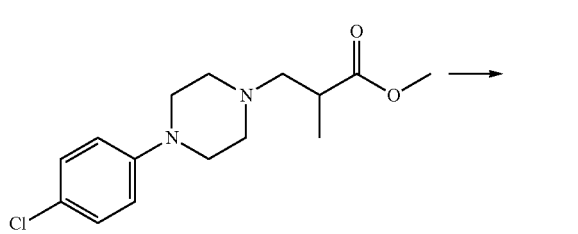

3-[4-(4-Chloro-phenyl)-piperazin-1-yl]-2-methyl-propionic acid methyl ester (586 mg; 1.98 mmol, prepared in accordance with Example 59) and lithium hydroxide (60 mg; 2.50 mmol) are suspended in a mixture of tetrahydrofuran (4 mL) and water (1 mL). The resulting mixture is irradiated in a mono-mode microwave oven for 50 minutes at 100° C. The mixture is then diluted with acetonitrile until precipitation occurs. The solid formed is then filtered and dried under high vacuum to afford the desired product (238 mg; 0.83 mmol).

Example 61

Preparation of 3-[4-(4-chloro-phenyl)-piperazin-1-yl]-2-methyl-1-[4-(4-nitro-3-trifluoromethyl-phenylamino)-piperidin-1-yl]-propan-1-one

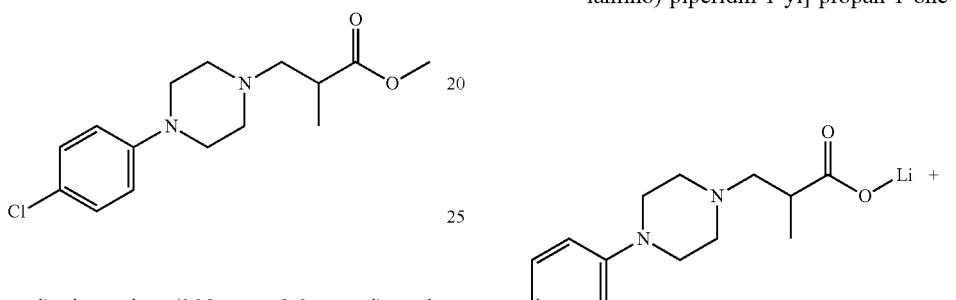

3-[4-(4-Chloro-phenyl)-piperazin-1-yl]-2-methyl-propionic acid lithium salt (62 mg; 0.22 mmol, prepared in accordance with Example 60), diisopropylethyl amine (87 µL; 0.50 mmol) and tetramethyl-O-(1H-benzotriazol-1-yl)uronium hexafluorophosphate (76 mg; 0.20 mmol) are diluted in a 2 to 1 mixture of dimethylformamide and tetrahydrofuran (1.5 mL) and the resulting solution is stirred for 5 minutes. A solution (4-nitro-3-trifluoromethyl-phenyl)-piperidin-4-yl-amine hydrochloride (63 mg; 0.20 mmol, prepared in accordance with Example 8) in dimethylformamide (0.5 mL) is added and the reaction is then stirred for 60 minutes at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (47 mg; 0.08 mmol). The structure was confirmed using Protocol I-A. Calculated mass=554; observed mass=554; HPLC retention time=3.45 min.

Example 62

Preparation of 3-[4-(4-trifluoromethyl-phenyl)-piperazin-1-yl]-2-methyl-propionic acid methyl ester intermediate

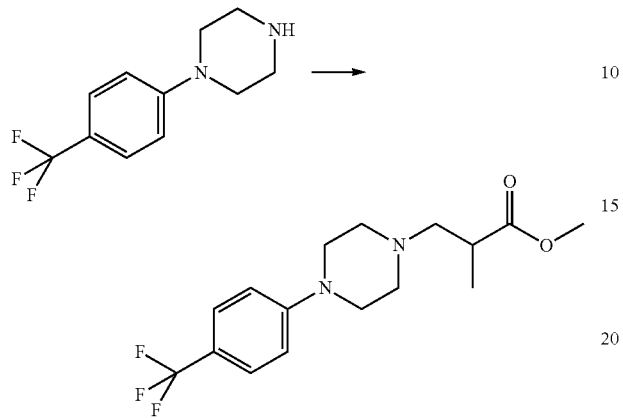

1-(4-Trifluoromethyl-phenyl)-piperazine (460 mg; 2.0 mmol) and sodium ethoxide (150 mg; 2.21 mmol) are dissolved in ethanol (2 mL) and irradiated for 5 minutes in a mono-mode microwave oven at 60° C. 2-Methyl-acrylic acid methyl ester (400 µL; 4.0 mmol) is then added and the resulting mixture is irradiated for 50 minutes in a mono-mode microwave oven at 100° C. The reaction is concentrated under reduced pressure, diluted in ethylacetate (10 mL) and extracted with water (2×5 mL). The organic phase is dried over magnesium sulphate, filtered and concentrated under reduced pressure to afford the desired product (623 mg; 1.89 mmol).

Example 63

Preparation of 3-[4-(4-trifluoromethyl-phenyl)-piperazin-1-yl]-2-methyl-propionic acid lithium salt intermediate

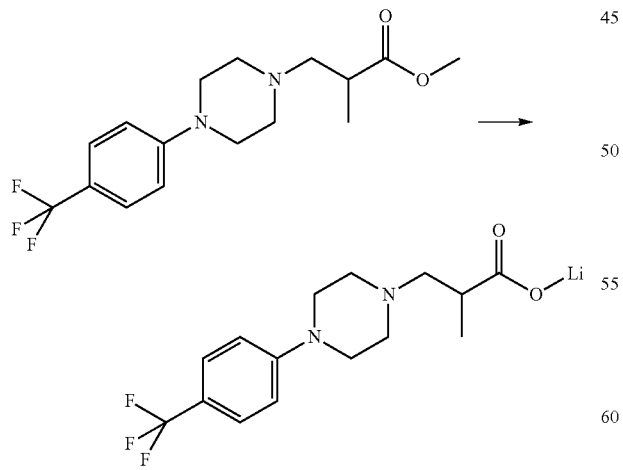

3-[4-(4-Trifluoromethyl-phenyl)-piperazin-1-yl]-2-methyl-propionic acid methyl ester (623 mg; 1.89 mmol, prepared in accordance with Example 62) and lithium hydroxide (60 mg; 2.50 mmol) are suspended in a mixture of tetrahydrofuran (4 mL) and water (1 mL). The resulting mixture is irradiated in a mono-mode microwave oven for 50 minutes at 100° C. The mixture is then diluted with acetonitrile until precipitation occurs. The solid formed is then filtered and dried under high vacuum to afford the desired product (465 mg; 1.44 mmol).

Example 64

Preparation of 2-methyl-1-[4-(4-nitro-3-trifluoromethyl-phenylamino)-piperidin-1-yl]-3-[4-(4-trifluoromethyl-phenyl)-piperazin-1-yl]-propan-1-one

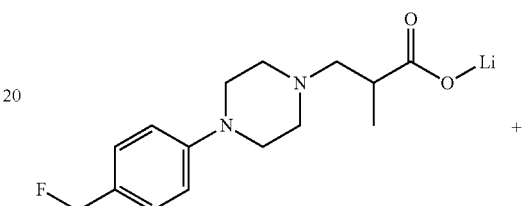

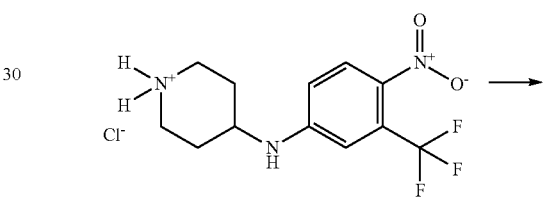

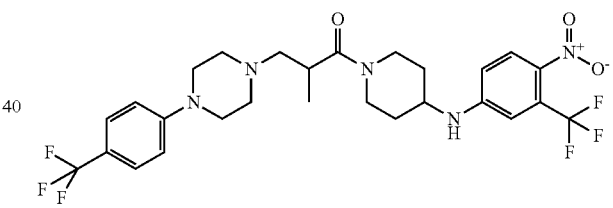

3-[4-(4-Trifluoromethyl-phenyl)-piperazin-1-yl]-2-methyl-propionic acid lithium salt (70 mg; 0.22 mmol, prepared in accordance with Example 63), diisopropylethyl amine (87 µL; 0.50 mmol) and tetramethyl-O-(1H-benzotriazol-1-yl) uronium hexafluorophosphate (76 mg; 0.20 mmol) are diluted in a 2 to 1 mixture of dimethylformamide and tetrahydrofuran (1.5 mL) and the resulting solution is stirred for 5 minutes. A solution (4-nitro-3-trifluoromethyl-phenyl)-piperidin-4-yl-amine hydrochloride (63 mg; 0.20 mmol, prepared in accordance with Example 8) in dimethylformamide (0.5 mL) is added and the reaction is then stirred for 60 minutes at room temperature. Following dilution with dichloromethane (10 mL), the organic layer is sequentially washed with water (5 mL), aq. sat. sodium hydrogen carbonate (5 mL), is dried over magnesium sulfate and concentrated under reduced pressure. The residue obtained is finally purified by preparative HPLC to deliver the desired product in pure form (64 mg; 0.11 mmol). The structure was confirmed using Protocol I-A. Calculated mass=588; observed mass=588; HPLC retention time=3.51 min.

Example 65

Preparation of (S)-2-methyl-3-[4-(4-trifluoromethyl-phenyl)-piperazin-1-yl]-propan-1-ol intermediate

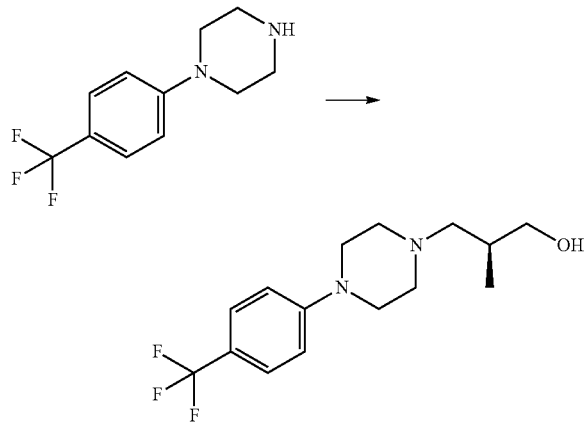

A solution of 1-(4-trifluoromethyl-phenyl)-piperazine (52.0 g; 221 mmol); (R)-3-bromo-2-methyl-propan-1-ol (36.0 g; 226 mmol) and triethylamine (61.7 mL; 443 mmol) in ethanol (350 mL) is heated at 95° C. for 45 hours. After cooling to room temperature, the mixture is concentrated under reduced pressure. The residue obtained is diluted with dichloromethane (500 mL) and the organic layer is washed with water (500 mL); with brine (500 mL) and the solvent is removed under reduced pressure. The crude residue obtained is re-crystallized from ethanol (200 mL), the re-crystallized product is washed with cold ethanol (100 mL). The mother liquor is concentrated under reduced pressure and is crystallized from ethanol (100 mL). The precipitate obtained is washed with cold ethanol (50 mL). The combined fractions are dried overnight at 40° C. under 3 mbar to deliver the enantiopure product (53.7 g; 178 mmol).

Example 66

Preparation of (S)-2-methyl-3-[4-(4-trifluoromethyl-phenyl)-piperazin-1-yl]-propionaldehyde intermediate

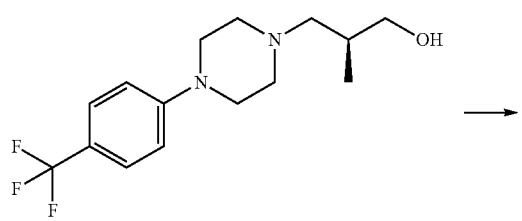

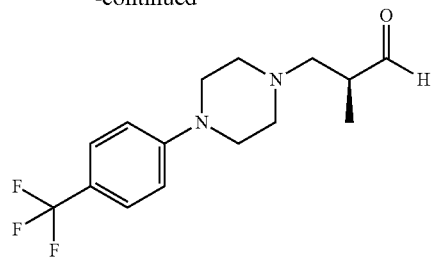

A 2 M solution of oxalyl dichloride in dichloromethane (4.96 mL; 13.2 mmol) is diluted with dichloromethane (35 mL); is cooled to −70° C. and dimethylsulfoxide (0.94 mL; 13.2 mmol) is added. The resulting mixture is stirred for 20 minutes. The temperature is allowed to reach −60° C. and a solution of (S)-2-methyl-3-[4-(4-trifluoromethyl-phenyl)-piperazin-1-yl]-propan-1-ol (2.0 g; 6.6 mmol, prepared in accordance with Example 65) in dichloromethane (20 mL) is added over 5 minutes. The resulting mixture is stirred at −60° C. for 2 hours before triethylamine (4.61 mL; 33.1 mmol) is added. After 10 minutes reaction time, the reaction mixture is allowed to slowly reach room temperature. The reaction is treated with water (100 mL), the organic layer is separated and is washed with water (2×100 mL) and concentrated to afford the desired product (1.99 g; 6.6 mmol). The crude product is engaged in the next step without further purification.

In many instances, the method of Example 66 can be adapted to make other compounds that are useful as intermediates for making the compounds and salts of this invention. An illustrative generic scheme is as follows:

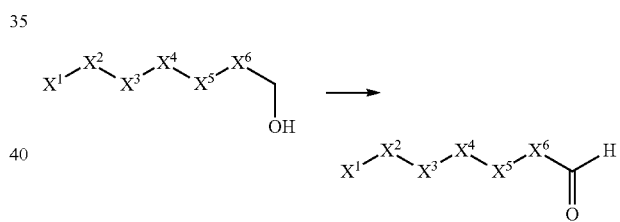

Here, $X^1$, $X^2$, $X^3$, $X^4$, $X^5$, $X^6$ are as defined above for the compounds of this invention. Determining the suitability of the method (and any necessary routine adaptations) or making a particular intermediate is generally with the skill of those in the art after reading this patent.

Example 67

Preparation of (S)-2-methyl-3-[4-(4-trifluoromethyl-phenyl)-piperazin-1-yl]-propionic acid intermediate

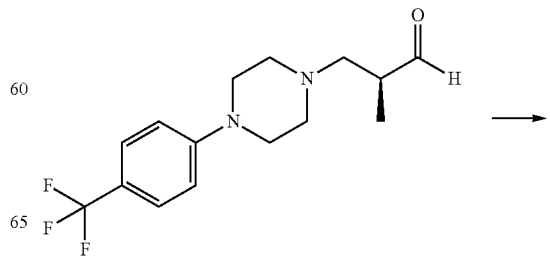

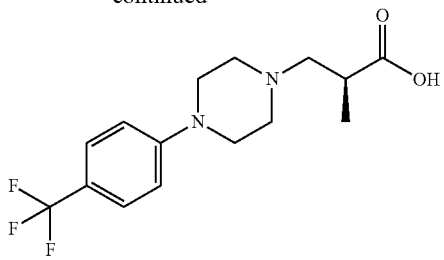

(S)-2-Methyl-3-[4-(4-trifluoromethyl-phenyl)-piperazin-1-yl]-propionaldehyde (1.99 g; 6.6 mmol, prepared in accordance with Example 66) is suspended in a mixture of tert-butanol (48 mL) and water (12 mL); sodium dihydrogenphosphate (1.59 g; 13.3 mmol) and 2-methyl-butene (13.94 g; 199 mmol) are added and the resulting mixture is stirred until a solution is obtained. Sodium chlorite (1.12 g; 9.9 mmol) is added and the reaction is stirred at room temperature for one hour. The precipitate formed is filtered, is washed with water and is dried at 40° C. under 3 mbar. Aqueous sat ammonium chloride (50 mL) is added to the filtrate which is then extracted with dichloromethane (2×50 mL). The combined organic layers are washed with brine (50 mL) and concentrated under reduced pressure. The residue obtained is dried at 40° C. under 3 mbar. The enantiopure product is obtained as colourless solid (1.3 g; 4.1 mmol).

In many instances, the method of Example 67 can be adapted to make other compounds that are useful as intermediates for making the compounds and salts of this invention. An illustrative generic scheme is as follows:

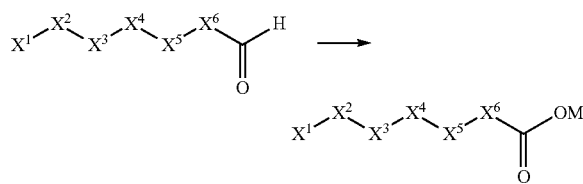

Here, $X^1$, $X^2$, $X^3$, $X^4$, $X^5$, $X^6$ are as defined above for the compounds of this invention. M is selected from the group consisting of hydrogen, lithium and potassium.

Example 68

Preparation of (S)-2-methyl-1-[4-(4-nitro-3-trifluoromethyl-phenylamino)-piperidin-1-yl]-3-[4-(4-trifluoromethyl-phenyl)-piperazin-1-yl]-propan-1-one

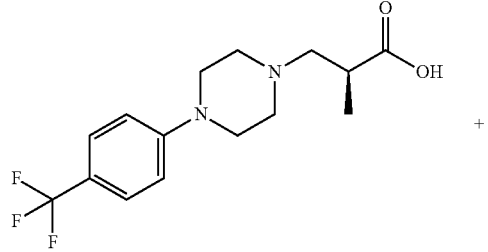

+

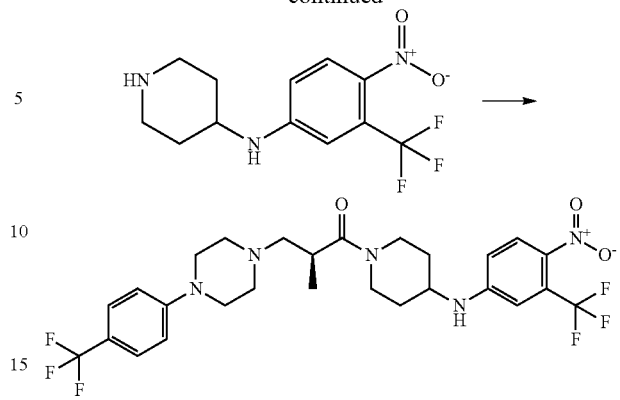

Tetramethyl-O-(1H-benzotriazol-1-yl)uronium hexafluorophosphate (8.74 g; 22.6 mmol) is added to a solution of (S)-2-methyl-3-[4-(4-trifluoromethyl-phenyl)-piperazin-1-yl]-propionic acid (13.0 g; 41.1 mmol, prepared in accordance with Example 67) is a mixture of dichloromethane (540 mL) and dimethylsulfoxide (10 mL). After stiffing for 10 minutes, (4-nitro-3-trifluoromethyl-phenyl)-piperidin-4-yl-amine (11.32 g; 39.1 mmol, free base of Example 8) and diisopropylethyl amine (15.15 g; 39.1 mmol) are added and the mixture is stirred at room temperature for 16 hours. The reaction mixture is then concentrated under reduced pressure and is dissolved in dichloromethane (250 mL). The organic phase is washed with water (2×500 mL), aq. sat. potassium carbonate (250 mL) and with brine (250 mL), is then dried over sodium sulfate and the solvent is removed under reduced pressure. The residue obtained is then diluted in ethyl acetate (250 mL), the organic phase is washed with water (2×1500 mL) is dried over sodium sulfate, filtered and concentrated under reduced pressure. The crude product is purified by column chromatography on silica gel (ethyl acetate:acetone 1:0 and then 9:1). After concentration of the fractions of interest, the product is dissolved in hot methanol (800 mL), and the solution is concentrated under vacuum. The solid obtained is finally dried at 40° C. under 3 mbar to afford the desired product (15.56 g; 26.5 mmol). The structure was confirmed using Protocol I-B. Calculated mass=588; observed mass=588; HPLC retention time=5.03 min.

Example 69

Preparation of 4-(4-methyl-5-nitro-pyridin-2-ylamino)-piperidine-1-carboxylic acid tert-butyl ester intermediate

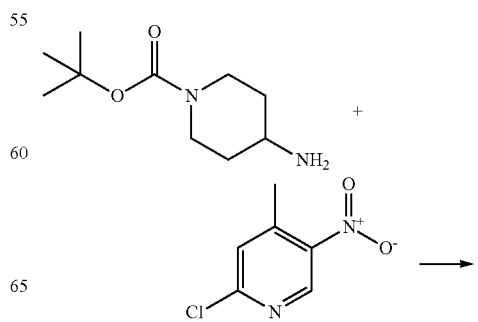

-continued

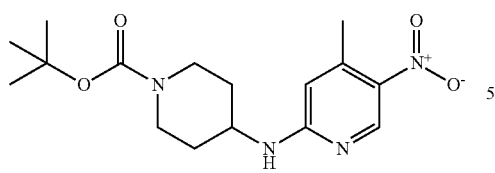

A mixture of 4-amino-piperidine-1-carboxylic acid tert-butyl ester (440 mg; 2.2 mmol), triethylamine (420 µL; 3.0 mmol) and 2-chloro-4-methyl-5-nitro-pyridine (346 mg; 2.0 mmol) is irradiated in a mono-mode microwave oven for 10 hours at 120° C. The mixture is then cooled to room temperature, water is added (5 mL) and the pH is adjusted to pH 4-5 by addition of aq. 1N hydrochloric acid. After extraction with dichloromethane (2×10 mL), the combined organic layers are dried over magnesium sulfate, filtered and the solvent removed under reduced pressure. The residue obtained is finally purified by column chromatography on silica gel (dichloromethane:ethyl acetate 1:0; 12:1; 2:1) to afford the desired product (480 mg; 1.43 mmol).

Example 70

Preparation of (4-methyl-5-nitro-pyridin-2-yl)-piperidin-4-yl-amine hydrochloride intermediate

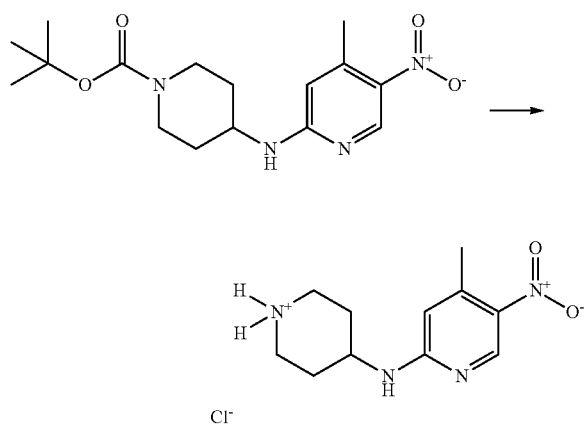 [SMILES: Cc1cc(NC2CCN(C(=O)OC(C)(C)C)CC2)ncc1[N+](=O)[O-] ; Cc1cc(NC2CC[NH2+]CC2)ncc1[N+](=O)[O-] ; [Cl-]]

Trifluoroacetic acid (1 mL) is added to a solution of 4-(4-methyl-5-nitro-pyridin-2-ylamino)-piperidine-1-carboxylic acid tert-butyl ester (170 mg; 0.51 mmol, prepared in accordance with Example 69) in dichloromethane (5 mL) under stiffing and the resulting mixture is stirred for 30 minutes at room temperature. The mixture is then concentrated under reduced pressure and co-evaporated with dichloromethane (2×10 mL). The residue obtained is diluted in dioxane (3 mL) and a 4N solution of hydrochloric acid in dioxane (3 mL) is added. The precipitate formed is filtered and is triturated with a small volume of acetone and dried under high vacuum to afford the desired product as hydrochloride (120 mg; 0.44 mmol).

Example 71

Preparation of 1-[4-(4-methyl-5-nitro-pyridin-2-ylamino)-piperidin-1-yl]-4-[4-(4-trifluoromethyl-phenyl)-piperazin-1-yl]-butan-1-one

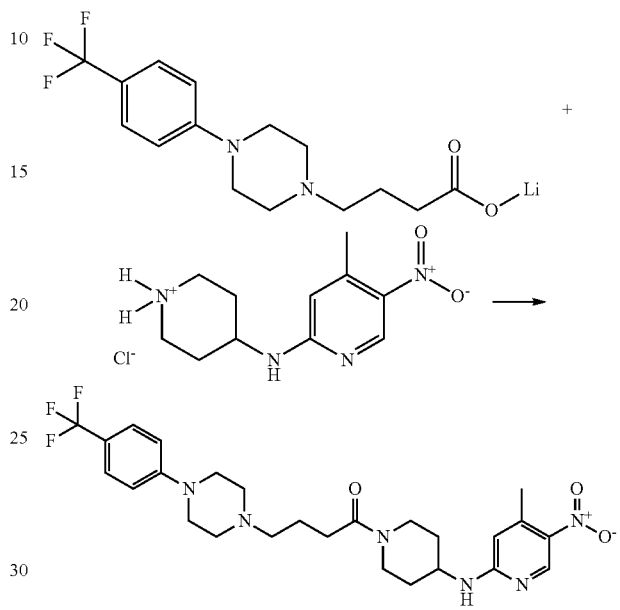

4-[4-(4-Trifluoromethyl-phenyl)-piperazin-1-yl]-butyric acid lithium salt (122 mg; 0.39 mmol, prepared in accordance with Example 3), diisopropylethyl amine (175 µL; 1.0 mmol) and tetramethyl-O-(1H-benzotriazol-1-yl)uronium hexafluorophosphate (133 mg; 0.35 mmol) are diluted in a 2 to 1 mixture of dimethylformamide and tetrahydrofuran (1.5 mL) and the resulting solution is stirred for 5 minutes. A solution of (4-methyl-5-nitro-pyridin-2-yl)-piperidin-4-yl-amine hydrochloride (95 mg; 0.35 mmol, prepared in accordance with Example 70) in dimethylformamide (0.5 mL) is added and the reaction is then stirred for 3 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (33 mg; 0.06 mmol). The structure was confirmed using Protocol II-A. Calculated mass=535; observed mass=535; HPLC retention time=3.29 min.

Example 72

Preparation of 1-(4-nitro-3-trifluoromethyl-phenyl)-piperidin-4-ylamine hydrochloride intermediate

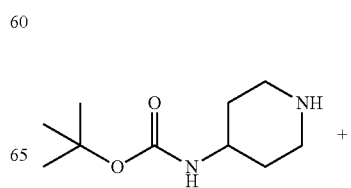

-continued

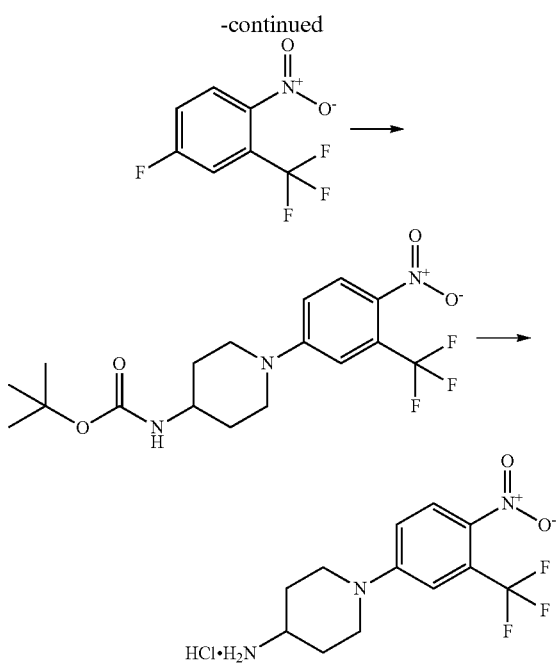

A solution of piperidin-4-yl-carbamic acid tert-butyl ester (400 mg; 2.0 mmol), 5-fluoro-2-nitrobenzotrifluoride (418 g; 2.0 mmol) and potassium carbonate (1.11 g; 8.0 mmol) in dimethylsulfoxide (5 mL) is heated at 100° C. for 5 hours. The mixture is allowed to reach room temperature, is diluted with ethyl acetate (50 mL) and filtered. The filtrate is washed with aq. sat. sodium hydrogencarbonate (2×10 mL) and with water (10 mL). The organic layer is then dried over magnesium sulfate and evaporated under reduced pressure to afford the desired product (797 mg; 2.0 mmol).

The [1-(4-Nitro-3-trifluoromethyl-phenyl)-piperidin-4-yl]-carbamic acid tert-butyl ester obtained (797 mg; 2.0 mmol) is dissolved in a 2 to 1 mixture of dichloromethane and trifluoroacetic acid (5 mL) and the resulting solution is stirred at room temperature for 1 hour. After concentration under reduced pressure, the residue obtained is co-evaporated with dichloromethane (2×10 mL), is then dissolved in diethylether (2 mL) and a molar solution of hydrochloric acid in diethyl-ether (5 mL) is added. The precipitate formed is triturated in ethylacetate (5 mL), filtered and is dried under high vacuum to yield the desired product as hydrochloride (624 mg; 1.6 mmol).

Example 73

Preparation of N-[1-(4-nitro-3-trifluoromethyl-phenyl)-piperidin-4-yl]-4-[4-(4-trifluoromethyl-phenyl)-piperazin-1-yl]-butyramide -continued

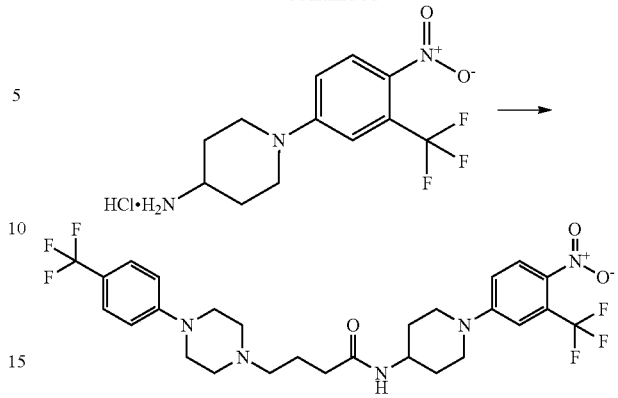

4-[4-(4-Trifluoromethyl-phenyl)-piperazin-1-yl]-butyric acid lithium salt (16 mg; 0.05 mmol, prepared in accordance with Example 3), diisopropylethyl amine (17 μL; 0.1 mmol) and tetramethyl-O-(1H-benzotriazol-1-yl)uronium hexafluorophosphate (19 mg; 0.05 mmol) are diluted in a 2 to 1 mixture of dimethylformamide and tetrahydrofuran (1.5 mL) and the resulting solution is stirred for 5 minutes. A solution of 1-(4-nitro-3-trifluoromethyl-phenyl)-piperidin-4-ylamine hydrochloride (16 mg; 0.05 mmol, prepared in accordance with Example 72) in dimethylformamide (0.5 mL) is added and the reaction is then stirred for 90 minutes at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (27 mg; 0.05 mmol). The structure was confirmed using Protocol I-B. Calculated mass=588; observed mass=588; HPLC retention time=5.09 min.

Example 74

Preparation of 4-{4-[4-(4-trifluoromethyl-phenyl)-piperazin-1-yl]-butyrylamino}-piperidine-1-carboxylic acid tert-butyl ester intermediate

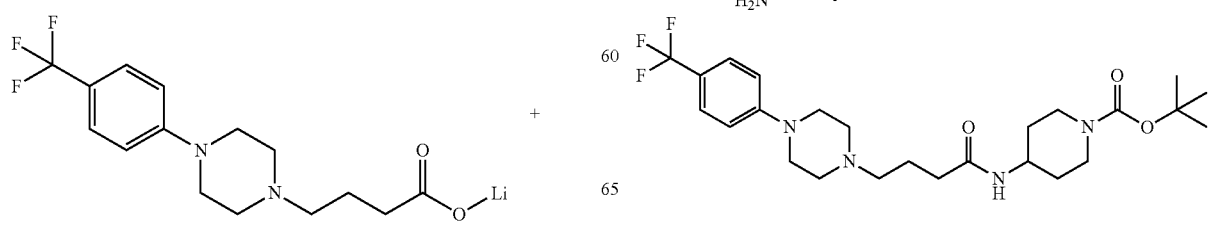

4-[4-(4-Trifluoromethyl-phenyl)-piperazin-1-yl]-butyric acid lithium salt (425 mg; 1.32 mmol, prepared in accordance with Example 3) and tetramethyl-O-(1H-benzotriazol-1-yl) uronium hexafluorophosphate (500 mg; 1.32 mmol) are diluted in a 5 to 1 mixture of dimethylformamide and tetrahydrofuran (6 mL) and the resulting solution is stirred for 5 minutes. 4-Amino-piperidine-1-carboxylic acid tert-butyl ester (264 mg; 1.32 mmol, free base of Example 73) and diisopropylethyl amine (460 µL; 2.64 mmol) are added and the reaction is then stirred for 90 minutes at room temperature. Following dilution with ethylacetate (30 mL), the organic layer is washed with aq. sat. sodium hydrogen carbonate (3×10 mL), is dried over magnesium sulfate and concentrated under reduced pressure to afford the desired product (660 mg; 1.32 mmol).

Example 75

Preparation of N-piperidin-4-yl-4-[4-(4-trifluoromethyl-phenyl)-piperazin-1-yl]-butyramide intermediate mg; 1.32 mmol, prepared in accordance with Example 74) in dichloromethane (4 mL) and the resulting mixture is stirred at room temperature. After 3 hours reaction time, the excess acid is neutralized by the addition of potassium carbonate, the mixture is filtered and the filtrate is concentrated under reduced pressure. The residue obtained is diluted in ethylacetate (20 mL) and the organic phase is extracted with water (2×10 mL). The combined aqueous phases are extracted with dichloromethane (10 mL) and diethylether (10 mL). The combined organic layers are dried over magnesium sulfate and the solvents removed under reduced pressure to afford the desired product (417 mg; 1.05 mmol).

Example 76

Preparation of 4-[4-(4-trifluoromethyl-phenyl)-piperazin-1-yl]-N-[1-(4-trifluoromethylsulfanyl-phenyl)-piperidin-4-yl]-butyramide

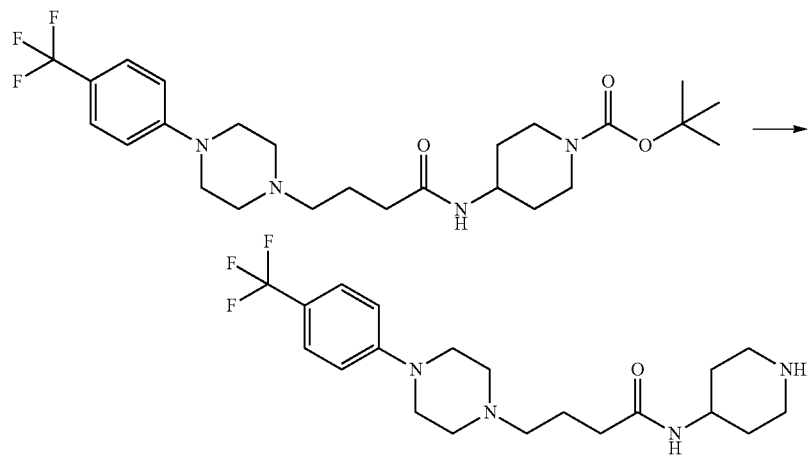

Trifluororoacetic acid (1 mL) is added to a solution of 4-{4-[4-(4-trifluoromethyl-phenyl)-piperazin-1-yl]-butyrylamino}-piperidine-1-carboxylic acid tert-butyl ester (660

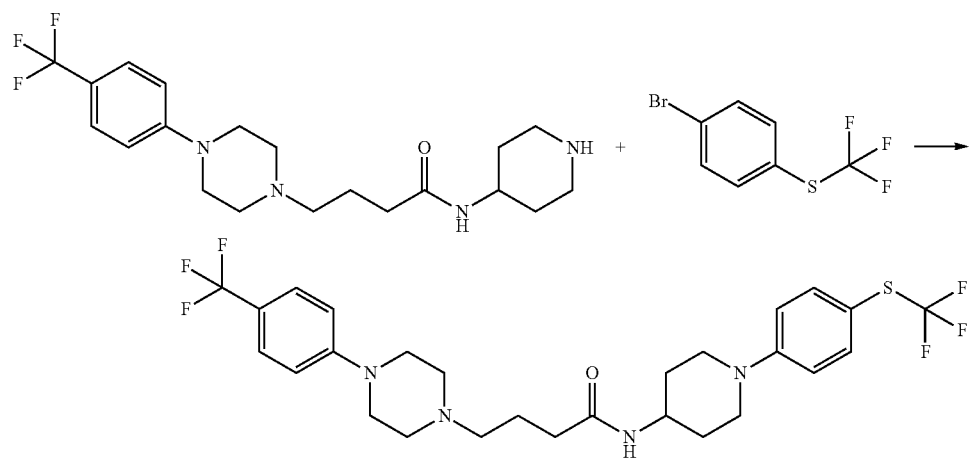

Tris(dibenzylideneacetone)dipalladium (13 mg; 0.01 mmol), 2,2'-bis(diphenylphosphino)-1,1'-binaphthyl (26 mg; 0.04 mmol), sodium tert-butoxide (120 mg; 1.20 mmol), 1-bromo-4-trifluoromethylsulfanyl-benzene (160 mg; 0.62 mmol) and N-piperidin-4-yl-4-[4-(4-trifluoromethyl-phenyl)-piperazin-1-yl]-butyramide (300 mg; 0.75 mmol, prepared in accordance with Example 75) are suspended in dry toluene (10 mL) and the mixture is irradiated in a mono-mode microwave oven for 90 minutes at 120° C. The mixture is then cooled down to room temperature, is diluted with ethyl acetate (50 mL), is filtered and the filtrate is concentrated under reduced pressure. The crude residue is then purified by column chromatography on silica gel (dichloromethane:isopropyl alcohol 9:1) to afford the desired product (155 mg; 0.27 mmol). The structure was confirmed using Protocol I-B. Calculated mass=575; observed mass=575; HPLC retention time=5.26 min.

Example 77

Preparation of 3-oxo-3-[4-(4-trifluoromethyl-phenyl)-piperazin-1-yl]-propionic acid lithium salt intermediate

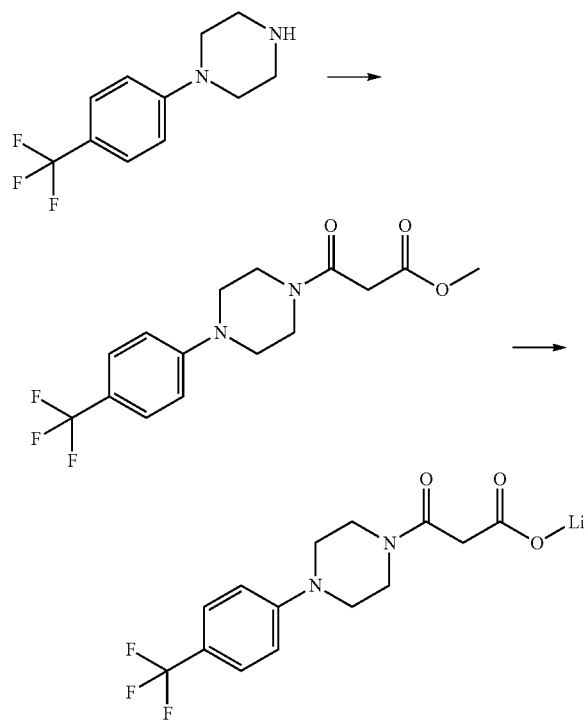

1-(4-Trifluoromethylphenyl)-piperazine (576 mg; 2.5 mmol) and triethylamine (348 µL; 2.5 mmol) are dissolved in dry tetrahydrofuran (5 mL) and chlorocarbonyl-acetic acid methyl ester (355 mg; 2.6 mmol) is slowly added. The resulting mixture is stirred for 30 minutes at room temperature to reach complete conversion of the educts. The reaction is then concentrated under reduced pressure and the residue obtained is co-evaporated with dichloromethane (2×5 mL).
The crude product is then dissolved in a mixture of tetrahydrofuran (3.5 mL) and water (1.5 mL) and lithium hydroxide is added (120 mg; 5 mmol). The resulting mixture is heated at 40° C. for 15 minutes, and cooled down to room temperature. After dilution with acetonitrile (30 mL), a precipitate is formed which is filtered and dried under high vacuum to afford the desired product as lithium salt (514 mg; 1.6 mmol).

In many instances, the method of Example 77 can be adapted to make other compounds that are useful as intermediates for making the compounds and salts of this invention. An illustrative generic scheme is as follows:

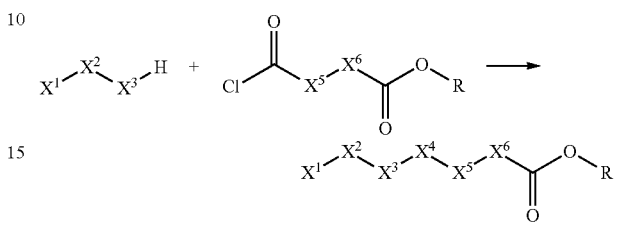

Here, $X^1$, $X^2$, $X^3$, $X^4$, $X^5$ and $X^6$ are as defined above for the compounds of this invention. R is alkyl. Determining the suitability of the method (and any necessary routine adaptations) or making a particular intermediate is generally with the skill of those in the art after reading this patent.

Example 78

Preparation of 1-[4-(4-nitro-3-trifluoromethyl-phenylamino)-piperidin-1-yl]-3-[4-(4-trifluoromethyl-phenyl)-piperazin-1-yl]-propane-1,3-dione

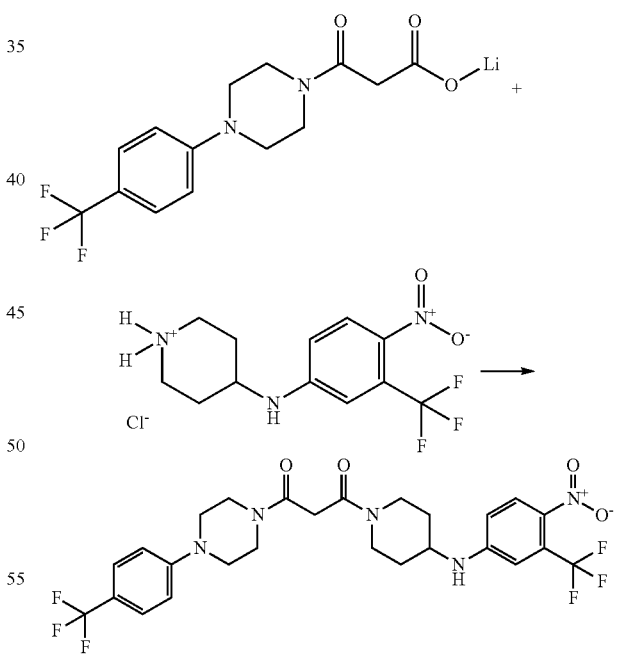

3-Oxo-3-[4-(4-trifluoromethyl-phenyl)-piperazin-1-yl]-propionic acid lithium salt (633 mg; 1.97 mmol, prepared in accordance with Example 77), diisopropylethyl amine (685 µL; 3.93 mmol) and tetramethyl-O-(1H-benzotriazol-1-yl) uronium hexafluorophosphate (670 mg; 1.77 mmol) are diluted in a 2 to 1 mixture of dimethylformamide and tetrahydrofuran (7.5 mL) and the resulting solution is stirred for 5 minutes. A solution of (4-methyl-5-nitro-pyridin-2-yl)-piperidin-4-yl-amine hydrochloride (576 mg; 1.77 mmol, prepared in accordance with Example 8) in dimethylformamide (2.5 mL) is added and the reaction is then stirred for 3 hours at room temperature. Following dilution with dichloromethane (50 mL), the organic layer is sequentially washed with water (25 mL), aq. sat. sodium hydrogen carbonate (3×25 mL), is dried over magnesium sulfate and concentrated under reduced pressure. The residue obtained is finally purified by preparative HPLC to deliver the desired product in pure form (382 mg; 0.65 mmol). The structure was confirmed using Protocol I-B. Calculated mass=588; observed mass=588; HPLC retention time=5.57 min.

Example 79

Preparation of 1-[4-(4-nitro-3-trifluoromethyl-phenoxy)-piperidin-1-yl]-4-[4-(4-trifluoromethyl-phenyl)-piperazin-1-yl]-butan-1-one

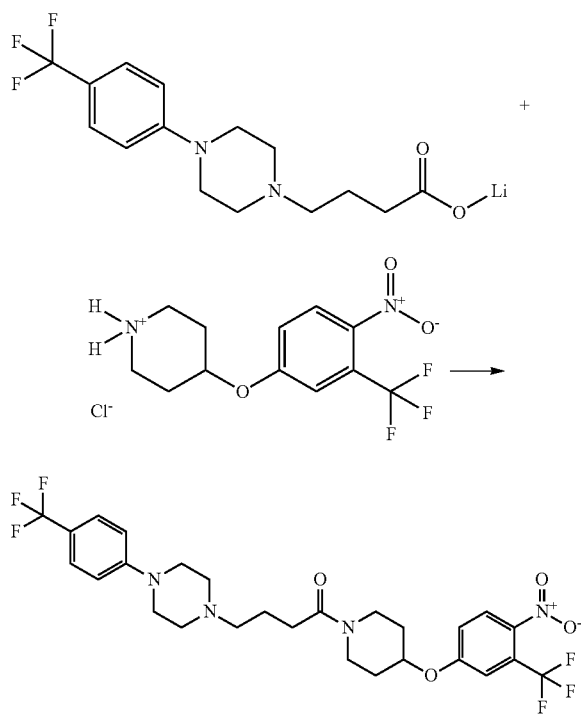

4-[4-(4-Trifluoromethyl-phenyl)-piperazin-1-yl]-butyric acid lithium salt (18 mg; 0.05 mmol, prepared in accordance with Example 3), diisopropylethyl amine (19 µL; 0.11 mmol) and tetramethyl-O-(1H-benzotriazol-1-yl)uronium hexafluorophosphate (21 mg; 0.05 mmol) are diluted in a 2 to 1 mixture of dimethylformamide and tetrahydrofuran (1.5 mL) and the resulting solution is stirred for 5 minutes. A solution of 4-(4-nitro-3-trifluoromethyl-phenoxy)-piperidine hydrochloride (18 mg; 0.05 mmol, prepared in accordance with Example 44) in dimethylformamide (0.5 mL) is added and the reaction is then stirred for 3 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (20 mg; 0.03 mmol). The structure was confirmed using Protocol I-C. Calculated mass=589; observed mass=589; HPLC retention time=3.08 min.

Example 80

Preparation of piperidin-4-yl-(3-trifluoromethyl-phenyl)-amine hydrochloride intermediate

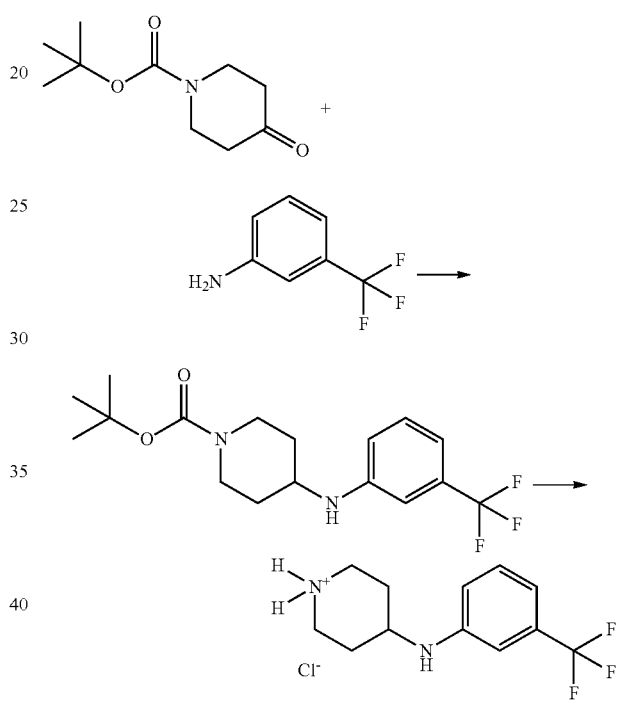

4-Oxo-piperidine-1-carboxylic acid tert-butyl ester (500 mg; 2.51 mmol), 3-trifluoromethyl-phenylamine (404 mg; 2.51 mmol) and sodium triacetoxyborohydride (1.59 g; 7.53 mmol) are suspended in dichloroethane (25 mL). After 1 day reaction time at room temperature, the mixture is diluted with dichloromethane (100 mL) and the organic layer is washed with aq. sat ammonium chloride (2×50 mL) and water (3×50 mL), is then dried over magnesium sulfate and is concentrated under reduced pressure. The residue obtained is triturated with cold diethylether (10 mL) until precipitation is observed. The precipitate is filtered and dried under vacuum.

The crude product is dissolved in dichloromethane (5 mL) and trifluoroacetic acid (5 mL) is added dropwise under vigorous stirring. After 30 minutes reaction time, the mixture is concentrated under reduced pressure and co-evaporated with dichloromethane (2×10 mL). The residue obtained is then dissolved in diethylether (5 mL) and a molar solution of hydrochloric acid in diethylether (5 mL) is added. The precipitate formed is filtered and dried under high vacuum to afford the desired product as hydrochloride (289 mg; 1.03 mmol).

Example 81

Preparation of 1-[4-(3-trifluoromethyl-phenylamino)-piperidin-1-yl]-4-[4-(4-trifluoromethyl-phenyl)-piperazin-1-yl]-butan-1-one

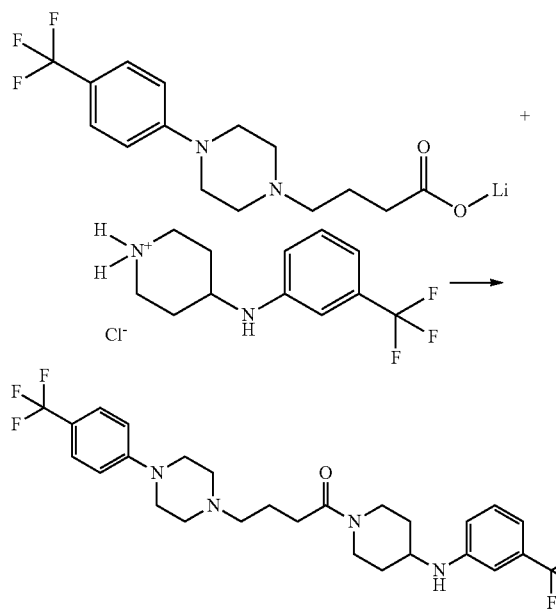

4-[4-(4-Trifluoromethyl-phenyl)-piperazin-1-yl]-butyric acid lithium salt (26 mg; 0.08 mmol, prepared in accordance with Example 3), diisopropylethyl amine (26 µL; 0.15 mmol) and tetramethyl-O-(1H-benzotriazol-1-yl)uronium hexafluorophosphate (28 mg; 0.08 mmol) are diluted in a 2 to 1 mixture of dimethylformamide and tetrahydrofuran (1.5 mL) and the resulting solution is stirred for 5 minutes. A solution of piperidin-4-yl-(3-trifluoromethyl-phenyl)-amine hydrochloride (21 mg; 0.08 mmol, prepared in accordance with Example 80) in dimethylformamide (0.5 mL) is added and the reaction is then stirred for 4 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (14 mg; 0.03 mmol). The structure was confirmed using Protocol I-B. Calculated mass=543; observed mass=543; HPLC retention time=5.20 min.

Example 82

Preparation of 4-(piperidin-4-ylamino)-benzonitrile hydrochloride intermediate

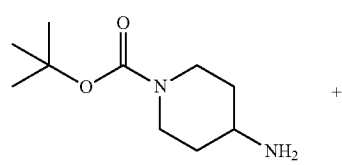

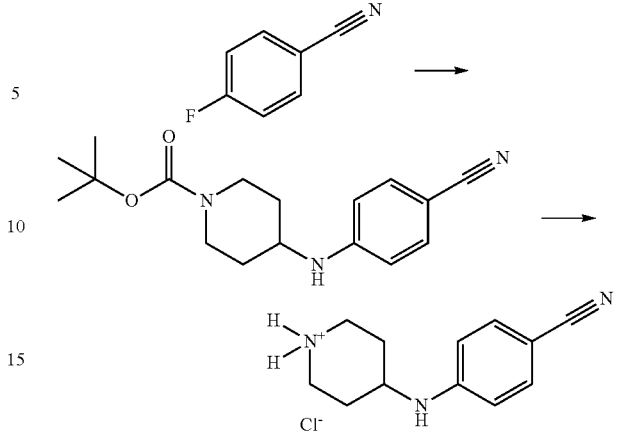

4-Amino-piperidine-1-carboxylic acid tert-butyl ester (300 mg; 1.50 mmol), 4-fluoro-benzonitrile (480 mg; 3.96 mmol) and potassium carbonate (415 mg; 3.0 mmol) are dissolved in dimethylsulfoxide (5 mL) and the resulting mixture is heated at 120° C. for 4 hours. After cooling to room temperature, the reaction is diluted with dichloromethane (40 mL) and the organic phase is washed with aq. sat. sodium carbonate (2×15 mL), aq. sat ammonium chloride (2×15 mL) and water (2×15 mL). The organic layer is dried over magnesium sulfate, filtered and concentrated under reduced pressure. The crude residue precipitated from cold diethylether (10 mL) to afford the desired intermediate.

The crude product is dissolved in dichloromethane (5 mL) and trifluoroacetic acid (5 mL) is added dropwise under vigorous stirring. After 30 minutes reaction time, the mixture is concentrated under reduced pressure and co-evaporated with dichloromethane (2×10 mL). The residue obtained is then dissolved in diethylether (5 mL) and a molar solution of hydrochloric acid in diethylether (5 mL) is added. The precipitate formed is filtered and dried under high vacuum to afford the desired product as hydrochloride (154 mg; 0.65 mmol).

Example 83

Preparation of 4-(1-{4-[4-(4-trifluoromethyl-phenyl)-piperazin-1-yl]-butyryl}-piperidin-4-ylamino)-benzonitrile

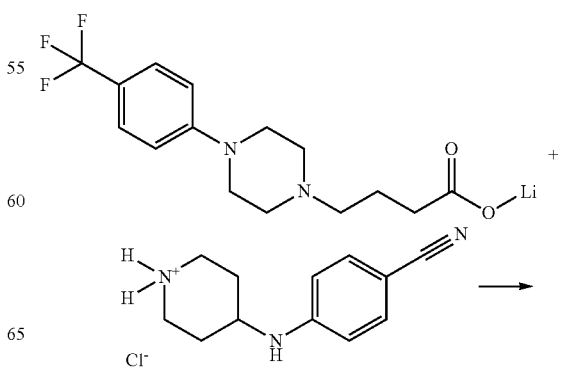

-continued

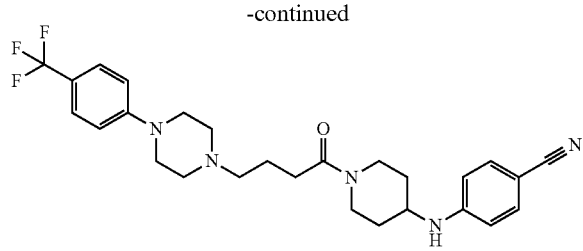

4-[4-(4-Trifluoromethyl-phenyl)-piperazin-1-yl]-butyric acid lithium salt (26 mg; 0.08 mmol, prepared in accordance with Example 3), diisopropylethyl amine (26 µL; 0.15 mmol) and tetramethyl-O-(1H-benzotriazol-1-yl)uronium hexafluorophosphate (28 mg; 0.08 mmol) are diluted in a 2 to 1 mixture of dimethylformamide and tetrahydrofuran (1.5 mL) and the resulting solution is stirred for 5 minutes. A solution of 4-(piperidin-4-ylamino)-benzonitrile hydrochloride (18 mg; 0.08 mmol, prepared in accordance with Example 82) in dimethylformamide (0.5 mL) is added and the reaction is then stirred for 4 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (21 mg; 0.04 mmol). The structure was confirmed using Protocol I-B. Calculated mass=500; observed mass=500; HPLC retention time=4.90 min.

Example 84

Preparation of (4-chloro-3-trifluoromethyl-phenyl)-piperidin-4-yl-amine hydrochloride intermediate

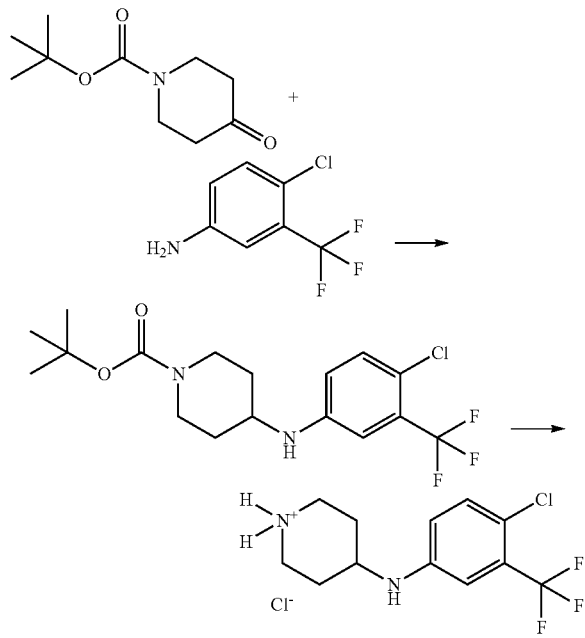

4-Oxo-piperidine-1-carboxylic acid tert-butyl ester (797 mg; 4.0 mmol), 4-chloro-3-trifluoromethyl-phenylamine (782 mg; 4.0 mmol) and sodium triacetoxyborohydride (2.54 g; 12.0 mmol) are suspended in dichloroethane (20 mL). After 8 days reaction time at room temperature, the mixture is diluted with dichloromethane (20 mL), water is added (20 mL) and the pH of the aqueous phase is set to 4 by the addition of aq. 1N hydrochloric acid. The organic layer is washed with water (2×10 mL) and brine (10 mL), is dried over magnesium sulfate and is concentrated under reduced pressure. The residue obtained is purified by column chromatography on silica gel (dichloromethane:methanol 1:0 and then 95:5) to afford the desired intermediate product.

The product is dissolved in dichloromethane (5 mL) and trifluoroacetic acid (5 mL) is added dropwise under vigorous stirring. After 30 minutes reaction time, the mixture is concentrated under reduced pressure and co-evaporated with dichloromethane (2×10 mL). The residue obtained is then dissolved in diethylether (5 mL) and a molar solution of hydrochloric acid in diethylether (5 mL) is added. The precipitate formed is filtered and dried under high vacuum to afford the desired product as hydrochloride (316 mg; 1.0 mmol).

Example 85

Preparation of 1-[4-(4-chloro-3-trifluoromethyl-phenylamino)-piperidin-1-yl]-4-[4-(4-trifluoromethyl-phenyl)-piperazin-1-yl]-butan-1-one

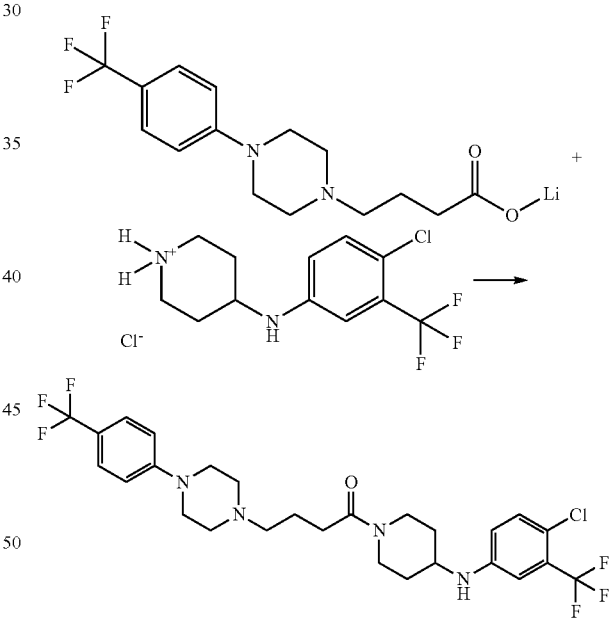

4-[4-(4-Trifluoromethyl-phenyl)-piperazin-1-yl]-butyric acid lithium salt (40 mg; 0.12 mmol, prepared in accordance with Example 3), diisopropylethyl amine (45 µL; 0.26 mmol) and tetramethyl-O-(1H-benzotriazol-1-yl)uronium hexafluorophosphate (48 mg; 0.12 mmol) are diluted in a 2 to 1 mixture of dimethylformamide and tetrahydrofuran 1.5 mL) and the resulting solution is stirred for 5 minutes. A solution of (4-chloro-3-trifluoromethyl-phenyl)-piperidin-4-yl-amine hydrochloride (35 mg; 0.11 mmol, prepared in accordance with Example 84) in dimethylformamide (0.5 mL) is added and the reaction is then stirred for 4 hours at room temperature. Following dilution with dichloromethane (10 mL), the organic layer is sequentially washed with water (5 mL), aq.

sat. sodium hydrogen carbonate (3×5 mL), is dried over magnesium sulfate and concentrated under reduced pressure. The residue obtained is finally purified by preparative HPLC to deliver the desired product in pure form (44 mg; 0.08 mmol). The structure was confirmed using Protocol I-B. Calculated mass=577; observed mass=577; HPLC retention time=5.38 min.

Example 86

Preparation of 1-[4-(4-nitro-3-trifluoromethyl-phenoxy)-piperidin-4-yl]-3-{4-[4-(4-trifluoromethyl-benzyloxy)-phenyl]-piperazin-4-yl}-propan-4-one tetrahydrofuran (1.5 mL) and the resulting solution is stirred for 5 minutes. A solution of 4-(4-nitro-3-trifluoromethyl-phenoxy)-piperidine hydrochloride (36 mg; 0.11 mmol, prepared in accordance with Example 44) in dimethylformamide (0.5 mL) is added and the reaction is then stirred for 4 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (19 mg; 0.03 mmol). The structure was confirmed using Protocol I-B. Calculated mass=795; observed mass=681; HPLC retention time=4.90 min.

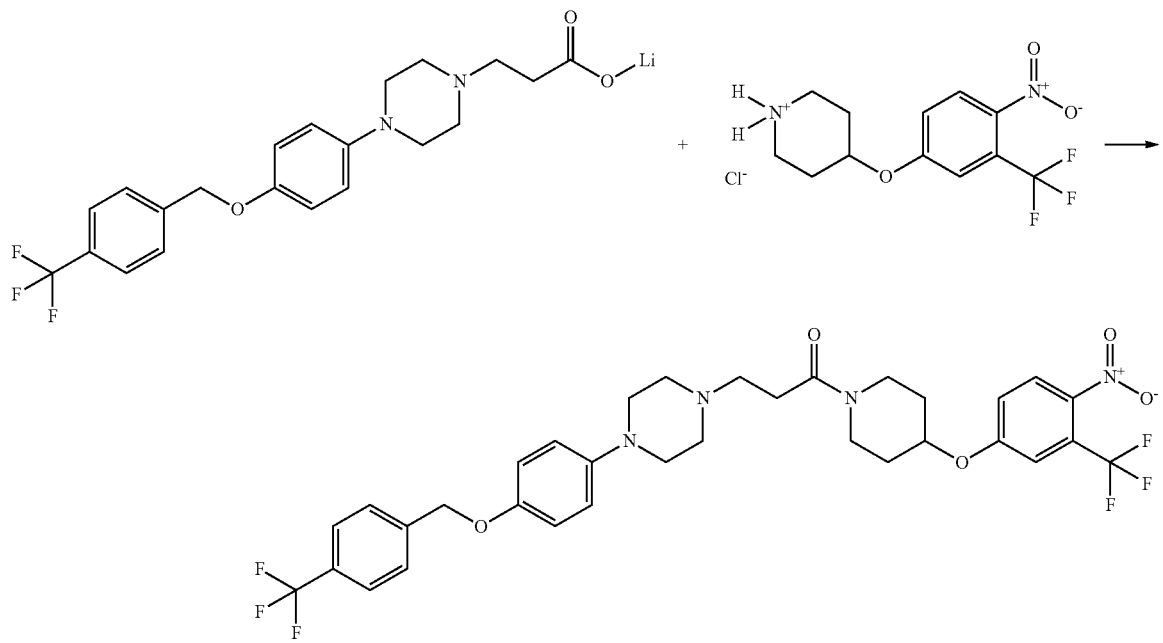

3-{4-[4-(4-Trifluoromethyl-benzyloxy)-phenyl]-piperazin-1-yl}-propionic acid lithium salt (41 mg; 0.10 mmol, prepared in accordance with Example 37), diisopropylethyl amine (35 µL; 0.20 mmol) and tetramethyl-O-(1H-benzotriazol-1-yl)uronium hexafluorophosphate (38 mg; 0.10 mmol) are diluted in a 2 to 1 mixture of dimethylformamide and Example 87

Preparation of 1-[4-(3-methoxy-4-nitro-phenoxy)-piperidin-1-yl]-3-{4-[4-(4-trifluoromethyl-benzyloxy)-phenyl]-piperazin-1-yl}-propan-1-one

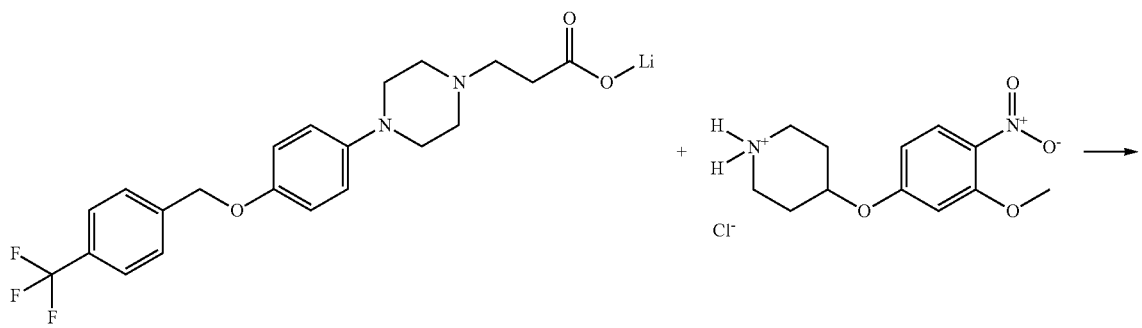

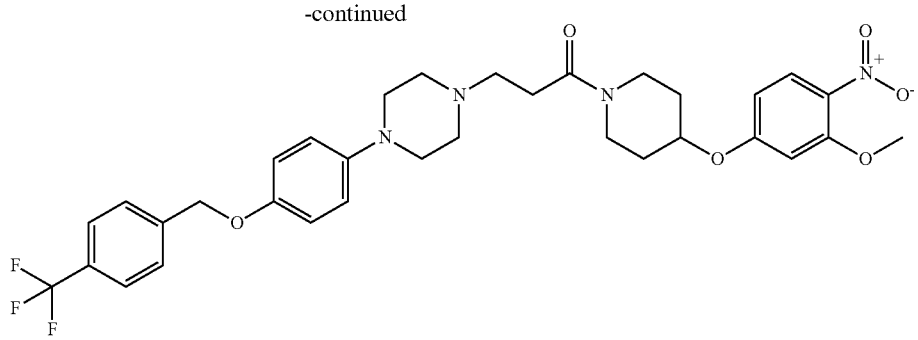

3-{4-[4-(4-Trifluoromethyl-benzyloxy)-phenyl]-piperazin-1-yl}-propionic acid lithium salt (41 mg; 0.10 mmol, prepared in accordance with Example 37), diisopropylethyl amine (35 μL; 0.20 mmol) and tetramethyl-O-(1H-benzotriazol-1-yl)uronium hexafluorophosphate (38 mg; 0.10 mmol) are diluted in a 2 to 1 mixture of dimethylformamide and tetrahydrofuran (1.5 mL) and the resulting solution is stirred for 5 minutes. A solution of 4-(3-methoxy-4-nitro-phenoxy)-piperidine hydrochloride (32 mg; 0.11 mmol) in dimethylformamide (0.5 mL) is added and the reaction is then stirred for 4 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (17 mg; 0.03 mmol). The structure was confirmed using Protocol I-B. Calculated mass=643; observed mass=643; HPLC retention time=4.66 min.

Example 88

Preparation of 1-[4-(4-nitro-3-trifluoromethyl-phenylamino)-piperidin-1-yl]-3-[4-(4-trifluoromethyl-phenyl)-piperazin-1-yl]-propan-1-one

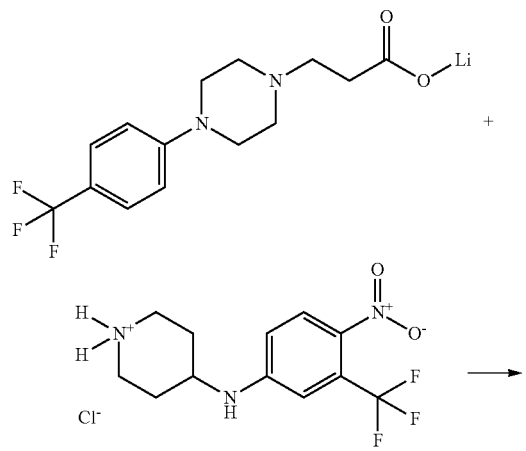

3-[4-(4-Trifluoromethyl-phenyl)-piperazin-1-yl]-propionic acid lithium salt (33 mg; 0.11 mmol, prepared in accordance with Example 13), diisopropylethyl amine (37 μL; 0.22 mmol) and tetramethyl-O-(1H-benzotriazol-1-yl)uronium hexafluorophosphate (36 mg; 0.10 mmol) are diluted in a 2 to 1 mixture of dimethylformamide and tetrahydrofuran (1.5 mL) and the resulting solution is stirred for 5 minutes. A solution of (4-nitro-3-trifluoromethyl-phenyl)-piperidin-4-yl-amine hydrochloride (33 mg; 0.10 mmol, prepared in accordance with Example 8) in dimethylformamide (0.5 mL) is added and the reaction is then stirred for 4 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (34 mg; 0.06 mmol). The structure was confirmed using Protocol II-F. Calculated mass=574; observed mass=575; HPLC retention time=11.47 min.

Example 89

Preparation of 1-[4-(4-nitro-3-trifluoromethyl-phenylamino)-piperidin-1-yl]-4-[4-(4-trifluoromethyl-phenyl)-piperazin-1-yl]-butan-1-one

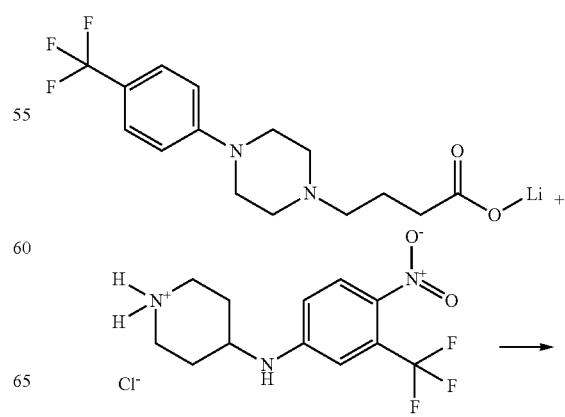

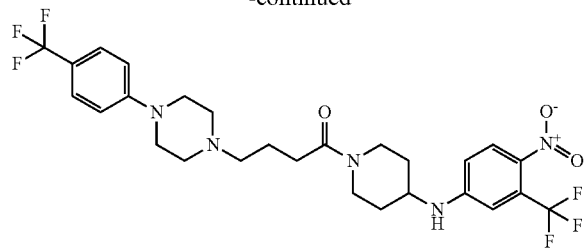

4-[4-(4-Trifluoromethyl-phenyl)-piperazin-1-yl]-butyric acid lithium salt (16 mg; 0.05 mmol, prepared in accordance with Example 3), diisopropylethyl amine (25 µL; 0.15 mmol) and tetramethyl-O-(1H-benzotriazol-1-yl)uronium hexafluorophosphate (19 mg; 0.05 mmol) are diluted in a 2 to 1 mixture of dimethylformamide and tetrahydrofuran (1.5 mL) and the resulting solution is stirred for 5 minutes. A solution of (4-nitro-3-trifluoromethyl-phenyl)-piperidin-4-yl-amine hydrochloride (16 mg; 0.05 mmol, prepared in accordance with Example 8) in dimethylformamide (0.5 mL) is added and the reaction is then stirred for 2 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (19 mg; 0.03 mmol). The structure was confirmed using Protocol I-C. Calculated mass=588; observed mass=588; HPLC retention time=3.03 min.

Example 90

Preparation of 4-[4-(4-tert-butyl-phenyl)-piperazin-1-yl]-1-[4-(4-nitro-3-trifluoromethyl-phenylamino)-piperidin-1-yl]-butan-1-one

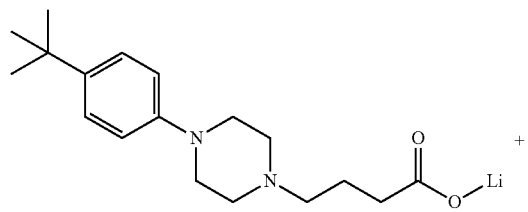

+

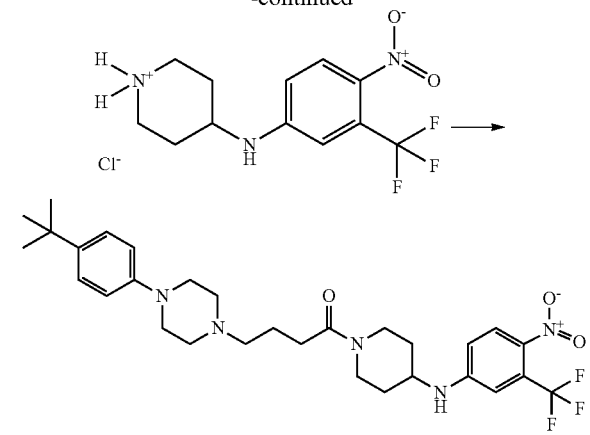

4-[4-(4-tert-Butyl-phenyl)-piperazin-1-yl]-butyric acid lithium salt (15 mg; 0.05 mmol, prepared in accordance with Example 167), diisopropylethyl amine (25 µL; 0.15 mmol) and tetramethyl-O-(1H-benzotriazol-1-yl)uronium hexafluorophosphate (19 mg; 0.05 mmol) are diluted in a 2 to 1 mixture of dimethylformamide and tetrahydrofuran (1.5 mL) and the resulting solution is stirred for 5 minutes. A solution of (4-nitro-3-trifluoromethyl-phenyl)-piperidin-4-yl-amine hydrochloride (16 mg; 0.05 mmol, prepared in accordance with Example 8) in dimethylformamide (0.5 mL) is added and the reaction is then stirred for 2 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (16 mg; 0.03 mmol). The structure was confirmed using Protocol I-C. Calculated mass=576; observed mass=576; HPLC retention time=3.16 min.

Example 91

Preparation of 1-[4-(4-nitro-3-trifluoromethyl-phenylamino)-piperidin-1-yl]-3-{4-[4-(4-trifluoromethyl-benzyloxy)-phenyl]-piperazin-1-yl}-propan-1-one

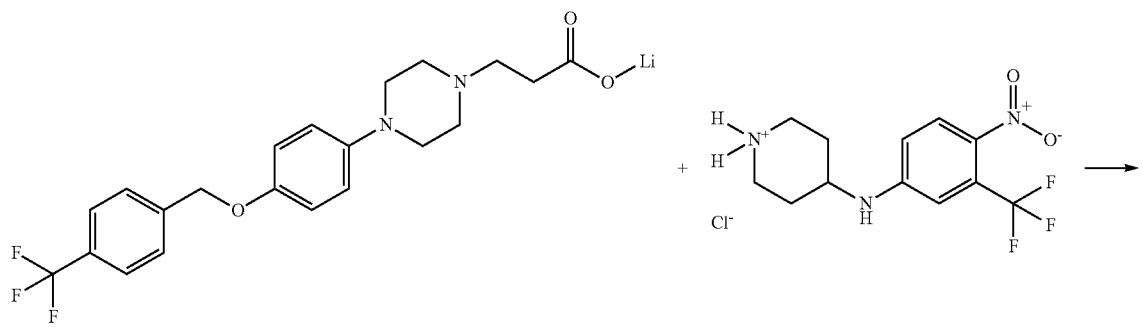

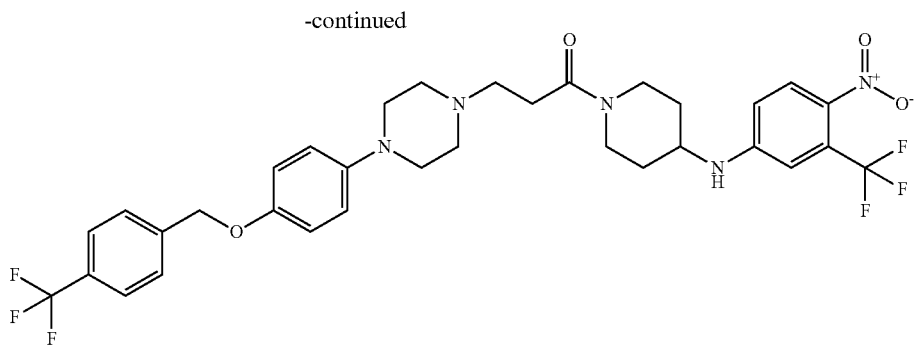

3-{4-[4-(4-Trifluoromethyl-benzyloxy)-phenyl]-piperazin-1-yl}-propionic acid lithium salt (134 mg; 0.32 mmol, prepared in accordance with Example 13), diisopropylethyl amine (174 µL; 1.0 mmol) and tetramethyl-O-(1H-benzotriazol-1-yl)uronium hexafluorophosphate (133 mg; 0.35 mmol) are diluted in a 2 to 1 mixture of dimethylformamide and tetrahydrofuran (1.5 mL) and the resulting solution is stirred for 5 minutes. A solution of (4-nitro-3-trifluoromethyl-phenyl)-piperidin-4-yl-amine hydrochloride (114 mg; 0.30 mmol, prepared in accordance with Example 8) in dimethylformamide (0.5 mL) is added and the reaction is then stirred for 2 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (34 mg; 0.05 mmol). The structure was confirmed using Protocol II-A. Calculated mass=680; observed mass=680; HPLC retention time=3.84 min.

Example 92

Preparation of 4-(1-{2-methyl-3-[4-(4-trifluoromethyl-phenyl)-piperazin-1-yl]-propionyl}-piperidin-4-ylamino)-2-trifluoromethyl-benzonitrile

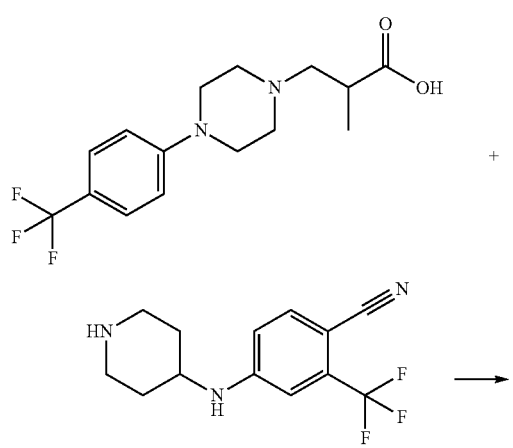

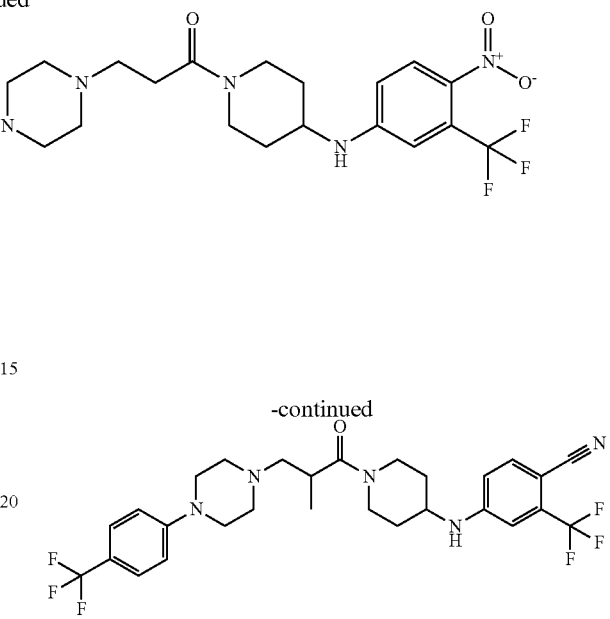

2-Methyl-3-[4-(4-trifluoromethyl-phenyl)-piperazin-1-yl]-propionic acid (57 mg; 0.18 mmol, prepared in accordance with Example 67), diisopropylethyl amine (140 µL; 0.8 mmol) and tetramethyl-O-(1H-benzotriazol-1-yl)uronium hexafluorophosphate (65 mg; 0.17 mmol) are diluted in a 2 to 1 mixture of dimethylformamide and tetrahydrofuran (1.5 mL) and the resulting solution is stirred for 5 minutes. A solution of 4-(Piperidin-4-ylamino)-2-trifluoromethyl-benzonitrile (50 mg; 0.17 mmol) in dimethylformamide (0.5 mL) is added and the reaction is then stirred for 1 hour at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. Upon addition of acetonitrile to the residue obtained a precipitation is observed. The precipitate is filtered, washed with acetonitrile (2×3 mL) and dried under high vacuum to afford the desired product (98 mg; 0.17 mmol). The structure was confirmed using Protocol II-B. Calculated mass=568; observed mass=568; HPLC retention time=4.812 min.

Example 93

Preparation of 4-(6-nitro-pyridin-3-ylamino)-piperidine-1-carboxylic acid tert-butyl ester intermediate

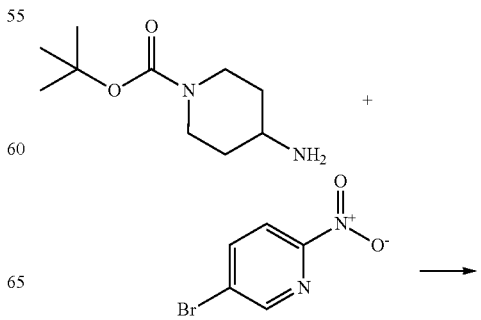

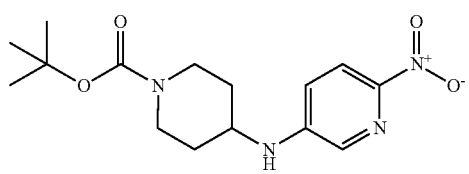

A mixture of 4-amino-piperidine-1-carboxylic acid tert-butyl ester (500 mg; 2.5 mmol), 5-bromo-2-nitro-pyridine (406 mg; 2.0 mmol), Tris(dibenzylideneacetone)dipalladium (36 mg; 0.04 mmol), 2,2'-bis(diphenylphosphino)-1,1'-binaphthyl (75 mg; 0.12 mmol), and sodium tert-butoxide (280 mg; 3.00 mmol) is suspended in toluene (5 mL) and is irradiated in a mono-mode microwave oven for 30 minutes at 120° C. The mixture is then concentrated under reduced pressure and the crude residue is purified by column chromatography on silica gel (dichloromethane:ethyl acetate 1:0 and then 4:1). The desired product is obtained with 78% purity (200 mg; 0.62 mmol).

Example 94

Preparation of (6-nitro-pyridin-3-yl)-piperidin-4-yl-amine hydrochloride intermediate

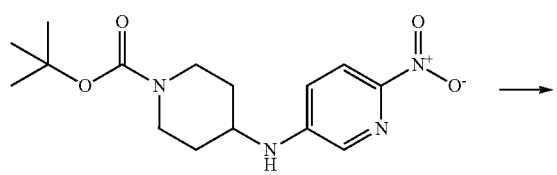

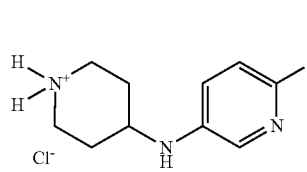

4-(6-nitro-pyridin-3-ylamino)-piperidine-1-carboxylic acid tert-butyl ester (200 mg; 0.62 mmol, prepared in accordance with Example 93) is dissolved in dichloromethane (5 mL) and trifluoroacetic acid (1 mL) is added under stirring. After 30 minutes, the reaction mixture is concentrated under reduced pressure and the residue obtained is co-evaporated with dichloromethane (2×10 mL). The product is then diluted in dioxane (3 mL) and a 4N solution of hydrochloric acid in dioxane (3 mL) is added. The precipitate formed is filtered and dried under high vacuum at 40° C. to afford the desired product as hydrochloride (159 mg; 0.61 mmol).

Example 95

Preparation of 1-[4-(6-nitro-pyridin-3-ylamino)-piperidin-1-yl]-4-[4-(4-trifluoromethyl-phenyl)-piperazin-1-yl]-butan-1-one

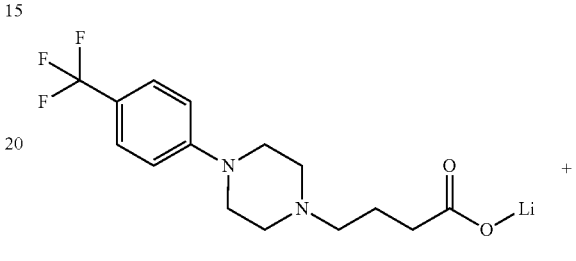

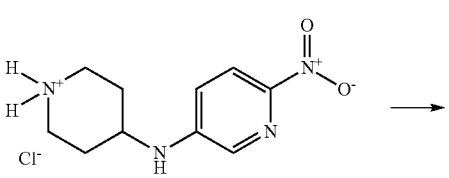

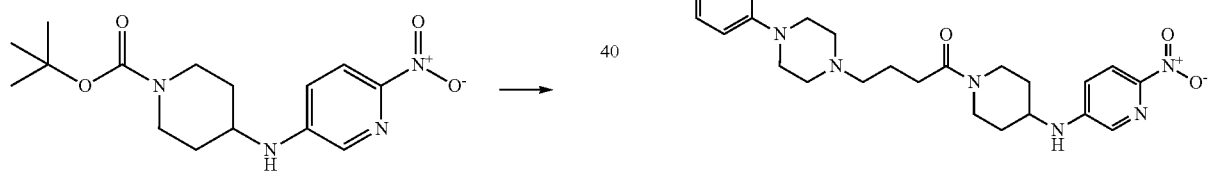

4-[4-(4-Trifluoromethyl-phenyl)-piperazin-1-yl]-butyric acid lithium salt (35 mg; 0.11 mmol, prepared in accordance with Example 3), diisopropylethyl amine (174 µL; 1.0 mmol) and tetramethyl-O-(1H-benzotriazol-1-yl)uronium hexafluorophosphate (37 mg; 0.1 mmol) are diluted in a 2 to 1 mixture of dimethylformamide and tetrahydrofuran (1.5 mL) and the resulting solution is stirred for 5 minutes. A solution of (6-nitro-pyridin-3-yl)-piperidin-4-yl-amine hydrochloride (27 mg; 0.1 mmol, prepared in accordance with Example 94) in dimethylformamide (0.5 mL) is added and the reaction is then stirred for 90 minutes at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (48 mg; 0.09 mmol). The structure was confirmed using Protocol II-A. Calculated mass=521; observed mass=521; HPLC retention time=3.08 min.

Example 96

Preparation of 4-(5-nitro-pyridin-2-ylamino)-piperidine-1-carboxylic acid tert-butyl ester intermediate

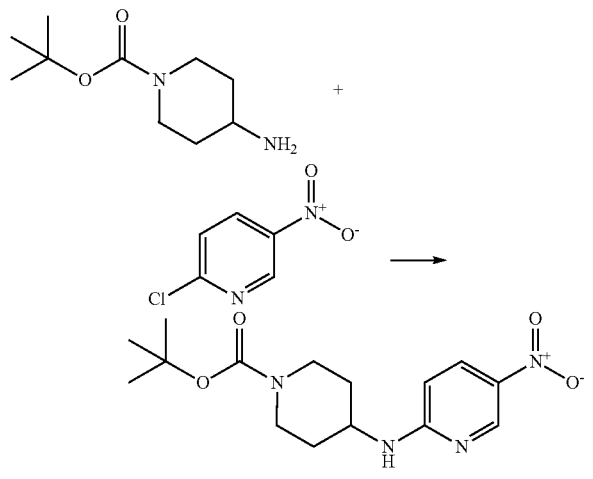

A mixture of 4-amino-piperidine-1-carboxylic acid tert-butyl ester (440 mg; 2.2 mmol), 2-chloro-5-nitro-pyridine (316 mg; 2.0 mmol), and triethylamine (420 µL; 3.0 mL) is dissolved in tetrahydrofuran (6 mL) and the resulting mixture is irradiated in a mono-mode microwave oven for 6 hours at 120° C. The reaction mixture is then treated by water (10 mL) and the pH of the aqueous phase is set to 4-5 by the addition of aqueous 1N hydrochloric acid. The aqueous phase is then extracted with dichloromethane (2×20 mL), the combined organic layers are washed with brine (10 mL), dried over magnesium sulphate, filtered and concentrated under reduced pressure. The crude residue is then purified by column chromatography on silica gel (dichloromethane:ethyl acetate 1:0 and then 5:1) to afford the desired product (533 mg; 1.65 mmol).

Example 97

Preparation of (5-nitro-pyridin-2-yl)-piperidin-4-yl-amine dihydrochloride intermediate

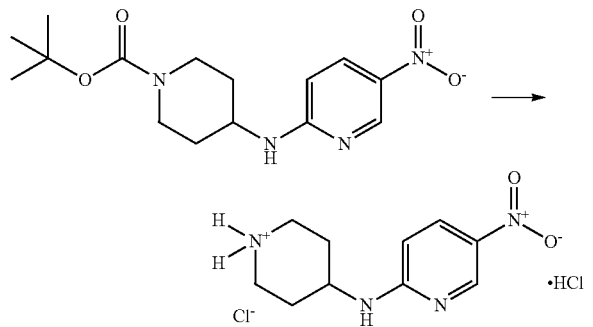

4-(5-nitro-pyridin-2-ylamino)-piperidine-1-carboxylic acid tert-butyl ester (533 mg; 1.65 mmol, prepared in accordance with Example 96) is dissolved in dichloromethane (5 mL) and trifluoroacetic acid (1 mL) is added under stirring. After 30 minutes, the reaction mixture is concentrated under reduced pressure and the residue obtained is co-evaporated with dichloromethane (2×10 mL). The product is then diluted in dioxane (3 mL) and a 4N solution of hydrochloric acid in dioxane (3 mL) is added. The precipitate formed is filtered and dried under high vacuum at 40° C. to afford the desired product as dihydrochloride (436 mg; 1.48 mmol).

Example 98

Preparation of 1-[4-(5-nitro-pyridin-2-ylamino)-piperidin-1-yl]-4-[4-(4-trifluoromethyl-phenyl)-piperazin-1-yl]-butan-1-one

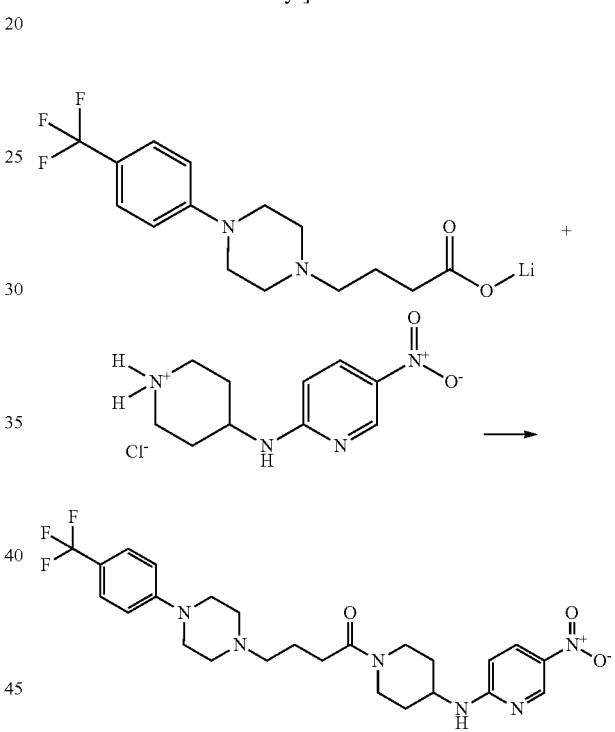

4-[4-(4-Trifluoromethyl-phenyl)-piperazin-1-yl]-butyric acid lithium salt (35 mg; 0.11 mmol, prepared in accordance with Example 3), diisopropylethyl amine (174 µL; 1.0 mmol) and tetramethyl-O-(1H-benzotriazol-1-yl)uronium hexafluorophosphate (37 mg; 0.1 mmol) are diluted in a 2 to 1 mixture of dimethylformamide and tetrahydrofuran (1.5 mL) and the resulting solution is stirred for 5 minutes. A solution of (5-nitro-pyridin-2-yl)-piperidin-4-yl-amine dihydrochloride (29 mg; 0.1 mmol, prepared in accordance with Example 97) in dimethylformamide (0.5 mL) is added and the reaction is then stirred for 90 minutes at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (41 mg; 0.08 mmol). The structure was confirmed using Protocol II-A. Calculated mass=521; observed mass=521; HPLC retention time=3.20 min.

Example 99

Preparation of 4-(6-methyl-5-nitro-pyridin-2-ylamino)-piperidine-1-carboxylic acid tert-butyl ester intermediate

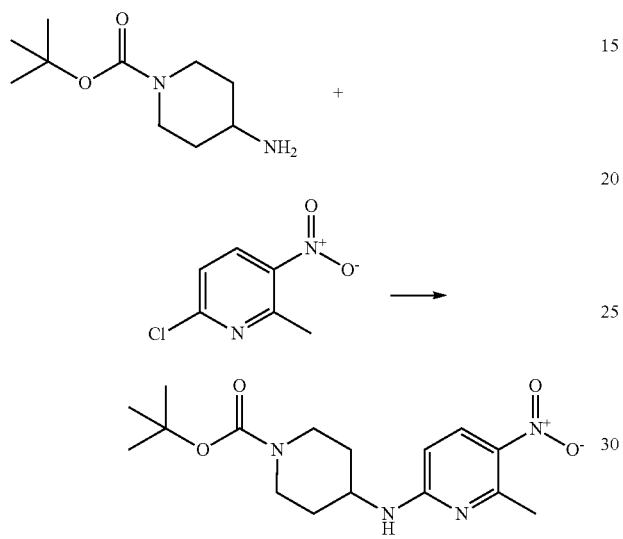

A mixture of 4-amino-piperidine-1-carboxylic acid tert-butyl ester (440 mg; 2.2 mmol), 6-chloro-2-methyl-3-nitro-pyridine (346 mg; 2.0 mmol), and triethylamine (420 µL; 3.0 mL) is dissolved in dimethylformamide (6 mL) and the resulting mixture is irradiated in a mono-mode microwave oven for 14 hours at 100° C. The reaction mixture is treated by aq. sat. ammonium chloride (5 mL), the precipitate formed is filtered, then rinsed with water (2 mL) and dried under high vacuum to afford the desired product (590 mg; 1.75 mmol).

Example 100

Preparation of (6-methyl-5-nitro-pyridin-2-yl)-piperidin-4-yl-amine hydrochloride intermediate

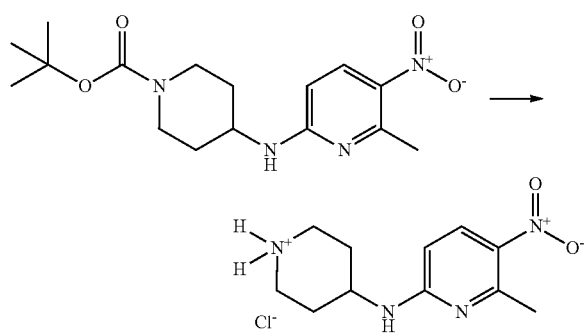

4-(6-Methyl-5-nitro-pyridin-2-ylamino)-piperidine-1-carboxylic acid tert-butyl ester (590 mg; 1.75 mmol, prepared in accordance with Example 99) is dissolved in dichloromethane (10 mL) and trifluoroacetic acid (2 mL) is added under stirring. After 30 minutes, the reaction mixture is concentrated under reduced pressure and the residue obtained is co-evaporated with dichloromethane (2×10 mL). The product is then diluted in dioxane (6 mL) and a 4N solution of hydrochloric acid in dioxane (3 mL) is added. The precipitate formed is filtered and dried under high vacuum at 40° C. to afford the desired product as hydrochloride (477 mg; 1.75 mmol).

Example 101

Preparation of 1-[4-(6-methyl-5-nitro-pyridin-2-ylamino)-piperidin-1-yl]-4-[4-(4-trifluoromethyl-phenyl)-piperazin-1-yl]-butan-1-one

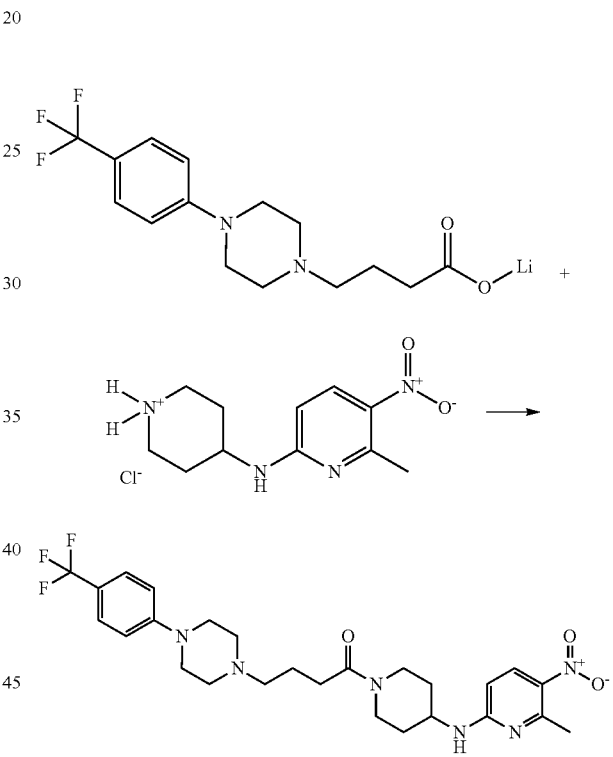

4-[4-(4-Trifluoromethyl-phenyl)-piperazin-1-yl]-butyric acid lithium salt (35 mg; 0.11 mmol, prepared in accordance with Example 3), diisopropylethyl amine (174 µL; 1.0 mmol) and tetramethyl-O-(1H-benzotriazol-1-yl)uronium hexafluorophosphate (37 mg; 0.1 mmol) are diluted in a 2 to 1 mixture of dimethylformamide and tetrahydrofuran (1.5 mL) and the resulting solution is stirred for 5 minutes. A solution of (6-methyl-5-nitro-pyridin-2-yl)-piperidin-4-yl-amine hydrochloride (27 mg; 0.1 mmol, prepared in accordance with Example 100) in dimethylformamide (0.5 mL) is added and the reaction is then stirred for 90 minutes at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (42 mg; 0.08 mmol).

The structure was confirmed using Protocol II-A. Calculated mass=535; observed mass=535; HPLC retention time=3.39 min.

Example 102

Preparation of 2-trifluoromethyl-4-(1-{4-[4-(4-trifluoromethyl-phenyl)-piperazin-1-yl]-butyryl}-piperidin-4-ylamino)-benzonitrile

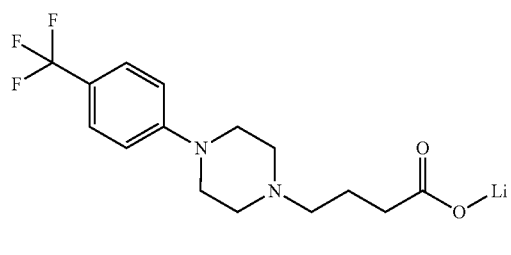

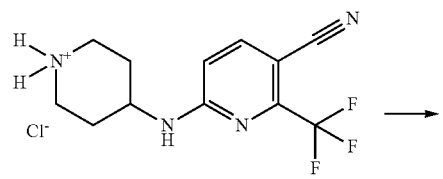

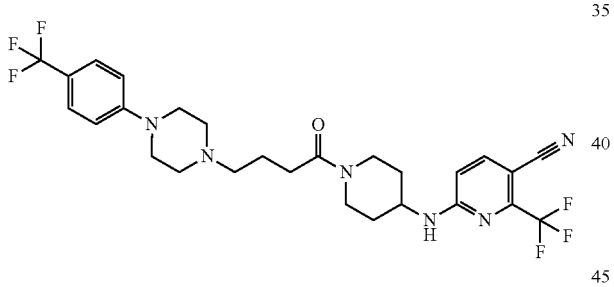

4-[4-(4-Trifluoromethyl-phenyl)-piperazin-1-yl]-butyric acid lithium salt (16 mg; 0.05 mmol, prepared in, prepared in accordance with Example 3), diisopropylethyl amine (25 µL; 0.15 mmol) and tetramethyl-O-(1H-benzotriazol-1-yl)uronium hexafluorophosphate (19 mg; 0.05 mmol) are diluted in a 2 to 1 mixture of dimethylformamide and tetrahydrofuran (1.5 mL) and the resulting solution is stirred for 5 minutes. A solution of 4-(piperidin-4-ylamino)-2-trifluoromethyl-benzonitrile hydrochloride (15 mg; 0.05 mmol) in dimethylformamide (0.5 mL) is added and the reaction is then stirred for 2 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (23 mg; 0.04 mmol). The structure was confirmed using Protocol I-B. Calculated mass=568; observed mass=568; HPLC retention time=5.10 min.

Example 103

Preparation of 4-(3-chloro-4-cyano-phenylamino)-piperidine-1-carboxylic acid tert-butyl ester intermediate

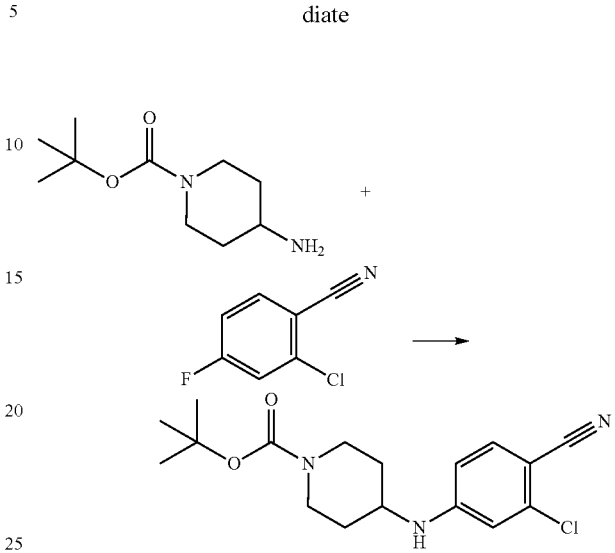

A mixture of 4-amino-piperidine-1-carboxylic acid tert-butyl ester (427 mg; 2.13 mmol), 2-chloro-4-fluoro-benzonitrile (302 mg; 1.94 mmol) and potassium carbonate (1.07 g; 7.76 mmol) is diluted in dimethylsulfoxide (5 mL) and is heated to 120° C. for 7 hours. After cooling to room temperature, the mixture is diluted with dichloromethane (50 mL) and is filtered. The filtrate is washed with 1N aq. hydrochlorid acid (2×15 mL), with water (20 mL) is then dried over magnesium sulfate, filtered and concentrated under reduced pressure. The crude product is finally purified by column chromatography on silica gel (dichloromethane:methanol 1:0 and then 98:2) to afford the desired product (290 mg; 0.87 mmol).

Example 104

Preparation of 2-chloro-4-(piperidin-4-ylamino)-benzonitrile Intermediate

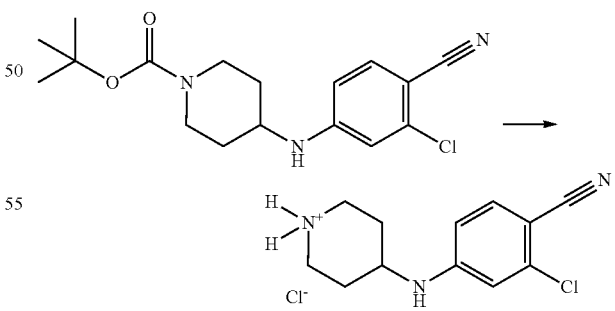

4-(3-Chloro-4-cyano-phenylamino)-piperidine-1-carboxylic acid tert-butyl ester (290 mg; 0.87 mmol, prepared according to Example 103) is dissolved in dichloromethane (1.3 mL) and trifluoroacetic acid (0.7 mL) is added under stiffing. After 60 minutes, the reaction mixture is concentrated under reduced pressure and the residue obtained is co-evaporated with dichloromethane (2×5 mL). The product is then diluted in dioxane (1 mL) and a 4N solution of hydrochloric acid in dioxane (2 mL) is added. The precipitate formed is filtered and dried under high vacuum at 40° C. to afford the desired product as hydrochloride (210 mg; 0.77 mmol).

Example 105

Preparation of 2-chloro-4-(1-{4-[4-(4-trifluoromethyl-phenyl)-piperazin-1-yl]-butyryl}-piperidin-4-ylamino)-benzonitrile

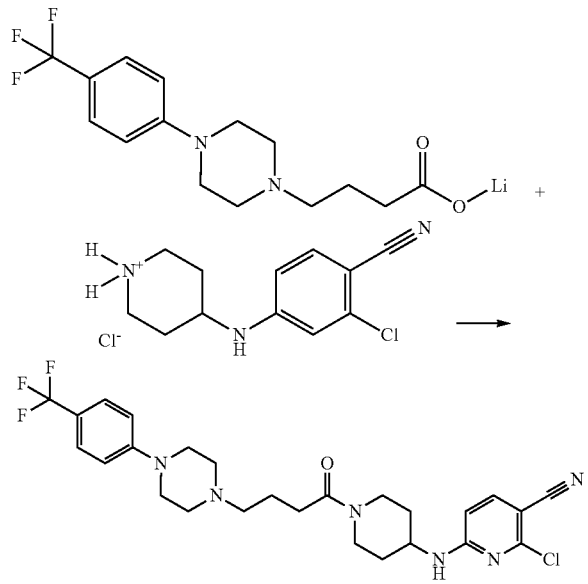

4-[4-(4-Trifluoromethyl-phenyl)-piperazin-1-yl]-butyric acid lithium salt (16 mg; 0.05 mmol, prepared in accordance with Example 3), diisopropylethyl amine (25 µL; 0.15 mmol) and tetramethyl-O-(1H-benzotriazol-1-yl)uronium hexafluorophosphate (19 mg; 0.05 mmol) are diluted in a 2 to 1 mixture of dimethylformamide and tetrahydrofuran (1.5 mL) and the resulting solution is stirred for 5 minutes. A solution of 2-chloro-4-(piperidin-4-ylamino)-benzonitrile hydrochloride (14 mg; 0.05 mmol, prepared in accordance with Example 104) in dimethylformamide (0.5 mL) is added and the reaction is then stirred for 2 hours at room temperature. Following dilution with dichloromethane (10 mL), the organic layer is sequentially washed with water (5 mL), aq. sat. sodium hydrogen carbonate (3×5 mL), is dried over magnesium sulfate and concentrated under reduced pressure. The residue obtained is finally purified by preparative HPLC to deliver the desired product in pure form (12 mg; 0.02 mmol). The structure was confirmed using Protocol I-B. Calculated mass=534; observed mass=534; HPLC retention time=4.52 min.

Example 106

Preparation of [1-(4-ethoxy-phenyl)-piperidin-4-ylmethyl]-carbamic acid tert-butyl ester intermediate

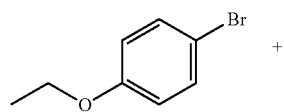

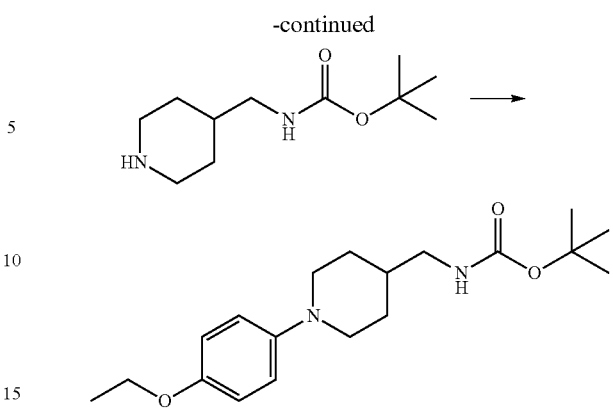

A suspension of piperidin-4-ylmethyl-carbamic acid tert-butyl ester (1.0 g; 4.67 mmol), 1-bromo-4-ethoxy-benzene (1.87 g; 9.33 mmol), tris(dibenzylideneacetone)dipalladium (174 mg; 0.19 mmol), sodium tert-butoxide (524 mg; 4.67 mmol) and 2-(dicyclohexylphosphino)-2-methylbiphenyl (135 mg; 0.37 mmol) in toluene (30 mL) is thoroughly flushed with argon. The reaction mixture is then heated at 70° C. for 17 hours. After dilution with ethyl acetate (50 mL), the suspension is filtered over Celite and the filtrate is washed with aq. sat ammonium chloride (2×25 mL), dried over sodium sulfate and concentrated under reduced pressure. The residue obtained is then further purified by flash column chromatography on silica gel (Ethyl acetate:heptane 25:75) to afford the desired product (963 mg; 2.88 mmol).

Example 107

Preparation of methyl-[1-(4-ethoxy-phenyl)-piperidin-4-ylmethyl]-amine intermediate

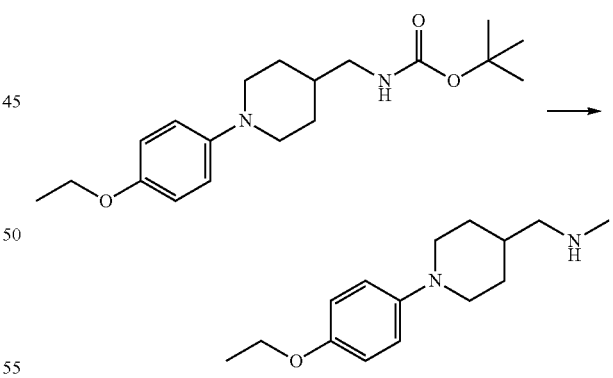

[1-(4-Ethoxy-phenyl)-piperidin-4-ylmethyl]-carbamic acid tert-butyl ester (963 mg, 2.88 mmol, prepared in accordance with Example 106) is added to a molar solution of lithium aluminium hydride in tetrahydrofuran (10 mL, 10 mmol) and the resulting mixture is refluxed for 2 hours. After cooling with an ice bath, water (1 mL) is added carefully and the mixture is stirred overnight at room temperature. The reaction is then filtered and the filtrate is concentrated under reduced pressure. The residue obtained is dried under high vacuum to afford the desired product (701 mg; 2.83 mmol).

Example 108

Preparation of 4-(4-nitro-3-trifluoromethyl-phenylamino)-piperidine-1-carboxylic acid [1-(4-ethoxy-phenyl)-piperidin-4-ylmethyl]-methyl-amide

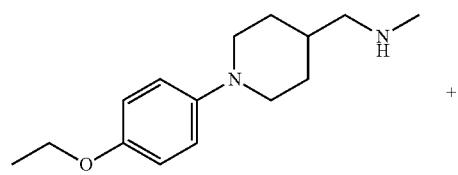

+

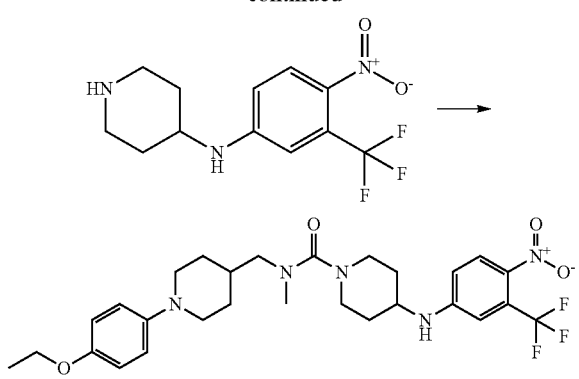

Triphosgene (60 mg; 0.20 mmol) is added to a solution of methyl-[1-(4-trifluoromethyl-phenyl)-piperidin-4-ylmethyl]-amine (150 mg; 0.60 mmol) and triethylamine (185 μL; 1.33 mmol) in acetonitrile (6 mL). After stirring for 15 minutes a solution of (4-nitro-3-trifluoromethyl-phenyl)-piperidin-4-yl-amine (173 mg; 0.60 mmol, in acetonitrile (10 mL) is added. After 2 hours reaction time at room temperature, the mixture is poured into water (10 m) and the aqueous layer is extracted with ethyl acetate (3×50 mL). The combined organic layers are dried over sodium sulfate, filtered and concentrated under reduced pressure. The crude product is purified by column chromatography on silica gel (Ethyl acetate:heptane 8:2) to afford the desired product (267 mg; 0.45 mmol). The structure was confirmed using Protocol II-E. Calculated mass=564; observed mass=564; HPLC retention time=7.73 min.

Example 109

Preparation of 4-(1-{4-[4-(4-trifluoromethyl-phenyl)-piperazin-1-yl]-thiobutyryl}-piperidin-4-ylamino)-benzonitrile

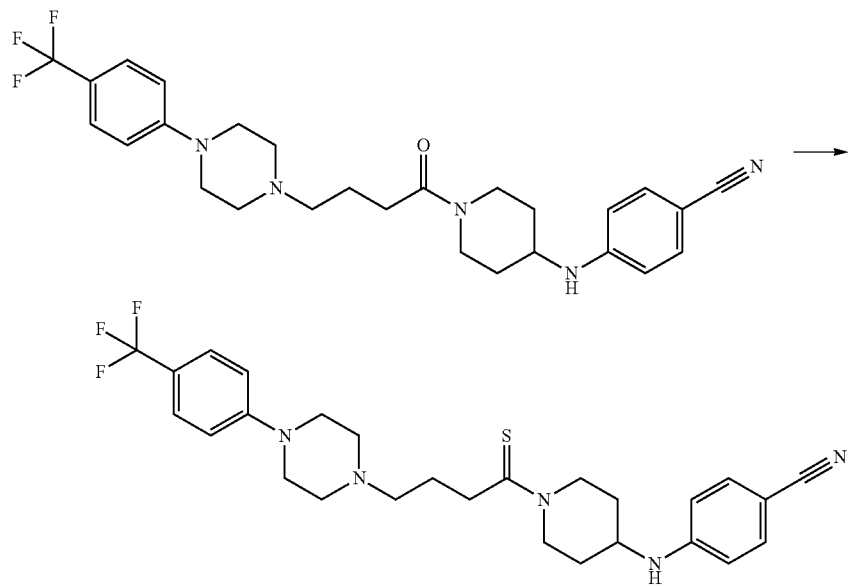

4-(1-{4-[4-(4-Trifluoromethyl-phenyl)-piperazin-1-yl]-butyryl}-piperidin-4-ylamino)-benzonitrile (7 mg; 0.014 mmol, prepared in accordance with Example 83) is reacted with Lawesson's reagent (3 mg; 0.007 mmol) and the resulting mixture is heated between at 95 to 110° C. for 2 hours. In cases where incomplete conversion of the starting amide is observed, additional portion of Lawesson's reagent is added and the mixture heated further until no evolution of the conversion is observed. The reaction mixture is concentrated under reduced pressure and the crude residue is purified by preparative HPLC (1 mg; 0.002 mmol). The structure was confirmed using Protocol I-B. Calculated mass=516; observed mass=516; HPLC retention time=4.53 min.

In many instances, the method of Example 109 can be adapted to make other compounds that are useful as intermediates for making the compounds and salts of this invention. An illustrative generic scheme is as follows:

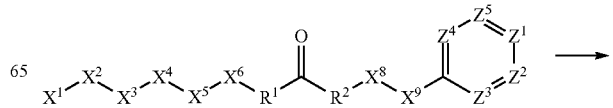

-continued

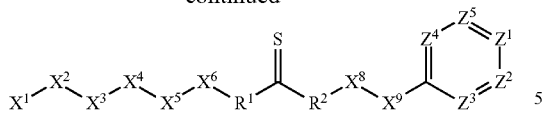

Here, $X^1, X^2, X^3, X^4, X^5, X^6, X^8, X^9, Z^1, Z^2, Z^3, Z^4, Z^5$ are as defined above for the compounds of this invention. $R^1$ and $R^2$ are independently selected from the group consisting of a bond and —NH—. Determining the suitability of the method (and any necessary routine adaptations) or making a particular intermediate is generally with the skill of those in the art after reading this patent.

Example 110

Preparation of 1-[4-(5-nitro-pyridin-2-ylamino)-piperidin-1-yl]-4-[4-(4-trifluoromethyl-phenyl)-piperazin-1-yl]-butane-1-thione

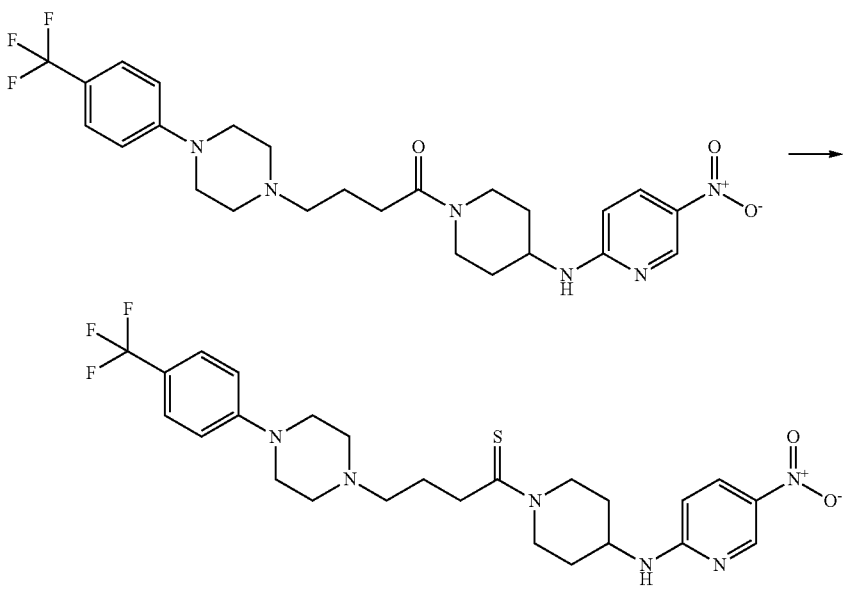

1-[4-(5-Nitro-pyridin-2-ylamino)-piperidin-1-yl]-4-[4-(4-trifluoromethyl-phenyl)-piperazin-1-yl]-butan-1-one (20 mg; 0.038 mmol, prepared in accordance with Example 95) is reacted with Lawesson's reagent (8 mg; 0.019 mmol) according to the general conditions described in Example 109. The desired product is obtained following purification by preparative HPLC (8 mg; 0.015 mmol). The structure was confirmed using Protocol I-B. Calculated mass=537; observed mass=537; HPLC retention time=4.39 min.

Example 111

Preparation of 1-[4-(4-methyl-5-nitro-pyridin-2-ylamino)-piperidin-1-yl]-4-[4-(4-trifluoromethyl-phenyl)-piperazin-1-yl]-butane-1-thione

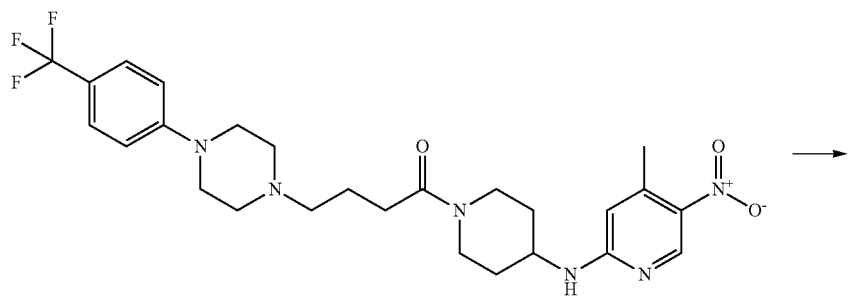

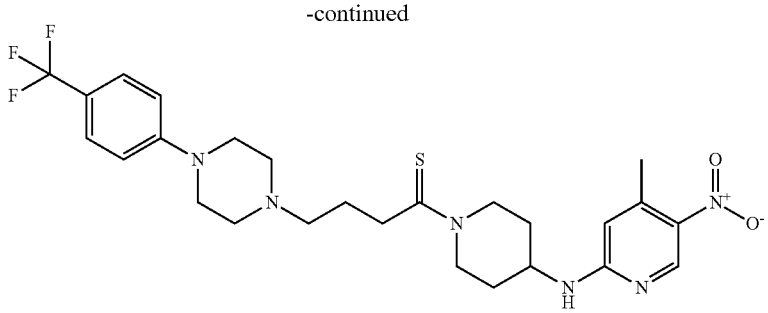

1-[4-(4-Methyl-5-nitro-pyridin-2-ylamino)-piperidin-1-yl]-4-[4-(4-trifluoromethyl-phenyl)-piperazin-1-yl]-butan-1-one (23 mg; 0.043 mmol, prepared in accordance with Example 71) is reacted with Lawesson's reagent (9 mg; 0.043 mmol) according to the general conditions described in Example 109. The desired product is obtained following purification by preparative HPLC (9 mg; 0.016 mmol). The structure was confirmed using Protocol 1-B. Calculated mass=551; observed mass=551; HPLC retention time=4.45 min.

Example 112

Preparation of 3-[4-(4-chloro-phenyl)-piperazin-1-yl]-2-methyl-1-[4-(4-nitro-3-trifluoromethyl-phenylamino)-piperidin-1-yl]-propane-1-thione pan-1-one (6 mg; 0.011 mmol, prepared in accordance with Example 61) is reacted with Lawesson's reagent (2 mg; 0.005 mmol) according to the general conditions described in Example 109. The desired product is obtained following purification by preparative HPLC (2 mg; 0.004 mmol). The structure was confirmed using Protocol I-B. Calculated mass=570; observed mass=570; HPLC retention time=4.69 min

Example 113

Preparation of 1-[4-(4-nitro-3-trifluoromethyl-phenylamino)-piperidin-1-yl]-3-[4-(4-trifluoromethyl-phenyl)-piperidin-1-yl]-propane-1-thione

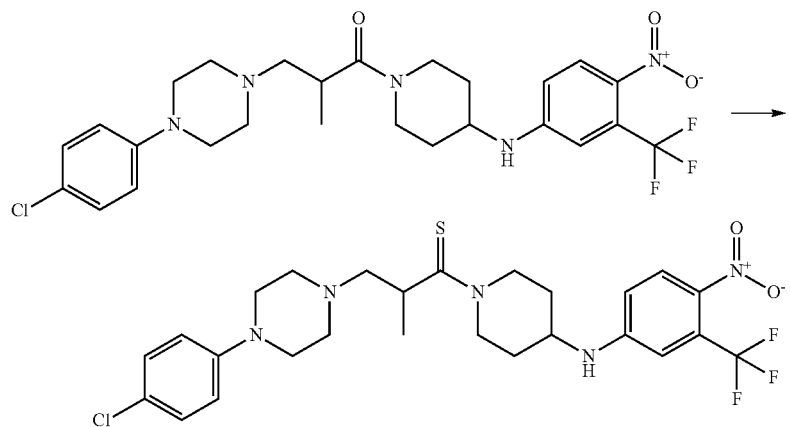

3-[4-(4-Chloro-phenyl)-piperazin-1-yl]-2-methyl-1-[4-(4-nitro-3-trifluoromethyl-phenylamino)-piperidin-1-yl]-pro-

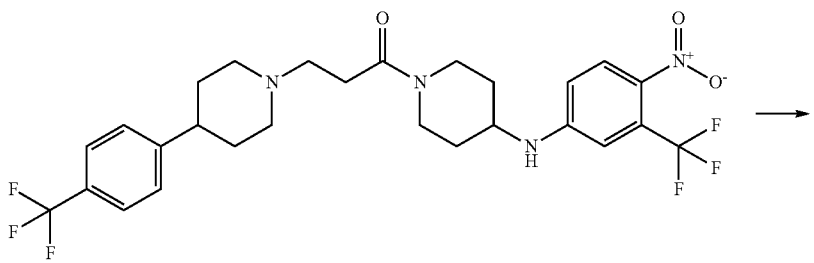

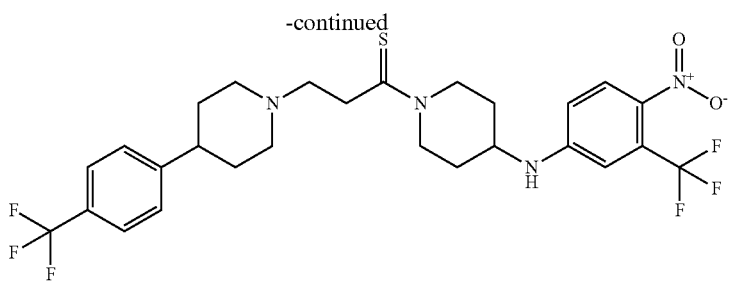

1-[4-(4-Nitro-3-trifluoromethyl-phenylamino)-piperidin-1-yl]-3-[4-(4-trifluoromethyl-phenyl)-piperidin-1-yl]-propan-1-one (20 mg; 0.035 mmol, prepared in accordance with Example 14) is reacted with Lawesson's reagent (7 mg; 0.018 mmol according to the general conditions described in Example 109. The desired product is obtained following purification by preparative HPLC (6 mg; 0.010 mmol). The structure was confirmed using Protocol 1-B. Calculated mass=589; observed mass=589; HPLC retention time=4.74 min.

Example 114

Preparation of 1-[4-(4-nitro-3-trifluoromethyl-phenoxy)-piperidin-4-yl]-4-[4-(4-trifluoromethyl-phenyl)-piperazin-4-yl]-butane-1-thione

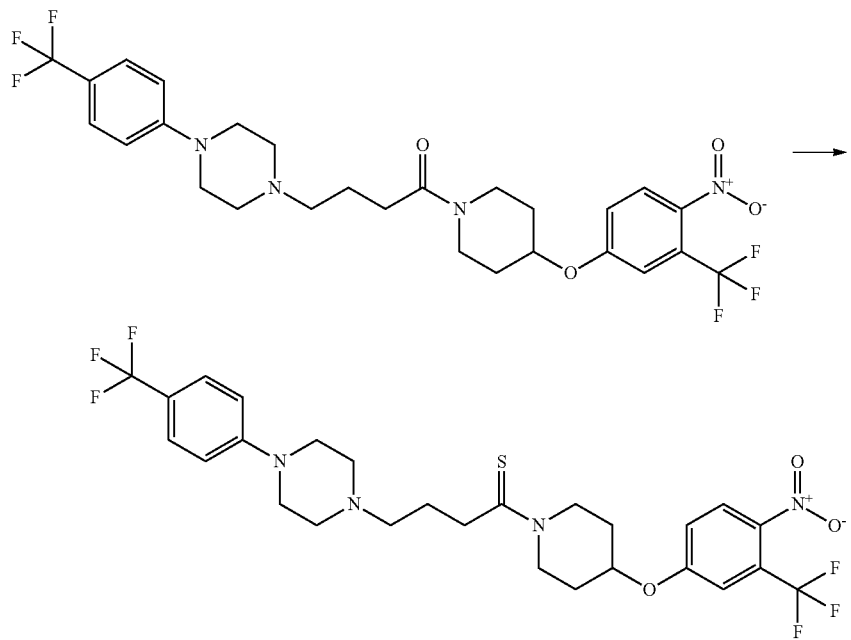

1-[4-(4-Nitro-3-trifluoromethyl-phenoxy)-piperidin-1-yl]-4-[4-(4-trifluoromethyl-phenyl)-piperazin-1-yl]-butan-1-one (24 mg; 0.041 mmol, prepared in accordance with Example 79) is reacted with Lawesson's reagent (8 mg; 0.020 mmol) according to the general conditions described in Example 109. The desired product is obtained following purification by preparative HPLC (8 mg; 0.013 mmol). The structure was confirmed using Protocol 1-B. Calculated mass=605; observed mass=605; HPLC retention time=4.72

Example 115

Preparation of 4-[4-(4-tert-butyl-phenyl)-piperazin-1-yl]-1-[4-(4-nitro-3-trifluoromethyl-phenylamino)-piperidin-1-yl]-butane-1-thione

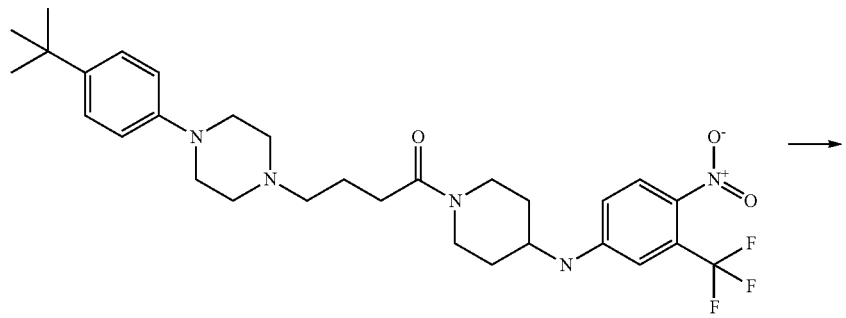

4-[4-(4-tert-Butyl-phenyl)-piperazin-1-yl]-1-[4-(4-nitro-3-trifluoromethyl-phenylamino)-piperidin-1-yl]-butan-1-one (28 mg; 0.049 mmol, prepared in accordance with Example 90) is reacted with Lawesson's reagent (10 mg; 0.024 mmol) according to the general conditions described in Example 109. The desired product is obtained following purification by preparative HPLC (13 mg; 0.023 mmol). The structure was confirmed using Protocol I-B. Calculated mass=592; observed mass=592; HPLC retention time=4.811 min.

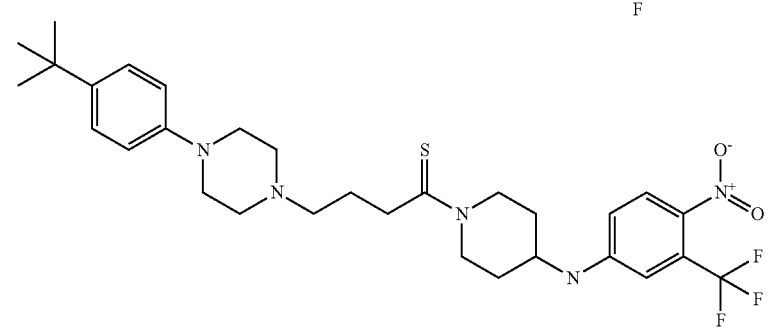

Example 116

Preparation of 1-[4-(4-methanesulfonyl-3-trifluoromethyl-phenylamino)-piperidin-1-yl]-4-[4-(4-trifluoromethyl-phenyl)-piperazin-1-yl]-butane-1-thione

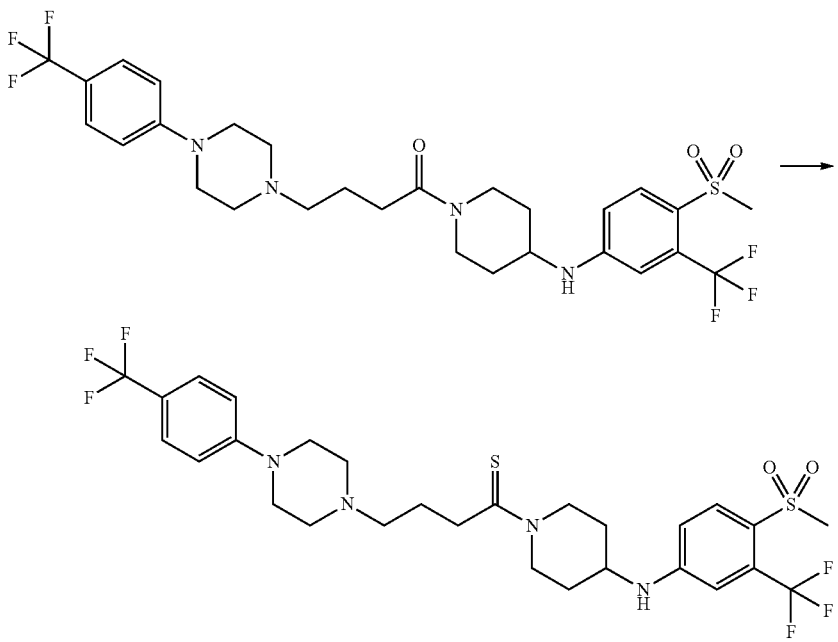

1-[4-(4-Methanesulfonyl-3-trifluoromethyl-phenylamino)-piperidin-1-yl]-4-[4-(4-trifluoromethyl-phenyl)-piperazin-1-yl]-butan-1-one (7 mg; 0.011 mmol, prepared in accordance with Example 30) is reacted with Lawesson's reagent (2 mg; 0.006 mmol) according to the general conditions described in Example 109. The desired product is obtained following purification by preparative HPLC (2 mg; 0.004 mmol). The structure was confirmed using Protocol I-B. Calculated mass=637; observed mass=637; HPLC retention time=4.48 min.

Example 117

Preparation of 1-[4-(4-nitro-3-trifluoromethyl-phenylamino)-piperidin-1-yl]-3-[4-(4-trifluoromethyl-benzyloxy)-piperidin-1-yl]-propane-1-thione

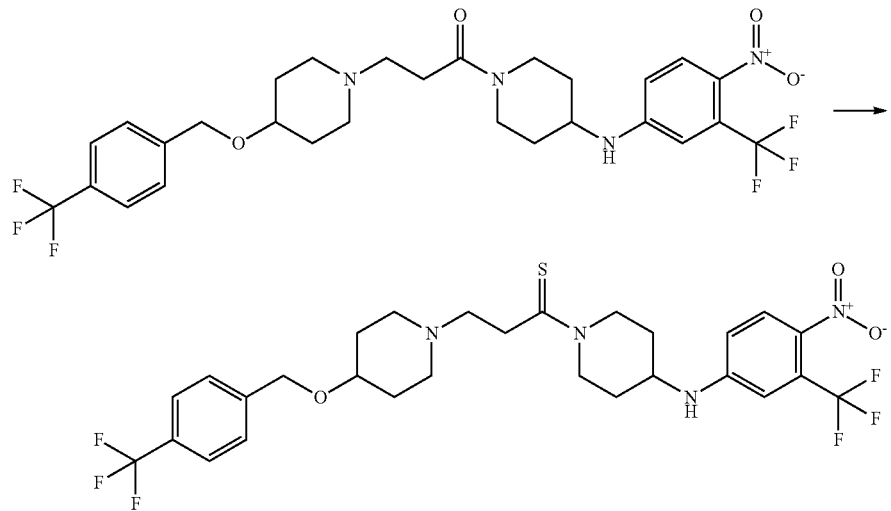

1-[4-(4-Nitro-3-trifluoromethyl-phenylamino)-piperidin-1-yl]-3-[4-(4-fluoromethyl-benzyloxy)-piperidin-1-yl]-propan-1-one (26 mg; 0.043 mmol, prepared in accordance with Example 57) is reacted with Lawesson's reagent (9 mg; 0.022 mmol) according to the general conditions described in Example 109. The desired product is obtained following purification by preparative HPLC (7 mg; 0.011 mmol). The structure was confirmed using Protocol I-B. Calculated mass=619; observed mass=619; HPLC retention time=4.79 min.

Example 118

Preparation of 2-methyl-1-[4-(4-nitro-3-trifluoromethyl-phenylamino)-piperidin-1-yl]-3-[4-(4-trifluoromethyl-phenyl)-piperazin-1-yl]-propane-1-thione

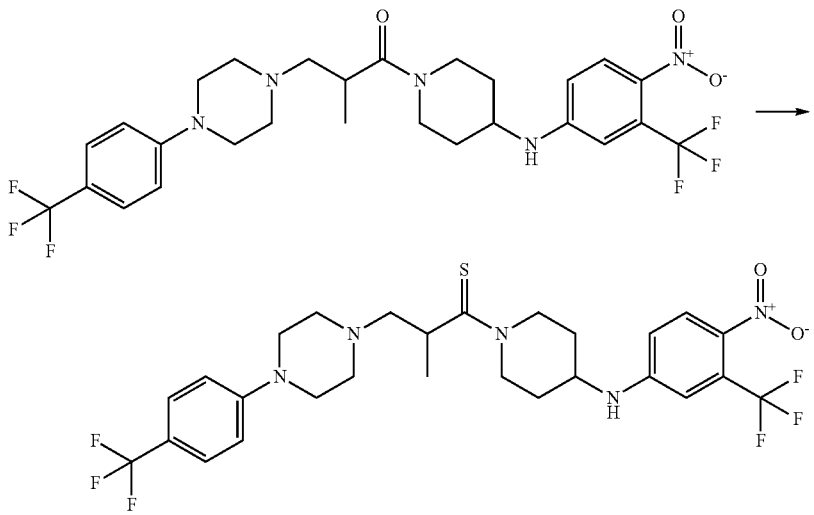

2-Methyl-1-[4-(4-nitro-3-trifluoromethyl-phenylamino)-piperidin-1-yl]-3-[4-(4-trifluoromethyl-phenyl)-piperazin-1-yl]-propane-1-thione (24 mg; 0.041 mmol, prepared in accordance with Example 68) is reacted with Lawesson's reagent (8 mg; 0.020 mmol) according to the general conditions described in Example 109. The desired product is obtained following purification by preparative HPLC (11 mg; 0.018 mmol). The structure was confirmed using Protocol I-B. Calculated mass=604; observed mass=604; HPLC retention time=4.74 min.

Example 119

Preparation of 1-[4-(4-nitro-3-trifluoromethyl-phenylamino)-piperidin-1-yl]-4-[4-(4-trifluoromethyl-phenyl)-piperazin-1-yl]-butane-1-thione

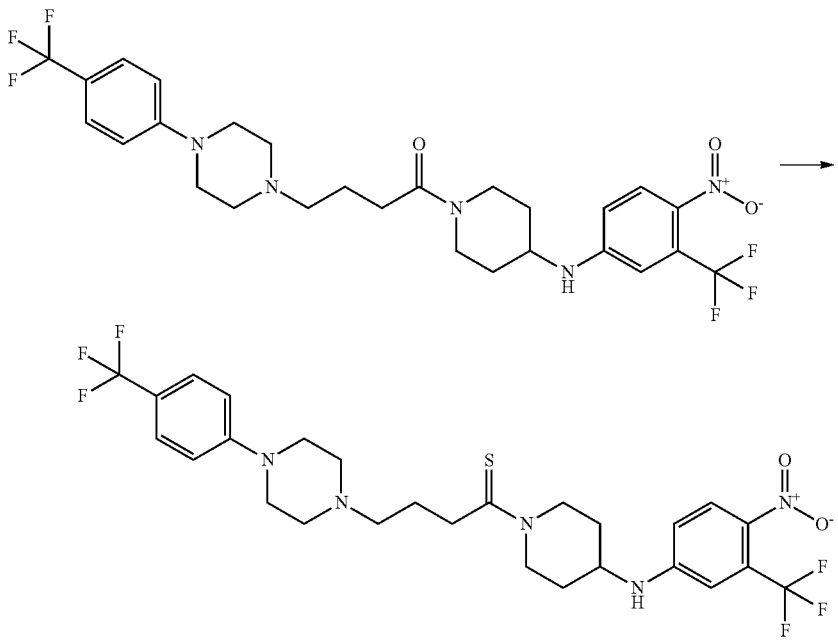

1-[4-(4-Nitro-3-trifluoromethyl-phenylamino)-piperidin-1-yl]-4-[4-(4-trifluoromethyl-phenyl)-piperazin-1-yl]-butan-1-one (20 mg; 0.034 mmol, prepared in accordance with Example 165) is reacted with Lawesson's reagent (7 mg; 0.017 mmol) according to the general conditions described in Example 109. The desired product is obtained following purification by preparative HPLC (11 mg; 0.018 mmol). The structure was confirmed using Protocol I-B. Calculated mass=604; observed mass=604; HPLC retention time=4.64 min.

Example 120

Preparation of 2-chloro-4-(1-{4-[4-(4-trifluoromethyl-phenyl)-piperazin-4-yl]-thiobutyryl}-piperidin-4-ylamino)-benzonitrile

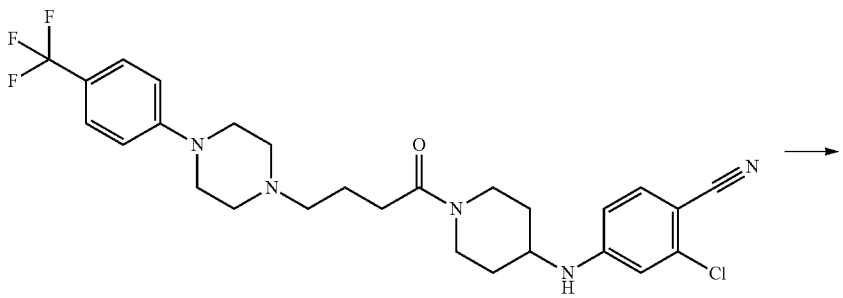

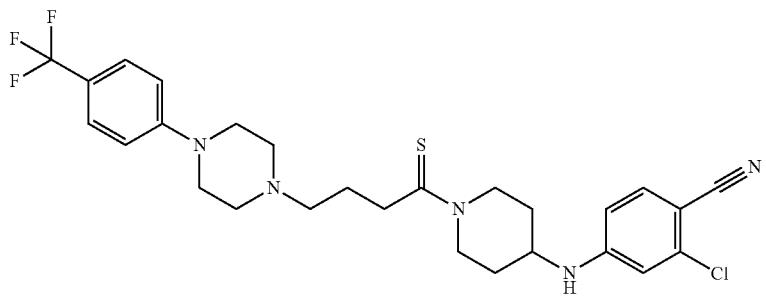

2-Chloro-4-(1-{4-[4-(4-trifluoromethyl-phenyl)-piperazin-1-yl]-butyryl}-piperidin-4-ylamino)-benzonitrile (5 mg; 0.009 mmol, prepared in accordance with Example 105) is reacted with Lawesson's reagent (2 mg; 0.005 mmol) according to the general conditions described in Example 109. The desired product is obtained following purification by preparative HPLC (2 mg; 0.004 mmol). The structure was confirmed using Protocol I-B. Calculated mass=550; observed mass=550; HPLC retention time=4.56 min.

Example 121

Preparation of 4-[4-(4-trifluoromethyl-phenyl)-piperazin-4-yl]-N-[1-(4-trifluoromethylsulfanyl-phenyl)-piperidin-4-yl]-thiobutyramide

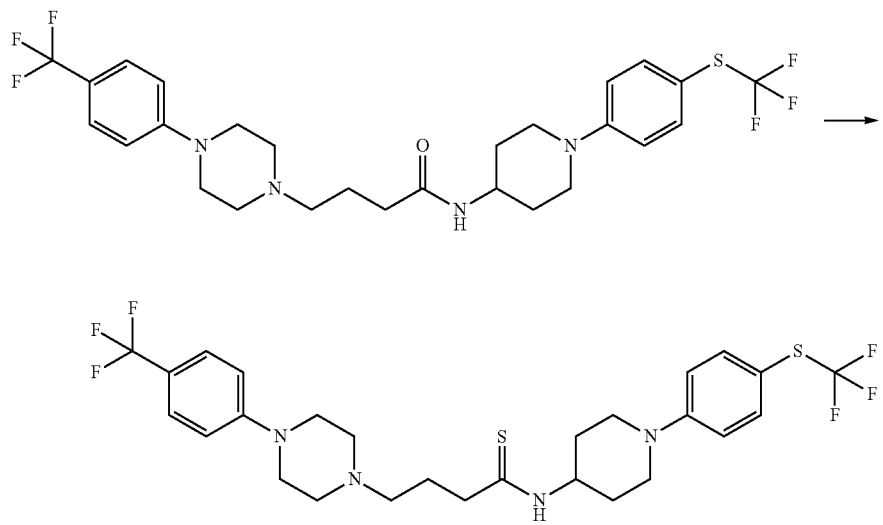 [SMILES: O=C(CCCN1CCN(c2ccc(C(F)(F)F)cc2)CC1)NC1CCN(c2ccc(SC(F)(F)F)cc2)CC1 ; FC(F)(F)Sc1ccc(N2CCC(NC(=S)CCCN3CCN(c4ccc(C(F)(F)F)cc4)CC3)CC2)cc1]

4-[4-(4-Trifluoromethyl-phenyl)-piperazin-1-yl]-N-[1-(4-trifluoromethylsulfanyl-phenyl)-piperidin-4-yl]-butyramide (10 mg; 0.017 mmol, prepared in accordance with Example 48) is reacted with Lawesson's reagent (4 mg; 0.009 mmol) according to the general conditions described in Example 109. The desired product is obtained following purification by preparative HPLC (4 mg; 0.007 mmol). The structure was confirmed using Protocol I-B. Calculated mass=591; observed mass=591; HPLC retention time=4.85 min.

Example 122

Preparation of 4-(1-{2-methyl-3-[4-(4-trifluoromethyl-phenyl)-piperazin-1-yl]-thiopropionyl}-piperidin-4-ylamino)-2-trifluoromethyl-benzonitrile

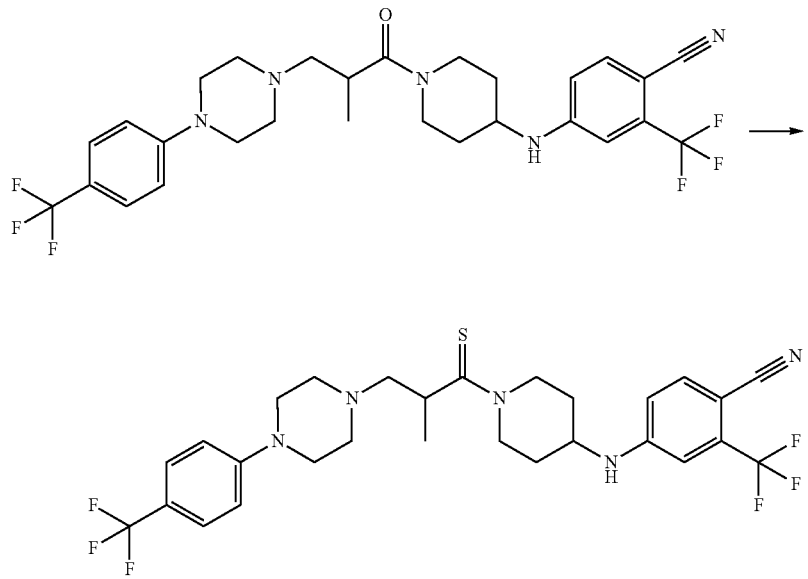 [SMILES: CC(CN1CCN(c2ccc(C(F)(F)F)cc2)CC1)C(=O)N1CCC(Nc2ccc(C#N)c(C(F)(F)F)c2)CC1 ; CC(CN1CCN(c2ccc(C(F)(F)F)cc2)CC1)C(=S)N1CCC(Nc2ccc(C#N)c(C(F)(F)F)c2)CC1]

4-(1-{2-Methyl-3-[4-(4-trifluoromethyl-phenyl)-piperazin-1-yl]-propionyl}-piperidin-4-ylamino)-2-trifluoromethyl-benzonitrile (15 mg; 0.026 mmol, prepared in accordance with Example 92) is reacted with Lawesson's reagent (5 mg; 0.013 mmol) according to the general conditions described in Example 109. The desired product is obtained following purification by preparative HPLC (9 mg; 0.015 mmol). The structure was confirmed using Protocol I-B. Calculated mass=584; observed mass=584; HPLC retention time=4.68 min

Example 123

Preparation of 3-[4-(5-trifluoromethyl-[1,3,4]thiadiazol-2-yl)-piperazin-1-yl]-propionic acid lithium salt intermediate

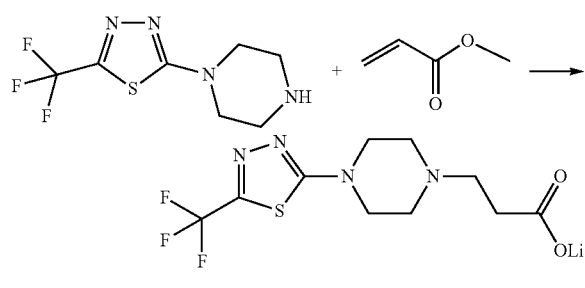

Acrylic acid methyl ester (189 mg; 2.20 mmol) is added to 1-(5-trifluoromethyl-[1,3,4]thiadiazol-2-yl)-piperazine (476 mg; 2.00 mmol) in water (1.6 mL) and the resulting mixture is irradiated in a mono-mode microwave oven for 30 minutes at 120° C. Lithium hydroxide (92 mg; 4.00 mmol) in water (2 mL) is then added and the reaction mixture is again irradiated in a mono-mode microwave oven for 10 minutes at 100° C. The mixture is then diluted with acetonitrile and the precipitate formed is filtered, collected and dried under high vacuum to afford the desired compound (580 mg; 1.84 mmol).

Example 124

Preparation of 1-[4-(4-nitro-3-trifluoromethyl-phenylamino)-piperidin-1-yl]-3-[4-(5-trifluoromethyl-1,3,4-thiadiazol-2-yl)-piperazin-1-yl]-propan-1-one

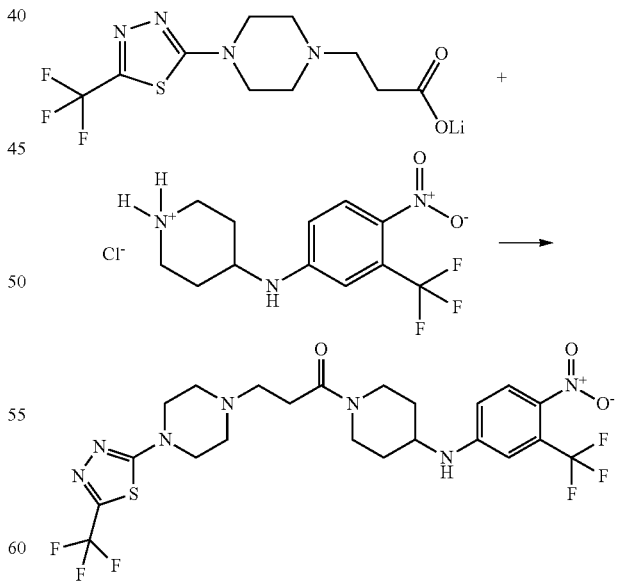

3-[4-(5-Trifluoromethyl-[1,3,4]thiadiazol-2-yl)-piperazin-1-yl]-propionic acid lithium salt (15 mg; 0.05 mmol, prepared in accordance with Example 123) and tetramethyl-O-(1H-benzotriazol-1-yl)uronium hexafluorophosphate (19 mg;

0.05 mmol) are diluted in a 2 to 1 mixture of dimethylformamide and tetrahydrofuran (0.75 mL). A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 μL; 0.15 mmol) are added and the reaction is then stirred. After 4 hours at room temperature, aluminium oxide (90 active basic) is added and stirring is continued for 40 minutes. The solids are removed by filtration and the filtrate is concentrated under high vacuum. The obtained residue is purified by preparative HPLC to afford the desired compound (16 mg; 0.027 mmol). The structure was confirmed using Protocol I-D. Calculated mass=582; observed mass=582; HPLC retention time=1.41 min.

Example 125

Preparation of 3-[4-(6-trifluoromethyl-pyridin-3-yl)-piperazin-1-yl]-propionic acid lithium salt intermediate

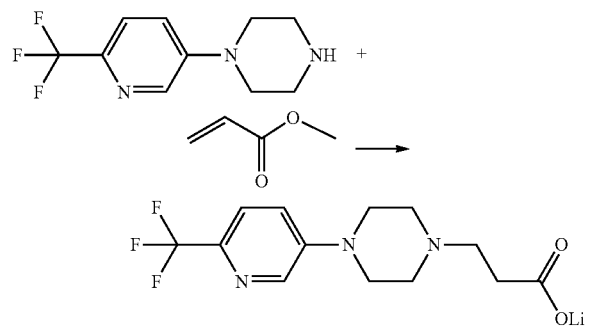

Acrylic acid methyl ester (189 mg; 2.20 mmol) and triethylamin (0.2 mL) are added to 1-(6-trifluoromethyl-pyridin-3-yl)-piperazine (420 mg; 1.82 mmol) in a 1 to 1 mixture of water and tetrahydrofuran (1.6 mL) and the resulting mixture is irradiated in a mono-mode microwave oven for 30 minutes at 120° C. Lithium hydroxide (92 mg; 3.84 mmol) in water (5 mL) is then added and the reaction mixture is again irradiated in a mono-mode microwave oven for 30 minutes at 100° C. The mixture is then diluted with acetonitrile and the precipitate formed is filtered, collected and dried under high vacuum to afford the desired product (363 mg; 1.20 mmol).

Example 126

Preparation of 1-[4-(4-nitro-3-trifluoromethyl-phenylamino)-piperidin-1-yl]-3-[4-(6-trifluoromethyl-pyridin-3-yl)-piperazin-1-yl]-propan-1-one

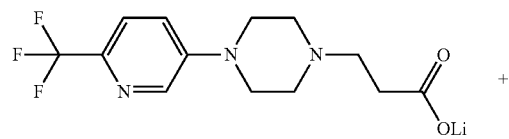

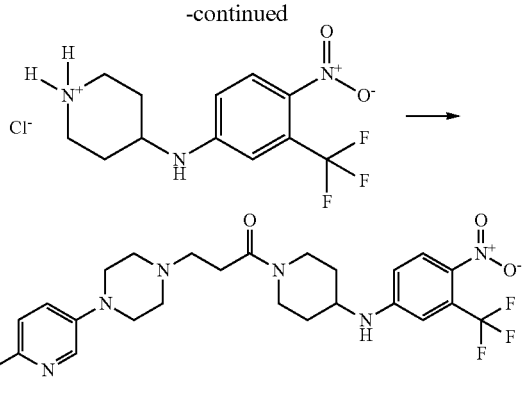

3-[4-(6-Trifluoromethyl-pyridin-3-yl)-piperazin-1-yl]-propionic acid lithium salt (15 mg; 0.05 mmol, prepared in accordance with Example 125) and tetramethyl-O-(1H-benzotriazol-1-yl)uronium hexafluorophosphate (19 mg; 0.05 mmol) are diluted in a 2 to 1 mixture of dimethylformamide and tetrahydrofuran (0.75 mL). A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 μL; 0.15 mmol) are added and the reaction is then stirred. After 4 hours at room temperature, aluminium oxide (90 active basic) is added and stirring is continued for 40 minutes. The solids are removed by filtration and the filtrate is concentrated under high vacuum. The obtained residue is purified by preparative HPLC to afford the desired compound (16 mg; 0.027 mmol). The structure was confirmed using Protocol I-D. Calculated mass=574; observed mass=575; HPLC retention time=1.42 min.

Example 127

Preparation of 3-[5-(4-tert-butyl-phenyl)-hexahydro-pyrrolo[3,4-c]pyrrol-2-yl]-propionic acid lithium salt intermediate

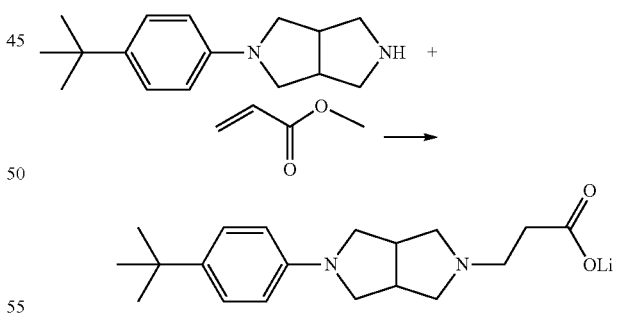

Acrylic acid methyl ester (189 mg; 2.20 mmol) and triethylamin (0.2 mL) are added to 2-(4-tert-butyl-phenyl)-octahydro-pyrrolo[3,4-c]pyrrole (450 mg; 1.84 mmol) in a 1 to 1 mixture of water and tetrahydrofuran (1.6 mL) and the resulting mixture is irradiated in a mono-mode microwave oven for 30 minutes at 120° C. Lithium hydroxide (92 mg; 3.84 mmol) in water (5 mL) is then added and the reaction mixture is again irradiated in a mono-mode microwave oven for 30 minutes at 100° C. The mixture is then diluted with acetonitrile and the precipitate formed is filtered, collected and dried under high vacuum to afford the desired product (425 mg; 1.34 mmol).

Example 128

Preparation of 3-[5-(4-tert-butyl-phenyl)-hexahydro-pyrrolo[3,4-c]pyrrol-2-yl]-1-[4-(4-nitro-3-trifluoromethyl-phenylamino)-piperidin-1-yl]-propan-1-one

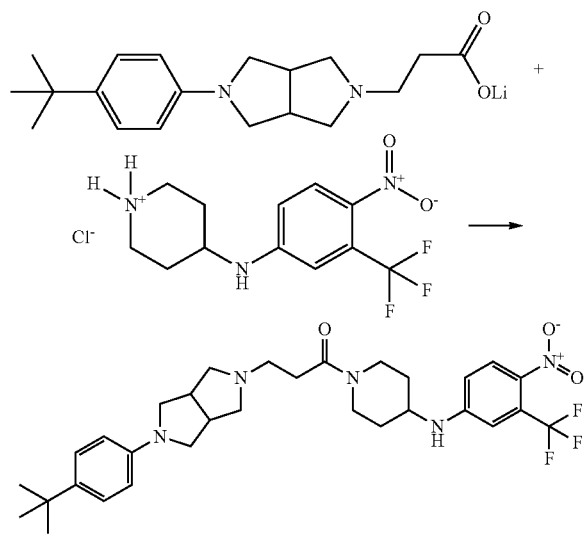

3-[5-(4-tert-Butyl-phenyl)-hexahydro-pyrrolo[3,4-c]pyrrol-2-yl]-propionic acid lithium salt (16 mg; 0.05 mmol, prepared in accordance with Example 127) and tetramethyl-O-(1H-benzotriazol-1-yl)uronium hexafluorophosphate (19 mg; 0.05 mmol) are diluted in a 2 to 1 mixture of dimethylformamide and tetrahydrofuran (0.75 mL). A solution of (4-nitro-3-trifluoromethyl-phenyl)-piperidin-4-yl-amine hydrochloride (16 mg; 0.05 mmol, prepared in accordance with Example 8) in dimethylformamide and (0.25 mL) diisopropylethyl amine (25 µL; 0.15 mmol) are added and the reaction is then stirred. After 4 hours at room temperature, aluminium oxide (90 active basic) is added and stirring is continued for 40 minutes. The solids are removed by filtration and the filtrate is concentrated under high vacuum. The obtained residue is purified by preparative HPLC to afford the desired compound (7 mg; 0.012 mmol). The structure was confirmed using Protocol I-D. Calculated mass=588; observed mass=588; HPLC retention time=1.66 min.

Example 129

Preparation of 3-[4-(4-tert-butyl-phenyl)-piperazin-1-yl]-2-methyl-propionic acid lithium salt intermediate

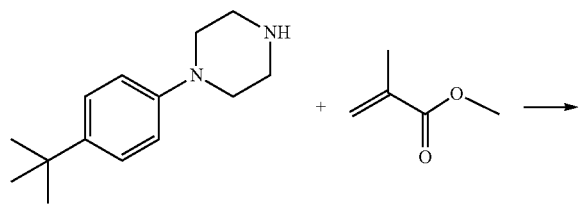

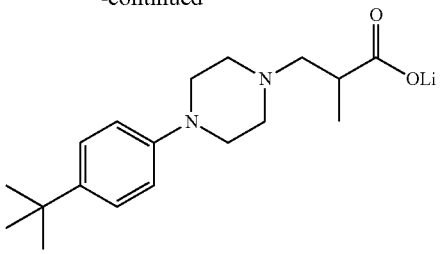

1-(4-tert-Butyl-phenyl)-piperazine (1.0 g; 4.58 mmol) and sodium methoxide (495 mg; 9.16 mmol) are dissolved in ethanol (5 mL) and irradiated for 5 minutes in a mono-mode microwave oven at 60° C. 2-Methyl-acrylic acid methyl ester (0.92 g; 9.16 mmol) is then added and the resulting mixture is irradiated for 90 minutes in a mono-mode microwave oven at 100° C. The reaction mixture is then transferred to a round-bottomed flask with ethanol and additional sodium methoxide and 2-methyl-acrylic acid methyl ester are added. Stirring at 100° C. was continued for one day and after removal of the heating bath, the reaction mixture was allowed to stand at room temperature for 2 weeks. All volatiles were then removed under high vacuum and the resulting residue taken up in ethyl acetate and water. The organic phase was separated, washed with water, dried over magnesium sulphate and concentrated under reduced pressure to give a residue with was subjected to column chromatography on silica gel (dichloromethane/ethyl acetate 100 to 30:70 v/v). The so obtained 3-[4-(4-tert-butyl-phenyl)-piperazin-1-yl]-2-methyl-propionic acid methyl ester and lithium hydroxide (150 mg; 6.25 mmol) are suspended in a mixture of tetrahydrofuran (10 mL) and water (2 mL). The resulting mixture is stirred at room temperature for 3 days and is then diluted with acetonitrile (90 mL). The precipitate formed is then filtered and dried under high vacuum to afford the desired product (730 mg; 2.40 mmol).

Example 130

Preparation of 3-[4-(4-tert-butyl-phenyl)-piperazin-1-yl]-2-methyl-1-[4-(4-nitro-3-trifluoromethyl-phenylamino)-piperidin-1-yl]-propan-1-one

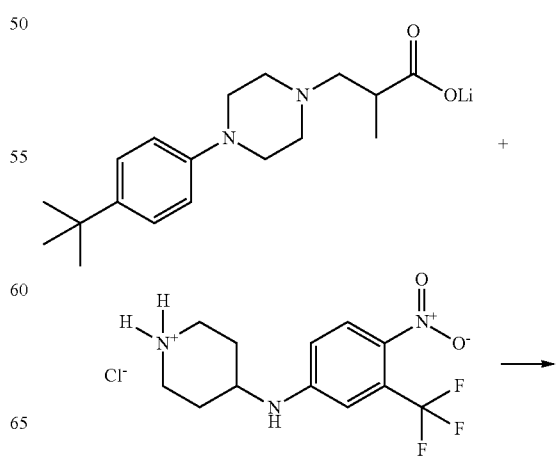

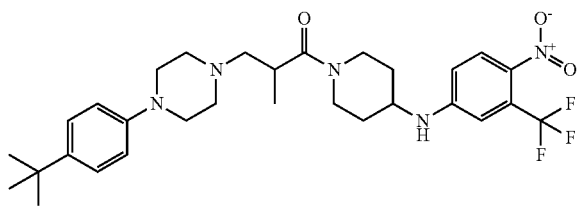

3-[4-(4-tert-Butyl-phenyl)-piperazin-1-yl]-2-methyl-propionic acid lithium salt (15 mg; 0.05 mmol, prepared in accordance with Example 129) and tetramethyl-O-(1H-benzotriazol-1-yl)uronium hexafluorophosphate (19 mg; 0.05 mmol) are diluted in a 2 to 1 mixture of dimethylformamide and tetrahydrofuran (0.75 mL). A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 µL; 0.15 mmol) are added and the reaction is then stirred. After 4 hours at room temperature, aluminium oxide (90 active basic) is added and stiffing is continued for 40 minutes. The solids are removed by filtration and the filtrate is concentrated under high vacuum. The obtained residue is purified by preparative HPLC to afford the desired compound (15 mg; 0.025 mmol). The structure was confirmed using Protocol I-D. Calculated mass=576; observed mass=576; HPLC retention time=1.61 min.

Example 131

Preparation of 4-piperidin-4-yl-butyric acid methyl ester hydrochloride intermediate

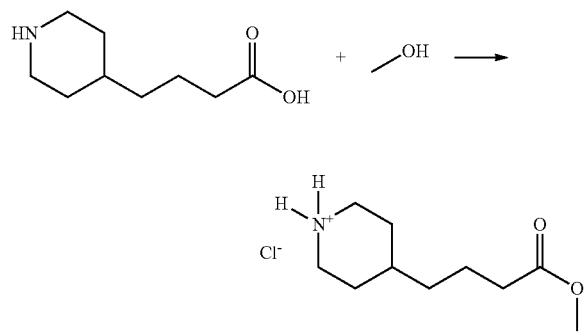

To a solution of 4-piperidin-4-yl-butyric acid (1.1 g; 5.30 mmol) in methanol (5 mL) is added thionylchloride (0.69 g; 5.80 mmol) and the reaction mixture is stirred at room temperature for 2 hours. All volatiles are then removed under high vacuum and the resulting residue triturated with diethyl ether, sucked to dryness and washed (diethyl ether) to afford the desired compound (1.06 g; 4.8 mmol).

Example 132

Preparation of 4-[1-(4-trifluoromethyl-phenyl)-piperidin-4-yl]-butyric acid methyl ester intermediate

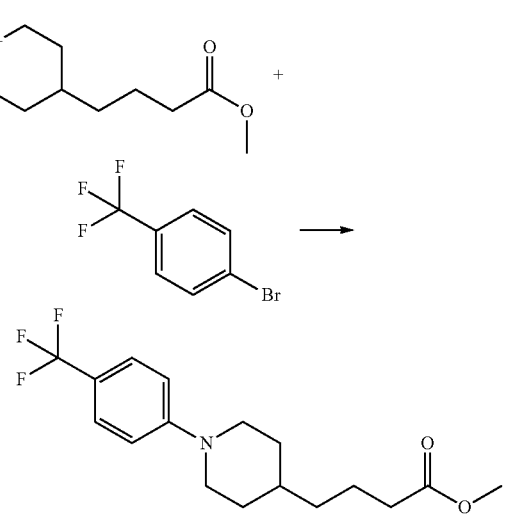

A mixture of palladium (II) acetate (42 mg; 0.185 mmol), (±)-2,2'-bis-diphenylphosphanyl-[1,1']binaphthalenyl (170 mg; 0.275 mmol), cesium carbonate (867 g; 2.66 mmol) in dioxane (5 mL) is placed in an ultrasonic bath for 30 minutes. 4-Piperidin-4-yl-butyric acid methyl ester hydrochloride (290 mg; 1.33 mmol, prepared in accordance with Example 131) and 1-bromo-4-trifluoromethyl-benzene (299 mg; 1.33 mmol) are then added and the reaction mixture is stirred for 2 hours under reflux. After dilution with ethyl acetate, the mixture is filtered and the filtrate concentrated under high vacuum. The obtained residue is purified by column chromatography on silica gel (hexanes/dichloromethane 50:50 v/v to 100) to afford the desired compound (284 mg; 0.86 mmol).

Example 133

Preparation of 4-[1-(4-trifluoromethyl-phenyl)-piperidin-4-yl]-butyric acid lithium intermediate

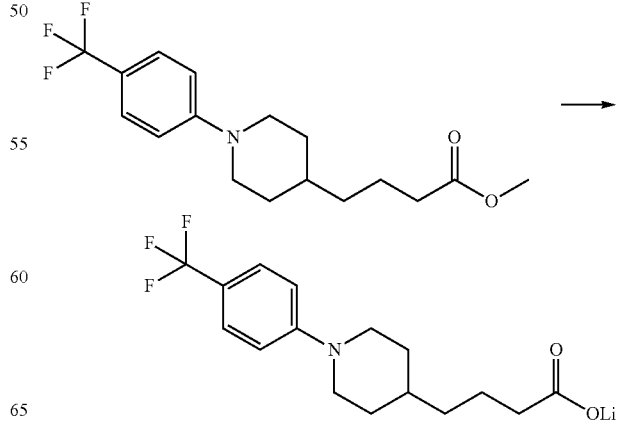

To 4-[1-(4-trifluoromethyl-phenyl)-piperidin-4-yl]-butyric acid methyl ester (311 mg; 0.95 mmol, prepared in accordance with Example 132) is added lithium hydroxide (72 mg; 3.00 mmol) dissolved in water (6.5 mL). After dilution with tetrahydrofuran (10 mL) the reaction mixture is stirred for 2-4 hours. The mixture is then diluted with acetonitrile until a precipitate is formed. The solid is collected by filtration and dried under high vacuum to deliver the desired product (100 mg; 0.31 mmol).

Example 134

Preparation of 1-[4-(4-nitro-3-trifluoromethyl-phenylamino)-piperidin-1-yl]-4-[1-(4-trifluoromethyl-phenyl)-piperidin-4-yl]-butan-1-one

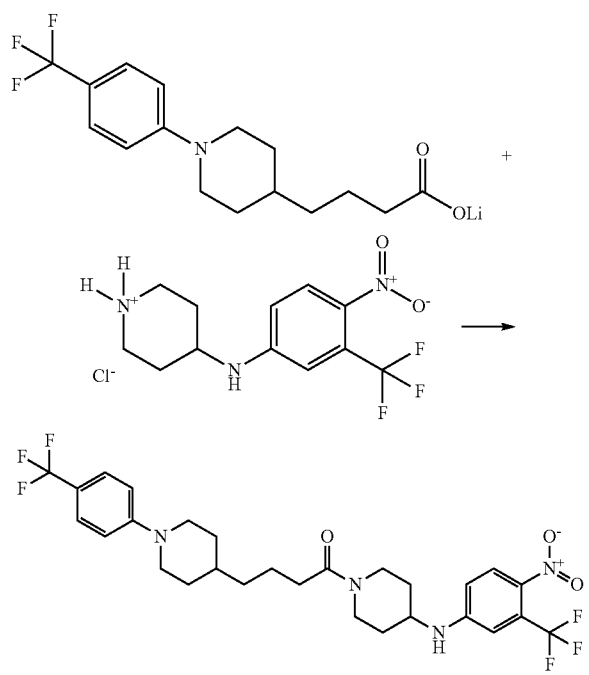

To a solution of 4-[1-(4-trifluoromethyl-phenyl)-piperidin-4-yl]-butyric acid lithium salt (16 mg; 0.05 mmol, prepared in accordance with Example 133) in tetrahydrofuran (0.5 mL) is added a solution of tetramethyl-O-(1H-benzotriazol-1-yl) uronium hexafluorophosphate (19 mg; 0.05 mmol) in dimethylformamide (0.25 mL). A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 µL; 0.15 mmol) are then added and the reaction is stirred. After 3 hours at room temperature, aluminium oxide (90 active basic) is added and stiffing is continued for 40 minutes. The solids are removed by filtration and the filtrate is concentrated under high vacuum. The obtained residue is purified by preparative HPLC to afford the desired compound (16 mg; 0.028 mmol). The structure was confirmed using Protocol I-D. Calculated mass=587; observed mass=587; HPLC retention time=2.20 min.

Example 135

Preparation of 4-[1-(4-tert-butyl-phenyl)-piperidin-4-yl]-butyric acid methyl ester intermediate

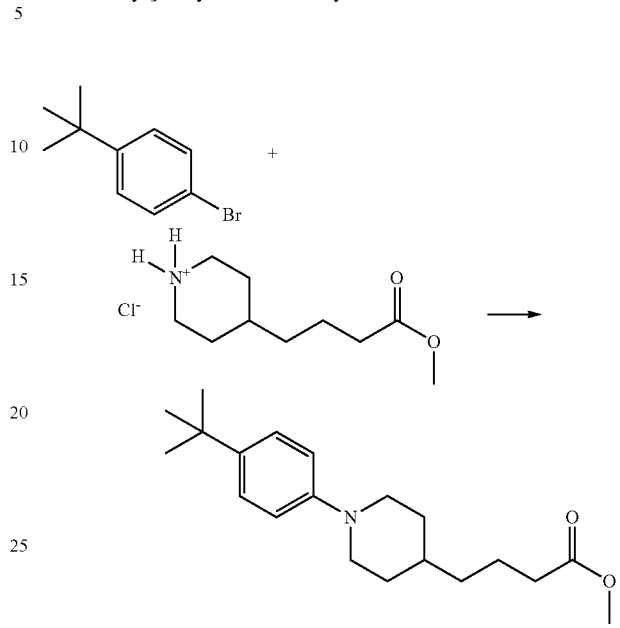

A mixture of palladium (II) acetate (63 mg; 0.28 mmol), (±)-2,2'-bis-diphenylphosphanyl-[1,1']binaphthalenyl (258 mg; 0.41 mmol) and cesium carbonate (1.30 g; 4.00 mmol) in dioxane (3 mL) is placed in an ultrasonic bath for 45 minutes. 4-Piperidin-4-yl-butyric acid methyl ester hydrochloride (415 mg; 2.0 mmol, prepared in accordance with Example 131) and 1-bromo-4-tert-butyl-benzene (426 mg; 2.00 mmol) are then added and the reaction mixture is stirred for 2 hours under reflux. New catalyst solution (prepared as above from palladium (II) acetate (63 mg; 0.28 mmol), (±)-2,2'-bis-diphenylphosphanyl-[1,1']binaphthalenyl (258 mg; 0.41 mmol), cesium carbonate (1.30 g; 4.00 mmol) and dioxane (3 mL) is prepared with the aid of an ultrasonic bath and added to the reaction mixture. After stirring under reflux for 3 hours, the mixture is diluted with ethyl acetate and is filtered. The filtrate is concentrated under high vacuum and the obtained residue is purified by column chromatography on silica gel (hexanes/dichloromethane 50:50 v/v to 100) to afford the desired compound (385 mg; 1.21 mmol).

Example 136

Preparation of 4-[1-(4-tert-butyl-phenyl)-piperidin-4-yl]-butyric acid lithium salt intermediate

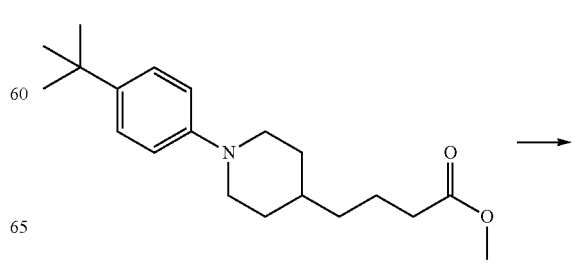

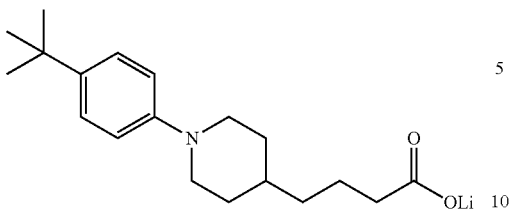

To 4-[1-(4-tert-butyl-phenyl)-piperidin-4-yl]-butyric acid methyl ester (385 mg; 1.21 mmol, prepared in accordance with Example 135) is added lithium hydroxide (72 mg; 3.00 mmol) dissolved in water (6.5 mL). After dilution with tetrahydrofuran (10 mL) the reaction mixture is stirred for 2-4 hours. The mixture is then diluted with acetonitrile until a precipitate is formed. The solid is collected by filtration and dried under high vacuum to afford the desired product (517 mg) which is used in the next step without further purification.

Example 137

Preparation of 4-[1-(4-tert-butyl-phenyl)-piperidin-4-yl]-1-[4-(4-nitro-3-trifluoromethyl-phenylamino)-piperidin-1-yl]-butan-1-one

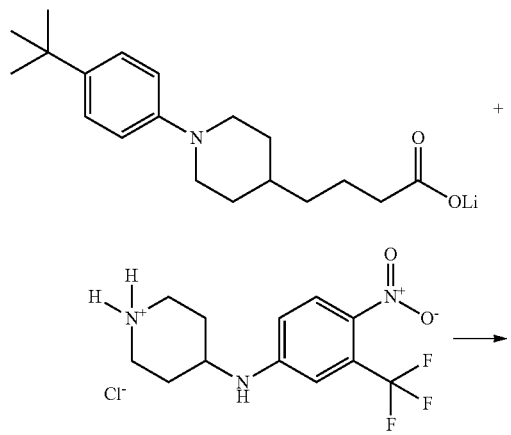

To a solution of 4-[1-(4-tert-butyl-phenyl)-piperidin-4-yl]-butyric acid lithium salt (15 mg; 0.05 mmol, prepared in accordance with Example 136) in tetrahydrofuran (0.5 mL) is added tetramethyl-O-(1H-benzotriazol-1-yl)uronium hexafluorophosphate (19 mg; 0.05 mmol) in dimethylformamide (0.25 mL). A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 μL; 0.15 mmol) are then added and the reaction is stirred. After 3 hours at room temperature, aluminium oxide (90 active basic) is added and stirring is continued for 40 minutes. The solids are removed by filtration and the filtrate is concentrated under high vacuum. The obtained residue is purified by preparative HPLC to afford the desired compound (14 mg; 0.023 mmol). The structure was confirmed using Protocol I-D. Calculated mass=575; observed mass=575; HPLC retention time=1.70 min.

Example 138

Preparation of 3-piperidin-4-yl-propionic acid methyl ester hydrochloride intermediate

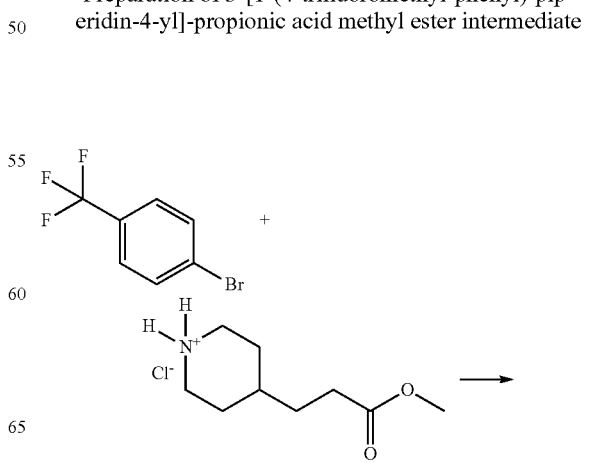

To a solution of 4-(2-carboxy-ethyl)-piperidine-1-carboxylic acid tert-butyl ester (1.95 g; 7.58 mmol) in methanol (5 mL) is slowly added thionylchloride (0.99 g; 8.34 mmol) and the reaction mixture is stirred at room temperature for 30 minutes. All volatiles are then removed under high vacuum and the resulting residue triturated with diethyl ether, sucked to dryness and washed (diethyl ether) to afford the desired compound (1.49 g; 7.18 mmol).

Example 139

Preparation of 3-[1-(4-trifluoromethyl-phenyl)-piperidin-4-yl]-propionic acid methyl ester intermediate

245

-continued

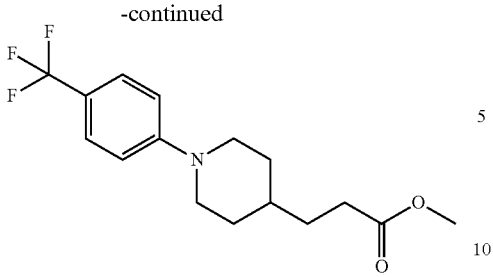

A mixture of palladium (II) acetate (63 mg; 0.28 mmol), (±)-2,2'-bis-diphenylphosphanyl-[1,1']binaphthalenyl (258 mg; 0.41 mmol) and cesium carbonate (1.30 g; 4.00 mmol) in dioxane (3 mL) is placed in an ultrasonic bath for 25 minutes. 3-Piperidin-4-yl-propionic acid methyl ester hydrochloride (415 mg; 2.0 mmol, prepared in accordance with Example 138) and 1-bromo-4-trifluoromethyl-benzene (443 mg; 2.00 mmol) are then added and the reaction mixture is stirred for 2 hours under reflux. New catalyst solution [prepared as above from palladium (II) acetate (63 mg; 0.28 mmol), (±)-2,2'-bis-diphenylphosphanyl-[1,1']binaphthalenyl (258 mg; 0.41 mmol), cesium carbonate (1.30 g; 4.00 mmol) and dioxane (3 mL)] is prepared with the aid of an ultrasonic bath and added to the reaction mixture. After stiffing under reflux for 3 hours, the mixture is diluted with ethyl acetate and is filtered. The filtrate is concentrated under high vacuum and the obtained residue is purified by column chromatography on silica gel (hexanes/dichloromethane 50:50 v/v to 100) to afford the desired compound (480 mg; 1.52 mmol).

Example 140

Preparation of 3-[1-(4-trifluoromethyl-phenyl)-piperidin-4-yl]-propionic acid lithium salt intermediate

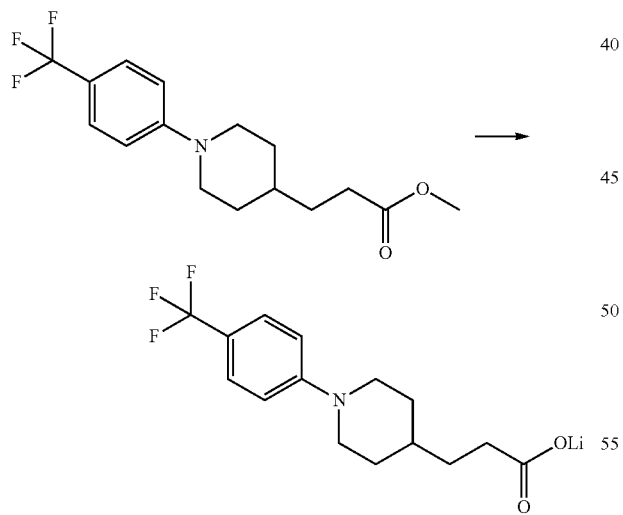

To 3-[1-(4-trifluoromethyl-phenyl)-piperidin-4-yl]-propionic acid methyl ester (480 mg; 1.52 mmol, prepared in accordance with Example 139) is added lithium hydroxide (72 mg; 3.00 mmol) dissolved in water (6.5 mL). After dilution with tetrahydrofuran (10 mL) the reaction mixture is stirred for 2-4 hours. The mixture is then diluted with acetonitrile until a precipitate is formed. The solid is collected by filtration and dried under high vacuum to deliver the desired compound (364 mg; 1.18 mmol).

246

Example 141

Preparation of 1-[4-(4-nitro-3-trifluoromethyl-phenylamino)-piperidin-1-yl]-3-[1-(4-trifluoromethyl-phenyl)-piperidin-4-yl]-propan-1-one

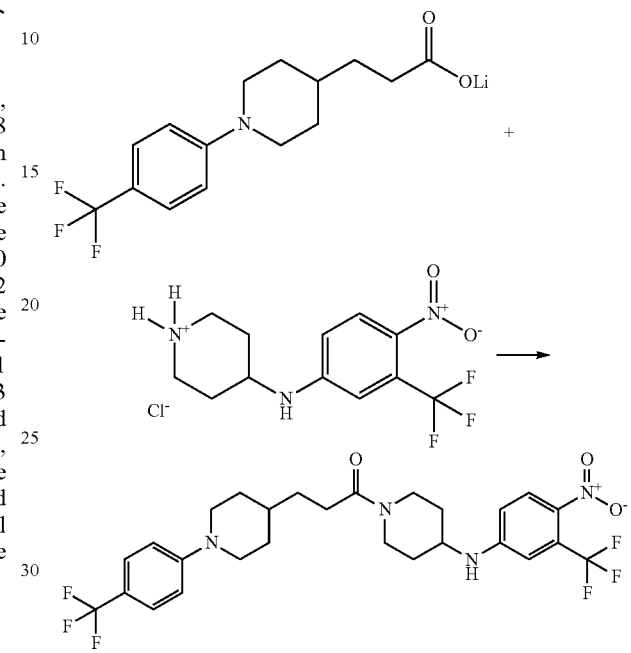

To a solution of 3-[1-(4-trifluoromethyl-phenyl)-piperidin-4-yl]-propionic acid lithium salt (15 mg; 0.05 mmol, prepared in accordance with Example 140) in tetrahydrofuran (1.0 mL) is added tetramethyl-O-(1H-benzotriazol-1-yl)uronium hexafluorophosphate (19 mg; 0.05 mmol) in dimethylformamide (0.25 mL). A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 µL; 0.15 mmol) are then added and the reaction is stirred. After 3 hours at room temperature, aluminium oxide (90 active basic) is added and stiffing is continued for 40 minutes. The solids are removed by filtration and the filtrate is concentrated under high vacuum. The obtained residue is purified by preparative HPLC to afford the desired compound (12 mg; 0.021 mmol). The structure was confirmed using Protocol I-D. Calculated mass=572; observed mass=573; HPLC retention time=1.13 min.

Example 142

Preparation of 3-[1-(4-chloro-phenyl)-piperidin-4-yl]-propionic acid methyl ester intermediate

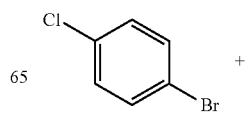

247

-continued

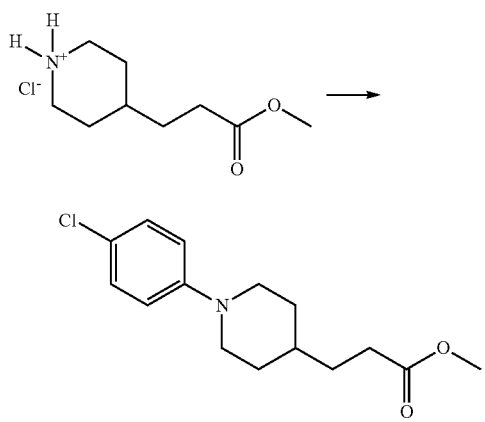

A mixture of palladium (II) acetate (63 mg; 0.28 mmol), (±)-2,2'-bis-diphenylphosphanyl-[1,1']binaphthalenyl (258 mg; 0.41 mmol) and cesium carbonate (1.30 g; 4.00 mmol) in dioxane (3 mL) is placed in an ultrasonic bath for 25 minutes. 3-Piperidin-4-yl-propionic acid methyl ester hydrochloride (415 mg; 2.0 mmol, prepared in accordance with Example 138) and 1-bromo-4-chloro-benzene (383 mg; 2.00 mmol) are then added and the reaction mixture is stirred for 2 hours under reflux. New catalyst solution [prepared as above from palladium (II) acetate (63 mg; 0.28 mmol), (±)-2,2'-bis-diphenylphosphanyl-[1,1']binaphthalenyl (258 mg; 0.41 mmol), cesium carbonate (1.30 g; 4.00 mmol) and dioxane (3 mL)] is prepared with the aid of an ultrasonic bath and added to the reaction mixture. After stirring under reflux for 6 hours, the mixture is diluted with ethyl acetate and is filtered. The filtrate is concentrated under high vacuum and the obtained residue is purified by column chromatography on silica gel (hexanes/dichloromethane 50:50 v/v to 100) to afford the desired compound (345 mg; 1.22 mmol).

Example 143

Preparation of 3-[1-(4-chloro-phenyl)-piperidin-4-yl]-propionic acid lithium salt intermediate

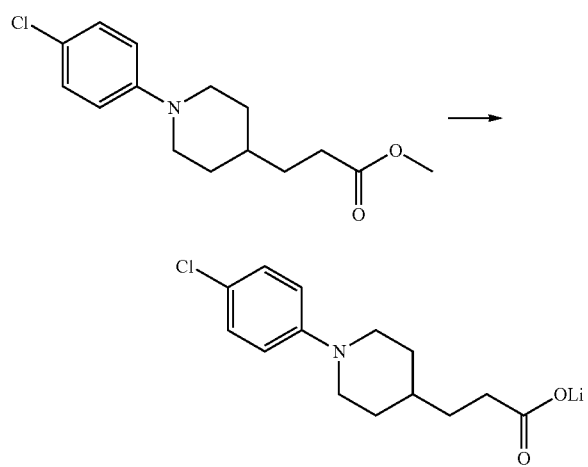

248

To 3-[1-(4-chloro-phenyl)-piperidin-4-yl]-propionic acid methyl ester (345 mg; 1.22 mmol, prepared in accordance with Example 142) is added lithium hydroxide (72 mg; 3.00 mmol) dissolved in water (6.5 mL). After dilution with tetrahydrofuran (10 mL) the reaction mixture is stirred for 2-4 hours. The mixture is then diluted with acetonitrile until a precipitate is formed. The solid is collected by filtration and dried under high vacuum to deliver the desired product (300 mg; 1.10 mmol).

Example 144

Preparation of 3-[1-(4-chloro-phenyl)-piperidin-4-yl]-1-[4-(4-nitro-3-trifluoromethyl-phenylamino)-piperidin-1-yl]-propan-1-one

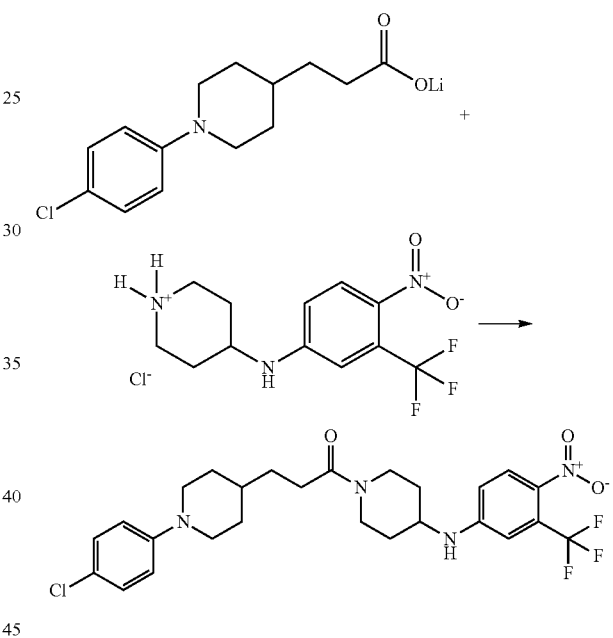

To a solution of 3-[1-(4-chloro-phenyl)-piperidin-4-yl]-propionic acid lithium salt (14 mg; 0.05 mmol, prepared in accordance with Example 143) in tetrahydrofuran (0.5 mL) is added tetramethyl-O-(1H-benzotriazol-1-yl)uronium hexafluorophosphate (19 mg; 0.05 mmol) in dimethylformamide (0.25 mL). A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 μL; 0.15 mmol) are then added and the reaction is stirred. After 3 hours at room temperature, aluminium oxide (90 active basic) is added and stirring is continued for 40 minutes. The solids are removed by filtration and the filtrate is concentrated under high vacuum. The obtained residue is purified by preparative HPLC to afford the desired compound (6 mg; 0.012 mmol). The structure was confirmed using Protocol I-D. Calculated mass=539; observed mass=539; HPLC retention time=1.88 min.

Example 145

Preparation of 3-[1-(4-tert-butyl-phenyl)-piperidin-4-yl]-propionic acid methyl ester intermediate

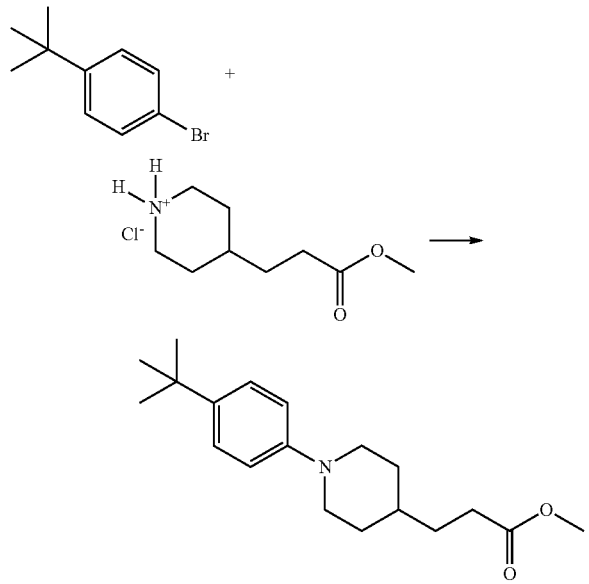

A mixture of palladium (II) acetate (63 mg; 0.28 mmol), (±)-2,2'-bis-diphenylphosphanyl-[1,1']binaphthalenyl (258 mg; 0.41 mmol) and cesium carbonate (1.30 g; 4.00 mmol) in dioxane (3 mL) is placed in an ultrasonic bath for 25 minutes. 3-Piperidin-4-yl-propionic acid methyl ester hydrochloride (415 mg, 2.0 mmol, prepared in accordance with Example 138) and 1-bromo-4-tert-butyl-benzene (426 mg; 2.00 mmol) are then added and the reaction mixture is stirred for 7 hours under reflux. The mixture is then diluted with ethyl acetate, filtered and the filtrate is concentrated under high vacuum. The obtained residue is purified by column chromatography on silica gel (hexanes/dichloromethane 50:50 v/v to 100) to afford the desired compound (295 mg; 0.97 mmol).

Example 146

Preparation of 3-[1-(4-tert-butyl-phenyl)-piperidin-4-yl]-propionic acid lithium salt intermediate

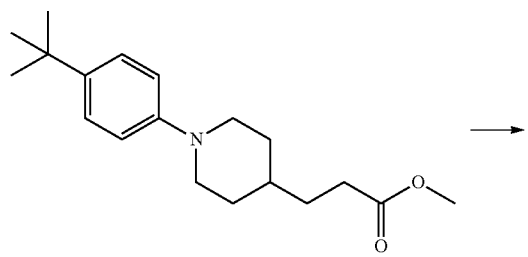

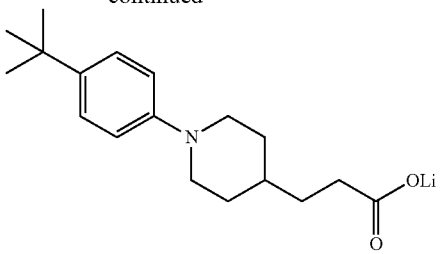

To 3-[1-(4-tert-butyl-phenyl)-piperidin-4-yl]-propionic acid methyl ester (295 mg; 0.97 mmol, prepared in accordance with Example 145) is added lithium hydroxide (72 mg; 3.00 mmol) dissolved in water (6.5 mL). After dilution with tetrahydrofuran (10 mL) the reaction mixture is stirred for 2-4 hours. The mixture is then diluted with acetonitrile until a precipitate is formed. The solid is collected by filtration and dried under high vacuum to deliver the desired product (468 mg) which is used in the next step without further purification.

Example 147

Preparation of 3-[1-(4-tert-butyl-phenyl)-piperidin-4-yl]-1-[4-(4-nitro-3-trifluoromethyl-phenylamino)-piperidin-1-yl]-propan-1-one

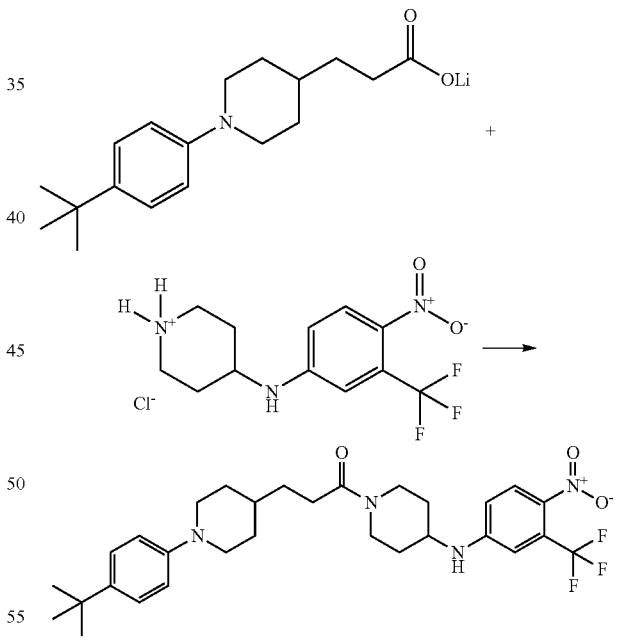

To a solution of 3-[1-(4-tert-butyl-phenyl)-piperidin-4-yl]-propionic acid lithium salt (15 mg; 0.05 mmol, prepared in accordance with Example 146) in tetrahydrofuran (0.5 mL) is added tetramethyl-O-(1H-benzotriazol-1-yl)uronium hexafluorophosphate (19 mg; 0.05 mmol) in dimethylformamide (0.25 mL). A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 µL; 0.15 mmol) are then added and the reaction is stirred. After 3 hours at room temperature, aluminium oxide (90 active basic) is added and stirring is continued for 40 minutes. The solids are removed by filtration and the filtrate is concentrated under high vacuum. The obtained residue is purified by preparative HPLC to afford the desired compound (6 mg; 0.011 mmol). The structure was confirmed using Protocol I-D. Calculated mass=561; observed mass=561; HPLC retention time=1.67 min.

Example 148

Preparation of 4-[4-(6-trifluoromethyl-pyridin-3-yl)-piperazin-1-yl]-butyric acid lithium salt intermediate

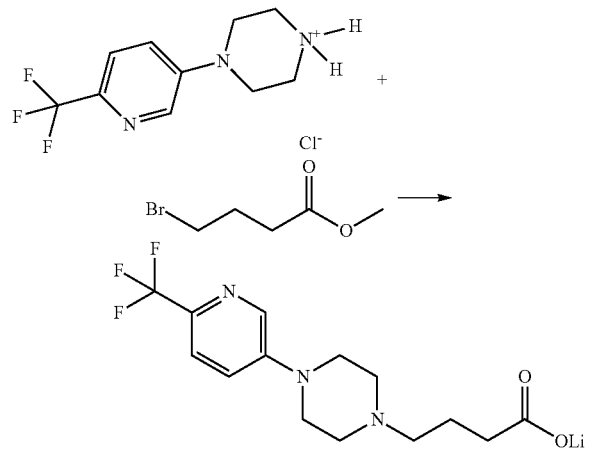

A mixture of 1-(6-trifluoromethyl-pyridin-3-yl)-piperazine hydrochloride (440 mg; 1.65 mmol), 4-bromo-butyric acid methyl ester (322 g; 1.65 mmol), potassium carbonate (456 mg; 3.30 mmol) and potassium iodide (274 mg; 1.65 mmol) in acetonitrile (6 mL) is heated to 100° C. for 2 hours. The reaction mixture is allowed to attain room temperature, filtered and the filtrate is concentrated under high vacuum. The resulting residue is taken up in tetrahydrofuran (10 mL) and a solution of lithium hydroxide (119 mg; 4.95 mmol) in water (2 mL) is added. The resulting mixture is stirred at room temperature over night and is then diluted with acetonitrile (90 mL). The precipitate formed is then filtered and dried under high vacuum to afford the desired compound (495 mg; 1.53 mmol).

Example 149

Preparation of 1-[4-(4-nitro-3-trifluoromethyl-phenylamino)-piperidin-1-yl]-4-[4-(6-trifluoromethyl-pyridin-3-yl)-piperazin-1-yl]-butan-1-one

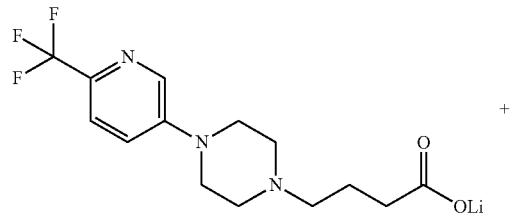

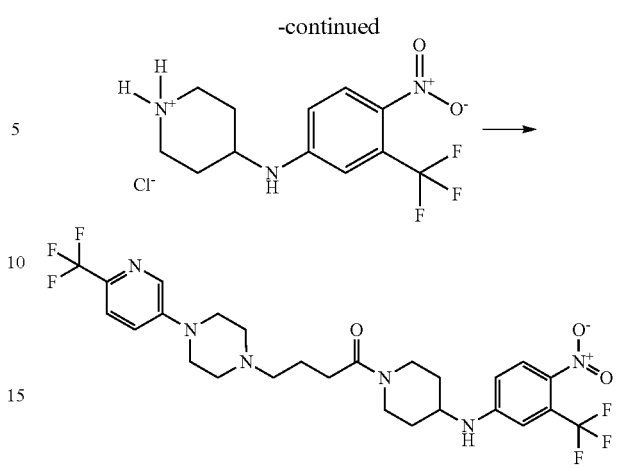

To a solution of 4-[4-(4-trifluoromethyl-phenyl)-piperazin-1-yl]-butyric acid lithium salt (16 mg; 0.05 mmol, prepared in accordance with Example 148) in tetrahydrofuran (0.5 mL) is added tetramethyl-O-(1H-benzotriazol-1-yl)uronium hexafluorophosphate (19 mg; 0.05 mmol) in dimethylformamide (0.25 mL). A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 µL; 0.15 mmol) are then added and the reaction is stirred. After 3 hours at room temperature, aluminium oxide (90 active basic) is added and stiffing is continued for 40 minutes. The solids are removed by filtration and the filtrate is concentrated under high vacuum. The obtained residue is purified by preparative HPLC to afford the desired compound (16 mg; 0.028 mmol). The structure was confirmed using Protocol I-D. Calculated mass=588; observed mass=588; HPLC retention time=1.44 min.

Example 150

Preparation of 4-[4-(5-trifluoromethyl-pyridin-2-yl)-piperazin-1-yl]-butyric acid lithium salt intermediate

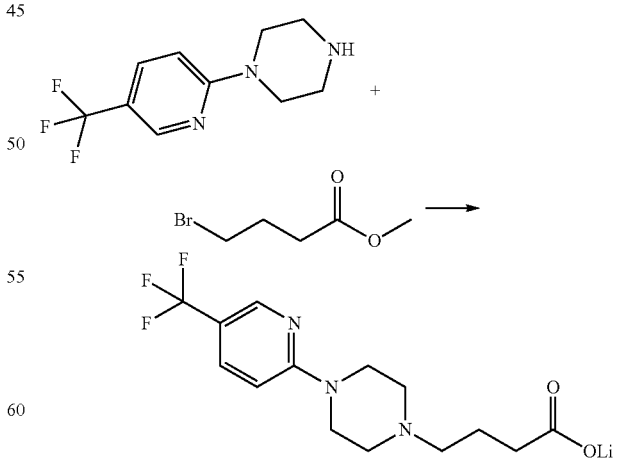

A mixture of 1-(5-trifluoromethyl-pyridin-2-yl)-piperazine (370 mg; 1.60 mmol), 4-bromo-butyric acid methyl ester (312 g; 1.60 mmol), potassium carbonate (442 mg; 3.30 mmol) and potassium iodide (265 mg; 1.65 mmol) in acetonitrile (6 mL)

is heated to 100° C. for 2 hours. The reaction mixture is allowed to attain room temperature, filtered and the filtrate is concentrated under high vacuum. The resulting residue is taken up in tetrahydrofuran (10 mL) and a solution of lithium hydroxide (115 mg; 4.80 mmol) in water (2 mL) is added. The resulting mixture is stirred at room temperature over night and is then diluted with acetonitrile (90 mL). The precipitate formed is then filtered and dried under high vacuum to afford the desired product (602 mg) which is used in the next step without further purification.

Example 151

Preparation of 1-[4-(4-nitro-3-trifluoromethyl-phenylamino)-piperidin-1-yl]-4-[4-(5-trifluoromethyl-pyridin-2-yl)-piperazin-1-yl]-butan-1-one

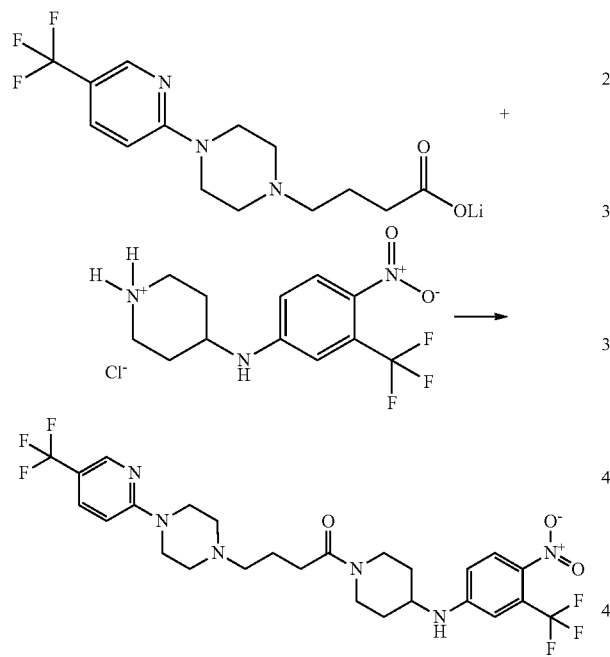

To a solution of 4-[4-(5-trifluoromethyl-pyridin-2-yl)-piperazin-1-yl]-butyric acid lithium salt (16 mg; 0.05 mmol, prepared in accordance with Example 150) in tetrahydrofuran (0.5 mL) is added tetramethyl-O-(1H-benzotriazol-1-yl)uronium hexafluorophosphate (19 mg; 0.05 mmol) in dimethylformamide (0.25 mL). A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 µL; 0.15 mmol) are then added and the reaction is stirred. After 3 hours at room temperature, aluminium oxide (90 active basic) is added and stiffing is continued for 40 minutes. The solids are removed by filtration and the filtrate is concentrated under high vacuum. The obtained residue is purified by preparative HPLC to afford the desired compound (18 mg; 0.031 mmol). The structure was confirmed using Protocol I-D. Calculated mass=588; observed mass=589; HPLC retention time=1.50 min.

Example 152

Preparation of 4-[4-(5-trifluoromethyl-[1,3,4]thiadiazol-2-yl)-piperazin-1-yl]-butyric acid lithium intermediate

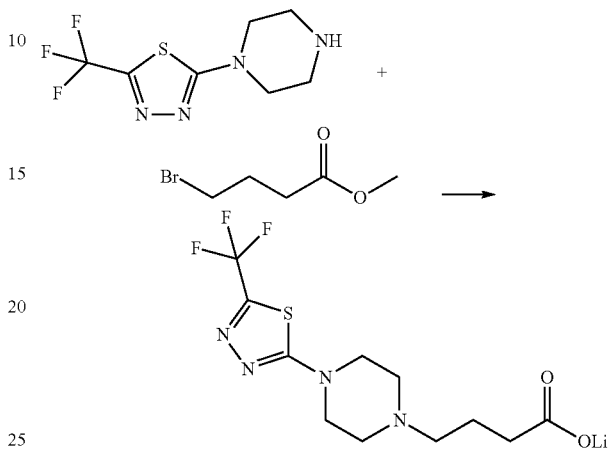

A mixture of 1-(5-trifluoromethyl-[1,3,4]thiadiazol-2-yl)-piperazine (381 mg; 1.60 mmol), 4-bromo-butyric acid methyl ester (312 g; 1.60 mmol), potassium carbonate (442 mg; 3.30 mmol) and potassium iodide (265 mg; 1.65 mmol) in acetonitrile (6 mL) is heated to 100° C. for 2 hours. The reaction mixture is allowed to attain room temperature, filtered and the filtrate is concentrated under high vacuum. The resulting residue is taken up in tetrahydrofuran (10 mL) and a solution of lithium hydroxide (115 mg; 4.80 mmol) in water (2 mL) is added. The resulting mixture is stirred at room temperature over night and is then diluted with acetonitrile (90 mL). The precipitate formed is then filtered and dried under high vacuum to afford the desired product (550 mg) which is used in the next step without further purification.

Example 153

Preparation of 1-[4-(4-nitro-3-trifluoromethyl-phenylamino)-piperidin-1-yl]-4-[4-(5-trifluoromethyl-1,3,4-thiadiazol-2-yl)-piperazin-1-yl]-butan-1-one

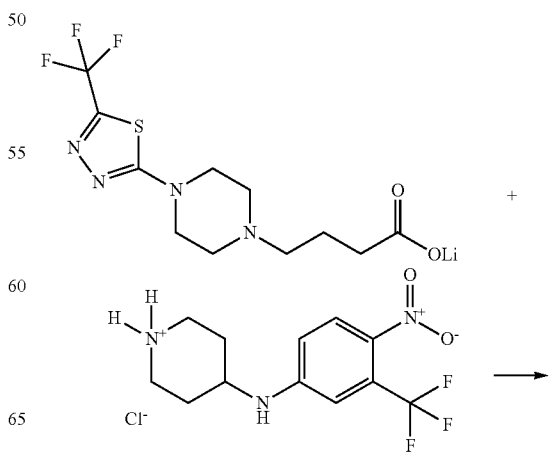

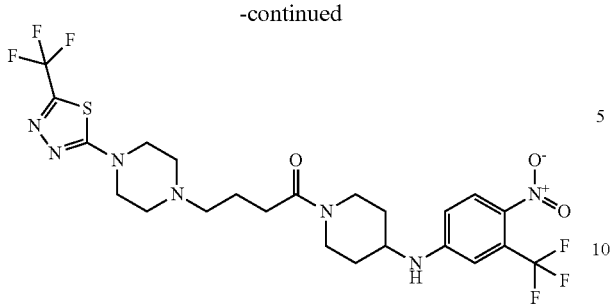

To a solution of 4-[4-(5-trifluoromethyl-[1,3,4]thiadiazol-2-yl)-piperazin-1-yl]-butyric acid lithium salt (17 mg; 0.05 mmol, prepared in accordance with Example 152) in tetrahydrofuran (0.5 mL) is added tetramethyl-O-(1H-benzotriazol-1-yl)uronium hexafluorophosphate (19 mg; 0.05 mmol) in dimethylformamide (0.25 mL) A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 µL; 0.15 mmol) are then added and the reaction is stirred. After 3 hours at room temperature, aluminium oxide (90 active basic) is added and stiffing is continued for 40 minutes. The solids are removed by filtration and the filtrate is concentrated under high vacuum. The obtained residue is purified by preparative HPLC to afford the desired compound (16 mg; 0.0271 mmol). The structure was confirmed using Protocol I-D. Calculated mass=596; observed mass=596; HPLC retention time=1.42 min Example 154

Preparation of 4-(4-cyano-3-trifluoromethyl-phenylamino)-piperidine-1-carboxylic acid tert-butyl ester intermediate

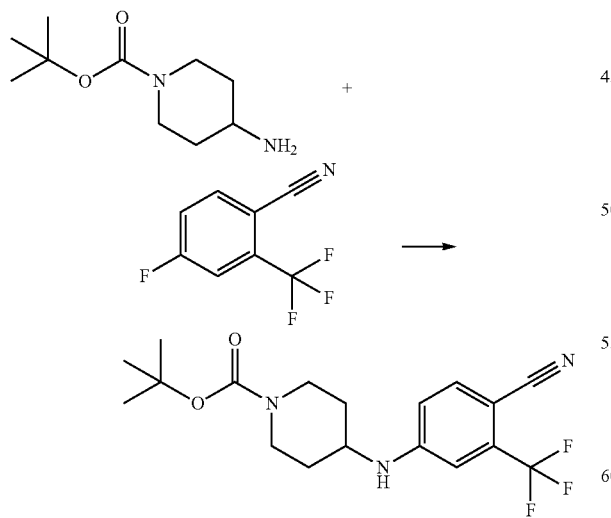

A mixture of 4-amino-piperidine-1-carboxylic acid tert-butyl ester (200 mg; 1.0 mmol), 4-fluoro-2-trifluoromethyl-benzonitrile (208 mg; 1.01 mmol) and potassium carbonate (276 mg; 2.0 mmol) in dimethylsulfoxide (3 mL) is heated to 100° C. over night. Water is then added and the precipitate formed is collected to afford the desired compound (250 mg; 0.68 mmol).

Example 155

Preparation of 4-(piperidin-4-ylamino)-2-trifluoromethyl-benzonitrile hydrochloride intermediate

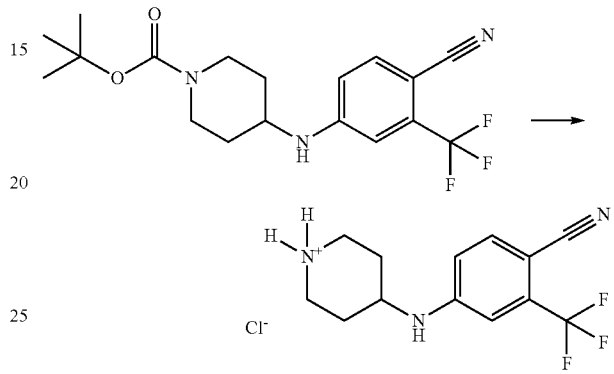

To a solution of 4-(4-cyano-3-trifluoromethyl-phenylamino)-piperidine-1-carboxylic acid tert-butyl ester (250 mg; 0.68 mmol, prepared in accordance with Example 154) in dichloromethane (5 mL) is added trifluoroacetic acid (1.5 mL) and the reaction mixture is stirred at room temperature for 30 minutes. All volatiles are then removed under high vacuum and the residue is taken up with diethyl ether and concentrated again. The residue is dissolved in a minimum amount of dioxane and a 4 molar solution of hydrochloric acid in dioxane is added. The precipitate formed is collected, washed with diethyl ether and dried under high vacuum to afford the desired compound (225 mg; 0.74 mmol).

Example 156

Preparation of 2-trifluoromethyl-4-(1-{4-[1-(4-trifluoromethyl-phenyl)-piperidin-4-yl]-butyryl}-piperidin-4-ylamino)-benzonitrile

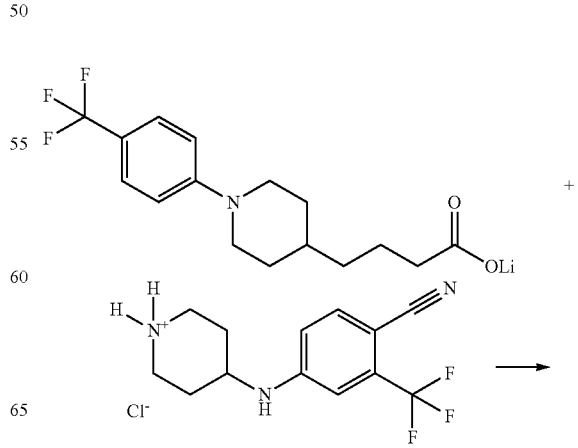

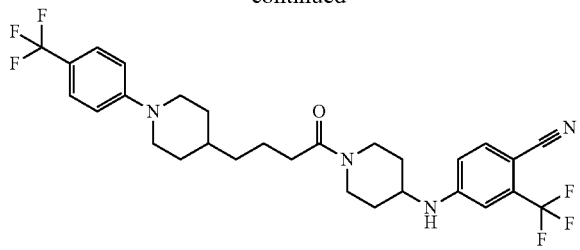

To a stirred suspension of 4-[1-(4-trifluoromethyl-phenyl)-piperidin-4-yl]-butyric acid lithium salt (16 mg; 0.05 mmol, prepared in accordance with Example 133) in tetrahydrofuran (1.0 mL) is added a solution of tetramethyl-O-(1H-benzotriazol-1-yl)uronium hexafluorophosphate (19 mg; 0.05 mmol) in dimethylformamide (0.5 mL). 15 minutes later, a solution of 4-(piperidin-4-ylamino)-2-trifluoromethyl-benzonitrile hydrochloride (15 mg; 0.05 mmol, prepared in accordance with Example 155) in dimethylformamide (10.5 mL) and diisopropylethyl amine (25 µL; 0.15 mmol) is added. After 2 hours at room temperature, aluminium oxide (90 active basic) is added and stirring is continued. The solids are removed by filtration and the filtrate is concentrated under high vacuum. The obtained residue is purified by preparative HPLC to afford the desired compound (20 mg; 0.035 mmol). The structure was confirmed using Protocol I-D. Calculated mass=567; observed mass=567; HPLC retention time=2.17 min.

Example 157

Preparation of 2-trifluoromethyl-4-(1-{4-[4-(5-trifluoromethyl-pyridin-2-yl)-piperazin-1-yl]-butyryl}-piperidin-4-ylamino)-benzonitrile

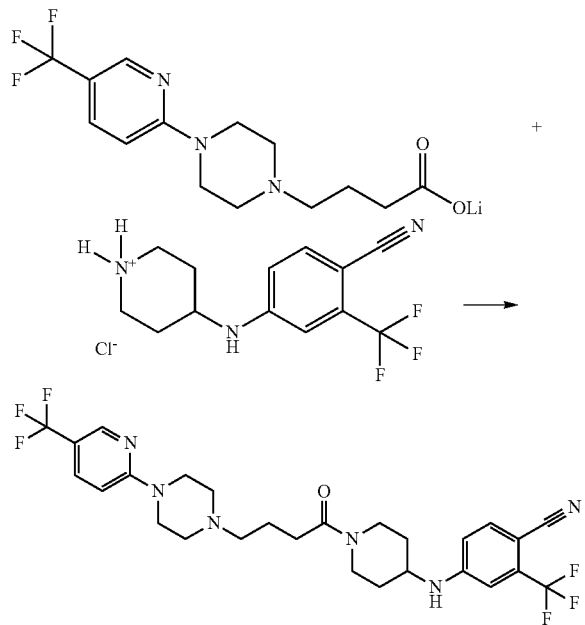

To a stirred suspension of 4-[4-(5-trifluoromethyl-[1,3,4]thiadiazol-2-yl)-piperazin-1-yl]-butyric acid lithium salt (17 mg; 0.05 mmol, prepared in accordance with Example 3) in tetrahydrofuran (1.0 mL) is added tetramethyl-O-(1H-benzotriazol-1-yl)uronium hexafluorophosphate (19 mg; 0.05 mmol) in dimethylformamide (0.5 mL). 15 minutes later, a solution of 4-(piperidin-4-ylamino)-2-trifluoromethyl-benzonitrile hydrochloride (15 mg; 0.05 mmol, prepared in accordance with Example 155) in dimethylformamide (0.5 mL) and diisopropylethyl amine (25 µL; 0.15 mmol) is added. After 2 hours at room temperature, aluminium oxide (90 active basic) is added and stirring is continued. The solids are removed by filtration and the filtrate is concentrated under high vacuum. The obtained residue is purified by preparative HPLC to afford the desired compound (9 mg; 0.016 mmol). The structure was confirmed using Protocol I-D. Calculated mass=569; observed mass=569; HPLC retention time=1.48 min.

Example 158

Preparation of 2-trifluoromethyl-4-(1-{4-[4-(5-trifluoromethyl-1,3,4-thiadiazol-2-yl)-piperazin-1-yl]-butyryl}-piperidin-4-ylamino)-benzonitrile

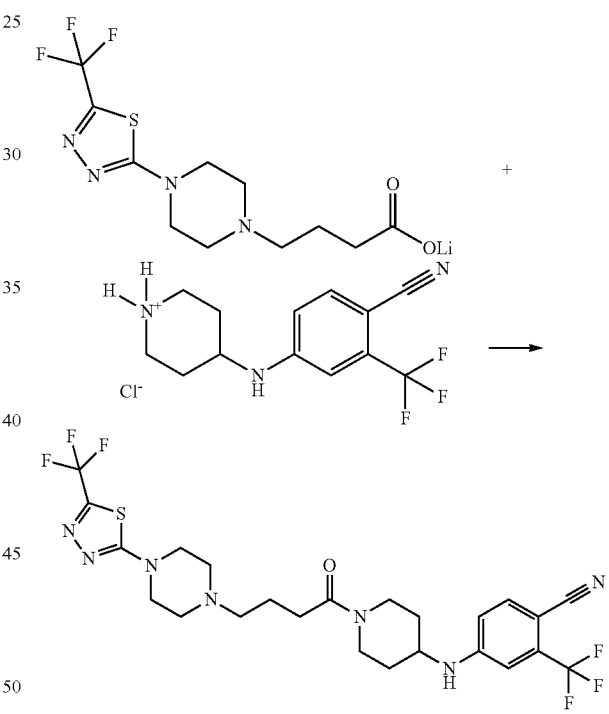

To a stirred suspension of 4-[4-(5-trifluoromethyl-pyridin-2-yl)-piperazin-1-yl]-butyric acid lithium salt (16 mg; 0.05 mmol, prepared in accordance with Example 152) in tetrahydrofuran (1.0 mL) is added tetramethyl-O-(1H-benzotriazol-1-yl)uronium hexafluorophosphate (19 mg; 0.05 mmol) in dimethylformamide (0.5 mL). 15 minutes later, a solution of 4-(piperidin-4-ylamino)-2-trifluoromethyl-benzonitrile hydrochloride (15 mg; 0.05 mmol, prepared in accordance with Example 155) in dimethylformamide (0.5 mL) and diisopropylethyl amine (25 µL; 0.15 mmol) is added. After 2 hours at room temperature, aluminium oxide (90 active basic) is added and stirring is continued. The solids are removed by filtration and the filtrate is concentrated under high vacuum. The obtained residue is purified by preparative HPLC to afford the desired compound (2 mg; 0.003 mmol). The structure was confirmed using Protocol I-D. Calculated mass=576; observed mass=576; HPLC retention time=1.41 min.

Example 159

Preparation of 4-(1-{3-[4-(4-tert-butyl-phenyl)-piperazin-1-yl]-2-methyl-propionyl}-piperidin-4-ylamino)-2-trifluoromethyl-benzonitrile

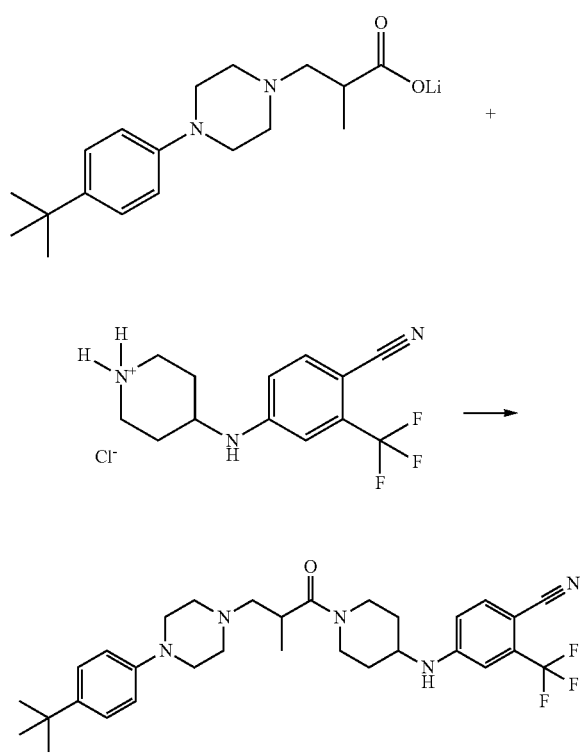

To a stirred suspension of 3-[4-(4-tert-butyl-phenyl)-piperazin-1-yl]-2-methyl-propionic acid lithium salt (16 mg; 0.05 mmol) in tetrahydrofuran (1.0 mL) is added tetramethyl-O-(1H-benzotriazol-1-yl)uronium hexafluorophosphate (19 mg; 0.05 mmol) in dimethylformaide (0.5 mL). 15 minutes later, diisopropylethyl amine (25 µL; 0.15 mmol) and a solution of 4-(piperidin-4-ylamino)-2-trifluoromethyl-benzonitrile hydrochloride (15 mg; 0.05 mmol, prepared in accordance with Example 155) in dimethylformamide (0.5 mL) are added. After 2 hours at room temperature, aluminium oxide (90 active basic) is added and stiffing is continued. The solids are removed by filtration and the filtrate is concentrated under high vacuum. The obtained residue is purified by preparative HPLC to afford the desired compound (2 mg; 0.004 mmol). The structure was confirmed using Protocol I-D. Calculated mass=556; observed mass=556; HPLC retention time=1.60 min.

Example 160

Preparation of 4-(4-tert-butyl-phenyl)-[1,4]diazepane-1-carboxylic acid tert-butyl ester intermediate

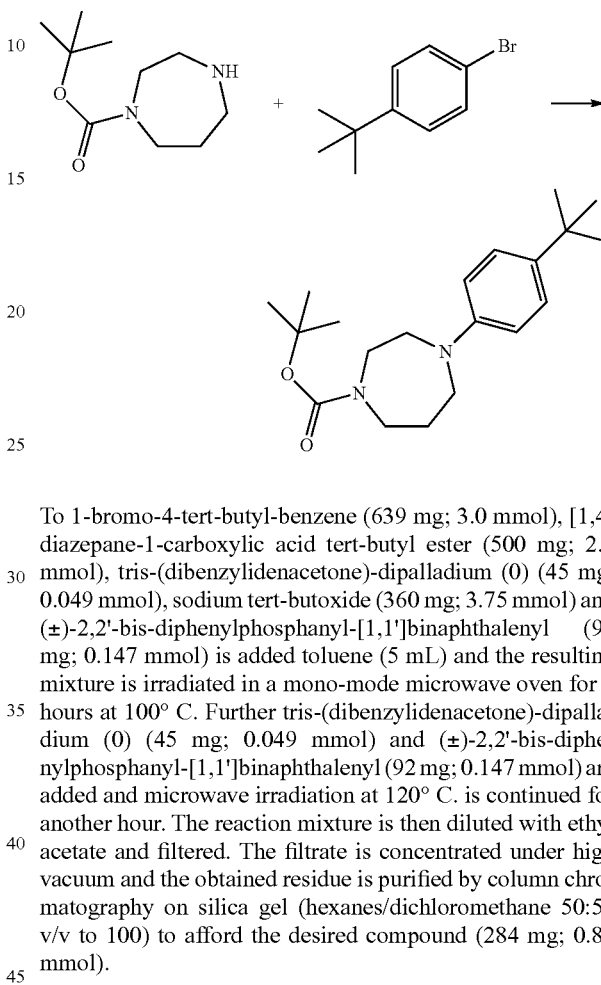

To 1-bromo-4-tert-butyl-benzene (639 mg; 3.0 mmol), [1,4] diazepane-1-carboxylic acid tert-butyl ester (500 mg; 2.5 mmol), tris-(dibenzylidenacetone)-dipalladium (0) (45 mg; 0.049 mmol), sodium tert-butoxide (360 mg; 3.75 mmol) and (±)-2,2'-bis-diphenylphosphanyl-[1,1']binaphthalenyl (92 mg; 0.147 mmol) is added toluene (5 mL) and the resulting mixture is irradiated in a mono-mode microwave oven for 2 hours at 100° C. Further tris-(dibenzylidenacetone)-dipalladium (0) (45 mg; 0.049 mmol) and (±)-2,2'-bis-diphenylphosphanyl-[1,1']binaphthalenyl (92 mg; 0.147 mmol) are added and microwave irradiation at 120° C. is continued for another hour. The reaction mixture is then diluted with ethyl acetate and filtered. The filtrate is concentrated under high vacuum and the obtained residue is purified by column chromatography on silica gel (hexanes/dichloromethane 50:50 v/v to 100) to afford the desired compound (284 mg; 0.85 mmol).

Example 161

Preparation of 1-(4-tert-butyl-phenyl)-[1,4]diazepane hydrochloride intermediate

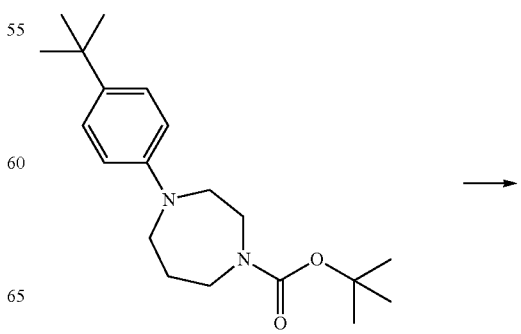

-continued

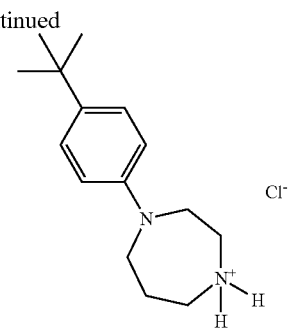

To 4-(4-tert-butyl-phenyl)-[1,4]diazepane-1-carboxylic acid tert-butyl ester (541 mg; 16.3 mmol, prepared in accordance with Example 160) is added a 2:3 mixture of trifluoroacetic acid and dichloromethane (5 mL) and the resulting reaction mixture is stirred at room temperature for 2 hours. All volatiles are then removed under high vacuum and the residue is taken up in a 4 molar solution of hydrochloric acid in dioxane. The solution is allowed to stand over night and the precipitate formed is filtered, washed (diethyl ether) and dried under high vacuum to afford the desired compound (452 mg) which is used in the next step without further purification.

Example 162

Preparation of 4-[4-(4-tert-butyl-phenyl)-[1,4]diazepan-1-yl]-butyric acid lithium salt intermediate

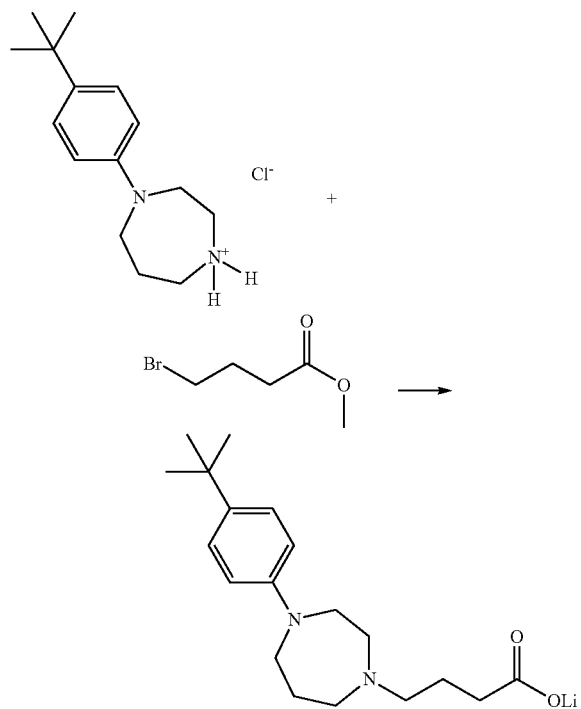

A mixture of 1-(4-tert-butyl-phenyl)-[1,4]diazepane hydrochloride (220 mg; 0.82 mmol, prepared in accordance with Example 161), 4-bromo-butyric acid methyl ester (160 mg; 0.82 mmol), potassium carbonate (113 mg; 0.82 mmol) and potassium iodide (136 mg; 0.82 mmol) in acetonitrile (5 mL) is heated to 100° C. for 3 hours. The reaction mixture is allowed to attain room temperature and filtered. The filtrate is diluted with a solution of lithium hydroxide (59 mg; 2.46 mmol) in water (2 mL) and the resulting mixture is stirred at room temperature over night. All volatiles are then removed under high vacuum and more lithium hydroxide solution is added to drive the reaction to completion. Acetonitrile is added and the precipitate formed is then filtered and dried under high vacuum to afford the desired product (514 mg) which is used in the next step without further purification.

Example 163

Preparation of 4-[4-(4-tert-butyl-phenyl)-[1,4]diazepan-1-yl]-1-[4-(4-nitro-3-trifluoromethyl-phenylamino)-piperidin-1-yl]-butan-1-one

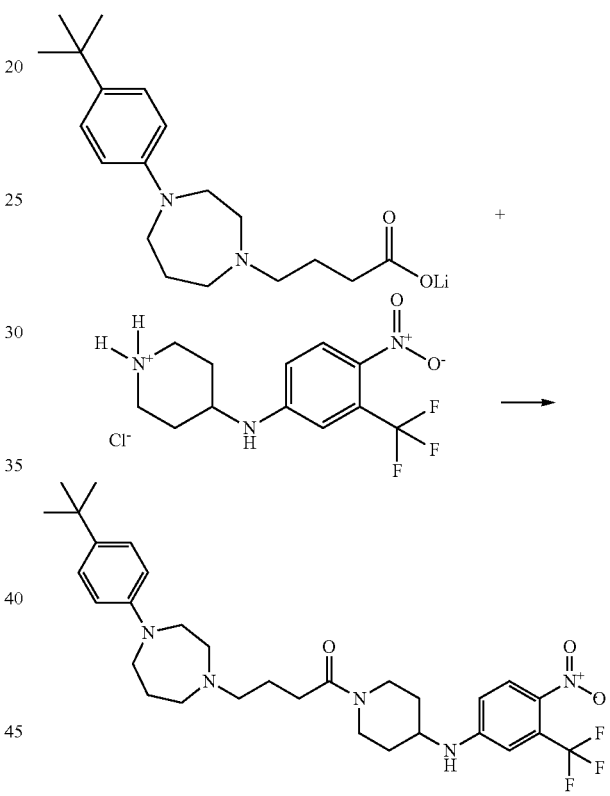

To a solution of 4-[4-(4-tert-butyl-phenyl)-[1,4]diazepan-1-yl]-butyric acid lithium salt (16 mg; 0.05 mmol, prepared in accordance with Example 162) in tetrahydrofuran (0.5 mL) is added tetramethyl-O-(1H-benzotriazol-1-yl)uronium hexafluorophosphate (19 mg; 0.05 mmol) in dimethylformamide (0.25 mL). A solution of (4-nitro-3-trifluoromethyl-phenyl)-piperidin-4-yl-amine hydrochloride (16 mg; 0.05 mmol, prepared in accordance with Example 8) in dimethylformamide (0.25 mL) and diisopropylethyl amine (25 µL; 0.15 mmol) are then added and the reaction is stirred. After 3 hours at room temperature, aluminium oxide (90 active basic) is added and stiffing is continued for 40 minutes. The solids are removed by filtration and the filtrate is concentrated under high vacuum. The obtained residue is purified by preparative HPLC to afford the desired compound (5 mg; 0.009 mmol). The structure was confirmed using Protocol I-D. Calculated mass=590; observed mass=590; HPLC retention time=1.66 min.

Example 164

Preparation of (R)-3-(4-nitro-3-trifluoromethyl-phenylamino)-pyrrolidine-1-carboxylic acid tert-butyl ester intermediate

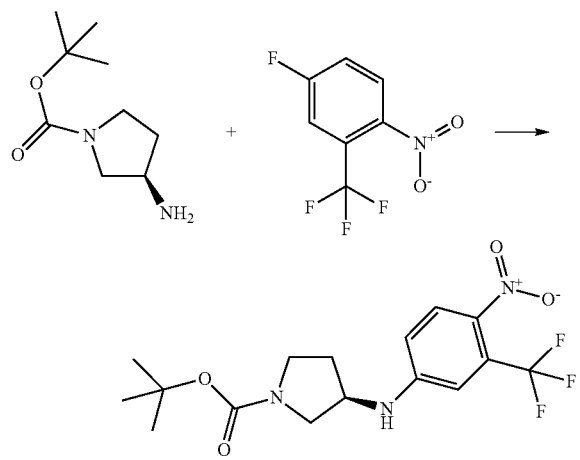

(R)-3-Amino-pyrrolidine-1-carboxylic acid tert-butyl ester (559 mg; 3.0 mmol), 4-fluoro-1-nitro-2-trifluoromethyl-benzene (627 mg; 3.0 mmol), potassium carbonate (1.24 g; 9.0 mmol), potassium iodide (498 mg; 3.0 mmol), acetonitrile (6 mL) and water (2 mL) are mixed together and the resulting reaction mixture heated to efflux for 5 hours. The phases are separated and the organic phase dried (MgSO$_4$) and concentrated under high vacuum. The residue is then triturated with diethyl ether, dried under high vacuum to afford the desired compound (1.12 g; 2.98 mmol).

Example 165

Preparation of (4-nitro-3-trifluoromethyl-phenyl)-(R)-pyrrolidin-3-yl-amine hydrochloride intermediate

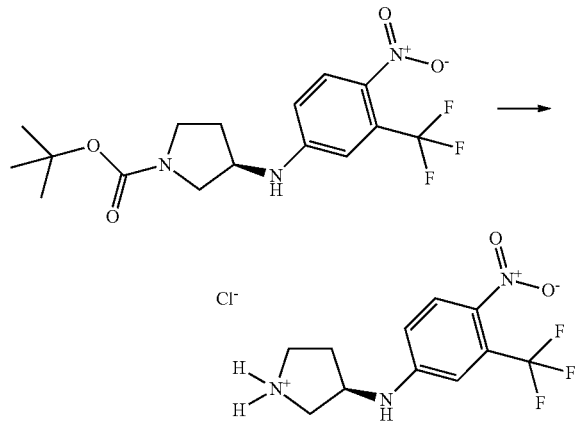

To solid (R)-3-(4-Nitro-3-trifluoromethyl-phenylamino)-pyrrolidine-1-carboxylic acid tert-butyl ester (1.12 g; 2.98 mmol, prepared in accordance with Example 164) is added a 3:2 mixture of dichloromethane and trifluoroacetic acid (5 mL) and the resulting solution is stirred at room temperature for 2 hours. All volatiles are then removed under high vacuum and the residue taken up in ethyl acetate. A 4 molar solution of hydrochloric acid in dioxane is then added and, after formation of an oily precipitate, all volatiles removed under high vacuum. The obtained residue is then taken up in methanol and treated with diethyl ether. This mixture is allowed to stand over night, concentrated under high vacuum and taken up in hot ethyl acetate. The solution is then allowed to stand at room temperature over night and the precipitate formed is collected and dried under high vacuum to afford the desired compound (1.07 g) which is used in the next step without further purification.

Example 166

Preparation of 4-[4-(4-tert-butyl-phenyl)-piperazin-1-yl]-butyric acid ethyl ester intermediate

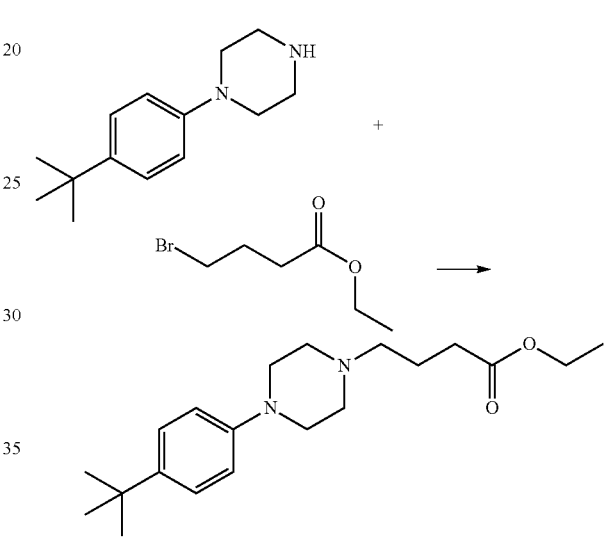

A mixture of 1-(4-tert-butyl-phenyl)-piperazine (1.09 mg; 5.0 mmol), 4-bromo-butyric acid ethyl ester (975 mg; 5.0 mmol), potassium carbonate (691 mg; 5.0 mmol) and potassium iodide (914 mg; 5.5 mmol) in acetonitrile (15 mL) is heated to reflux for 2 hours. The reaction mixture is allowed to attain room temperature and all solids removed by filtration. The filtration residue is washed with acetonitrile and the filtrate concentrated under high vacuum to afford the desired compound (1.41 g; 4.24 mmol).

Example 167

Preparation of 4-[4-(4-tert-butylphenyl)-piperazin-1-yl]-butyric acid lithium salt intermediate

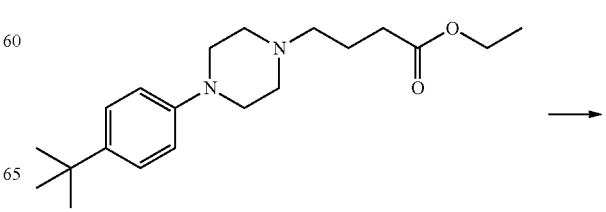

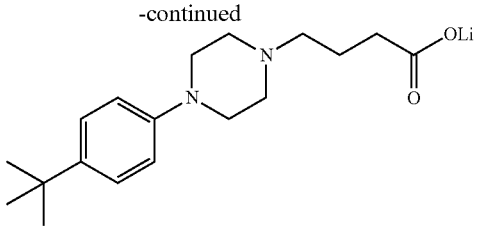

To 4-[4-(4-tert-butyl-phenyl)-piperazin-1-yl]-butyric acid ethyl ester (1.41 g; 4.24 mmol, prepared in accordance with Example 166) is added a solution of lithium hydroxide (59 mg; 2.46 mmol in 3 mL of water) diluted with tetrahydrofuran (3 mL) and the resulting mixture is stirred at room temperature for one hour. Acetonitrile (50 mL) is added and the precipitate formed is then filtered and dried under high vacuum to afford the desired product (1.45 g) which is used in the next step without further purification.

Example 168

Preparation of 4-[4-(4-tert-butyl-phenyl)-piperazin-1-yl]-1-[(R)-3-(4-nitro-3-trifluoromethyl-phenylamino)-pyrrolidin-1-yl]-butan-1-one

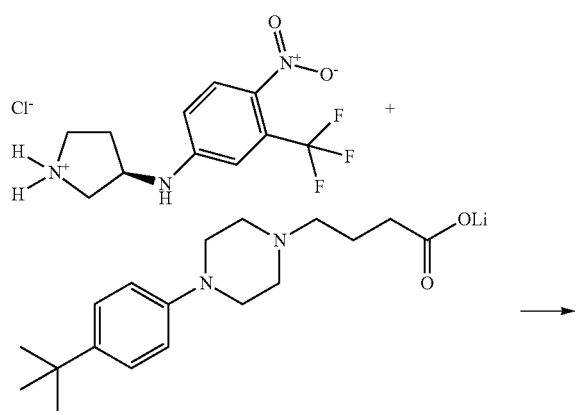

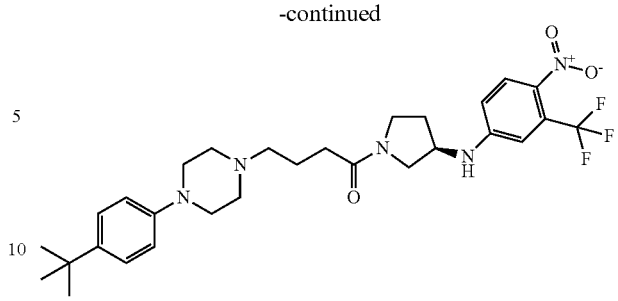

To as suspension of 4-[4-(4-tert-butylphenyl)-piperazin-1-yl]-butyric acid lithium salt (15 mg; 0.05 mmol, prepared in accord with Example 167) in tetrahydrofuran (1 mL) is added a solution of tetramethyl-O-(1H-benzotriazol-1-yl)uronium hexafluorophosphate (19 mg; 0.05 mmol) in dimethylformamide (0.5 mL). After 15 minutes at room temperature, diisopropylethyl amine (25 µL; 0.15 mmol) and a solution of (4-nitro-3-trifluoromethyl-phenyl)-(R)-pyrrolidin-3-yl-amine hydrochloride (16 mg; 0.05 mmol, prepared in accord with Example 165) in dimethylformamide (0.5 mL) is added and the reaction mixture is stirred at room temperature for one hour. Aluminium oxide (90 active basic) is then added and stiffing is continued. The solids are removed by filtration and the filtrate is concentrated under high vacuum. The obtained residue is purified by preparative HPLC to afford the desired compound (17 mg; 0.030 mmol). The structure was confirmed using Protocol I-D. Calculated mass=562; observed mass=562; HPLC retention time=1.60 min.

Examples 169-996

Examples of Additional Compounds Prepared by Applicants in Accordance with this Invention Applicants have prepared various other compounds using the above protocols alone or in combination methods generally known in the art. Such compounds include those listed in the following Table V. Table V also provides the protocol used to confirm each compound structure, as well as the calculated mass, the observed mass, and the HPLC retention time.

TABLE V

Additional Compounds Prepared by Applicants in Accordance with this Invention

| Compound Structure | Analysis Method | Retention Time (min) | Calc. Mass | Obs. Mass |
|---|---|---|---|---|
| Example 169 | II-F | 10.75 | 620 | 506 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 170 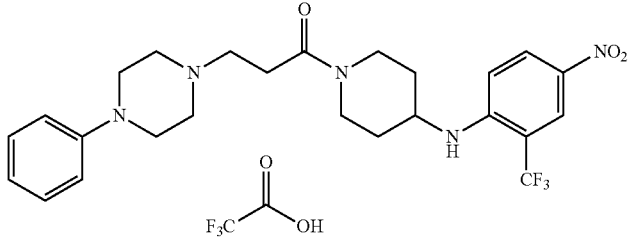 | II-A | 3.82 | 620 | 506 |
| Example 171 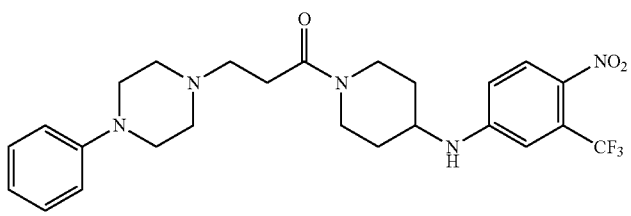 | II-F | 10.75 | 506 | 507 |
| Example 172 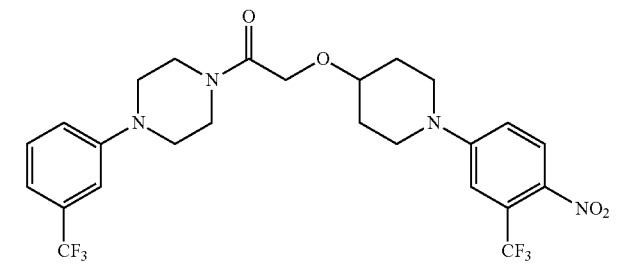 | II-A | 4.56 | 560 | 561 |
| Example 173 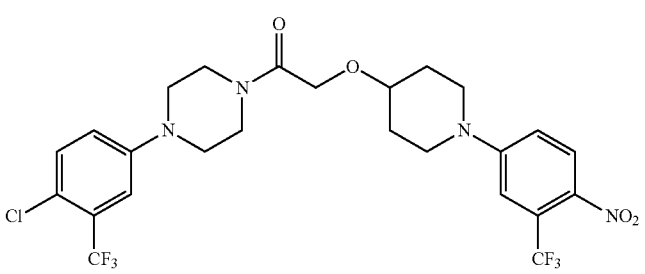 | II-A | 4.69 | 595 | 595 |
| Example 174 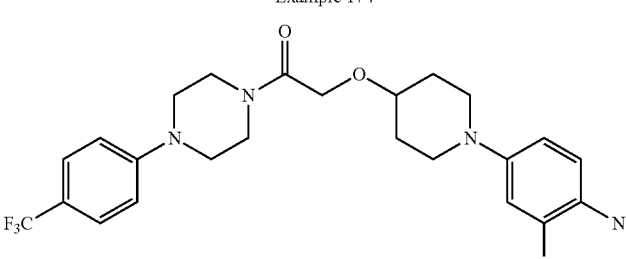 | II-A | 4.54 | 560 | 561 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 175 | II-A | 4.84 | 549 | 549 |
| Example 176 | II-A | 4.69 | 561 | 561 |
| Example 177 | II-A | 4.52 | 527 | 527 |
| Example 178 | II-A | 4.67 | 561 | 561 |
| Example 179 | II-A | 4.49 | 527 | 527 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 180 | II-A | 4.12 | 518 | 518 |
| Example 181 | II-A | 4.33 | 586 | 586 |
| Example 182 | II-A | 4.63 | 576 | 577 |
| Example 183 | I-B | 4.83 | 574 | 574 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 184 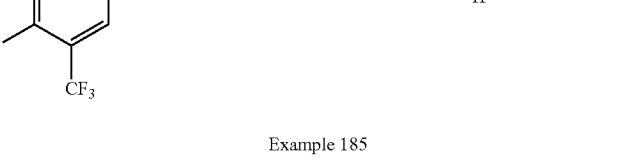 | I-B | 4.92 | 608 | 608 |
| Example 185 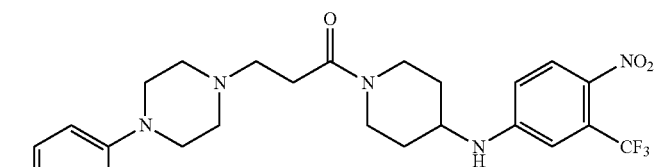 | I-B | 4.85 | 574 | 574 |
| Example 186 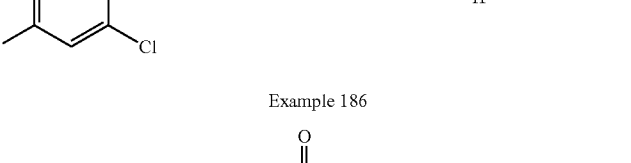 | I-B | 4.76 | 540 | 540 |
| Example 187 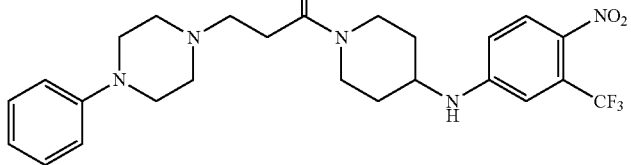 | I-B | 4.86 | 574 | 574 |
| Example 188 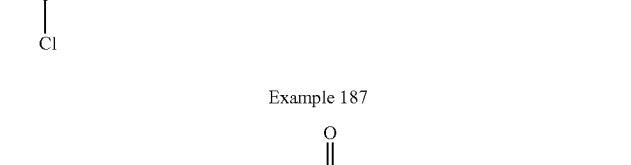 | II-F | 11.30 | 540 | 541 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 189 | I-B | 4.58 | 530 | 531 |
| Example 190 | I-B | 4.73 | 598 | 599 |
| Example 191 | I-B | 4.87 | 590 | 590 |
| Example 192 | I-B | 4.84 | 574 | 574 |
| Example 193 | I-B | 4.96 | 608 | 608 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 194 | I-B | 4.85 | 574 | 574 |
| Example 195 | I-B | 4.99 | 562 | 562 |
| Example 196 | I-B | 4.94 | 574 | 574 |
| Example 197 | I-B | 4.76 | 540 | 540 |
| Example 198 | I-B | 4.89 | 574 | 574 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 199 | I-B | 4.74 | 540 | 540 |
| Example 200 | I-B | 4.58 | 530 | 531 |
| Example 201 | I-B | 5.57 | 588 | 588 |
| Example 202 | I-B | 5.70 | 622 | 622 |
| Example 203 | I-B | 5.76 | 576 | 576 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 204 | I-B | 5.67 | 588 | 588 |
| Example 205 | I-B | 5.52 | 554 | 554 |
| Example 206 | I-B | 5.67 | 588 | 588 |
| Example 207 | I-B | 5.51 | 554 | 554 |
| Example 208 | I-B | 5.76 | 545 | 576 |

TABLE V-continued

Additional Compounds Prepared by Applicants in Accordance with this Invention

| Compound Structure | Analysis Method | Retention Time (min) | Calc. Mass | Obs. Mass |
| --- | --- | --- | --- | --- |
| Example 209 | I-B | 5.43 | 612 | 613 |
| Example 210 | I-B | 5.62 | 604 | 604 |
| Example 211 | I-B | 4.96 | 642 | 642 |
| Example 212 | I-B | 4.84 | 572 | 573 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 213 | I-B | 4.86 | 570 | 571 |
| Example 214 | I-B | 4.66 | 506 | 507 |
| Example 215 | I-B | 5.97 | 572 | 573 |
| Example 216 | I-B | 4.73 | 504 | 505 |
| Example 217 | I-C | 2.96 | 574 | 575 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 218 | I-C | 3.03 | 609 | 609 |
| Example 219 | I-C | 2.96 | 574 | 575 |
| Example 220 | I-C | 3.09 | 563 | 563 |
| Example 221 | I-C | 3.00 | 575 | 575 |
| Example 222 | I-C | 2.92 | 541 | 541 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 223 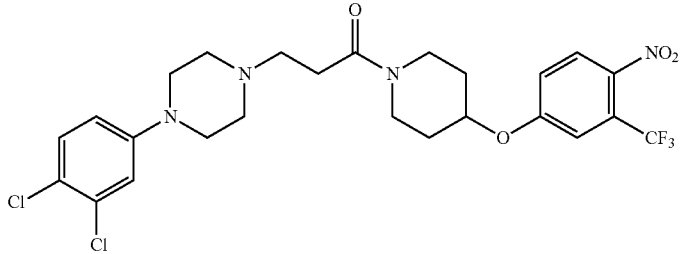 | I-C | 2.99 | 575 | 575 |
| Example 224 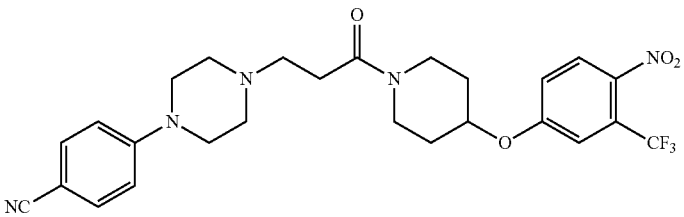 | I-C | 2.82 | 532 | 532 |
| Example 225 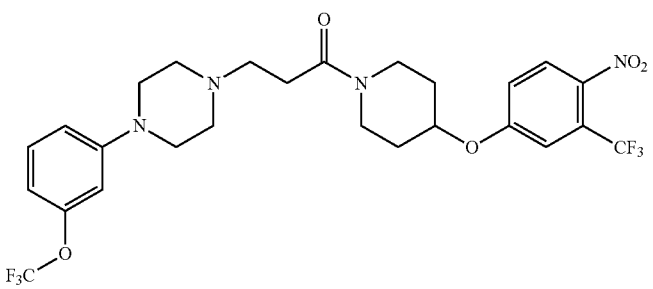 | I-C | 2.99 | 590 | 591 |
| Example 226 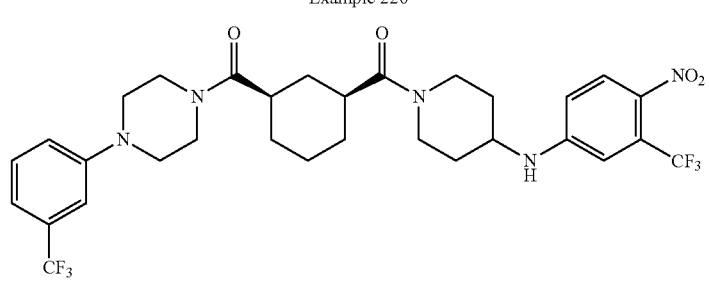 | I-C | 3.61 | 656 | 656 |
| Example 227 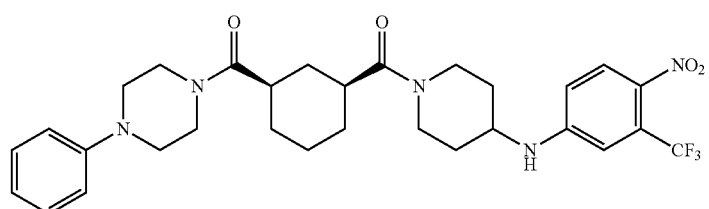 | I-C | 3.47 | 588 | 588 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 228 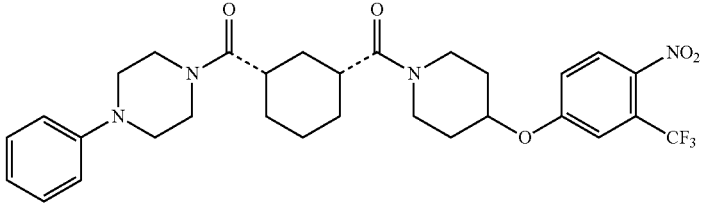 | I-C | 3.55 | 589 | 589 |
| Example 229 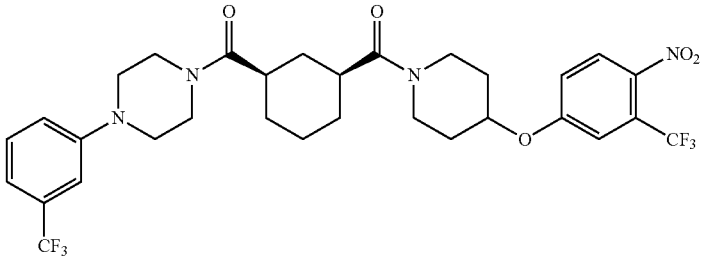 | I-A | 4.72 | 657 | 657 |
| Example 230 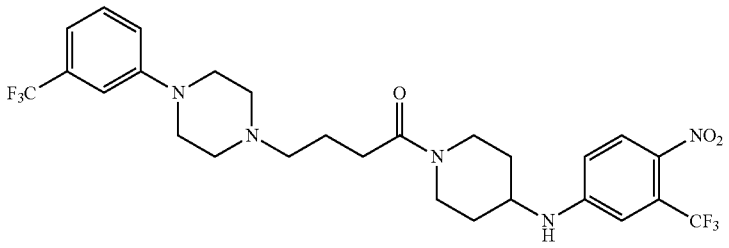 | I-B | 4.97 | 588 | 588 |
| Example 231  | I-B | 5.45 | 589 | 589 |
| Example 232 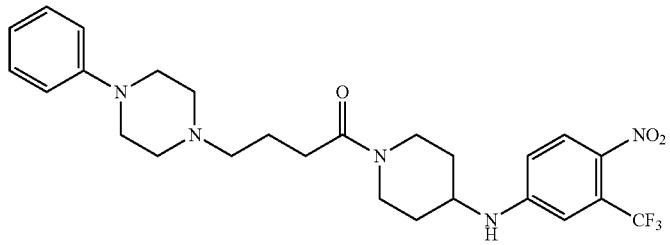 | I-B | 4.79 | 520 | 520 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 233 | I-B | 4.88 | 520 | 522 |
| Example 234 | I-C | 3.47 | 588 | 588 |
| Example 235 | I-A | 4.46 | 589 | 589 |
| Example 236 | I-B | 4.78 | 520 | 520 |
| Example 237 | II-F | 10.82 | 550 | 551 |
| Example 238 | II-F | 10.49 | 486 | 487 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 239 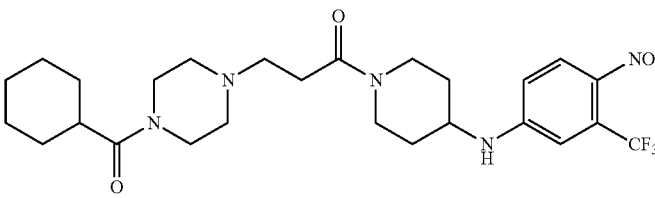 | II-F | 10.16 | 540 | 540 |
| Example 240 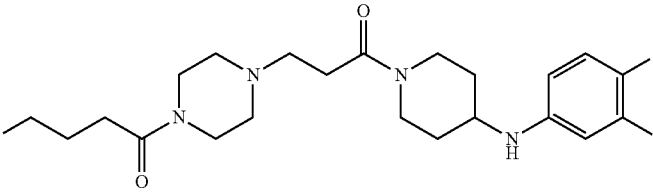 | II-F | 9.75 | 515 | 514 |
| Example 241 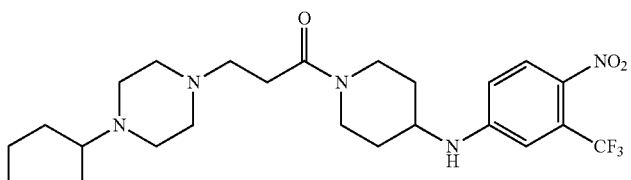 | II-F | 11.16 | 512 | 513 |
| Example 242 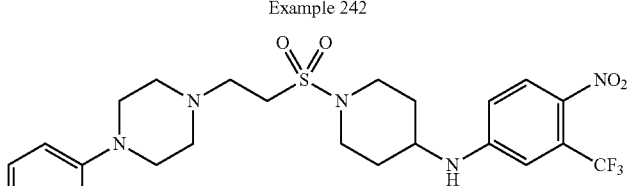 | II-F | 11.15 | 542 | 543 |
| Example 243 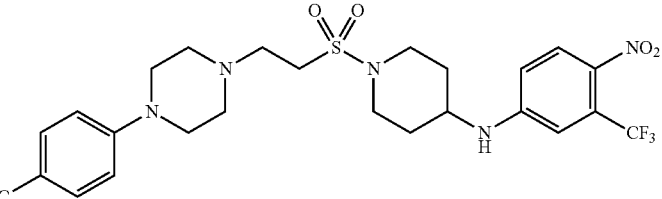 | II-F | 11.44 | 556 | 557 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 244 | II-F | 12.29 | 598 | 599 |
| Example 245 | II-F | 11.66 | 610 | 611 |
| Example 246 | II-F | 11.63 | 576 | 574 |
| Example 247 | II-F | 11.22 | 586 | 587 |
| Example 248 | II-F | 11.46 | 548 | 549 |
| Example 249 | II-F | 11.01 | 522 | 523 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 250 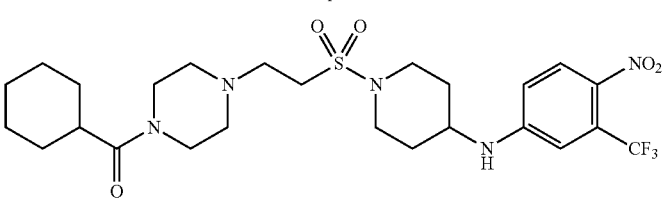 | II-F | 10.86 | 576 | 577 |
| Example 251 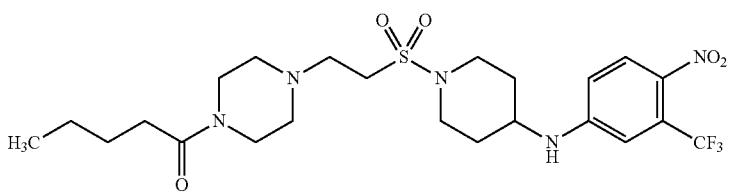 | II-F | 10.44 | 550 | 551 |
| Example 252 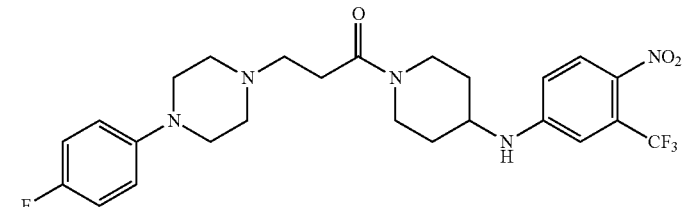 | I-B | 4.77 | 524 | 524 |
| Example 253 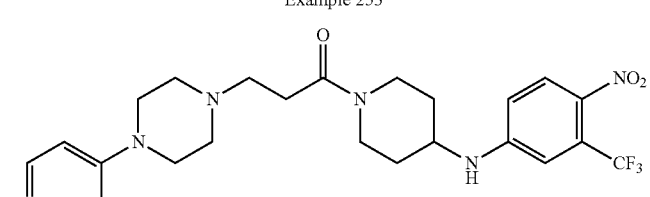 | I-B | 4.04 | 506 | 507 |
| Example 254 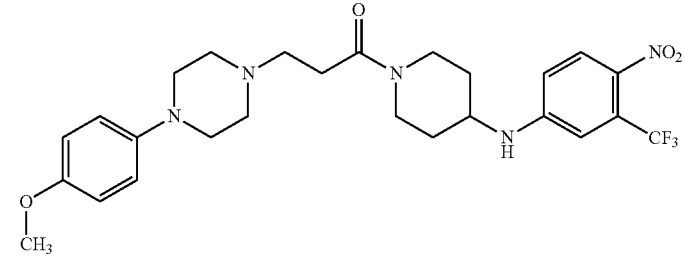 | I-B | 4.71 | 536 | 536 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 255 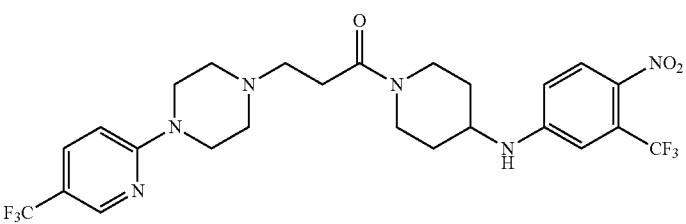 | I-B | 4.86 | 575 | 575 |
| Example 256 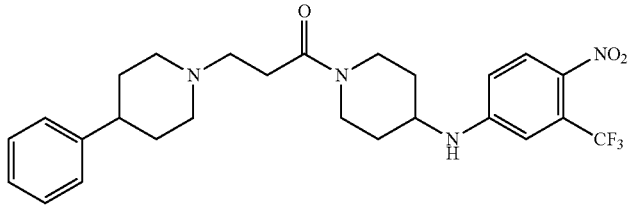 | I-B | 4.80 | 504 | 505 |
| Example 257 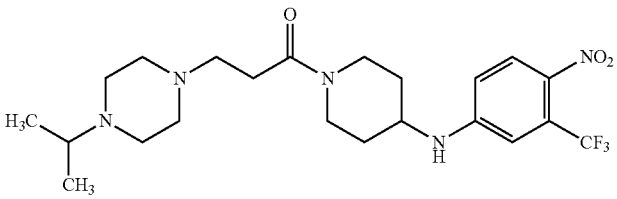 | I-B | 4.21 | 472 | 472 |
| Example 258 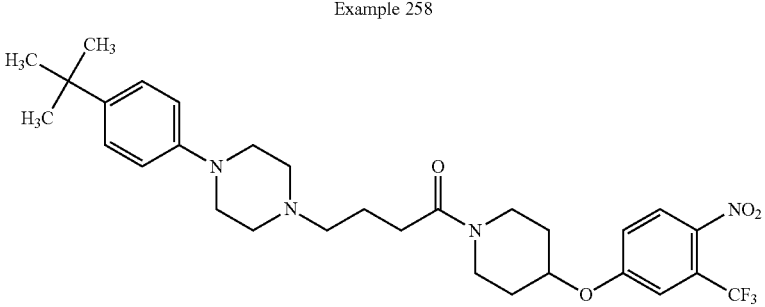 [SMILES: "Example 258" ; CC(C)(C)c1ccc(N2CCN(CCCC(=O)N3CCC(Oc4ccc([N+](=O)[O-])c(C(F)(F)F)c4)CC3)CC2)cc1] | I-C | 3.18 | 577 | 577 |
| Example 259 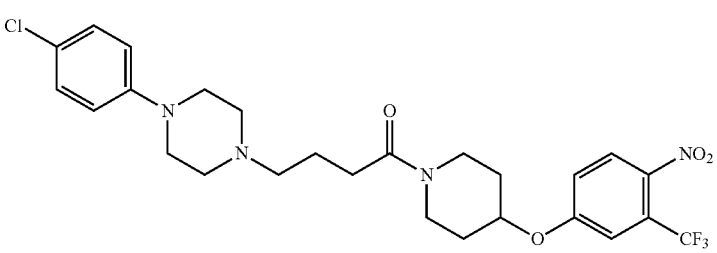 | I-C | 3.01 | 555 | 555 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 260 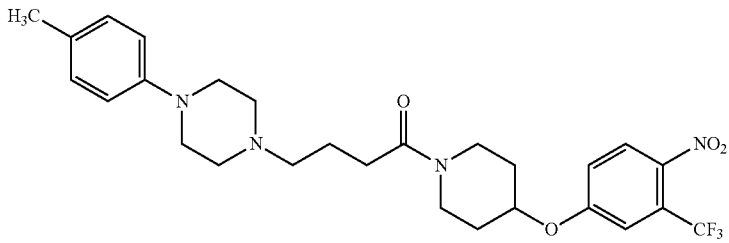 | I-C | 2.98 | 535 | 535 |
| Example 261 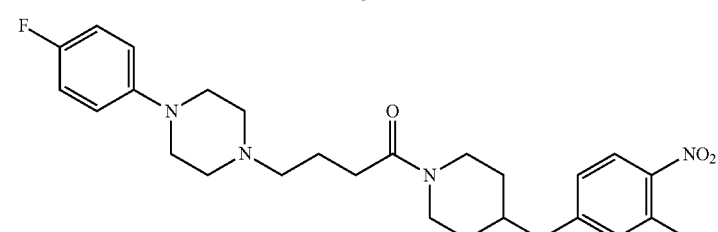 | I-C | 2.90 | 538 | 539 |
| Example 262 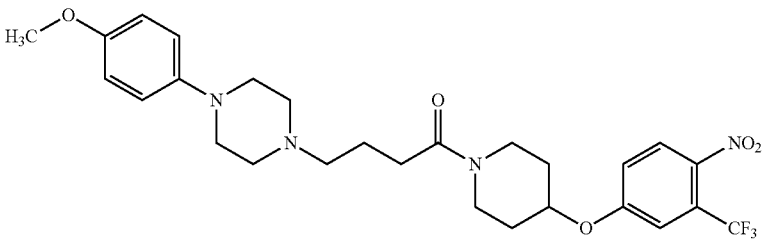 | I-C | 2.89 | 551 | 551 |
| Example 263 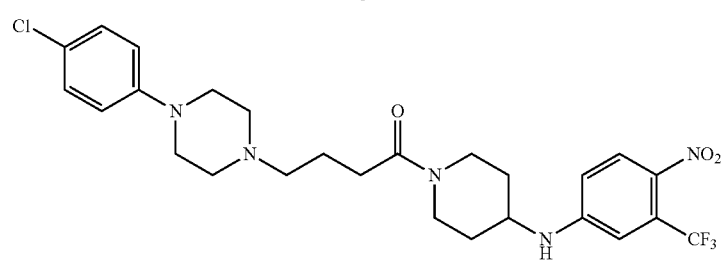 | I-D | 1.50 | 554 | 554 |
| Example 264 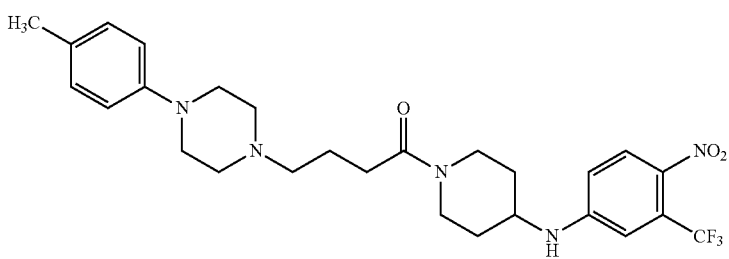 | I-C | 2.95 | 534 | 534 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 265 | I-C | 2.91 | 538 | 538 |
| Example 266 | I-A | 2.47 | 489 | 489 |
| Example 267 | II-A | 2.93 | 485 | 485 |
| Example 268 | II-A | 3.19 | 539 | 539 |
| Example 269 | I-B | 5.20 | 543 | 543 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 270 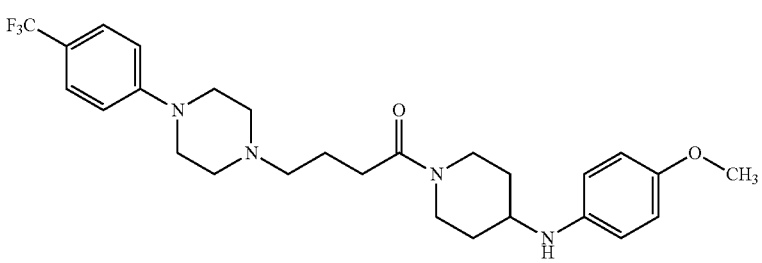 | I-B | 4.26 | 505 | 505 |
| Example 271 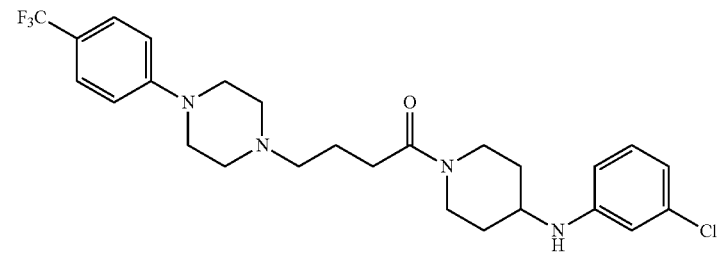 | I-B | 5.11 | 509 | 509 |
| Example 272 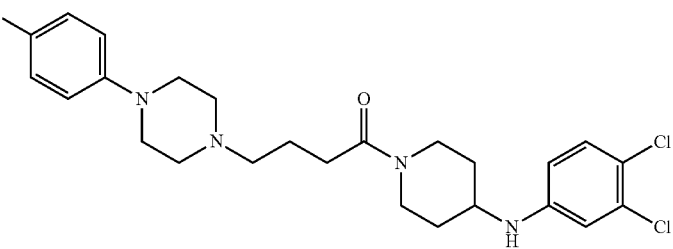 | I-B | 5.30 | 544 | 543 |
| Example 273 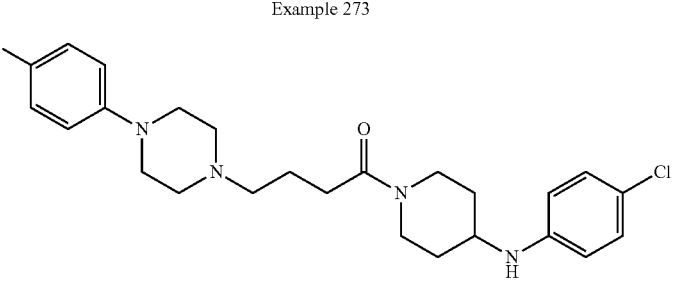 | I-B | 5.13 | 509 | 509 |
| Example 83 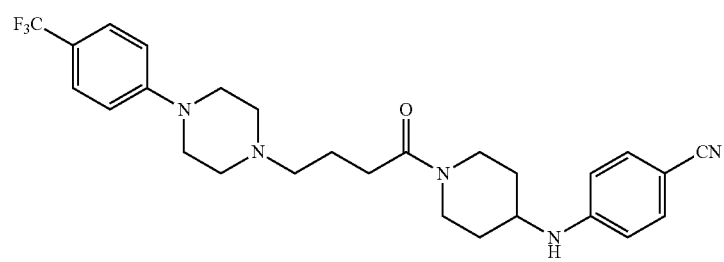 | I-B | 4.90 | 500 | 500 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 85 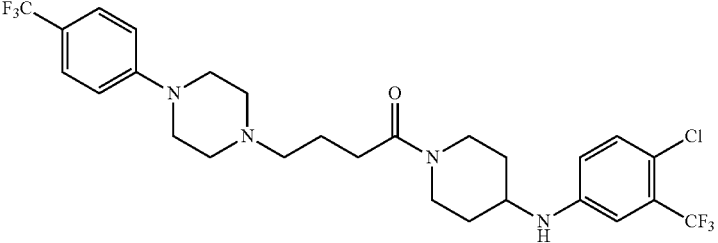 | I-B | 5.38 | 577 | 577 |
| Example 274 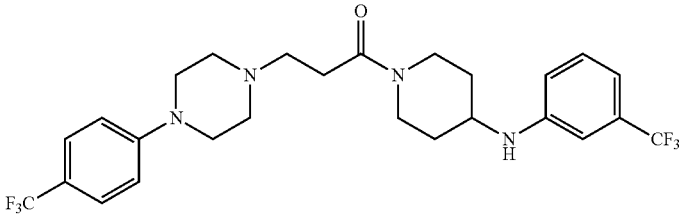 | I-B | 5.18 | 528 | 529 |
| Example 275 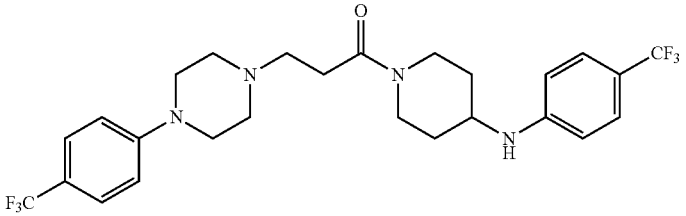 | I-C | 3.14 | 528 | 529 |
| Example 276 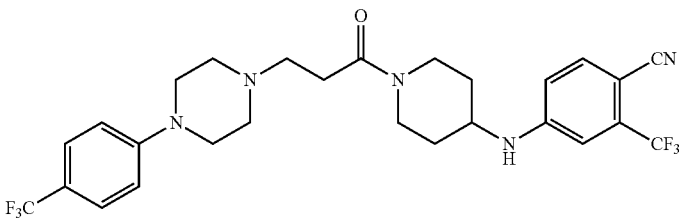 | I-C | 3.06 | 554 | 554 |
| Example 277 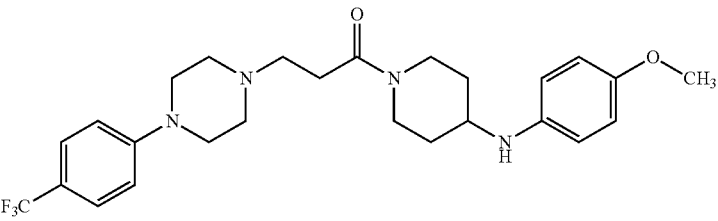 | I-C | 2.53 | 491 | 491 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 278 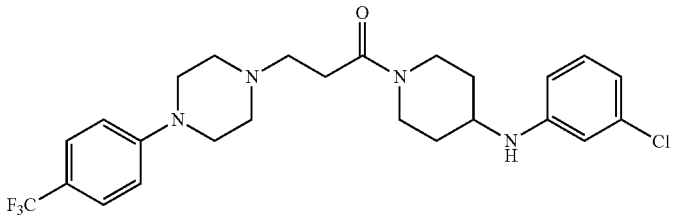 | I-B | 5.00 | 495 | 495 |
| Example 279 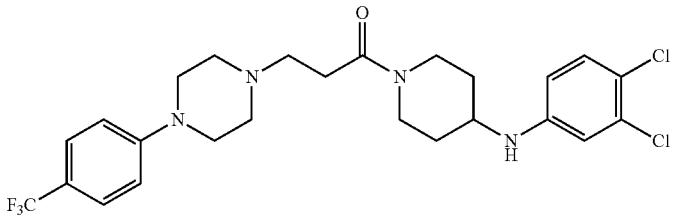 | I-B | 5.18 | 529 | 529 |
| Example 280 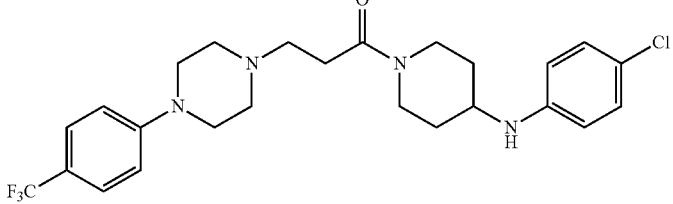 | I-B | 4.99 | 495 | 495 |
| Example 281 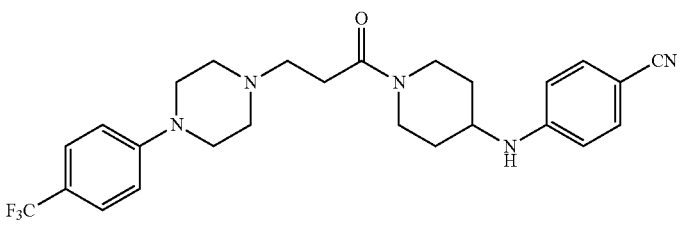 | I-C | 2.92 | 486 | 486 |
| Example 282 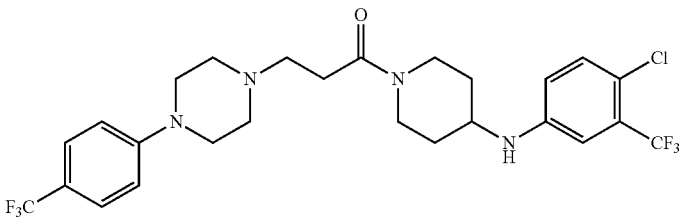 | I-B | 5.32 | 563 | 563 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 283 | I-D | 1.50 | 560 | 560 |
| Example 284 | I-D | 1.56 | 548 | 548 |
| Example 285 | I-B | 5.03 | 558 | 559 |
| Example 286 | I-D | 1.45 | 526 | 526 |
| Example 287 | I-B | 4.75 | 522 | 522 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 288 | II-F | 10.31 | 541 | 542 |
| Example 289 | II-F | 9.86 | 514 | 516 |
| Example 290 | II-E | 6.55 | 513 | 514 |
| Example 291 | II-A | 3.39 | 619 | 619 |
| Example 292 | II-A | 3.65 | 607 | 607 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 293 | II-A | 3.30 | 585 | 585 |
| Example 294 | II-A | 3.70 | 621 | 621 |
| Example 295 | I-B | 4.83 | 599 | 599 |
| Example 296 | II-A | 2.94 | 591 | 591 |
| Example 297 | II-A | 3.14 | 579 | 579 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 298 | II-A | 2.81 | 557 | 557 |
| Example 299 | II-C | 7.48 | 605 | 605 |
| Example 300 | II-A | 3.16 | 593 | 593 |
| Example 301 | II-A | 2.84 | 571 | 571 |
| Example 302 | II-A | 3.61 | 561 | 561 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 303 | I-D | 1.71 | 549 | 549 |
| Example 304 | I-D | 1.61 | 527 | 527 |
| Example 305 | I-D | 1.73 | 563 | 563 |
| Example 306 | I-D | 1.63 | 541 | 541 |
| Example 307 | I-B | 4.69 | 544 | 545 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 308 | I-B | 4.85 | 533 | 533 |
| Example 309 | I-B | 4.63 | 511 | 511 |
| Example 310 | I-B | 4.92 | 547 | 547 |
| Example 311 | I-B | 4.69 | 525 | 525 |
| Example 312 | I-B | 4.78 | 575 | 575 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 313 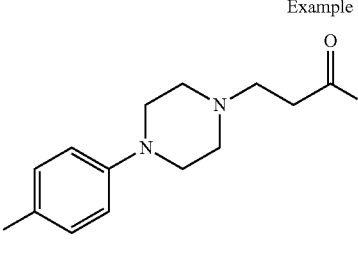 | I-B | 4.95 | 563 | 563 |
| Example 314 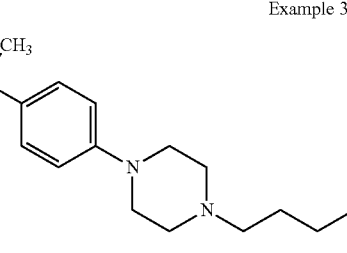 | I-B | 4.71 | 541 | 541 |
| Example 315 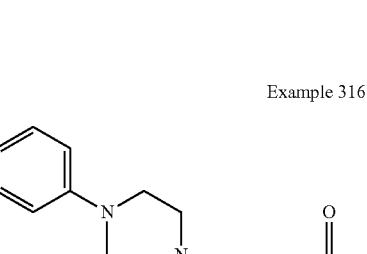 | I-B | 4.99 | 577 | 577 |
| Example 316 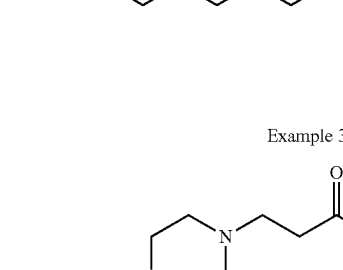 | I-B | 4.75 | 555 | 555 |
| Example 317 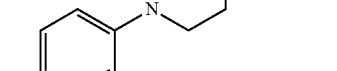 | I-B | 4.51 | 520 | 520 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 318 | I-B | 4.63 | 508 | 508 |
| Example 319 | I-B | 4.41 | 486 | 486 |
| Example 320 | I-B | 4.70 | 522 | 522 |
| Example 321 | I-B | 4.45 | 500 | 500 |
| Example 322 | I-B | 4.73 | 542 | 542 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 323 | I-D | 1.44 | 520 | 520 |
| Example 324 | I-B | 4.76 | 556 | 556 |
| Example 325 | I-B | 4.54 | 534 | 534 |
| Example 326 | I-D | 1.39 | 530 | 530 |
| Example 327 | I-D | 1.46 | 518 | 518 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 328 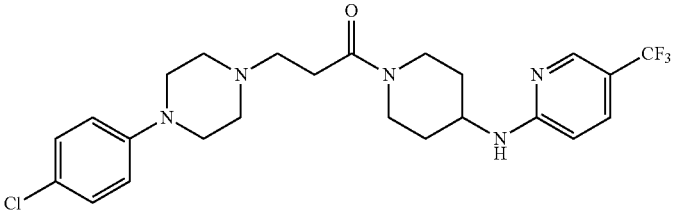 | I-D | 1.32 | 496 | 496 |
| Example 329 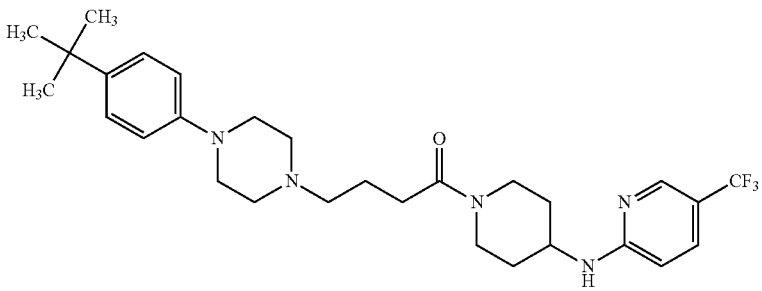 | I-D | 1.49 | 532 | 532 |
| Example 330 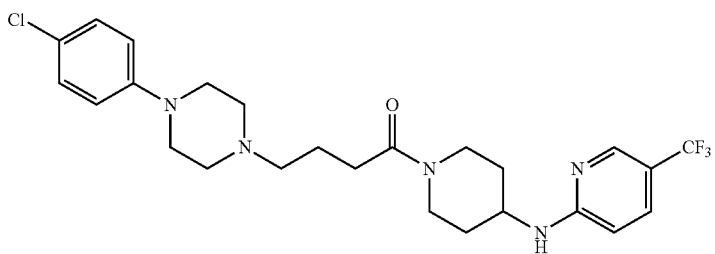 | I-D | 1.34 | 510 | 510 |
| Example 331 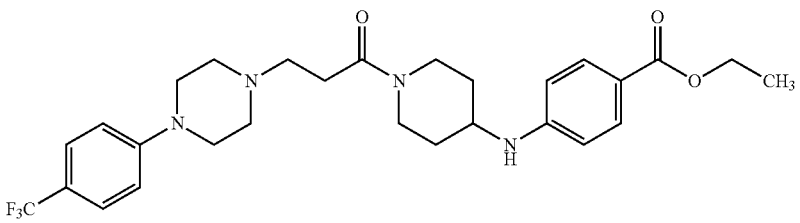 | I-B | 4.36 | 533 | 533 |
| Example 332 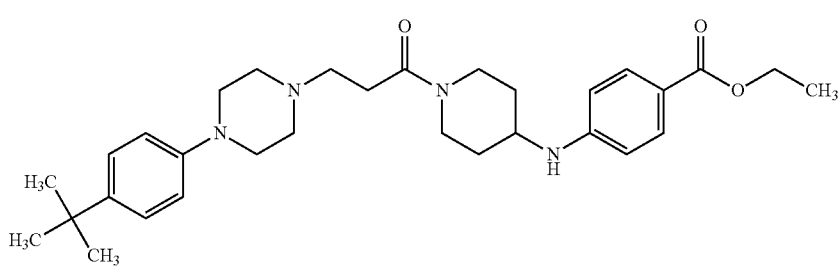 | I-B | 4.52 | 521 | 521 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 333 | I-B | 4.28 | 499 | 499 |
| Example 334 | I-B | 4.42 | 547 | 547 |
| Example 335 | I-B | 4.59 | 535 | 535 |
| Example 336 | I-B | 4.34 | 513 | 513 |
| Example 337 | I-B | 4.34 | 607 | 607 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 338 | I-B | 4.53 | 595 | 595 |
| Example 339 | I-B | 4.27 | 573 | 573 |
| Example 340 | I-B | 4.57 | 609 | 609 |
| Example 341 | I-B | 4.30 | 587 | 587 |
| Example 342 | I-B | 4.47 | 636 | 636 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 343 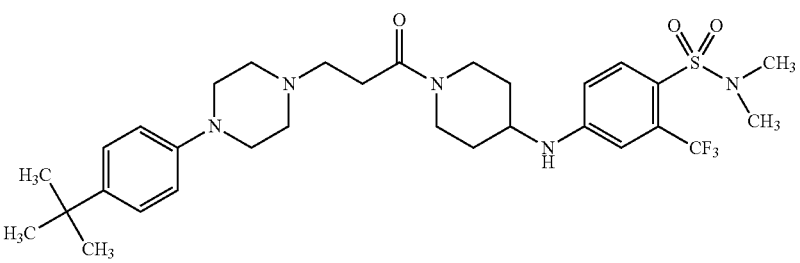 | I-B | 4.62 | 624 | 624 |
| Example 344 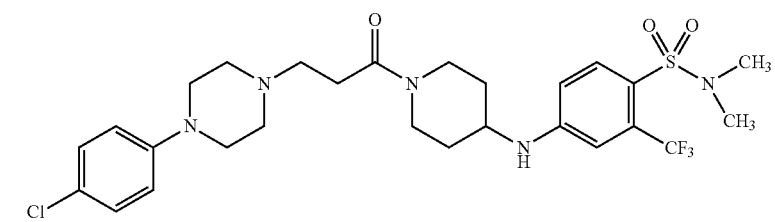 | I-B | 4.40 | 602 | 602 |
| Example 345 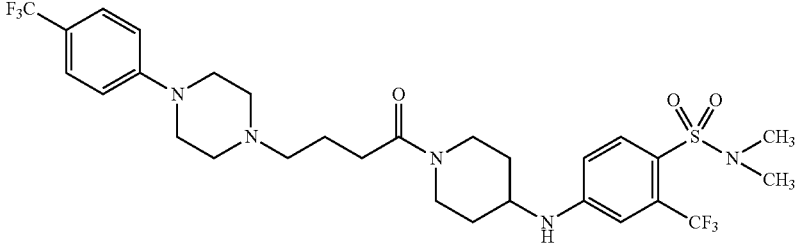 | I-B | 4.51 | 650 | 650 |
| Example 346 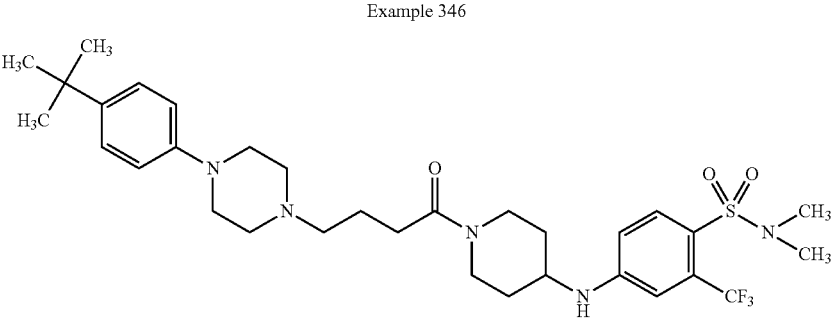 [SMILES: "Example 346" ; CN(C)S(=O)(=O)c1ccc(NC2CCN(C(=O)CCCN3CCN(c4ccc(C(C)(C)C)cc4)CC3)CC2)cc1C(F)(F)F] | I-B | 4.64 | 638 | 638 |
| Example 347 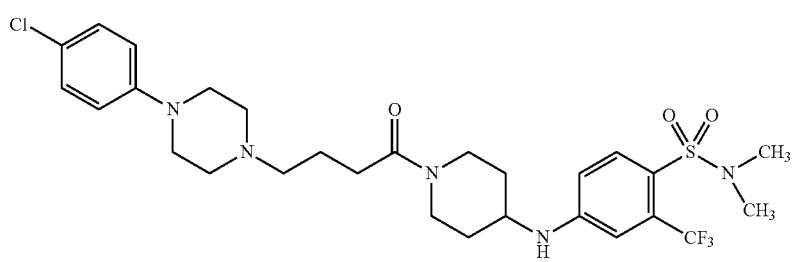 | I-B | 4.42 | 616 | 616 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 348 | I-B | 4.37 | 486 | 486 |
| Example 349 | I-B | 4.54 | 474 | 474 |
| Example 350 | I-B | 4.27 | 452 | 452 |
| Example 351 | I-B | 4.55 | 488 | 488 |
| Example 352 | I-B | 4.31 | 466 | 466 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 353 | I-B | 4.83 | 595 | 595 |
| Example 354 | I-B | 5.00 | 583 | 583 |
| Example 355 | I-B | 4.78 | 562 | 561 |
| Example 356 | I-B | 5.04 | 597 | 597 |
| Example 357 | I-B | 4.82 | 576 | 575 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 358 | II-A | 3.42 | 540 | 541 |
| Example 359 | II-A | 3.77 | 581 | 581 |
| Example 360 | II-A | 3.46 | 519 | 519 |
| Example 361 | II-A | 3.35 | 535 | 535 |
| Example 362 | II-A | 3.82 | 597 | 597 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 363 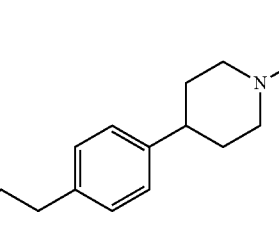 | II-A | 3.70 | 582 | 582 |
| Example 364 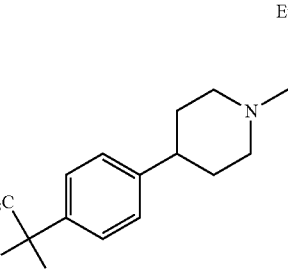 | II-A | 3.79 | 547 | 547 |
| Example 365 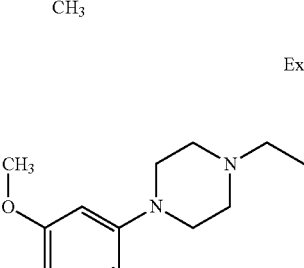 | II-A | 3.88 | 561 | 561 |
| Example 366 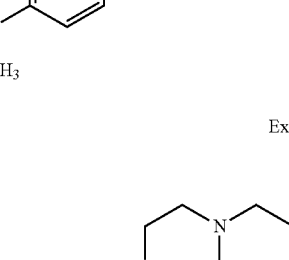 | I-B | 4.29 | 566 | 566 |
| Example 367 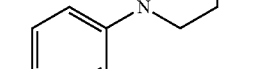 | II-A | 3.30 | 558 | 558 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 368 | II-A | 3.17 | 542 | 542 |
| Example 369 | I-B | 4.22 | 481 | 481 |
| Example 370 | I-B | 4.45 | 524 | 524 |
| Example 371 | I-B | 4.27 | 501 | 501 |
| Example 372 | I-B | 4.13 | 497 | 497 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 373 | I-B | 4.17 | 503 | 503 |
| Example 374 | I-B | 4.45 | 559 | 559 |
| Example 375 | I-B | 4.30 | 535 | 535 |
| Example 376 | I-B | 4.42 | 544 | 544 |
| Example 377 | I-B | 4.43 | 509 | 509 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 378 | I-B | 4.47 | 523 | 523 |
| Example 379 | I-B | 4.48 | 543 | 543 |
| Example 380 | I-B | 4.31 | 536 | 536 |
| Example 381 | I-B | 4.13 | 482 | 482 |
| Example 382 | I-B | 4.38 | 570 | 570 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 383 | I-B | 4.18 | 502 | 502 |
| Example 384 | I-B | 4.27 | 536 | 536 |
| Example 385 | II-A | 3.39 | 574 | 574 |
| Example 386 | I-B | 3.98 | 528 | 528 |
| Example 387 | I-B | 4.02 | 498 | 498 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 388 | I-B | 4.41 | 540 | 540 |
| Example 389 | I-B | 4.23 | 520 | 520 |
| Example 390 | I-B | 4.08 | 504 | 504 |
| Example 391 | I-B | 4.40 | 565 | 565 |
| Example 392 | I-B | 4.53 | 538 | 538 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 393 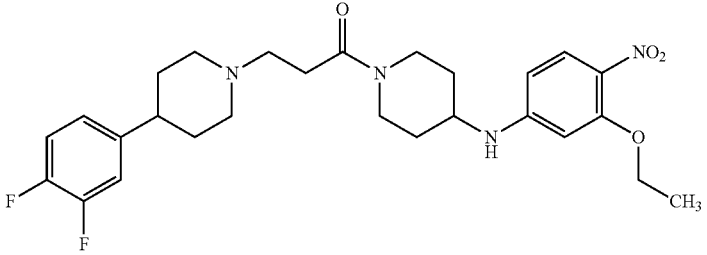 | I-B | 4.31 | 517 | 517 |
| Example 394 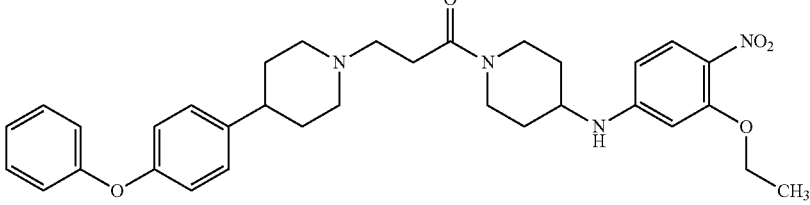 | I-B | 4.58 | 573 | 573 |
| Example 395 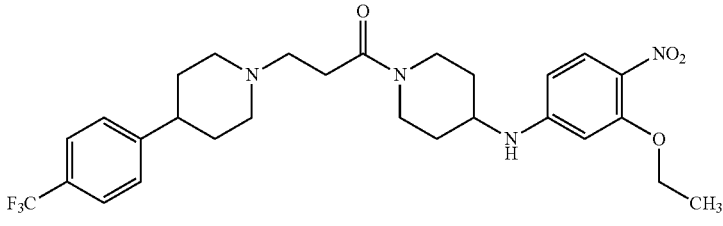 | I-B | 4.44 | 549 | 549 |
| Example 396 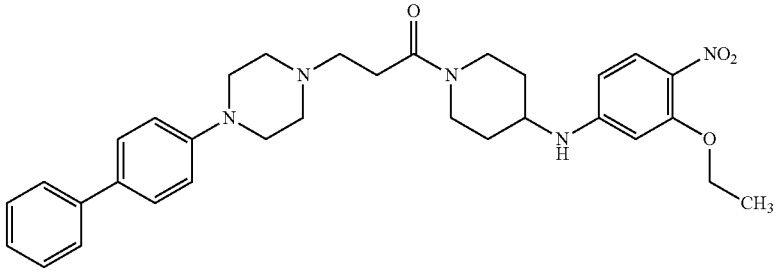 | I-B | 4.51 | 558 | 558 |
| Example 397 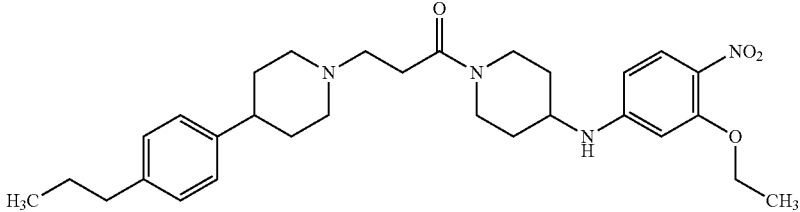 | I-B | 4.57 | 523 | 523 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 398 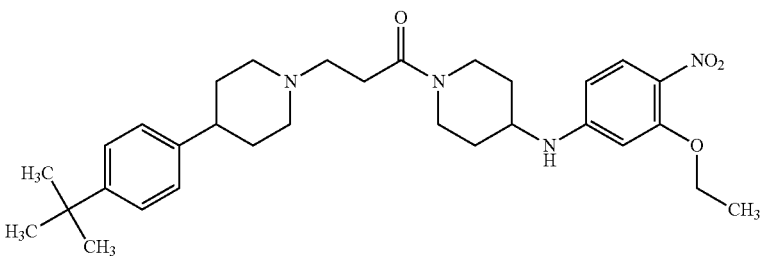 | I-B | 5.64 | 537 | 537 |
| Example 399 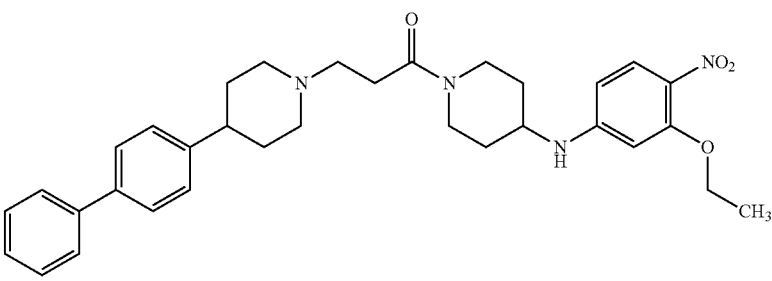 | I-B | 4.56 | 557 | 557 |
| Example 400 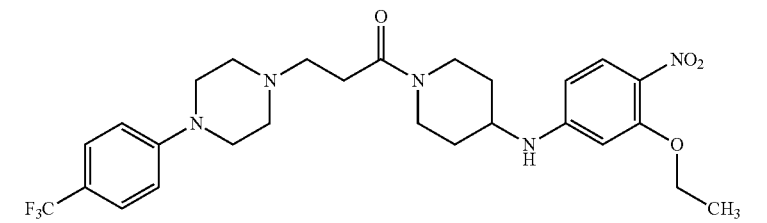 | I-B | 4.41 | 550 | 550 |
| Example 401 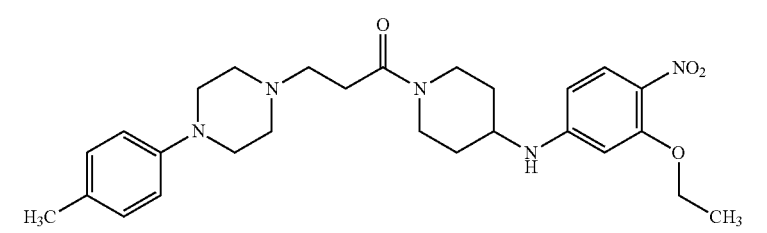 | I-B | 4.27 | 496 | 496 |
| Example 402 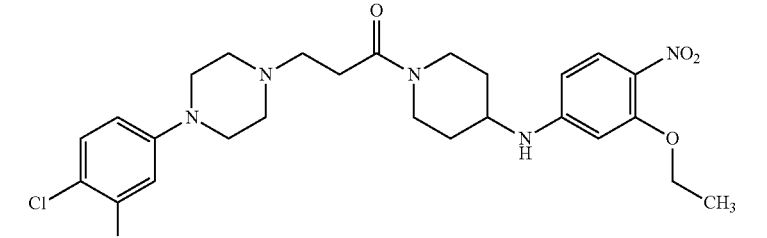 | I-B | 4.53 | 584 | 584 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 403 | I-B | 4.31 | 516 | 516 |
| Example 404 | I-B | 4.39 | 550 | 550 |
| Example 405 | I-B | 4.51 | 588 | 588 |
| Example 406 | I-B | 4.16 | 512 | 512 |
| Example 407 | I-B | 4.54 | 554 | 554 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 408 | I-B | 4.36 | 534 | 534 |
| Example 409 | I-B | 4.24 | 518 | 518 |
| Example 410 | I-B | 4.50 | 579 | 579 |
| Example 411 | I-B | 4.33 | 495 | 495 |
| Example 412 | I-B | 4.34 | 515 | 515 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 413 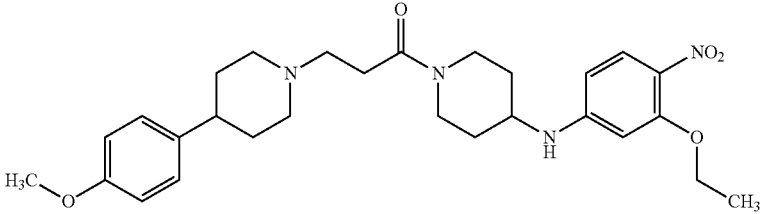 | I-B | 4.25 | 511 | 511 |
| Example 414 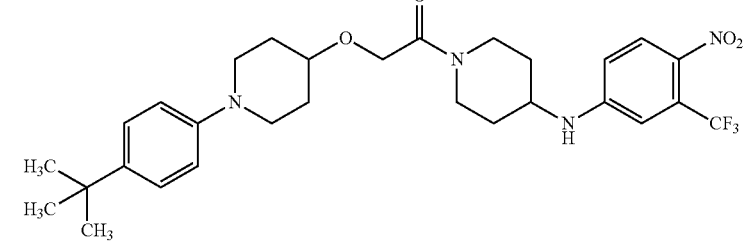 | II-E | 9.49 | 563 | 564 |
| Example 415 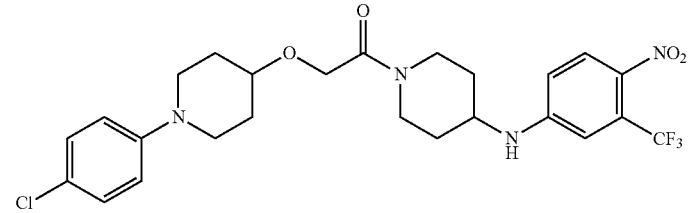 | II-E | 11.06 | 541 | 542 |
| Example 416 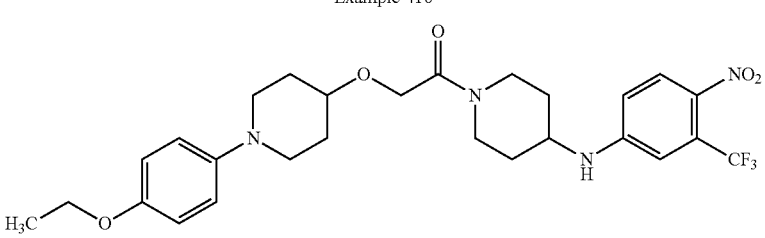 | II-E | 7.49 | 551 | 552 |
| Example 417 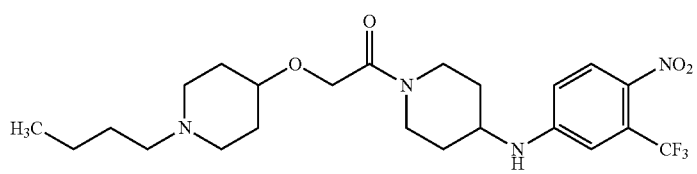 | II-E | 6.49 | 486 | 488 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 418 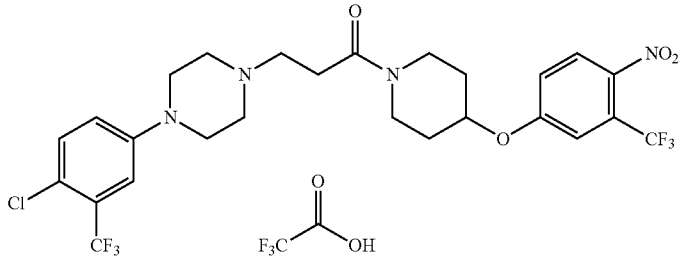 | I-B | 4.71 | 723 | 609 |
| Example 419 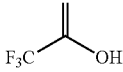 | I-B | 4.56 | 655 | 541 |
| Example 420 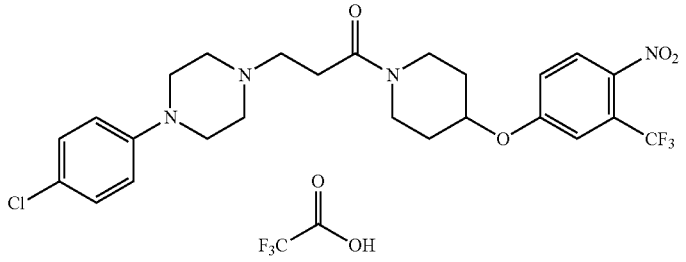 | I-B | 4.52 | 689 | 575 |
| Example 421 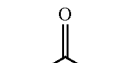 | I-B | 4.74 | 727 | 613 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 422 | I-B | 4.37 | 681 | 567 |
| Example 423 | I-B | 4.44 | 651 | 537 |
| Example 424 | I-B | 4.75 | 693 | 579 |
| Example 425 | I-B | 4.60 | 673 | 559 |
| Example 426 | I-B | 4.51 | 656 | 543 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 427 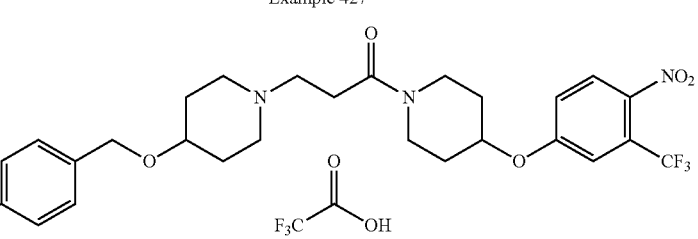 | I-B | 4.71 | 718 | 604 |
| Example 428 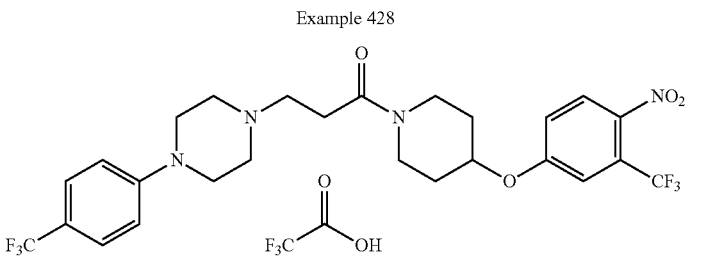 [SMILES: "Example 428" ; O=C(CCN1CCN(c2ccc(C(F)(F)F)cc2)CC1)N1CCC(Oc2ccc([N+](=O)[O-])c(C(F)(F)F)c2)CC1 ; O=C(O)C(F)(F)F] | I-B | 4.65 | 689 | 575 |
| Example 429 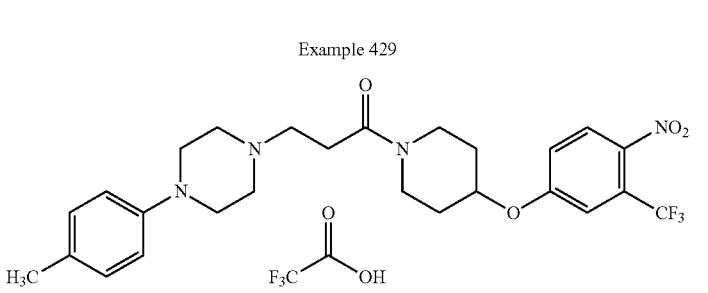 [SMILES: "Example 429" ; Cc1ccc(N2CCN(CCC(=O)N3CCC(Oc4ccc([N+](=O)[O-])c(C(F)(F)F)c4)CC3)CC2)cc1 ; O=C(O)C(F)(F)F] | I-B | 4.54 | 635 | 521 |
| Example 430 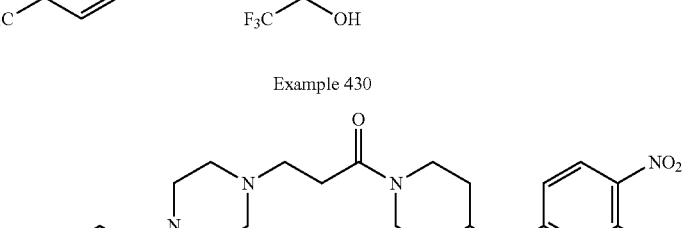 | I-B | 4.77 | 677 | 563 |
| Example 431 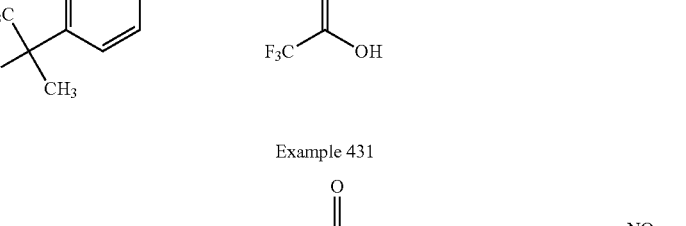 | I-B | 4.64 | 654 | 540 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 432 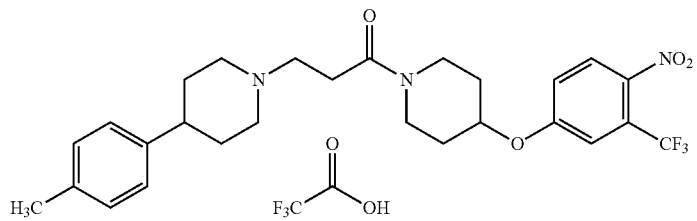 | I-B | 4.60 | 634 | 520 |
| Example 433 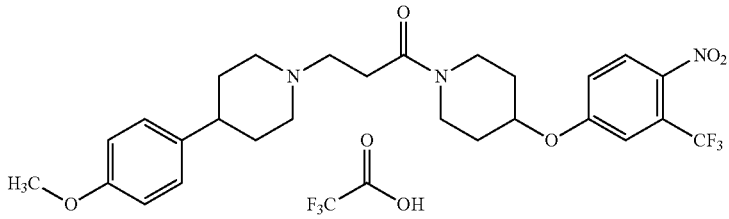 | I-B | 4.48 | 650 | 563 |
| Example 434 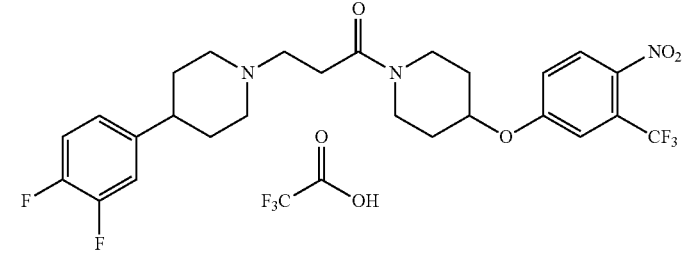 | I-B | 4.58 | 656 | 542 |
| Example 435 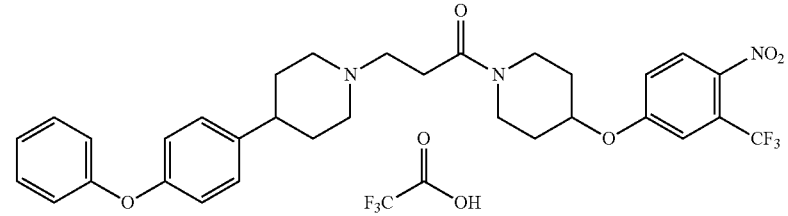 | I-B | 4.78 | 712 | 598 |
| Example 436 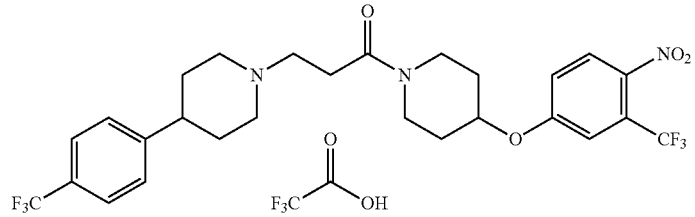 | I-B | 4.68 | 688 | 574 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 437 | I-B | 4.73 | 697 | 583 |
| Example 438 | I-B | 4.81 | 662 | 548 |
| Example 439 | I-B | 4.85 | 676 | 562 |
| Example 440 | I-B | 4.80 | 696 | 582 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 441 | I-B | 4.32 | 543 | 543 |
| Example 442 | I-B | 4.48 | 531 | 531 |
| Example 443 | I-B | 4.23 | 509 | 509 |
| Example 444 | I-B | 4.52 | 545 | 545 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 445 | I-B | 4.26 | 523 | 523 |
| Example 446 | I-B | 4.56 | 523 | 523 |
| Example 447 | I-B | 4.85 | 566 | 565 |
| Example 448 | I-B | 4.62 | 543 | 543 |
| Example 449 | I-B | 4.51 | 539 | 539 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 450 | I-B | 4.56 | 545 | 545 |
| Example 451 | n | n | n | n |
| Example 452 | I-B | 4.69 | 577 | 577 |
| Example 453 | I-B | 4.73 | 586 | 586 |
| Example 454 | I-B | 4.82 | 551 | 551 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 455 | I-B | 4.84 | 565 | 565 |
| Example 456 | I-B | 4.79 | 585 | 585 |
| Example 457 | I-B | 4.64 | 578 | 578 |
| Example 458 | I-B | 4.53 | 524 | 524 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 459 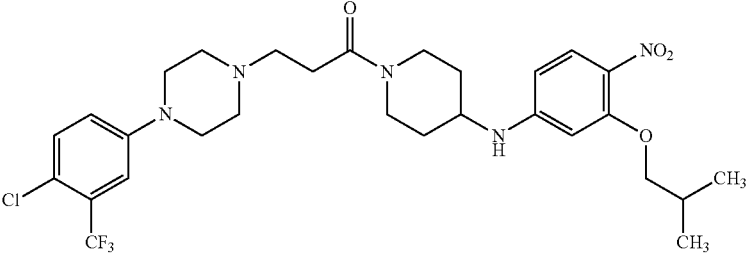 | I-B | 4.65 | 612 | 612 |
| Example 460 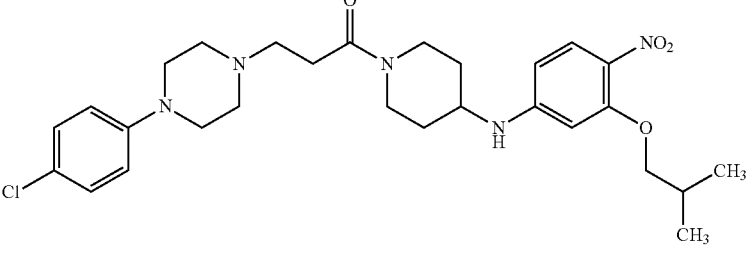 | I-B | 4.51 | 544 | 544 |
| Example 461 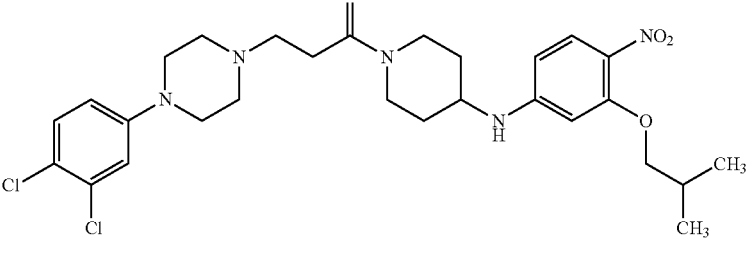 | I-B | 4.62 | 578 | 578 |
| Example 462 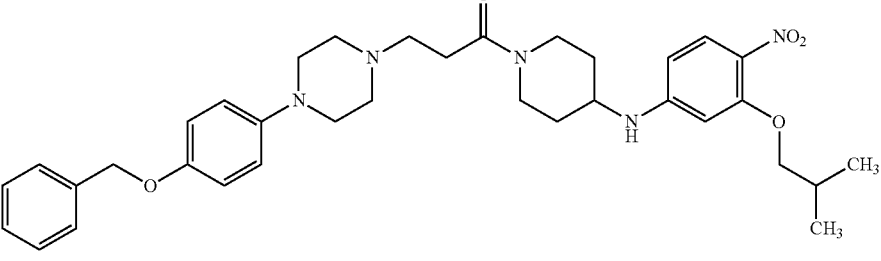 | I-B | 4.70 | 616 | 616 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 463 | I-B | 4.36 | 570 | 570 |
| Example 464 | I-B | 4.42 | 540 | 540 |
| Example 465 | n | 4.56 | 582 | N |
| Example 466 | I-B | 4.57 | 562 | 562 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 467 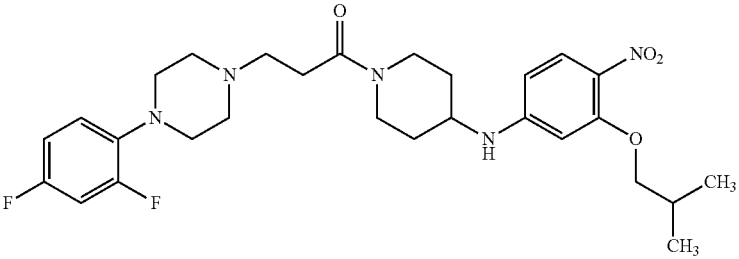 | I-B | 4.50 | 546 | 546 |
| Example 468 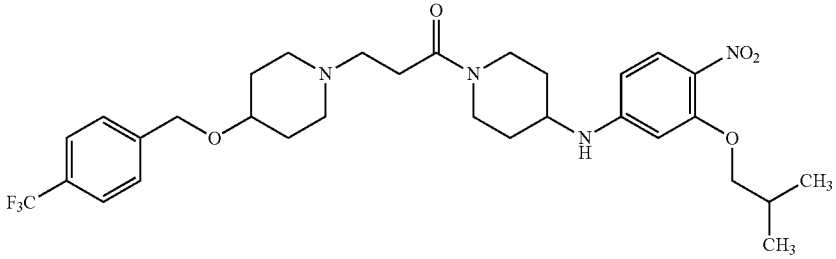 | I-B | 4.69 | 607 | 607 |
| Example 469 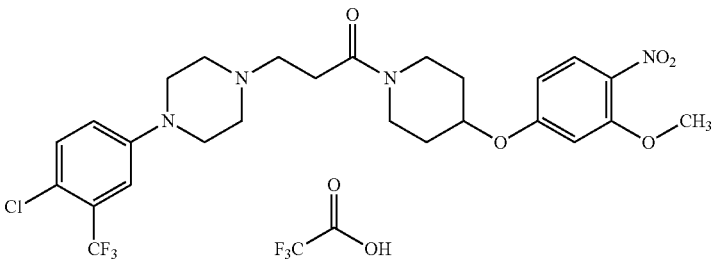 | I-B | 4.47 | 685 | 571 |
| Example 470 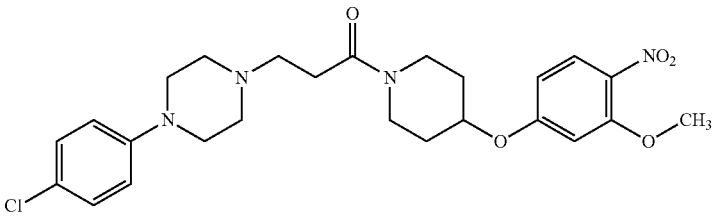 | I-B | 4.26 | 503 | 503 |
| Example 471 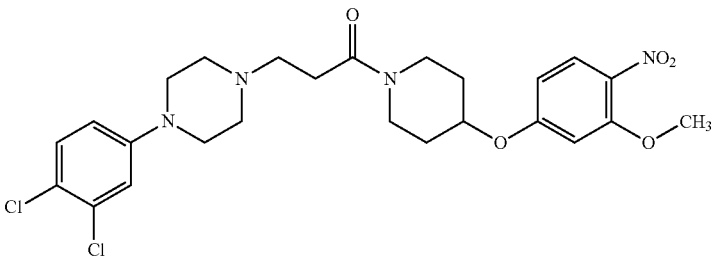 | I-B | 4.40 | 537 | 537 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 472 | I-B | 4.50 | 575 | 575 |
| Example 473 | I-B | 4.47 | 541 | 541 |
| Example 474 | I-B | 4.34 | 521 | 521 |
| Example 475 | I-B | 4.23 | 504 | 505 |
| Example 476 | I-B | 4.47 | 566 | 566 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 477 | I-B | 4.35 | 651 | 537 |
| Example 478 | I-B | 4.22 | 483 | 483 |
| Example 479 | I-B | 4.52 | 525 | 525 |
| Example 480 | I-B | 4.38 | 502 | 502 |
| Example 481 | I-B | 4.32 | 482 | 482 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 482 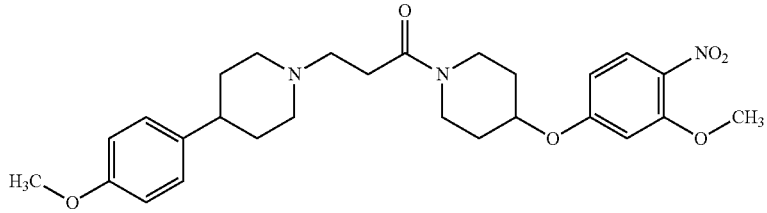 | I-B | 4.21 | 498 | 498 |
| Example 483 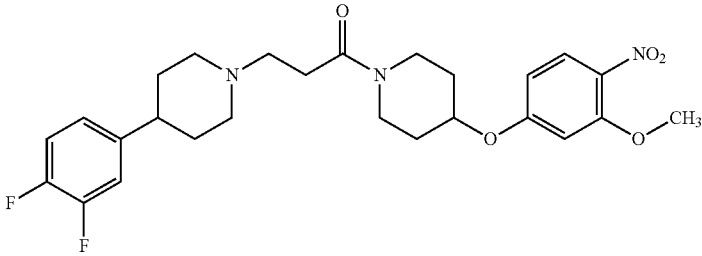 | I-B | 4.29 | 504 | 504 |
| Example 484 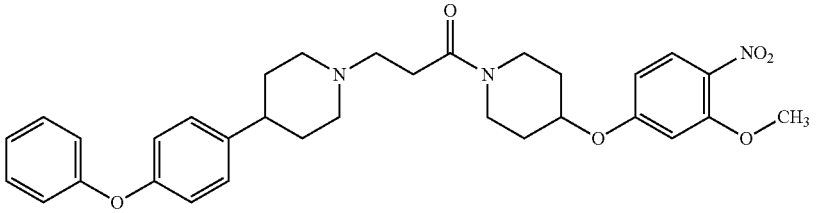 | I-B | 4.54 | 560 | 560 |
| Example 485 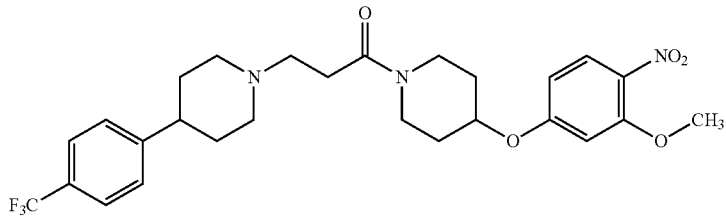 | I-B | 4.43 | 536 | 536 |
| Example 486 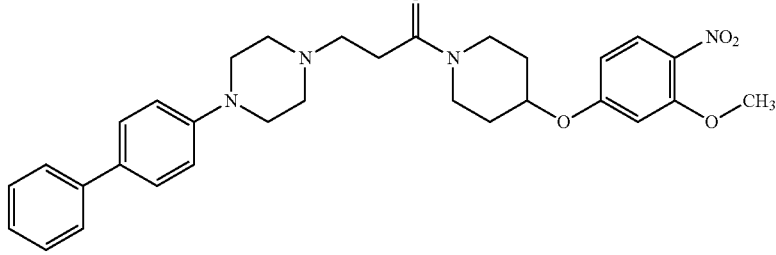 | I-B | 4.49 | 545 | 545 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 487 | I-B | 4.55 | 510 | 510 |
| Example 488 | I-B | 4.54 | 544 | 544 |
| Example 489 | I-B | 4.56 | 585 | 585 |
| Example 490 | I-B | 4.39 | 517 | 517 |
| Example 491 | I-B | 4.50 | 552 | 551 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 492 | I-B | 4.64 | 589 | 589 |
| Example 493 | I-B | 4.22 | 543 | 543 |
| Example 494 | I-B | 4.26 | 513 | 513 |
| Example 495 | I-B | 4.76 | 657 | 657 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 496 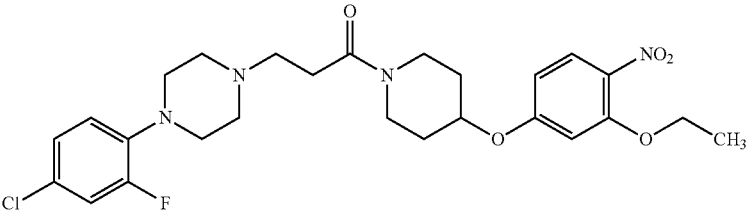 | I-B | 4.42 | 535 | 535 |
| Example 497 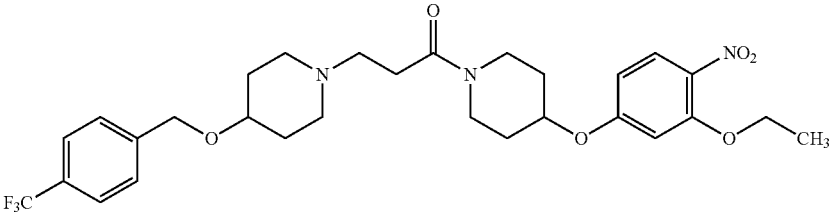 | I-B | 4.55 | 580 | 580 |
| Example 498 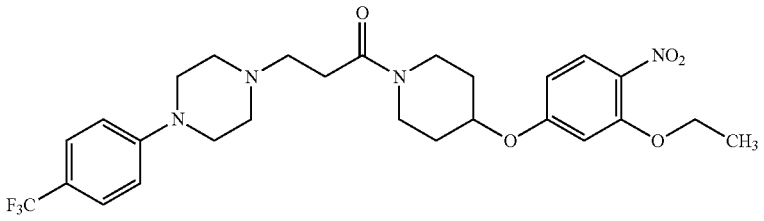 | I-B | 4.48 | 551 | 551 |
| Example 499 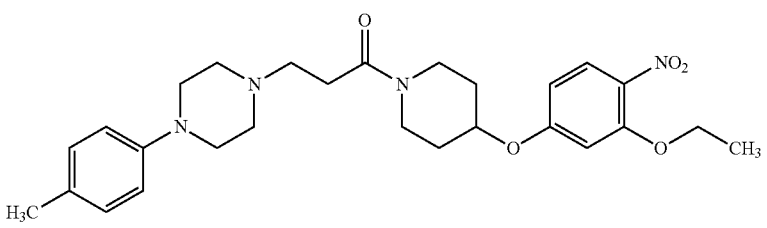 | I-B | 4.36 | 497 | 497 |
| Example 500 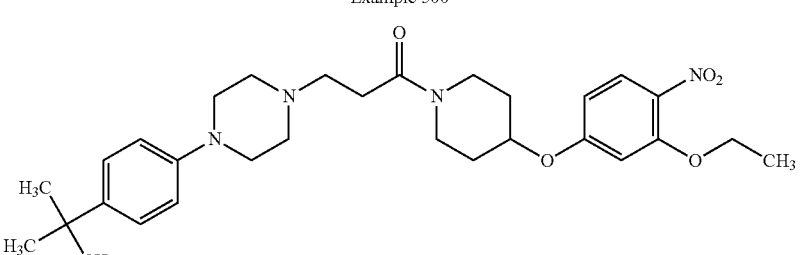 | I-B | 4.62 | 539 | 539 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 501 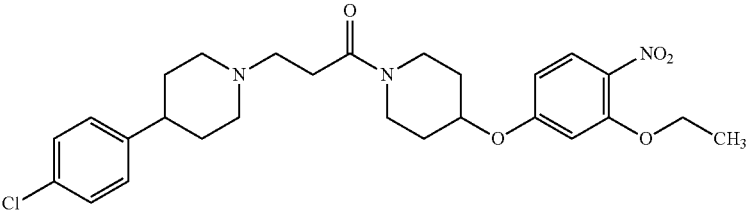 | I-B | 4.45 | 516 | 516 |
| Example 502 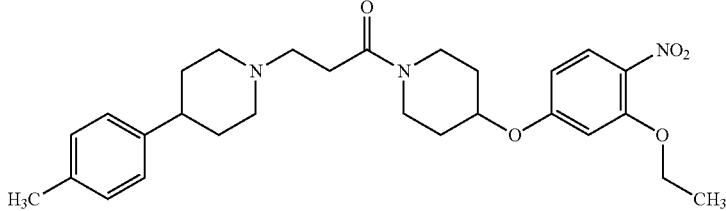 | I-B | 4.43 | 496 | 496 |
| Example 503 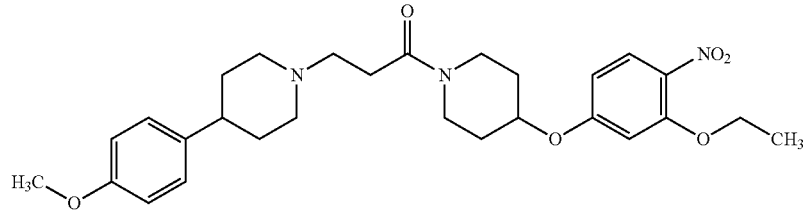 | I-B | 4.32 | 512 | 512 |
| Example 504 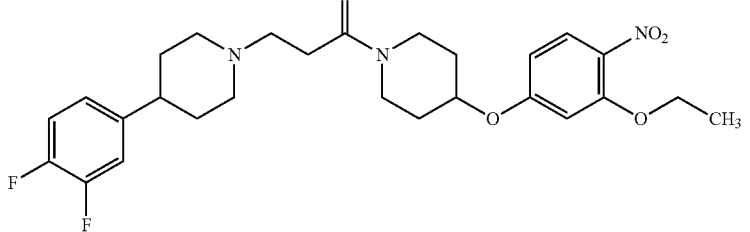 | I-B | 4.39 | 518 | 518 |
| Example 505 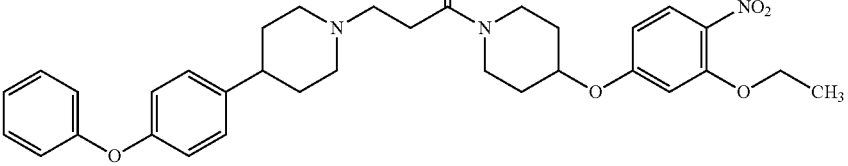 | I-B | 4.64 | 574 | 574 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 506 | I-B | 4.52 | 550 | 550 |
| Example 507 | I-B | 4.66 | 652 | 538 |
| Example 508 | I-B | 4.63 | 672 | 558 |
| Example 509 | I-B | 4.72 | 727 | 613 |
| Example 510 | I-B | 4.57 | 659 | 545 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 511 | I-B | 4.67 | 694 | 579 |
| Example 512 | I-B | 4.74 | 731 | 617 |
| Example 513 | I-B | 4.43 | 685 | 571 |
| Example 514 | I-B | 4.47 | 655 | 541 |
| Example 515 | I-B | 4.77 | 697 | 583 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 516 | I-B | 4.91 | 799 | 685 |
| Example 517 | I-B | 4.63 | 677 | 563 |
| Example 518 | I-B | 4.54 | 661 | 547 |
| Example 519 | I-B | 4.73 | 722 | 608 |
| Example 520 | I-B | 4.67 | 693 | 579 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 521 | I-B | 4.57 | 639 | 525 |
| Example 522 | I-B | 4.79 | 681 | 567 |
| Example 523 | I-B | 4.65 | 658 | 544 |
| Example 524 | I-B | 4.65 | 638 | 524 |
| Example 525 | I-B | 4.55 | 654 | 540 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 526 | I-B | 4.61 | 660 | 546 |
| Example 527 | I-B | 4.82 | 716 | 602 |
| Example 528 | I-B | 4.71 | 692 | 578 |
| Example 529 | I-B | 4.77 | 701 | 587 |
| Example 530 | I-B | 4.82 | 666 | 552 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 531 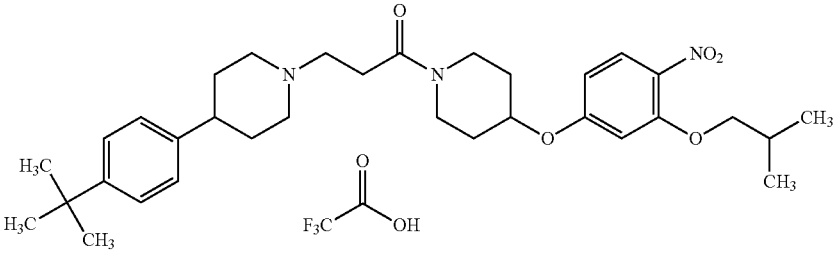 | I-B | 4.87 | 680 | 566 |
| Example 532 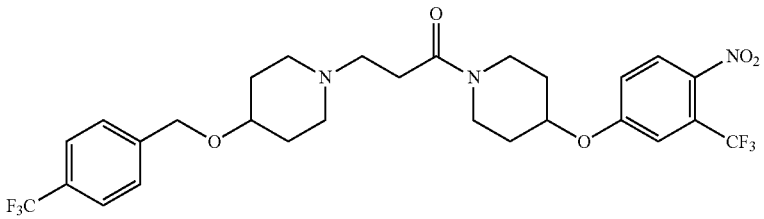 | I-B | 4.71 | 604 | 604 |
| Example 533 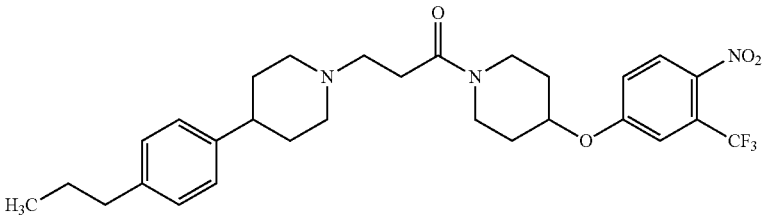 | I-B | 4.81 | 548 | 548 |
| Example 534 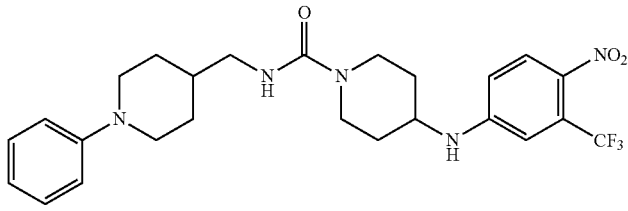 | II-E | 7.45 | 506 | 506 |
| Example 535 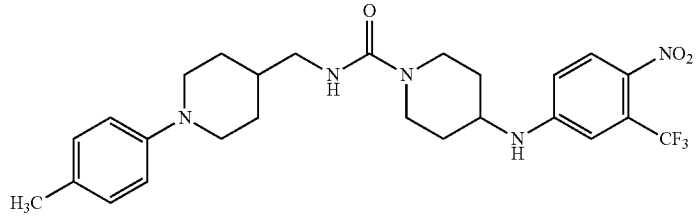 | II-E | 7.43 | 520 | 520 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 536 | II-E | 8.50 | 562 | 562 |
| Example 537 | II-E | 10.96 | 574 | 574 |
| Example 538 | II-E | 10.75 | 540 | 540 |
| Example 539 | II-E | 7.24 | 550 | 550 |
| Example 540 | II-E | 6.74 | 512 | 512 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 541 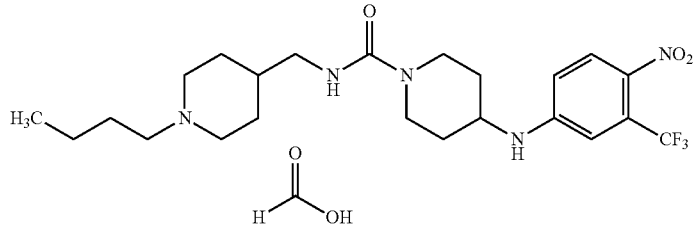 | II-E | 6.61 | 632 | 486 |
| Example 542 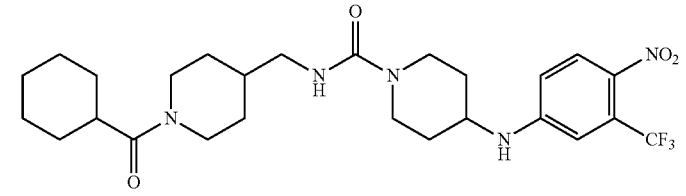 | II-E | 10.47 | 540 | 540 |
| Example 543 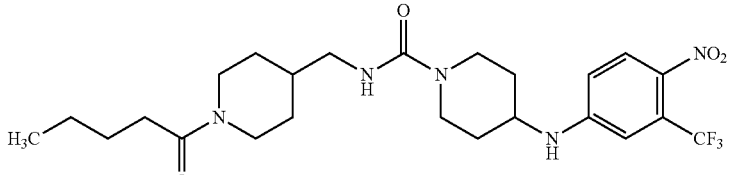 | II-E | 10.05 | 514 | 514 |
| Example 544 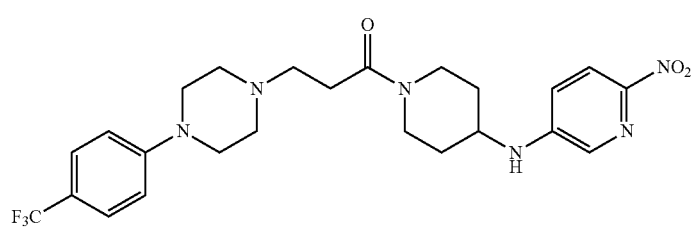 | II-A | 3.01 | 506 | 507 |
| Example 545 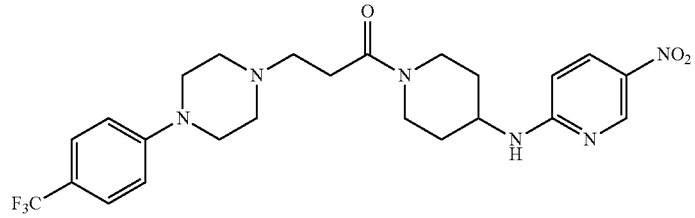 | II-A | 3.16 | 506 | 507 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 546 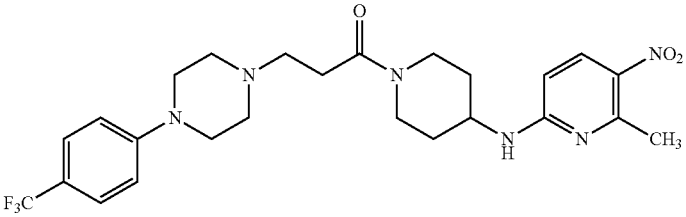 | II-A | 3.35 | 521 | 521 |
| Example 547 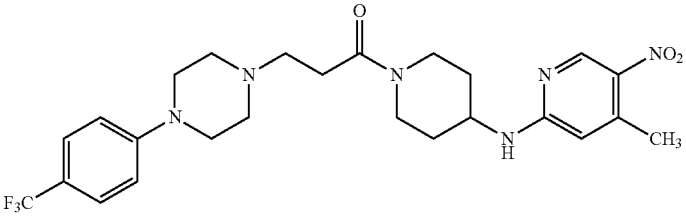 | II-A | 3.28 | 521 | 521 |
| Example 548 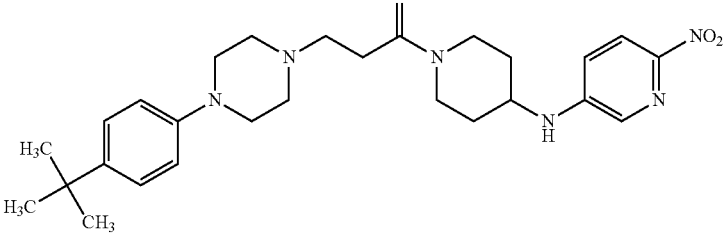 | II-A | 3.25 | 495 | 495 |
| Example 549 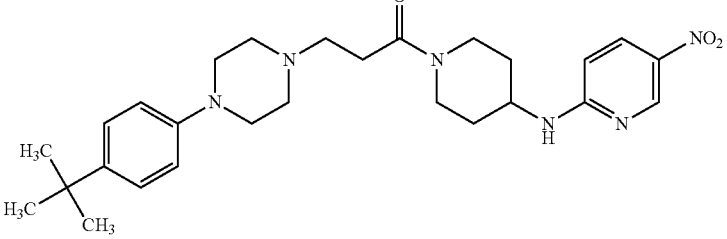 | II-A | 3.41 | 495 | 495 |
| Example 550 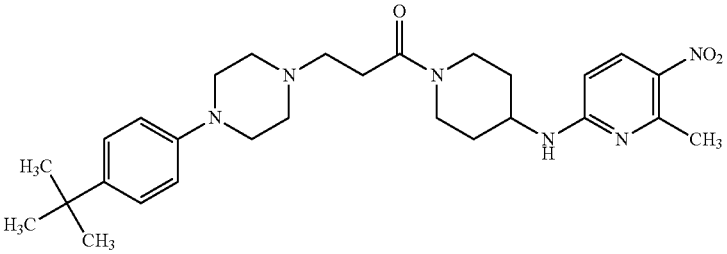 | II-A | 3.56 | 509 | 509 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 551 | II-A | 3.44 | 509 | 509 |
| Example 552 | II-A | 2.83 | 473 | 473 |
| Example 553 | II-A | 3.02 | 473 | 473 |
| Example 554 | II-A | 3.20 | 487 | 487 |
| Example 555 | II-A | 3.11 | 487 | 487 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 556 | II-A | 2.94 | 487 | 487 |
| Example 557 | II-A | 3.08 | 487 | 487 |
| Example 558 | II-A | 3.26 | 501 | 501 |
| Example 559 | I-A | 3.26 | 602 | 602 |
| Example 560 | I-A | 3.25 | 568 | 568 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 561 | I-A | 3.25 | 602 | 602 |
| Example 562 | II-E | 7.73 | 564 | 564 |
| Example 563 | II-E | 8.82 | 520 | 520 |
| Example 564 | II-E | 8.17 | 534 | 534 |
| Example 565 | II-E | 9.80 | 576 | 576 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 566 | II-E | 12.33 | 588 | 588 |
| Example 567 | II-E | 11.87 | 554 | 554 |
| Example 568 | II-E | 6.90 | 526 | 526 |
| Example 569 | II-E | 6.80 | 500 | 500 |
| Example 570 | II-E | 11.17 | 554 | 554 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 571 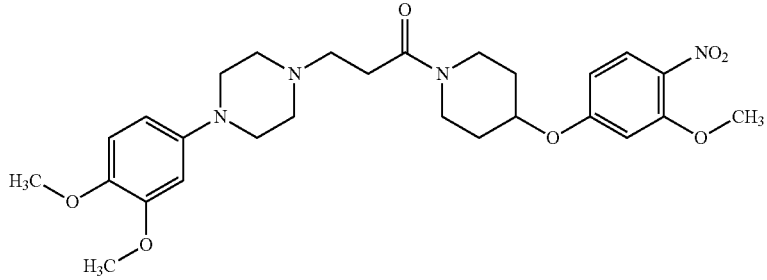 | I-B | 3.09 | 529 | 528 |
| Example 572 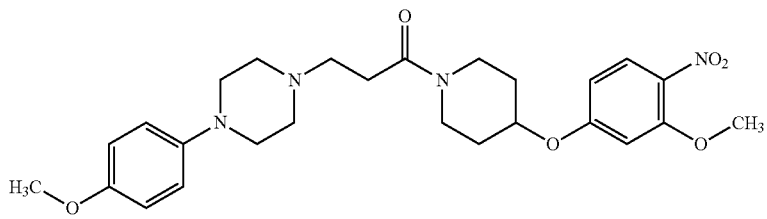 | I-B | 4.08 | 499 | 498 |
| Example 573 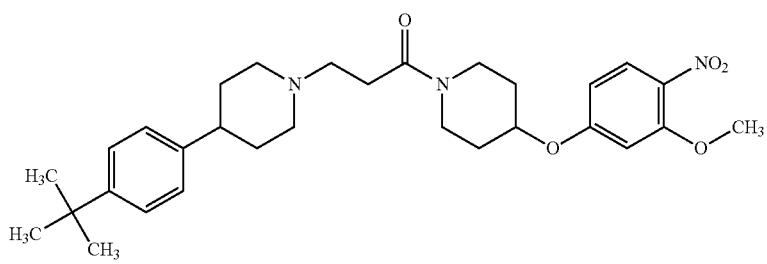 | I-B | 3.54 | 524 | 524 |
| Example 574 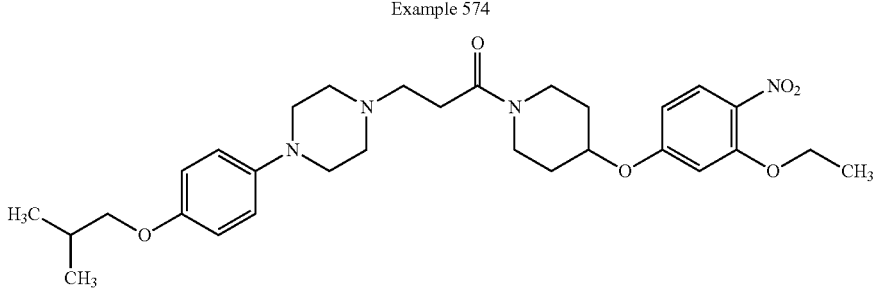 [SMILES: "Example 574" ; CCOc1cc(OC2CCN(C(=O)CCN3CCN(c4ccc(OCC(C)C)cc4)CC3)CC2)ccc1[N+](=O)[O-]] | I-B | 3.50 | 555 | 555 |
| Example 575 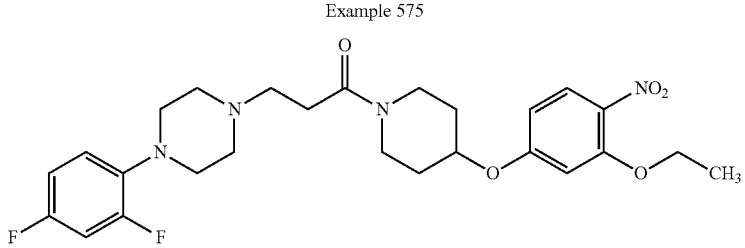 | II-D | 4.43 | 519 | 518 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 576 | II-D | 5.05 | 559 | 558 |
| Example 577 | II-D | 5.16 | 524 | 524 |
| Example 578 | II-A | 3.97 | 528 | 528 |
| Example 579 | I-A | 3.29 | 534 | 534 |
| Example 580 | II-B | 4.70 | 500 | 500 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 581 | I-A | 3.34 | 534 | 534 |
| Example 582 | I-A | 3.76 | 568 | 568 |
| Example 583 | I-A | 3.71 | 602 | 602 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 584 | II-B | 5.45 | 582 | 582 |
| Example 585 | II-B | 5.13 | 602 | 602 |
| Example 586 | II-B | 5.50 (5.65) | 590 | 590 |
| Example 587 | II-B | 5.48 | 616 | 616 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 588 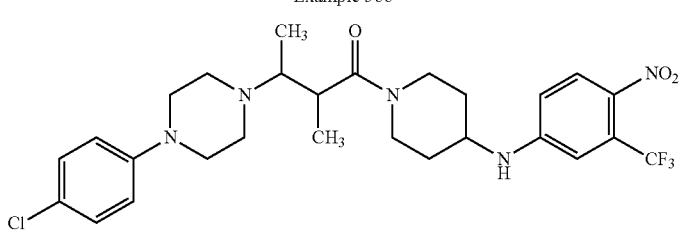 | II-B | 5.05 | 568 | 568 |
| Example 589 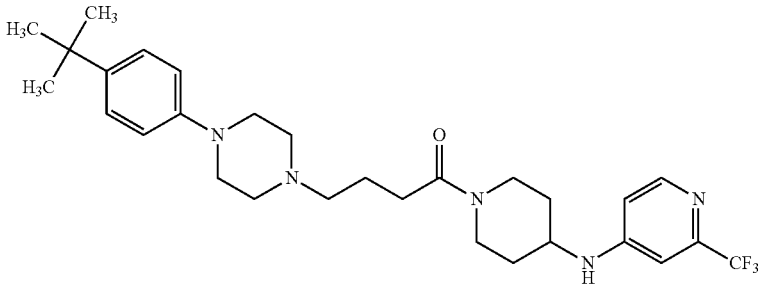 | I-D | 1.33 | 532 | 532 |
| Example 590 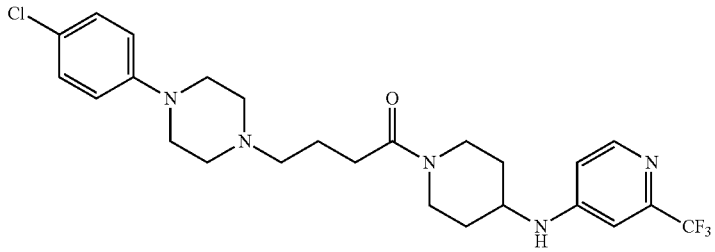 | I-D | 1.14 | 510 | 510 |
| Example 591 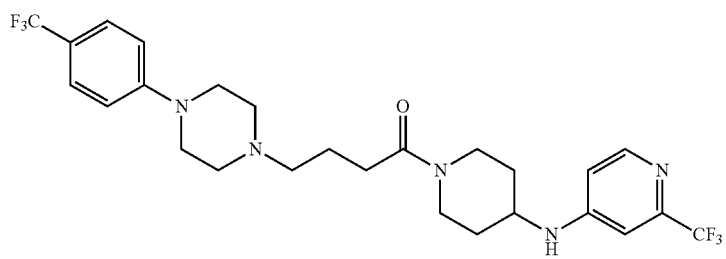 | I-D | 1.20 | 544 | 544 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 592 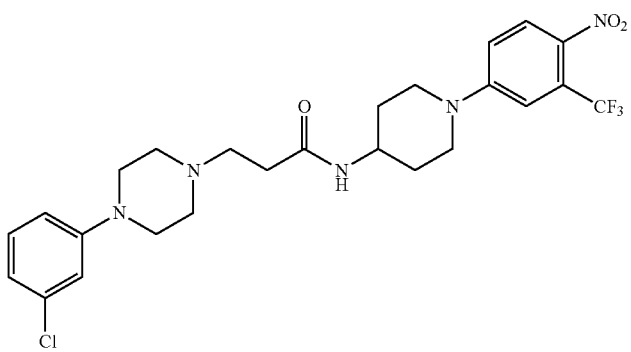 | I-B | 4.89 | 540 | 540 |
| Example 593 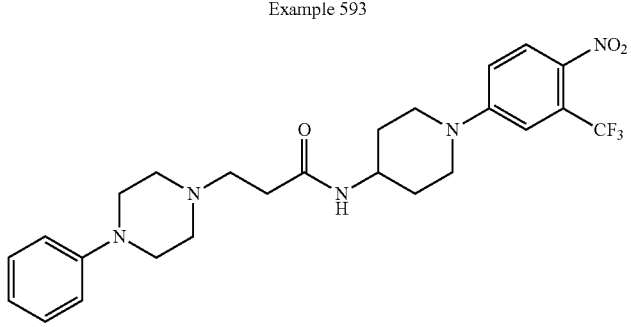 [SMILES: "Example 593" ; O=C(CCN1CCN(c2ccccc2)CC1)NC1CCN(c2ccc([N+](=O)[O-])c(C(F)(F)F)c2)CC1] | I-B | 4.82 | 506 | 506 |
| Example 594 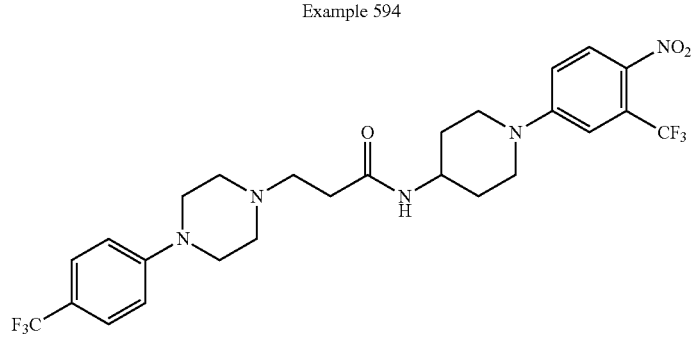 [SMILES: "Example 594" ; O=C(CCN1CCN(c2ccc(C(F)(F)F)cc2)CC1)NC1CCN(c2ccc([N+](=O)[O-])c(C(F)(F)F)c2)CC1] | I-B | 5.04 | 574 | 574 |
| Example 595 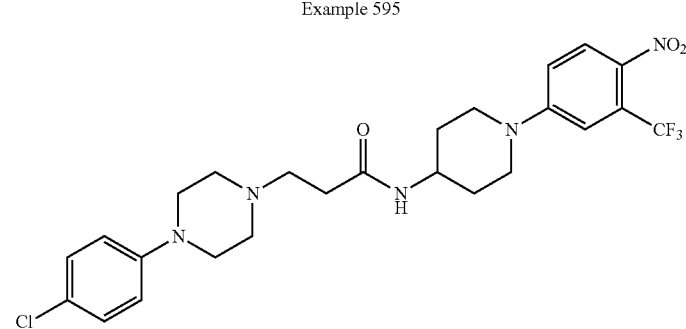 [SMILES: "Example 595" ; O=C(CCN1CCN(c2ccc(Cl)cc2)CC1)NC1CCN(c2ccc([N+](=O)[O-])c(C(F)(F)F)c2)CC1] | I-B | 4.96 | 540 | 540 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 596 | I-B | 5.20 | 562 | 562 |
| Example 597 | I-B | 4.81 | 536 | 536 |
| Example 598 | I-B | 4.92 | 520 | 520 |
| Example 599 | I-B | 4.94 | 540 | 540 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 600 | I-B | 4.94 | 554 | 554 |
| Example 601 | I-B | 4.88 | 520 | 520 |
| Example 602 | I-B | 5.00 | 554 | 554 |
| Example 603 | I-B | 5.26 | 576 | 576 |
| Example 604 | I-B | 4.81 | 550 | 550 |
| Example 605 | I-B | 4.97 | 534 | 534 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 606 | I-B | 4.99 | 554 | 554 |
| Example 607 | I-B | 4.87 | 520 | 520 |
| Example 608 | I-B | 4.72 | 486 | 486 |
| Example 609 | I-B | 4.91 | 554 | 554 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 610 | I-B | 4.85 | 520 | 520 |
| Example 611 | I-B | 5.10 | 542 | 542 |
| Example 612 | I-B | 4.69 | 516 | 516 |
| Example 613 | I-B | 4.80 | 500 | 500 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 614 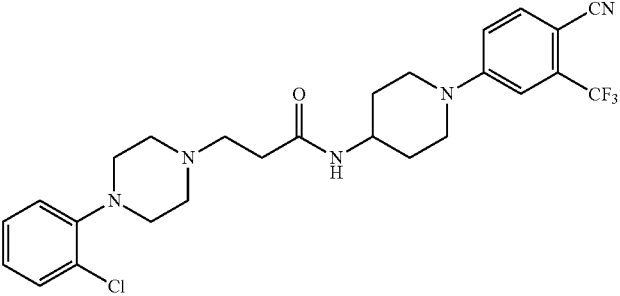 | I-B | 4.83 | 520 | 520 |
| Example 615 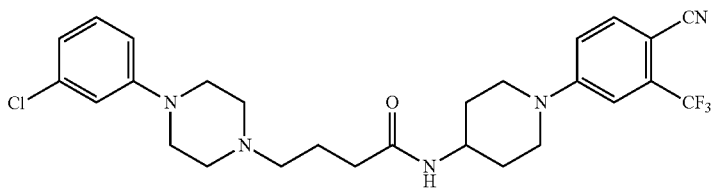 | I-B | 4.92 | 534 | 534 |
| Example 616 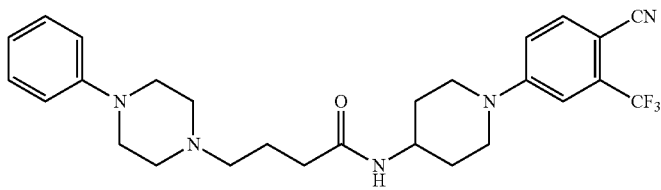 | I-B | 4.76 | 500 | 500 |
| Example 617 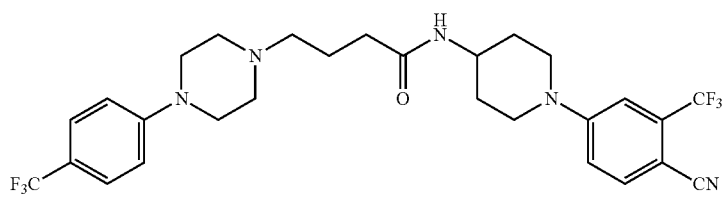 | I-B | 4.98 | 568 | 568 |
| Example 618 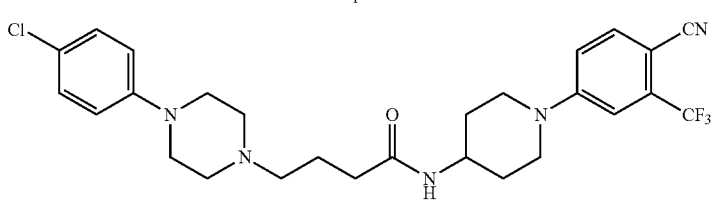 | I-B | 4.90 | 534 | 534 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 619 | I-B | 5.16 | 556 | 556 |
| Example 620 | I-B | 4.73 | 530 | 530 |
| Example 621 | I-B | 4.86 | 514 | 514 |
| Example 622 | I-B | 4.87 | 534 | 534 |
| Example 623 | I-B | 5.13 | 527 | 527 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 624 | I-B | 5.11 | 493 | 493 |
| Example 625 | I-B | 5.20 | 561 | 561 |
| Example 626 | I-B | 5.14 | 527 | 527 |
| Example 627 | I-B | 5.38 | 549 | 549 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 628 | I-B | 5.00 | 523 | 523 |
| Example 629 | I-B | 5.11 | 507 | 507 |
| Example 630 | I-B | 5.13 | 527 | 527 |
| Example 631 | I-B | 5.22 | 541 | 541 |
| Example 632 | I-B | 5.10 | 507 | 507 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 633 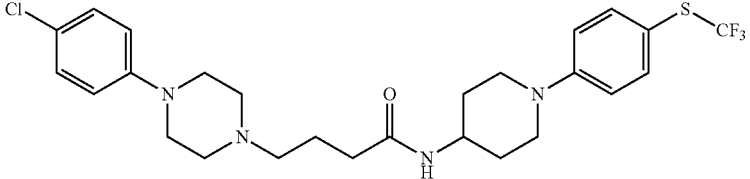 | I-B | 5.21 | 541 | 541 |
| Example 634 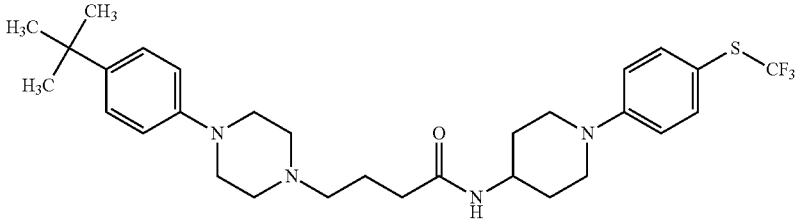 | I-B | 5.47 | 563 | 563 |
| Example 635 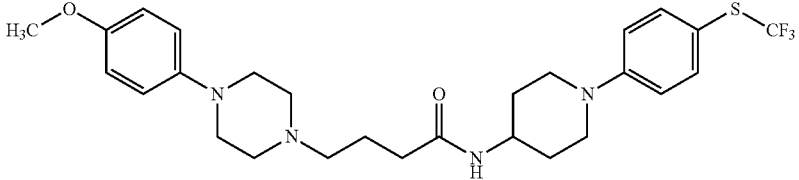 | I-B | 5.05 | 537 | 537 |
| Example 636 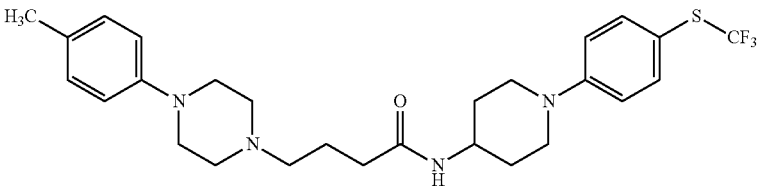 | I-B | 5.18 | 521 | 521 |
| Example 637 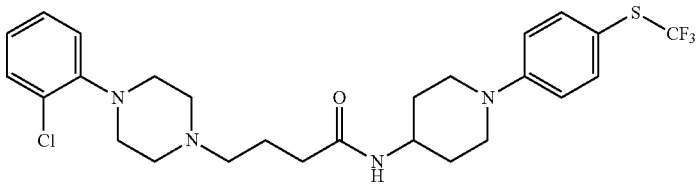 | I-B | 5.20 | 541 | 541 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 638 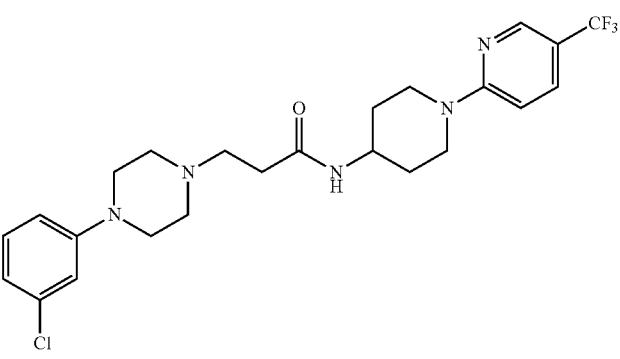 | I-B | 4.76 | 496 | 496 |
| Example 639 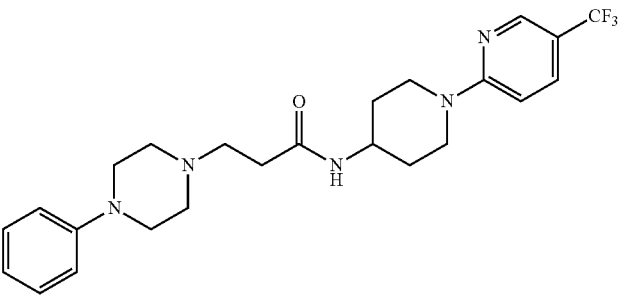 | I-B | 4.59 | 462 | 462 |
| Example 640 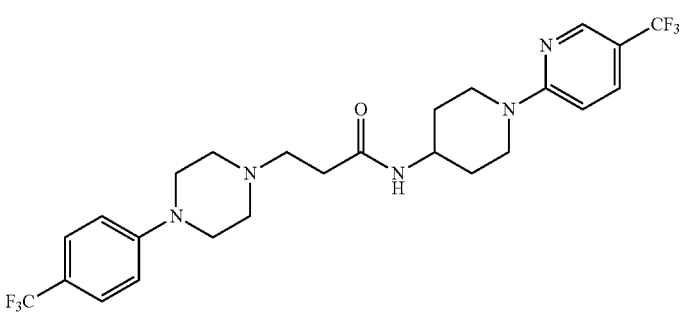 | I-B | 4.85 | 530 | 530 |
| Example 641 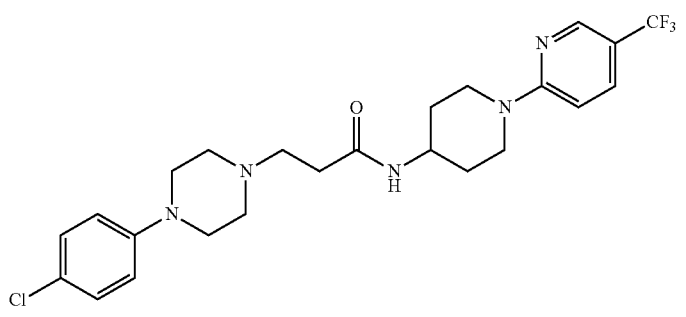 | I-B | 4.76 | 496 | 496 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 642 | I-B | 5.02 | 518 | 518 |
| Example 643 | I-B | 4.58 | 492 | 492 |
| Example 644 | I-B | 4.71 | 476 | 476 |
| Example 645 | I-B | 4.73 | 496 | 496 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 646 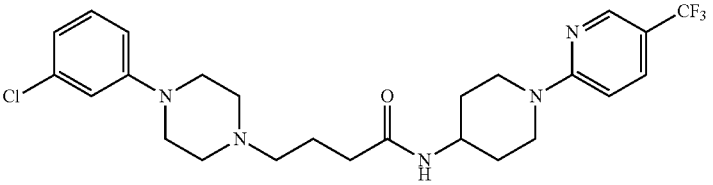 | I-B | 4.84 | 510 | 510 |
| Example 647 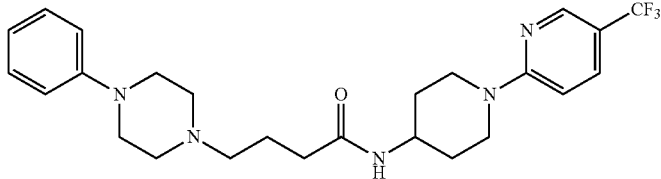 | I-B | 4.66 | 476 | 476 |
| Example 648 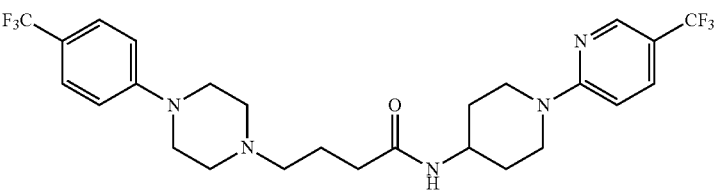 | I-B | 4.91 | 544 | 544 |
| Example 649 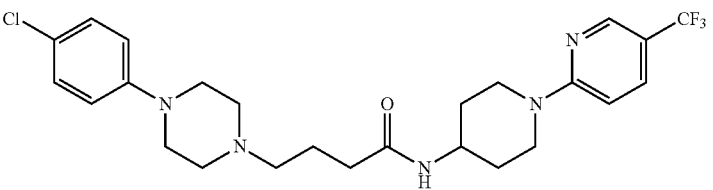 | I-B | 4.82 | 510 | 510 |
| Example 650 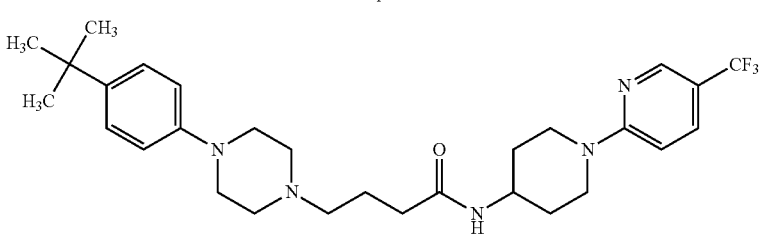 | I-B | 5.12 | 532 | 532 |
| Example 651 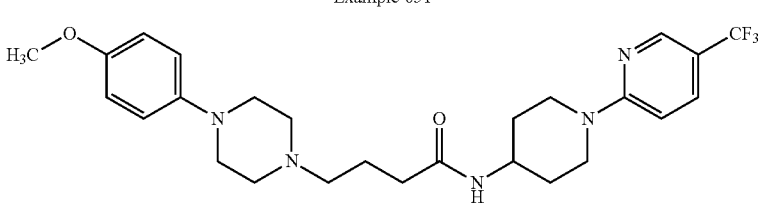 | I-B | 4.63 | 506 | 506 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 652 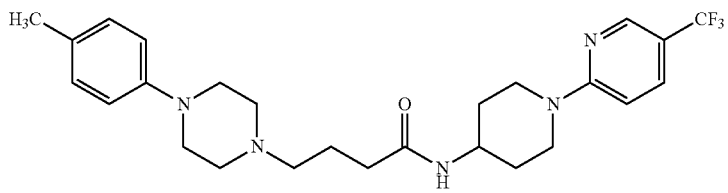 | I-B | 4.76 | 490 | 490 |
| Example 653 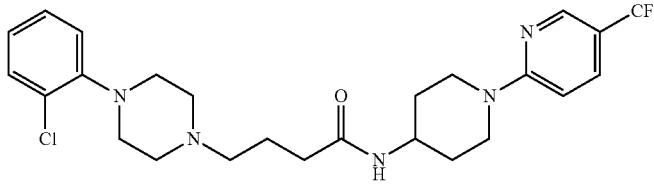 | I-B | 4.78 | 510 | 510 |
| Example 654 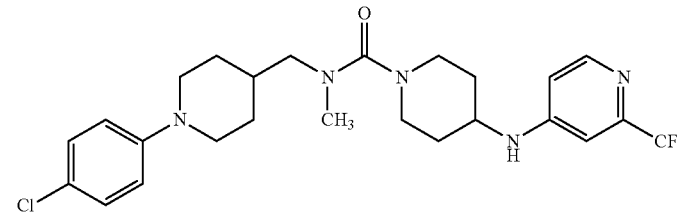 | I-B | 4.32 | 510 | 510 |
| Example 655 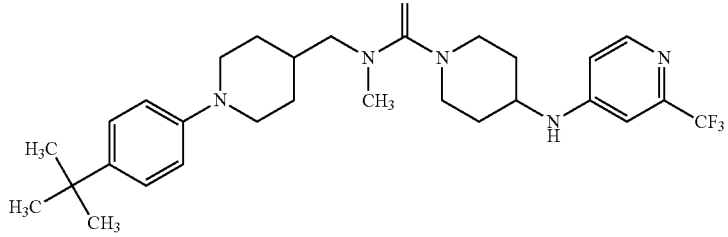 | I-B | 4.48 | 532 | 532 |
| Example 656 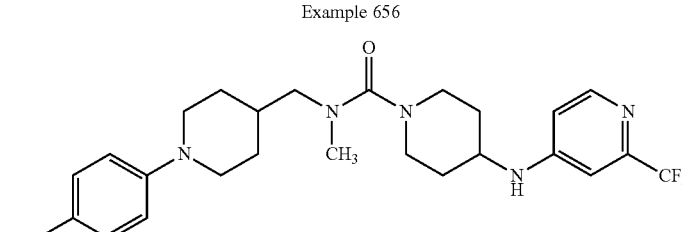 | I-B | 5.45 | 544 | 544 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 657 | I-B | 5.01 | 588 | 588 |
| Example 658 | I-D | 1.60 | 541 | 541 |
| Example 659 | I-D | 1.64 | 574 | 575 |
| Example 660 | I-B | 4.63 | 584 | 584 |
| Example 661 | I-B | 4.80 | 558 | 558 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 662 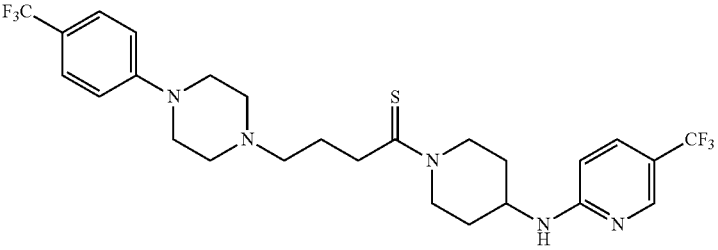 | I-B | 4.52 | 560 | 560 |
| Example 663 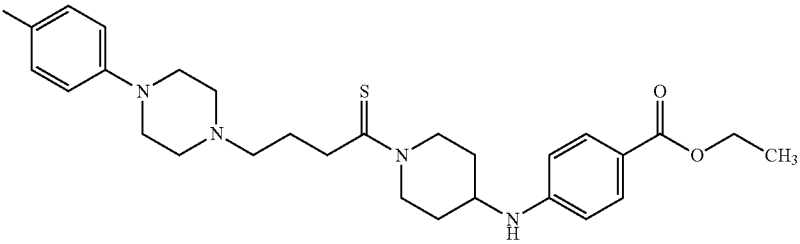 | I-D | 1.64 | 575 | 575 |
| Example 664 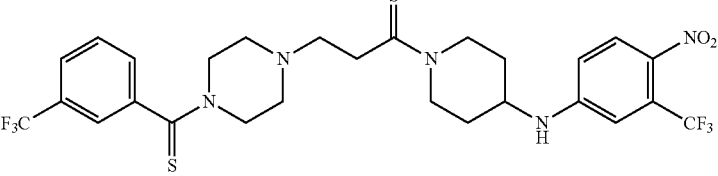 | I-B | | | |
| Example 665 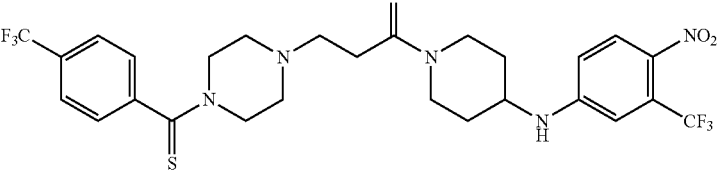 | I-B | 4.79 | 634 | 634 |
| Example 666 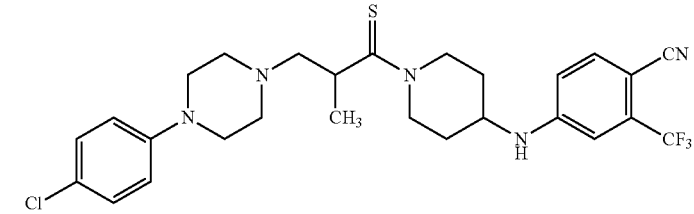 | I-B | 4.67 | 550 | 550 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 667 | I-B | 4.98 | 696 | 696 |
| Example 668 | I-B | 5.49 | 579 | 579 |
| Example 669 | I-B | 4.89 | 629 | 629 |
| Example 670 | I-B | 4.81 | 516 | 516 |
| Example 671 | I-B | 4.77 | 615 | 615 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 672 | I-B | 4.87 | 639 | 649 |
| Example 673 | I-B | 4.58 | 590 | 590 |
| Example 674 | I-B | 5.83 | 570 | 570 |
| Example 675 | I-B | 4.66 | 580 | 580 |
| Example 676 | I-B | 4.81 | 628 | 628 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 677 | I-B | 4.56 | 550 | 550 |
| Example 678 | I-B | 4.53 | 522 | 522 |
| Example 679 | I-B | 4.73 | 605 | 605 |
| Example 680 | I-B | 4.51 | 551 | 551 |
| Example 681 | I-B | 4.63 | 550 | 550 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 682 | I-B | 4.69 | 604 | 604 |
| Example 683 | I-B | 4.65 | 604 | 604 |
| Example 684 | I-B | 4.61 | 536 | 536 |
| Example 685 | I-B | 5.46 | 544 | 544 |
| Example 686 | I-B | 4.89 | 563 | 563 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 687 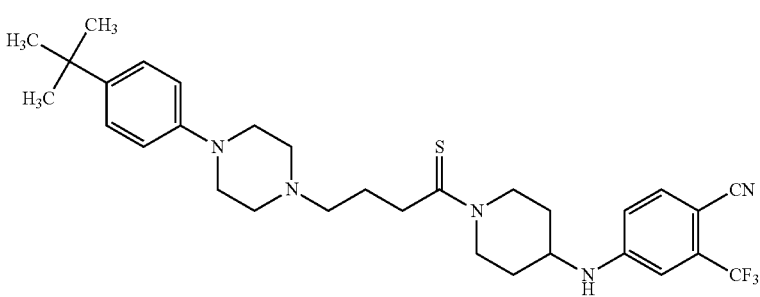 | I-B | 4.75 | 572 | 572 |
| Example 688 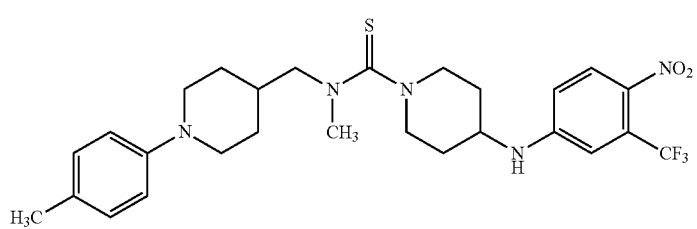 | I-B | 4.76 | 550 | 550 |
| Example 689 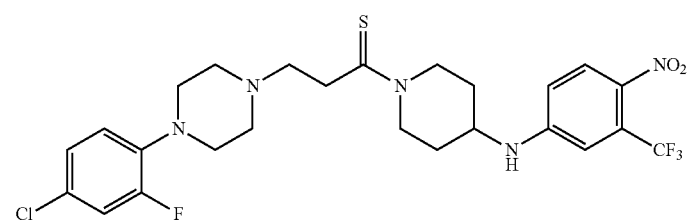 | I-B | 4.70 | 574 | 574 |
| Example 690 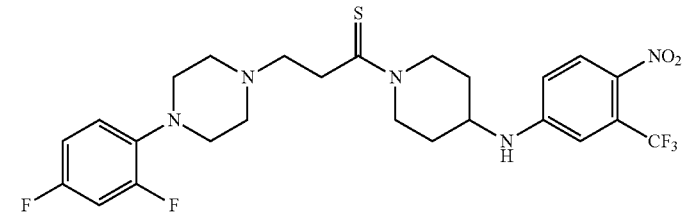 | I-B | 4.60 | 558 | 558 |
| Example 691 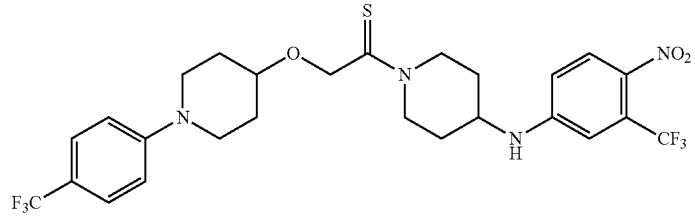 | I-B | 5.87 | 591 | 591 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 692 | I-B | 4.75 | 567 | 567 |
| Example 693 | I-B | 4.86 | 620 | 620 |
| Example 694 | I-B | 4.91 | 614 | 614 |
| Example 695 | I-B | 4.78 | 590 | 590 |
| Example 696 | I-B | 4.94 | 564 | 564 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 697 | I-B | 4.56 | 666 | 666 |
| Example 698 | I-B | 4.65 | 512 | 512 |
| Example 699 | I-B | 4.70 | 575 | 575 |
| Example 700 | I-B | 4.57 | 536 | 536 |
| Example 701 | I-D | 1.43 | 541 | 541 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 702 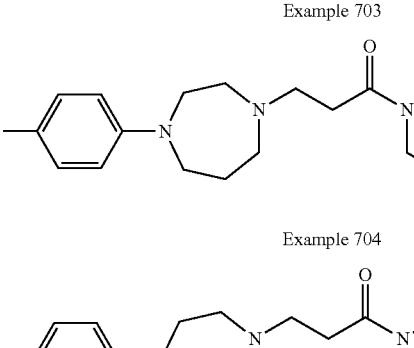 | I-D | 1.54 | 566 | 566 |
| Example 703 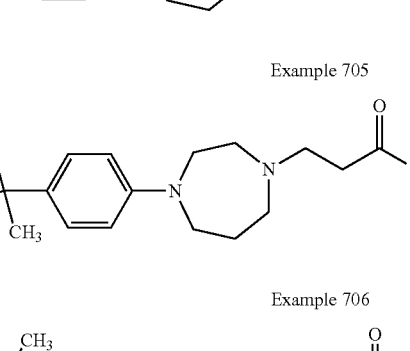 | I-D | 1.56 | 588 | 588 |
| Example 704 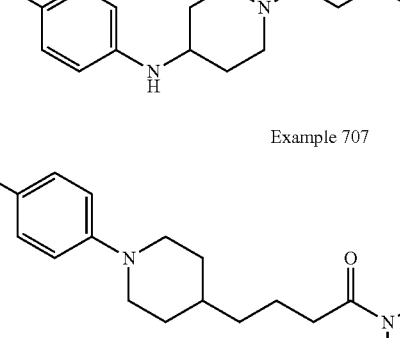 | I-D | 1.52 | 554 | 554 |
| Example 705  | I-D | 1.64 | 576 | 576 |
| Example 706 | I-D | 1.58 | 576 | 576 |
| Example 707  | I-D | 1.93 | 553 | 553 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 708 | I-D | 1.58 | 602 | 602 |
| Example 709 | I-D | 1.54 | 568 | 568 |
| Example 710 | I-D | 1.56 | 602 | 602 |
| Example 711 | I-D | 1.52 | 568 | 568 |
| Example 712 | I-D | 1.60 | 590 | 590 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 713 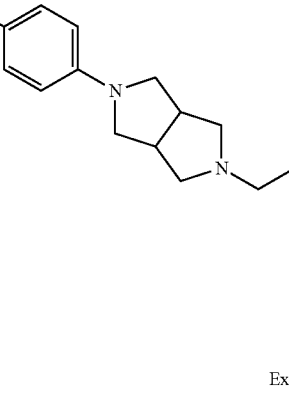 | I-D | 1.60 | 614 | 614 |
| Example 714 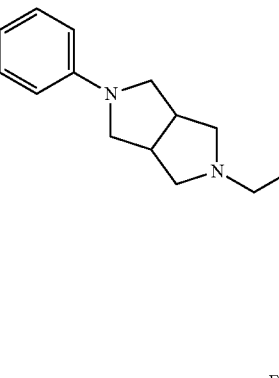 | I-D | 1.57 | 580 | 580 |
| Example 715 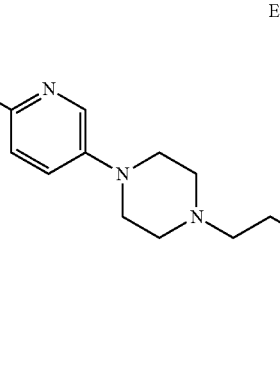 | I-D | 1.36 | 551 | 551 |
| Example 716  | I-D | 1.46 | 555 | 555 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 717 | I-D | 1.46 | 561 | 561 |
| Example 718 | I-D | 1.38 | 568 | 568 |
| Example 719 | I-D | 1.40 | 527 | 527 |
| Example 720 | I-D | 1.40 | 560 | 561 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 721 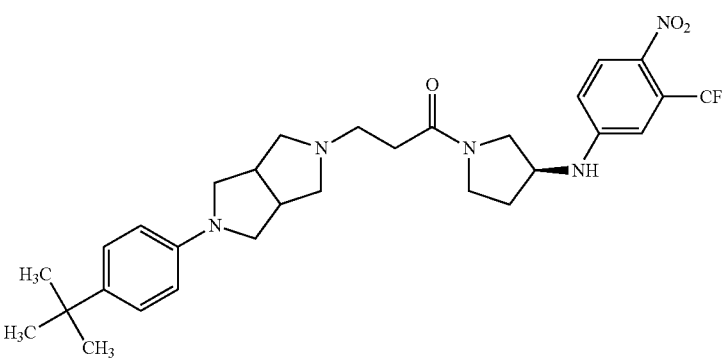 | I-D | 1.63 | 574 | 574 |
| Example 722 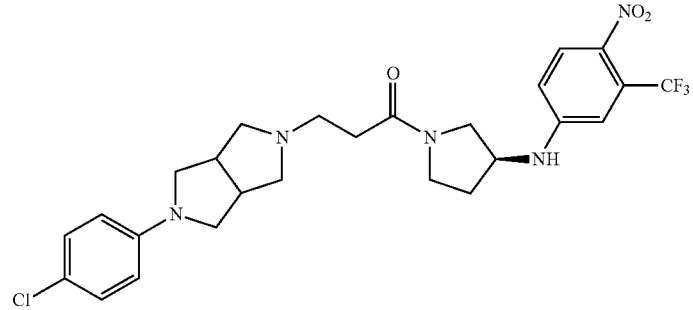 | I-D | 1.52 | 552 | 552 |
| Example 723 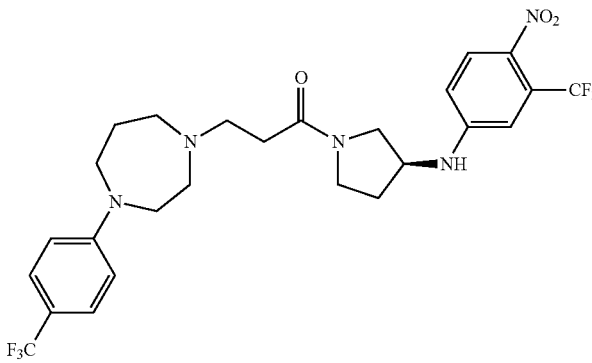 | I-D | 1.54 | 574 | 574 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 724 | I-D | 1.49 | 540 | 540 |
| Example 725 | I-D | 1.56 | 562 | 562 |
| Example 726 | I-D | 1.52 | 574 | 574 |
| Example 727 | I-D | 1.58 | 562 | 562 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 728 | I-D | 1.51 | 574 | 574 |
| Example 729 | I-D | 1.47 | 540 | 540 |
| Example 730 | I-D | 1.59 | 562 | 562 |
| Example 731 | I-D | 2.14 | 573 | 573 |
| Example 732 | I-D | 1.86 | 539 | 539 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 733 | I-D | 2.08 | 559 | 559 |
| Example 734 | I-D | 1.81 | 525 | 525 |
| Example 735 | I-D | 1.54 | 588 | 588 |
| Example 736 | I-D | 1.51 | 554 | 554 |
| Example 737 | I-D | 1.62 | 576 | 576 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 738 | I-D | 1.53 | 588 | 588 |
| Example 739 | I-D | 1.49 | 554 | 554 |
| Example 740 | I-D | 1.57 | 576 | 576 |
| Example 741 | I-D | 1.57 | 600 | 600 |
| Example 742 | I-D | 1.53 | 566 | 566 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 743 | I-D | 1.64 | 588 | 588 |
| Example 744 | I-D | 1.31 | 537 | 537 |
| Example 745 | I-D | 1.38 | 575 | 575 |
| Example 746 | I-D | 1.46 | 575 | 575 |
| Example 747 | I-D | 1.35 | 582 | 582 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 748 | I-D | 1.41 | 541 | 541 |
| Example 749 | I-D | 1.66 | 561 | 561 |
| Example 750 | I-D | 1.49 | 540 | 540 |
| Example 751 | I-D | 1.32 | 523 | 523 |
| Example 752 | I-D | 1.89 | 533 | 533 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 753 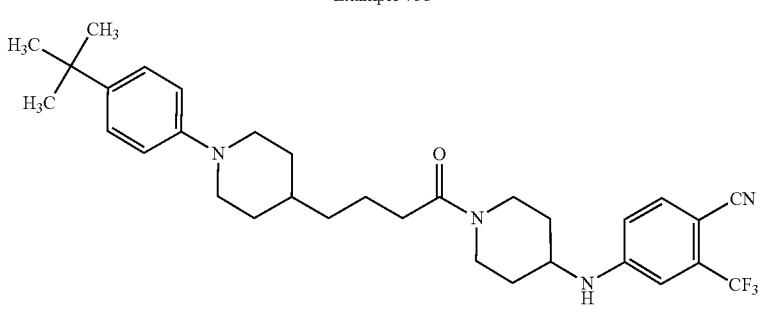 | I-D | 1.67 | 555 | 555 |
| Example 754 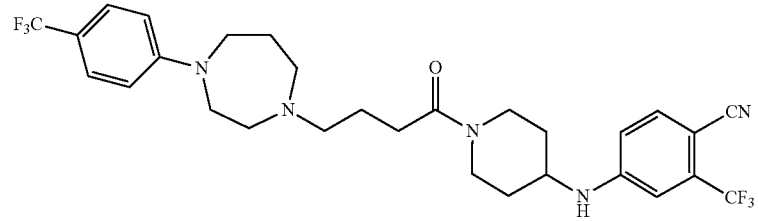 | I-D | 1.54 | 582 | 582 |
| Example 755 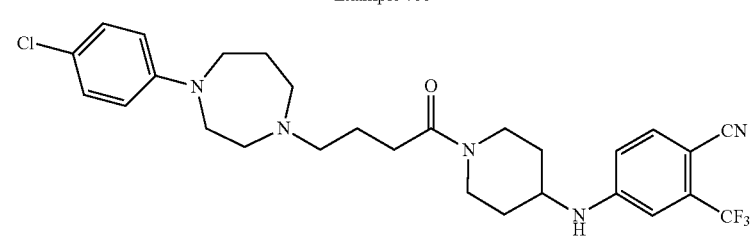 | I-D | 1.54 | 548 | 548 |
| Example 756 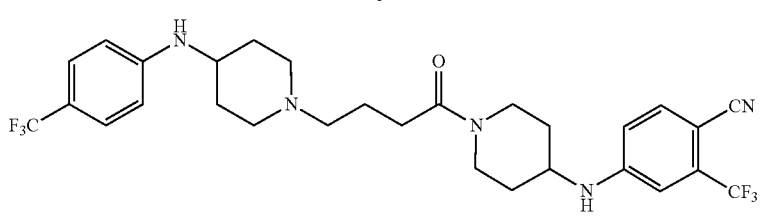 | I-D | 1.55 | 582 | 582 |
| Example 757 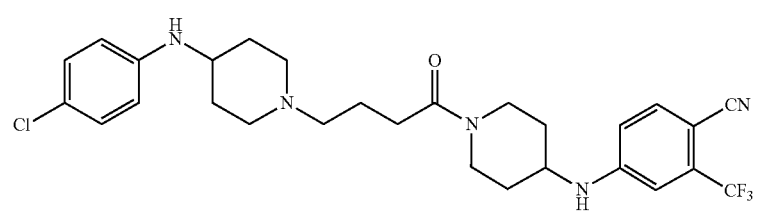 | I-D | 1.50 | 548 | 548 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 758 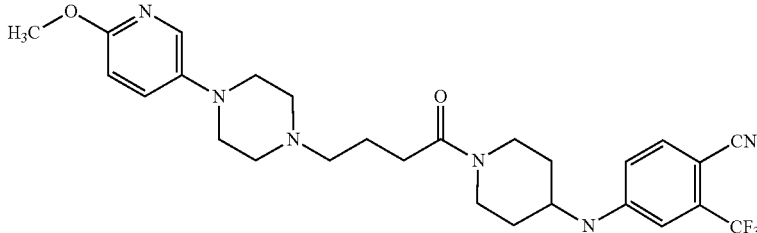 | I-D | 1.34 | 531 | 531 |
| Example 760 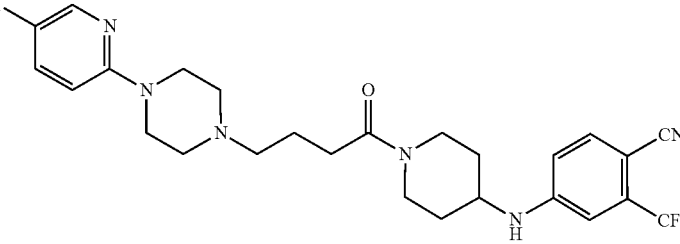 | I-D | 1.43 | 535 | 535 |
| Example 761 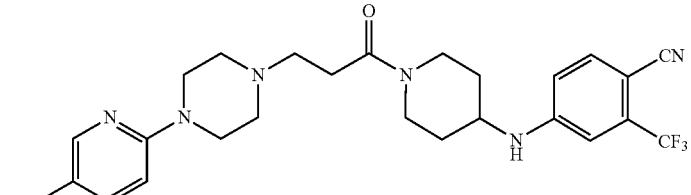 | I-D | 1.44 | 555 | 555 |
| Example 762 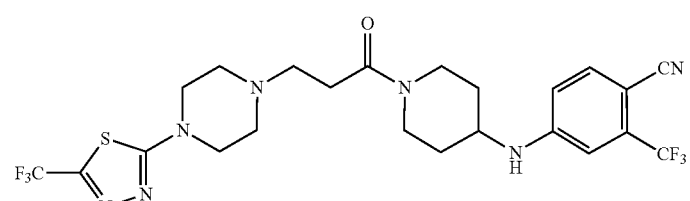 | I-D | 1.37 | 562 | 562 |
| Example 763 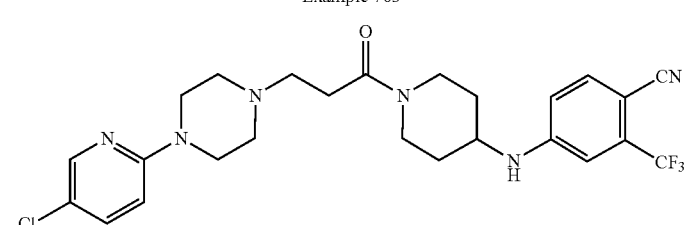 | I-D | 1.40 | 521 | 521 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 764 | I-D | 1.31 | 517 | 517 |
| Example 765 | I-D | 1.39 | 555 | 555 |
| Example 766 | I-D | 1.64 | 568 | 568 |
| Example 767 | I-D | 1.51 | 546 | 546 |
| Example 768 | I-D | 1.55 | 568 | 568 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 769 | I-D | 1.49 | 534 | 534 |
| Example 770 | I-D | 1.61 | 556 | 556 |
| Example 771 | I-D | 1.57 | 556 | 556 |
| Example 772 | I-D | 2.14 | 573 | 573 |
| Example 773 | I-D | 1.89 | 539 | 539 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 774 | I-D | 2.07 | 559 | 559 |
| Example 775 | I-D | 1.56 | 588 | 588 |
| Example 776 | I-D | 1.53 | 554 | 554 |
| Example 777 | I-D | 1.64 | 576 | 576 |
| Example 778 | I-D | 1.55 | 588 | 588 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 779 | I-D | 1.49 | 554 | 554 |
| Example 780 | I-D | 1.34 | 537 | 537 |
| Example 781 | I-D | 1.43 | 575 | 575 |
| Example 782 | I-D | 1.49 | 575 | 575 |
| Example 783 | I-D | 1.41 | 582 | 582 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 784 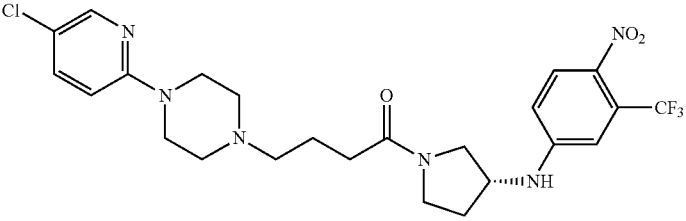 | I-D | 1.44 | 541 | 541 |
| Example 785 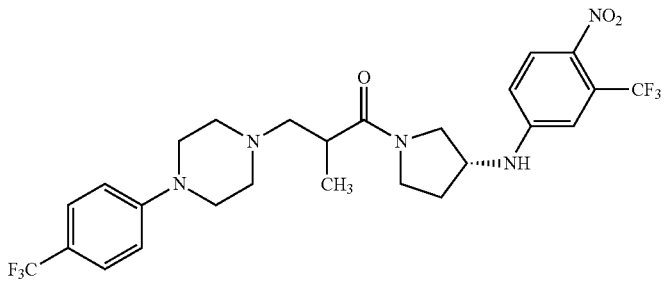 | I-D | 1.54 | 574 | 574 |
| Example 786 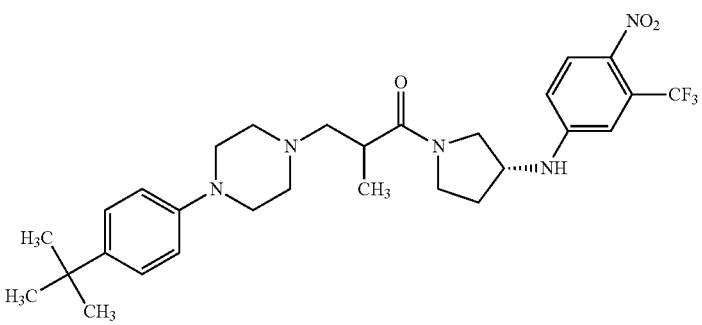 | I-D | 1.61 | 562 | 562 |
| Example 787 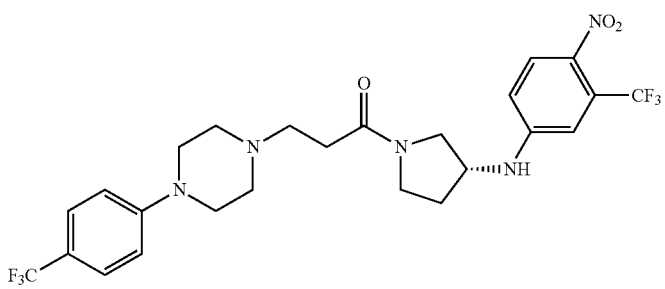 | I-D | 1.51 | 560 | 560 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 788 | I-D | 1.49 | 526 | 526 |
| Example 789 | I-D | 1.56 | 548 | 548 |
| Example 790 | I-D | 1.53 | 574 | 574 |
| Example 791 | I-D | 1.49 | 540 | 540 |
| Example 792 | I-D | 1.48 | 560 | 561 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 793 | I-D | 1.42 | 568 | 568 |
| Example 794 | I-D | 1.41 | 527 | 527 |
| Example 795 | I-D | 1.40 | 560 | 561 |
| Example 796 | I-D | 1.65 | 574 | 574 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 797 | I-D | 1.53 | 552 | 552 |
| Example 798 | I-D | 1.50 | 540 | 540 |
| Example 799 | I-D | 1.66 | 588 | 588 |
| Example 800 | I-D | 1.55 | 562 | 562 |
| Example 801 | I-D | 1.50 | 528 | 528 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 802 | I-D | 1.43 | 524 | 524 |
| Example 803 | I-D | 1.50 | 562 | 562 |
| Example 804 | I-D | 1.60 | 553 | 553 |
| Example 805 | I-D | 1.64 | 575 | 575 |
| Example 806 | I-D | 1.59 | 541 | 541 |
| Example 807 | I-D | 1.73 | 563 | 563 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 808 | I-D | 1.62 | 575 | 575 |
| Example 809 | I-D | 1.66 | 563 | 563 |
| Example 810 | I-D | 1.62 | 575 | 575 |
| Example 811 | I-D | 1.58 | 541 | 541 |
| Example 812 | I-D | 1.67 | 563 | 563 |
| Example 813 | I-D | 1.59 | 561 | 561 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 814 | I-D | 1.55 | 527 | 527 |
| Example 815 | I-D | 1.66 | 549 | 549 |
| Example 816 | I-D | 1.60 | 575 | 575 |
| Example 817 | I-D | 1.57 | 541 | 541 |
| Example 818 | I-D | 1.68 | 563 | 563 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 819 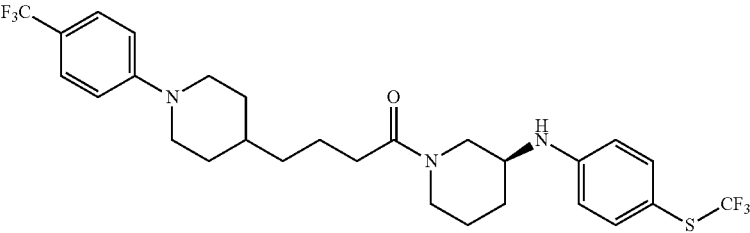 | I-D | 2.36 | 574 | 574 |
| Example 820 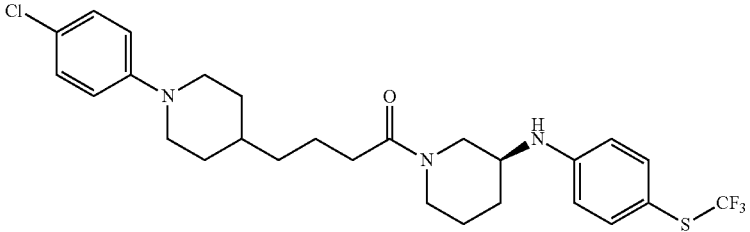 | I-D | 2.19 | 540 | 540 |
| Example 821 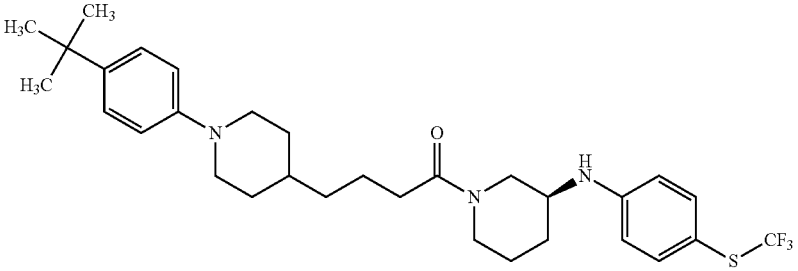 | I-D | 1.85 | 562 | 562 |
| Example 822 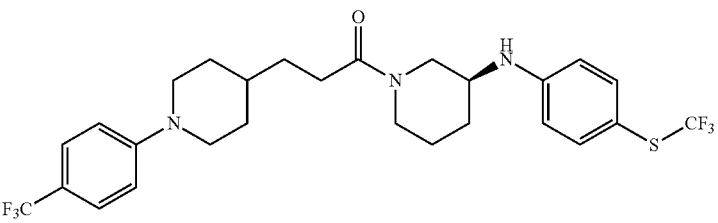 | I-D | 2.30 | 560 | 560 |
| Example 823 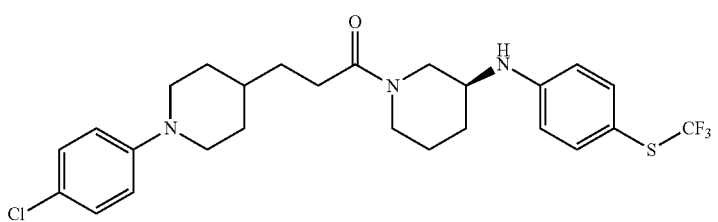 | I-D | 1.82 | 526 | 526 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 824 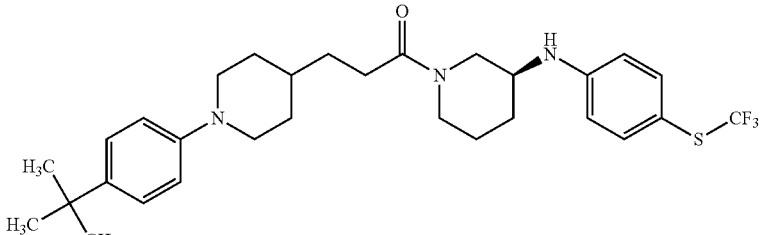 | I-D | 1.82 | 548 | 548 |
| Example 825 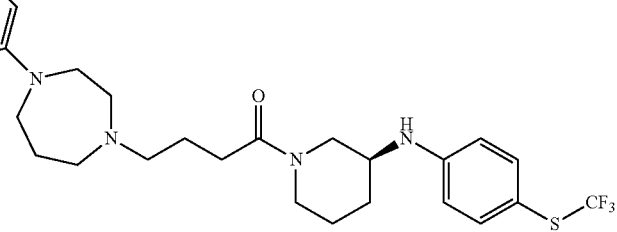 | I-D | 1.64 | 589 | 589 |
| Example 826 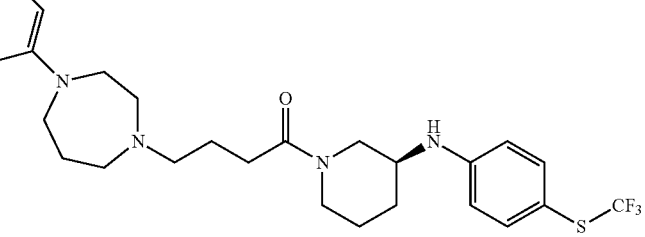 | I-D | 1.63 | 555 | 555 |
| Example 827 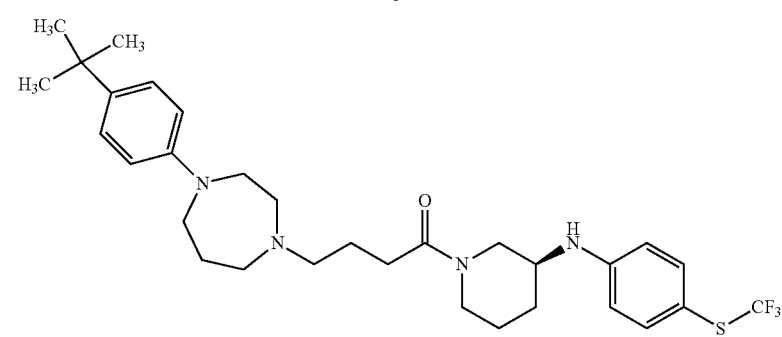 | I-D | 1.76 | 577 | 577 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 828 | I-D | 1.65 | 589 | 589 |
| Example 829 | I-D | 1.60 | 555 | 555 |
| Example 830 | I-D | 1.70 | 577 | 577 |
| Example 831 | I-D | 1.65 | 587 | 587 |
| Example 832 | I-D | 1.67 | 567 | 567 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 833 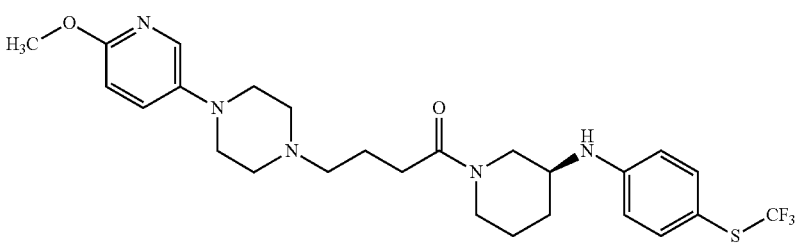 | I-D | 1.45 | 538 | 538 |
| Example 834 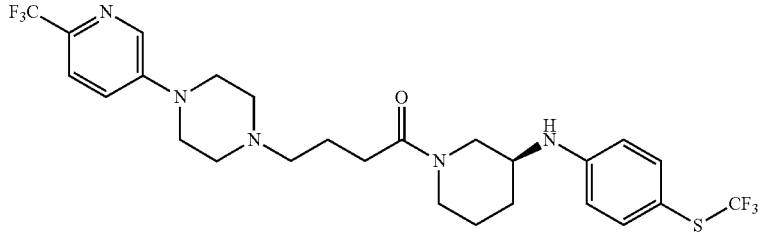 | I-D | 1.51 | 576 | 576 |
| Example 835 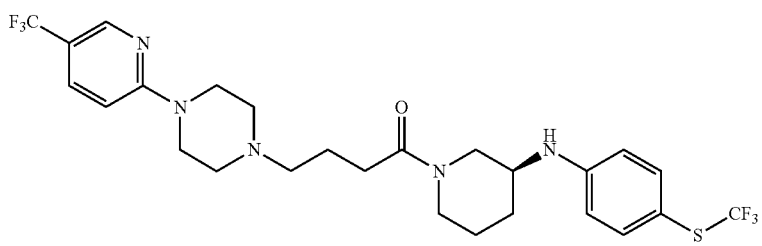 | I-D | 1.57 | 576 | 576 |
| Example 836 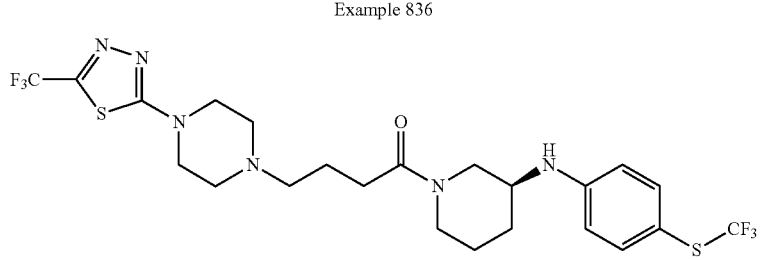 | I-D | 1.52 | 583 | 583 |
| Example 837 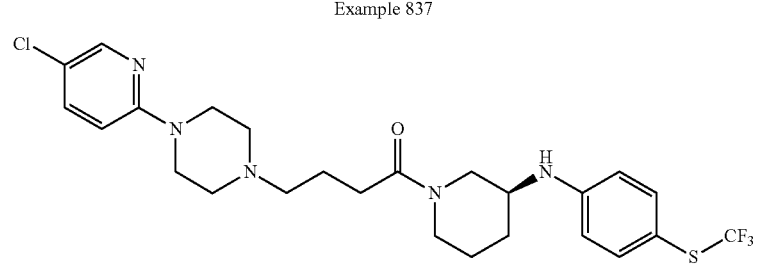 [SMILES: "Example 817" ; O=C(CCCN1CCN(c2ccc(Cl)cc2)CC1)N1CCC[C@H](Nc2ccc(SC(F)(F)F)cc2)C1] | I-D | 1.54 | 542 | 542 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 838 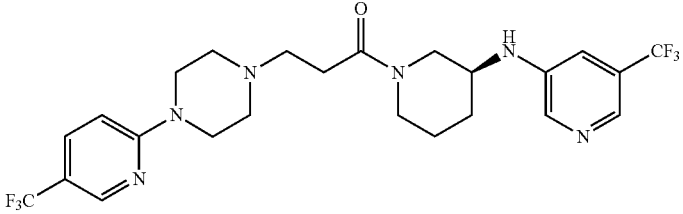 | I-D | 1.34 | 531 | 531 |
| Example 839 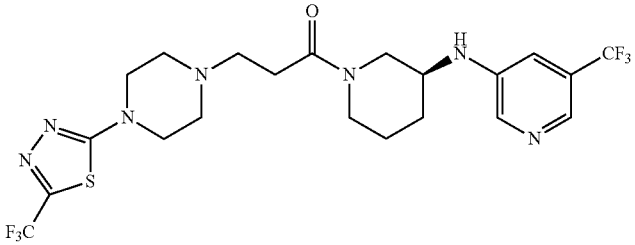 | I-D | 1.22 | 538 | 538 |
| Example 840 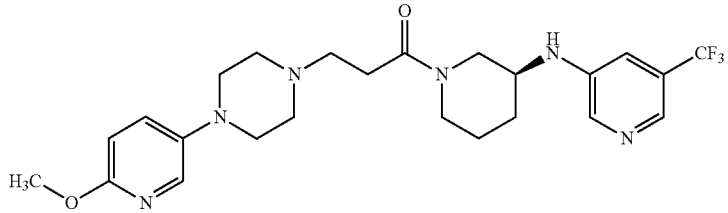 | I-D | 1.12 | 493 | 493 |
| Example 841 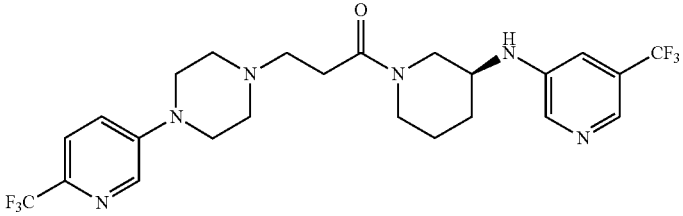 | I-D | 1.24 | 531 | 531 |
| Example 842 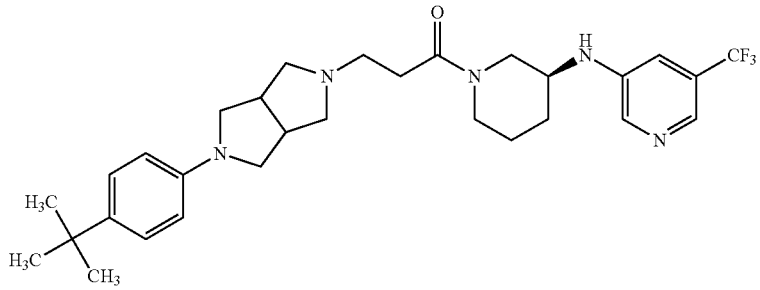 | I-D | 1.55 | 544 | 544 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 843 | I-D | 1.40 | 522 | 522 |
| Example 844 | I-D | 1.43 | 544 | 544 |
| Example 845 | I-D | 1.38 | 510 | 510 |
| Example 846 | I-D | 1.53 | 532 | 532 |
| Example 847 | I-D | 1.43 | 544 | 544 |
| Example 848 | I-D | 1.46 | 532 | 532 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 849 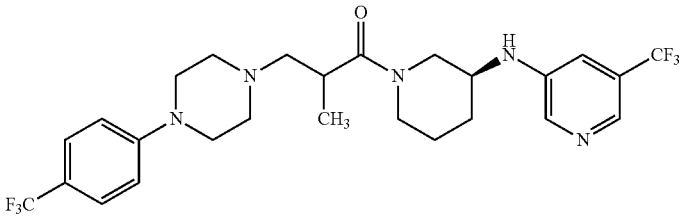 | I-D | 1.41 | 544 | 544 |
| Example 850 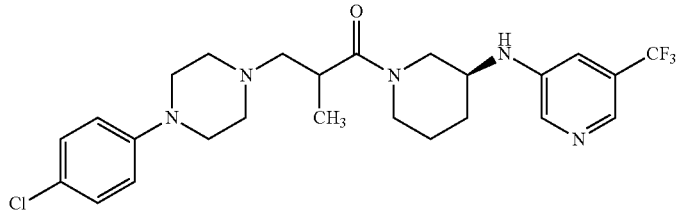 | I-D | 1.34 | 510 | 510 |
| Example 851 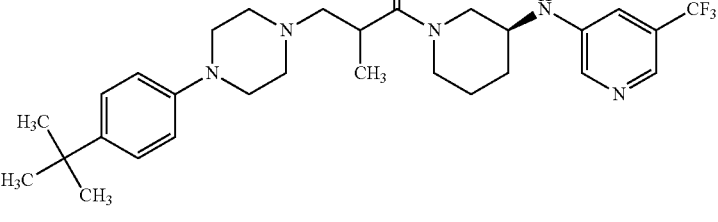 | I-D | 1.48 | 532 | 532 |
| Example 852 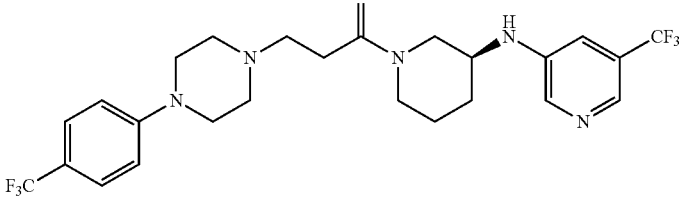 | I-D | 1.39 | 530 | 530 |
| Example 853 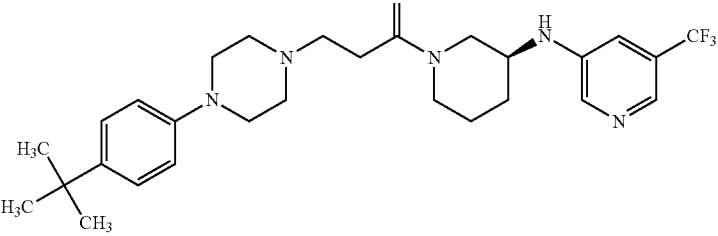 | I-D | 1.46 | 518 | 518 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 854 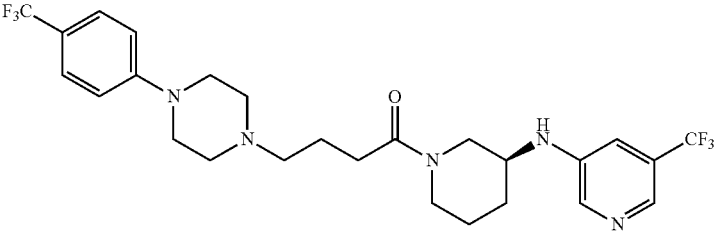 | I-D | 1.41 | 544 | 544 |
| Example 855 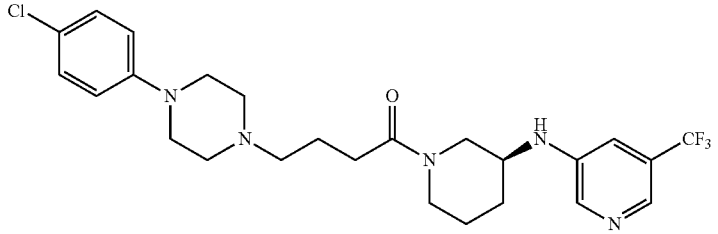 | I-D | 1.34 | 510 | 510 |
| Example 856 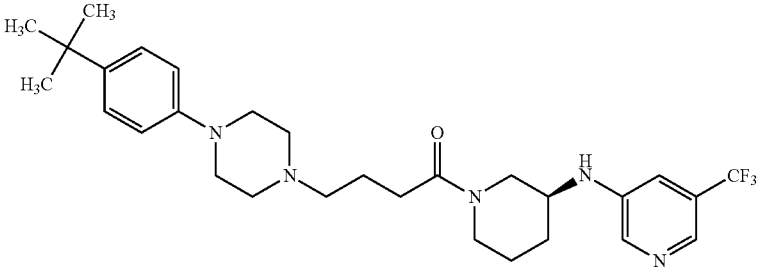 | I-D | 1.47 | 532 | 532 |
| Example 857 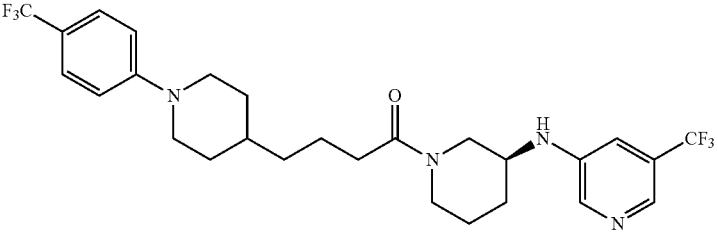 | I-D | 2.12 | 543 | 543 |
| Example 858 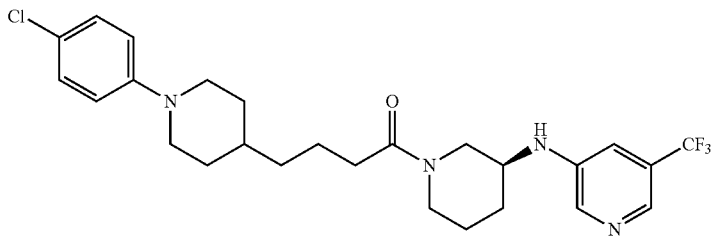 | I-D | 1.77 | 509 | 509 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 859 | I-D | 1.87 | 543 | 543 |
| Example 860 | I-D | 1.46 | 509 | 509 |
| Example 861 | I-D | 1.37 | 531 | 531 |
| Example 862 | I-D | 1.79 | 529 | 529 |
| Example 863 | I-D | 1.38 | 495 | 495 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 864 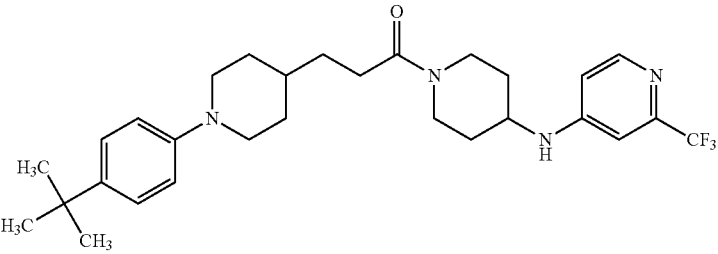 | I-D | 1.33 | 517 | 517 |
| Example 865 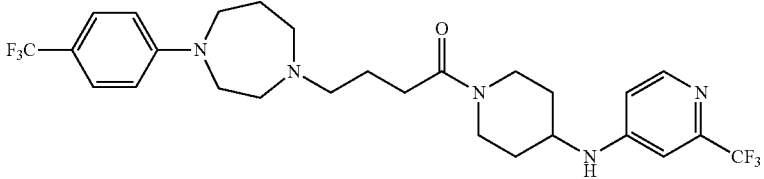 | I-D | 1.31 | 558 | 558 |
| Example 866 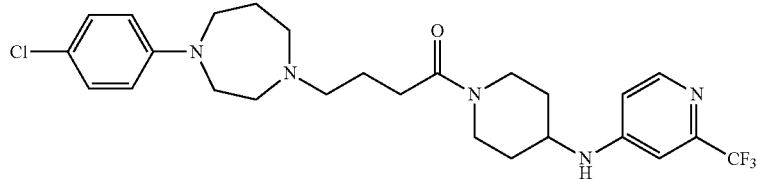 | I-D | 1.26 | 524 | 524 |
| Example 867 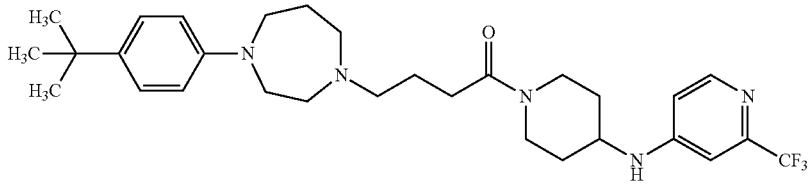 | I-D | 1.41 | 546 | 546 |
| Example 868 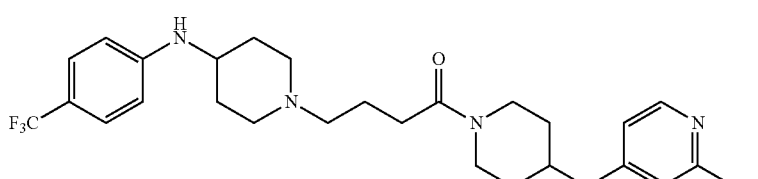 | I-D | 1.28 | 558 | 558 |
| Example 869 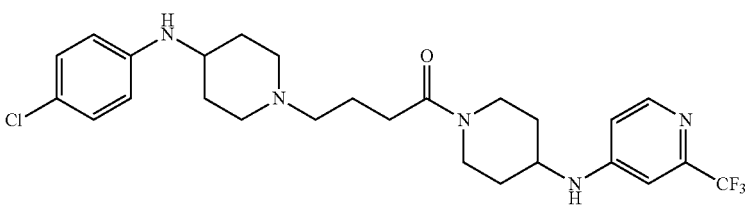 | I-D | 1.20 | 524 | 524 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 870 | I-D | 1.33 | 546 | 546 |
| Example 871 | I-D | 1.34 | 570 | 570 |
| Example 872 | I-D | 1.27 | 536 | 536 |
| Example 873 | I-D | 1.44 | 558 | 558 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 874 | I-C | 1.31 | 507 | 507 |
| Example 875 | I-D | 1.04 | 545 | 545 |
| Example 876 | I-D | 1.17 | 545 | 545 |
| Example 877 | I-D | 0.92 | 552 | 552 |
| Example 878 | I-D | 1.09 | 511 | 511 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 879 | I-D | 1.22 | 544 | 544 |
| Example 880 | I-D | 1.15 | 510 | 510 |
| Example 881 | I-D | 1.33 | 532 | 532 |
| Example 882 | I-D | 1.20 | 530 | 530 |
| Example 883 | I-D | 1.11 | 496 | 496 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 884 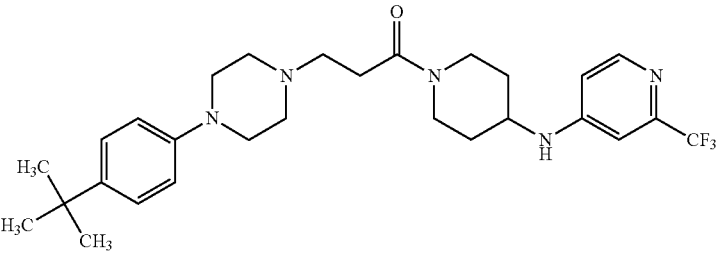 | I-D | 1.30 | 518 | 518 |
| Example 885 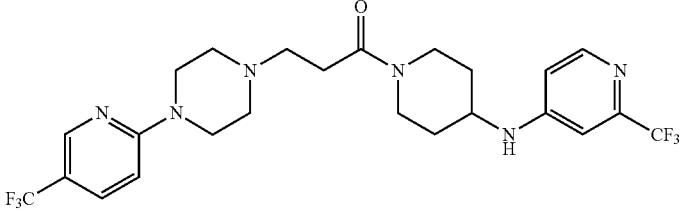 | I-D | 1.14 | 531 | 531 |
| Example 886 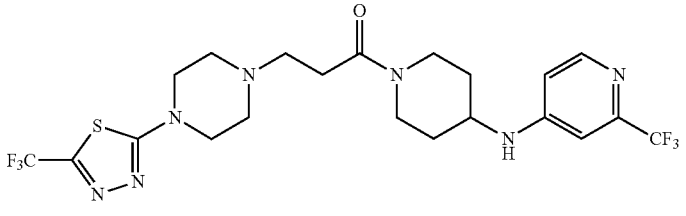 | I-D | 0.82 | 538 | 538 |
| Example 887 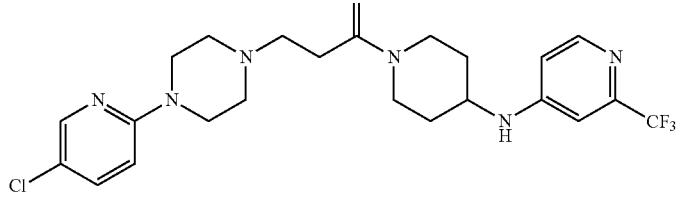 | I-D | 0.98 | 497 | 497 |
| Example 888 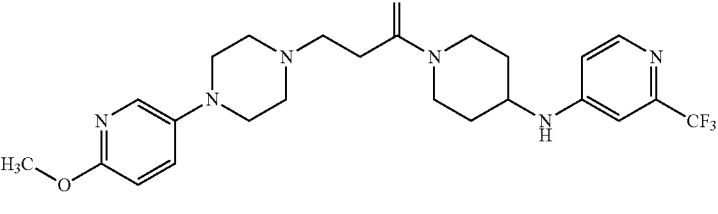 | I-C | 1.29 | 493 | 493 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 889 | I-D | 0.96 | 531 | 531 |
| Example 890 | I-D | 1.40 | 544 | 544 |
| Example 891 | I-D | 1.24 | 522 | 522 |
| Example 892 | I-D | 1.29 | 544 | 544 |
| Example 893 | I-D | 1.20 | 510 | 510 |
| Example 894 | I-D | 1.40 | 532 | 532 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 895 | I-D | 1.30 | 532 | 532 |
| Example 896 | I-D | 2.12 | 543 | 523 |
| Example 897 | I-D | 1.77 | 509 | 509 |
| Example 898 | I-D | 1.58 | 531 | 531 |
| Example 899 | I-D | 2.04 | 529 | 529 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 900 | I-D | 1.70 | 495 | 495 |
| Example 901 | I-D | 1.54 | 517 | 517 |
| Example 902 | I-D | 1.48 | 558 | 558 |
| Example 903 | I-D | 1.40 | 524 | 524 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 904 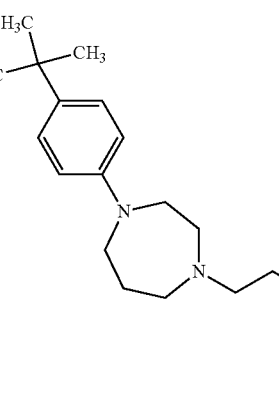 | I-D | 1.54 | 546 | 546 |
| Example 905 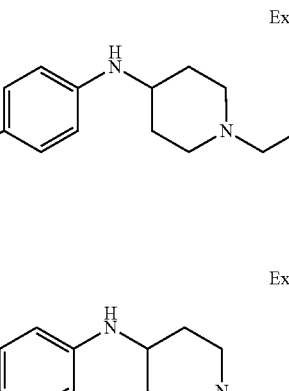 | I-D | 1.46 | 558 | 558 |
| Example 906 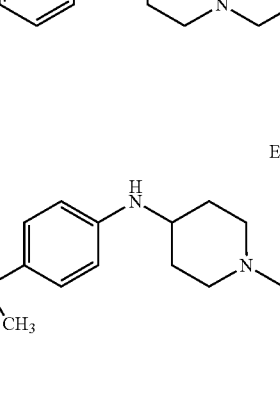 | I-D | 1.39 | 524 | 524 |
| Example 907 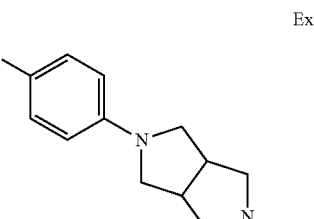 | I-D | 1.47 | 546 | 546 |
| Example 908  | I-D | 1.49 | 570 | 570 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 909 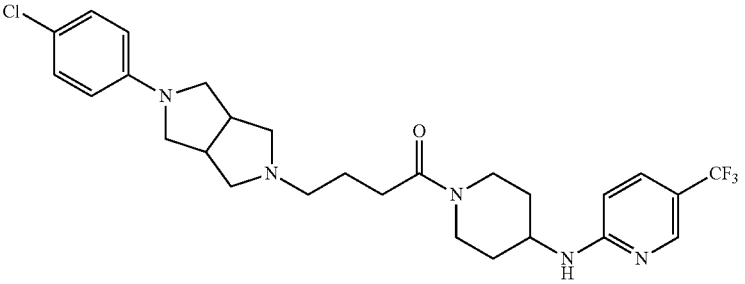 | I-D | 1.44 | 536 | 536 |
| Example 910 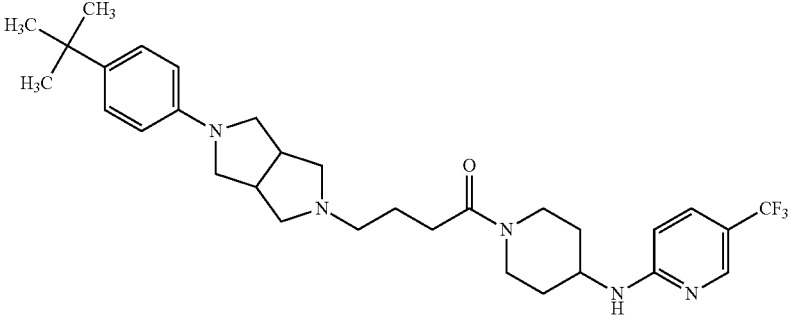 | I-D | 1.57 | 558 | 558 |
| Example 911 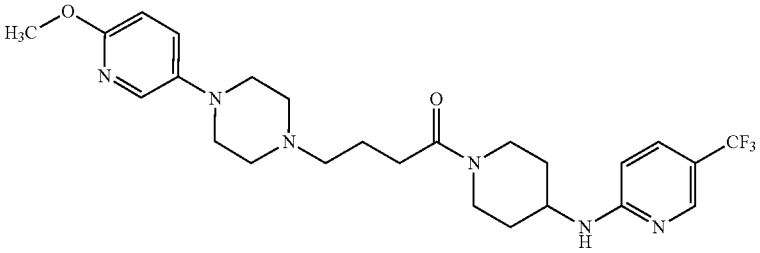 | I-D | 1.63 | 507 | 507 |
| Example 912 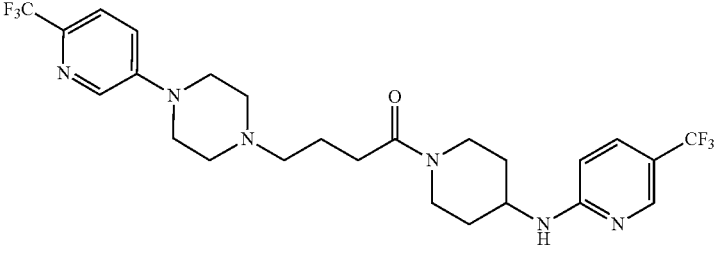 | I-D | 1.29 | 545 | 545 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 913 | I-D | 1.36 | 545 | 545 |
| Example 914 | I-D | 1.24 | 552 | 552 |
| Example 915 | I-D | 1.28 | 511 | 511 |
| Example 916 | I-D | 1.44 | 544 | 544 |
| Example 917 | I-D | 1.38 | 510 | 510 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 918 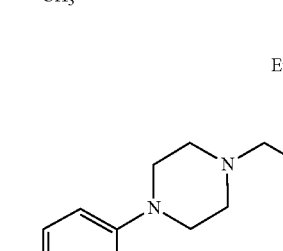 | I-D | 1.51 | 532 | 532 |
| Example 919 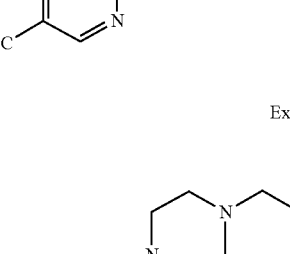 | I-D | 1.32 | 531 | 531 |
| Example 920 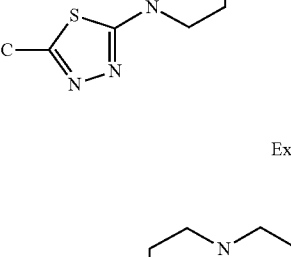 | I-D | 1.22 | 538 | 538 |
| Example 921 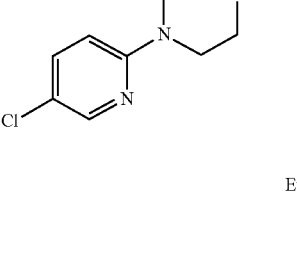 | I-D | 1.26 | 497 | 497 |
| Example 922 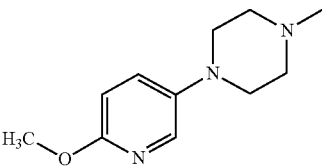 | I-D | 1.12 | 493 | 493 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 923 | I-D | 1.25 | 531 | 531 |
| Example 924 | I-D | 1.55 | 544 | 544 |
| Example 925 | I-D | 1.44 | 522 | 522 |
| Example 926 | I-D | 1.48 | 544 | 544 |
| Example 927 | I-D | 1.38 | 510 | 510 |
| Example 928 | I-D | 1.52 | 532 | 532 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 929 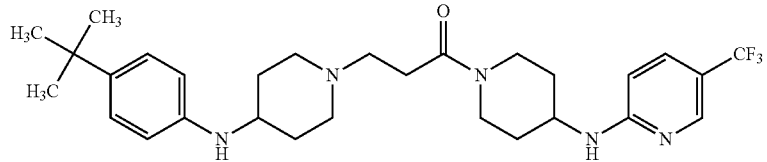 | I-D | 1.47 | 532 | 532 |
| Example 930 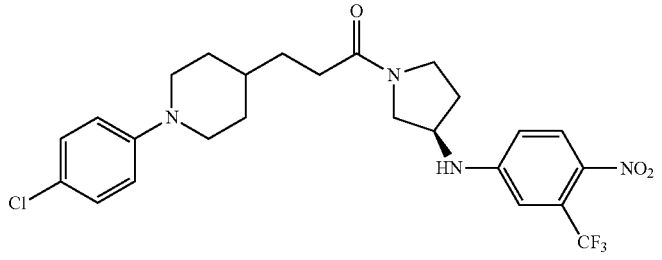 | I-D | 1.80 | 525 | 525 |
| Example 931 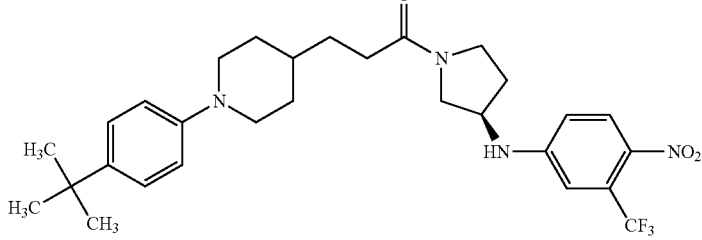 | I-D | 1.62 | 547 | 547 |
| Example 932 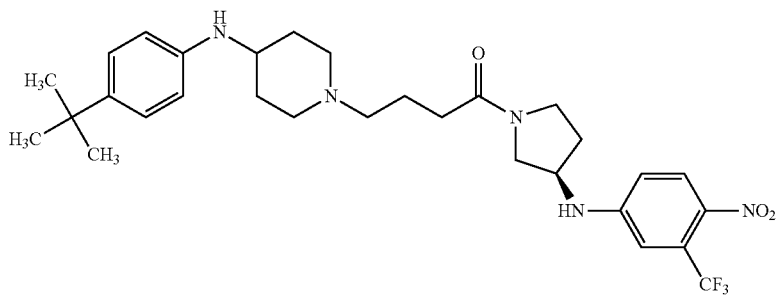 | I-D | 1.60 | 576 | 576 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 933 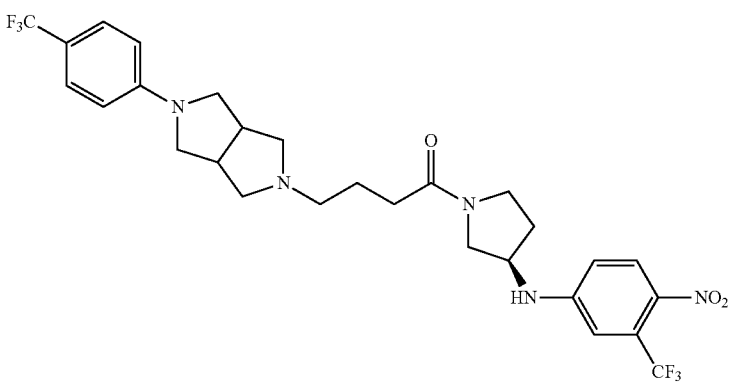 | I-D | 1.57 | 600 | 600 |
| Example 934 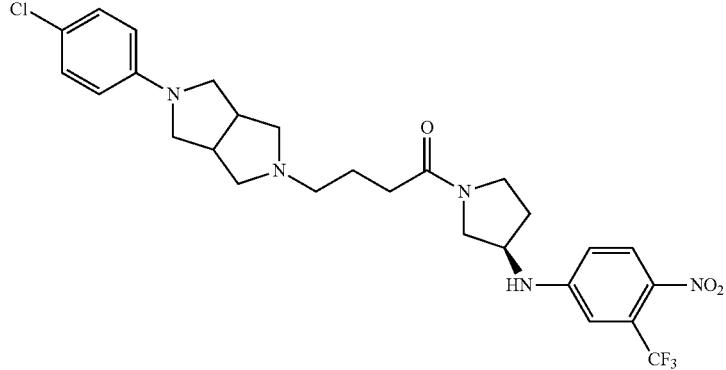 | I-D | 1.55 | 566 | 566 |
| Example 935 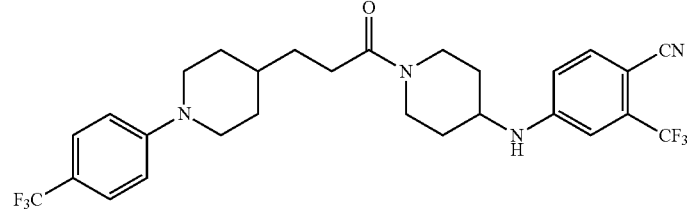 | I-D | 2.12 | 553 | 553 |
| Example 936 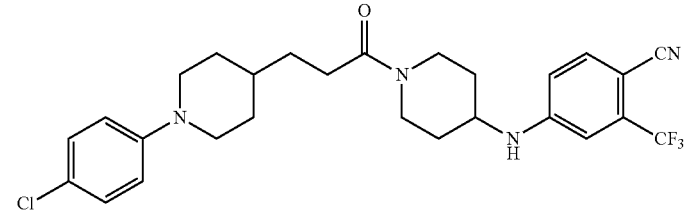 | I-D | 1.82 | 519 | 519 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 937 | I-D | 1.644 | 541 | 541 |
| Example 938 | I-D | 1.64 | 570 | 570 |
| Example 939 | I-D | 1.52 | 560 | 560 |
| Example 940 | I-D | 1.61 | 582 | 582 |
| Example 941 | I-D | 1.41 | 569 | 569 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 942 | I-D | 2.35 | 574 | 574 |
| Example 943 | I-D | 2.14 | 540 | 540 |
| Example 944 | I-D | 1.84 | 562 | 562 |
| Example 945 | I-D | 2.29 | 560 | 560 |
| Example 946 | I-D | 1.81 | 548 | 548 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 947 | I-D | 1.68 | 589 | 589 |
| Example 948 | I-D | 1.65 | 555 | 555 |
| Example 949 | I-D | 1.74 | 577 | 577 |
| Example 950 | I-B | 4.97 | 589 | 589 |
| Example 951 | I-B | 4.92 | 555 | 555 |
| Example 952 | I-D | 1.68 | 577 | 577 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 953 | I-D | 1.66 | 567 | 567 |
| Example 954 | I-D | 1.78 | 589 | 589 |
| Example 955 | I-D | 1.46 | 538 | 538 |
| Example 956 | I-D | 1.54 | 576 | 576 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 957 | I-D | 1.60 | 576 | 576 |
| Example 958 | I-D | 1.54 | 583 | 583 |
| Example 959 | I-D | 1.56 | 542 | 542 |
| Example 960 | I-D | 1.71 | 563 | 563 |
| Example 961 | I-D | 2.12 | 526 | 526 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 962 | I-D | 1.62 | 562 | 562 |
| Example 963 | I-D | 1.56 | 569 | 569 |
| Example 964 | I-D | 1.56 | 528 | 528 |
| Example 965 | I-D | 1.47 | 524 | 524 |
| Example 966 | I-D | 1.56 | 562 | 562 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 967 | I-D | 1.78 | 575 | 575 |
| Example 968 | I-D | 1.66 | 553 | 553 |
| Example 969 | I-D | 1.66 | 575 | 575 |
| Example 970 | I-D | 1.65 | 541 | 541 |
| Example 971 | I-D | 1.78 | 563 | 563 |
| Example 972 | I-D | 1.68 | 575 | 575 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 973 | I-D | 1.71 | 563 | 563 |
| Example 974 | I-D | 1.68 | 541 | 541 |
| Example 975 | I-D | 1.70 | 587 | 587 |
| Example 976 | I-D | 1.71 | 601 | 601 |
| Example 977 | I-D | 2.47 | 608 | 608 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 978 | I-D | 1.95 | 596 | 596 |
| Example 979 | I-D | 2.42 | 594 | 594 |
| Example 980 | I-D | 2.22 | 561 | 560 |
| Example 981 | I-D | 1.91 | 582 | 582 |
| Example 982 | I-D | 1.75 | 623 | 623 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 983 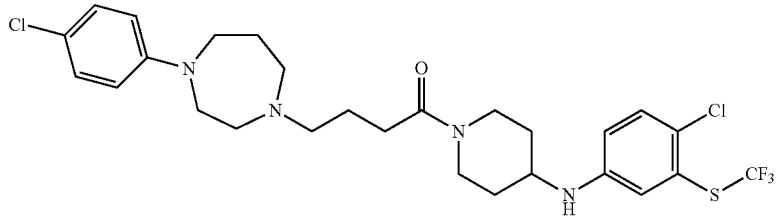 | I-D | 1.72 | 589 | 589 |
| Example 984 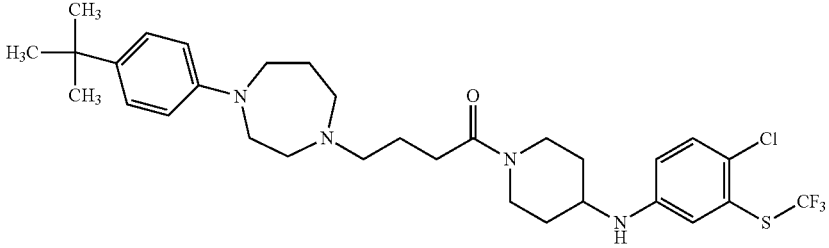 | I-D | 1.81 | 611 | 611 |
| Example 985 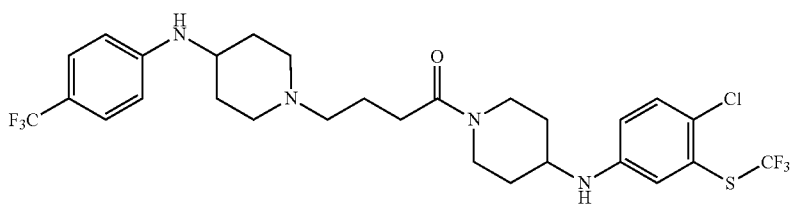 | I-D | 1.72 | 623 | 623 |
| Example 986 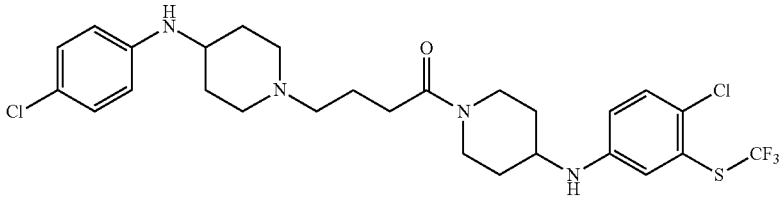 | I-D | 1.69 | 590 | 589 |
| Example 987 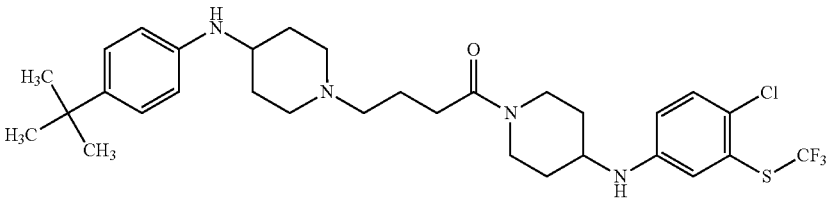 | I-D | 1.76 | 611 | 611 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 988 | I-D | 1.73 | 602 | 601 |
| Example 989 | I-D | 1.85 | 623 | 623 |
| Example 990 | I-D | 1.54 | 572 | 572 |
| Example 991 | I-D | 1.62 | 610 | 610 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 992 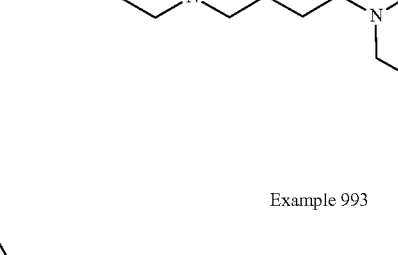 | I-D | 1.67 | 610 | 610 |
| Example 993 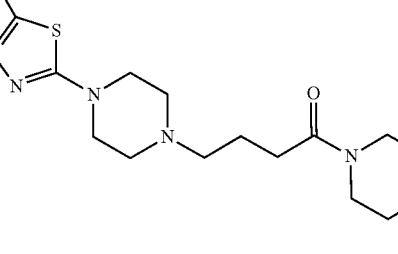 | I-D | 1.60 | 617 | 617 |
| Example 994 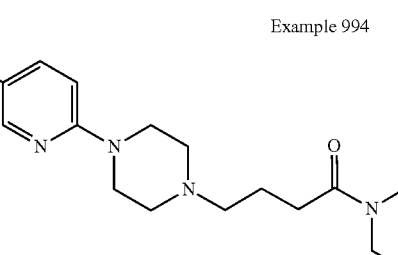 | I-D | 1.64 | 577 | 576 |
| Example 995 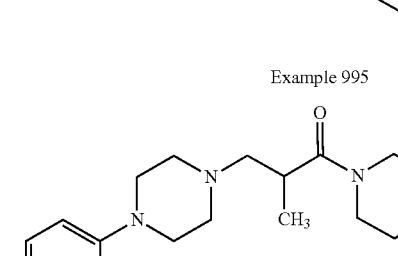 | I-D | 1.71 | 609 | 609 |
| Example 996 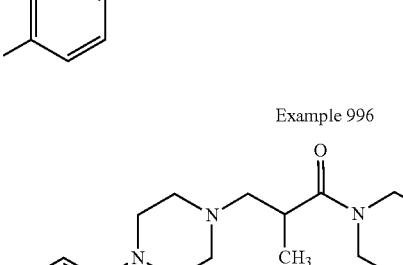 | I-D | 1.67 | 576 | 575 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 997 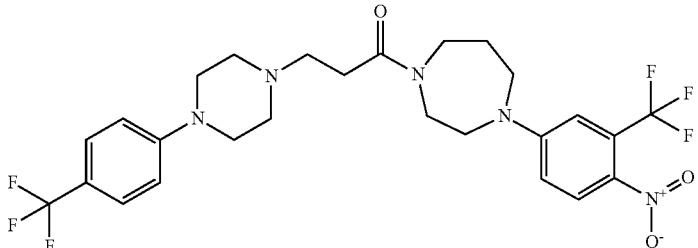 | I-B | 4.991 | 573.5 | 574.2 |
| Example 998 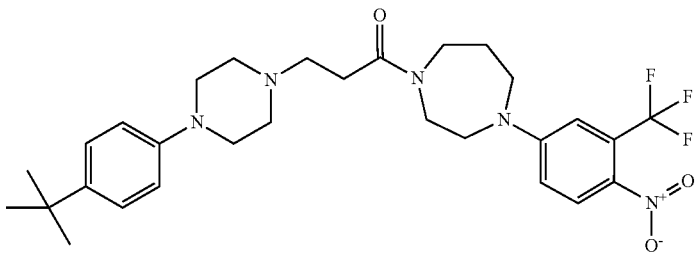 | I-B | 5.183 | 561.6 | 562.3 |
| Example 999 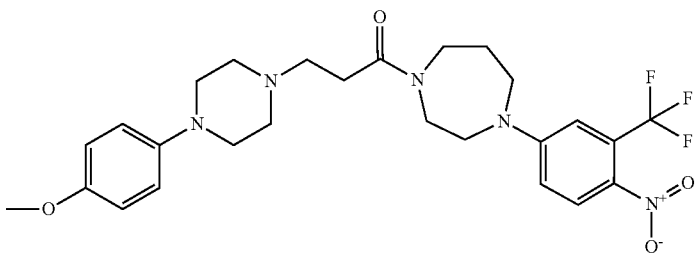 | I-B | 4.730 | 535.6 | 536.2 |
| Example 1000 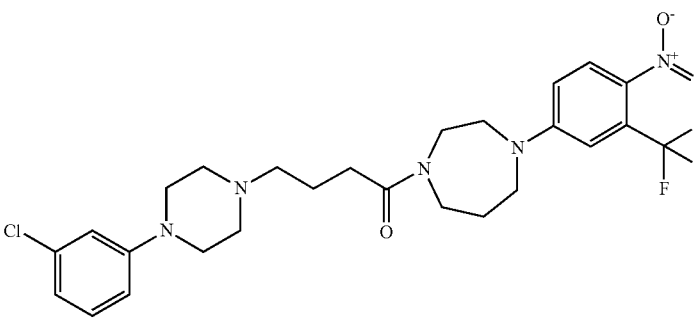 | I-B | 4.950 | 554.0 | 554.2 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 1001 | I-B | 5.011 | 587.6 | 588.2 |
| Example 1002 | I-B | 4.947 | 554.0 | 554.2 |
| Example 1003 | I-B | 5.184 | 575.7 | 576.3 |
| Example 1004 | I-B | 4.775 | 549.6 | 550.2 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 1005 | I-B | 4.866 | 533.6 | 534.2 |
| Example 1006 | I-B | 4.923 | 553.5 | 554.2 |
| Example 1007 | I-B | 5.111 | 541.7 | 542.3 |
| Example 1008 | I-B | 4.942 | 567.6 | 568.2 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 1009 | I-B | 4.860 | 534.0 | 534.2 |
| Example 1010 | I-B | 5.149 | 555.7 | 556.3 |
| Example 1011 | I-B | 4.698 | 529.6 | 530.2 |
| Example 1012 | I-B | 4.823 | 513.6 | 514.2 |

TABLE V-continued
Additional Compounds Prepared by Applicants in Accordance with this Invention
| Compound Structure | Analysis Method | Retention Time (min) | Calc. Mass | Obs. Mass |
|---|---|---|---|---|
| Example 1013 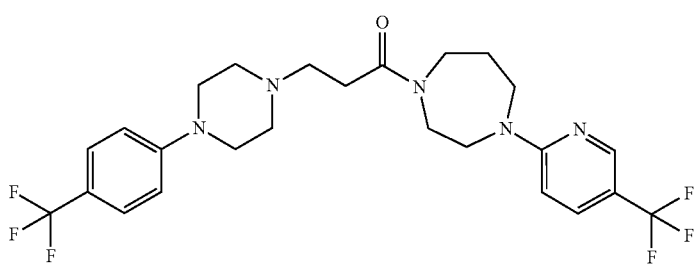 | I-B | 4.947 | 529.5 | 530.2 |
| Example 1014 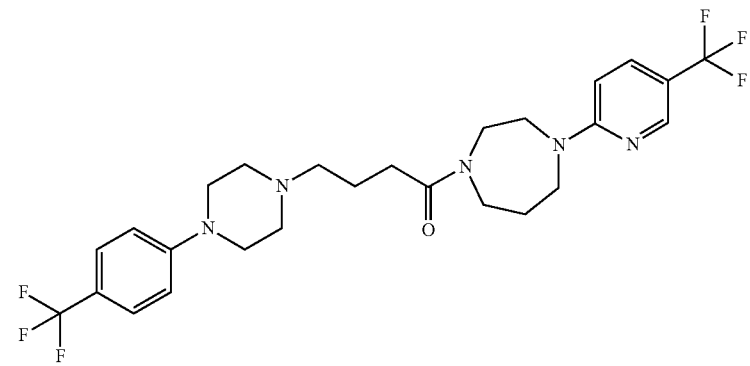 | I-B | 4.953 | 543.6 | 544.2 |
| Example 1015 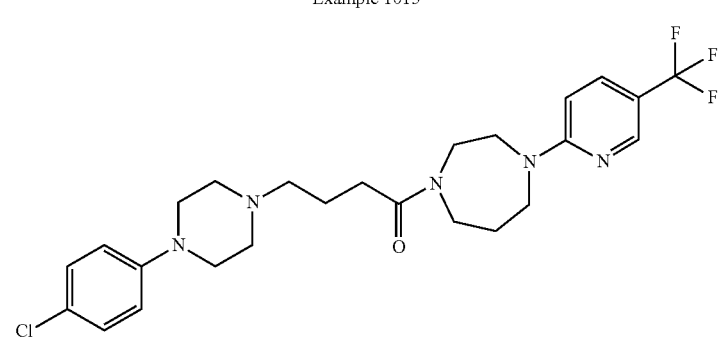 | I-B | 4.881 | 510.0 | 510.2 |
| Example 1016 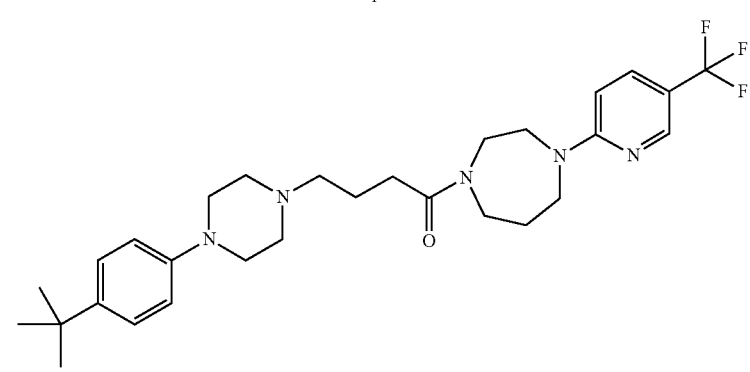 | I-B | 5.194 | 531.7 | 532.3 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 1017 | I-B | 5.234 | 560.6 | 561.2 |
| Example 1018 | I-B | 5.179 | 527.1 | 527.1 |
| Example 1019 | I-B | 5.479 | 548.7 | 549.2 |
| Example 1020 | I-B | 5.005 | 522.6 | 523.2 |
| Example 1021 | I-B | 5.142 | 506.6 | 507.2 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 1022 | I-B | 5.159 | 527.1 | 527.2 |
| Example 1023 | I-B | 5.165 | 527.1 | 527.1 |
| Example 1024 | I-B | 5.042 | 492.6 | 493.2 |
| Example 1025 | I-B | 5.236 | 541.1 | 541.2 |
| Example 1026 | I-B | 5.089 | 506.6 | 507.2 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 1027 | I-B | 5.281 | 574.6 | 575.2 |
| Example 1028 | I-B | 5.238 | 541.1 | 541.2 |
| Example 1029 | I-B | 5.515 | 562.7 | 563.3 |
| Example 1030 | I-B | 5.058 | 536.7 | 537.2 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 1031 | I-B | 5.200 | 520.7 | 521.2 |
| Example 1032 | I-B | 5.235 | 541.1 | 541.2 |
| Example 1033 | I-B | 5.228 | 560.6 | 561.2 |
| Example 1034 | I-B | 5.170 | 527.1 | 527.1 |

TABLE V-continued

Additional Compounds Prepared by Applicants in Accordance with this Invention

| Compound Structure | Analysis Method | Retention Time (min) | Calc. Mass | Obs. Mass |
|---|---|---|---|---|
| Example 1035 | I-B | 5.435 | 548.7 | 549.3 |
| Example 1036 | I-B | 5.041 | 522.6 | 523.2 |

Example 1037

Determining Activity Against *Ascaridia galli* and *Oesophagostomum dentatum*

Anthelmintic effects of compounds of this invention were tested in vitro using gut-welling larval stages of two parasitic nematode species: *A. galli* (intestinal roundworm of chicken), larval stage 3 ("L3"); and *O. dentatum* (nodular worm of swine), larval stages 3 and 4 (respectively "L3" and "L4"). When conducting these experiments, various concentrations of the compounds were incubated in 96-well microtiter plates. Parasites were then distributed at 20 larvae per well. The anthelmintic effects were classified by microscopic examination. The microscopic examination included assessing mortality, damage, motility, progression of development, and neutral red uptake by the larvae in comparison to a DMSO-control and standard anthelmintics. The anthelmintic effects were defined by the minimum effective concentration ("MEC"). Nearly all the tested compounds showed at least some activity against one or more of the nematodes. The following compounds exhibited an MEC of less than 7 µM against one or more of the tested nematodes: Examples 5, 7, 12, 14, 17, 21, 23, 26, 30, 33, 35, 40, 48, 51, 54, 57, 61, 64, 68, 71, 73, 76, 78, 79, 81, 83, 85-92, 95, 98, 101, 102, 105, 108-122, 124, 126, 128, 130, 134, 137, 141, 144, 147, 149, 151, 153, 156, 157-159, 163, 168, 169, 171, 173-176, 178-181, 183-252, 254-256, 258-265, 268-330, 334-336, 338-341, 343-347, 349, 351-368, 370, 374-377, 379, 380, 382, 384, 385, 388-391, 394-398, 399, 400, 402, 405, 407, 408, 410, 414-440, 442, 444, 445, 457, 459, 469, 471-474, 476, 477, 479, 484-489, 495, 497, 498, 502, 505-509, 512, 515, 516, 519, 520, 527-529, 534-570, 572-591, 593-598, 600-613, 615-636, 640-643, 647-713, 715-718, 720-723, 725-731, 733, 734, 737-741, 743, 745-749, 751-758, 760-799, 997, 998, 1001, 1003, 1006-1010, 1014-1022, 1024-1031, and 1033-1036. The following compounds exhibited an MEC of less than 1 µM against one or more of the tested nematodes: Examples 5, 7, 12, 14, 17, 21, 23, 26, 30, 33, 35, 40, 48, 51, 54, 57, 61, 64, 68, 71, 73, 76, 78, 79, 81, 83, 85-92, 95, 98, 101, 102, 105, 108-122, 124, 126, 128, 130, 134, 137, 141, 144, 147, 149, 151, 153, 156, 157-159, 163, 168, 171, 173-175, 179, 180, 183-191, 193-197, 199, 200, 202-204, 206-208, 210, 212, 215, 216, 218-221, 223-234, 236-248, 250-252, 254-256, 258, 259, 261, 263-265, 268-276, 278-283, 285, 289, 291, 294-296, 299-309, 311-317, 321-326, 329, 334, 338, 340, 341, 343, 345-347, 351, 353-357, 359, 361-368, 376, 380, 385, 400, 402, 414-421, 423-431, 433, 435-439, 444, 445, 459, 484, 489, 495, 502, 509, 516, 534-539, 544-547, 550, 551, 555-557, 559-570, 578-591, 594, 596, 602-605, 609, 611, 617-621, 624-629, 633-635, 640, 648, 650-652, 655-663, 665-668, 670-672, 674-691, 694, 695, 697, 699-708, 710-713, 715, 716, 720, 725-728, 730, 731, 733, 746, 749, 752-754, 756-758, 760-768, 770-772, 774, 775, 777, 778, 781-783, 784, 787, 789, 790, 792, 795, 799, 1008, 1010, 1014, 1017, 1019, 1020, 1027, 1028, and 1033-1036. The following compounds exhibited an MEC of less than 1 µM against two or more of the tested nematodes: Examples 5, 7, 12, 14, 17, 21, 23, 26, 30, 33, 35, 40, 48, 51, 54, 57, 61, 64, 68, 71, 73, 76, 78, 79, 81, 83, 85-92, 95, 98, 101, 102, 105, 108-122, 124, 126, 128, 130, 134, 137, 141, 144, 147, 149, 151, 153, 156, 157-159, 163, 168, 171, 183, 187-189, 191, 202, 203, 206-208, 215, 216, 218, 220, 225, 227, 228, 230-233, 236-238, 241, 243, 245, 248, 254, 255, 263-265, 269, 270, 272, 273, 276, 282, 283, 289, 294, 295, 299, 317, 322, 324, 325, 334, 341, 345, 346, 363-365, 367, 368, 382, 385, 402, 414-416, 421, 423, 424, 427-430, 435, 436, 438, 444, 445, 495, 535-539, 551, 559, 561, 564-567, 578, 579, 581-583, 585, 586, 588, 591, 602-604, 617, 619, 661, 662, 667, 668, 675, 676, 678, 680-691, 695, 697, 699, 701, 705-707, 710-712, 715, 716, 725, 730, 752, 754, 757, 759, 760, 764, 770, 774, 778, 789, and 1033.

Example 1038

Determining Resistance-Breaking Activity Against *Haemonchus contortus*

Anthelmintic resistance-breaking effects of compounds of this invention were tested in vitro using larval stage 4 ("L4") of the parasitic nematode species *Haemonchus contortus* (Barber's pole worm in ruminants). One isolate of *Haemonchus contortus* with a resistance to benzimidazoles and ivermectin was tested in comparison to the anthelmintic-sensitive isolate of *Haemonchus contortus*. When conducting these experiments, various concentrations of the compounds were incubated in 96-well microtiter plates. Parasites were then distributed at 20 larvae per well. The anthelmintic effects were classified by microscopic examination. The microscopic examination included assessing mortality, damage, motility, progression of development, and neutral red uptake by the larvae in comparison to a DMSO-control and standard anthelmintics. The anthelmintic effects were defined by the minimum effective concentration ("MEC"). Compounds from Examples 45, 48, 64, and 325 demonstrated the same activity against the resistant and the sensitive isolate of *Haemonchus contortus*, whereas benzimidazoles and ivermectin were less sensitive against the resistant isolate of *Haemonchus contortus*.

Example 1039

Determining Efficacy Against *Haemonchus contortus* in Jirds

Anthelmintic effects of compounds of this invention were tested in vivo using *Haemonchus contuortus* in jirds (*Meriones unguiculatus*). The jirds were orally infected with approximately 750-3,000 third-stage larvae of *Haemonchus contortus*. Ten days after infection, the jirds in the treatment groups were treated once orally or subcutaneously at a dose of 2, 10, and/or 50 mg per kg bodyweight. Three days after treatment, the jirds were necropsied, and the larvae burden in the stomach is determined. The efficacy is defined as the reduction of the mean larvae count in the jirds of the treatment groups in comparison to the infected jirds in the untreated negative control group. Results are shown in Table VI.

TABLE VI

Efficacy against *Haemonchus contortus* in jirds

| Compound | Dose (mg/kg) | Administration Route | % Reduction in H. |
|---|---|---|---|
| Example 5 | 50 | subcutaneous | 99 |
| Example 5 | 50 | oral | 87 |
| Example 7 | 50 | subcutaneous | 98 |
| Example 7 | 50 | oral | 99 |
| Example 12 | 50 | subcutaneous | 100 |
| Example 12 | 50 | oral | 96 |
| Example 14 | 50 | subcutaneous | 99 |
| Example 14 | 50 | oral | 87 |
| Example 17 | 50 | subcutaneous | 96 |
| Example 17 | 50 | oral | 100 |
| Example 21 | 50 | subcutaneous | 38 |
| Example 21 | 50 | oral | 95 |
| Example 23 | 50 | subcutaneous | 92 |
| Example 23 | 50 | oral | 66 |
| Example 26 | 50 | subcutaneous | 91 |
| Example 26 | 50 | oral | 64 |
| Example 30 | 50 | subcutaneous | 69 |
| Example 30 | 50 | oral | 62 |
| Example 33 | 50 | subcutaneous | 69 |
| Example 33 | 50 | oral | 55 |
| Example 35 | 50 | subcutaneous | 93 |
| Example 35 | 50 | oral | 45 |
| Example 40 | 50 | subcutaneous | 74 |
| Example 40 | 50 | oral | 0 |
| Example 45 | 50 | subcutaneous | 94 |
| Example 45 | 50 | oral | 94 |
| Example 48 | 10 | subcutaneous | 92 |
| Example 48 | 10 | oral | 99 |
| Example 51 | 50 | subcutaneous | 63 |
| Example 51 | 50 | oral | 86 |
| Example 54 | 50 | subcutaneous | 58 |
| Example 54 | 50 | oral | 95 |
| Example 57 | 50 | subcutaneous | 84 |
| Example 57 | 50 | oral | 85 |
| Example 58 | 50 | subcutaneous | 59 |
| Example 58 | 50 | oral | 0 |
| Example 416 | 50 | subcutaneous | 98 |
| Example 416 | 50 | oral | 88 |
| Example 532 | 50 | subcutaneous | 99 |
| Example 532 | 50 | oral | 90 |
| Example 533 | 50 | subcutaneous | 74 |
| Example 533 | 50 | oral | 83 |
| Example 322 | 50 | subcutaneous | 73 |
| Example 322 | 50 | oral | 67 |
| Example 324 | 50 | subcutaneous | 90 |
| Example 324 | 50 | oral | 89 |
| Example 325 | 50 | subcutaneous | 97 |
| Example 325 | 50 | oral | 92 |
| Example 334 | 50 | subcutaneous | 82 |
| Example 334 | 50 | oral | 78 |
| Example 345 | 50 | subcutaneous | 61 |
| Example 345 | 50 | oral | 76 |
| Example 367 | 50 | subcutaneous | 45 |
| Example 367 | 50 | oral | 73 |
| Example 414 | 50 | subcutaneous | 98 |
| Example 414 | 50 | oral | 0 |
| Example 444 | 50 | subcutaneous | 52 |
| Example 444 | 50 | oral | 78 |
| Example 295 | 50 | subcutaneous | 0 |
| Example 295 | 50 | oral | 97 |
| Example 385 | 50 | subcutaneous | 83 |
| Example 385 | 50 | oral | 0 |
| Example 61 | 50 | subcutaneous | 100 |
| Example 61 | 50 | oral | 100 |
| Example 64 | 50 | subcutaneous | 100 |
| Example 64 | 50 | oral | 100 |
| Example 539 | 50 | subcutaneous | 73 |
| Example 539 | 50 | oral | 82 |
| Example 71 | 50 | subcutaneous | 35 |
| Example 71 | 50 | oral | 55 |
| Example 565 | 50 | subcutaneous | 90 |
| Example 565 | 50 | oral | 70 |
| Example 566 | 50 | subcutaneous | 93 |
| Example 566 | 50 | oral | 83 |
| Example 579 | 50 | subcutaneous | 96 |
| Example 579 | 50 | oral | 96 |
| Example 92 | 50 | subcutaneous | 91 |
| Example 92 | 50 | oral | 100 |
| Example 581 | 50 | subcutaneous | 10 |
| Example 581 | 50 | oral | 68 |
| Example 73 | 10 | subcutaneous | 63 |
| Example 73 | 10 | oral | 54 |

TABLE VI-continued

Efficacy against *Haemonchus contortus* in jirds

| Compound | Dose (mg/kg) | Administration Route | % Reduction in H. |
|---|---|---|---|
| Example 76 | 10 | subcutaneous | 13 |
| Example 76 | 10 | oral | 67 |
| Example 68 | 10 | subcutaneous | 99 |
| Example 68 | 10 | oral | 99 |
| Example 124 | 10 | subcutaneous | 75 |
| Example 124 | 10 | oral | 47 |
| Example 126 | 10 | subcutaneous | 86 |
| Example 126 | 10 | oral | 64 |
| Example 157 | 10 | subcutaneous | 93 |
| Example 157 | 10 | oral | 96 |
| Example 89 | 10 | subcutaneous | 98 |
| Example 89 | 10 | oral | 99 |
| Example 90 | 10 | subcutaneous | 42 |
| Example 90 | 10 | oral | 46 |
| Example 151 | 10 | subcutaneous | 84 |
| Example 151 | 10 | oral | 88 |
| Example 134 | 10 | subcutaneous | 99 |
| Example 134 | 10 | oral | 99 |

Example 1040

Determining Efficacy Against *Haemonchus contortus* in Sheep

Anthelmintic effects of compounds of this invention were tested in vivo using *Haemonchus contortus* in sheep. The sheep were orally infected with approximately 5,000 third-stage larvae of *Haemonchus contortus*. Thirty-five days after infection, the sheep in the treatment groups were treated once orally at a dose of 2, 5, 10, and/or 50 mg per kg bodyweight. Seven days after treatment, the sheep were necropsied, and the worm burden in the abomasum was determined. The efficacy was defined as the reduction of the mean worm count in the infected sheep of the treatment groups in comparison to the infected sheep in the untreated negative control group. Results for the compounds of Examples 64 and 325 are shown in Table VII.

TABLE VII

Efficacy against *Haemonchus contortus* in sheep

| Compound | Dose (mg/kg) | Administration Route | % Reduction in H. |
|---|---|---|---|
| Example 325 | 50 | oral | 96 |
| Example 64 | 10 | oral | 75 |

Example 1041

Determining Efficacy Against *Haemonchus contortus* and *Trichostrongylus colubriformis* in Cattle Anthelmintic effects of compounds of this invention are tested in vivo using *Haemonchus contortus* and *Trichostrongylus colubriformis* in cattle. The cattle are orally infected with approximately 10,000 third-stage larvae of *Haemonchus contortus* and approximately 30,000 third-stage larvae of *Trichostrongylus colubriformis*. Thirty-two days after infection, the cattle in the treatment group are treated once orally with a compound of the invention at a dose of 10 mg/kg bodyweight. Seven days after treatment, the cattle are necropsied, and the worm burden in the abomasum and the small intestine is determined. The efficacy is defined as the reduction of the mean worm count in the infected cattle of the treatment group in comparison to the infected cattle in the untreated negative control group.

DEFINITIONS

The term "alkyl" (alone or in combination with another term(s)) means a straight- or branched-chain saturated hydrocarbyl substituent (i.e., a substituent containing only carbon and hydrogen) typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, iso-butyl, sec-butyl, tert-butyl, pentyl, iso-amyl, hexyl, and octyl.

The term "alkenyl" (alone or in combination with another term(s)) means a straight- or branched-chain hydrocarbyl substituent containing one or more double bonds and typically from 2 to about 20 carbon atoms, more typically from about 2 to about 10 carbon atoms, even more typically from about 2 to about 8 carbon atoms, and still even more typically from about 2 to about 6 carbon atoms. Examples of such substituents include ethenyl(vinyl); 2-propenyl; 3-propenyl; 1,4-pentadienyl; 1,4-butadienyl; 1-butenyl; 2-butenyl; 3-butenyl; and decenyl.

The term "alkynyl" (alone or in combination with another term(s)) means a straight- or branched-chain hydrocarbyl substituent containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, decynyl, 1-butynyl, 2-butynyl, and 3-butynyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent typically containing from 3 to 14 carbon ring atoms ("ring atoms" are the atoms bound together to form the ring or rings of a cyclic moiety). A carbocyclyl may be a single ring, which typically contains from 3 to 6 ring atoms. Examples of such single-ring carbocyclyls include cyclopropanyl, cyclobutanyl, cyclopentyl, cyclopentenyl, cyclopentadienyl, cyclohexyl, cyclohexenyl, cyclohexadienyl, and phenyl. A carbocyclyl alternatively may be multiple (typically 2 or 3) rings fused together, such as naphthalenyl, tetrahydronaphthalenyl (also known as "tetralinyl"), indenyl, isoindenyl, indanyl, bicyclodecanyl, anthracenyl, phenanthrene, benzonaphthenyl (also known as "phenalenyl"), fluoreneyl, decalinyl, and norpinanyl.

The term "cycloalkyl" (alone or in combination with another term(s)) means a saturated cyclic hydrocarbyl substituent typically containing from 3 to 14 carbon ring atoms. A cycloalkyl may be a single carbon ring, which typically contains from 3 to 6 carbon ring atoms. Examples of single-ring cycloalkyls include cyclopropyl (or "cyclopropanyl"), cyclobutyl (or "cyclobutanyl"), cyclopentyl (or "cyclopentanyl"), and cyclohexyl (or "cyclohexanyl"). A cycloalkyl alternatively may be multiple (typically 2 or 3) carbon rings fused together, such as, decalinyl or norpinanyl.

The term "aryl" (alone or in combination with another term(s)) means an aromatic carbocyclyl typically containing from 6 to 14 carbon ring atoms. Examples of aryls include phenyl, naphthalenyl, and indenyl.

In some instances, the number of carbon atoms in a hydrocarbyl group (e.g., alkyl, alkenyl, alkynyl, or cycloalkyl) is indicated by the prefix "$C_x$-$C_y$-", wherein x is the minimum and y is the maximum number of carbon atoms in the group.

Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical (or "hydrido"), and may be depicted as —H.

The term "hydroxy" (alone or in combination with another term(s)) means —OH.

The term "nitro" (alone or in combination with another term(s)) means —$NO_2$.

The term "cyano" (alone or in combination with another term(s)) means —CN, which also may be depicted:

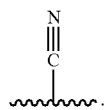

The term "oxo" (alone or in combination with another term(s)) means an oxo radical, and may be depicted as:

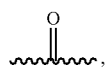

The term "carboxy" (alone or in combination with another term(s)) means —C(O)—OH, which also may be depicted as:

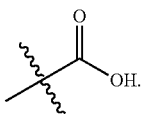 [SMILES: *C(=O)O]

The term "amino" (alone or in combination with another term(s)) means —$NH_2$.

The term "halogen" (alone or in combination with another term(s)) means a fluorine radical ("fluoro", which may be depicted as —F), chlorine radical ("chloro", which may be depicted as —Cl), bromine radical ("bromo", which may be depicted as —Br), or iodine radical ("iodo", which may be depicted as —I). Typically, fluoro or chloro is preferred, with fluoro often being particularly preferred.

If a substituent is described as being "substituted", a non-hydrogen substituent is in the place of a hydrogen on a carbon, nitrogen, oxygen, or sulfur of the substituent. Thus, for example, a substituted alkyl substituent is an alkyl substituent wherein at least one non-hydrogen substituent is in the place of a hydrogen on the alkyl substituent. To illustrate, monofluoroalkyl is alkyl substituted with a fluoro, and difluoroalkyl is alkyl substituted with two fluoros. It should be recognized that if there are more than one substitutions on a substituent, each non-hydrogen substituent may be identical or different (unless otherwise stated).

If a substituent is described as being "optionally substituted", the substituent may be either (1) not substituted or (2) substituted. If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 substituents, then any heteroaryl with less than 3 substitutable positions would be optionally substituted by up to only as many non-hydrogen substituents as the heteroaryl has substitutable positions. To illustrate, tetrazolyl (which has only one substitutable position when it is bonded to a single non-hydrogen moiety by a single bond) would be optionally substituted with up to one non-hydrogen substituent. To illustrate further, if an amino nitrogen is described as being optionally substituted with up to 2 non-hydrogen substituents, then a primary amino nitrogen will be optionally substituted with up to 2 non-hydrogen substituents, whereas a secondary amino nitrogen will be optionally substituted with up to only one non-hydrogen substituent.

The term "substitutable position" means a position where the substituent moiety provides a pharmacokinetic and pharmacodynamic stable compound for the intended use.

The prefix "halo" indicates that the substituent to which the prefix is attached is substituted with one or more independently selected halogens. For example, haloalkyl means an alkyl substituent having a halogen in the place of a hydrogen, or multiple halogens in the place of the same number of hydrogens. Examples of haloalkyls include chloromethyl, 1-bromoethyl, fluoromethyl, difluoromethyl, trifluoromethyl, and 1,1,1-trifluoro ethyl. Illustrating further, "haloalkoxy" means an alkoxy substituent wherein a halogen is in the place of a hydrogen, or multiple halogens are in the place of the same number of hydrogens. Examples of haloalkoxy substituents include chloromethoxy, 1-bromoethoxy, fluoromethoxy, difluoromethoxy, trifluoromethoxy (also known as "perfluoromethyloxy"), and 1,1,1,-trifluoroethoxy. It should be recognized that if a substituent is substituted by more than one halogen, the halogens may be identical or different (unless otherwise stated).

The term "carbonyl" (alone or in combination with another term(s)) means —C(O)—, which also may be depicted as:

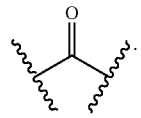 [SMILES: *C(*)=O]

This term also is intended to encompass a hydrated carbonyl substituent, i.e., —$C(OH)_2$—.

The term "aminocarbonyl" (alone or in combination with another term(s)) means —C(O)—$NH_2$, which also may be depicted as:

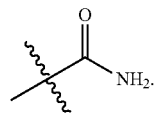

The term "oxy" (alone or in combination with another term(s)) means an ether substituent, and may be depicted as —O—.

The term "alkoxy" (alone or in combination with another term(s)) means an alkylether substituent, i.e., —O-alkyl. Examples of such a substituent include methoxy (—O—$CH_3$), ethoxy, n-propoxy, iso-propoxy, n-butoxy, iso-butoxy, sec-butoxy, and tert-butoxy.

The term "alkylcarbonyl" (alone or in combination with another term(s)) means —C(O)-alkyl. For example, "ethylcarbonyl" may be depicted as:

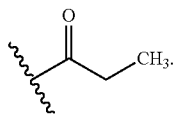

The term "alkoxycarbonyl" (alone or in combination with another term(s)) means —C(O)—O-alkyl. For example, "ethoxycarbonyl" may be depicted as:

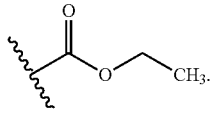 [SMILES: *C(=O)OCC]

The term "carbocyclylcarbonyl" (alone or in combination with another term(s)) means —C(O)-carbocyclyl. For example, "phenylcarbonyl" may be depicted as:

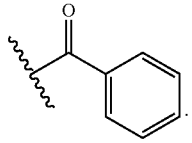

Similarly, the term "heterocyclylcarbonyl" (alone or in combination with another term(s)) means —C(O)-heterocyclyl.

The term "sulfanyl" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-sulfanyl-alkyl" means alkyl-S-alkyl.

The term "thiol" or "mercapto" (alone or in combination with another term(s)) means a sulfhydryl substituent, and may be depicted as —SH.

The term "thiocarbonyl" (alone or in combination with another term(s)) means a carbonyl wherein a sulfur is in the place of the oxygen. Such a substituent may be depicted as —C(S)—, and also may be depicted as:

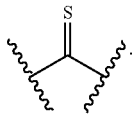 [SMILES: *C(*)=S]

The term "sulfonyl" (alone or in combination with another term(s)) means —S(O)$_2$—, which also may be depicted as:

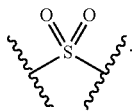 [SMILES: *S(*)(=O)=O]

Thus, for example, "alkyl-sulfonyl-alkyl" means alkyl-S(O)$_2$-alkyl.

The term "aminosulfonyl" (alone or in combination with another term(s)) means —S(O)$_2$—NH$_2$, which also may be depicted as:

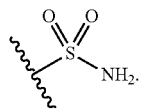

The term "sulfinyl" (alone or in combination with another term(s)) means —S(O)—, which also may be depicted as:

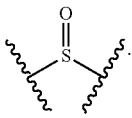

Thus, for example, "alkyl-sulfinyl-alkyl" means alkyl-S(O)-alkyl.

The term "heterocyclyl" (alone or in combination with another term(s)) means a saturated (i.e., "heterocycloalkyl"), non-aromatic partially-saturated (i.e., "heterocycloalkenyl"), or heterocyclic aromatic (i.e., "heteroaryl") ring structure typically containing a total of 3 to 14 ring atoms. At least one of the ring atoms is a heteroatom (typically oxygen, nitrogen, or sulfur), with the remaining ring atoms generally being independently selected from the group typically consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, thienyl (also known as "thiophenyl" and "thiofuranyl"), oxazolyl, isoxazolyl, thiazolyl, isothiazolyl, thiodiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), pyrrolyl, pyrazolyl, imidazolyl, triazolyl, tetrazolyl, oxathiazolyl, oxatriazolyl (including 1,2,3,4-oxatriazolyl and 1,2,3,5-oxatriazolyl), pyridinyl, diazinyl (including pyridazinyl (also known as "1,2-diazinyl"), pyrimidinyl (also known as "1,3-diazinyl"), and pyrazinyl (also known as "1,4-diazinyl")), triazinyl (including s-triazinyl (also known as "1,3,5-triazinyl"), as-triazinyl (also known 1,2,4-triazinyl), and v-triazinyl (also known as "1,2,3-triazinyl")), oxathiazinyl (including 1,2,5-oxathiazinyl and 1,2,6-oxathiazinyl), oxepinyl, thiepinyl, dihydrofuranyl, tetrahydrofuranyl, dihydrothienyl (also known as "dihydrothiophenyl"), tetrahydrothienyl (also known as "tetrahydrothiophenyl"), isopyrrolyl, pyrrolinyl, pyrrolidinyl, isoimidazolyl, imidazolinyl, imidazolidinyl, pyrazolinyl, pyrazolidinyl, dithiolyl, oxathiolyl, oxathiolanyl, oxazolidinyl, isoxazolidinyl, thiazolinyl, isothiazolinyl, thiazolidinyl, isothiazolidinyl, dioxazolyl (including 1,2,3-dioxazolyl, 1,2,4-dioxazolyl, 1,3,2-dioxazolyl, and 1,3,4-dioxazolyl), pyranyl (including 1,2-pyranyl and 1,4-pyranyl), dihydropyranyl, tetrahydropyranyl, piperidinyl, piperazinyl, oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxadiazinyl (including 1,4,2-oxadiazinyl and 1,3,5,2-oxadiazinyl), morpholinyl, azepinyl, and diazepinyl.

A heterocyclyl alternatively may be 2 or 3 rings fused together, such as, for example, indolizinyl, pyranopyrrolyl, purinyl, imidazopyrazinyl, imidazolopyridazyl, pyridopyridinyl (including pyrido[3,4-b]-pyridinyl, pyrido[3,2-b]-pyridinyl, pyrido[4,3-b]-pyridinyl, and naphthyridinyl), pteridinyl, pyridazinotetrazinyl, pyrazinotetrazinyl, pyrimidinotetrazinyl, pyrindinyl, pyrazolopyrimidinyl, pyrazolopyrazinyl, pyrazolopyridazyl, or 4H-quinolizinyl. In some embodiments, the preferred multi-ring heterocyclyls are indolizinyl, pyranopyrrolyl, purinyl, pyridopyridinyl, pyrindinyl, and 4H-quinolizinyl.

Other examples of fused-ring heterocyclyls include benzo-fused heterocyclyls, such as, for example, benzofuranyl (also known as "coumaronyl"), isobenzofuranyl, benzoxazolyl, benzoisoxazolyl (also known as "indoxazinyl"), anthranilyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, benzoisothiazolyl, benzothiadiazolyl, benzoxadiazolyl, indolyl, isoindazolyl (also known as "benzpyrazolyl"), benzoimidazolyl, benzotriazolyl, benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzoimidazothiazolyl, carbazolyl, acridinyl, isoindolyl, indoleninyl (also known as "pseudoindolyl"), benzodioxolyl, chromanyl, isochromanyl, thiochromanyl, isothiochromanyl, chromenyl, isochromenyl, thiochromenyl, isothiochromenyl, benzodioxanyl, tetrahydroisoquinolinyl, benzoxazinyl (including 1,3,2-benzoxazinyl, 1,4,2-benzoxazinyl, 2,3,1-benzoxazinyl, and 3,1,4-benzoxazinyl), benzoisoxazinyl (including 1,2-benzisoxazinyl and 1,4-benzisoxazinyl), benzoxadiazinyl, and xanthenyl. In some embodiments, the preferred benzo-fused heterocyclyls are benzofuranyl, isobenzofuranyl, benzoxazolyl, benzoisoxazolyl, anthranilyl, benzothienyl, isobenzothienyl, benzothiazolyl, benzothiadiazolyl, benzoxadiazolyl, indolyl, isoindazolyl, benzoimidazolyl, benzotriazolyl, benzazinyl, phthalazinyl, quinoxalinyl, benzodiazinyl, carbazolyl, acridinyl, isoindolyl, indoleninyl, benzodioxolyl, chromanyl, isochromanyl, thiochromanyl, benzodioxanyl, tetrahydroisoquinolinyl, benzoxazinyl, benzoisoxazinyl, and xanthenyl.

The term "2-fused-ring" heterocyclyl (alone or in combination with another term(s)) means a saturated, non-aromatic partially-saturated, or heteroaryl containing two fused rings. Such heterocyclyls include, for example, benzofuranyl, isobenzofuranyl, benzoxazolyl, benzoisoxazolyl, anthranilyl, benzothienyl, isobenzothienyl, benzothiazolyl, benzoisothiazolyl, benzothiadiazolyl, indolizinyl, pyranopyrrolyl, benzoxadiazolyl, indolyl, isoindazolyl, benzoimidazolyl, benzotriazolyl, purinyl, imidazopyrazinyl, imidazolopyridazyl, quinolinyl, isoquinolinyl, pyridopyridinyl, phthalazinyl, quinoxalinyl, benzodiazinyl, pteridinyl, pyridazinotetrazinyl, pyrazinotetrazinyl, pyrimidinotetrazinyl, pyrindinyl, isoindolyl, indoleninyl, pyrazolopyrimidinyl, pyrazolopyrazinyl, pyrazolopyridazyl, benzodioxolyl, chromanyl, isochromanyl, thiochromanyl, isothiochromanyl, chromenyl, isochromenyl, thiochromenyl, isothiochromenyl, benzodioxanyl, tetrahydroisoquinolinyl, 4H-quinolizinyl, benzoxazinyl, and benzoisoxazinyl. In some embodiments, preferred 2-fused-ring heterocyclyls include benzofuranyl, isobenzofuranyl, benzoxazolyl, benzoisoxazolyl, anthranilyl, benzothienyl, isobenzothienyl, benzothiazolyl, benzothiadiazolyl, indolizinyl, pyranopyrrolyl, benzoxadiazolyl, indolyl, isoindazolyl, benzoimidazolyl, benzotriazolyl, purinyl, quinolinyl, isoquinolinyl, pyridopyridinyl, phthalazinyl, quinoxalinyl, benzodiazinyl, pteridinyl, pyrindinyl, isoindolyl, indoleninyl, benzodioxolyl, benzodioxanyl, tetrahydroisoquinolinyl, 4H-quinolizinyl, benzoxazinyl, and benzoisoxazinyl.

The term "heteroaryl" (alone or in combination with another term(s)) means an aromatic heterocyclyl typically containing from 5 to 14 ring atoms. A heteroaryl may be a single ring or multiple (typically 2 or 3) fused rings. Such moieties include, for example, 5-membered rings such as furanyl, thienyl, oxazolyl, isoxazolyl, thiazolyl, isothiazolyl, thiodiazolyl, oxadiazolyl, pyrrolyl, pyrazolyl, imidazolyl, triazolyl, tetrazolyl, oxathiazolyl, and oxatriazolyl; 6-membered rings such as pyridinyl, pyrazinyl, pyrimidinyl, pyridazinyl, triazinyl, and oxathiazinyl; 7-membered rings such as oxepinyl and thiepinyl; 6/5-membered fused-ring systems such as benzofuranyl, isobenzofuranyl, benzoxazolyl, benzoisoxazolyl, anthranilyl, benzothienyl, isobenzothienyl, benzothiazolyl, benzoisothiazolyl, benzothiadiazolyl, indolizinyl, pyranopyrrolyl, benzoxadiazolyl, indolyl, isoindazolyl, benzoimidazolyl, benzotriazolyl, purinyl, imidazopyrazinyl, and imidazolopyridazyl; and 6/6-membered fused-ring systems such as quinolinyl, isoquinolinyl, pyridopyridinyl, phthalazinyl, quinoxalinyl, benzodiazinyl, pteridinyl, pyridazinotetrazinyl, pyrazinotetrazinyl, pyrimidinotetrazinyl, benzoimidazothiazolyl, carbazolyl, and acridinyl. In some embodiments, the preferred 5-membered rings include furanyl, thienyl, oxazolyl, isoxazolyl, thiazolyl, isothiazolyl, oxadiazolyl, pyrazolyl, and imidazolyl; the preferred 6-membered rings include pyridinyl, pyrazinyl, pyrimidinyl, pyridazinyl, and triazinyl; the preferred 6/5-membered fused-ring systems include benzoxazolyl, benzoisoxazolyl, anthranilyl, benzothienyl, isobenzothienyl, and purinyl; and the preferred 6/6-membered fused-ring systems include quinolinyl, isoquinolinyl, and benzodiazinyl.

A carbocyclyl or heterocyclyl can optionally be substituted with, for example, one or more substituents independently selected from the group consisting of halogen, hydroxy, carboxy, oxo, alkyl, alkoxy, alkoxyalkyl, alkylcarbonyl, aryl, arylalkyl, arylalkoxy, arylalkoxyalkyl, arylalkoxycarbonyl, cycloalkyl, cycloalkylalkyl, cycloalkylalkoxy, cycloalkylalkoxyalkyl, and cycloalkylalkoxycarbonyl. More typically, a carbocyclyl or heterocyclyl may optionally be substituted with, for example, one or more substituents independently selected from the group consisting of halogen, —OH, —C(O)—OH, oxo, $C_1$-$C_6$-alkyl, $C_1$-$C_6$-alkoxy, $C_1$-$C_6$-alkoxy-$C_1$-$C_6$-alkyl, $C_1$-$C_6$-alkylcarbonyl, aryl, aryl-$C_1$-$C_6$-alkyl, aryl-$C_1$-$C_6$-alkoxy, aryl-$C_1$-$C_6$-alkoxy-$C_1$-$C_6$-alkyl, aryl-$C_1$-$C_6$-alkoxycarbonyl, cycloalkyl, cycloalkyl-$C_1$-$C_6$-alkyl, cycloalkyl-$C_1$-$C_6$-alkoxy, cycloalkyl-$C_1$-$C_6$-alkoxy-$C_1$-$C_6$-alkyl, and cycloalkyl-$C_1$-$C_6$-alkoxycarbonyl. The alkyl, alkoxy, alkoxyalkyl, alkylcarbonyl, aryl, arylalkyl, arylalkoxy, arylalkoxyalkyl, or arylalkoxycarbonyl substituent(s) may further be substituted with, for example, one or more halogen. The aryl and cycloalkyl portions of such optional substituents are typically single-rings containing from 3 to 6 ring atoms, and more typically from 5 to 6 ring atoms.

An aryl or heteroaryl can optionally be substituted with, for example, one or more substituents independently selected from the group consisting of halogen, —OH, —CN, —NO₂, —SH, —C(O)—OH, amino, aminoalkyl, alkyl, alkylsulfanyl, carboxyalkylsulfanyl, alkylcarbonyloxy, alkoxy, alkoxyalkyl, alkoxycarbonylalkoxy, alkoxyalkylsulfanyl, alkoxycarbonylalkylsulfanyl, carboxyalkoxy, alkoxycarbonylalkoxy, carbocyclyl, carbocyclylalkyl, carbocyclyloxy, carbocyclylsulfanyl, carbocyclylalkylsulfanyl, carbocyclylamino, carbocyclylalkylamino, carbocyclylcarbonylamino, carbocyclylalkyl, carbocyclylcarbonyloxy, carbocyclyloxyalkoxycarbocyclyl, carbocyclylsulfanylalkylsulfanylcarbocyclyl, carbocyclylsulfanylalkoxycarbocyclyl, carbocyclyloxyalkylsulfanylcarbocyclyl, heterocyclyl, heterocyclylalkyl, heterocyclyloxy, heterocyclylsulfanyl, heterocyclylalkylsulfanyl, heterocyclylamino, heterocyclylalkylamino, heterocyclylcarbonylamino, heterocyclylcarbonyloxy, heterocyclyloxyalkoxyheterocyclyl, heterocyclylsulfanylalkylsulfanylheterocyclyl, heterocyclylsulfanylalkoxyheterocyclyl, and heterocyclyloxyalkylsulfanylheterocyclyl. More typically, an aryl or heteroaryl may, for example, optionally be substituted with one or more substituents independently selected from the group consisting of halogen, —OH, —CN, —NO$_2$, —SH, —C(O)—OH, amino, amino-$C_1$-$C_6$-alkyl, $C_1$-$C_6$-alkyl, $C_1$-$C_6$-alkylsulfanyl, carboxy-$C_1$-$C_6$-alkylsulfanyl, $C_1$-$C_6$-alkylcarbonyloxy, $C_1$-$C_6$-alkoxy, $C_1$-$C_6$-alkoxy-$C_1$-$C_6$-alkyl, $C_1$-$C_6$-alkoxycarbonyl-$C_1$-$C_6$-alkoxy, $C_1$-$C_6$-alkoxy-$C_1$-$C_6$-alkylsulfanyl, $C_1$-$C_6$-alkoxycarbonyl-$C_1$-$C_6$-alkylsulfanyl, carboxy-$C_1$-$C_6$-alkoxy, $C_1$-$C_6$-alkoxycarbonyl-$C_1$-$C_6$-alkoxy, aryl, aryl-$C_1$-$C_6$-alkyl, aryloxy, arylsulfanyl, aryl-$C_1$-$C_6$-alkylsulfanyl, arylamino, aryl-$C_1$-$C_6$-alkylamino, arylcarbonylamino, arylcarbonyloxy, aryloxy-$C_1$-$C_6$-alkoxyaryl, arylsulfanyl-$C_1$-$C_6$-alkylsulfanylaryl, arylsulfanyl-$C_1$-$C_6$-alkoxyaryl, aryloxy-$C_1$-$C_6$-alkylsulfanylaryl, cycloalkyl, cycloalkyl-$C_1$-$C_6$-alkyl, cycloalkyloxy, cycloalkylsulfanyl, cycloalkyl-$C_1$-$C_6$-alkylsulfanyl, cycloalkylamino, cycloalkyl-$C_1$-$C_6$-alkylamino, cycloalkylcarbonylamino, cycloalkylcarbonyloxy, heteroaryl, heteroaryl-$C_1$-$C_6$-alkyl, heteroaryloxy, heteroarylsulfanyl, heteroaryl-$C_1$-$C_6$-alkylsulfanyl, heteroarylamino, heteroaryl-$C_1$-$C_6$-alkylamino, heteroarylcarbonylamino, and heteroarylcarbonyloxy. Here, one or more hydrogens bound to a carbon in any such substituent may, for example, optionally be replaced with halogen. In addition, any cycloalkyl, aryl, and heteroaryl portions of such optional substituents are typically single-rings containing 3 to 6 ring atoms, and more typically 5 or 6 ring atoms.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component.

If substituents are described as being "independently selected," each substituent is selected independent of the other. Each substituent, therefore, may be identical to or different from the other selected substituent(s).

When words are used to describe a substituent, the rightmost-described component of the substituent is the component that has the free valence. To illustrate, benzene substituted with methoxyethyl has the following structure:

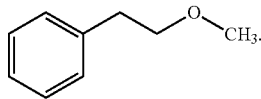

As can be seen, the ethyl is bound to the benzene, and the methoxy is the component of the substituent that is the component furthest from the benzene. As further illustration, benzene substituted with cyclohexanylsulfanylbutoxy has the following structure:

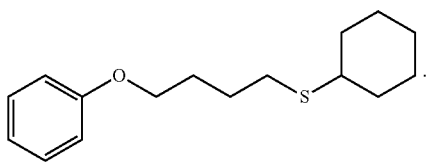 [SMILES: c1ccc(OCCCCSC2CCCCC2)cc1]

When a chemical formula is used to describe a monovalent substituent, the dash on the left side of the formula indicates the portion of the substituent that has the free valence. To illustrate, benzene substituted with —C(O)—OH has the following structure:

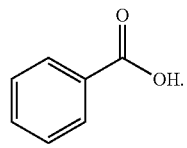

When a chemical formula is used to describe a di-valent (or "linking") component between two other components of a depicted chemical structure (the right and left components), the leftmost dash of the linking component indicates the portion of the linking component that is bound to the left component in the depicted structure. The rightmost dash, on the other hand, indicates the portion of the linking component that is bound to the right component in the depicted structure. To illustrate, if the depicted chemical structure is X-L-Y and L is described as —C(O)—N(H)—, then the chemical would be:

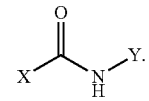

Dashes are not used to characterize a tri-valent component when standing alone. Thus, for example, a tri-valent nitrogen is identified as "N" and a tri-valent carbon bonded to hydrogen is identified as "CH" in this patent.

The words "comprise", "comprises", and "comprising" are to be interpreted inclusively rather than exclusively. This interpretation is intended to be the same as the interpretation that these words are given under United States patent law.

The term "pharmaceutically acceptable" is used adjectivally to mean that the modified noun is appropriate for use in a pharmaceutical product. When it is used, for example, to describe a salt or excipient, it characterizes the salt or excipient as being compatible with the other ingredients of the composition, and not deleterious to the intended recipient animal to the extent that the deleterious effect(s) outweighs the benefit(s) of the salt.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:
1. A compound or salt thereof of Formula (I-8), wherein the compound corresponds in structure to:

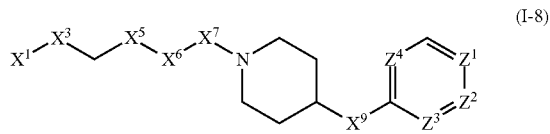

(I-8)

$X^1$ is selected from the group consisting of phenyl, 5-member heteroaryl, and 6-member heteroaryl, wherein:
the 5-member heteroaryl is optionally substituted with one or more independently selected alkyl; wherein:

the alkyl is optionally substituted with one or more independently selected halogen,
the phenyl and 6-member heteroaryl are optionally substituted at the meta and para positions by one or more substituents selected from the group consisting of alkyl and arylalkoxy wherein:
the alkyl is optionally substituted with one or more independently selected halogen;
the arylalkoxy is optionally substituted with one or more haloalkyl;
$X^3$ is a linker selected from the group consisting of:

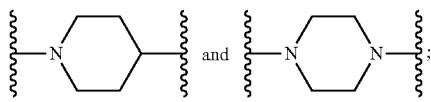

$X^5$ is selected from the group consisting of a bond and —CH$_2$—;
$X^6$ is —CH$_2$—, wherein:
the —CH$_2$— is optionally substituted with up to two independently selected alkyl;
$X^7$ is selected from the group consisting of —C(O)—, —C(S), —C(O)—NH—, and —C(S)—NH—;
$X^9$ is selected from the group consisting of —NH—, and —O—;
$Z^1$ is CH, wherein:
the CH is optionally substituted with a substituent selected from the group consisting of nitro, cyano, alkyl, alkylsulfanyl and alkylsulfonyl, wherein:
the alkyl and alkylsulfanyl are optionally substituted with one or more halogen;
$Z^2$ is CH, wherein:
the CH is optionally substituted with a substituent selected from the group consisting of alkyl, cyano, alkoxy and haloalkyl; and
$Z^3$ and $Z^4$ are independently selected from the group consisting of N and CH.

2. A compound or salt thereof of Formula (I-9), wherein the compound corresponds in structure to:

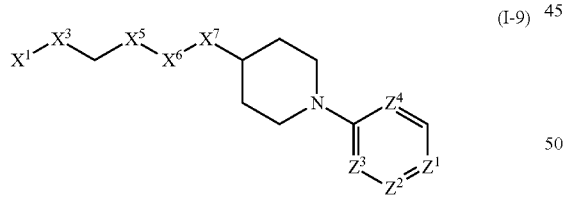

(I-9)

$X^1$ is selected from the group consisting of phenyl, 5-member heteroaryl, and 6-member heteroaryl, wherein:
the 5-member heteroaryl is optionally substituted with one or more independently selected alkyl; wherein:
the alkyl is optionally substituted with one or more independently selected halogen,
the phenyl and 6-member heteroaryl are optionally substituted at the meta and para positions by one or more substituents selected from the group consisting of alkyl and arylalkoxy wherein:
the alkyl is optionally substituted with one or more independently selected halogen;
the arylalkoxy is optionally substituted with one or more haloalkyl;

$X^3$ is a linker selected from the group consisting of:

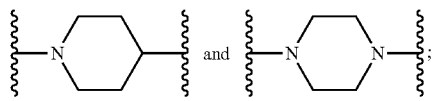

$X^5$ is selected from the group consisting of a bond and —CH$_2$—;
$X^6$ is —CH$_2$—, wherein:
the —CH$_2$— is optionally substituted with up to two independently selected alkyl;
$X^7$ is selected from the group consisting of —C(O)—, —C(S), —C(O)—NH—, and —C(S)—NH—;
$Z^1$ is CH, wherein:
the CH is optionally substituted with a substituent selected from the group consisting of nitro, cyano, alkyl, alkylsulfanyl and alkylsulfonyl, wherein:
the alkyl and alkylsulfanyl are optionally substituted with one or more halogen;
$Z^2$ is CH, wherein:
the CH is optionally substituted with a substituent selected from the group consisting of alkyl, cyano, alkoxy and haloalkyl; and
$Z^3$ and $Z^4$ are independently selected from the group consisting of N and CH.

3. The compound or salt of claim 1, wherein:

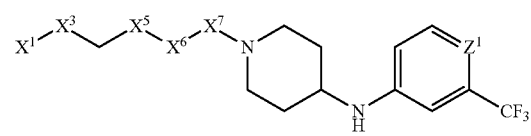

$X^1$ is selected from the group consisting of phenyl, 5-member heteroaryl, and 6-member heteroaryl, wherein:
the 5-member heteroaryl is optionally substituted with one or more independently selected haloalkyl;
the phenyl and 6-member heteroaryl are optionally substituted at the meta and para positions by one or more independently selected haloalkyl;
$X^3$ is a linker selected from the group consisting of:

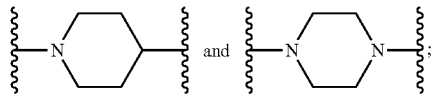

$X^5$ is selected from the group consisting of a bond and —CH$_2$—;
$X^6$ is —CH$_2$—, wherein:
the —CH$_2$— is optionally substituted with up to two independently selected alkyl;
$X^7$ is selected from the group consisting of —C(O)— and —C(S); and
$Z^1$ is CH optionally substituted with a substituent selected from the group consisting of nitro and cyano.

4. A method of treating a parasitic infection in an animal, wherein the method comprises administering at least one compound or salt of Formula (I) or a pharmaceutical composition comprising at least one compound or salt of Formula (I)

and at least one excipient and/or one or more active ingredients which differ in structure from the compound of Formula (I) to the animal, wherein:
the compound corresponds in structure to Formula (I):

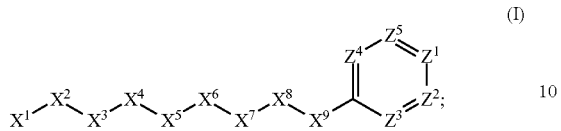

(I)

$X^1$ is selected from the group consisting of $C_3$-$C_6$-alkyl, $C_3$-$C_6$-alkenyl, $C_3$-$C_6$-alkynyl, cyclopentyl, cyclohexyl, phenyl, 5-member heterocycloalkyl, 5-member heterocycloalkenyl, 5-member heteroaryl, 6-member heterocycloalkyl, 6-member heterocycloalkenyl, and 6-member heteroaryl, wherein:
  the $C_3$-$C_6$-alkyl, $C_3$-$C_6$-alkenyl, $C_3$-$C_6$-alkynyl, cyclopentyl, 5-member heterocycloalkyl, 5-member heterocycloalkenyl, and 5-member heteroaryl are optionally substituted by one or more substituents independently selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl, wherein:
    the alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl,
  the cyclohexyl, phenyl, 6-member heterocycloalkyl, 6-member heterocycloalkenyl, and 6-member heteroaryl are optionally substituted by one or more substituents independently selected from the group consisting of halogen, cyano, alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl, wherein:
    the alkyl, alkoxy, alkylsulfanyl, aryl, aryloxy, arylalkoxy, arylsulfanyl, arylalkylsulfanyl, heteroaryl, heteroaryloxy, heteroarylalkoxy, heteroarylsulfanyl, and heteroarylalkylsulfanyl substituents are optionally substituted with one or more substituents independently selected from the group consisting of halogen, cyano, alkyl, alkoxy, haloalkyl, haloalkoxy, alkylsulfanyl, and haloalkylsulfanyl;
$X^2$ is selected from the group consisting of a bond, —O—, —C(O)—, —C(S)—, —NH—, —S—, —S(O)—, —S(O)$_2$—, —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$—, wherein:
  the —NH— is optionally substituted with alkyl, and
  the —CH$_2$—, —CH$_2$CH$_2$—, —C(O)—CH$_2$—, —CH$_2$—C(O)—, —O—CH$_2$—, —CH$_2$—O—, —NH—CH$_2$—, —CH$_2$—NH—, —S—CH$_2$—, —CH$_2$—S—, —S(O)—CH$_2$—, —CH$_2$—S(O)—, —S(O)$_2$—CH$_2$—, and —CH$_2$—S(O)$_2$— are optionally substituted with one or more independently selected alkyl;
$X^3$ is a linker, wherein:
  the linker is selected from the group of linkers consisting of:

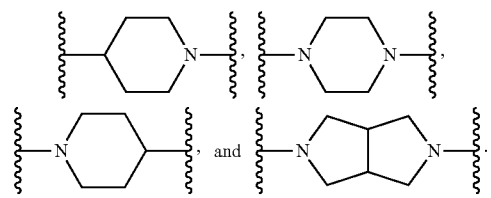

$X^4$ is selected from the group consisting of a bond, —CH$_2$—, —O—, —C(S)—, —C(O)—, —S(O)—, and —S(O)$_2$—, wherein:
  the —CH$_2$— is optionally substituted with up to two substituents independently selected from the group consisting of alkyl, alkenyl, and carbocyclyl;
$X^5$ is selected from the group consisting of a bond, —CH$_2$—, and carbocyclyl, wherein:
  the —CH$_2$— is optionally substituted with up to two substituents independently selected from the group consisting of alkyl, alkenyl, and carbocyclyl;
$X^6$ is selected from the group consisting of a bond, —CH$_2$—, and carbocyclyl, wherein:
  the —CH$_2$— is optionally substituted with up to two substituents independently selected from the group consisting of alkyl, alkenyl, and carbocyclyl;
$X^7$ is selected from the group consisting of —CH$_2$—, —O—, —C(O)—, —C(S)—, —S—, —S(O)—, —S(O)$_2$—, —NH—, —C(O)—NH—, —C(S)—NH—, —NH—C(O)—, —NH—C(S)—, wherein:
  the —CH$_2$— is optionally substituted with up to two substituents independently selected from the group consisting of alkyl, alkenyl, and carbocyclyl, and
  any —NH— is optionally substituted at a substitutable position with a substituent selected from the group consisting of alkyl, alkenyl, alkynyl, alkoxyalkyl, carbocyclyl, and carbocyclylalkyl, wherein:
    any such substituent is optionally substituted with one or more independently selected halogen;
$X^8$ is selected from the group consisting of piperidinyl, piperazinyl, homopiperazinyl or pyrrolidinyl, wherein:
  the piperidinyl, piperazinyl, homopiperazinyl or pyrrolidinyl is optionally substituted with one or more independently selected alkyl;
$X^4$-$X^5$-$X^6$-$X^7$ comprises at least one chain of 3 to 5 atoms that links $X^3$ to $X^8$;
$X^4$-$X^5$-$X^6$-$X^7$ comprises no chain of less than 3 atoms that links $X^3$ to $X^8$;
$X^9$ is selected from the group consisting of a bond, —O—, —C(O)—, —S—, —S(O)$_2$—, and —NH—, wherein:
  the —NH— is optionally substituted at a substitutable position with a substituent selected from the group consisting of alkyl, alkenyl, alkynyl, alkoxyalkyl, carbocyclyl, and carbocyclylalkyl, wherein:
    any such substituent is optionally substituted with one or more independently selected halogen;
$Z^1$ is selected from the group consisting of N and CH, wherein:
  the CH is optionally substituted with a substituent selected from the group consisting of halogen, nitro, cyano, aminosulfonyl, alkyl, alkoxy, alkoxycarbonyl, alkylsulfanyl, alkylsulfinyl, alkylsulfonyl, aryl, arylsulfanyl, arylsulfinyl, arylsulfonyl, heteroaryl, heteroarylsulfanyl, heteroarylsulfinyl, and heteroarylsulfonyl, wherein:

the alkyl, alkoxy, alkoxycarbonyl, alkylsulfanyl, alkylsulfinyl, alkylsulfonyl, aryl, arylsulfanyl, arylsulfinyl, arylsulfonyl, heteroaryl, heteroarylsulfanyl, heteroarylsulfinyl, and heteroarylsulfonyl are optionally substituted with one or more substituents independently selected from the group consisting of halogen and alkyl, and the aminosulfonyl is optionally substituted with up to two independently selected alkyl;

$Z^2$ is selected from the group consisting of N and CH, wherein:

the CH is optionally substituted with a substituent selected from the group consisting of cyano, halogen, nitro, alkyl, alkoxy, haloalkyl, alkylsulfanyl, and haloalkylsulfanyl;

$Z^3$, $Z^4$, and $Z^5$ are each independently selected from the group consisting of N and CH, wherein:

the CH is optionally substituted with a substituent selected from the group consisting of halogen, cyano, nitro, alkyl, alkoxy, alkylsulfanyl, haloalkyl, haloalkoxy, and haloalkylsulfanyl; and only one of $Z^1$, $Z^2$, $Z^3$, $Z^4$, and $Z^5$ may be N.

5. The method of claim 4, wherein the parasitic infection comprises a nematode infection.

6. The method of claim 4, wherein the parasitic infection comprises an infection by at least one of *Trichostrongylus axei, Trichostrongylus colubriformis, Haemonchus contortus, Ascaridia galli,* and *Oesophagostomum dentatum.*

7. The method of claim 4, wherein the animal is a sheep.

8. The method of claim 4, wherein the animal is a bovine animal.

9. A compound or salt of claim 1, wherein: the compound corresponds in structure to:

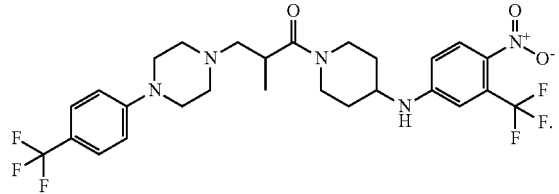 [SMILES: CC(CN1CCN(c2ccc(C(F)(F)F)cc2)CC1)C(=O)N1CCC(Nc2ccc([N+](=O)[O-])c(C(F)(F)F)c2)CC1]

* * * * *